US012799479B2

(12) United States Patent
Regev et al.

(10) Patent No.: US 12,799,479 B2
(45) Date of Patent: Nov. 17, 2026

(54) HIGH-THROUGHPUT METHODS FOR IDENTIFYING GENE INTERACTIONS AND NETWORKS

(71) Applicants: The Broad Institute, Inc., Cambridge, MA (US); Massachusetts Institute of Technology, Cambridge, MA (US)

(72) Inventors: Aviv Regev, Cambridge, MA (US); Atray Dixit, Cambridge, MA (US); Orit Rozenblatt-Rosen, Cambridge, MA (US)

(73) Assignees: The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 1376 days.

(21) Appl. No.: 16/770,346

(22) PCT Filed: Dec. 7, 2018

(86) PCT No.: PCT/US2018/064553

§ 371 (c)(1),
(2) Date: Jun. 5, 2020

(87) PCT Pub. No.: WO2019/113499

PCT Pub. Date: Jun. 13, 2019

(65) Prior Publication Data

US 2020/0362334 A1 Nov. 19, 2020

Related U.S. Application Data

(60) Provisional application No. 62/698,778, filed on Jul. 16, 2018, provisional application No. 62/595,904, filed on Dec. 7, 2017.

(51) Int. Cl.

| | |
|---|---|
| ***C12Q 1/6869*** | (2018.01) |
| ***C12N 9/22*** | (2006.01) |
| ***C12N 15/10*** | (2006.01) |
| ***C12N 15/113*** | (2010.01) |
| *C12N 15/90* | (2006.01) |

(52) U.S. Cl.

CPC .......... *C12N 15/1079* (2013.01); *C12N 9/22* (2013.01); *C12N 15/1065* (2013.01); *C12N 15/1096* (2013.01); *C12N 15/113* (2013.01); *C12Q 1/6869* (2013.01); *A01K 2217/072* (2013.01); *A01K 2267/0393* (2013.01); *C12N 15/907* (2013.01); *C12N 2310/20* (2017.05); *C12N 2320/12* (2013.01); *C12N 2800/80* (2013.01)

(58) Field of Classification Search

CPC .............................. C12N 15/10; C12Q 1/6869
See application file for complete search history.

(56) References Cited

U.S. PATENT DOCUMENTS

| | | | |
|---|---|---|---|
| 4,971,903 | A | 11/1990 | Hyman |
| 5,202,231 | A | 4/1993 | Drmanac et al. |
| 5,210,015 | A | 5/1993 | Gelfand et al. |
| 5,403,708 | A | 4/1995 | Brennan et al. |
| 5,445,934 | A | 8/1995 | Fodor et al. |
| 5,525,464 | A | 6/1996 | Drmanac et al. |
| 5,547,839 | A | 8/1996 | Dower et al. |
| 5,580,737 | A | 12/1996 | Polisky et al. |
| 5,604,097 | A | 2/1997 | Brenner |
| 5,636,400 | A | 6/1997 | Young |
| 5,641,870 | A | 6/1997 | Rinderknecht et al. |
| 5,660,985 | A | 8/1997 | Pieken et al. |
| 5,695,934 | A | 12/1997 | Brenner |
| 5,695,940 | A | 12/1997 | Drmanac et al. |
| 5,795,782 | A | 8/1998 | Church et al. |
| 5,846,719 | A | 12/1998 | Brenner et al. |
| 5,863,722 | A | 1/1999 | Brenner |
| 5,869,326 | A | 2/1999 | Hofmann |
| 5,902,723 | A | 5/1999 | Dower et al. |
| 6,138,077 | A | 10/2000 | Brenner |
| 6,150,516 | A | 11/2000 | Brenner et al. |
| 6,172,214 | B1 | 1/2001 | Brenner |
| 6,172,218 | B1 | 1/2001 | Brenner |
| 6,235,475 | B1 | 5/2001 | Brenner et al. |
| 6,352,828 | B1 | 3/2002 | Brenner |
| 7,041,481 | B2 | 5/2006 | Anderson et al. |
| RE39,793 | E | 8/2007 | Brenner |

(Continued)

FOREIGN PATENT DOCUMENTS

| | | | |
|---|---|---|---|
| AU | 2015101792 | A4 | 1/2016 |
| CA | 3028158 | A1 | 12/2017 |

(Continued)

OTHER PUBLICATIONS

Parnas et al., A Genome-Wide CRISPR Screen in Primary Immune Cells to Dissect Regulatory Networks, 2015, 162, 675-686. (Year: 2015).*

(Continued)

*Primary Examiner* — Amy M Bunker

(74) *Attorney, Agent, or Firm* — Sunit Talapatra; Foley & Lardner LLP

(57) ABSTRACT

The present disclosure provides compositions, systems, and methods for pooled screening of perturbations correlating to a phenotype. The present disclosure also provides for methods of in vivo perturbation screening. The present disclosure also provides for high-throughput sample multiplexing. The present disclosure also provides for methods to determine the clonal effects associated with millions of genetic perturbation combinations using standard pooled screening reagents.

10 Claims, 190 Drawing Sheets

Specification includes a Sequence Listing.

(56) References Cited

U.S. PATENT DOCUMENTS

| | | | |
|---|---|---|---|
| 7,393,665 B2 | 7/2008 | Brenner | |
| 7,537,897 B2 | 5/2009 | Brenner et al. | |
| 7,544,473 B2 | 6/2009 | Brenner | |
| 7,708,949 B2 | 5/2010 | Stone et al. | |
| RE41,780 E | 9/2010 | Anderson et al. | |
| 8,003,312 B2 | 8/2011 | Krutzik et al. | |
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,932,814 B2 | 1/2015 | Cong et al. | |
| 8,945,839 B2 | 2/2015 | Zhang | |
| 8,993,233 B2 | 3/2015 | Zhang et al. | |
| 8,999,641 B2 | 4/2015 | Zhang et al. | |
| 9,790,490 B2 | 10/2017 | Zhang et al. | |
| 11,149,267 B2 * | 10/2021 | Wang | C12N 15/113 |
| 2004/0171156 A1 | 9/2004 | Hartley et al. | |
| 2005/0172476 A1 | 8/2005 | Stone et al. | |
| 2006/0163385 A1 | 7/2006 | Link et al. | |
| 2007/0003442 A1 | 1/2007 | Link et al. | |
| 2007/0184489 A1 | 8/2007 | Griffiths et al. | |
| 2007/0195127 A1 | 8/2007 | Ahn et al. | |
| 2008/0003142 A1 | 1/2008 | Link et al. | |
| 2008/0014589 A1 | 1/2008 | Link et al. | |
| 2008/0081330 A1 | 4/2008 | Kahvejian | |
| 2009/0005254 A1 | 1/2009 | Griffiths et al. | |
| 2009/0131543 A1 | 5/2009 | Weitz et al. | |
| 2010/0002241 A1 | 1/2010 | Hirose et al. | |
| 2010/0137163 A1 | 6/2010 | Link et al. | |
| 2010/0172803 A1 | 7/2010 | Stone et al. | |
| 2011/0265198 A1 | 10/2011 | Gregory et al. | |
| 2012/0017290 A1 | 1/2012 | Cui et al. | |
| 2012/0219947 A1 | 8/2012 | Yurkovetsky et al. | |
| 2013/0236946 A1 | 9/2013 | Gouble | |
| 2013/0337441 A1 | 12/2013 | Lohse | |
| 2014/0170753 A1 | 6/2014 | Zhang | |
| 2014/0179006 A1 | 6/2014 | Zhang | |
| 2014/0179770 A1 | 6/2014 | Zhang et al. | |
| 2014/0186843 A1 | 7/2014 | Zhang et al. | |
| 2014/0186919 A1 | 7/2014 | Zhang et al. | |
| 2014/0186958 A1 | 7/2014 | Zhang et al. | |
| 2014/0189896 A1 | 7/2014 | Zhang et al. | |
| 2014/0227787 A1 | 8/2014 | Zhang | |
| 2014/0234972 A1 | 8/2014 | Zhang | |
| 2014/0242664 A1 | 8/2014 | Zhang et al. | |
| 2014/0242699 A1 | 8/2014 | Zhang | |
| 2014/0242700 A1 | 8/2014 | Zhang et al. | |
| 2014/0248702 A1 | 9/2014 | Zhang et al. | |
| 2014/0256046 A1 | 9/2014 | Zhang et al. | |
| 2014/0256595 A1 | 9/2014 | Link et al. | |
| 2014/0273231 A1 | 9/2014 | Zhang et al. | |
| 2014/0273232 A1 | 9/2014 | Zhang et al. | |
| 2014/0273234 A1 | 9/2014 | Zhang et al. | |
| 2014/0287938 A1 | 9/2014 | Zhang et al. | |
| 2014/0310830 A1 | 10/2014 | Zhang et al. | |
| 2015/0051088 A1 | 2/2015 | Kim | |
| 2015/0184139 A1 | 7/2015 | Zhang et al. | |
| 2015/0259674 A1 | 9/2015 | Steelman et al. | |
| 2016/0060691 A1 | 3/2016 | Giresi et al. | |
| 2016/0208323 A1 | 7/2016 | Bernstein et al. | |
| 2016/0370266 A1 | 12/2016 | White et al. | |
| 2017/0211142 A1 | 7/2017 | Smargon et al. | |
| 2017/0349894 A1 | 12/2017 | Dahlman et al. | |
| 2018/0112255 A1 | 4/2018 | Chen et al. | |
| 2018/0320224 A1 | 11/2018 | Gaublomme et al. | |
| 2018/0341744 A1 | 11/2018 | Regev et al. | |
| 2019/0085324 A1 * | 3/2019 | Regev | G16B 5/00 |
| 2020/0308560 A1 | 10/2020 | Zhang et al. | |

FOREIGN PATENT DOCUMENTS

| | | | |
|---|---|---|---|
| CN | 108513582 | A | 9/2018 |
| EP | 0 404 097 | A2 | 12/1990 |
| EP | 2 047 910 | A2 | 4/2009 |
| EP | 2 047 910 | B1 | 4/2009 |
| EP | 2 771 468 | B1 | 2/2015 |
| EP | 2 784 162 | B1 | 4/2015 |
| EP | 2 764 103 | B1 | 8/2015 |
| EP | 3 009 511 | A2 | 4/2016 |
| WO | 93/11161 | A1 | 6/1993 |
| WO | 93/23564 | A1 | 11/1993 |
| WO | 96/39154 | A1 | 12/1996 |
| WO | 97/03211 | A1 | 1/1997 |
| WO | 97/49450 | A1 | 12/1997 |
| WO | 98/13523 | A1 | 4/1998 |
| WO | 98/28440 | A1 | 7/1998 |
| WO | 98/52609 | A1 | 11/1998 |
| WO | 01/89788 | A2 | 11/2001 |
| WO | 2004/002627 | A2 | 1/2004 |
| WO | 2004/091763 | A2 | 10/2004 |
| WO | 2005/021151 | A1 | 3/2005 |
| WO | 2006/040551 | A2 | 4/2006 |
| WO | 2006/040554 | A1 | 4/2006 |
| WO | 2006/096571 | A2 | 9/2006 |
| WO | 2007/081385 | A2 | 7/2007 |
| WO | 2007/089541 | A2 | 8/2007 |
| WO | 2007/133710 | A2 | 11/2007 |
| WO | 2008/063227 | A2 | 5/2008 |
| WO | 2009/012418 | A2 | 1/2009 |
| WO | 2010/056728 | A1 | 5/2010 |
| WO | 2011/079176 | A2 | 6/2011 |
| WO | 2012/106385 | A2 | 8/2012 |
| WO | 2014/018423 | A2 | 1/2014 |
| WO | 2014/047556 | A1 | 3/2014 |
| WO | 2014/047561 | A1 | 3/2014 |
| WO | 2014/085802 | A1 | 6/2014 |
| WO | 2014/093595 | A1 | 6/2014 |
| WO | 2014/093622 | A2 | 6/2014 |
| WO | 2014/093635 | A1 | 6/2014 |
| WO | 2014/093655 | A2 | 6/2014 |
| WO | 2014/093661 | A2 | 6/2014 |
| WO | 2014/093694 | A1 | 6/2014 |
| WO | 2014/093701 | A1 | 6/2014 |
| WO | 2014/093709 | A1 | 6/2014 |
| WO | 2014/093712 | A1 | 6/2014 |
| WO | 2014/093718 | A1 | 6/2014 |
| WO | 2014/143157 | A1 | 9/2014 |
| WO | 2014/204723 | A1 | 12/2014 |
| WO | 2014/204724 | A1 | 12/2014 |
| WO | 2014/204725 | A1 | 12/2014 |
| WO | 2014/204726 | A1 | 12/2014 |
| WO | 2014/204727 | A1 | 12/2014 |
| WO | 2014/204728 | A1 | 12/2014 |
| WO | 2014/204729 | A1 | 12/2014 |
| WO | WO-2014/210353 | A2 | 12/2014 |
| WO | 2015/058052 | A1 | 4/2015 |
| WO | WO-2015/050998 | A2 | 4/2015 |
| WO | 2015/070083 | A1 | 5/2015 |
| WO | 2015/089351 | A1 | 6/2015 |
| WO | 2015/089354 | A1 | 6/2015 |
| WO | 2015/089364 | A1 | 6/2015 |
| WO | 2015/089419 | A2 | 6/2015 |
| WO | 2015/089427 | A1 | 6/2015 |
| WO | 2015/089462 | A1 | 6/2015 |
| WO | 2015/089465 | A1 | 6/2015 |
| WO | 2015/089473 | A1 | 6/2015 |
| WO | 2015/089486 | A2 | 6/2015 |
| WO | 2015/130968 | A2 | 9/2015 |
| WO | 2015/188839 | A2 | 12/2015 |
| WO | 2016/028682 | A1 | 2/2016 |
| WO | 2016/049024 | A2 | 3/2016 |
| WO | 2016/049163 | A2 | 3/2016 |
| WO | 2016/049251 | A1 | 3/2016 |
| WO | 2016/049258 | A2 | 3/2016 |
| WO | 2016040476 | A1 | 3/2016 |
| WO | 2016/094867 | A1 | 6/2016 |
| WO | 2016/094872 | A1 | 6/2016 |
| WO | 2016/094874 | A1 | 6/2016 |

(56) References Cited

FOREIGN PATENT DOCUMENTS

| | | | |
|---|---|---|---|
| WO | 2016/094880 | A1 | 6/2016 |
| WO | 2016/100974 | A1 | 6/2016 |
| WO | 2016/106236 | A1 | 6/2016 |
| WO | 2016/106244 | A1 | 6/2016 |
| WO | 2016/149422 | A1 | 9/2016 |
| WO | 2016/161516 | A1 | 10/2016 |
| WO | 2016/168584 | A1 | 10/2016 |
| WO | 2016/205749 | A1 | 12/2016 |
| WO | 2016/205759 | A1 | 12/2016 |
| WO | 2017/044893 | A1 | 3/2017 |
| WO | 2017/070605 | A1 | 4/2017 |
| WO | 2017/075292 | A1 | 5/2017 |
| WO | 2017075265 | A1 | 5/2017 |
| WO | 2017075294 | A1 | 5/2017 |
| WO | 2017/156336 | A1 | 9/2017 |
| WO | 2017/161325 | A1 | 9/2017 |
| WO | WO-2017/164936 | A1 | 9/2017 |
| WO | 2017/219027 | A1 | 12/2017 |
| WO | 2018/035250 | A1 | 2/2018 |
| WO | 2018/170333 | A1 | 9/2018 |
| WO | 2019/005866 | A1 | 1/2019 |
| WO | 2019/113506 | A1 | 6/2019 |

OTHER PUBLICATIONS

Parnas et al., A Genome-Wide CRISPR Screen in Primary Immune Cells to Dissect Regulatory Networks, Supplementary Information, 2015, 162, 675-686. (Year: 2015).*

O'Duibhir et al., Cell Cycle Population Effects in Perturbation Studies, Molecular Systems Biology, 2014, 10(732), 1-14. (Year: 2014).*

Adamson et. al., A Multiplexed Single-Cell CRISPR Screening Platform Enables Systematic Dissection of the Unfolded Protein Response, Cell, 2016, 167, 167-1882; and e1-12. (Year: 2016).*

Adamson et al., A Multiplexed Single-Cell CRISPR Screening Platform Enables Systematic Dissection of the Unfolded Protein Response, Supplementary Material, Cell, 2016, 167, 1. (Year: 2016).*

Gewirtz et al., Constitutive Expression of Platelet Glycoproteins by the Human Leukemia Cell Line K562, Blood, 1982, 60(3), 785-789. (Year: 1982).*

Tim Wang, Thesis, Development and Application of a General Method for Somatic Cell Genetics, Massachusetts Institute of Technology (MIT), May 2017, 1-270. (Year: 2017).*

The Broad Institute, Inc., International Preliminary Report on Patentability issued in International Application No. PCT/US2018/064553, mailed on Jun. 18, 2020, 9 pages.

The Broad Institute, Inc., International Preliminary Report on Patentability issued in International Application No. PCT/US2018/064563, mailed on Jun. 18, 2020, 11 pages.

The Broad Institute, Inc., International Search Report and Written Opinion issued in International Application No. PCT/US2018/064563, mailed on Feb. 26, 2019, 14 pages.

Aguirre et al., "Genomic Copy Number Dictates a Gene-Independent Cell Response to CRISPR/Cas9 Targeting", Cancer Discovery, vol. 6, No. 8, Jun. 3, 2016, 914-929.

Amit et al., "Unbiased Reconstruction of a Mammalian Transcriptional Network Mediating Pathogen Responses", Science, vol. 326, Issue 5950, Oct. 9, 2009, 257-263.

Anders et al., "Structural Basis of PAM-Dependent Target DNA Recognition by the Cas9 Endonuclease", Nature, vol. 513, No. 7519, Sep. 25, 2014, 22 pages.

Bandyopadhyay et al., "Rewiring of Genetic Networks in Response to DNA Damage", Science, vol. 330, No. 6009, Dec. 3, 2010, 9 pages.

Bassik et al., "A Systematic Mammalian Genetic Interaction Map Reveals Pathways Underlying Ricin Susceptibility", Cell, vol. 152, No. 4, Feb. 14, 2013, 28 pages.

Berger et al., "High-throughput Phenotyping of Lung Cancer Somatic Mutations", Cancer Cell, vol. 30, No. 2, Aug. 8, 2016, 31 pages.

Briner et al., "Guide RNA Functional Modules Direct Cas9 Activity and Orthogonality", Molecular Cell, vol. 56, Issue 2, Oct. 23, 2014, 7 pages.

Butler et al., "Integrating Single-cell Transcriptomic Data Across different Conditions, Technologies, and Species", Nature Biotechnology, vol. 36, No. 5, May 2018, 17 pages.

Cao et al., "Comprehensive Single Cell Transcriptional Profiling of a Multicellular Organism by Combinatorial Indexing", Available at: BioRxiv https://doi.org/10.1101/104844, Feb. 2, 2017, 35 pages.

Cao et al., "Comprehensive Single-cell Transcriptional Profiling of a Multicellular Organism", Science, vol. 357, No. 6352, Aug. 18, 2017, 7 pages.

Capaldi et al., "Structure and Function of a Transcriptional Network Activated by the MAPK Hog1", Nature Genetics, vol. 40, No. 11, Nov. 2008, 18 pages.

Chavez et al., "Highly Efficient Cas9-mediated Transcriptional Programming", Nature Methods, vol. 12, No. 4, Apr. 2015, 11 pages.

Chen et al., "Genome-Wide CRISPR Screen in a Mouse Model of Tumor Growth and Metastasis", Cell, vol. 160, No. 6, Mar. 12, 2015, 28 pages.

Datlinger et al., "Pooled CRISPR Screening with Single-cell Transcriptome Readout", Nature Methods, vol. 14, No. 3, Mar. 2017, 20 pages.

Zheng et al., "Massively Parallel Digital Transcriptional Profiling of Single Cells", Nature Communications, vol. 8, No. 14049, Jan. 16, 2017, 12 pages.

Duan et al., "LINCS Canvas Browser: Interactive Web App to Query, Browse and Interrogate Lincs L1000 Gene Expression Signatures", Nucleic Acids Research, vol. 42, Issue W1, May 13, 2014, 13 pages.

Fan et al., "Combinatorial Labeling of Single Cells for Gene Expression Cytometry", Science, vol. 347, Issue 6222, Feb. 6, 2015, 10 pages.

Feldman et al., "Lentiviral Co-Packaging Mitigates the Effects of Intermolecular Recombination and Multiple Integrations in Pooled Genetic Screens", BioRxiv, Feb. 8, 2018, 6 pages.

Gehring et al., "Highly Multiplexed Single-Cell RNA-seq for Defining Cell Population and Transcriptional Spaces", Retrieved as : https://doi.org/10.1101/315333. on Jul. 25, 2020, May 5, 2018, 19 pages.

Gierahn et al., "Seq-Well: Portable, Low-Cost RNA Sequencing of Single Cells at High Throughput", Nature Methods, vol. 14, No. 4, Apr. 2017., 9 pages.

Gilbert et al., "CRISPR-Mediated Modular RNA-Guided Regulation of Transcription in Eukaryotes", Cell, vol. 154, No. 2, Jul. 18, 2013, 20 pages.

Gilbert et al., "Genome-Scale CRISPR-Mediated Control of Gene Repression and Activation", Cell, vol. 159, No. 3, Oct. 23, 2014, 647-661.

Haber et al., "Systematic Triple-Mutant Analysis Uncovers Functional Connectivity Between Pathways Involved in Chromosome Regulation", Cell, vol. 3, No. 6, Jun. 27, 2013, 2168-2178.

Habib et al., "Div-Seq: Single-Nucleus RNA-Seq Reveals Dynamics of Rare Adult Newborn Neurons", Science, vol. 353, No. 6302, Jul. 28, 2016, 925-928.

Habib et al., "Massively Parallel Single-Nucleus RNA-seq with DroNc-seq", Nature Methods, vol. 14, No. 10, Oct. 2017, 18 pages.

Hill et al., "On the design of CRISPR-based Single-Cell Molecular Screens", Nature Methods, vol. 15, No. 4, Apr. 2018, 22 pages.

Hughes et al., "Functional Discovery via a Compendium of Expression Profiles", Cell, vol. 102, Jul. 7, 2000, 109-126.

Jaitin et al., "Dissecting Immune Circuits by Linking CRISPR-Pooled Screens with Single-Cell RNA-Seq", Cell, vol. 167, No. 7, Dec. 15, 2016, 29 pages.

Kabadi et al., "Multiplex CRISPR/Cas9-Based Genome Engineering from a Single Lentiviral Vector", Nucleic Acids Research, vol. 42, No. 19, Aug. 13, 2014, 11 pages.

Kampmann et al., "Functional Genomics Platform for Pooled Screening and Generation of Mammalian Genetic Interaction Maps", Nature Protocols, vol. 9, No. 8, Aug. 2014, 48 pages.

(56) References Cited

OTHER PUBLICATIONS

Kang et al., "Multiplexed Droplet Single-cell RNA-sequencing using Natural Genetic Variation", Nature Biotechnology, vol. 36, No. 1, Jan. 2018, 89-94.
Kemmeren et al., "Largescale Genetic Perturbations Reveal Regulatory Networks and An Abundance of Gene-Specific Repressors", Cell, vol. 157, No. 3, Apr. 24, 2014, 740-752.
Klein et al., "Droplet Barcoding for Single-Cell Transcriptomics Applied to Embryonic Stem Cells", Cell, vol. 161, No. 5, May 21, 2015, 24 pages.
Konermann et al., "Genome-Scale Transcriptional Activation by an Engineered CRISPR-Cas9 Complex", Nature, vol. 517, No. 7536, Jan. 29, 2015, 583-588.
Lamb et al., "The Connectivity Map: Using Gene-Expression Signatures to Connect Small Molecules, Genes, and Disease", Science, vol. 313, Issue 5795, Sep. 29, 2006, 1929-1935.
Liberali et al., "Single-Cell and Multivariate Approaches in Genetic Perturbation Screens", Nature Reviews Genetics, vol. 16, No. 1, Dec. 2, 2014, 15 pages.
Macosko et al., "Highly Parallel Genome-Wide Expression Profiling of Individual Cells Using Nanoliter Droplets", Cell, vol. 161, No. 5, May 21, 2015, 25 pages.
Melnikov et al., "Systematic Dissection and Optimization of Inducible Enhancers in Human Cells using a Massively Parallel Reporter Assay", Nature Biotechnology, vol. 30, Feb. 26, 2012, 9 pages.
Nagy et al., "Single-nucleus RNA Sequencing shows Convergent Evidence from Different Cell Types for Altered Synaptic Plasticity in Major Depressive Disorder", Retrieved from : https://doi.org/10.1101/384479 as on Jul. 25, 2020, Aug. 3, 2018, 37 pages.
Parnas et al., "A Genome-Wide CRISPR Screen in Primary Immune Cells to Dissect Regulatory Networks", Cell, vol. 162, No. 3, Jul. 30, 2015, 24 pages.
Picelli et al., "Full-Length RNA-Seq from Single Cells using Smart-seq2", Nature Protocols, vol. 9, No. 1, Jan. 2, 2014, 171-181.
Platt et al., "CRISPR-Cas9 Knockin Mice for Genome Editing and Cancer Modeling", Cell, vol. 159, No. 2, Oct. 9, 2014, 31 pages.
Rajagopal et al., "High-throughput Mapping of Regulatory DNA", Nature Biotechnology, vol. 34, No. 2, Feb. 2016, 22 pages.
Rosenberg et al., "Scaling Single Cell Transcriptomics Through Split Pool Barcoding", Available at:Bio Rxiv http://dx.doi.org/10.1101/105163, Feb. 2, 2017, 13 pages.
Rosenberg et al., "Single-Cell Profiling of the Developing Mouse Brain and Spinal Cord with Split-Pool Barcoding", Science, vol. 360, No. 6385, Apr. 13, 2018, 8 pages.
Sanjana et al., "Improved Vectors and Genome-Wide Libraries for CRISPR Screening", Nature Methods, vol. 11, No. 8, Aug. 2014, 5 pages.
Satija et al., "Spatial Reconstruction of Single-Cell Gene Expression Data", Nature Biotechnology, vol. 33, No. 5, May 2015, 495-502.
Zilionis et al., "Single-cell Barcoding and Sequencing Using Droplet Microfluidics", Nature Protocols, vol. 12, No. 1, Jan. 2017, 44-73.
Shalem et al., "Genome-Scale CRISPR-Cas9 Knockout Screening in Human Cells", Science, vol. 343, No. 6166, Jan. 3, 2014, 10 pages.
Shalem et al., "High-Throughput Functional Genomics Using CRISPR-Cas9", Nature Reviews Genetics, vol. 16, No. 5, May 2015, 28 pages.
Shendure et al., "Massively Parallel Genetics", Genetics, vol. 203, Jun. 2016, 617-619.
Smith et al., "Massively Parallel Decoding of Mammalian Regulatory Sequences Supports a Flexible Organizational Model", Nature Genetics, vol. 45, No. 9, Jul. 2013, 11 pages.
Stoeckius et al., "Cell Hashing with Barcoded Antibodies Enables Multiplexing and Doublet Detection for Single Cell Genomics", Genome Biology, vol. 19, No. 224, 2018, 12 pages.
Stoeckius et al., "Simultaneous Epitope and Transcriptome Measurement in Single Cells", Nature Methods, vol. 14, No. 9, Jul. 31, 2017, 10 pages.
Swiech et al., "In Vivo Interrogation of Gene Function in the Mammalian Brain Using CRISPR-Cas9", Nature Biotechnology, vol. 33, No. 1, Jan. 2015, 102-106.
Tanenbaum et al., "A Protein-Tagging System for Signal Amplification in Gene Expression and Fluorescence Imaging", Cell, vol. 159, Issue 3, Oct. 23, 2014, 635-646.
Tsumura et al., "Maintenance of Self-Renewal Ability of Mouse Embryonic Stem Cells in the Absence of DNA Methyltransferases Dnmt1, Dnmt3a and Dnmt3b", Genes Cells, vol. 11, No. 7, Jul. 2006, 805-814.
Vitak et al., "Sequencing Thousands of Single-Cell Genomes with Combinatorial Indexing", Nature Methods, vol. 14, No. 3, Mar. 2017, 19 pages.
Wang et al., "Genetic Screens in Human Cells Using the CRISPR/Cas9 System", Science, vol. 343, No. 6166., Jan. 3, 2014, 12 pages.
Wang et al., "Identification and Characterization of Essential Genes in the Human Genome", Science, vol. 350, No. 6264, Nov. 15, 2015, 1096-1101.
Wong et al., "Multiplexed Barcoded CRISPR-Cas9 Screening Enabled by CombiGEM", Proceedings of the National Academy of Sciences of the United States of America, vol. 113, No. 9, Mar. 1, 2016, 2544-2549.
Zheng et al., "Haplotyping Germline and Cancer Genomes with High-Throughput Linked-Read Sequencing", Nature Biotechnology, vol. 34, No. 3, Mar. 2016, 303-311.
Adamson, et al., "A Multiplexed Single-Cell CRISPR Screening Platform Enables Systematic Dissection of the Unfolded Protein Response", Cell, vol. 167, No. 7, Dec. 15, 2016, 49 pages.
Amit, et al., "Strategies to Discover Regulatory Circuits of the Mammalian Immune System", Nat. Rev. Immunol., Nov. 18, 2011, pp. 873-880.
Dixit, et al., "Perturb-Seq: Dissecting Molecular Circuits with Scalable Singe-Cell RNA Profiling of Pooled Genetic Screens", Cell, 167, Dec. 15, 2016, 1853-1866.
The Broad Institute, Inc., et al., "Notification of Transmittal of The International Search Report and the Written Opinion of the International Searching Authority, or the Declaration", PCT/US2018/064553, Feb. 26, 2019, 12 pages.
Abhyankar et al., "Characterization of a membrane-based gradient generator for use in cell-signaling studies," Lab on a Chip, 2006, vol. 6 (pp. 389-393).
Abudayyeh et al., "C2c2 is a single-component programmable RNA-guided RNA targeting CRISPR effector," Science, Aug. 5, 2016, vol. 353, No. 6299 (pp. 1-23).
Acosta-Alvear et al., "XBPI controls diverse cell type- and condition-specific transcriptional regulatory networks," Molecular Cell, Jul. 6, 2007, vol. 27, No. 1 (pp. 53-66).
Adiconis et al., "Comparative analysis of RNA sequencing methods for degraded or low-input samples," Nature Methods, Jul. 2013, vol. 10, No. 7 (pp. 623-629).
Allerson et al., "Fully 2'-Modified Oligonucleotide Duplexes with Improved in Vitro Potency and Stability Compared to Unmodified Small Interfering RNA," American Chemical Society, Journal of Medicinal Chemistry, Feb. 2005, vol. 48 (pp. 901-904).
Altschul et al., "Basic Local Alignment Search Tool," Journal of Molecular Biology, May 15, 1990, vol. 215 (pp. 403-410).
Altshuler et al., "Genetic Mapping in Human Disease," Science, Nov. 2008, vol. 322, No. 5903 (pp. 881-888).
Ashworth et al., "Genetic Interactions in Cancer Progression and Treatment," Cell, Apr. 2011, vol. 145, No. 1 (pp. 30-38).
Assarsson et al., "Homogenous 96-plex PEA immunoassay exhibiting high sensitivity, specificity, and excellent scalability," PloS one, Apr. 2014, vol. 9, e95192 (pp. 1-11).
Ausubel, "A botanical macroscope" Proceedings of the National Academy of Sciences, Aug. 4, 2009, vol. 106, No. 31 (pp. 12569-12570).
Bamshad et al., "Exome sequencing as a tool for Mendelian disease gene discovery," Nature Reviews Genetics, Nov. 2011, vol. 12 (pp. 745-755).
Banks et al., Comparison of three common amine reactive fluorescent probes used for conjugation to biomolecules by capillary zone electrophoresis, Bioconjugate Chemistry, Jul.-Aug. 1995, vol. 6, No. 4 (pp. 447-458).

(56) References Cited

OTHER PUBLICATIONS

Bao et al., "Mitochondrial dysfunction remodels one-carbon metabolism in human cells," eLife, Jun. 16, 2016 (pp. 1-24).
Baserga et al., "Beta-globin nonsense mutation: deficient accumulation of mRNA occurs despite normal cytoplasmic stability," Proceedings of the National Academy of Sciences, USA, Genetics, Apr. 1992, vol. 89 (pp. 2935-2939).
Beerenwinkle et al., "Epistasis and Shapes of Fitness Landscapes," Statistica Sinica, 2007, vol. 17 (pp. 1317-1342) retrieved from: http://arxiv.org/abs/q-bio/0603034v2.
Bendall et al., "Single-cell mass cytometry of differential immune and drug responses across a human hematopoietic continuum," Science, May 6, 2011, vol. 332, No. 6030 (pp. 687-696).
Benharouga et al., "COOH-Terminal Truncations Promote Proteasome-Dependent Degradation of Mature Cystic Fibrosis Transmembrane Conductance Regulator from Post-Golgi Compartments," Journal of Cell Biology, May 28, 2001, vol. 153, No. 5 (pp. 957-997).
Birrell et al., "A genome-wide screen in *Saccharomyces cerevisiae* for genes affecting UV radiation sensitivity," Proceedings of the National Academy of Sciences, USA, Oct. 23, 2001, vol. 98, No. 22 (pp. 12608-12613).
Blanco et al., "Highly efficient DNA synthesis by the phage Phi 29 DNA polymerase: Symmetrical mode of DNA replication," The Journal of Biological Chemistry, May 25, 1989, vol. 264, No. 15 (pp. 8935-8940).
Blecher-Gonen et al., "High-throughput chromatin immunoprecipitation for genome-wide mapping of in vivo protein-DNA interactions and epigenomic states," Nature Protocols, 2013, vol. 8 (pp. 539-554).
Bloom et al., "The role of genetic interactions in yeast quantitative traits," bioRxiv preprint first posted online May 19, 2015; doi: http://dx.doi.org/10.1101/01951 (pp. 1-22).
Bochkis et al., "Changes in nucleosome occupancy associated with metabolic alterations in aged mammalian liver," Cell Reports, 2014, vol. 9, No. 3 (pp. 996-1006).
Boone et al., "Exploring genetic interactions and networks with yeast," Nature Reviews Genetics, Jun. 2007, vol. 8 (pp. 437-449).
Bornstein et al., "A negative feedback loop of transcription factors specifies alternative dendritic cell chromatin States," Molecular Cell, Dec. 18, 2014, vol. 56 (pp. 749-762).
Botstein et al., "Discovering genotypes underlying human phenotypes: past successes for mendelian disease, future approaches for complex disease," Nature Genetics, Mar. 2003, vol. 33 (pp. 228-237).
Boyle et al., "An Expanded View of Complex Traits: From Polygenic to Omnigenic," Cell, Jun. 2017, vol. 169 (pp. 1177-1186).
Bramsen et al., "Development of Therapeutic-Grade Small Interfering RNAs by Chemical Engineering," Frontiers in Genetics, Aug. 20, 2012, vol. 3, Article 154 (pp. 1-22).
Buenrostro et al. "Transposition of native chromatin for fast and sensitive epigenomic profiling of open chromatin, DNA-binding proteins and nucleosome position," Nature Methods, Dec. 2013, vol. 10, No. 12 (pp. 1213-1218).
Buenrostro et al., "Single-cell chromatin accessibility reveals principles of regulatory variation," Nature, Jul. 23, 2015, vol. 523, No. 7561 (pp. 486-490).
Buettner et al., "Computational analysis of cell-to-cell heterogeneity in single-cell RNA-sequencing data reveals hidden subpopulations of cells," Nature Biotechnology, Feb. 2015, vol. 33, No. 2 (pp. 155-160).
Cabili et al., "A Localization and abundance analysis of human IncRNAs at single-cell and single-molecule resolution," Genome Biology, 2015, vol. 16, No. 20 (pp. 1-16).
Cabili et al., "Integrative annotation of human large intergenic noncoding RNAs reveals global properties and specific subclasses," Genes Development, 2011, vol. 25 (pp. 1915-1927).
Calfon et al., "IRE1 couples endoplasmic reticulum load to secretory capacity by processing the XBP-1 mRNA," Nature, Jan. 3, 2002, vol. 415, No. 6867 (pp. 92-96).
Canard et al., "DNA polymerase fluorescent substrates with reversible 3'-tags," Gene, Oct. 11, 1994, vol. 148, No. 1 (pp. 1-6).
Candes et al., "Exact Matrix Completion via Convex Optimization," Forty-Sixth Annual Allerton Conference, Allerton House, UIUC, Illinois, USA, Sep. 23-26, 2008 (pp. 806-812).
Candes et al., "Matrix Completion with Noise," Proceedings of the IEEE, Jun. 2010, vol. 98, No. 6 (pp. 925-936).
Candes et al., "Robust principal component analysis?" Journal of the ACM (JACM), Dec. 17, 2009 (pp. 1-39) retrieved from: arXiv:0912.3599v1 Sep. 12, 2024.
Candes, E.J., "Compressive sampling," Proceedings of the International Congress of Mathematicians, Madrid, Spain, 2006 (pp. 1-20).
Candes, E.J., "Mathematics of sparsity (and a few other things)," Proceedings of the International Congress of Mathematicians, Seoul, South Korea, 2014 (pp. 1-27).
Cannoodt et al., "SCORPIUS improves trajectory inference and identifies novel modules in dendritic cell development," bioRxiv preprint doi: https://doi.org/10.1101/079509; this version posted Oct. 7, 2016 (pp. 1-15).
Canver et al., "BCL11A enhancer dissection by Cas9-mediated in situ saturating mutagenesis," Nature, vol. 527, 2015 [including Supplementary Material] (pp. 192-197).
Carbon et al., "AmiGO: online access to ontology and annotation data," Bioinformatics, 2009, vol. 25, No. 2 (pp. 288-289).
Carr et al., "Genome Engineering," Nature Biotechnology, Dec. 2009, vol. 27, No. 12 (pp. 1151-1162).
Carter et al., "Prediction of phenotype and gene expression for combinations of mutations," Molecular Systems Biology, 2007, vol. 3, No. 96 (pp. 1-9).
Cartwright et al., "NFKB1: a suppressor of inflammation, ageing and cancer," FEBS Journal, 2016, vol. 283 (pp. 1812-1822).
CBOL Plant Working Group, "A DNA barcode for land plants," Proceedings of the National Academy of Sciences, Aug. 4, 2009, vol. 106, No. 31 (pp. 12794-12797).
Chan et al., "A Mouse ooplasm confers context-specific reprogramming capacity," Nature genetics, Sep. 2013, vol. 44 (pp. 978-980).
Chang et al., "Copper-free click chemistry in living animals," Proceedings of the National Academy of Sciences, Feb. 2, 2010, vol. 107, No. 5 (pp. 1821-1826).
Chen et al., "Characterization of 582 natural and synthetic terminators and quantification of their design constraints," Nature Methods, Jul. 2013, vol. 10, No. 7 (pp. 659-664).
Chen et al., "Dynamic Imaging of Genomic Loci in Living Human Cells by an Optimized CRISPR/Cas System," Cell, 2013, vol. 155 (pp. 1479-1491).
Cheng et al., "Semiconductor-based DNA sequencing of histone modification states," Nature Communications, 2013, vol. 4, No. 2672 (pp. 1-7).
Chevrier et al., "Systematic discovery of TLR signaling components delineates viral-sensing circuits," Cell, Nov. 11, 2011, vol. 147 (pp. 853-867).
Chu et al., "Efficient Generation of Rosa26 Knock-in Mice using Crispr/Cas9 in C57bl/6 Zygotes," BMC Biotechnology, Jan. 16, 2016, vol. 16, No. 4 (15 pages).
Chuang et al., "Porcine type III RNA polymerase III promoters for short hairpin RNA expression," Animal Biotechnology, 2009, vol. 20, No. 1 (pp. 34-39).
Chung et al., "Polycistronic RNA polymerase II expression vectors for RNA interference based on BIC/miR-155," Nucleic Acids Research, 2006, vol. 34, No. 7 (14 pages).
Chung et al., "Statistical significance of variables driving systematic variation in high-dimensional data," Bioinformatics, 2015, vol. 31, No. 4 (pp. 545-554).
Chung et al., "Structural and molecular interrogation of intact biological systems," Nature, May 16, 2013, vol. 497 (pp. 332-337).
Claeboe et al., "3'-Modified oligonucleotides by reverse DNA synthesis," Nucleic Acids Research, Oct. 1, 2003, vol. 31, No. 19 (pp. 5685-5691).
Cleary et al., "Composite measurements and molecular compressed sensing for highly efficient transcriptomics," bioRxiv preprint doi: https://doi.org/10.1101/091926; this version posted Jan. 2, 2017 (pp. 1-54).

(56) References Cited

OTHER PUBLICATIONS

Cohen, A., "Hidden Markov models in biomedical signal processing," Proceedings of the 20th Annual International Conference of the IEEE Engineering in Medicine and Biology Society, 1998, vol. 20, No. 3 (pp. 1145-1150).
Collins et al., "A branched DNA signal amplification assay for quantification of nucleic acid targets below 100 molecules," Nucleic Acids Research, 1997, vol. 25, No. 15 (pp. 2979-2984).
Cong et al., "CRISPR-Assisted Mammalian Genome Engineering," published as "Multiplex Genome Engineering Using CRISPR-Cas Systems," Science, Oct. 5, 2012, vol. 339 (pp. 819-823) [Manuscript including Supplementary Materials—36 pages].
Costanzo et al., "A global genetic interaction network maps a wiring diagram of cellular function," Science, Sep. 2016, vol. 353, No. 6306 (pp. 1-34).
Costanzo et al., "The genetic landscape of a cell," Science, Jan. 22, 2010, vol. 327 (pp. 425-431).
Cox et al., "RNA editing with CRISPR-Cas13," Science, Nov. 24, 2017, vol. 358, No. 6366 (pp. 1019-1027).
Cusanovich et al., "Multiplex single-cell profiling of chromatin accessibility by combinatorial cellular indexing" Science, May 22, 2015, vol. 348, No. 6237 (34 pages—Supplementary materials).
Dahlman et al., "Orthogonal gene knockout and activation with a catalytically active Cas9 nuclease," Nature Biotechnology, Nov. 2015, vol. 33, No. 11 (pp. 1159-1161).
Dang et al., "Optimizing sgRNA structure to improve CRISPR-Cas9 knockout efficiency," Genome Biology, 2015, vol. 16, No. 280 (pp. 1-10).
Datlinger et al., "Pooled CRISPR Screening with Single-Cell Transcriptome Read-Out," Nature Methods, Mar. 2017, vol. 14, No. 3 (20 pages—includes supplemental materials).
Dean et al., "Comprehensive human genome amplification using multiple displacement amplification," Proceedings of the National Academy of Sciences, 2002, vol. 99, No. 8 (pp. 5261-5266).
Dellinger et al., "Streamlined Process for the Chemical Synthesis of RNA Using 2 '-O-Thionocarbamate-Protected Nucleoside Phosphoramidites in the Solid Phase," Journal of the American Chemical Society, 2011, vol. 133, No. 30 (pp. 11540-11556).
Deng et al., "CASFISH: CRISPR/Cas9-mediated in situ labeling of genomic loci in fixed cells," Proceedings of the National Academy of Sciences, USA, Sep. 22, 2015, vol. 112, No. 38 (pp. 11870-11875).
Doench et al., "Optimized sgRNA design to maximize activity and minimize off-target effects of CRISPR-Cas9," Nature Biotechnology, Feb. 2016, vol. 34, No. 2 (pp. 184-191).
Doench et al., "Rational design of highly active sgRNAs for CRISPR-Cas9-mediated gene inactivation," Nature Biotechnology, 2014, vol. 32 (pp. 1262-1267) [including Supplementary Material, 17 pages].
Drmanac et al., "Sequencing of megabase plus DNA by hybridization: theory of the method," Genomics, Feb. 1989, vol. 4, No. 2 (pp. 114-128).
Dyatkina et al., "Terminating substrates of DNA polymerases: synthesis and functional study," Nucleic Acids Symposium Series, Jan. 1, 1987, vol. 18 (pp. 117-120).
East-Seletsky et al., "Two distinct RNase activities of CRISPR-C2c2 enable guide-RNA processing and RNA detection," Nature, Oct. 13, 2016, vol. 538, No. 7624 (pp. 270-273).
Edd et al., "Controlled encapsulation of single-cells into monodisperse picolitre drops," Lab Chip, 2008, vol. 8, No. 8 (pp. 1262-1264).
Elgen et al., "Sorting single molecules: application to diagnostics and evolutionary biotechnology," Proceedings of the National Academy of Sciences, USA, Jun. 1994, vol. 91 (pp. 55740-5747).
Elsharkawy et al., "The NF-kappaB p50:p50:HDAC-I repressor complex orchestrates transcriptional inhibition of multiple pro-inflammatory genes," Journal of Hepatology, 2010, vol. 53 (pp. 519-527).
Empedocles et al., "Three-dimensional orientation measurements of symmetric single chromophores using polarization microscopy," Nature, 1999, vol. 399 (pp. 126-130).
Engreitz et al., "The Xist IncRNA exploits three-dimensional genome architecture to spread across the X chromosome," Science, Aug. 16, 2013, vol. 341 (pp. 1-8).
Fogli et al., "The large spectrum of elF2B-related diseases," Biochemical Society Transactions, 2006, vol. 34 (pp. 22-29).
Fredriksson et al., "Protein detection using proximity-dependent DNA ligation assays," Nature Biotechnology, May 2002, vol. 20 (pp. 473-477).
Fulco, C. P. et al., "Systematic mapping of functional enhancer-promoter connections with CRISPR interference," Science, vol. 354, No. 6313, Sep. 15, 2016, pp. 769-773 (5 pages).
Galonska et al., "In Vivo and in vitro dynamics of undifferentiated embryonic cell transcription factor 1," Stem Cell Reports, 2014, vol. 2 (pp. 245-252).
Gao et al., "Engineered Cpf1 Enzymes with Altered PAM Specificities," Nature Biotechnology, Aug. 2017, vol. 35, No. 8 (pp. 789-792).
Garber et al., "A High-Throughput Chromatin Immunoprecipitation Approach Reveals Principles of Dynamic Gene Regulation in Mammals," Molecular Cell, 2012, vol. 47 (pp. 810-822).
Gat-Viks et al., "Deciphering molecular circuits from genetic variation underlying transcriptional responsiveness to stimuli," Nature Biotechnology, Apr. 2013, vol. 31, No. 4 (pp. 342-349).
Gate et al., "Genetic determinants of chromatin accessibility and gene regulation in T cell activation across human individuals," bioRxiv preprint first posted online Dec. 2, 2016 (pp. 1-50).
Gaublomme et al., "Single-cell Genomics Unveils Critical Regulators of Th17 Cell Pathogenicity," Dec. 3, 2015, vol. 163, No. 6 (pp. 1400-1412).
Gaudelli et al., "Programmable base editing of A-T to G-C in genomic DNA without DNA cleavage," Nature, Nov. 23, 2017, vol. 551, No. 7681 (pp. 464-471).
Giaever et al., "Functional profiling of the *Saccharomyces cerevisiae* genome," Nature, Jul. 25, 2002, vol. 418 (pp. 387-391).
Gomez et al., "Detection of histone modifications at specific gene loci in single cells in histological sections," Nature Methods, Feb. 2013, vol. 10, No. 2 (pp. 171-177).
Goodwin et al., "The 3'-flanking sequence of the bovine growth hormone gene contains novel elements required for efficient and accurate polyadenylation," The Journal of Biological Chemistry, Aug. 15, 1992, vol. 267, No. 23 (p. 16330-16334).
Gruber et al., "The Vienna RNA Websuite," Nucleic Acids Research, Apr. 19, 2008, vol. 36 (pp. W70-W74).
Grun et al., "Design and Analysis of Single-Cell Sequencing Experiments," Cell, Nov. 5, 2015, vol. 163, No. 4 (pp. 799-810).
Gu et al., "Depletion of Abundant Sequences by Hybridization (DASH): using Cas9 to remove unwanted high-abundance species in sequencing libraries and molecular counting applications," Genome Biology, 2016, vol. 17 (p. 41).
Gullberg et al., "Cytokine detection by antibody-based proximity ligation," Proceedings of the National Academy of Sciences, USA, Jun. 1, 2004, vol. 101 (pp. 8420-8424).
Guo et al., "Droplet microfluidics for high-throughput biological assays" Lab Chip, 2012, vol. 12 (pp. 2146-2155).
Gustafsdottir et al., "In vitro analysis of DNA-protein interactions by proximity ligation," Proceedings of the National Academy of Sciences, USA, Feb. 27, 2007, vol. 104, No. 9 (pp. 3067-3072).
Guttman et al., "lincRNAs act in the circuitry controlling pluripotency and differentiation," Nature, Sep. 15, 2011, vol. 477, No. 7364 (pp. 295-300).
Haas et al., "A De novo transcript sequence reconstruction from RNA-seq using the Trinity platform for reference generation and analysis," Nature Protocols, Aug. 2013, vol. 8, No. 8 (pp. 1494-1512).
Hacisuleyman et al., "Topological organization of multichromosomal regions by the long intergenic noncoding RNA Firre," Nature Structure Molecular Biology, Feb. 2014, vol. 21, No. 2 (pp. 198-206).
Haldimann et al., "Conditional-replication, integration, excision, and retrieval plasmid-host systems for gene structure-function studies of bacteria," Journal of Bacteriology, 2001, vol. 183, No. 21 (pp. 6384-6393).

(56) References Cited

OTHER PUBLICATIONS

Hamanaka et al., "PERK and GCN2 Contribute to elF2a Phosphorylation and Cell Cycle Arrest after Activation of the Unfolded Protein Response Pathway," Molecular Biology of the Cell, Dec. 2005, vol. 16, No. 12 (pp. 5493-5501).
Hammond et al., "Profiling cellular protein complexes by proximity ligation with dual tag m1croarray readout," PLoS One, Jul. 2012, vol. 7, No. 7 (pp. 1-9).
Han et al., "ER-stress-induced transcriptional regulation increases protein synthesis leading to cell death," Nature Cell Biology, May 2013, vol. 15, No. 5 (pp. 481-490).
Han et al., "Synergistic drug combinations for cancer identified in a CRISPR screen for pairwise genetic interactions," Nature Biotechnology, May 2017, vol. 35, No. 5 (pp. 463-474).
Harrington et al., "Programmed DNA destruction by miniature CRISPR-Cas14 enzymes," Science, Nov. 16, 2018, vol. 362, No. 6416 (pp. 839-842).
Hartl et al., "What can Applicants learn from fitness landscapes?," Current Opinion Microbiology, Oct. 2014, vol. 21 (pp. 51-57).
Hashimshony, et al., "CEL-Seq: Single-Cell RNA-Seq by Multiplexed Linear Amplification," Cell Reports, 2012, vol. 2, No. 3 (pp. 666-673).
Heckl et al., "Generation of mouse models of myeloid malignancy with combinatorial genetic lesions using CRISPR-Cas9 genome editing," Nature Biotechnology, Sep. 2014, vol. 32 (pp. 941-946).
Heimberg et al., "Low Dimensionality in Gene Expression Data Enables the Accurate Extraction of Transcriptional Programs from Shallow Sequencing," Cell Systems, Apr. 27, 2016, vol. 2 (pp. 239-250).
Helft et al., "GM-CSF Mouse Bone Marrow Cultures Comprise a Heterogeneous Population of CD11c+ MHCII+ Macrophages and Dendritic Cells," Immunity, 2015, vol. 42 (pp. 1197-1211).
Hendel et al., "Chemically modified guide RNAs enhance CRISPR-Cas genome editing in human primary cells," Nature Biotechnology, Sep. 2015, vol. 33, No. 9 (pp. 985-989).
Hess et al., "Directed evolution using dCas9-targeted somatic hypermutation in mammalian cells," Nature Methods, Dec. 2016, vol. 13, No. 12 (pp. 1036-1042).
Hetz, C., "The unfolded protein response: controlling cell fate decisions under ER stress and beyond," Nature Reviews, Molecular Cell Biology, 2012, vol. 13, No. 2 (pp. 89-102).
Hicke et al., "Escort aptamers: a delivery service for diagnosis and therapy," The Journal of Clinical Investigation, Oct. 2000, vol. 106, No. 8 (pp. 923-928).
Higgins et al., "CLUSTAL: a package for performing multiple sequence alignment on a microcomputer," Gene, Dec. 15, 1998, vol. 73, No. 1 (pp. 237-244).
Hong et al., "Labeling Live Cells by Copper-Catalyzed Alkyne-Azide Click Chemistry," Bioconjugate chemistry, Oct. 20, 2010, vol. 21, No. 10 (pp. 1912-1916).
Horlbeck et al., "Compact and highly active next-generation libraries for CRISPR-mediated gene repression and activation," eLife, 2016, vol. 5 (pp. 1-20).
Horn et al., "Hybridization properties of the 5-methy-isocytidine/isoguanosine base pair in synthetic oligodeoxynucleotides," Tetrahedron Letters, 1995, vol. 36, No. 12 (pp. 2033-2036).
Howie et al., "High-throughput pairing of T cell receptor alpha and beta sequences," Science Translational Medicine, Aug. 2015, vol. 7, No. 301 (pp. 1-12).
Hoyle et al., "Thiol-Ene Click Chemistry," Angewandte Chemie International Edition, Feb. 22, 2010, vol. 49, No. 9 (pp. 1540-1573).
Hsu et al., "Development and Applications of CRISPR-Cas9 for Genome Engineering," Cell, 2014, vol. 157 (pp. 1262-1278).
Hsu et al., "DNA targeting specificity of RNA-guided Cas9 nucleases," Nature Biotechnology, Sep. 2013, vol. 31, No. 9 (pp. 827-832).
Hu et al., "Cloning and functional analysis of sheep U6 promoters," Animal Biotechnology, 2011, vol. 22, No. 3 (pp. 170-174).
Huang et al., "Bioinformatics enrichment tools: paths toward the comprehensive functional analysis of large gene lists," Nucleic Acids Research, 2009, vol. 37, No. 1 (pp. 1-13).
Huang et al., "Systematic and integrative analysis of large gene lists using DAVID bioinformatics resources," Nature Protocols, 2009, vol. 4, No. 1 (pp. 44-57).
Hyman et al., "A new method of sequencing DNA," Analytical Biochemistry, Nov. 1, 1988, vol. 174, No. 2 (pp. 423-436).
Illumina Inc., "Whole-Genome Chromatin IP Sequencing(ChIP-Seq)," 2010, www.illumina.com/Documents/products/datasheets/datasheet_chip_sequence.pdf; retrieved from the internet on Mar. 25, 2025 (pp. 1-3).
Inoue et al., "An inducible translocation strategy to rapidly activate and inhibit small GTPase signaling pathways," Nature Methods, Jun. 2005, vol. 2, No. 6 (pp. 415-418).
Islam et al., "Characterization of the single-cell transcriptional landscape by highly multiplex RNA-seq," Genome Research, 2011, vol. 21, No. 7 (pp. 1160-1167).
Islam et al., "Quantitative single-cell RNA-seq with unique molecular identifiers," Nature Methods, Feb. 2014, vol. 11, No. 2 (pp. 163-166).
Jaenisch et al., "Stem cells, the molecular circuitry of pluripotency and nuclear reprogramming," Cell, Feb. 22, 2008, vol. 132, No. 4 (pp. 567-582).
Jaitin et al., "Massively parallel single-cell RNA-seq for marker-free decomposition of tissues into cell types," Science, 2014, vol. 343 (pp. 776-779).
Janssen et al., "Nucleic acids for ultrasensitive protein detection," Sensors, 2013, vol. 13 (pp. 1353-1384).
Jerby-Arnon et al., "Predicting cancer-specific vulnerability via data-driven detection of synthetic lethality," Cell, Aug. 2014, vol. 158 (pp. 1199-1209).
Jiang et al., "RNA-guided editing of bacterial genomes using CRISPR-Cas systems," Nature Biotechnology, Mar. 2013, vol. 31 [including supplementary information—30 pages] (pp. 233-239).
Jiang et al., Structural Biology: "A Cas9-guide RNA complex preorganized for target DNA recognition," Science, Jun. 26, 2015, vol. 348, No. 6242 (pp. 1477-1481).
Jin et al., "A pooling-deconvolution strategy for biological network elucidation," Nature Methods, 2006, vol. 3 (pp. 183-189).
Joensson et al., "Droplet Microfluidics—A Tool for Single-Cell Analysis," Angewandte Chemie International Edition, 2012, vol. 51 (pp. 12176-12192).
Johnson et al., "Continuous assay for DNA polymerization by light scattering," Analytical Biochemistry, Jan. 1984, vol. 136, No. 1 (pp. 192-194).
Johnson et al., "Genome-wide mapping of in vivo protein-DNA interactions," Science, Jun. 8, 2007, vol. 316 (pp. 1497-1502).
Johnson et al., "A third base pair for the polymerase chain reaction: inserting isoC and isoG," Nucleic Acids Research, 2004 vol. 32, No. 6 (pp. 1937-1941).
Jones, D.H., "An iterative and regenerative method for DNA sequencing," BioTechniques, May 1997, vol. 22 (pp. 938-946).
Jonikas et al., "Comprehensive characterization of genes required for protein folding in the endoplasmic reticulum," Science, 2009, vol. 323, No. 5922 (pp. 1693-1697).
Jovanovic et al., "A Dynamic profiling of the protein life cycle in response to pathogens," Science, Mar. 2015, vol. 347, No. 6226 (pp. 1-8).
Kalisky et al., "Genomic Analysis at the Single-Cell Level," Annual Review of Genetics, 2011, vol. 45 (pp. 431-445).
Kalisky et al., "Single-cell genomics," Nature Methods, Apr. 2011, vol. 8, No. 4 (pp. 311-314).
Kanda et al., "Autonomous translational pausing is required for XBP1u mRNA recruitment to the ER via the SRP pathway," Proceedings of the National Academy of Sciences of the, USA, 2016, vol. 113, No. 40 (pp. E5886-E5895).
Kang et al., "Multiplexing droplet-based single cell RNA-sequencing using natural genetic barcodes," bioRxiv preprint doi: https://doi.org/10.1101/118778; this version posted May 15, 2017 (pp. 1-25).
Kantlehner et al., "A high-throughput DNA methylation analysis of a single cell," Nucleic Acids Research, Jan. 25, 2011, vol. 39, No. 7 (pp. 1-9).

(56) References Cited

OTHER PUBLICATIONS

Kearns et al., "Cas9 effector-mediated regulation of transcription and differentiation in human pluripotent stem cells," Development, 2014, vol. 141 (pp. 219-223).
Keefe et al., "Aptamers as therapeutics," Nature Reviews, Jul. 2010, vol. 9 (pp. 537-550).
Keenan et al., "Biomolecular gradients in cell culture systems," Lab on a Chip, Jan. 2008, vol. 8, No. 1 (pp. 1-44).
Kelley et al., "Transposable elements reveal a stem cell-specific class of long noncoding RNAs," Genome Biology, 2012, vol. 13 (pp. 1-14).
Kelley et al., "Versatility of chemically synthesized guide RNAs for CRISPR-Cas9 genome editing," Journal of Biotechnology, Sep. 2016, vol. 233, 10 (pp. 74-83).
Keskin et al., "Transcript-RNA-templated DNA recombination and repair," Nature, Nov. 20, 2014, vol. 515, No. 7527 (pp. 436-439).
Kharchenko et al., "Bayesian Approach to Single-Cell Differential Expression Analysis, " Nature Methods, Jul. 2014 Vol. 11, No. 7 (pp. 1-11).
Kim et al., "Highly efficient RNA-guided genome editing in human cells via delivery of purified Cas9 ribonucleoproteins," Genome Research, Jun. 2014, vol. 24, No. 6 (pp. 1012-1019).
Kivioja et al., "Counting Absolute Numbers of Molecules Using Unique Molecular Identifiers," Nature Methods, 2012 vol. 9 (pp. 72-74).
Kleinstiver et al., "Engineered CRISPR-Cas9 nucleases with altered PAM specificities," Nature, Jul. 23, 2015, vol. 523 (pp. 1-27) [includes supplemental information].
Klopfenstein et al., "Goatools: A Python Library for Gene Ontology analyses," Scientific Reports, 2018, vol. 8, 10872 (pp. 1-17).
Koch, H., "Combining morphology and DNA barcoding resolves the taxonomy of Western Malagasy Liotrigona Moure, 1961," African Invertebrates, Dec. 2010, vol. 51, No. 2 (pp. 413-421).
Kolb et al., "Click Chemistry: Diverse Chemical Function from a Few Good Reactions," Angewandte Chemie International Edition, 2001, vol. 40 (pp. 2004-2021).
Komor et al., "Programmable editing of a target base in genomic DNA without double-stranded DNA cleavage," Nature, 2016, vol. 533 (pp. 420-424).
Konermann et al., "Optical control of mammalian endogenous transcription and epigenetic states," Nature, Aug. 22, 2013, vol. 500, Includes Supplemental Information (pp. 472-476).
Koster et al., "A strategy for rapid and efficient DNA sequencing by mass spectrometry," Nature Biotechnology, Sep. 1996, vol. 14 (pp. 1123-1128).
Kowalczyk et al., "Single-cell RNA-seq reveals changes in cell cycle and differentiation programs upon aging of hematopoietic stem cells," Genome Research, 2015, vol. 25 (pp. 1860-1872).
Kress et al., "DNA barcodes: Genes, genomics, and bioinformatics," Proceedings of the National Academy of Sciences, Feb. 26, 2008, vol. 105, No. 8 (pp. 2761-2762).
Kress et al., "Use of DNA barcodes to identify flowering plants" Proceedings of the National Academy of Sciences, USA, vol. 102, No. 23 (pp. 8369-8374).
Kroepfl et al., "Identification of a basolateral membrane targeting signal within the cytoplasmic domain of myelin/oligodendrocyte glycoprotein," Journal of Neurochemistry, Jun. 2001, vol. 77, No. 5 (pp. 1301-1309).
Kuleshov et al., "Enrichr: a comprehensive gene set enrichment analysis web server 2016 update," Nucleic Acids Research, May 2016, vol. 44 (pp. W90-W97).
Kumar et al., "Deconstructing transcriptional heterogeneity in pluripotent stem cells," Nature, Dec. 4, 2014, vol. 516, No. 7529 (pp. 56-61).
Kuzmin et al., "Systematic analysis of complex genetic interactions," Science, Apr. 2018, vol. 360, No. 6386 (pp. 1-25).
Labzin et al., "ATF3 Is a Key Regulator of Macrophage IFN Responses," Journal of Immunology, 2015, vol. 195 (pp. 4446-4455).
Lacoste et al. "Ultrahigh-resolution multicolor colocalization of single fluorescent probes," Proceedings of the National Academy of Sciences, USA, Aug. 15, 2000, vol. 97, No. 17 (pp. 9461-9466).
Lambeth et al., "Comparison of bovine RNA polymerase III promoters for short hairpin RNA expression," Animal Genetics, 2006, vol. 37, No. 4 (pp. 369-372).
Lara-Astiaso et al., "Chromatin state dynamics during blood formation," Science, 2014, vol. 345 (pp. 943-949).
Lasken et al., "Whole genome amplification: abundant supplies of DNA from precious samples or clinical specimens," Trends in Biotechnology, Dec. 2003, vol. 21, No. 12 (pp. 531-535).
Laufer et al., "Mapping genetic interactions in human cancer cells with RNAi and multiparametric phenotyping," Nature Methods, May 2013, vol. 10, No. 5 (pp. 427-431).
Lawrence et al., "Discovery and saturation analysis of cancer genes across 21 tumour types," Nature, Jan. 23, 2014, vol. 505, No. 7484 (pp. 495-501).
Lee et al., "A rhizavidin monomer with nearly multimeric avidin-like binding stability against biotin conjugates," Angewandte Chemie, Feb. 2, 2016, vol. 55 (pp. 3393-3397).
Lee et al., "Common genetic variants modulate pathogen-sensing responses in human dendritic cells," Science, Mar. 7, 2014, vol. 343, No. 6175 (pp. 1-19).
Lee et al., "Synthetically modified guide RNA and donor DNA are a versatile platform for CRISPR-Cas9 engineering," Elife, May 2, 2017, vol. 6 e25312 (17 pages).
Lee et al., "XBP-1 regulates a subset of endoplasmic reticulum resident chaperone genes in the unfolded protein response," Molecular Cell Biology, Nov. 2003, vol. 23, No. 21 (pp. 7448-7459).
Leuchowius et al., "Flow cytometric in situ proximity ligation analyses of protein interactions and post-translational modification of the epidermal growth factor receptor family," Cytometry, Part A, Oct. 2009, vol. 75A, No. 10 (pp. 833-839).
Levy-Nissenbaum et al., Nanotechnology and aptamers: applications in drug delivery, Trends in Biotechnology, Aug. 2008, vol. 26, No. 8 (pp. 442-449).
Li et al., "Engineering CRISPR-Cpf1 crRNAs and mRNAs to maximize genome editing efficiency," Nature Biomedical Engineering, May 2017, vol. 1, No. 5 (21 pages).
Liang et al., "PERK (elF2alpha kinase) is required to activate the stress-activated MAPKs and induce the expression of immediate-early genes upon disruption of ER calcium homoeostasis," The Biochemical Journal, 2006, vol. 393, No. Pt 1 (pp. 201-209).
Lin et al., "IRE1 signaling affects cell fate during the unfolded protein response," Science, Nov. 9, 2007, vol. 318, No. 5852 (pp. 944-949).
Lin et al., "The augmented lagrange multiplier method for exact recovery of corrupted low-rank matrices," arXiv, 2010 (23 pages).
Lizardi et al. "Mutation detection and single-molecule counting using isothermal rolling-circle amplification," Nature Genetics, Jul. 1998, vol. 19 (pp. 225-232).
Lorthongpanich et al., "Single-cell DNA-methylation analysis reveals epigenetic chimerism in preimplantation embryos," Science, 2013, vol. 341 (pp. 1110-1112).
Lundberg et al., "Homogeneous antibody-based proximity extension assays provide sensitive and specific detection of low-abundant proteins in human blood," Nucleic Acids Research, Jun. 6, 2011, vol. 39, No. 15 (pp. 1-8).
Lutz et al., "Independent and tight regulation of transcriptional units in *Escherichia coli* via the LacR/O, the TetR/O and AraC/I1-12 regulatory elements," Nucleic Acids Research, 1997, vol. 25, No. 6 (pp. 1203-1210).
Makarova et al., "Evolution and Classification of the CRISPR-CAS Systems," Nature Reviews Microbiology, Jun. 2011, vol. 9 (pp. 467-477—[23 pages—Including Supplemental information].
Manolio et al., "Finding the missing heritability of complex diseases," Nature, Oct. 8, 2009, vol. 461, No. 7265 (pp. 747-753).
Marmorstein et al., "The polarity of the plasma membrane protein RET-PE2 in retinal pigment epithelium is developmentally regulated," Journal of cell science, 1996, vol. 109 (pp. 3025-3034).
Martincorena et al. "Somatic mutation in cancer and normal cells," Science, Sep. 25, 2015, Vo. 349, No. 6255 (pp. 1483-1489).

(56) References Cited

OTHER PUBLICATIONS

Meerbrey et al., "The pINDUCER lentiviral toolkit for inducible RNA interference in vitro and in vivo," Proceedings of the National Academy of Sciences of the United States of America, Mar. 1, 2011, vol. 108, No. 9 (pp. 3665-3670).
Meier et al., "Toward a new STATe: the role of STATs in mitochondrial function," Seminars in Immunology, Feb. 2014, vol. 26, No. 1 (pp. 20-28).
Metzker et al., "Termination of DNA synthesis by novel 3'-modified-deoxyribonucleoside 5'-triphosphates," Nucleic Acids Research, 1994, vol. 22, No. 20 (pp. 4259-4267).
Michlits et al., "CRISPR-UMI: single-cell lineage tracing of pooled CRISPR-Cas9 screens," Nature Methods, Dec. 2017, vol. 14, No. 12 (pp. 1191-1197).
Miyamoto et al., "Rapid and orthogonal logic gating with a gibberellin-induced dimerization system," Nature Chemical Biology, 2012, vol. 8, No. 5 (pp. 465-470).
Morgens et al., "Genome-scale measurement of off-target activity using Cas9 toxicity in high-throughput screens," Nature Communications, 2017, vol. 8 (pp. 1-8).
Morocz et al., "Brain edema development after MRI-guided focused ultrasound treatment," Journal of Magnetic Resonance Imaging, Jan.-Feb. 1998, vol. 8, No. 1 (pp. 136-142).
Moussatov et al., "A Possible Approach to the Treatment of Polycystic Ovarian Syndrome Using Focused Ultrasound," Ultrasonics, 1998, vol. 36, No. 8 (pp. 893-900).
Muller-Kuller et al., "A minimal ubiquitous chromatin opening element (UCOE) effectively prevents silencing of juxtaposed heterologous promoters by epigenetic remodeling in multipotent and pluripotent stem cells," Nucleic Acids Research, 2015 (pp. 1577-1592).
Munoz et al., "CRISPR Screens Provide a Comprehensive Assessment of Cancer Vulnerabilities but Generate False-Positive Hits for Highly Amplified Genomic Regions," Cancer Discovery, 2016, vol. 6, No. 8 (pp. 900-913).
Na et al., "Probing enzymatic activity inside living cells using a nanowire-cell 'sandwich' assay," Nano Letters, Jan. 9, 2013, vol. 13, No. 1 (pp. 153-158).
Nagano et al. "Single-cell Hi-C reveals cell-to-cell variability in chromosome structure," Nature, Sep. 25, 2013, vol. 502, No. 7469 (pp. 59-64).
Najm et al., "Orthologous CRISPR-Cas9 enzymes for combinatorial genetic screens," Nature Biotechnology, Feb. 2018, vol. 36, No. 2 (pp. 179-189).
Nakamura et al., "Codon usage tabulated from the international DNA sequence databases: status for the year 2000," Nucleic Acids Research, 2000, vol. 28, No. 1 (p. 292).
Neumann et al., "Phenotypic profiling of the human genome by time-lapse microscopy reveals cell division genes," Nature, Apr. 1, 2010, vol. 464, No. 7289 (pp. 721-727).
Niemeyer et al., "Detecting antigens by quantitative immuno-PCR," Nature Protocols, Aug. 2007, vol. 2, No. 8 (pp. 1918-1930).
Nikic et al., "Labeling proteins on live mammalian cells using click chemistry," Nature Protocols, May 2015, vol. 10, No. 5 (pp. 780-791).
Nishida et al., "Targeted nucleotide editing using hybrid prokaryotic and vertebrate adaptive immune systems," Science, Sep. 16, 2016, vol. 353, No. 6305 (9 Pages).
Nishimasu et al., "Crystal Structure of Cas9 in Complex with Guide RNA and Target DNA," Cell, Feb. 27, 2014, vol. 156 (pp. 935-949).
Nishimasu et al., "Crystal Structure of *Staphylococcus aureus* Cas9", Cell, 2015, vol. 162 (pp. 1113-1126).
Nissim et al., "Multiplexed and programmable regulation of gene networks with an integrated RNA and CRISPR/Cas toolkit in human cells," Molecular Cell, May 22, 2014, vol. 54, No. 4 (pp. 698-710).
Nong et al., "Solid-phase proximity ligation assays for individual or parallel protein analyses with readout via real-time PCR or sequencing," Nature protocols, 2013, vol. 8, No. 6 (pp. 1234-1248).
Nowak et al., "Survey and Summary—Guide RNA engineering for versatile Cas9 functionality," Nucleic Acids Research, Oct. 12, 2016, vol. 44, No. 20 (pp. 9555-9564).
Nyren et al., "Enzymatic method for continuous monitoring of inorganic pyrophosphate synthesis," Analytical Biochemistry, Dec. 1985, vol. 151, No. 2 (pp. 504-509).
O'Neil et al., "Synthetic lethality and cancer," Nature Reviews, Genetics, Oct. 2017, vol. 18 (pp. 613-623).
Okabe et al., "Tissue-Specific Signals Control Reversible Program of Localization and Functional Polarization of Macrophages," Cell, May 8, 2014, vol. 157 (pp. 832-844).
Overwijk et al., "B16 as a Mouse Model for Human Melanoma," Current Protocols in Immunology, Tumor Immunology, 2000, Suppl. 39 (pp. 20.1.1-20.1.29).
Paige et al., "RNA mimics of green fluorescent protein," Science, Jul. 29, 2011, vol. 333, No. 6042 (pp. 642-646).
Paix et al., "High Efficiency, Homology-Directed Genome Editing in Caenorhabditis elegans Using CRISPR-Cas9 Ribonucleoprotein Complexes," Genetics, Sep. 2015, vol. 201 (pp. 47-54).
Pardon et al., "A general protocol for the generation of Nanobodies for structural biology," Nature protocols, Mar. 2014, vol. 9, No. 3 (pp. 674-693).
Perfetto et al., "Seventeen-colour flow cytometry: unravelling the immune system," Nature Reviews Immunology, Aug. 2004, vol. 4 (pp. 648-655).
Phillips et al., "Epistasis-the essential role of gene interactions in the structure and evolution of genetic systems," Nature reviews Genetics, Nov. 2008, vol. 9, No. 11 (pp. 855-867).
Plumb et al., "A functional link between the co-translational protein translocation pathway and the UPR," eLife, 2015, vol. 4 (pp. 1-18).
Pollen et al., "Low-coverage single-cell mRNA sequencing reveals cellular heterogeneity and activated signaling pathways in developing cerebral cortex," Nature Biotechnology, Oct. 2014, vol. 32, No. 10 (pp. 1053-1058).
Pott et al., "Single-cell ATAC-seq: strength in numbers," Genome Biology, Aug. 21, 2015, vol. 16, No. 172 (pp. 1-4).
Qi et al., "Repurposing CRISPR as an RNA-Guided Platform for Sequence-Specific Control of Gene Expression," Cell, Feb. 28, 2013, vol. 152 (pp. 1173-1183).
Rabani et al., "A Metabolic labeling of RNA uncovers principles of RNA production and degradation dynamics in mammalian cells," Nature biotechnology, May 2011, vol. 29, No. 5 (pp. 436-442).
Rabani et al., "High-resolution sequencing and modeling identifies distinct dynamic RNA regulatory strategies," Cell, Dec. 18, 2014, vol. 159 (pp. 1698-1710).
Rahdar et al., "Synthetic CRISPR RNA-Cas9-guided genome editing in human cells," Proceedings of the American Academy of Sciences, U.S.A. Nov. 16, 2015 (pp. E7110-E7117).
Ram et al., "Combinatorial Patterning of Chromatin Regulators Uncovered by Genome-wide Location Analysis in Human Cells," Cell, 2011, vol. 147 (pp. 1628-1639).
Ramanan et al., "CRISPR-Cas9 cleavage of viral DNA efficiently suppresses hepatitis B virus," Nature/Scientific Reports, Jun. 2015 (9 pages).
Ramsauer et al., "Distinct modes of action applied by transcription factors STAT1 and IRF1 to initiate transcription of the IFN-gamma-inducible gbp2 gene," Proceedings of the National Academy of Sciences, USA, Feb. 20, 2007, vol. 104, No. 8 (pp. 2849-2854).
Ramskold et al., "Full-length mRNA-Seq from single-cell levels of RNA and individual circulating tumor cells," Nature Biotechnology, Aug. 2012, vol. 30, No. 8 (pp. 777-782).
Ran et al., "Double Nicking by RNA-guided CRISPR Cas9 for enhanced genome editing specificity," Cell, Sep. 12, 2013, vol. 154 (pp. 1380-1389).
Ran et al., "Genome engineering using the CRISPR-Cas9 system," Nature Protocols, 2013, vol. 8 (pp. 2281-2308).
Ran et al., "In vivo genome editing using *Staphylococcus aureus* Cas9," Nature, 2015, vol. 520 (pp. 186-191). [Includes Supplemental information, 12 pages].
Rauscher et al., "Toward an integrated map of genetic interactions in cancer cells," Molecular Systems Biology, 2018, vol. 14 (pp. 1-17).

(56) References Cited

OTHER PUBLICATIONS

Ray et al., "Cell surface presenilin-1 participates in the gamma-secretase-like proteolysis of Notch," The Journal of Biological Chemistry, Dec. 17, 1999, vol. 217, No. 51 (pp. 36801-36807).
Reichert et al., "Chip-Based Optical Detection of DNA Hybridization by Means of Nanobead Labeling," Analytical Chemistry, Dec. 15, 2000, vol. 72, No. 24 (pp. 6025-6029).
Richard et al., "Estimation of Simultaneously Sparse and Low Rank Matrices," Appearing in Proceedings of the 29th International Conference on Machine Learning, Edinburgh, Scotland, UK, 2012, (pp. 1-8).
Ron et al., "Signal integration in the endoplasmic reticulum unfolded protein response," Nature Reviews, Molecular Cell Biology, Jul. 2007, vol. 8, No. 7 (pp. 519-529).
Ronaghi et al., "A Sequencing Method Based on Real-Time Pyrophosphate," Science, Jul. 17, 1988, vol. 281, No. 5375 (pp. 363-365).
Ronaghi et al., "Real-time DNA sequencing using detection of pyrophosphate release," Analytical Biochemistry, 1996, vol. 242, Article 0432 (pp. 84-89).
Rosvall et al., "Maps of Random Walks on Complex Networks Reveal Community Structure," Proceedings of the National Academy of Sciences, USA, Jan. 29, 2008, vol. 105, No. 4 (pp. 1118-1123).
Sack et al., "Sources of Error in Mammalian Genetic Screens," G3, Genes, Genomics, Genetics, Sep. 2016, vol. 6, No. 9 (pp. 2781-2790).
Sackton et al., "Perspective Genotypic Context and Epistasis in Individuals and Populations," Cell, Jul. 14, 2016, vol. 166 (pp. 279-287).
Sanger et al., "DNA sequencing with chain-terminating inhibitors," Proceedings of the National Academy of Sciences, USA, Dec. 1977, vol. 74, No. 12 (pp. 5463-5467).
Sauvageau et al., "Multiple knockout mouse models reveal lincRNAs are required for life and brain development," eLife, 2013, vol. 2, e01749 (pp. 1-24).
Sawyers, C., "Targeted cancer therapy," Nature, Nov. 18, 2004, vol. 432 (pp. 294-297).
Scaringe et al., "Advanced 5'-silyl-2'-orthoester approach to RNA oligonucleotide synthesis," Methods in Enzymology, 2000, vol. 317 (pp. 3-18).
Scaringe et al., "Novel RNA Synthesis Method Using 5'-O-Silyl-2'-O-orthoester Protecting Groups," Journal of the American Chemical Society, 1998, vol. 120, No. 45 (pp. 11820-11821).
Schmierer et al., "CRISPR/Cas9 screening using unique molecular identifiers," Molecular Systems Biology, 2017, vol. 13, No. 945 (pp. 1-8).
Scholkopf et al., "Estimating the support of a high-dimensional distribution," Neural Computation, 2001, vol. 13, No. 7 (pp. 1443-1471) procured as: Technical Report MSR-TR-99-87; Microsoft Research, Microsoft Corporation, One Microsoft Way, Redmond, WA 98052, Nov. 27, 1999 (pp. 1-28).
Schwartz et al., "High-resolution mapping reveals a conserved, widespread, dynamic mRNA methylation program in yeast meiosis," Cell, Dec. 5, 2013, vol. 155 (pp. 1409-1421).
Schwartz et al., "Perturbation of m6A writers reveals two distinct classes of mRNA methylation at internal and 5' sites," Cell Reports, Jul. 10, 2014, vol. 8 (pp. 284-296).
Schwartz et al., "Transcriptome-wide mapping reveals widespread dynamic-regulated pseudouridylation of ncRNA and mRNA," Cell, Sep. 25, 2014, vol. 159 (pp. 148-162).
Seberg et al., "How many loci does it take to DNA barcode a crocus?" PLoS One, Feb. 2009, vol. 4, No. 2 e4598 (pp. 1-6).
Shahni et al., "Signal transducer and activator of transcription 2 deficiency is a novel disorder of mitochondrial fission," Brain, 2015, vol. 138 (pp. 2834-2846).
Shakya et al., "Pluripotency transcription factor Oct4 mediates stepwise nucleosome demethylation and depletion," Molecular Cell Biology, Mar. 2015, vol. 35, No. 6 (pp. 1014-1025).
Shalek et al., "Nanowire-mediated delivery enables functional interrogation of primary immune cells: application to the analysis of chronic lymphocytic leukemia," Nano Letters, Nov. 28, 2012, vol. 12 (pp. 6498-6504).
Shalek et al., "Single-Cell RNA-Seq Reveals Dynamic Paracrine Control of Cellular Variation," Nature, Jun. 19, 2014, vol. 510 (pp. 363-369).
Shalek et al., "Single-Cell Transcriptomics Reveals Bimodality in Expression and Splicing in Immune Cells," Nature, Jun. 13, 2013, vol. 498, No. 7453 (pp. 236-240).
Shalek et al., "Vertical silicon nanowires as a universal platform for delivering biomolecules into living cells," Proceedings of the National Academy of Sciences, USA Feb. 2, 2010, vol. 107, No. 5 (pp. 1870-1875).
Shao et al., "Genetic architecture of complex traits: large phenotypic effects and pervasive epistasis," Proceedings of the National Academy of Sciences, USA, 2008, vol. 105 (pp. 19910-19914).
Sharei et al., "A vector-free microfluidic platform for intracellular delivery," Proceedings of the National Academy of Sciences, USA, Feb. 5, 2013, vol. 110, No. 6, (pp. 2082-2087).
Sharma et al., "Antisense oligonucleotides: modifications and clinical trials," Medical Chemistry Journal, 2014, vol. 5 (pp. 1454-1471).
Sharma et al., "Immunologic applications of conditional gene modification technology in the mouse," Current Protocols, Immunology 2014, vol. 105 (pp. 1-17).
Shen et al., "Combinatorial CRISPR-Cas9 screens for de novo mapping of genetic interactions," Nature Methods, Jun. 2017, vol. 14, No. 6 (pp. 573-576).
Shendure et al., "The origins, determinants, and consequences of human mutations," Science, Sep. 25, 2015, vol. 349, No. 6255 (pp. 1478-1483).
Shi et al., "Discovery of cancer drug targets by CRISPR-Cas9 screening of protein domains," Nature Biotechnology, Jun. 2015, vol. 33, No. 6 (pp. 661-667).
Shmakov et al., "Discovery and Functional Characterization of Diverse Class 2 CRISPR-Cas Systems," Molecular Cell, Nov. 1, 2015, vol. 60, No. 3 (pp. 385-397).
Shoulders et al., "Stress-independent activation of XBP1s and/or ATF6 reveals three functionally diverse ER proteostasis environments," Cell Reports, Apr. 25, 2013, vol. 3, No. 4 (pp. 1279-1292).
Sidrauski et al., "Pharmacological dimerization and activation of the exchange factor eIF2B antagonizes the integrated stress response," eLife, 2015, vol. 4, e07314 (pp. 1-27).
Sisler et al., "The Signal Transducer and Activator of Transcription 1 (STAT1) Inhibits Mitochondrial Biogenesis in Liver and Fatty Acid Oxidation in Adipocytes," PLoS One, Dec. 21, 2015, vol. 10, e0144444 (pp. 1-19).
Sismour et al., "The use of thymidine analogs to improve the replication of an extra DNA base pair: a synthetic biological system," Nucleic Acids Research, 2005, vol. 33, No. 17 (pp. 5640-5646).
Slaymaker et al., "Rationally engineered Cas9 nucleases with improved specificity," Science, Jan. 1, 2016, vol. 351, No. 6268 (pp. 84-88).
Smargon et al., "Cas13b Is a Type VI-B CRISPR-Associated RNA-Guided RNases Differentially Regulated by Accessory Proteins Csx27 and Csx28," Cell Press: Molecular Cell, Feb. 16, 2017, vol. 65, No. 4 (pp. 618-630).
Smith et al., "A unique regulatory phase of DNA methylation in the early mammalian embryo," Nature, 2012, vol. 484, No. 7394 (pp. 339-344).
Smith et al., "DNA methylation dynamics of the human preimplantation embryo," Nature, Jul. 31, 2014, vol. 511, No. 7511 (pp. 611-615).
Smyth et al., "The origin of genetic diversity in HIV-1," Virus Research, Nov. 2012, vol. 169, No. 2 (pp. 415-429).
Snijder et al., "Population context determines cell-to-cell variability in endocytosis and virus infection," Nature, Sep. 24, 2009, vol. 461, No. 7263 (pp. 520-523).
Sohail et al., "Negative selection in humans and fruit flies involves synergistic epistasis," Science, May 2017, vol. 356 (pp. 539-542).

(56) References Cited

OTHER PUBLICATIONS

Soininen et al., "Analysing diet of small herbivores: the efficiency of DNA barcoding coupled with high-throughput pyrosequencing for deciphering the composition of complex plant mixtures," Frontiers in Zoology, Aug. 2009, vol. 6, No. 16 (pp. 1-9).
Sokolov et al., "Pathway-Based Genomics Prediction using Generalized Elastic Net," PLoS, Computational Biology, Mar. 9, 2016, vol. 12, e1004790 (pp. 1-23).
Stahlberg et al., "Quantitative PCR analysis of DNA, RNAs, and proteins in the same single cell," Clinical chemistry, Dec. 1, 2012, vol. 58, No. 12 (pp. 1682-1691).
Stanley et al., "Radio-Wave Heating of Iron Oxide Nanoparticles Can Regulate Plasma Glucose in Mice," Science, May 4, 2012 vol. 336, No. 6081 (pp. 604-608).
Stegle et al., "Computational and analytical challenges in single-cell transcriptomics," Nature Reviews Genetics, Mar. 2015, vol. 16 (pp. 133-145).
Strona et al., "A fast and unbiased procedure to randomize ecological binary matrices with fixed row and column totals," Nature Communications, 2014, vol. 5, No. 4114 (pp. 1-9).
Sun et al., "Long noncoding RNAs regulate adipogenesis," Proceedings of the National Academy of Sciences of the United States of America, Feb. 26, 2013, vol. 110, No. 9 (pp. 3387-3392).
Switzer et al., "Enzymatic incorporation of a new base pair into DNA and RNA," Journal of the American Chemical Society, 1989, vol. 111 (pp. 8322-8323).
Takahashi et al., "Induction of pluripotent stem cells from mouse embryonic and adult fibroblast cultures by defined factors," Cell, 2006, vol. 126, No. 4 (pp. 663-676).
Tang et al., "mRNA-Seq whole-transcriptome analysis of a single cell," Nature Methods, May 2009, vol. 6, No. 5 (pp. 377-382).
Tang et al., "RNA-Seq analysis to capture the transcriptome landscape of a single cell," Nature Protocols, Mar. 2010, vol. 5, No. 3 (pp. 516-535).
Tatusova et al., "Blast 2 sequences, a new tool for comparing protein and nucleotide sequences," FEMS Microbiology Letters, 1999 vol. 174 (pp. 247-250).
Tatusova et al., Erratum to: "BLAST 2 Sequences, a new tool for comparing protein and nucleotide sequences," FEMS Microbiology Letters, 1999, vol. 177 (pp. 187-188).
Tehranirokh et al., "Microfluidic devices for cell cultivation and proliferation," Biomicrofluidics, Oct. 29, 2013, vol. 7, No. 051502 (pp. 1-33).
Theile et al., "Site-specific N-terminal labeling of proteins using sortase-mediated reactions," Nature protocols, Sep. 2013, vol. 8, No. 9 (pp. 1800-1807).
Thomason et al., "*E. coli* Genome Manipulation by P1 Transduction," Current Protocols in Molecular Biology, Supplement 79, 2007 (pp. 1.17.1-1.17.8).
Thomason et al., "Recombineering: genetic engineering in bacteria using homologous recombination," Current Protocols in Molecular Biology, 2014, Suppl. 106 (pp. 1-39).
Tong et al., "Global mapping of the yeast genetic interaction network," Science, Feb. 6, 2004, vol. 303 (pp. 808-813).
Tran-Huu-Hue et al., "Practical Systems for the Generation of High Power Continuous Wave-Non Focused Ultrasound in the MHz Range," Acustica, acta acustica, 1997, vol. 83 (pp. 1103-1106).
Trapnell et al., "Differential analysis of gene regulation at transcript resolution with RNA-seq," Nature Biotechnology, Jan. 2013, vol. 31, No. 1 (pp. 46-53).
Trapnell et al., "The Dynamics and Regulators of Cell Fate Decisions are Revealed by Pseudotemporal Ordering of Single Cells," Nature Biotechnology, Apr. 2014, vol. 32, No. 4 (pp. 381-386).
Trapnell, C. "Defining cell types and states with single-cell genomics," Genome Research, 2015, vol. 25, No. 10 (pp. 1491-1498).
Trombetta et al., "Preparation of Single-Cell RNA-Seq Libraries for Next Generation Sequencing," Current Protocols in Molecular Biology, Jul. 2014, vol. 107, No. 1 (pp. 1-25).
Tsai et al., "Dimeric CRISPR RNA-guided FokI nucleases for highly specific genome editing," Nature Biotechnology, 2014, vol. 32, No. 6 (pp. 569-576).
Tuerk et al., "Systematic evolution of ligands by exponential enrichment: RNA ligands to bacteriophage T4 DNA polymerase," Science, Aug. 3, 1990, vol. 249, No. 4968 (pp. 505-510).
Tussiwand et al., "Compensatory dendritic cell development mediated by BATF-IRF interactions," Nature, Oct. 25, 2012, vol. 490, No. 7421 (pp. 502-507).
Tyynismaa et al., "Mitochondrial myopathy induces a starvation-like response," Human Molecular Genetics, 2010, vol. 19, No. 20 (pp. 3948-3958).
Udeshi et al., "Antibodies to biotin enable large-scale detection of biotinylation sites on proteins," Nature Methods, Dec. 2017, vol. 14, No. 12 (pp. 1167-1170).
Van Der Maaten, "Accelerating t-SNE using Tree-Based Algorithms," Journal of Machine Learning Research, Oct. 2014, vol. 15, No. 1 (pp. 3221-3245).
Visscher et al., "Five Years of GWAS Discovery," Discovery, American Journal of Human Genetics, Jan. 13, 2012, vol. 90 (pp. 7-24).
Walter et al., "The Unfolded Protein Response: From Stress Pathway to Homeostatic Regulation," Science, Nov. 25, 2011, vol. 334, No. 6059 (pp. 1081-1086).
Wang et al., "Activation of ATF6 and an ATF6 Dna binding site by the endoplasmic reticulum stress response," The Journal of Biological Chemistry, Sep. 1, 2000, vol. 275, No. 35 (pp. 27013-27020).
Wang et al., "CD5L/AIM Regulates Lipid Biosynthesis and Restrains Th17 Cell Pathogenicity," Cell, Dec. 3, 2015, vol. 163, No. 6 (pp. 1413-1427).
Wang et al., "Somatic mutation as a mechanism of Wnt/beta-catenin pathway activation in CLL," Blood, Aug. 14, 2014, vol. 124, No. 7 (pp. 1089-1098).
Wang et al., "One-Step Generation of Mice Carrying Mutations In Multiple Genes By CRISPR/Cas-Mediated Genome Engineering," Cell, May 9, 2013, vol. 153 (pp. 910-918).
Washietl et al., "Evolutionary dynamics and tissue specificity of human long noncoding RNAs in six mammals," Genome Research, 2014, vol. 24 (pp. 616-628).
Wei et al., "Bioinformatic analysis reveals cRel as a regulator of a subset of interferon-stimulated genes," Journal of Interferon & Cytokine Research, Sep. 2008, vol. 28, No. 9 (pp. 541-551).
Weinberger, E., "Fourier and Taylor series on fitness landscapes," Biological Cybernetics, 1991, vol. 65 (pp. 321-330).
Weinreich et al., "Should evolutionary geneticists worry about higher-order epistasis?," Current opinion in genetics & development, Dec. 2013, vol. 23, No. 6 (pp. 700-707).
Winzeler et al., "Functional characterization of the *S. cerevisiae* genome by gene deletion and parallel analysis," Science, Aug. 6, 1999, vol. 285, No. 5429 (pp. 901-906).
Wu et al., "Induction of pathogenic TH17 cells by inducible salt-sensing kinase SGK1," Nature, Apr. 25, 2013, vol. 497, No. 7446 (pp. 513-517).
Wu et al., "Genome-wide binding of the CRISPR endonuclease Cas9 in mammalian cells," Nature Biotechnology, 2014, Including Supplemental information (pp. 1-9).
Xu et al., "Design of 240,000 orthogonal 25mer DNA barcode probes," Proceedings of the National Academy of Sciences, USA, Feb. 17, 2009, vol. 106, No. 7 (pp. 2289-2294).
Xu et al., "Sequence determinants of improved CRISPR sgRNA design," Genome Research, Aug. 2015, vol. 25 (pp. 1147-1157).
Yan et al., "Cas13d Is a Compact RNA-Targeting Type VI CRISPR Effector Positively Modulated by a WYL-Domain-Containing Accessory Protein," Molecular Cell, Apr. 19, 2018, vol. 70, No. 2 (pp. 327-339).
Yang et al., "Engineering and optimising deaminase fusions for genome editing," Nature Communications, 2017 Vol. 7. No. 13330 (pp. 1-12).
Yosef et al., "Dynamic regulatory network controlling TH17 cell differentiation," Nature, Mar. 6, 2013, vol. 496 (pp. 461-468).

(56) References Cited

OTHER PUBLICATIONS

Yosef et al., "Writ large: Genomic dissection of the effect of cellular environment on immune response," Science, Oct. 7, 2016, vol. 354, No. 6308 (pp. 64-68).
Yu et al., "High-throughput identification of genotype-specific cancer vulnerabilities in mixtures of barcoded tumor cell lines," Nature Biotechnology, Apr. 2016, vol. 34, No. 4 (pp. 419-423).
Zalatan et al., "Engineering Complex Synthetic Transcriptional Programs with CRISPR RNA Scaffolds," Cell, Jan. 15, 2015, vol. 160 (pp. 339-350).
Zetsche et al., "A split-Cas9 architecture for inducible genome editing and transcription modulation," Nature Biotechnology, Feb. 2015, vol. 33, No. 2 (pp. 139-142).
Zetsche et al., "Cpf1 is a single RNA-guided endonuclease of a Class 2 CRISPR-Cas system," Cell, Oct. 22, 2015, vol. 163, No. 3 (pp. 759-771) [with Supplemental Information]—36 Pages).
Zetsche et al., "Multiplex gene editing by CRISPR-Cpf1 through autonomous processing of a single crRNA array," bioRxiv preprint first posted online Oct. 1, 2016; doi: http://dx.doi.org/10.1101/04912 (pp. 1-15).
Zhang et al., "Identification and characterization of buffalo 7SK and U6 pol III promoters and application for expression of short hairpin RNAs," International Journal of Molecular Sciences, 2014, vol. 15 (pp. 2596-2607).
Zhou et al., "Aptamer-targeted cell-specific RNA interference," Silence, Feb. 1, 2010, vol. 1, No. 4 (10 pages).
Zimmer et al., "N-glycans of F protein differentially affect fusion activity of human respiratory syncytial virus," Journal of Virology, May 2001, vol. 75, No. 10 (pp. 4744-4751).
Zuk et al., "The mystery of missing heritability: Genetic interactions create phantom heritability," Proceedings of the National Academy of Sciences, U.S.A., Jan. 24, 2012, vol. 109, No. 4 (pp. 1193-1198).
Zuker et al., "Optimal computer folding of large RNA sequences using thermodynamics and auxiliary information," Nucleic Acids Research, Jan. 10, 1981, vol. 9, No. 1 (pp. 133-148).

* cited by examiner

FIG. 10
1. Synthesize ssDNA with the following structure:
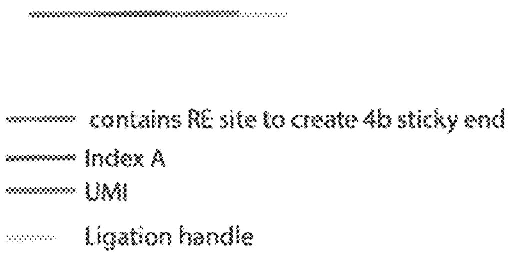
2. hybridize primer providing sticky end at 3' end
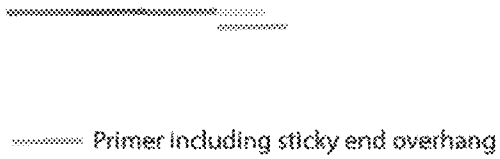
3. DNA polymerase for second strand synthesis
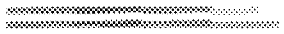
4. Restriction enzyme digestion to generate 5' sticky end
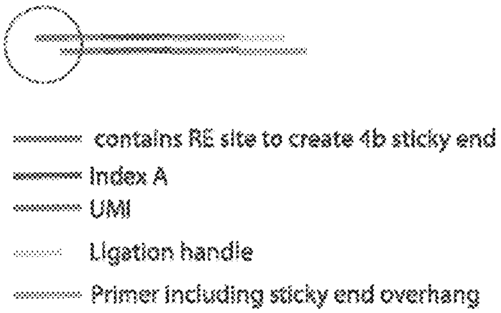

FIG. 18
1. Synthesize ssDNA with the following structure:
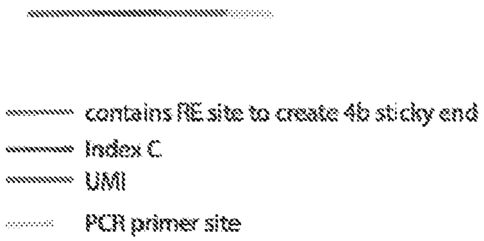
2. Hybridize universal primer
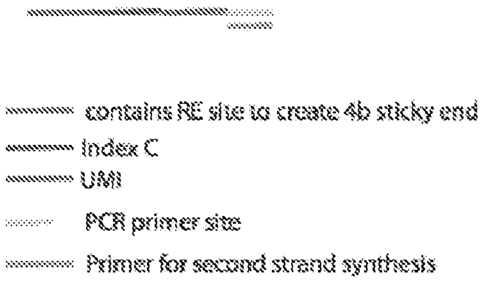
3. DNA polymerase for second strand synthesis
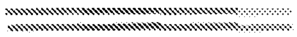
4. Restriction enzyme digest
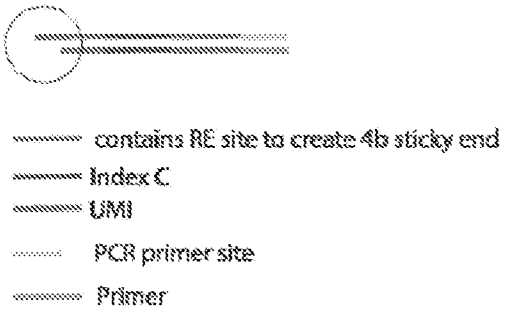

5) Release oligo's from ligand and PCR or T7 amplify, each sequence to amplify (top strand) has:
PCR FWD + UCI + universal hybridization site + ULI + USI + UMI + PCR Rev FIG. 48A-B
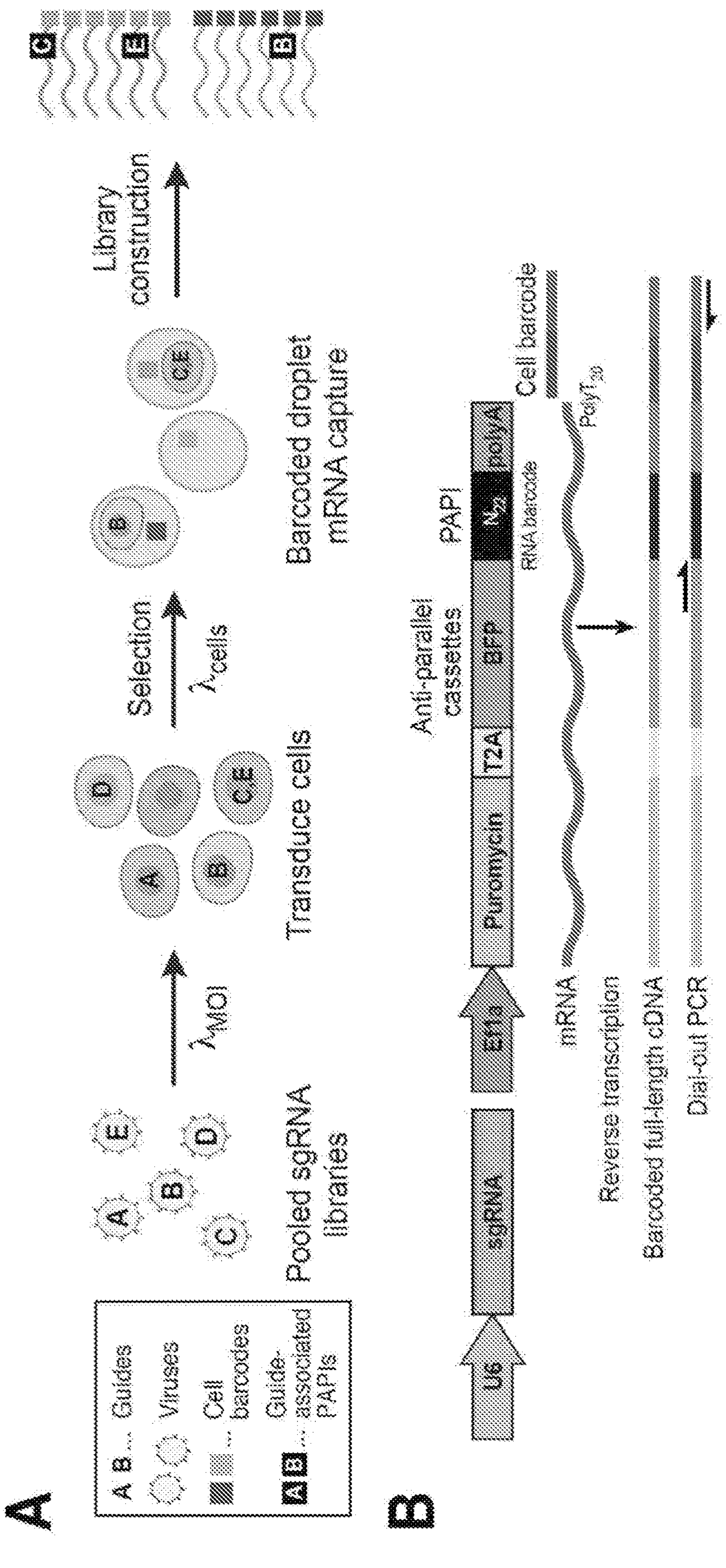

FIG. 48C-G
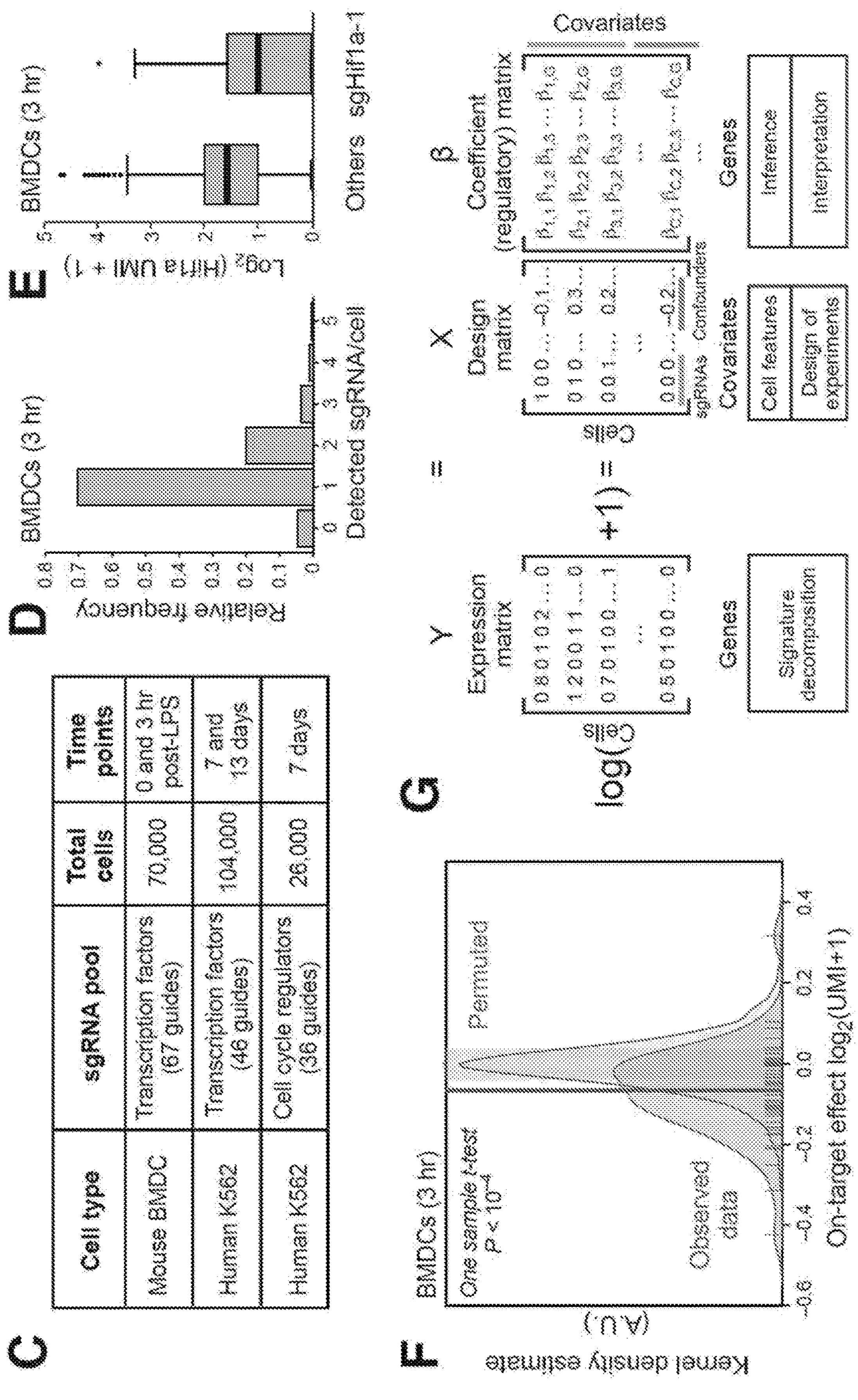
| Cell type | sgRNA pool | Total cells | Time points |
|---|---|---|---|
| Mouse BMDC | Transcription factors (67 guides) | 70,000 | 0 and 3 hr post-LPS |
| Human K562 | Transcription factors (46 guides) | 104,000 | 7 and 13 days |
| Human K562 | Cell cycle regulators (36 guides) | 26,000 | 7 days |

FIG. 49A-G
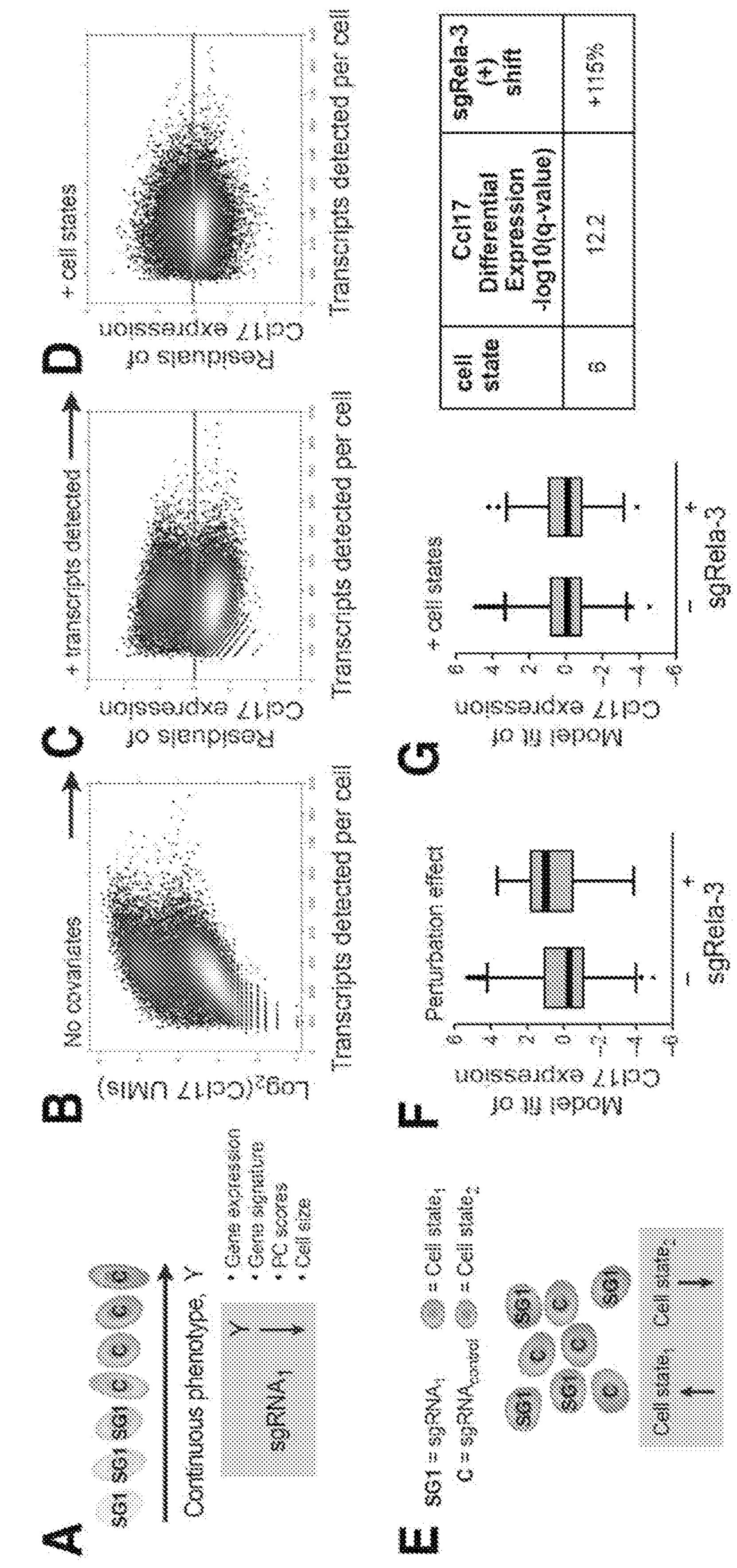
| cell state | Ccl17 Differential Expression -log10(q-value) | sgRela-3 (+) shift |
|---|---|---|
| 6 | 12.2 | +115% |

FIG. 49H-J
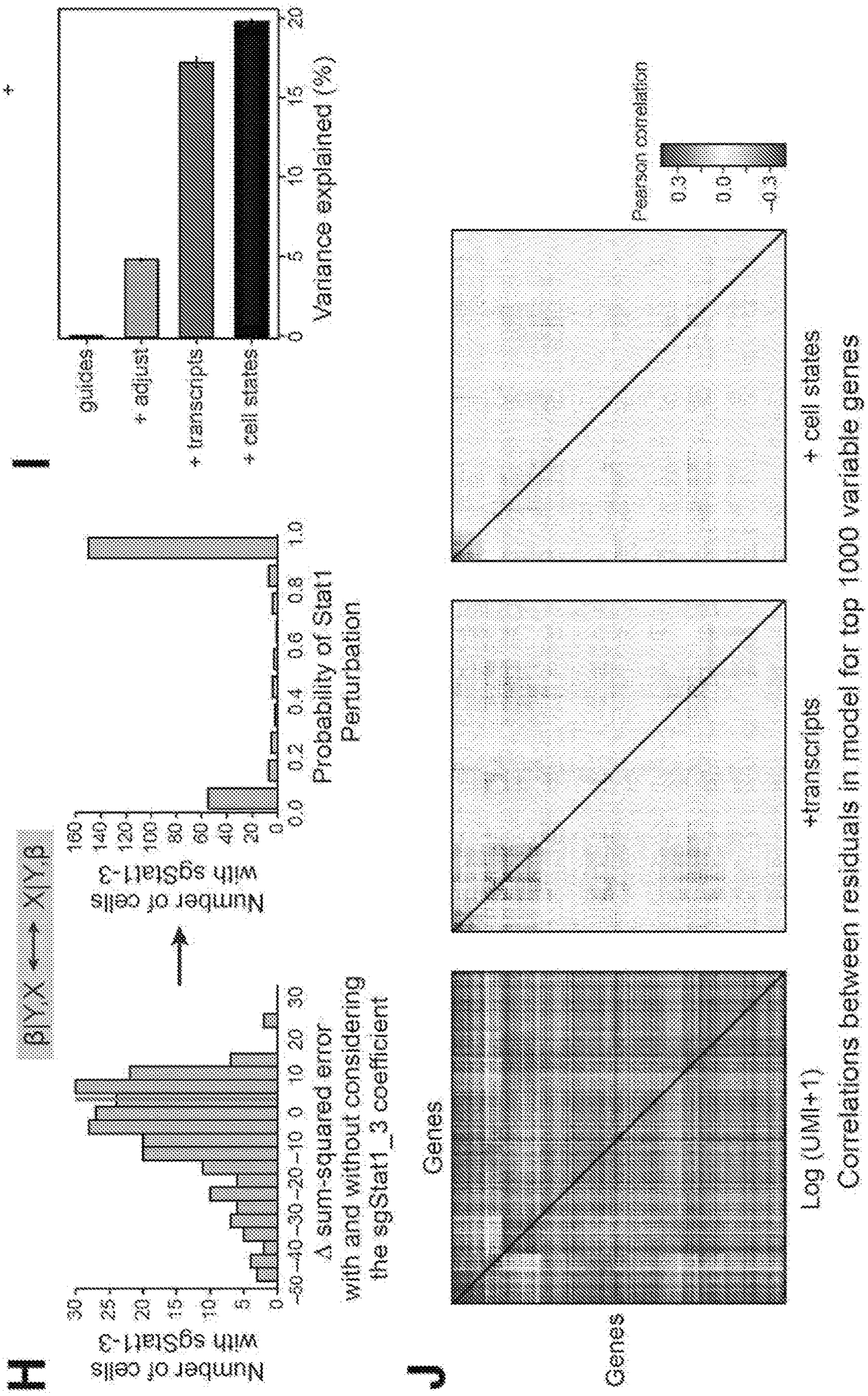

FIG. 50A-B
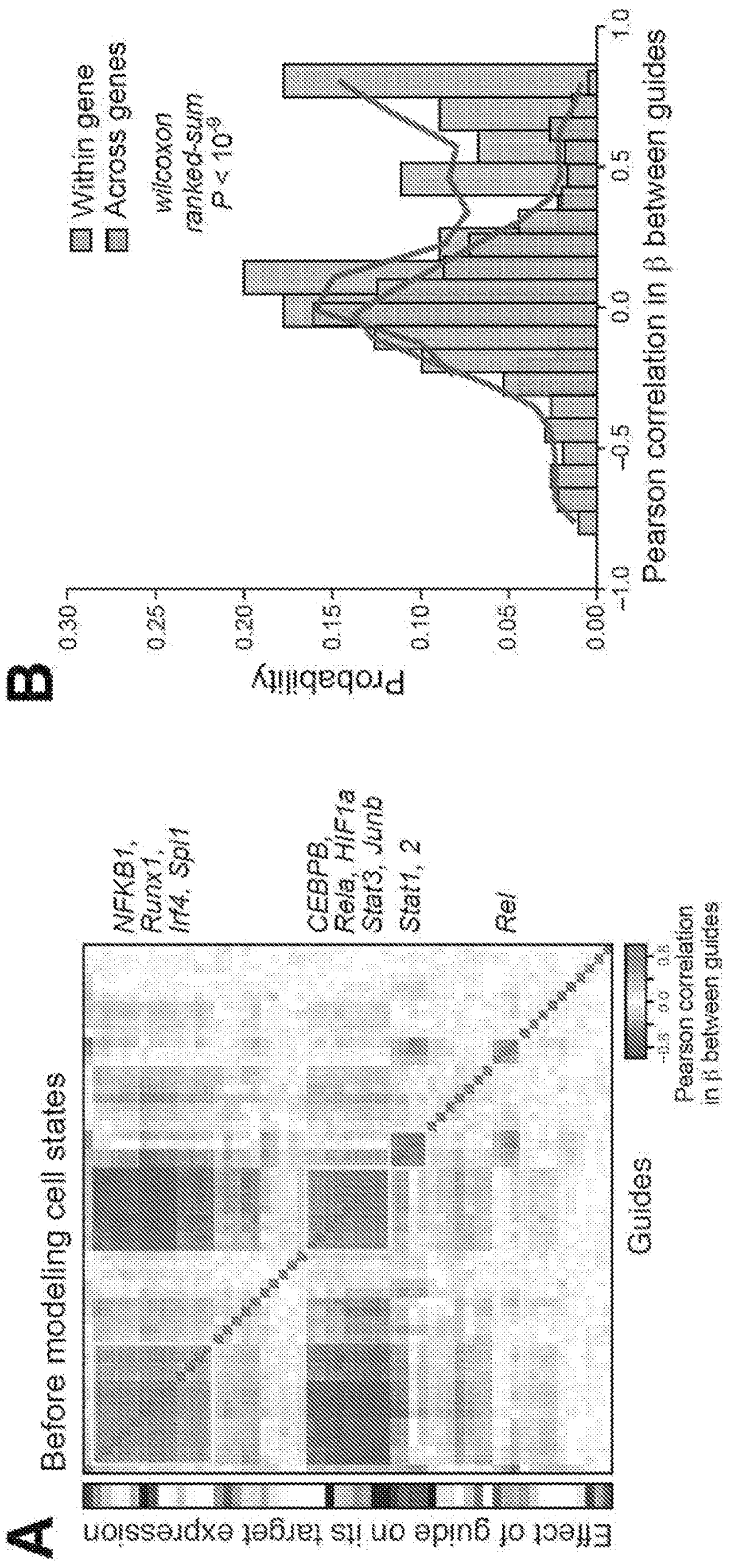

FIG. 50C-D
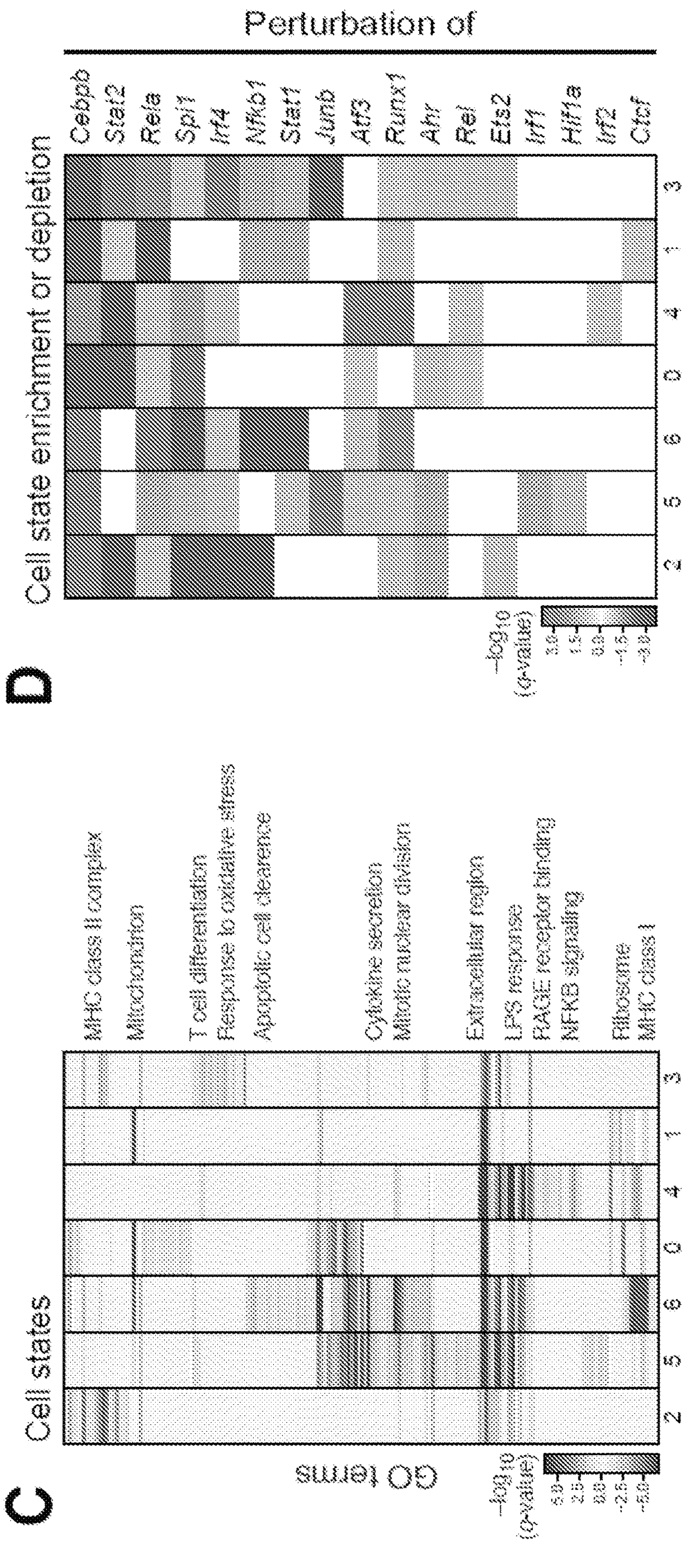

FIG. 50E-F
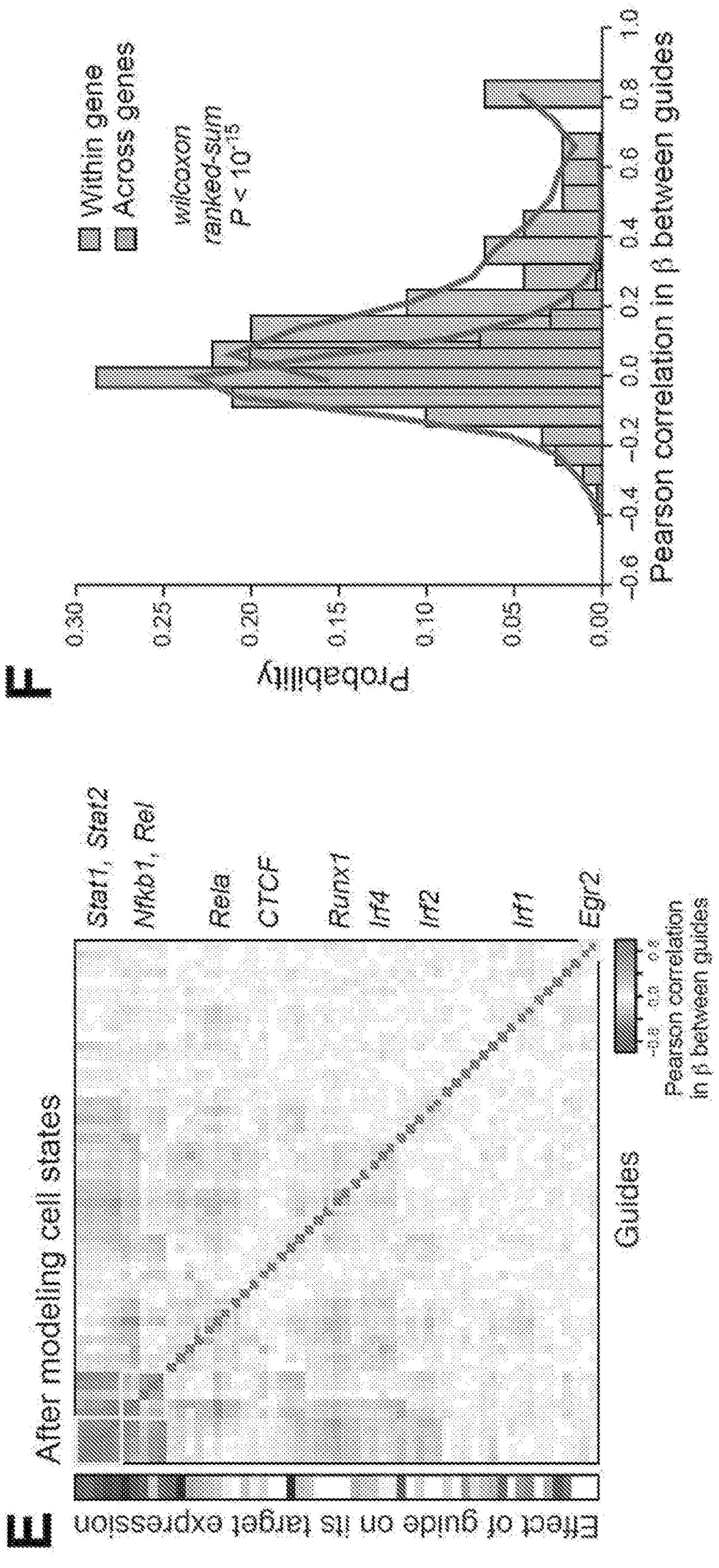

C

FIG. 53A-B
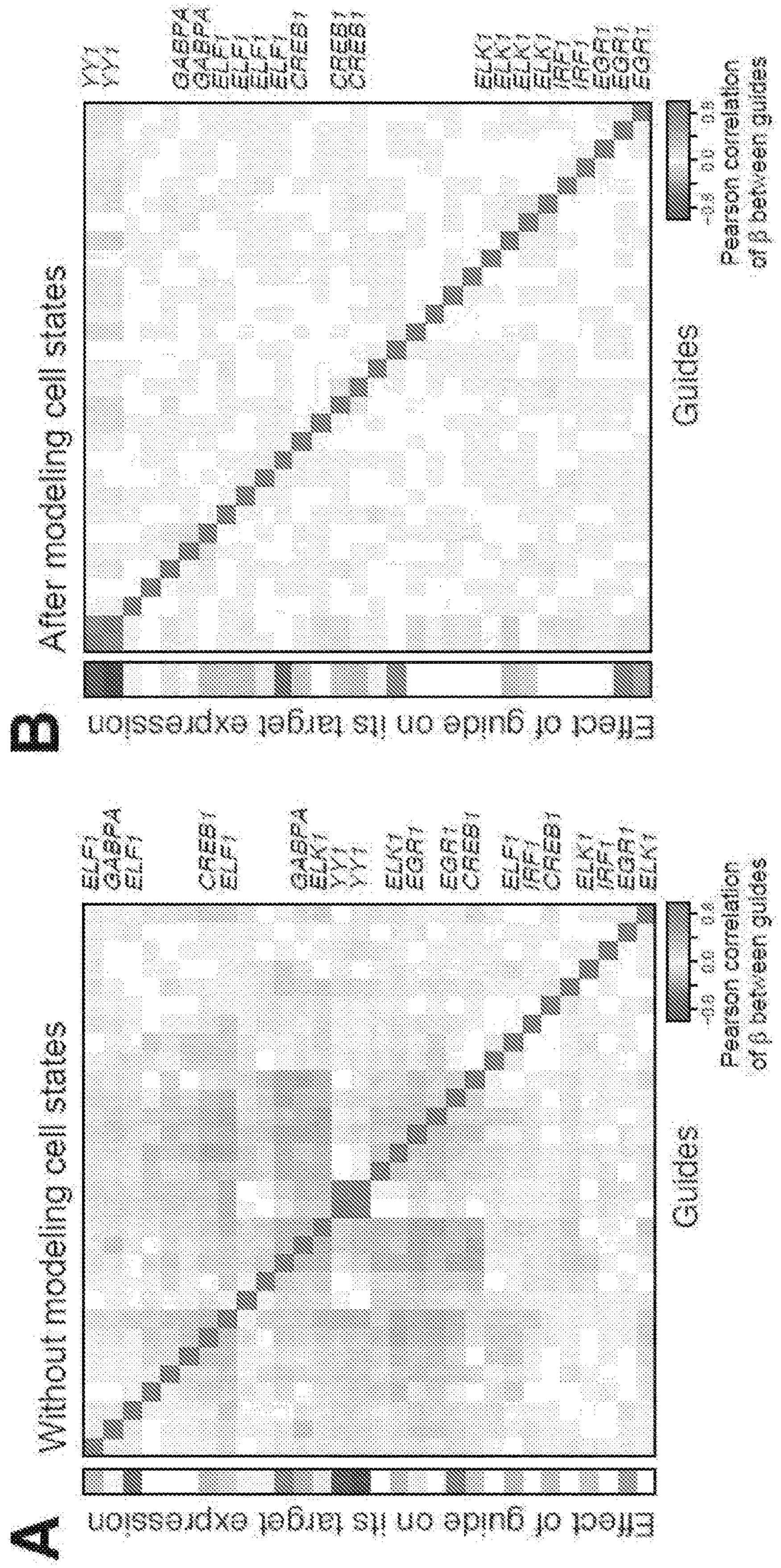

FIG. 53E-F
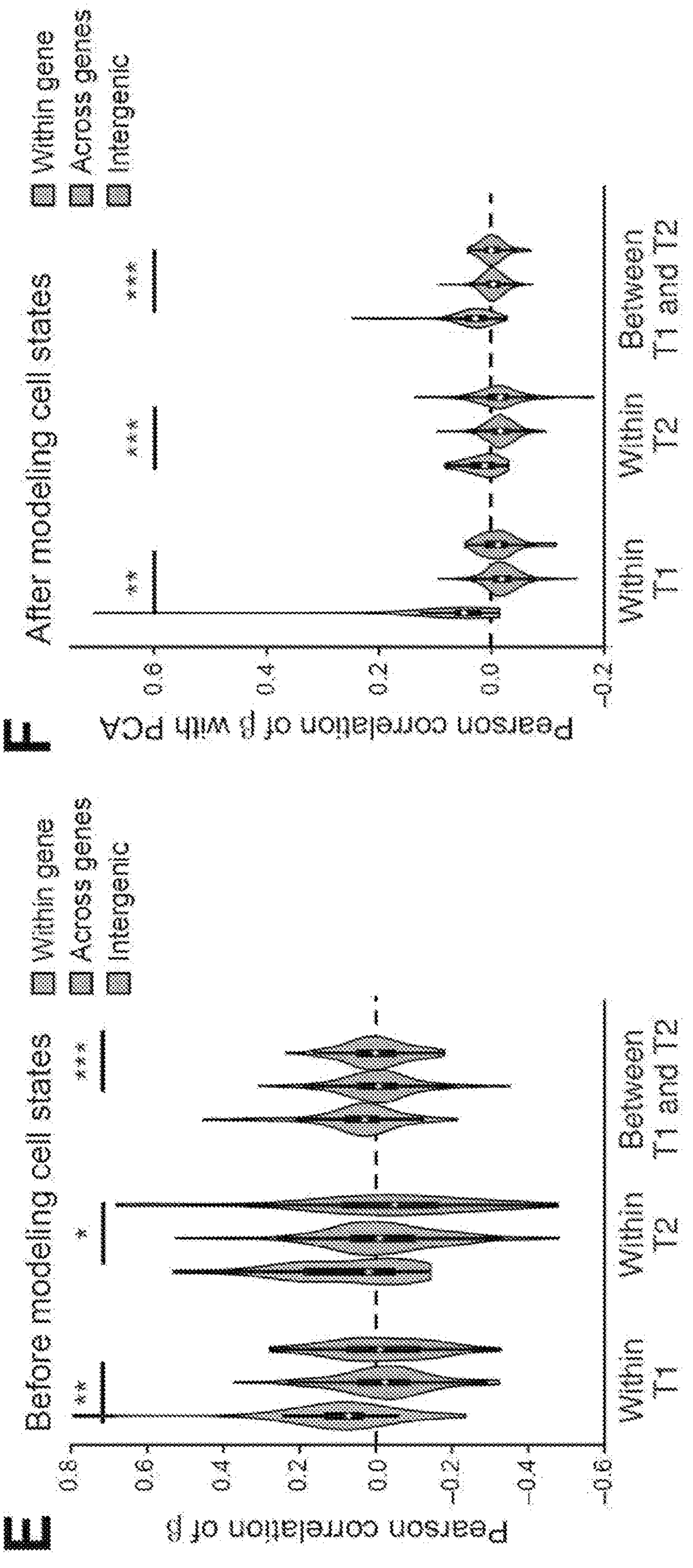

FIG. 53H-I
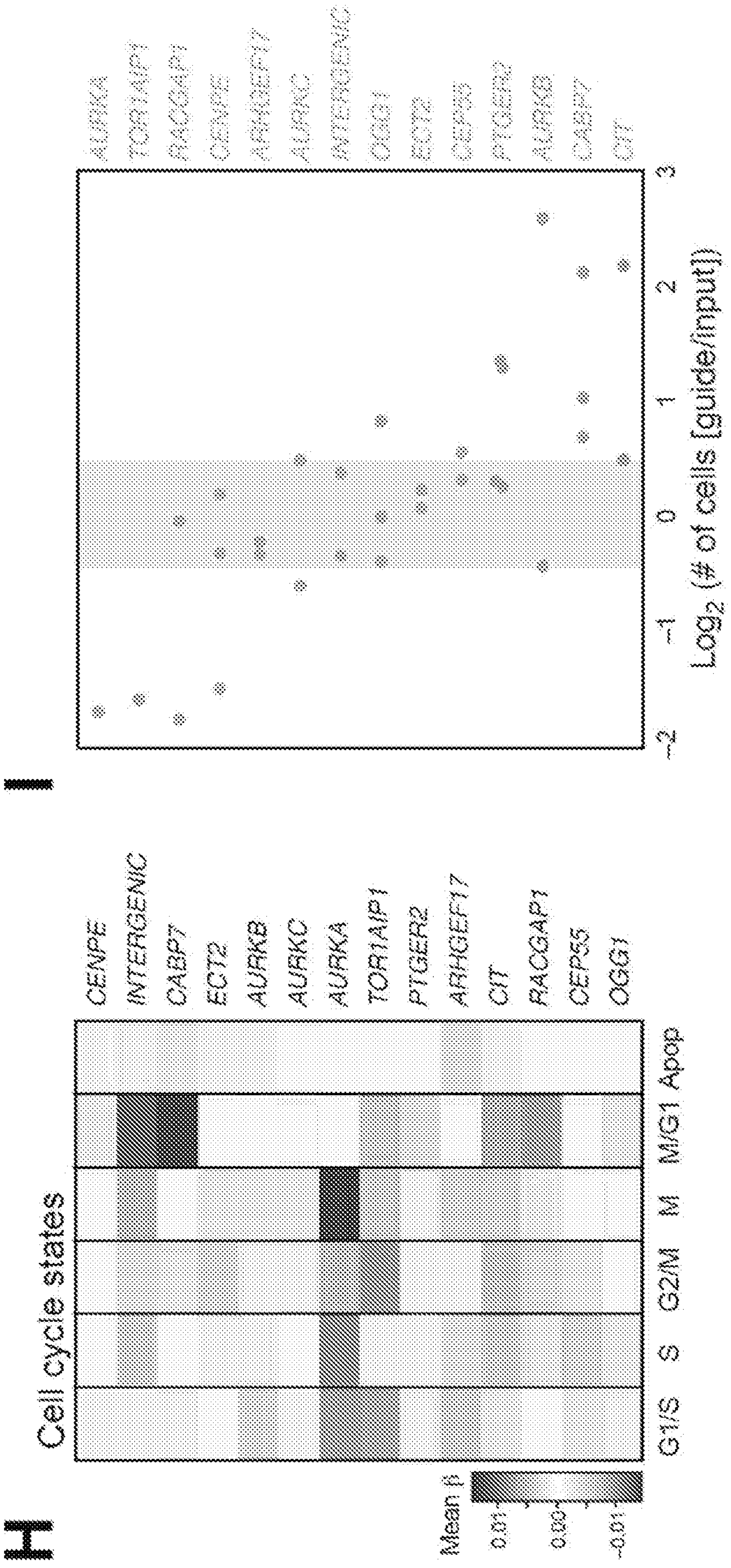

FIG. 54A-B
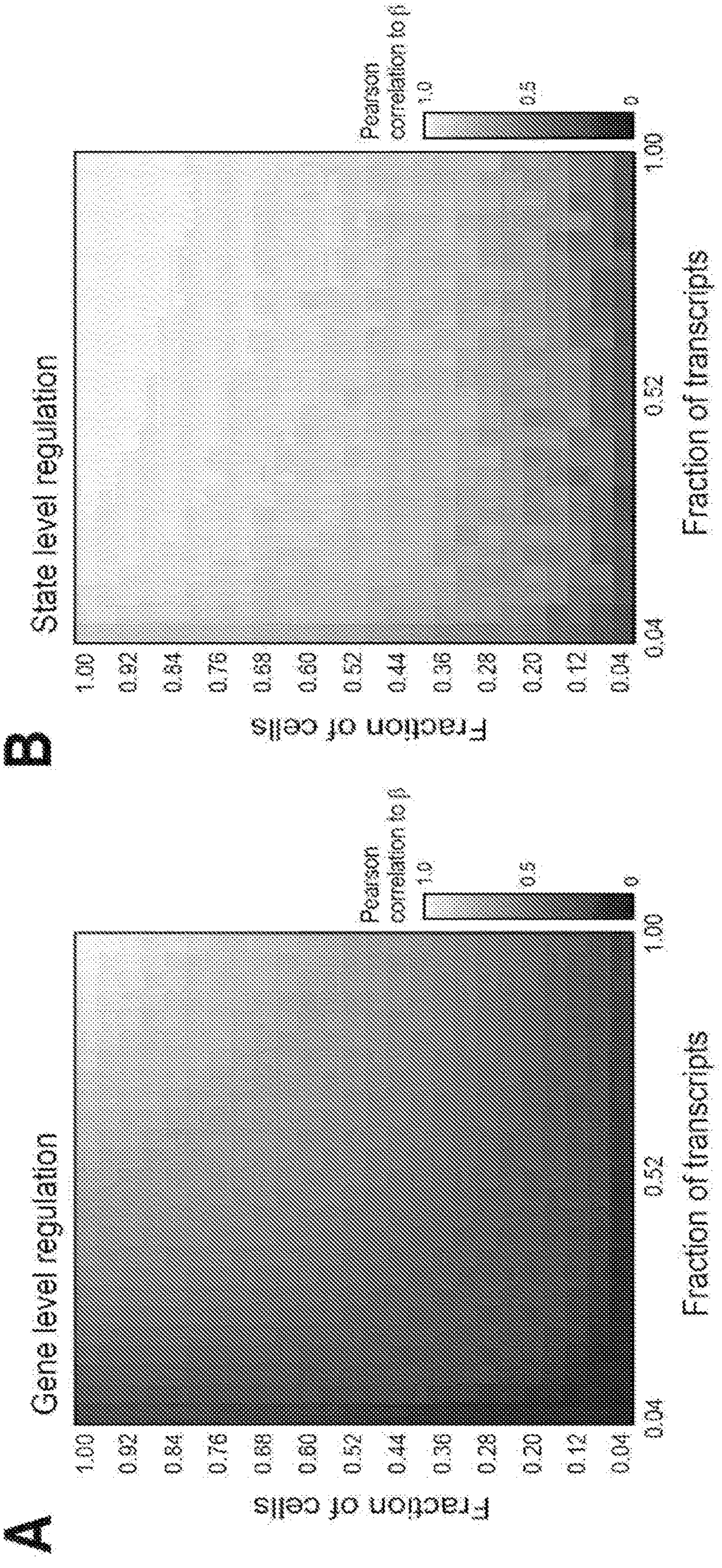

FIG. 55A-C
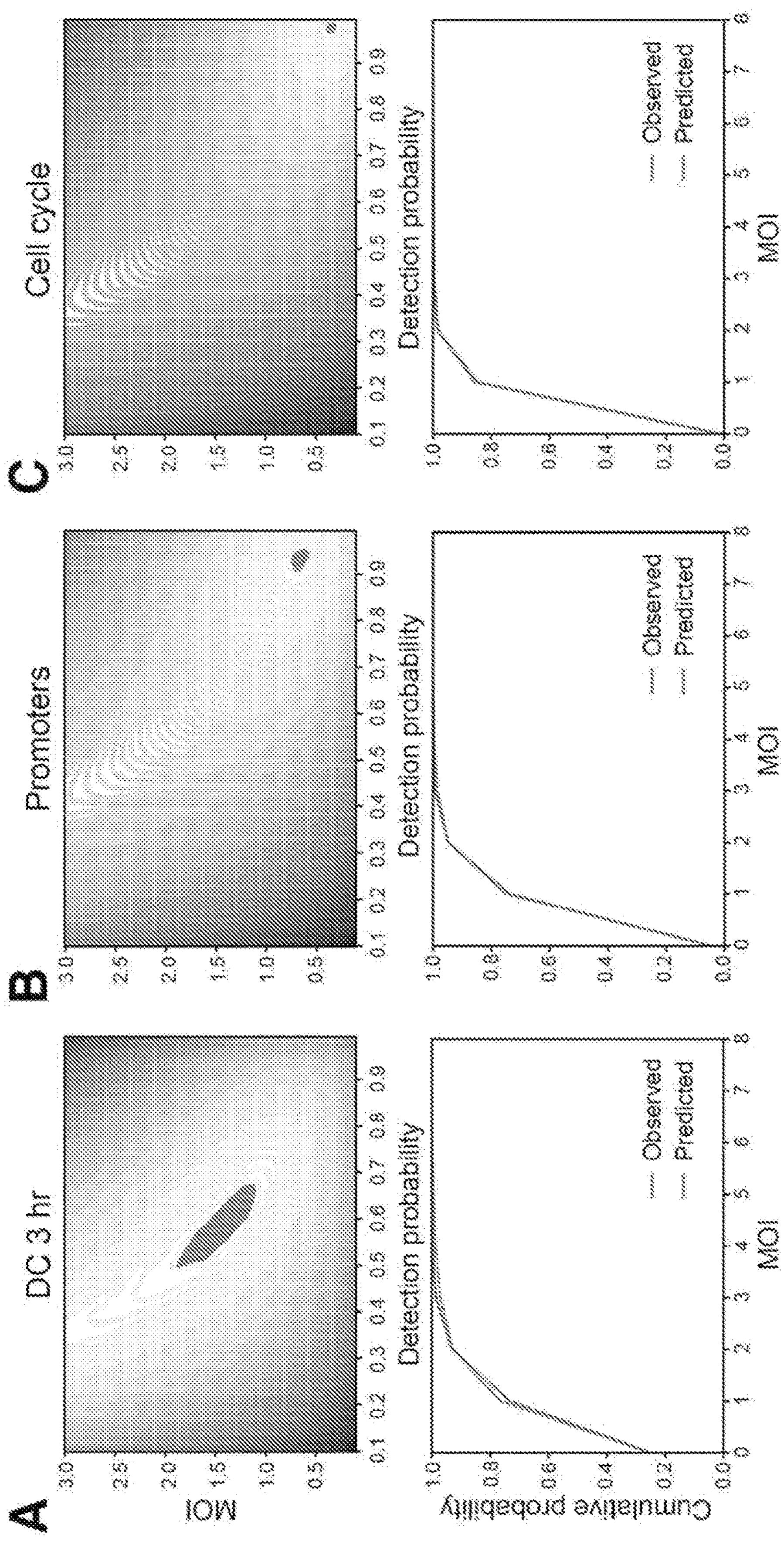

FIG. 55D-J
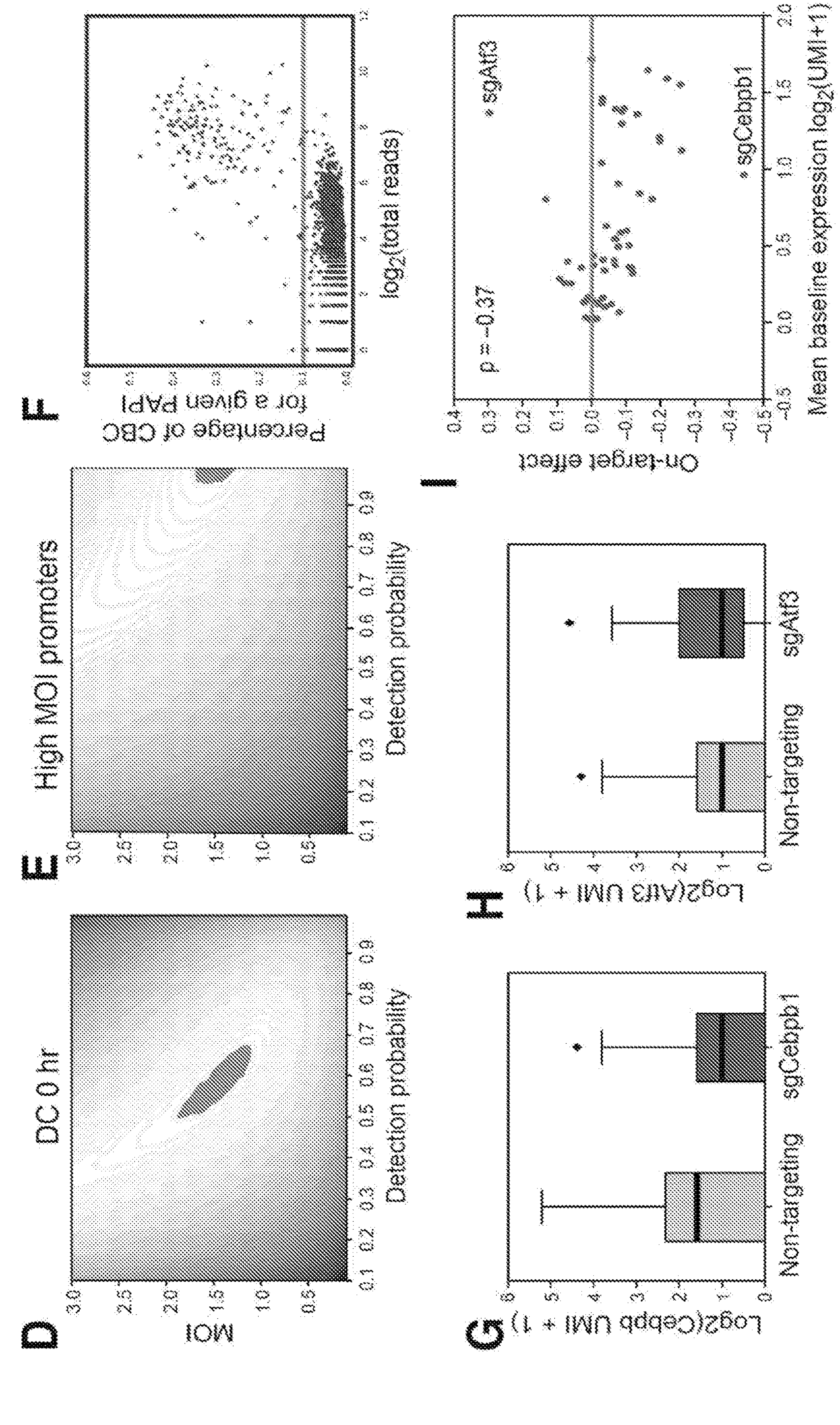

FIG. 55J-L
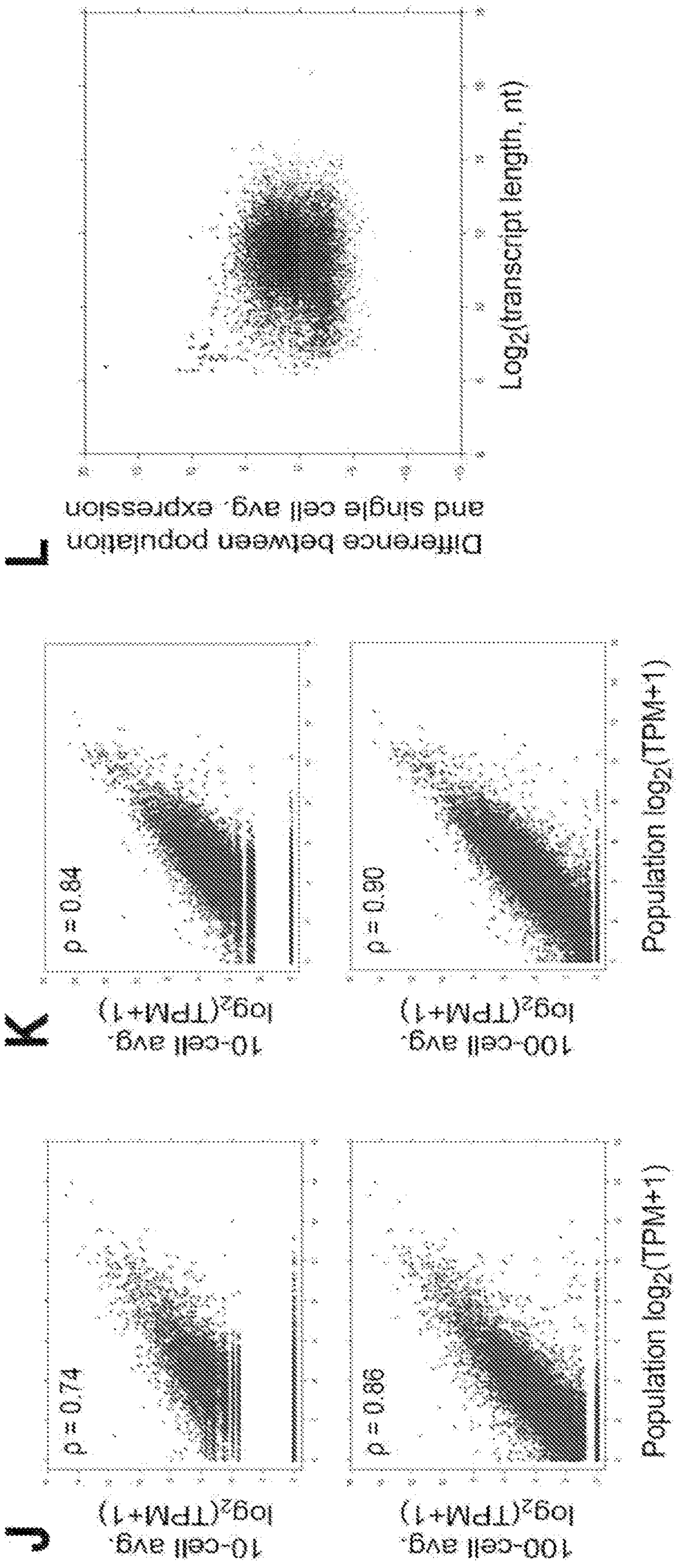

FIG. 56A-C
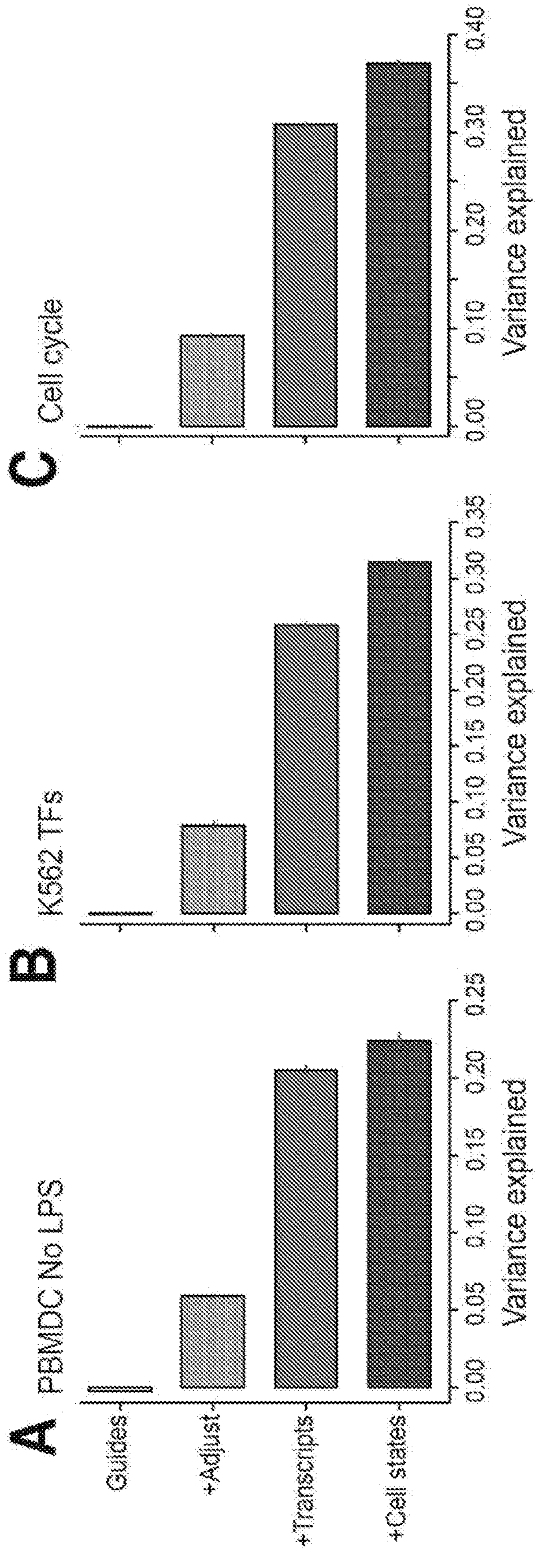

FIG. 56D-G
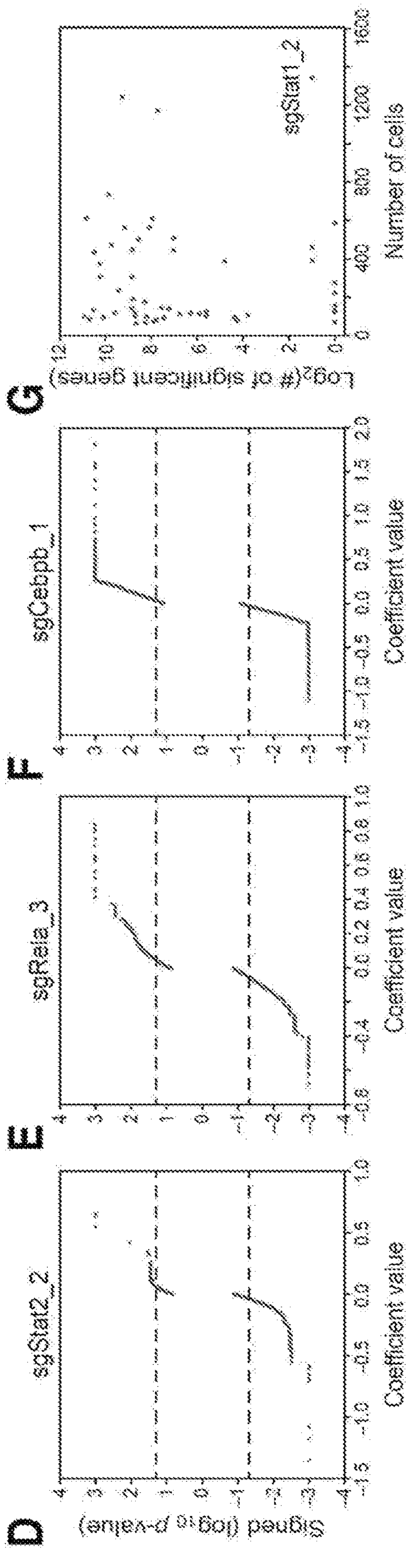

FIG. 57A-B
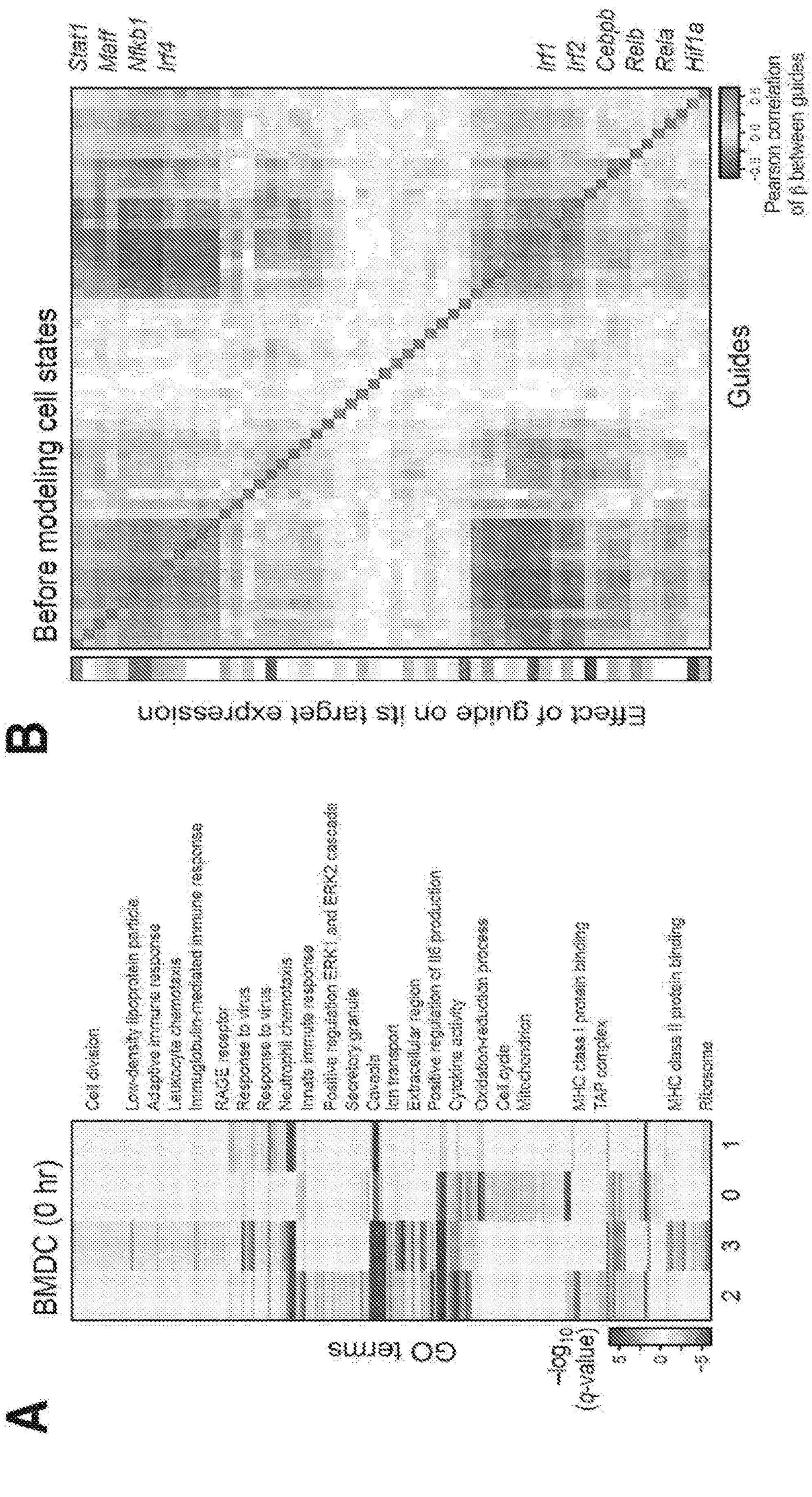

Gene Signatures

Gene Signatures

Gene Signatures

Fraction of transcripts

Individual Gene

Fraction of transcripts

Individual Gene

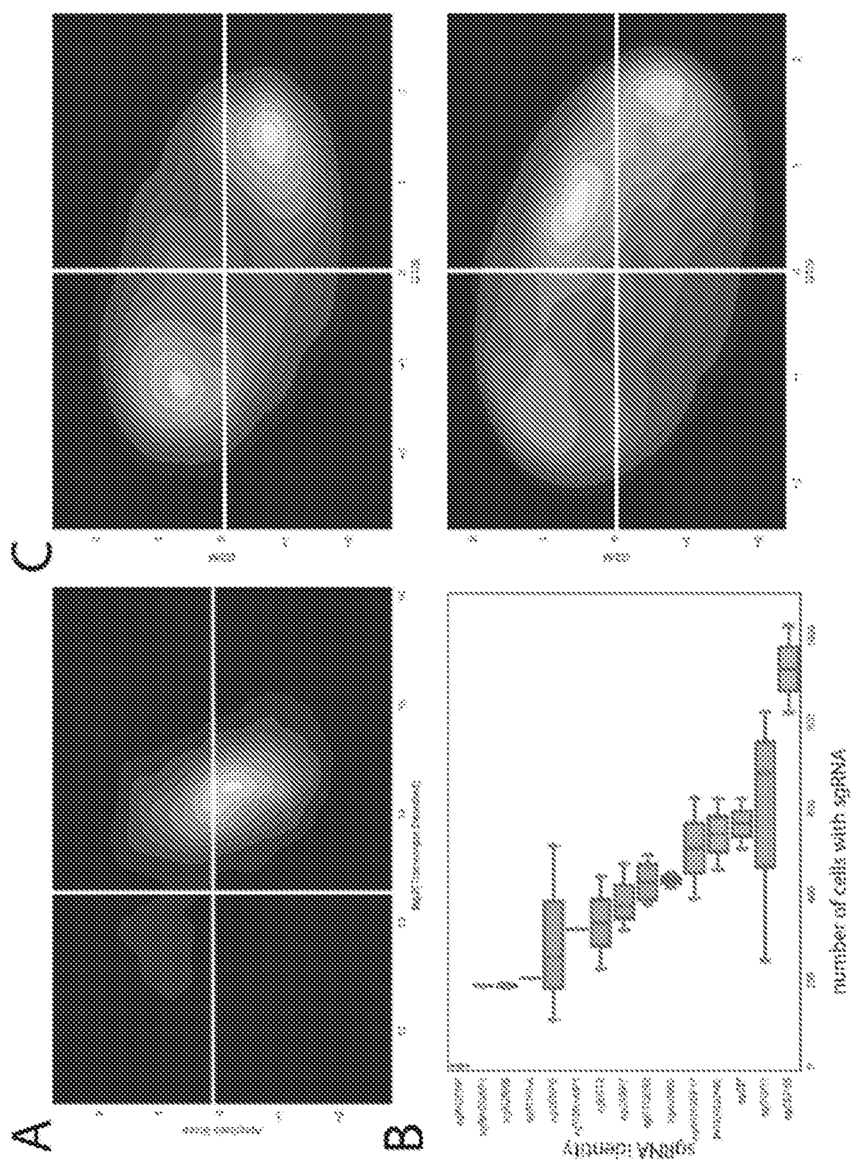
Figure 63A-C.

A.

B.

| | |
|---|---|
| Number of Cells | 5,768 |
| Fraction Reads in Cells | 90.9% |
| Mean Reads per Cell | 75,001 |
| Median Genes per Cell | 3,804 |
| Median UMI Counts per Cell | 20,760 |

Figure 80

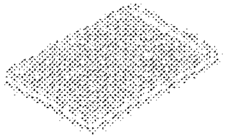
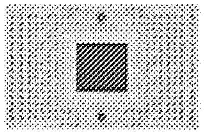
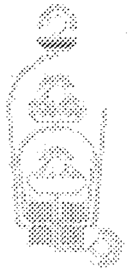
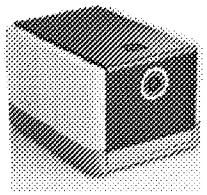

| | Plate-based | Fluidigm C1 Autoprep | Drop-seq/InDrop | 10X GemCode |
|---|---|---|---|---|
| Capture method | FACS into plate | Microfluidic wells | Random droplet encapsulation | Random droplet encapsulation |
| Throughput | 96 per plate | 96 (average: 72) or 800 per chip | ~5000 – 10000 per hour | 1000 – 6000 per 10 minutes |
| Volume "scale" | 4 μL to 25 μL | 4.5 nL to 5 μL | ~1 nL to 50 nL | |
| mRNA capture efficiency | ~20-40% | ~48% | 12.8% (DropSeq) 7% (InDrop) | Comparable to dropseq |
| Cost per cell | ~$10 | $3.50 | $0.07 (DropSeq) | |

FIG. 81C-F
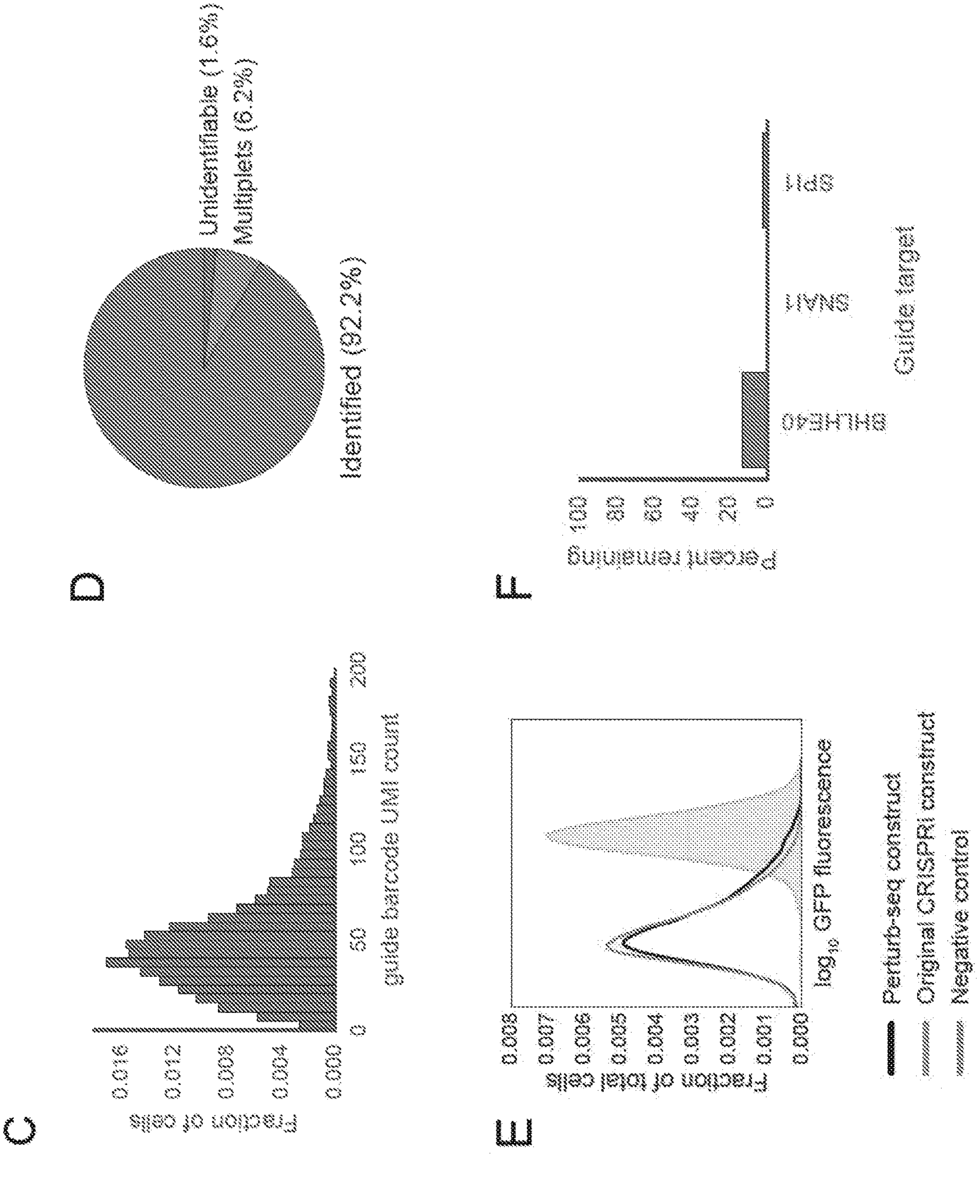

FIG. 82A-C
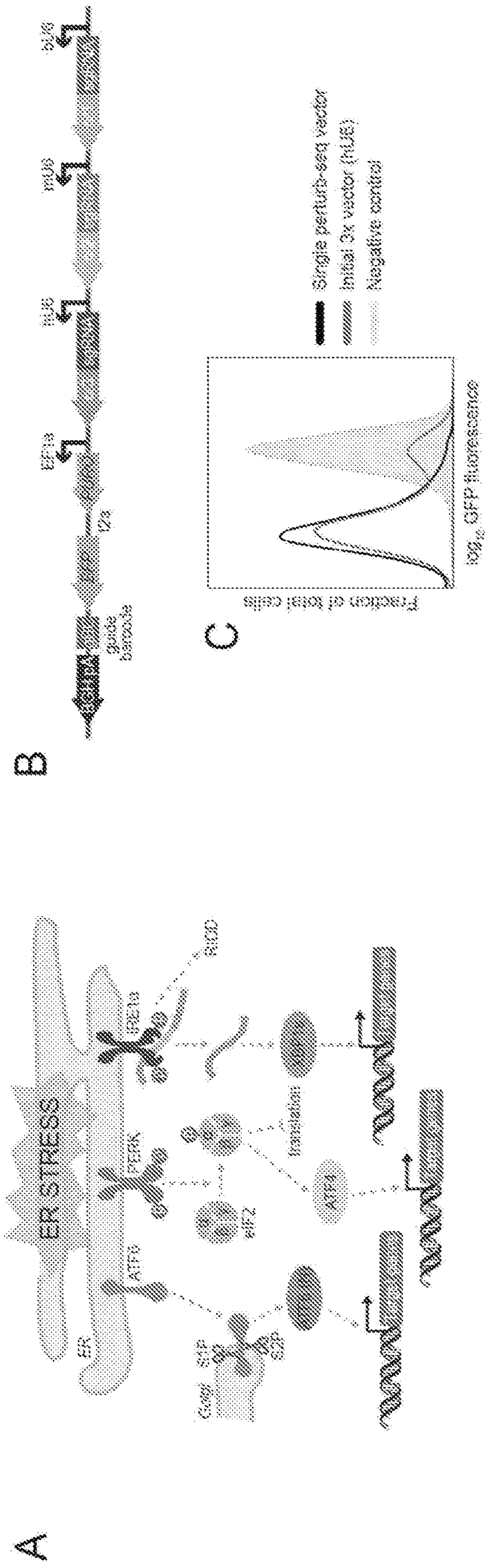

FIG. 82E-G
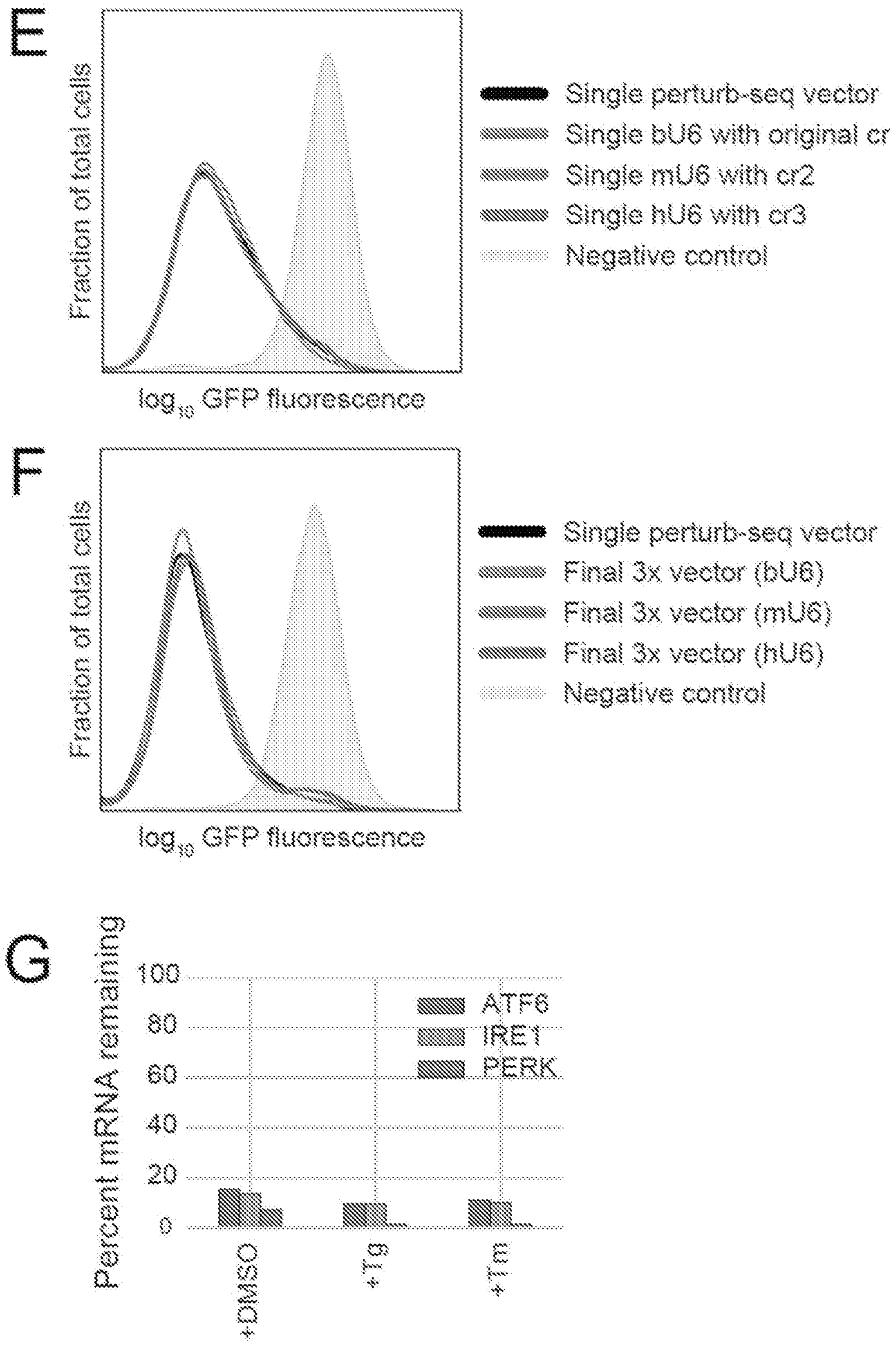

FIG. 83A-C
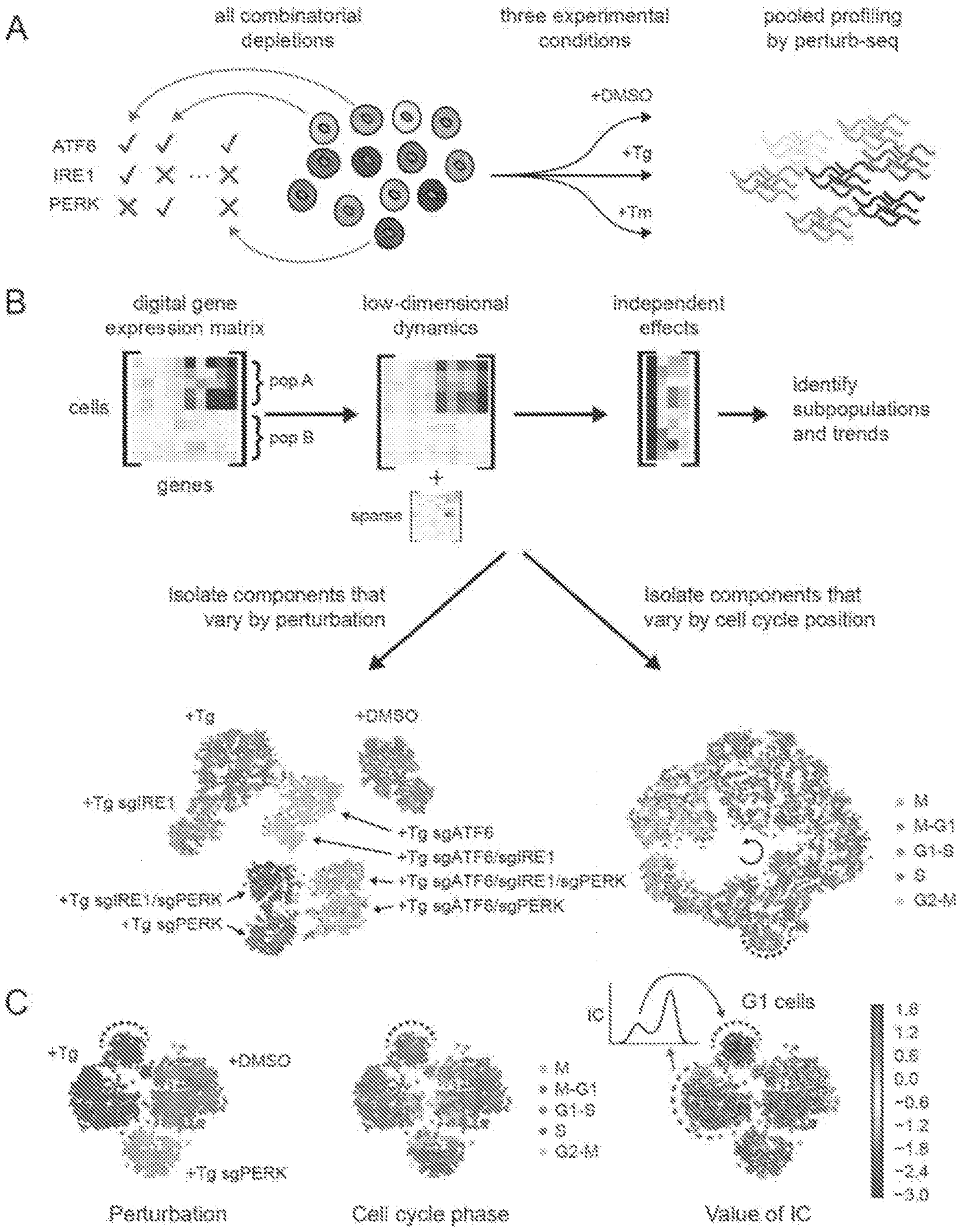

FIG. 84A-C
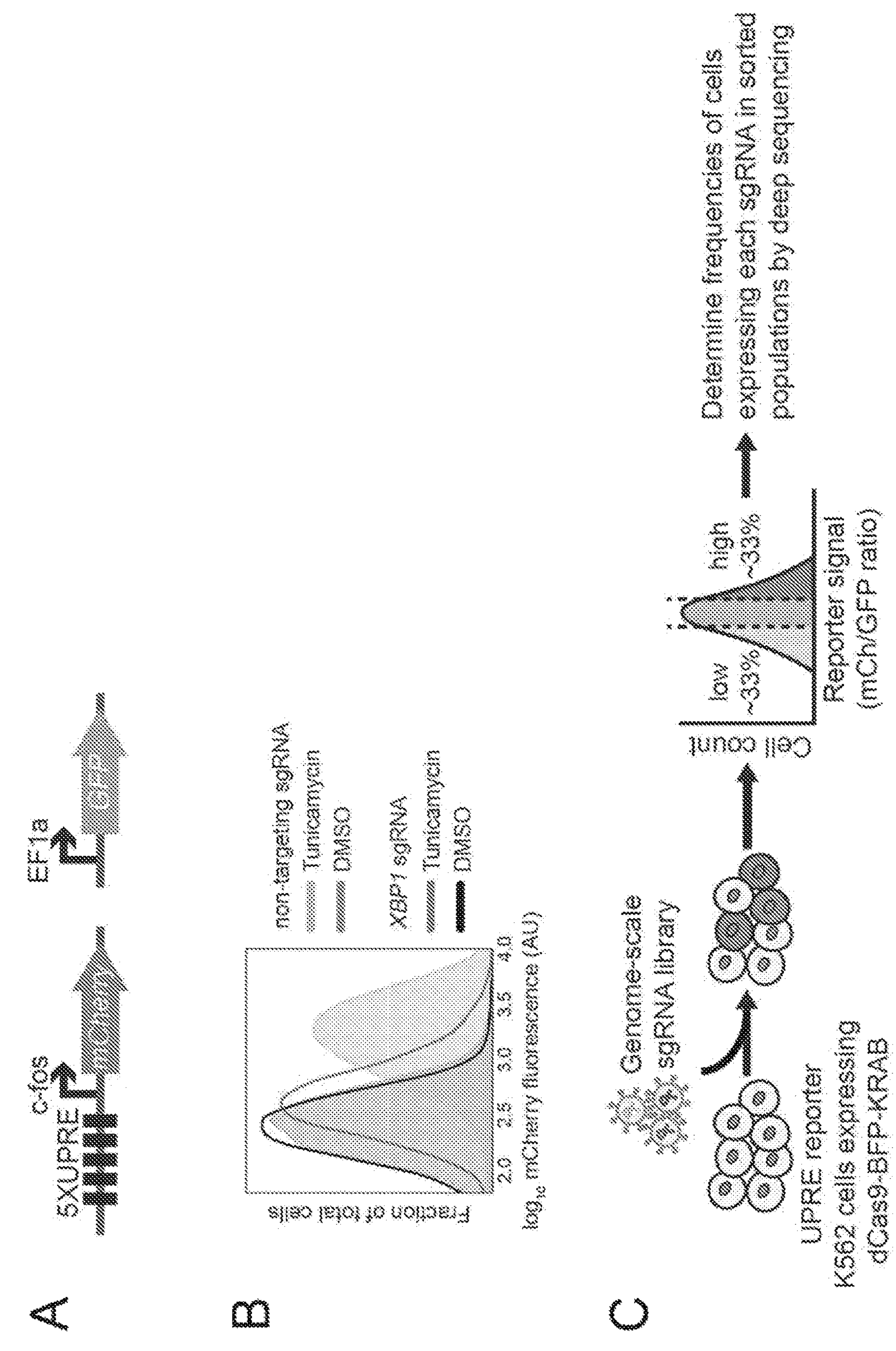

FIG. 84D-E
D
E
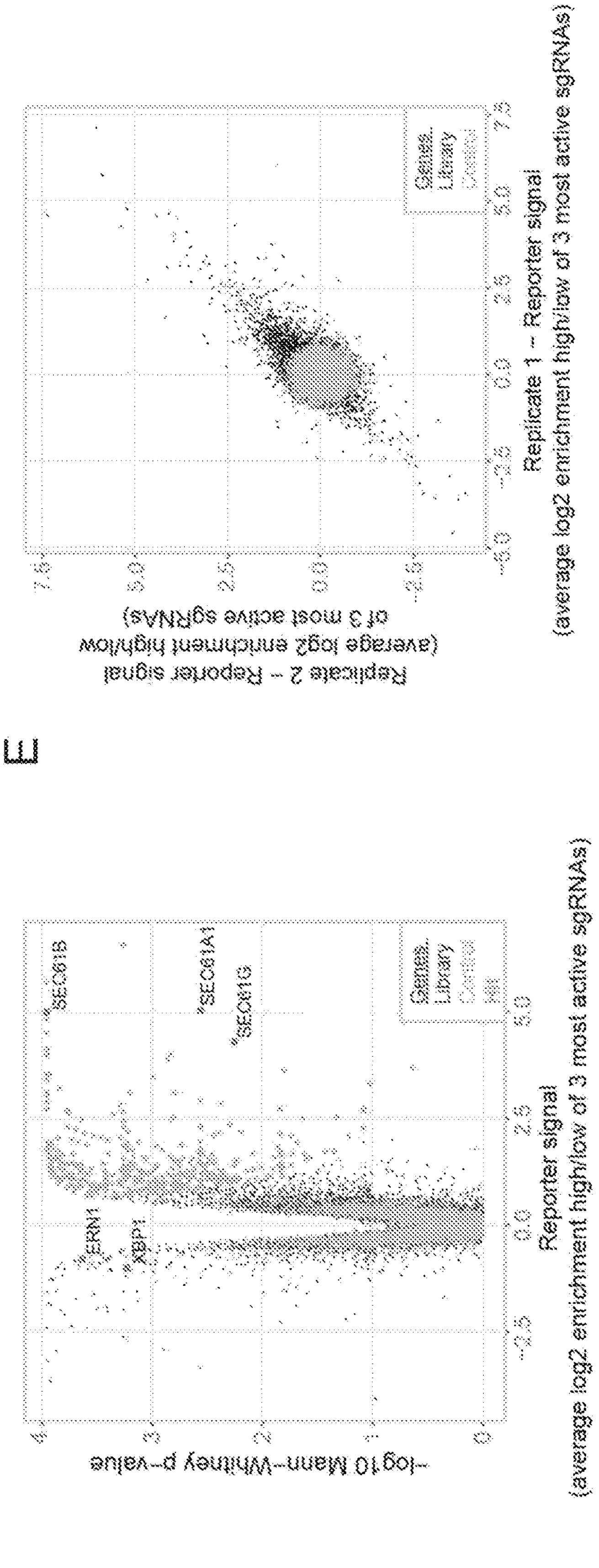

F

FIG. 85B-D
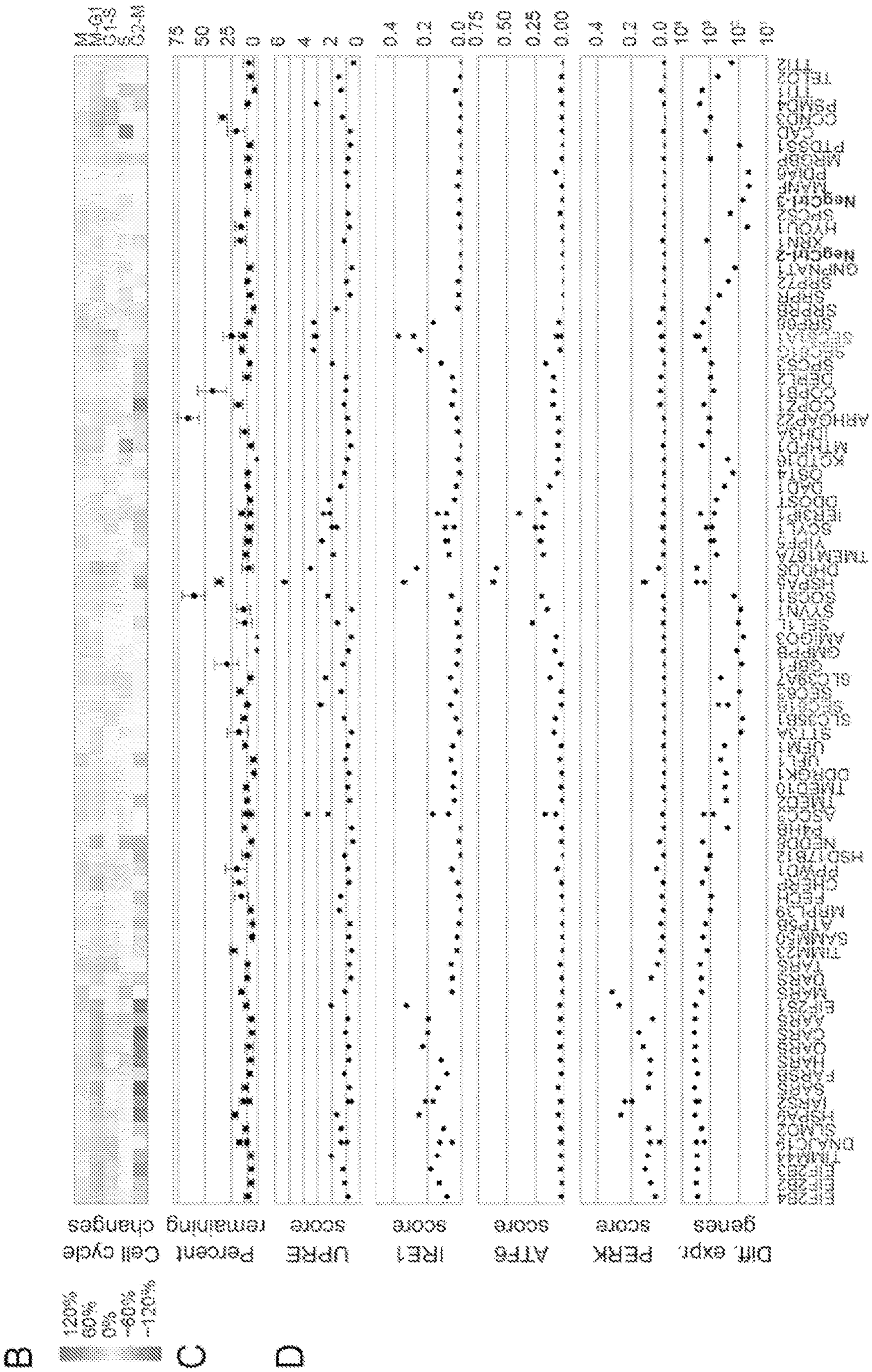

FIG. 86A-C
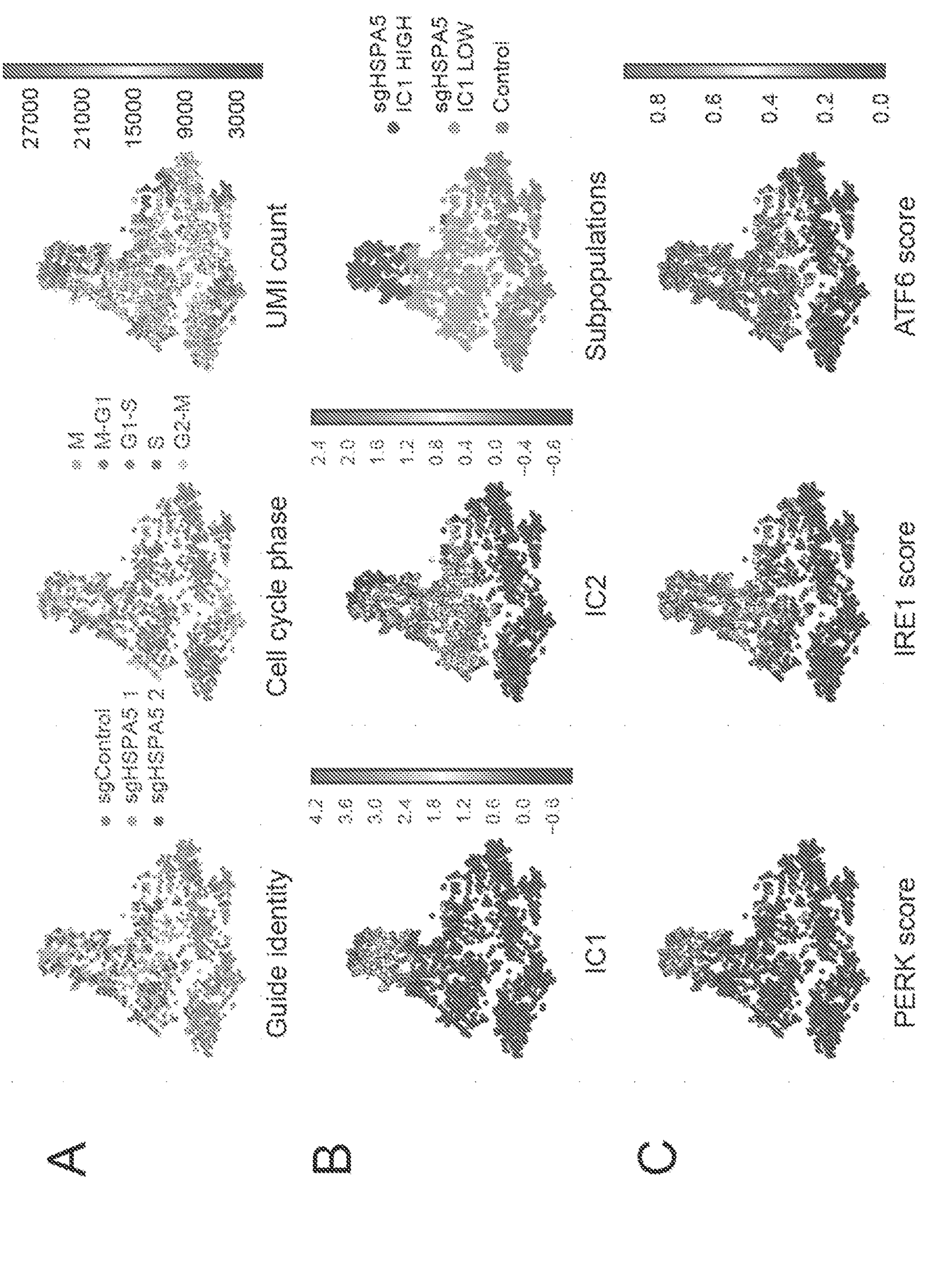

FIG. 86D-F
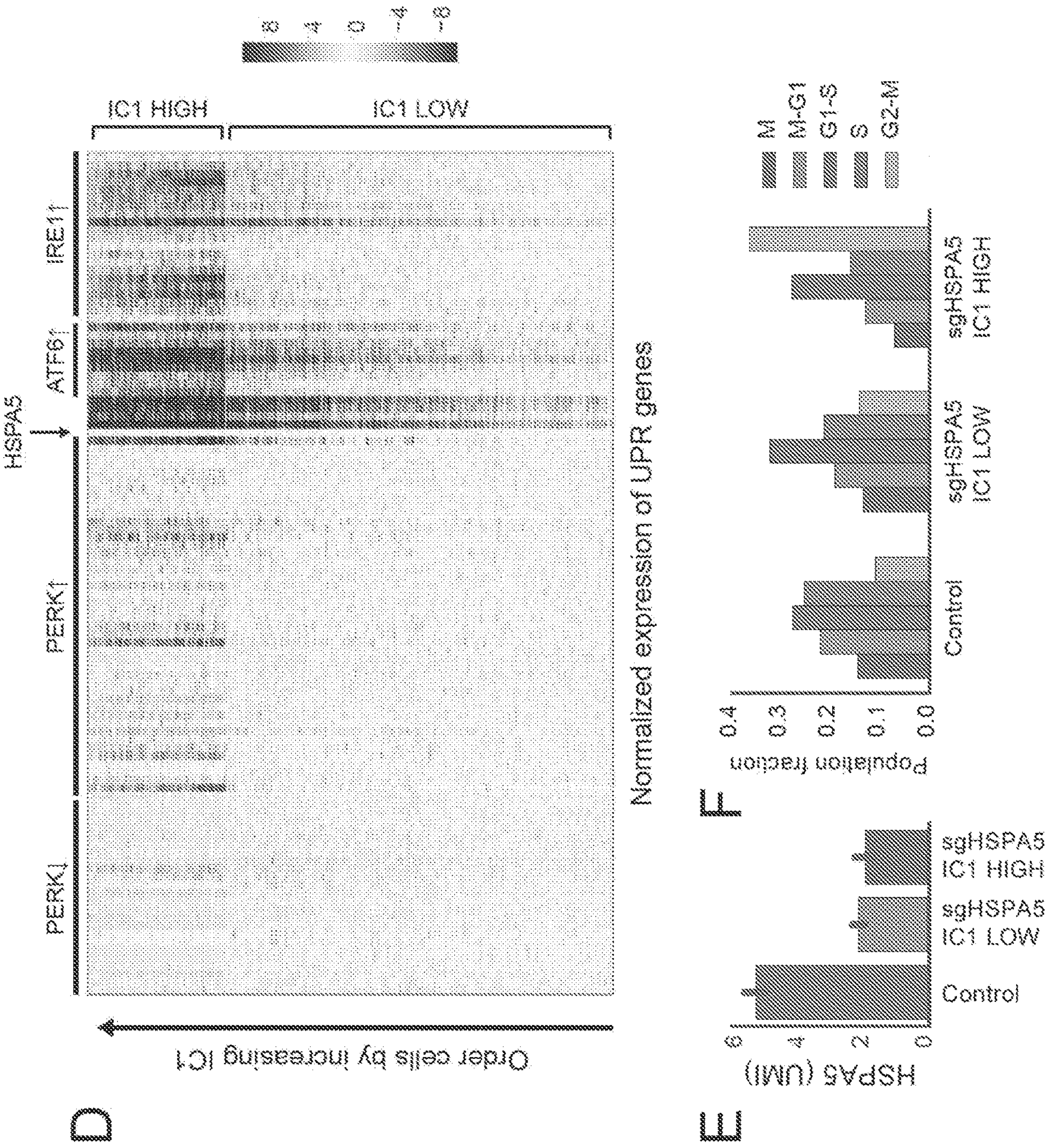

FIG. 86G-H
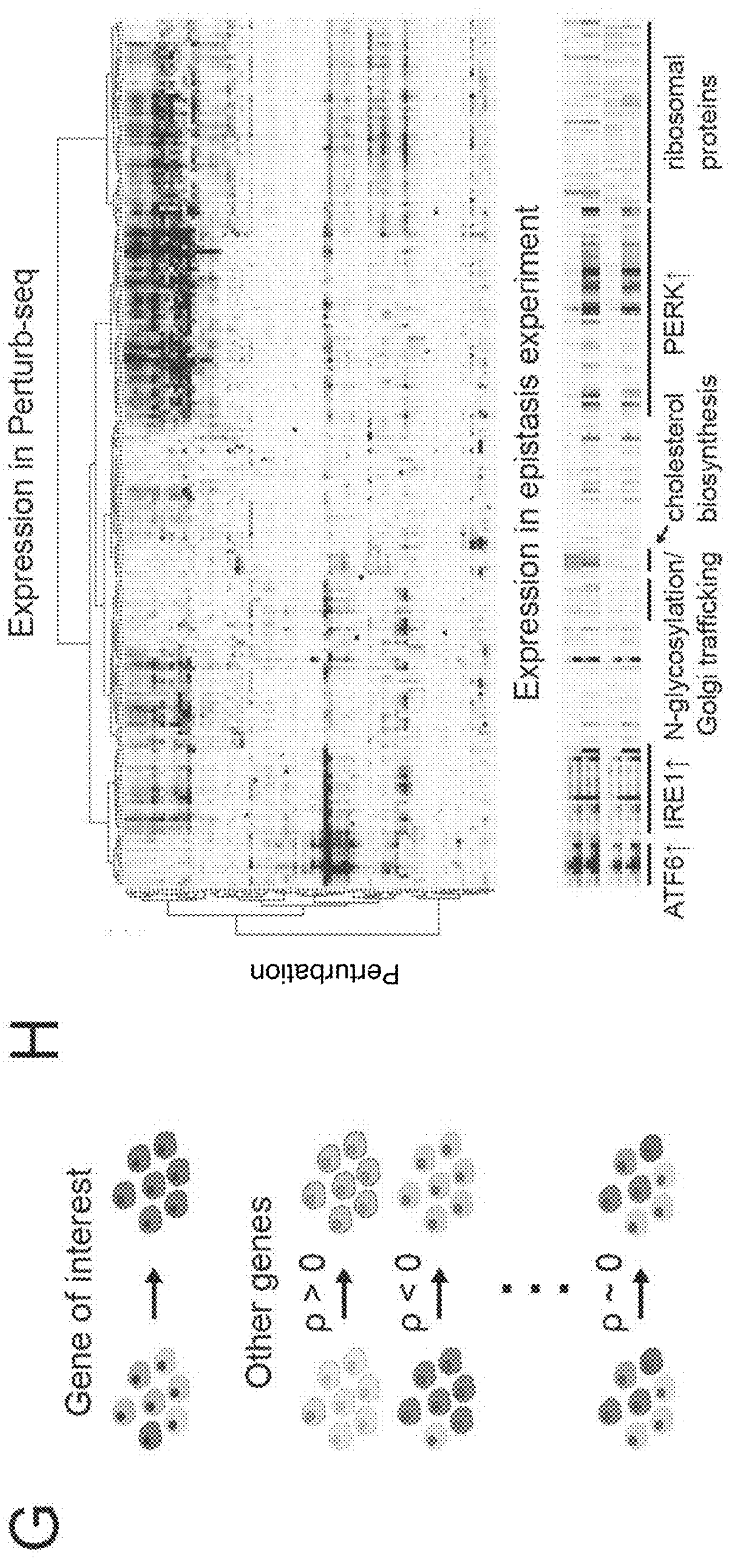

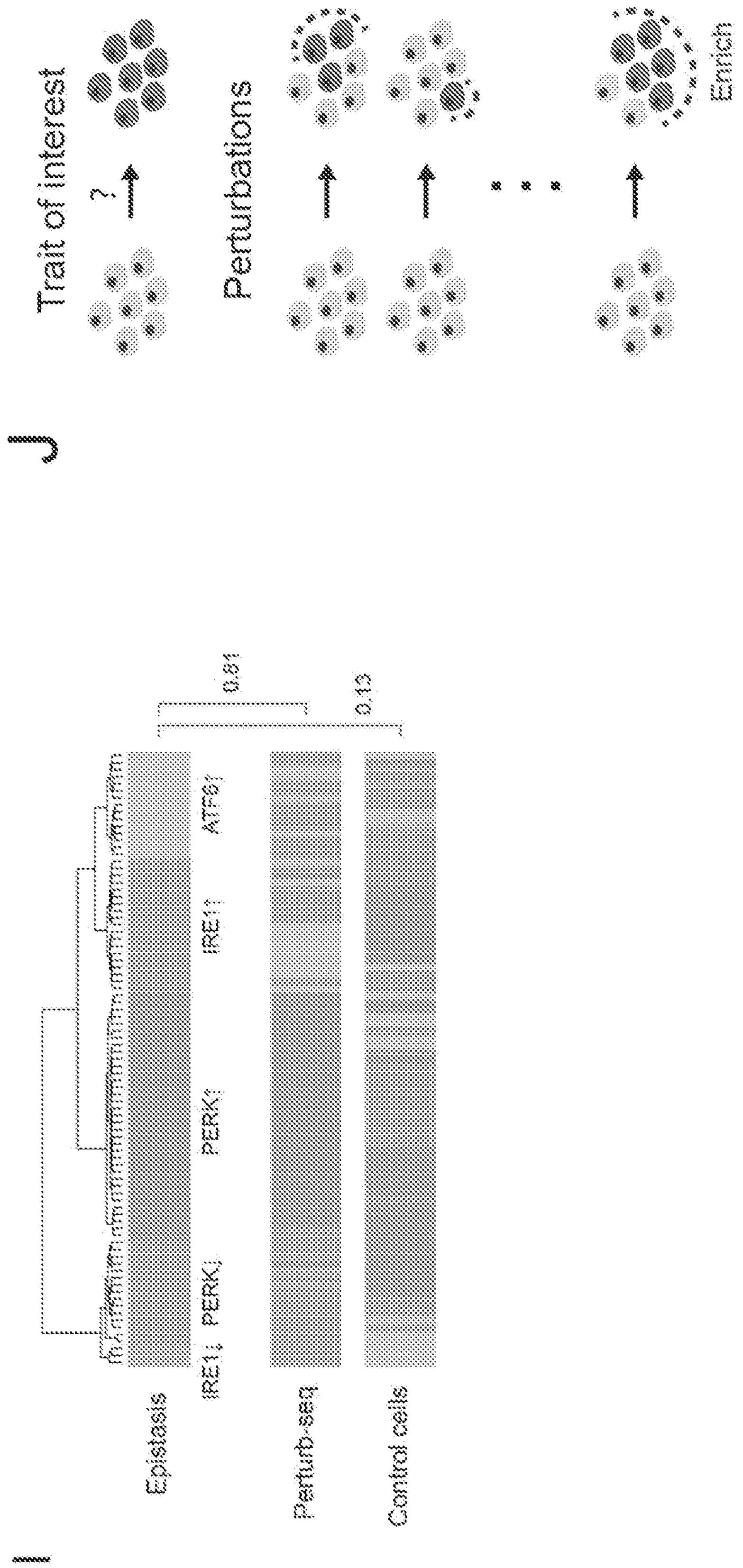
FIG. 86I-J

FIG. 86K-L
K
L
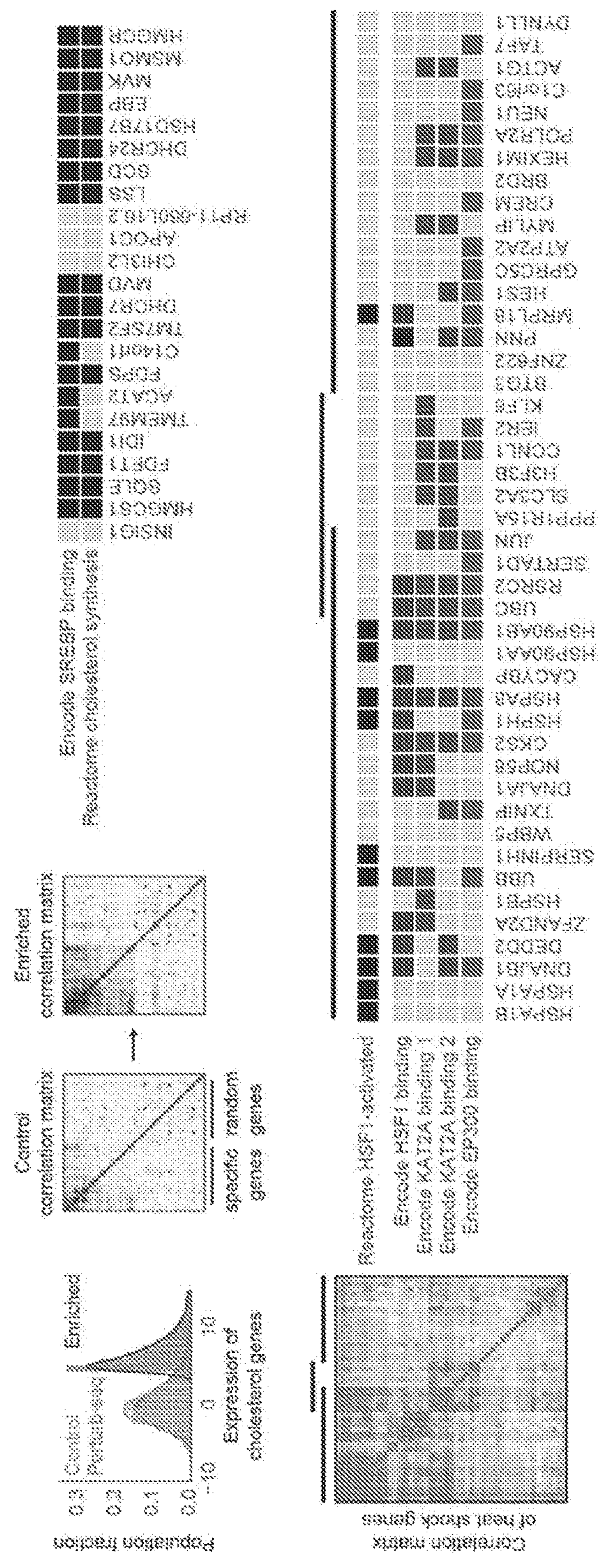

FIG. 87A-C
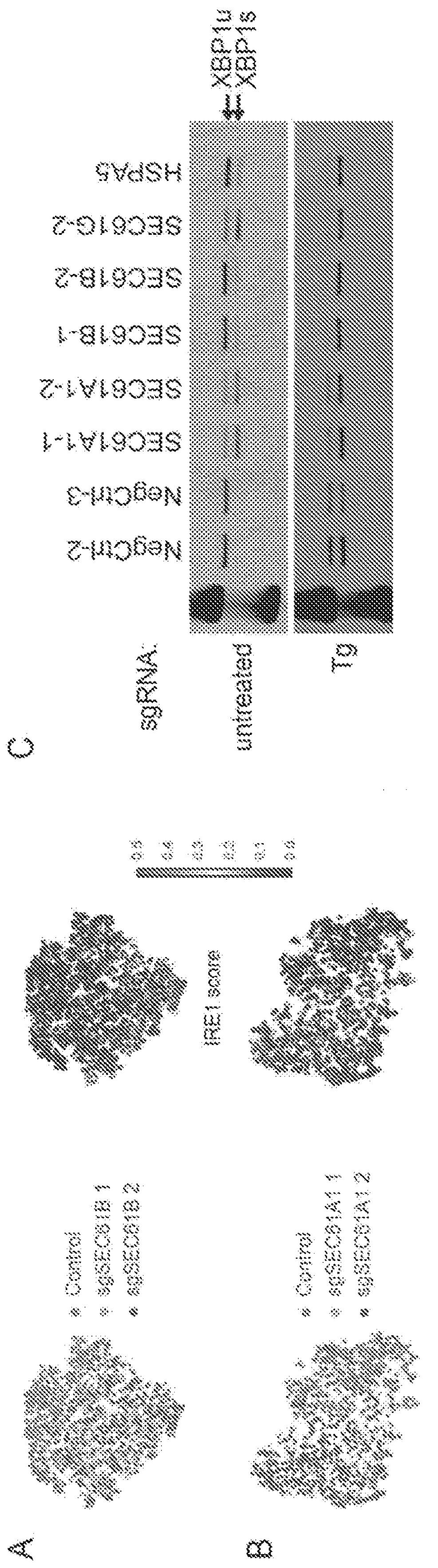

FIG. 87D-F
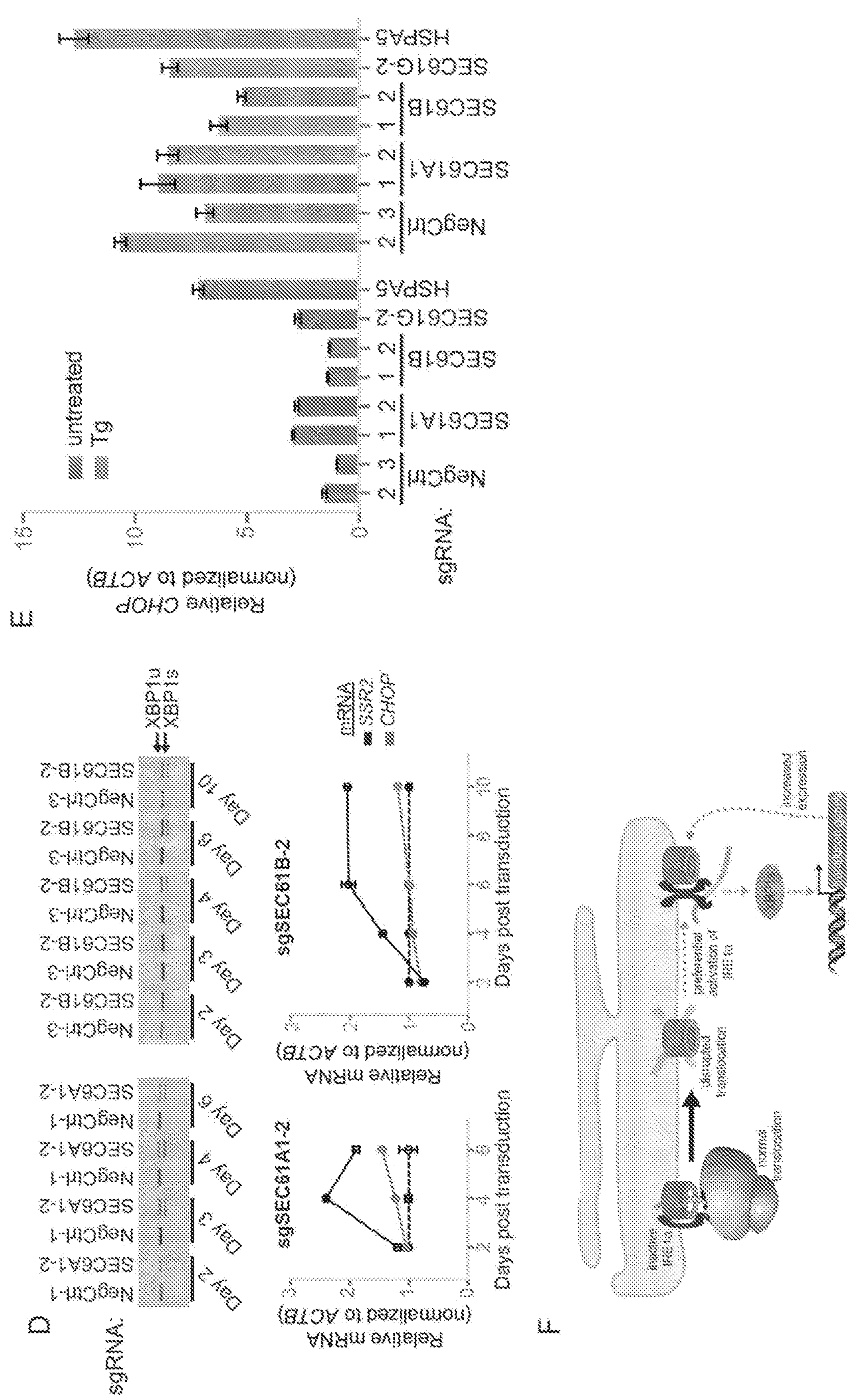

FIG. 88A-E
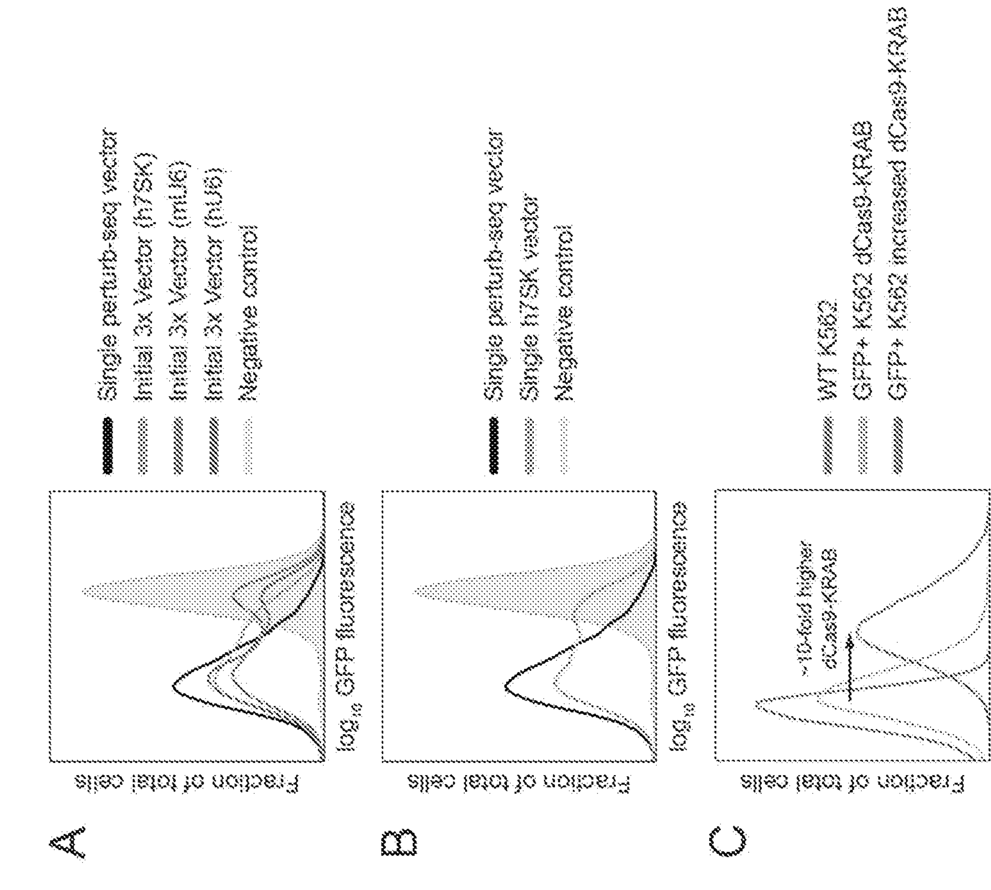
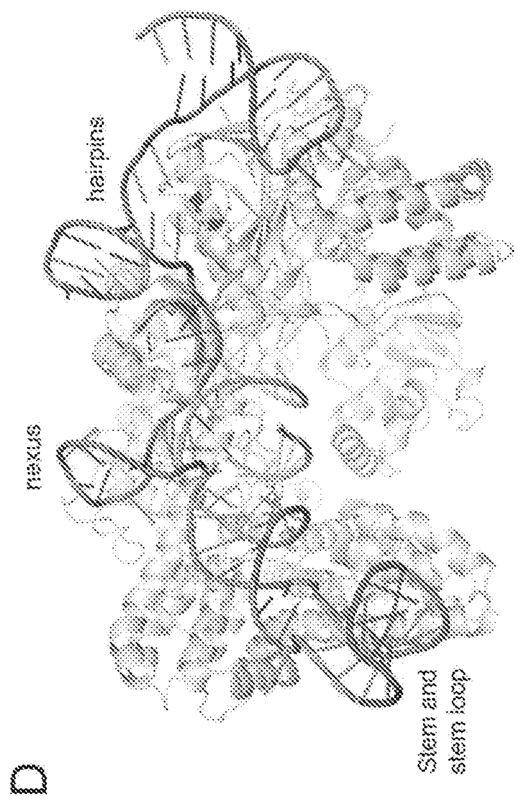
E
| promoter | % knockdown (GFP) |
|---|---|
| mU6 (perturb-seq vector, exp 1) | 95.2 |
| bU6-2 | 95.4 |
| bU6-3 | 93.4 |
| sU6-1 | 94.9 |
| sU6-2 | 95.1 |
| mU6 (perturb-seq vector, exp 2) | 94.4 |
| buU6 | 94.8 |
| pU6 | 94.4 |

FIG. 90A-B
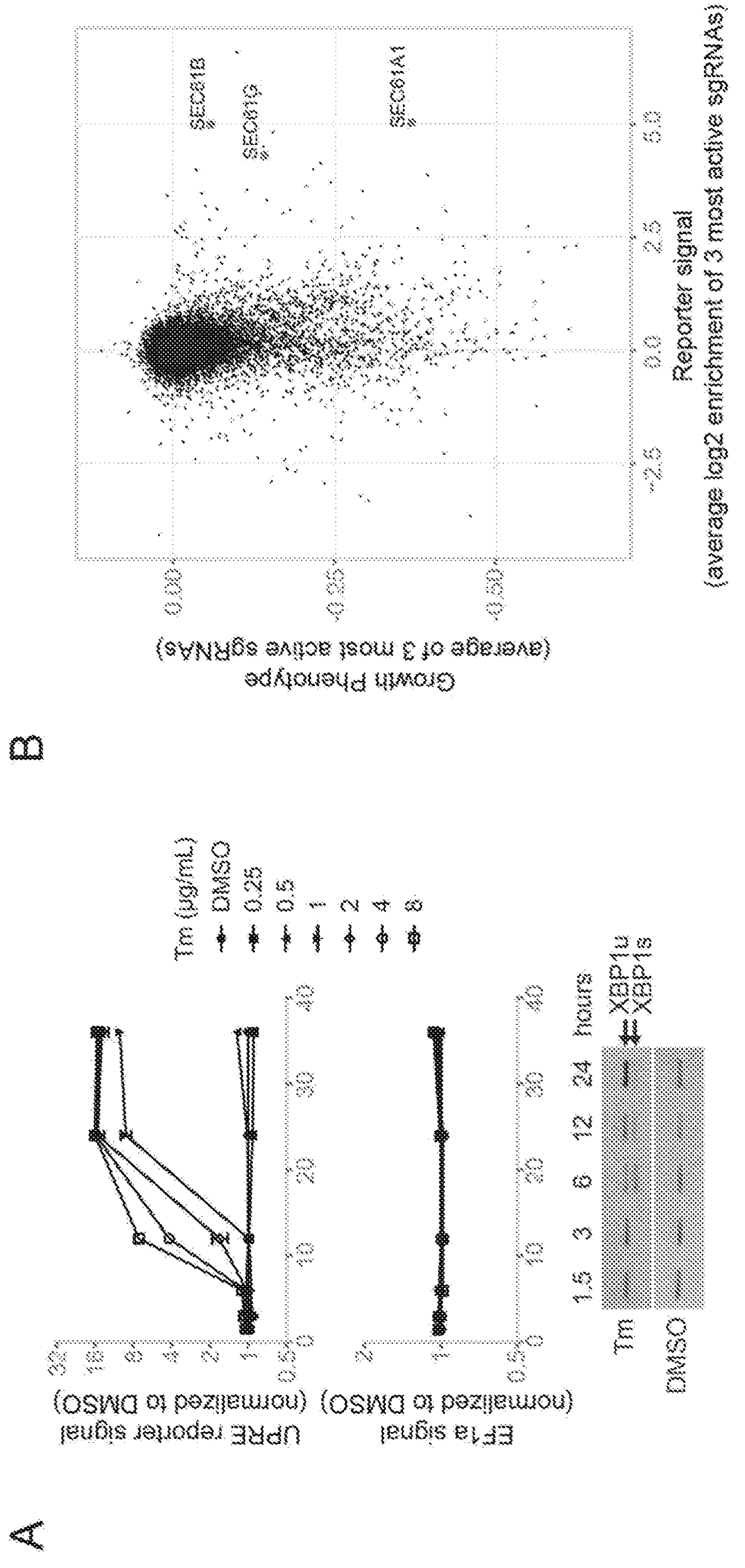

FIG. 90C-D
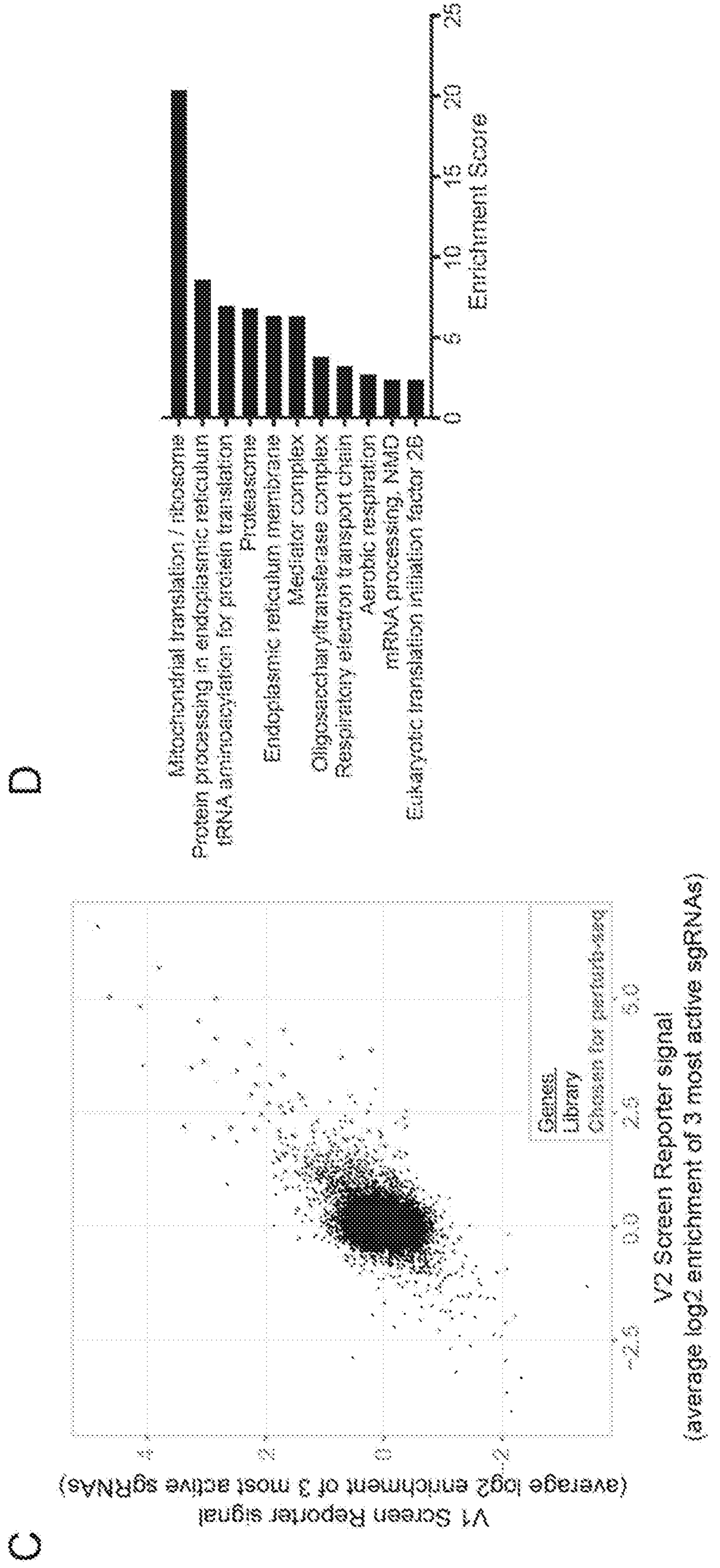

FIG. 91A-B
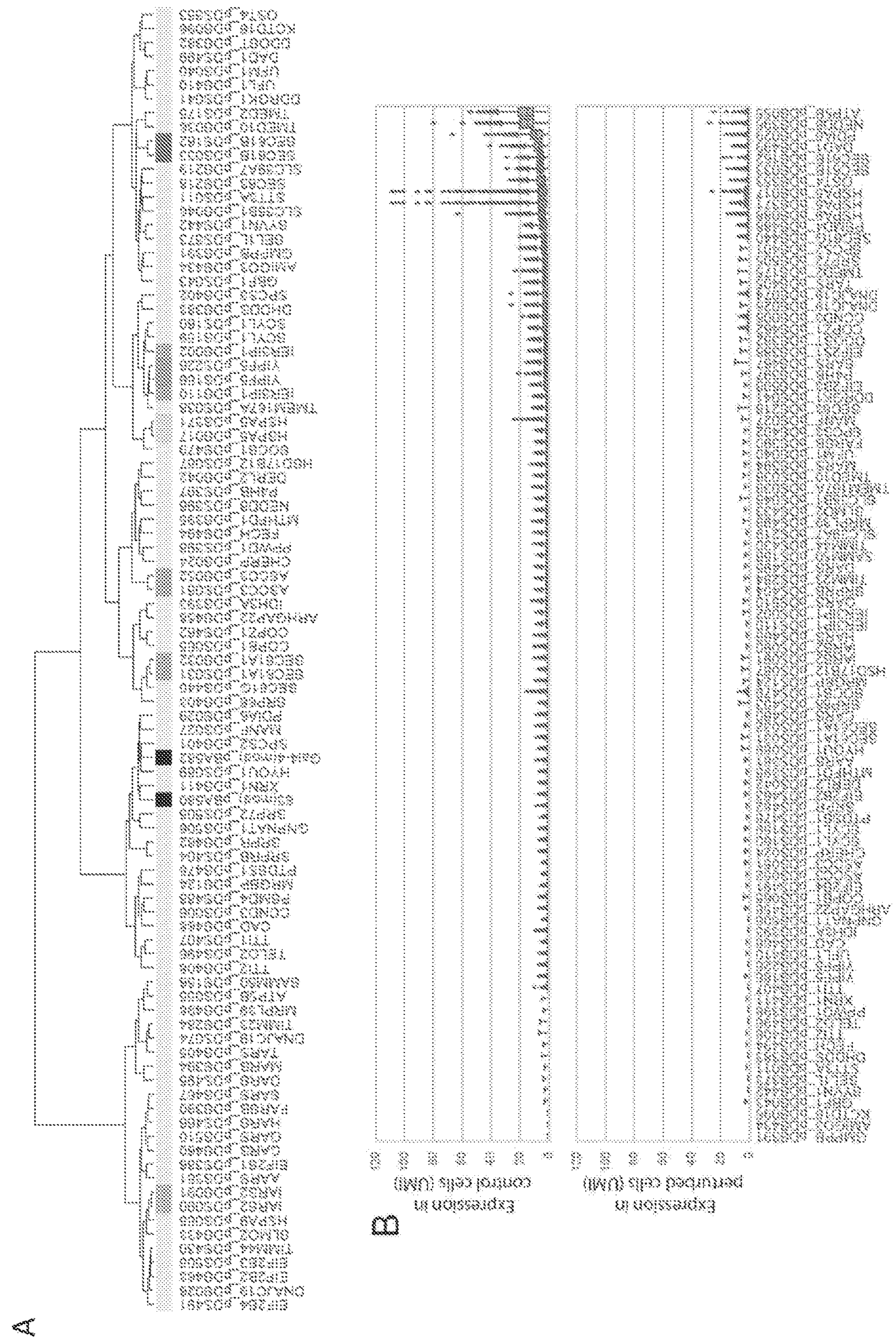

FIG. 91D-E
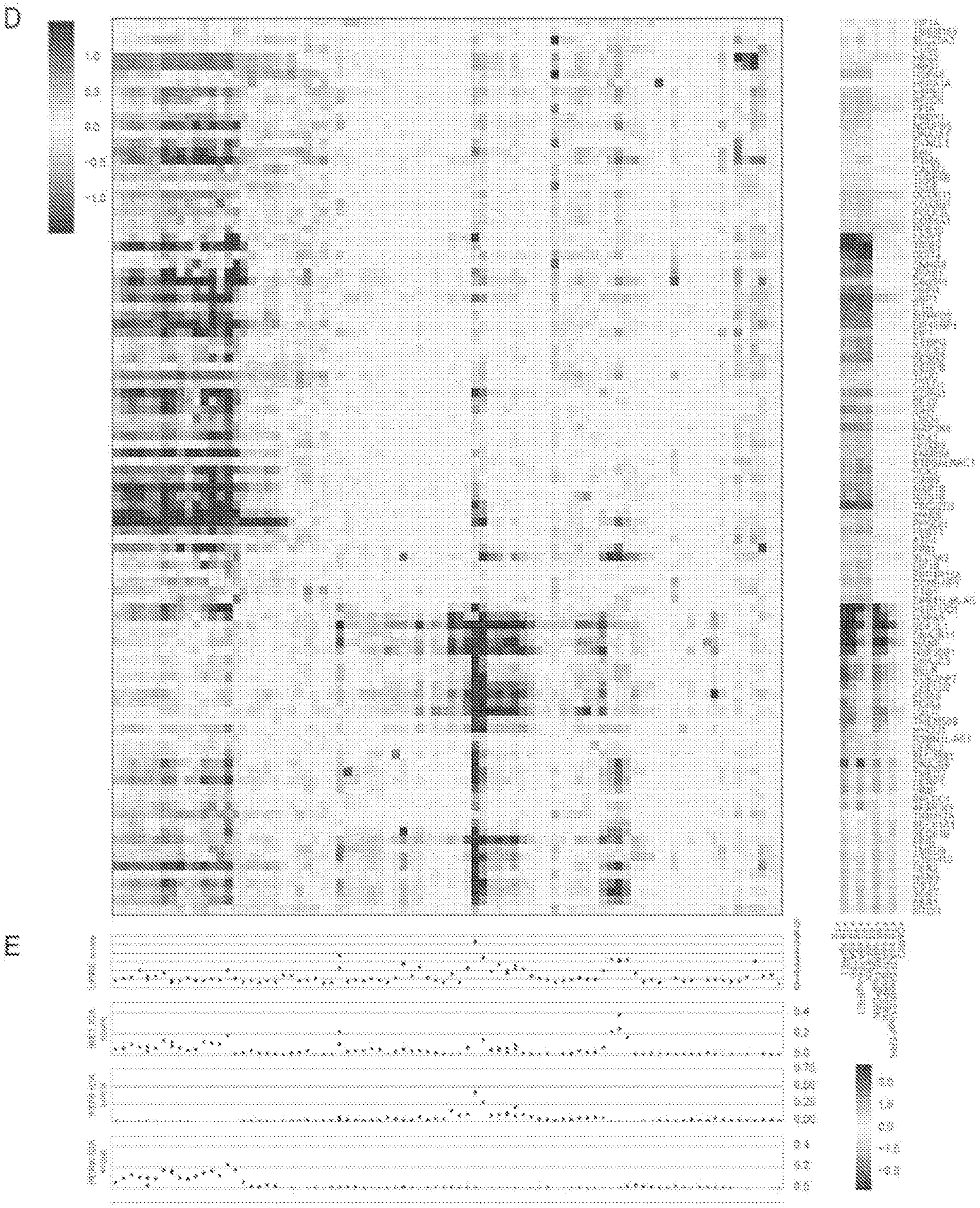

F

FIG. 93A-C
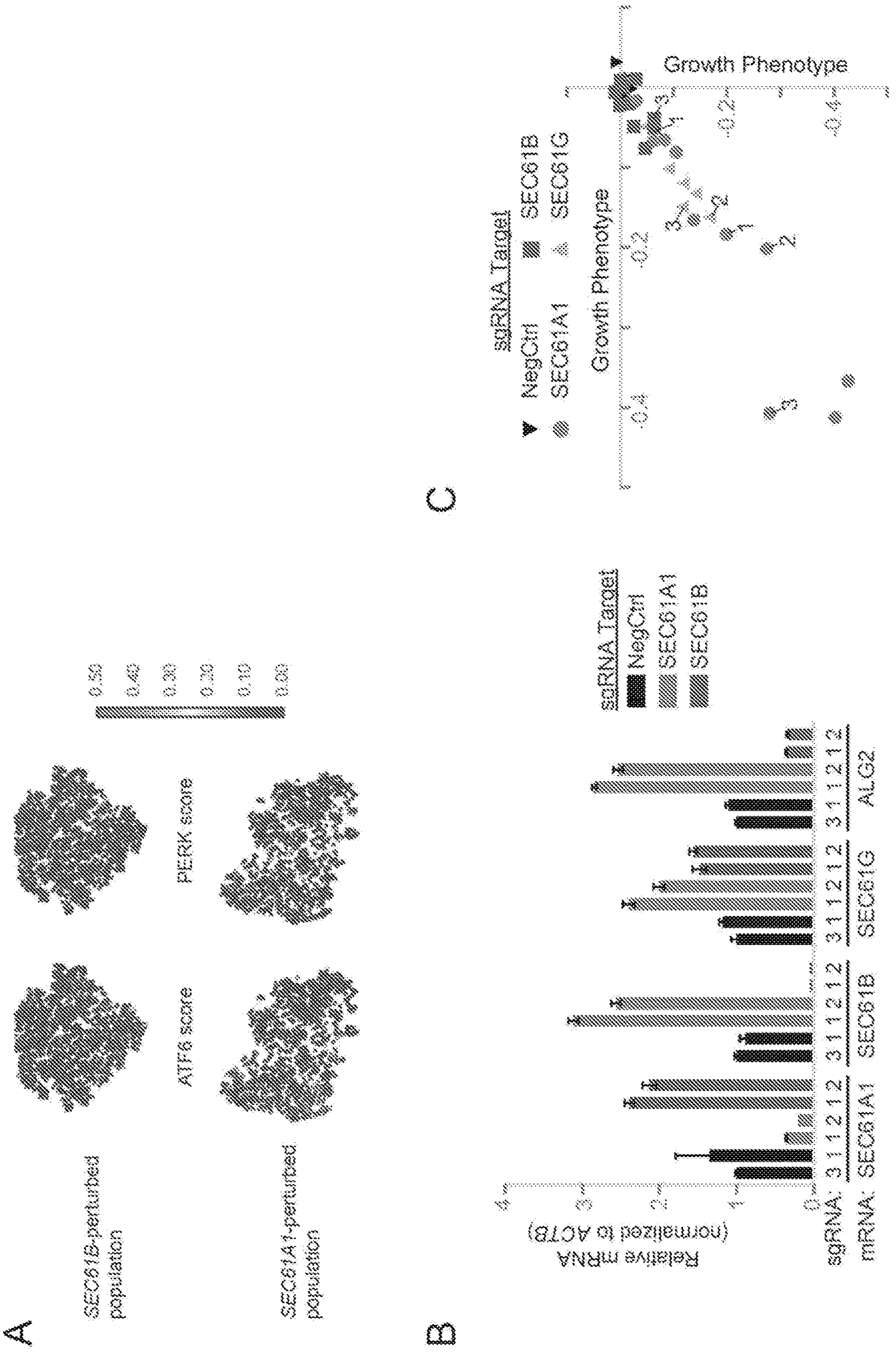

| Pair | Number of Occurrences |
|---|---|
| A-B | 3 |
| A-C | 3 |
| B-C | 3 |
| A-D | 1 |
| A-F | 1 |
| A-G | 1 |
| A-K | 1 |
| A-H | 0 |

True Pairs (A-B, A-C, B-C)

False Pairs (A-D, A-F, A-G, A-K)

SEQUENCE LISTING

```
<160> NUMBER OF SEQ ID NOS: 68

<210> SEQ ID NO 1
<211> LENGTH: 14
<212> TYPE: DNA
<213> ORGANISM: Artificial Sequence
<220> FEATURE:
<223> OTHER INFORMATION: Synthetic

<400> SEQUENCE: 1

agcctcacag gcga                                                       14


<210> SEQ ID NO 2
<211> LENGTH: 14
<212> TYPE: DNA
<213> ORGANISM: Artificial Sequence
<220> FEATURE:
<223> OTHER INFORMATION: Synthetic
```

<400> SEQUENCE: 2
atagcgtgca acca 14

<210> SEQ ID NO 3
<211> LENGTH: 29
<212> TYPE: DNA
<213> ORGANISM: Artificial Sequence
<220> FEATURE:
<223> OTHER INFORMATION: Synthetic

<400> SEQUENCE: 3
aatgatacgg cgaccaccga gatctacac 29

<210> SEQ ID NO 4
<211> LENGTH: 33
<212> TYPE: DNA
<213> ORGANISM: Artificial Sequence
<220> FEATURE:
<223> OTHER INFORMATION: Synthetic

<400> SEQUENCE: 4
tcgtcggcag cgtcagatgt gtataagaga cag 33

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
tagcaaactg gggcacaagc 20

<210> SEQ ID NO 6
<211> LENGTH: 29
<212> TYPE: DNA
<213> ORGANISM: Artificial Sequence
<220> FEATURE:
<223> OTHER INFORMATION: Synthetic

<400> SEQUENCE: 6
aatgatacgg cgaccaccga gatctacac 29

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
tcgtcggcag cgtcagatgt gtataagaga cag 33

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tagcaaactg gggcacaagc 20

<210> SEQ ID NO 9
<211> LENGTH: 29

<212> TYPE: DNA
<213> ORGANISM: Artificial Sequence
<220> FEATURE:
<223> OTHER INFORMATION: Synthetic

<400> SEQUENCE: 9
aatgatacgg cgaccaccga gatctacac 29

<210> SEQ ID NO 10
<211> LENGTH: 33
<212> TYPE: DNA
<213> ORGANISM: Artificial Sequence
<220> FEATURE:
<223> OTHER INFORMATION: Synthetic

<400> SEQUENCE: 10
tcgtcggcag cgtcagatgt gtataagaga cag 33

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
tagcaaactg gggcacaagc 20

<210> SEQ ID NO 12
<211> LENGTH: 29
<212> TYPE: DNA
<213> ORGANISM: Artificial Sequence
<220> FEATURE:
<223> OTHER INFORMATION: Synthetic

<400> SEQUENCE: 12
aatgatacgg cgaccaccga gatctacac 29

<210> SEQ ID NO 13
<211> LENGTH: 33
<212> TYPE: DNA
<213> ORGANISM: Artificial Sequence
<220> FEATURE:
<223> OTHER INFORMATION: Synthetic

<400> SEQUENCE: 13
tcgtcggcag cgtcagatgt gtataagaga cag 33

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
tagcaaactg gggcacaagc 20

<210> SEQ ID NO 15
<211> LENGTH: 29
<212> TYPE: DNA
<213> ORGANISM: Artificial Sequence
<220> FEATURE:
<223> OTHER INFORMATION: Synthetic

<400> SEQUENCE: 15
aatgatacgg cgaccaccga gatctacac 29

<210> SEQ ID NO 16
<211> LENGTH: 33
<212> TYPE: DNA
<213> ORGANISM: Artificial Sequence
<220> FEATURE:
<223> OTHER INFORMATION: Synthetic

<400> SEQUENCE: 16
tcgtcggcag cgtcagatgt gtataagaga cag 33

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
tagcaaactg gggcacaagc 20

<210> SEQ ID NO 18
<211> LENGTH: 29
<212> TYPE: DNA
<213> ORGANISM: Artificial Sequence
<220> FEATURE:
<223> OTHER INFORMATION: Synthetic

<400> SEQUENCE: 18
aatgatacgg cgaccaccga gatctacac 29

<210> SEQ ID NO 19
<211> LENGTH: 33
<212> TYPE: DNA
<213> ORGANISM: Artificial Sequence
<220> FEATURE:
<223> OTHER INFORMATION: Synthetic

<400> SEQUENCE: 19
tcgtcggcag cgtcagatgt gtataagaga cag 33

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
tagcaaactg gggcacaagc 20

<210> SEQ ID NO 21
<211> LENGTH: 29
<212> TYPE: DNA
<213> ORGANISM: Artificial Sequence
<220> FEATURE:
<223> OTHER INFORMATION: Synthetic

<400> SEQUENCE: 21
aatgatacgg cgaccaccga gatctacac 29

<210> SEQ ID NO 22
<211> LENGTH: 33
<212> TYPE: DNA
<213> ORGANISM: Artificial Sequence
<220> FEATURE:
<223> OTHER INFORMATION: Synthetic

<400> SEQUENCE: 22
tcgtcggcag cgtcagatgt gtataagaga cag 33

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
tagcaaactg gggcacaagc 20

<210> SEQ ID NO 24
<211> LENGTH: 24
<212> TYPE: DNA
<213> ORGANISM: Artificial Sequence
<220> FEATURE:
<223> OTHER INFORMATION: Synthetic

<400> SEQUENCE: 24
caagcagaag acggcatacg agat 24

<210> SEQ ID NO 25
<211> LENGTH: 14
<212> TYPE: DNA
<213> ORGANISM: Artificial Sequence
<220> FEATURE:
<223> OTHER INFORMATION: Synthetic

<400> SEQUENCE: 25
gggggggggg gggg 14

<210> SEQ ID NO 26
<211> LENGTH: 22
<212> TYPE: DNA
<213> ORGANISM: Artificial Sequence
<220> FEATURE:
<223> OTHER INFORMATION: Synthetic

<400> SEQUENCE: 26
ggcacaagct taattaagaa tt 22

<210> SEQ ID NO 27
<211> LENGTH: 22
<212> TYPE: DNA
<213> ORGANISM: Artificial Sequence
<220> FEATURE:
<223> OTHER INFORMATION: Synthetic

<400> SEQUENCE: 27
ggcacaagct taattaagaa tt 22

<210> SEQ ID NO 28
<211> LENGTH: 8
<212> TYPE: DNA
<213> ORGANISM: Artificial Sequence
<220> FEATURE:
<223> OTHER INFORMATION: Synthetic

<400> SEQUENCE: 28 tcgcataa 8

<210> SEQ ID NO 29
<211> LENGTH: 55
<212> TYPE: DNA
<213> ORGANISM: Artificial Sequence
<220> FEATURE:
<223> OTHER INFORMATION: Synthetic

<400> SEQUENCE: 29
cgcaaactgg ggcacaagct taattaagaa ttcgatcaac gcagagacgg cctag 55

<210> SEQ ID NO 30
<211> LENGTH: 10
<212> TYPE: DNA
<213> ORGANISM: Artificial Sequence
<220> FEATURE:
<223> OTHER INFORMATION: Synthetic

<400> SEQUENCE: 30
gcgtataagt 10

<210> SEQ ID NO 31
<211> LENGTH: 14
<212> TYPE: DNA
<213> ORGANISM: Artificial Sequence
<220> FEATURE:
<223> OTHER INFORMATION: Synthetic

<400> SEQUENCE: 31
tcgagcctta tggc 14

<210> SEQ ID NO 32
<211> LENGTH: 8
<212> TYPE: DNA
<213> ORGANISM: Artificial Sequence
<220> FEATURE:
<223> OTHER INFORMATION: Synthetic

<400> SEQUENCE: 32 tcgcataa 8

<210> SEQ ID NO 33
<211> LENGTH: 55
<212> TYPE: DNA
<213> ORGANISM: Artificial Sequence
<220> FEATURE:
<223> OTHER INFORMATION: Synthetic

<400> SEQUENCE: 33
cgcaaactgg ggcacaagct taattaagaa ttgcttgact cgttagcgag cctag 55

<210> SEQ ID NO 34
<211> LENGTH: 10
<212> TYPE: DNA
<213> ORGANISM: Artificial Sequence
<220> FEATURE:
<223> OTHER INFORMATION: Synthetic

<400> SEQUENCE: 34
cacgataccg 10

<210> SEQ ID NO 35
<211> LENGTH: 14
<212> TYPE: DNA
<213> ORGANISM: Artificial Sequence
<220> FEATURE:
<223> OTHER INFORMATION: Synthetic

<400> SEQUENCE: 35
actcgagagt tcga 14

<210> SEQ ID NO 36
<211> LENGTH: 8
<212> TYPE: DNA
<213> ORGANISM: Artificial Sequence
<220> FEATURE:
<223> OTHER INFORMATION: Synthetic

<400> SEQUENCE: 36 tcgcataa 8

<210> SEQ ID NO 37
<211> LENGTH: 55
<212> TYPE: DNA
<213> ORGANISM: Artificial Sequence
<220> FEATURE:
<223> OTHER INFORMATION: Synthetic

<400> SEQUENCE: 37
cgcaaactgg ggcacaagct taattaagaa ttcgatcaac gcagagacgg cctag 55

<210> SEQ ID NO 38
<211> LENGTH: 10
<212> TYPE: DNA
<213> ORGANISM: Artificial Sequence
<220> FEATURE:
<223> OTHER INFORMATION: Synthetic

<400> SEQUENCE: 38
gtctaatgaa 10

<210> SEQ ID NO 39
<211> LENGTH: 14
<212> TYPE: DNA
<213> ORGANISM: Artificial Sequence
<220> FEATURE:
<223> OTHER INFORMATION: Synthetic

<400> SEQUENCE: 39
gcacgtctac tagc 14

<210> SEQ ID NO 40
<211> LENGTH: 8
<212> TYPE: DNA
<213> ORGANISM: Artificial Sequence
<220> FEATURE:
<223> OTHER INFORMATION: Synthetic

<400> SEQUENCE: 40 tcgcataa 8

<210> SEQ ID NO 41
<211> LENGTH: 55
<212> TYPE: DNA
<213> ORGANISM: Artificial Sequence
<220> FEATURE:
<223> OTHER INFORMATION: Synthetic

<400> SEQUENCE: 41
cgcaaactgg ggcacaagct taattaagaa ttctaactca gcgactggag cctag 55

<210> SEQ ID NO 42

<211> LENGTH: 10
<212> TYPE: DNA
<213> ORGANISM: Artificial Sequence
<220> FEATURE:
<223> OTHER INFORMATION: Synthetic

<400> SEQUENCE: 42
catgtgcccg 10

<210> SEQ ID NO 43
<211> LENGTH: 14
<212> TYPE: DNA
<213> ORGANISM: Artificial Sequence
<220> FEATURE:
<223> OTHER INFORMATION: Synthetic

<400> SEQUENCE: 43
atagattgtc cgaa 14

<210> SEQ ID NO 44
<211> LENGTH: 8
<212> TYPE: DNA
<213> ORGANISM: Artificial Sequence
<220> FEATURE:
<223> OTHER INFORMATION: Synthetic

<400> SEQUENCE: 44 tcgcataa 8

<210> SEQ ID NO 45
<211> LENGTH: 55
<212> TYPE: DNA
<213> ORGANISM: Artificial Sequence
<220> FEATURE:
<223> OTHER INFORMATION: Synthetic

<400> SEQUENCE: 45
cgcaaactgg ggcacaagct taattaagaa ttgcttgact cgttagcgag cctag 55

<210> SEQ ID NO 46
<211> LENGTH: 10
<212> TYPE: DNA
<213> ORGANISM: Artificial Sequence
<220> FEATURE:
<223> OTHER INFORMATION: Synthetic

<400> SEQUENCE: 46
aaaaggatgg 10

<210> SEQ ID NO 47
<211> LENGTH: 14
<212> TYPE: DNA
<213> ORGANISM: Artificial Sequence
<220> FEATURE:
<223> OTHER INFORMATION: Synthetic

<400> SEQUENCE: 47
gagcaggagc tatg 14

<210> SEQ ID NO 48
<211> LENGTH: 8
<212> TYPE: DNA
<213> ORGANISM: Artificial Sequence
<220> FEATURE:
<223> OTHER INFORMATION: Synthetic

<400> SEQUENCE: 48 tcgcataa 8

<210> SEQ ID NO 49
<211> LENGTH: 55
<212> TYPE: DNA
<213> ORGANISM: Artificial Sequence
<220> FEATURE:
<223> OTHER INFORMATION: Synthetic

<400> SEQUENCE: 49
cgcaaactgg ggcacaagct taattaagaa ttaaaccctc actgccgacg cctag 55

<210> SEQ ID NO 50
<211> LENGTH: 10
<212> TYPE: DNA
<213> ORGANISM: Artificial Sequence
<220> FEATURE:
<223> OTHER INFORMATION: Synthetic

<400> SEQUENCE: 50
acctgttacg 10

<210> SEQ ID NO 51
<211> LENGTH: 14
<212> TYPE: DNA
<213> ORGANISM: Artificial Sequence
<220> FEATURE:
<223> OTHER INFORMATION: Synthetic

<400> SEQUENCE: 51
ggaggcctgt tacg 14

<210> SEQ ID NO 52
<211> LENGTH: 8
<212> TYPE: DNA
<213> ORGANISM: Artificial Sequence
<220> FEATURE:
<223> OTHER INFORMATION: Synthetic

<400> SEQUENCE: 52 tcgcataa 8

<210> SEQ ID NO 53
<211> LENGTH: 55
<212> TYPE: DNA
<213> ORGANISM: Artificial Sequence
<220> FEATURE:
<223> OTHER INFORMATION: Synthetic

<400> SEQUENCE: 53
cgcaaactgg ggcacaagct taattaagaa ttagggcttg cagtgcacgg cctag 55

<210> SEQ ID NO 54
<211> LENGTH: 10
<212> TYPE: DNA
<213> ORGANISM: Artificial Sequence
<220> FEATURE:
<223> OTHER INFORMATION: Synthetic

<400> SEQUENCE: 54
aacgtcaaga 10

<210> SEQ ID NO 55
<211> LENGTH: 14
<212> TYPE: DNA

<213> ORGANISM: Artificial Sequence
<220> FEATURE:
<223> OTHER INFORMATION: Synthetic

<400> SEQUENCE: 55
cgactcacgt tcag 14

<210> SEQ ID NO 56
<211> LENGTH: 8
<212> TYPE: DNA
<213> ORGANISM: Artificial Sequence
<220> FEATURE:
<223> OTHER INFORMATION: Synthetic

<400> SEQUENCE: 56 tcgcataa 8

<210> SEQ ID NO 57
<211> LENGTH: 55
<212> TYPE: DNA
<213> ORGANISM: Artificial Sequence
<220> FEATURE:
<223> OTHER INFORMATION: Synthetic

<400> SEQUENCE: 57
cgcaaactgg ggcacaagct taattaagaa ttcgatcaac gcagagacgg cctag 55

<210> SEQ ID NO 58
<211> LENGTH: 10
<212> TYPE: DNA
<213> ORGANISM: Artificial Sequence
<220> FEATURE:
<223> OTHER INFORMATION: Synthetic

<400> SEQUENCE: 58
cagactgggc 10

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gaccaggatg ggcaccaccc 20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
ggggatctga gaatgtacca 20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
gcgggctgag acgtggccag 20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
gagaactgac taggcagcgg 20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
gacgactagt taggcgtgta 20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
ggccaaacgt gccctgacgg 20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
gccttggcta aaccgctccc 20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
aactttcagt ttagcggtct 20

<210> SEQ ID NO 67
<211> LENGTH: 60
<212> TYPE: DNA
<213> ORGANISM: Artificial Sequence
<220> FEATURE:
<223> OTHER INFORMATION: Synthetic Primer

<400> SEQUENCE: 67
taacttgaaa gtatttcgat ttcttggctt tatatatctt gtggaaagga cgaaacaccg 60

<210> SEQ ID NO 68
<211> LENGTH: 90
<212> TYPE: DNA
<213> ORGANISM: Artificial Sequence
<220> FEATURE:

-continued

```
<223> OTHER INFORMATION: Synthetic Primer
<220> FEATURE:
<221> NAME/KEY: misc_feature
<222> LOCATION: (27)..(40)
<223> OTHER INFORMATION: n is a, c, g, or t

<400> SEQUENCE: 68

tctcaagatc tagttacgcc aagcttnnnn nnnnnnnnnn aaaaaagcac cgactcggtg     60

ccactttttc aagttgataa cggactagcc                                      90
```

HIGH-THROUGHPUT METHODS FOR IDENTIFYING GENE INTERACTIONS AND NETWORKS

CROSS-REFERENCE TO RELATED APPLICATIONS

This application is a U.S. National Phase Application under 35 U.S.C. § 371 of International Application No. PCT/US2018/064553, filed Dec. 7, 2018, and claims the benefit of U.S. Provisional Application Nos. 62/595,904, filed Dec. 7, 2017, and 62/698,778, filed Jul. 16, 2018. The entire contents of the above-identified applications are hereby fully incorporated herein by reference.

REFERENCE TO AN ELECTRONIC SEQUENCE LISTING

The contents of the electronic sequence listing (BROD_2117WP_ST25.txt "; Size is 13 Kilobytes and it was created on Dec. 4, 2018) is herein incorporated by reference in its entirety.

TECHNICAL FIELD

The present invention provides methods and tools for analyzing genetic interactions. The present invention relies on a systematic approach of causing single and combinatorial genome-wide perturbations in cells, with subsequent molecular profiling at the single cell level. Applications include dissection of cell circuitry and delineation of functional or molecular pathways. The present invention is also relevant for therapeutics target discovery.

BACKGROUND

Regulatory circuits in cells process signals, trigger decisions, and orchestrate physiological responses under diverse conditions. Diseases, in turn, arise from circuit malfunctions: one or more components are missing or defective; a key component is over- or under-active. To understand mechanisms underlying disease and develop more effective treatments, it would be highly advantageous to be able to provide a comprehensive picture of all cellular components, to identify the circuits in which they function, and to delineate how these components and circuits are integrated to form cellular responses.

Genomic research on dissecting cellular circuitry has generally had distinct phases: genomic observations and perturbation of single components.

Early advances in functional genomics made it possible to observe molecular profiles in different cells. Such global analysis has been very powerful in drawing hypotheses that relate regulators to their targets from statistical correlations. However, it is also very limited: the hypotheses were mostly not tested, and because correlation is not causation, many hypotheses may be found partially or fully incorrect.

In recent years, efforts were implemented in order to determine causation. Genomic profiles were used to infer a molecular model, on an increasingly large scale, based on genetic manipulations. However, the approach of testing genes individually has limitations: because genes involved in biological circuits have non-linear interactions, one cannot predict how a cellular circuit functions simply by summing up the individual effects. Indeed, biological systems are not linear: the combined effect of multiple factors is not simply the sum of their individual effects. This is a direct outcome of the biochemistry underlying molecular biology, from allosteric protein changes to cooperative binding, and is essential for cells to process complex signals.

It has remained an insurmountable stumbling block to achieving a quantitative and predictive understanding of circuits on a genomic scale, with far-reaching implications for basic and translational science. For example, despite decades of work, one still cannot predict how the enhancer controlling the transcription of the interferon beta gene (IFNβ) behaves in response to viral and other stimuli. In another example, p38α, a serine/threonine kinase with key roles in inflammation, has been studied for two decades, and yet it remains unclear how it balances control of inflammatory and anti-inflammatory cytokines, and many therapeutics programs launched to target this protein were hampered by unwarranted and unexpected effects. Finally, in genomic studies ranging from yeast to mammals, many molecular events (e.g., transcription factor binding) appear 'functionally silent' upon factor perturbation, and only some expression variation is explained with available mechanistic data.

Citation or identification of any document in this application is not an admission that such document is available as prior art to the present invention.

SUMMARY

A current phase of genomic research on dissecting cellular circuitry involves combinatorial probing of circuits. It would be desirable to provide a combinatorial approach: perturbing multiple components, at a large enough scale that will allow one to reliably reconstruct cellular circuits; for example, simultaneously or at or about the same time or in parallel. Such a combinatorial genomics approach has generally been considered intractable, because it required: (1) the ability to perturb many genes simultaneously (or at or about the same time or in parallel) in the same cell; (2) the ability to readout genomic profiles in individual cells, so that the effect of many perturbations can be assessed in parallel in a pool of cells; and (3) the development of mathematics and computational tools, because even millions of experiments are very few compared to the staggering size of the possible combinatorial space.

The invention involves Massively Parallel Combinatorial Perturbation Profiling (MCPP) to address or identify genetic interactions. Biological systems are not linear: the combined effect of multiple factors is not simply the sum of their individual effects. This is a direct outcome of the biochemistry underlying molecular biology, from allosteric protein changes to cooperative binding, and is essential for cells to process complex signals. However, heretofore, it has remained an insurmountable stumbling block to quantitative and predictive biology on a genomic scale, with far-reaching implications e.g., from basic research to clinical translation. The invention provides a combinatorial approach: perturbing multiple components simultaneously. Yet, even recent experimental advances in genetics and genomics heretofore have not been enough; for instance, studying all 2-way, 3-way and 4-way interactions would, prior to the instant invention, require performing ~$10^8$, ~$10^{12}$, and ~$10^{16}$ combinations of perturbations, respectively; and, beyond the technological and cost issues, the sheer number of mammalian cells required becomes infeasible because, for example, even if one focused on 100 genes, exhaustive analysis of 5-way interactions would require 70 million perturbations.

It would be desirable to provide tools and methods for the systematic analysis of genetic interactions, including higher order interactions.

It would be desirable to provide tools and/or methods for combinatorial probing of cellular circuits, for instance, for dissecting cellular circuitry, for delineating molecular pathways and/or interactions (e.g., intercellular and/or intracellular pathways or interactions), for identifying relevant targets and/or for identifying impact or effect of perturbations or stimuli or mutation; for instance for therapeutics development and/or cellular engineering and/or any cellular manipulation and/or ascertaining internal cell function and/or for bioproduction (e.g., production of antibodies from new sources, expression of products from organisms or cells that previously did not naturally express such products, increasing or decreasing expression of endogenous products, and the like), new plants or animal models.

The present invention involves cellular circuits (both intracellular and extracellular circuits). For instance, a cellular, e.g., regulatory circuit combines trans inputs (such as the levels and activities of factors, e.g., transcription factors, non-coding RNAs, e.g., regulatory RNAs and signalling molecules) and cis inputs (such as sequences, e.g., regulatory sequences in the promoter and enhancer of a gene); for instance, to determine the level of mRNA produced from a gene.

Reconstruction of a cellular, e.g., regulatory circuit is to identify inputs, e.g., all identifiable inputs (for example, proteins, non-coding RNAs and cis-regulatory elements), their physical 'wirings' (or connections) and the transcriptional functions that they implement; for instance, as to regulation of the level of mRNA.

A model should address (advantageously simultaneously or in parallel) providing a functional description of the input-output relationships (for example, if regulator A is induced, then target gene B is repressed to a particular extent), and providing a physical description of the circuit (for example, regulator A binds to the promoter of gene B in sequence Y, modifies its chromatin and leads to repression). Networks, e.g., regulatory networks, control complex downstream cellular phenotypes (such as cell death, proliferation and migration).

Reconstructing the connectivity of a network can be through the monitoring of hundreds to thousands of cellular parameters (massively parallel monitoring or hundreds to thousands of cellular parameters), such as the levels of mRNAs. Hence "massively parallel" can mean undertaking a particular activity hundreds to thousands to millions, e.g., from 100 to 1000 or to 10,000 or to 100,000 or to 1,000,000 or up to 1,000,000,000 times (or as otherwise indicated herein or in figures herewith), in parallel, e.g., simultaneously or at or about the same time. See, e.g., Amit et al., "Strategies to discover regulatory circuits of the mammalian immune system," NATURE REVIEWS (IMMUNOLOGY) 11: 873-880 (December 2011).

The present invention relates to methods of measuring or determining or inferring RNA levels, e.g., massively parallel measuring or determining or inferring of RNA levels in a single cell or a cellular network or circuit in response to at least one perturbation parameter or advantageously a plurality of perturbation parameters or massively parallel perturbation parameters involving sequencing DNA of a perturbed cell, whereby RNA level and optionally protein level may be determined in the single cell in response to the at least one perturbation parameter or advantageously a plurality of perturbation parameters or massively parallel perturbation parameters. The invention thus may involve a method of inferring or determining or measuring RNA in a single cell or a cellular network or circuit, e.g., massively parallel inferring or determining or measuring of RNA level in a single cell or a cellular network or circuit in response to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 or massively parallel perturbation parameter(s) comprising optionally so perturbing the cell or the cells or each cell of the cellular network or circuit with the perturbation parameter(s) and sequencing of the perturbed cell(s), whereby RNA level(s) and optionally protein level(s) is/are determined in the cell(s) in response to the perturbation parameter(s).

Genetic screens are used to infer gene function in mammalian cells, but it has remained difficult to assay complex phenotypes-such as genome-wide transcriptional profiles—in large-scale screens. Moreover, it has been traditionally difficult to assay the transcriptional phenotype of genetic perturbations at scale. Preferably, a genome-wide scale transcriptome phenotype associated with a perturbation would be possible.

Applicants developed Perturb-seq, which combines single cell RNA-seq and CRISPR/Cas9 based perturbations identified by unique polyadenylated barcodes to perform many, tens of thousands in certain embodiments, of such assays in a single pooled experiment. By randomly integrating more than one sgRNA in each cell, Perturb-Seq is extended to test transcriptional phenotypes caused by genetic interactions. Applicants developed a computational framework, MIMOSCA (Multi-Input Multi-Output Single Cell Analysis) to identify the regulatory effects of individual perturbations and their combinations at different levels of resolution: from effects on each individual gene to functional signatures to proportional changes in cell types. Applicants demonstrated Perturb-seq by analyzing 200,000 cells across three screens: transcription factors controlling the immune response of dendritic cells to LPS, transcription factors bound in the K562 cell line, and cell cycle regulators in the same cell line. Perturb-Seq accurately identified known regulatory relations, and its individual gene target predictions were validated by ChIP-Seq binding profiles. Applicants posit new functions for regulatory factors affecting cell differentiation, the anti-viral response and mitochondrial function during immune activation, and uncovered an underlying circuit that balances these different programs through positive and negative feedback loops. Using Perturb-Seq Applicants identified genetic interactions including synergistic, buffering and dominant genetic interactions that could not be predicted from individual perturbations alone. Perturb-Seq can be flexibly applied to diverse cell metadata, to customize design and scope of pooled genomic assays.

Applicants also applied perturb-seq to dissect the mammalian unfolded protein response (UPR). First, Applicants used perturb-seq to build an epistatic map of UPR-mediated transcription. Then, Applicants conducted a genome-scale CRISPRi screen to identify genes whose depletion perturbs ER homeostasis and subjected a subset of our hits (using a ~100 element sublibrary) to perturb-seq, revealing high precision functional gene clusters. Single-cell analyses revealed both bifurcations in behavior in cells subject to the same perturbation as well as differential activation of the three UPR branches across hits, including an isolated feedback loop between the translocon and the IRE1α branch of the UPR. These studies provide insight into how the three separate sensors of ER homeostasis allow the cell to monitor distinct types of ER stress and, more generally, highlight the ability of perturb-seq to dissect complex cellular responses.

By combining droplet based single cell transcriptomics with CRISPR-Cas based perturbations, Applicants demonstrate an approach that allow researchers to perform thousands of these assays in a single pooled experiment. This pooled approach represents a 10-fold improvement in cost over current methods for obtaining perturbation transcription profiles. Leveraging the discrete nature of the single cell measurements, the screening approach also has the ability to resolve novel phenotypes such as the effect of a perturbation on cell type composition or cell cycle phase, and filter unperturbed cells whose presence otherwise dilutes the measured effect in population measurements. Finally, by randomly integrating more than one sgRNA in each cell, applicants show the ability to extend the method to test combinatorial effects. Together, these statistical and experimental methods enable researchers to perform large-scale screening of perturbations, including systematic dissection of epistatic effects, using RNA transcription as a phenotype.

In one aspect, the present invention provides for a method of reconstructing a cellular network or circuit, comprising introducing at least 1, 2, 3, 4 or more single-order or combinatorial perturbations to a plurality of cells in a population of cells, wherein each cell in the plurality of the cells receives at least 1 perturbation; measuring comprising: detecting genomic, genetic, proteomic, epigenetic and/or phenotypic differences in single cells compared to one or more cells that did not receive any perturbation, and detecting the perturbation(s) in single cells; and determining measured differences relevant to the perturbations by applying a model accounting for co-variates to the measured differences, whereby intercellular and/or intracellular networks or circuits are inferred. The measuring in single cells may comprise single cell sequencing. The single cell sequencing may comprise cell barcodes, whereby the cell-of-origin of each RNA is recorded. The single cell sequencing may comprise unique molecular identifiers (UMI), whereby the capture rate of the measured signals, such as transcript copy number or probe binding events, in a single cell is determined. The model may comprise accounting for the capture rate of measured signals, whether the perturbation actually perturbed the cell (phenotypic impact), the presence of subpopulations of either different cells or cell states, and/or analysis of matched cells without any perturbation.

The single-order or combinatorial perturbations may comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 perturbations. The perturbation(s) may target genes in a pathway or intracellular network.

The measuring may comprise detecting the transcriptome of each of the single cells. The perturbation(s) may comprise one or more genetic perturbation(s). The perturbation(s) may comprise one or more epigenetic or epigenomic perturbation(s). At least one perturbation may be introduced with RNAi- or a CRISPR-Cas system. At least one perturbation may be introduced via a chemical agent, biological agent, an intracellular spatial relationship between two or more cells, an increase or decrease of temperature, addition or subtraction of energy, electromagnetic energy, or ultrasound.

The cell(s) may comprise a cell in a model non-human organism, a model non-human mammal that expresses a Cas protein, a mouse that expresses a Cas protein, a mouse that expresses Cpf1, a cell in vivo or a cell ex vivo or a cell in vitro. The cell(s) may also comprise a human cell.

The measuring or measured differences may comprise measuring or measured differences of DNA, RNA, protein or post translational modification; or measuring or measured differences of protein or post translational modification correlated to RNA and/or DNA level(s).

The perturbing or perturbation(s) may comprise(s) genetic perturbing. The perturbing or perturbation(s) may comprise(s) single-order perturbations. The perturbing or perturbation(s) may comprise(s) combinatorial perturbations. The perturbing or perturbation(s) may comprise gene knock-down, gene knock-out, gene activation, gene insertion, or regulatory element deletion. The perturbing or perturbation(s) may comprise genome-wide perturbation. The perturbing or perturbation(s) may comprise performing CRISPR-Cas-based perturbation. The perturbing or perturbation(s) may comprise performing pooled single or combinatorial CRISPR-Cas-based perturbation with a genome-wide library of sgRNAs. The perturbations may be of a selected group of targets based on similar pathways or network of targets.

The perturbing or perturbation(s) may comprises performing pooled combinatorial CRISPR-Cas-based perturbation with a genome-wide library of sgRNAs. Each sgRNA may be associated with a unique perturbation barcode. Each sgRNA may be co-delivered with a reporter mRNA comprising the unique perturbation barcode (or sgRNA perturbation barcode).

The perturbing or perturbation(s) may comprise subjecting the cell to an increase or decrease in temperature. The perturbing or perturbation(s) may comprise subjecting the cell to a chemical agent. The perturbing or perturbation(s) may comprise subjecting the cell to a biological agent. The biological agent may be a toll like receptor agonist or cytokine. The perturbing or perturbation(s) may comprise subjecting the cell to a chemical agent, biological agent and/or temperature increase or decrease across a gradient.

The cell may be in a microfluidic system. The cell may be in a droplet. The population of cells may be sequenced by using microfluidics to partition each individual cell into a droplet containing a unique barcode, thus allowing a cell barcode to be introduced.

The perturbing or perturbation(s) may comprise transforming or transducing the cell or a population that includes and from which the cell is isolated with one or more genomic sequence-perturbation constructs that perturbs a genomic sequence in the cell. The sequence-perturbation construct may be a viral vector, preferably a lentivirus vector. The perturbing or perturbation(s) may comprise multiplex transformation or transduction with a plurality of genomic sequence-perturbation constructs.

In another aspect, or in alternative embodiments of aspects described herein, the present invention provides for a method wherein proteins or transcripts expressed in single cells are determined in response to a perturbation, wherein the proteins or transcripts are detected in the single cells by binding of more than one labeling ligand comprising an oligonucleotide tag, and wherein the oligonucleotide tag comprises a unique constituent identifier (UCI) specific for a target protein or transcript. The single cells may be fixed in discrete particles. The discrete particles may be washed and sorted, such that cell barcodes may be added, e.g. sgRNA perturbation barcodes as described above. The oligonucleotide tag and sgRNA perturbation barcode may comprise a universal ligation handle sequence, whereby a unique cell barcode may be generated by split-pool ligation. The labeling ligand may comprise an oligonucleotide label comprising a regulatory sequence configured for amplification by T7 polymerase. The labeling ligands may comprise oligonucleotide sequences configured to hybridize to a transcript specific region. Not being bound by a theory, both proteins and RNAs may be detected after perturbation. The oligonucleotide label may further comprise a photocleavable linker. The oligonucleotide label may further comprise a restriction enzyme site between the labeling ligand and unique constituent identifier (UCI). The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle. The method may further comprise quantitating the relative amount of UCI sequence associated with a first cell to the amount of the same UCI sequence associated with a second cell, whereby the relative differences of a cellular constituent between cell(s) are determined. The labeling ligand may comprise an antibody or an antibody fragment. The antibody fragment may be a nanobody, Fab, Fab', (Fab')2, Fv, ScFv, diabody, triabody, tetrabody, Bis-scFv, minibody, Fab2, or Fab3 fragment. The labeling ligand may comprise an aptamer. The labeling ligand may be a nucleotide sequence complementary to a target sequence.

Single cell sequencing may comprise whole transcriptome amplification.

The method in aspects of the invention may comprise comparing an RNA profile of the perturbed cell with any mutations in the cell to also correlate phenotypic or transcriptome profile and genotypic profile.

In another aspect, or in alternative embodiments of aspects described herein, the present invention provides for a method comprising determining genetic interactions by causing a set of P genetic perturbations in single cells of the population of cells, wherein the method comprises: determining, based upon random sampling, a subset of $\pi$ genetic perturbations from the set of P genetic perturbations; performing said subset of $\pi$ genetic perturbations in a population of cells; performing single-cell molecular profiling of the population of genetically perturbed cells; inferring, from the results and based upon the random sampling, single-cell molecular profiles for the set of P genetic perturbations in cells. The method may further comprises: from the results, determining genetic interactions. The method may further comprise: confirming genetic interactions determined with additional genetic manipulations.

The set of P genetic perturbations or said subset of $\pi$ genetic perturbations may comprise single-order genetic perturbations. The set of P genetic perturbations or said subset of $\pi$ genetic perturbations may comprise combinatorial genetic perturbations. The genetic perturbation may comprise gene knock-down, gene knock-out, gene activation, gene insertion, or regulatory element deletion. The set of P genetic perturbations or said subset of a genetic perturbations may comprise genome-wide perturbations. The set of P genetic perturbations or said subset of $\pi$ genetic perturbations may comprise k-order combinations of single genetic perturbations, wherein k is an integer ranging from 2 to 15, and wherein the method comprises determining k-order genetic interactions. The set of P genetic perturbations may comprise combinatorial genetic perturbations, such as k-order combinations of single-order genetic perturbations, wherein k is an integer ranging from 2 to 15, and wherein the method comprises determining j-order genetic interactions, with $j<k$.

The method in aspects of this invention may comprise performing RNAi- or CRISPR-Cas-based perturbation. The method may comprise an array-format or pool-format perturbation. The method may comprise pooled single or combinatorial CRISPR-Cas-based perturbation with a genome-wide library of sgRNAs. The method may comprise pooled combinatorial CRISPR-Cas-based perturbation with a genome-wide library of sgRNAs.

The random sampling may comprise matrix completion, tensor completion, compressed sensing, or kernel learning. The random sampling may comprise matrix completion, tensor completion, or compressed sensing, and wherein $\pi$ is of the order of log P.

The cell may comprise a eukaryotic cell. The eukaryotic cell may comprise a mammalian cell. The mammalian cell may comprise a human cell. The cell may be from a population comprising $10^2$ to $10^8$ cells and DNA or RNA or protein or post translational modification measurements or variables per cell comprise 50 or more.

The perturbation of the population of cells may be performed in vivo. The perturbation of the population of cells may be performed ex vivo and the population of cells may be adoptively transferred to a subject. The population of cells may comprise tumor cells. The method may comprise a lineage barcode associated with single cells, whereby the lineage or clonality of single cells may be determined.

The perturbing may be across a library of cells to thereby obtain RNA level and/or optionally protein level, whereby cell-to-cell circuit data at genomic or transcript or expression level is determined. The library of cells may comprise or is from a tissue sample. The tissue sample may comprise or is from a biopsy from a mammalian subject. The mammalian subject may comprise a human subject. The biopsy may be from a tumor. The method may further comprise reconstructing cell-to-cell circuits.

The method may comprise measuring open chromatin and may comprise fragmenting chromatin inside isolated intact nuclei from a cell, adding universal primers at cutting sites, and uniquely tagging DNA that originated from the cell.

The method may comprise measuring protein and RNA levels and may comprise CyTOF.

In another aspect, the present invention provides for a method of determining any combination of protein detection, RNA detection, open chromatin detection, protein-protein interactions, protein-RNA interactions, or protein-DNA interactions comprising any of the preceding methods.

In another aspect, the present invention provides for a method for screening compounds or agents capable of modifying a cellular network or circuit comprising performing any method as described herein, wherein perturbing further comprises exposing the cell to each compound or agent.

In another aspect, the present invention provides for a method of identifying a therapeutic, and to a therapeutic identified by the method described herein.

In another aspect, the present invention provides a method of reconstructing a cellular network or circuit, comprising introducing at least 1, 2, 3, 4 or more single-order or combinatorial perturbations to each cell in a population of cells; measuring genomic, genetic and/or phenotypic differences of each cell and coupling combinatorial perturbations with measured differences to infer intercellular and/or intracellular networks or circuits. The single-order or combinatorial perturbations can comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 or massively parallel perturbations. The perturbation(s) can comprise one or more genetic perturbation. The perturbation(s) can comprise one or more epigenetic or epigenomic perturbation. The perturbation can be introduced with RNAi- or a CRISPR-Cas system. For example, reference is also made to Dahlman et al., Nature Biotechnology (2015) doi:10.1038/nbt.3390 Published online 5 Oct. 2015 to allow efficient orthogonal genetic and epigenetic manipulation. Dahlman et al., Nature Biotechnology (2015) doi:10.1038/nbt.3390 have developed a CRISPR-based method that uses catalytically active Cas9 and distinct single guide (sgRNA) constructs to knock out and activate different genes in the same cell. These sgRNAs, with 14- to 15-bp target sequences and MS2 binding loops, can activate gene expression using an active *Streptococcus pyogenes* Cas9 nuclease, without inducing double-stranded breaks. Dahlman et al., Nature Biotechnology (2015) doi: 10.1038/nbt.3390 use these 'dead RNAs' to perform orthogonal gene knockout and transcriptional activation in human cells.

The at least one perturbation can be introduced via a chemical agent, an intracellular spatial relationship between two or more cells, an increase or decrease of temperature, addition or subtraction of energy, electromagnetic energy, or ultrasound. The cell can comprise a cell in a model non-human organism, a model non-human mammal that expresses a Cas protein, a mouse that expresses a Cas protein, a cell in vivo or a cell ex vivo or a cell in vitro. The measuring or measured differences can comprise measuring or measured differences of DNA, RNA, protein or post translational modification; or measuring or measured differences of protein or post translational modification correlated to RNA and/or DNA level(s). The method can include sequencing, and prior to sequencing: perturbing and isolating a single cell with at least one labeling ligand specific for binding at one or more target RNA transcripts, or isolating a single: cell with at least one labeling ligand specific for binding at one or more target RNA transcripts and perturbing the cell; and/or lysing the cell under conditions wherein the labeling ligand binds to the target RNA transcript(s).

The method in aspects of this invention may also include, prior to sequencing perturbing and isolating a single cell with at least one labeling ligand specific for binding at one or more target RNA transcripts, or isolating a single cell with at least one labeling ligand specific for binding at one or more target RNA transcripts and perturbing the cell; and lysing the cell under conditions wherein the labeling ligand binds to the target RNA transcript(s). The perturbing and isolating a single cell may be with at least one labeling ligand specific for binding at one or more target RNA transcripts. The isolating a single cell may be with at least one labeling ligand specific for binding at one or more target RNA transcripts and perturbing the cell.

The perturbing of the present invention may involve genetic perturbing, single-order genetic perturbations or combinatorial genetic perturbations. The perturbing may also involve gene knock-down, gene knock-out, gene activation, gene insertion or regulatory element deletion. The perturbation may be genome-wide perturbation. The perturbation may be performed by RNAi- or CRISPR-Cas-based perturbation, performed by pooled single or combinatorial CRISPR-Cas-based perturbation with a genome-wide library of sgRNAs or performing pooled combinatorial CRISPR-Cas-based perturbation with a genome-wide library of sgRNAs.

In another aspect, the methods described herein may be used for a diagnostic assay. In one embodiment, T cells are obtained from a subject and perturb-seq is performed on the cells. In another embodiment, T cells are obtained from a subject and gene expression of single cells is determined. Upon determining gene expression, perturb-seq is performed on a subset of genes differentially expressed. Perturb-seq can inform proper therapies to administer to a subject and can test many targets in a single experiment. In another embodiment, tumor cells are obtained from a subject. The tumor cells may also include cells of the tumor microenvironment, such as immune cells. The cells may be assayed for gene expression and differentially expressed genes can be assayed using the perturb-seq methods described herein. Not being bound by a theory, perturb-seq may allow assaying many targets and perturbations in a single experiment.

In another aspect, the present invention provides for a method of multiplexing samples for single cell sequencing comprising: labeling single cells from each of a plurality of samples with a sample barcode oligonucleotide unique to each sample; and constructing a multiplexed single cell sequencing library for the plurality of samples comprising cell of origin barcodes, wherein the sample barcode oligonucleotide on each labeled cell receives a cell of origin barcode. The method may further comprise sequencing the library and demultiplexing in silico based on the cell of origin barcodes and the sample barcodes.

In certain embodiments, the sample barcode oligonucleotide comprises a polyA tail.

In certain embodiments, the single cells are labeled with one or more antibodies linked to the sample barcode oligonucleotide. The one or more antibodies may be specific for one or more surface markers present on single cells in the plurality of samples. In other words, one or more antibodies are selected such that all of the cells in the plurality of samples express a surface marker detected by the one or more antibodies and every cell in each sample is labeled.

In certain embodiments, the single cells are modified to accept covalent linkage of the sample barcode oligonucleotide and the cells are labeled by covalent linkage of the sample barcode oligonucleotide. The cells may be modified with an acceptor molecule capable of being covalently linked to the sample barcode oligonucleotide by click chemistry and the cells may be labeled with sample barcode oligonucleotides modified for click chemistry. In other words, the cells are modified to have functional groups that allow for click chemistry and the sample barcode oligonucleotides are functionalized for click chemistry. The cells can be labeled with sample barcode oligonucleotides using click chemistry without the need for specific surface markers.

In certain embodiments, the cells are modified with a biotin moiety and the sample barcode oligonucleotide comprises avidin, whereby the cells are labeled by biotin-avidin binding.

In certain embodiments, constructing a single cell sequencing library comprises droplet based single cell sequencing or split and pool single cell sequencing.

In certain embodiments, the method comprises: labeling the single cells for each of the plurality of samples; and segregating the labeled cells into droplets comprising cell of origin barcodes, whereby a cell of origin barcode is added to the sample barcode oligonucleotide.

In certain embodiments, the method comprises: fixation of the cells from each of the plurality of samples; labeling the fixed cells for each of the plurality of samples; and barcoding by splitting and pooling the labeled cells, whereby a cell of origin barcode is added to the sample barcode oligonucleotide.

In certain embodiments, the multiplexed single cell sequencing library is an RNA sequencing library. In certain embodiments, the multiplexed single cell sequencing library is an ATAC sequencing library.

In another aspect, the present invention provides for multiplexing single nuclei or any membrane bound organelle. In certain embodiments, the single nuclei or organelles are labeled with a sample barcode oligonucleotide.

In another aspect, the present disclosure provides methods for screening a combination of perturbations correlating to a phenotype: introducing a plurality of perturbations to a plurality of cells, wherein each perturbation comprises a barcode and each cell receives at least one perturbation; expanding the plurality of cells introduced with the plurality of perturbations, thereby generating a plurality of clonal cell populations wherein each clonal cell population results from expanding one of the plurality of cells introduced with the plurality of perturbations; selecting a subpopulation from the clonal cell populations, wherein cells in the subpopulation has the phenotype; and identifying perturbations in the cells in the subpopulation.

In some embodiments, the plurality of perturbations is a pooled plurality of perturbations. The plurality of perturbations may comprise polynucleotides with guide RNA sequences. Each of the polynucleotides may comprise a barcode sequence. The methods herein may further comprise identifying the correlation between the barcode and the perturbation. The barcode may be a unique transduction barcode. The plurality of perturbations may be introduced via a chemical agent, biological agent, an intracellular spatial relationship between two or more cells, an increase or decrease of temperature, addition or subtraction of energy, electromagnetic energy, ultrasound, or combination thereof. The plurality of perturbations may be CRISPR-Cas-based perturbations. For example, the plurality of perturbations may comprise a genome-wide library of sgRNA. In some cases, introducing the plurality of perturbations to the plurality of cells comprise transducing, transfecting, transforming, or a combination thereof.

In some embodiments, selecting the subpopulation comprises sorting cells into multiple containers. The multiple containers may be wells in a multi-well plate.

In some embodiments, identifying the perturbations in the cells in the subpopulation comprise sequencing. The sequencing may be deep sequencing. In some case, the methods further comprise detecting the phenotype. The phenotype may indicate the subpopulation's response to a treatment of a disease. For example, the plurality of cells may be derived from a patient or a disease model.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

An understanding of the features and advantages of the present invention will be obtained by reference to the following detailed description that sets forth illustrative embodiments, in which the principles of the invention may be utilized, and the accompanying drawings of which:

FIG. 10 illustrates an example of the generation of an Index A+UMI.

FIG. 18 illustrates the generation of an Index C+UMI.

FIG. 48A-G illustrates Perturb-seq: pooled approach to obtain screening of transcriptional profiles of perturbations. (A) Overview of approach. From left: A complex pool of lentiviruses, each carrying a guide targeting a specific genes (A-E) in a vector including matched PAPIs is transduced at a given MOI ($\gamma_{MOI}$) into cells that are subsequently selected ($\gamma_{MOI}$) through growth and/or fluorescence. Individual cells are profiled with droplet scRNA-seq, to simultaneously recover their RNA profiles and PAPIs. (B) Perturb-Seq vector. A transcribed PAPI is pre-associated with a specific sgRNA, and enriched after WTA using dial-out PCR. (C) Perturb-Seq screens in this study. (D) The observed distribution of number of guides detected per cell (X axis) in BMDCs at 3 h post-LPS stimulation. (E) Effect on target. Hif1a transcript expression (Y axis) in cells carrying a sgRNA targeting Hif1a (sgHif1a-1, right) compared to all other cell (left). Box plots denote [describe all aspects: mean/median? Percentiles, outliers etc]. (F) Distribution of on-target effects in BMDC at 3 h post-LPS. Shown is the distribution of on-target expression (X axis) in cells carrying the corresponding targeting guides (blue) and permuted results for a single permutation (green). Rectangle is the 99% confidence interval for the permuted mean. Mean on-target effect of individual guides are in tickmarks, including one outlier exceeding even the permuted data. (G) Linear modeling framework. Applicants fit the coefficients of a (regulatory) matrix (B) to best explain the observed expression profiles of each cell (matrix Y) given the covariates in the design matrix (X), including the observed sgRNAs in each cell and additional cell covariates. See also FIG. 55.

FIG. 49A-J illustrates MIMOSCA: A linear model stratifies analysis framework to stratify the observed expression variation. (A) A linear modeling framework for continuous phenotypes. A linear model relates a continuous phenotype (gene expression, PC scores, etc; arrow) to a covariate (here guide identity). (B-D) Accounting for differences in cell complexity and state. Scatter plots show the relation for every cell (dot) between the expression levels of the highly expressed Ccl17 gene (B, Y axis) or its residual expression after a model is fit (C, D; Y axis) and the number of transcripts in the same cell (X axis); sum (log (transcripts detected)) in the original data (B), after including the quality measure as a covariate residuals (C) and after also including in addition cell state proportion (D). (E) Effect on cell states. Cartoon illustration of a hypothetical scenario where cells belong to either of two states (red, blue) and perturbation by sgRNA1 increases the proportion of cells in one state over the other. (F,G) Accounting for cell states. Shown is the effect on Ccl17 expression (Y axis) in cells with (right box) and without (left box) sg-Rela-3 in the original model (left) and when conditioned on cell state proportions (right). (H) Expectation maximization-like framework to separate effectively wild type cells within the set of cells containing a particular sgRNA. Left: The distribution of number of cells with the sgStat1-3 guide with a given fit (X axis) to the model of the effect of the Stat1-3 perturbation. Right: the distribution of inferred probabilities of an actual perturbation in the same cells. (I) Contribution of each component in the model (Y axis) to the % variance explained (X axis) based on the $r^2$ values from cross-validation. (J) Correlation matrix between genes in the residuals of the model. The addition of our covariates reduces the residual structure in the data. See also FIG. 56.

FIG. 50A-F illustrates the analysis of the role of 24 TFs in the response of BMDCs to LPS. (A) Key TF modules in BMDCs at 3 h post-LPS. Heat map shows the Pearson correlation (red-blue colorbar) between the coefficients of the regulatory matrix β for every pair of guides (rows, columns), based on a model that does not include the cell state covariates. Yellow rectangles: four key TF modules high (members marked on right). Leftmost column: effect of the guide on-target. (B) Agreement between guides targeting the same gene. Shown is the distribution of correlations between guides targeting the same gene (grey) or different genes (blue). (C) Cell states. Shown are enrichments (−log 10 (P-value) for induced (red) and repressed (blue) genes) for GO gene sets (rows) in each of seven cell states (columns) defined for genetically unperturbed BMDC at 3 h post-LPS. Key terms are marked on right. (D) TFs group by their effects on cell state proportion. Show are the Z-score for enrichment (red) or depletion (blue) of guides in cells with each of seven states (columns; as in C). (E, F) Accounting for cell states emphasizes TF-specific effects. (E) Heat map shows the Pearson correlation (red-blue colorbar) between the coefficients of the regulatory matrix β for every pair of guides (rows, columns), based on a model that accounts for cell states as covariates. Yellow rectangles: specific modules all with guides to a single gene (gene marked on right). Leftmost column: effect of the guide on-target. (F) The distribution of correlations between guides targeting the same gene (grey) or different genes (blue), with a model including cell state covariates. See also FIG. 57.

FIG. 53A-I illustrates the analysis of the role of 10 non-essential TFs and 14 cell cycle regulators in K562 cells. (A,B) Grouping of TFs by their regulatory coefficients. Shown are the Pearson correlation matrix of the coefficients of the regulatory matrix β of the TFs without including the cell state covariates (A) and after including them (B). (C) Cell states in genetically unperturbed K562 cells. Shown are enrichments (−log 10 (P-value) for induced (red) and repressed (blue) genes) for GO gene sets (rows) in each of seven cell states (columns) defined for genetically unperturbed BMDC at 3 h post-LPS. Key terms are marked on right. (D) TFs effects on cell state proportions. Shown are the Z-score for enrichment (red) or depletion (blue) of guides in cells in each of seven states (columns; as in C). (E,F) Agreement of guide effects across time points. Violin plots show the distribution of correlations between guides targeting the same gene (grey), different genes (blue) and a gene and an intergenic region (red) with each of two time points (T1=7 d, T2=14 d) and across the two time points, in either a model that does not (E) or does (F) include cell state covariates. (G) Pearson correlation matrix of the coefficients of the regulatory matrix β of the cell cycle regulators without including the cell state covariates. (H) The regulatory effect (color bar, defined by the average regulatory coefficients in our model) or the guides targeting each cell cycle gene (rows) on the genes associated with each of six signatures of phases of the cell cycle and apoptosis (columns). (I) Distribution of fitness effects (X axis) across the guides targeting each gene (Y axis) by comparing the number of cells with the guide to its abundance in the initial pool. See also FIG. 60.

FIG. 54A-D illustrates a power analysis and prospects for Perturb-seq. (A,B) Saturation analysis. Shown is the effect of the number of cells (Y axis) and reads (X axis) on our ability to recover a given level of correlation (color bar) with either the per gene transcriptional defects (A) or gene signature effects (e.g., cell type proportions) (B) Applicants observed with our full data. (C) The tradespace of number of cells (X axis) and measurements per cell (Y axis) required for screening scale transcriptome measurements. (D) Extensions of Perturb-Seq. The perturb seq framework can be extended by scaling the number of cells (arrow, left) or by incorporating additional types of cell covariates, such as lineage, marker expression, or temporal tracers.

FIG. 55A-L illustrates the performance of Perturb-seq (A-E) Log-likelihood functions as a function of detection probability (X axis) and MOI (Y axis) for our zero-truncated zero inflated Poisson distribution for the indicated experiment (label on top). (A-C) Line plots are cumulative distributions for the observed distribution of guides per cell (blue) and the expectation from the maximum likelihood estimate (green). (F) Specificity of PAPI detection. Scatter plot shows the percentage of reads for a PAPI within a given cell (CBC-cell barcode) (Y axis) as a function of the log 2 (reads) it received in that cell (X axis). (G) Effect on target. Cebpb transcript expression (Y axis) in cells carrying an sgRNA targeting Cebpb (sgCebpb_1, right) compared to all other cell (left). Box plots. (I) Relationship between overall mean expression of the on-target gene (X axis) and the observed effect on its expression (Y axis) by the guides that target it, in BMDCs at 3 h post-LPS. (J,K) Relationship between population expression measurements and 10 cell average (top) and 100 cell average for BMDCs (J) and K562 cells (H). (L) Relationship between transcript length (X axis) and the difference between population expression and single cell average expression (Y axis).

FIG. 56A-I illustrates the performance of MIMOSCA framework. (A-C) Contribution of each component in the model (Y axis) to the % variance explained (X axis) based on the $r^2$ values from cross-validation in each of 3 screens (labeled on top). (D-F) Significance of regulatory coefficients. Shown are the distributions of signed $\log_{10}$ (FDR) for each of three sgRNAs (marked on top). Values capped at 3; Zero coefficients (due to shrinkage by regularization) have no assigned FDR. (G) Relationship between number of cells/sgRNA (X axis) and number of significant genes for each sgRNA (Y axis). One outlier guide (sgStat1_2) is marked and—while included in all subsequent plots—was not considered in subsequent biological analysis. (H) Computational flowchart for MIMOSCA. Raw input data (orange) is processed into intermediate data types that require little computation (purple) or a more intensive processing (green). Finally, output data (blue) is generated and interpreted biologically. (I) Significant guide effects. Scatter plots show conceptual (left) and real (middle and right) examples of the sum of difference in the sum of the squared residuals between a model fit including a guide covariate and a model not including the guide covariate for positive and negative values. Each dot is a cell. Conceptually (left column), a pure population of perturbed cells that is well separated from the other cells should have few genes that are better fit without the guide covariate (left column, top and middle), whereas a poor performing guide (or a well-performing control) should have few such genes (left column, bottom panel). A guide targeting Rela in BMDC (3 h post-LPS) (top middle and top right) has a distinguishable effect compared to a non-targeting guide (below) in a model without cell state covariates (middle) and even when considering cell states (right). Bottom middle and right plots show the mean deviation of each guide (X axis). Red line: the non-targeting control.

FIG. 57A-F illustrates analysis analyses of the role of 24 TFs in BMDCs. (A) Cell states in BMDCs pre-stimulation. Shown are enrichments (−log 10(P-value) for induced (red) and repressed (blue) genes) for GO gene sets (rows) in each of four cell states (columns) defined for genetically unperturbed BMDC at 0 h (pre-stimulation). Key terms are marked on right. (B) TFs group by their effects on cell state proportions pre-stimulation. Shown are the Z-score for enrichment (red) or depletion (blue) of guides in cells with each of four states (columns; as in A). (C) Distinct effects pre- and post-stimulation. Boxplots comparing the correlations of regulatory coefficients between guides targeting the same genes within the 3 hr LPS stimulated cells (light blue) or within unstimulated cells (white), and across the two conditions either without modeling cell state co-variates (dark grey) or with modeling cell states (blue). (D) Distribution of number of detected transcripts per cell (X axis) for cells harboring guides targeting distinct genes (Y axis). (E) Relationship between the relative abundance of an sgRNA in the input plasmid pool (X axis) and the relative amount of cells with that sgRNA (Y axis). (F) Assessing potential fitness effects. Shown is the distribution of fold changes of sgRNA abundance compared to the input abundance (X axis) for the guides (dots) targeting each gene (Y axis).

FIG. 63A-D illustrates Perturb-Seq analysis of the role of cell cycle regulators in K562 cells. (A) Regulation of apoptosis ["virtual FACS": control, all guides, selected example. (B) Individual and synthetic effects on cell fitness (Livnat model). (C) Individual and synthetic effects on G1/S and G2/M cell states ("virtual FACS" plus Livnat model). (D) Transcriptional patterns underlying effect on cell states.

FIG. 80 illustrates a comparison of methods for single cell RNA-seq.

FIG. 81A-F A robust strategy for systematic genetic modifier screens using single cell expression profiling. (A) Schematic of the perturb-seq platform. (1) Cells transduced with a complex pool of CRISPRi guide RNAs (2) are encapsulated with cell lysis buffer and gel beads, which deliver DNA oligos, in droplets using the Chromium™ instrument (10× Genomics). DNA oligos encode cell barcodes (unique to each bead), unique molecular identifiers or UMIs (unique to each bead oligo), and an oligo-dT homopolymer region. (3) After capture, beads dissolve and released oligos prime cellular mRNAs for cDNA synthesis within droplets. (4-6) The cDNA libraries are prepared for deep sequencing in pooled format, and transcripts of particular interest are separately enriched by specific amplification. (B) Method for introducing and identifying perturbations using CRISPR guide RNAs. A lentiviral vector designed for single copy integration into cells expressing Cas9 or dCas9 fused to effector domains (for CRISPRi/a) carries two expression units: (1) a polymerase III-driven sgRNA and (2) a guide barcode selection cassette (top) in reverse orientation. The later transcript can be selectively amplified during library preparation (bottom). (C) Performance of guide barcode capture by specific amplification. The plot shows the distribution of guide barcode UMIs counted per cell in a pilot experiment of ~5,700 cells containing different perturbations. (D) Performance of perturbation identification. The high coverage of the guide barcode enables efficient identification of perturbation identity, and confident rejection of cell doublets (apparent as multiple guide barcodes attached to a single cell barcode). (E) Characterization of perturb-seq vector by GFP knockdown. GFP+K562 cells with dCas9-KRAB were transduced with either the perturb-seq vector or the original CRISPRi vector expressing a GFP-targeting sgRNA or a perturb-seq vector expressing a negative control sgRNA. GFP levels were measured by flow cytometry 11 d after transduction. Plotted are kernel density estimates of normalized flow cytometry counts for infected (BFP+) cells. (F) Characterization of perturb-seq vector in pooled format via single-cell RNA-seq. Using identities inferred from the capture of guide barcodes, Applicants computationally separate our pilot perturb-seq experiment into subpopulations of cells containing each sgRNA. The single-cell RNA-seq profiles allow us to assess average knockdown of the gene targeted within each subpopulation (relative to cells containing a control sgRNA). The plot shows three examples.

FIG. 82A-G Strategy for multiplexed delivery of CRISPR guide RNAs in a single expression vector. (A) Schematic of the unfolded protein response. (B) Schematic of three-guide vector. Three guide RNA expression cassettes (a U6 promoter, a sgRNA targeting sequence, and a sgRNA constant region (cr)) are fused to express the three sgRNAs. The lentiviral backbone is the same as that of the perturb-seq vector. (C) Characterization of initial three-guide vector by GFP knockdown. GFP+K562 cells with UCOE-dCas9-KRAB were transduced with either the single perturb-seq vector expressing a GFP-targeting sgRNA, an initial three-guide vector expressing a GFP-targeting sgRNA from the hU6 promoter, or a single vector expressing a negative control sgRNA. Cells were selected to purity with puromycin and GFP levels measured by flow cytometry 7 d after transduction. Plotted are kernel density estimates of normalized flow cytometry counts. (D) Design and characterization of constant region variants. Top: Schematic representation of sgRNA constant region, with location and description of changes indicated. Changes that were combined to generate cr2 and cr3 are labeled in orange and purple, respectively. Bottom: RFP levels of *E. coli* CRISPRi reporter strain expressing a mRFP-targeting sgRNA and the denoted constant region variant. RFP levels, determined by flow cytometry, are plotted as mean fluorescence of three replicates relative to a strain expressing a negative control sgRNA. Error bars denote standard deviations. (E) Characterization of new sgRNA expression cassettes by GFP knockdown. GFP+K562 cells with dCas9-KRAB were transduced with different constructs expressing a GFP-targeting sgRNA from different U6 promoters and with different constant regions, as indicated. GFP levels were measured by flow cytometry 10 d after transduction. Plotted are kernel density estimates of normalized flow cytometry counts for infected (BFP+) cells. (F) Characterization of final three-guide vector by GFP knockdown. GFP+K562 cells with UCOE-dCas9-KRAB were transduced with three-guide vectors expressing a GFP-targeting sgRNA from the position indicated in parentheses and two different negative control sgRNAs from the other two positions or a three-guide vector expressing three negative control sgRNAs. Cells were treated as described in (B). Plotted are kernel density estimates of normalized flow cytometry counts. Plot for the single perturb-seq construct is the same as in panel (B). (G) Characterization of the three-guide vector via perturb-seq. Using the three-guide vector, Applicants simultaneously targeted the three main UPR sensors and determined the average reduction in expression (relative to cells containing three negative control guides) via perturb-seq. Each target showed >80% depletion, and depletion was stable across two chemical treatments that induce the UPR. See also FIG. 88.

FIG. 83A-F Epistatic analysis of the three transcriptional arms of the unfolded proteins response using perturb-seq (A) Schematic of perturb-seq epistasis experiment. (B) Unbiased identification and decoupling of single-cell behaviors via low rank independent component analysis. Individual single-cell RNA-seq profiles are noisy, but shared regulation and correlated gene expression mean that patterns exist within the population. To identify these patterns, Applicants computationally construct a low-dimensional approximation of gene expression within the population to remove noise, and then use ICA to identify a small number of independent programs of gene expression. The figure shows this approach applied to our combinatorial knockdowns treated with thapsigargin. Low rank ICA identifies distinct sets of components that vary either across perturbation or across the cell cycle. When the first set of components are projected via t-sne, the cells (each dot) group via perturbation. Conversely when Applicants project the second set, the cells arrange in a circular pattern by cell cycle position. The "bulge" highlighted by the dashed line is enriched for cells that have PERK active. (C) Identification of a PERK- and cell-cycle-dependent subpopulation in thapsigargin-treated cells. The plots show t-sne projections of control (+DMSO) and thapsigargin-treated cells with or without PERK. Low rank ICA identifies a component (IC) that is bimodal within each perturbation subpopulation and marks G1 cells, and that is particularly disenriched in G1 cells within the thapsigargin-treated subpopulation. (D) Cell cycle composition of +DMSO, +Tg, and +Tg cells with PERK depleted. (E) Genetic interactions between G1 and PERK activation. Applicants split each perturbation subpopulation into G1 and non-G1 cells based on the value of IC, and constructed average expression profiles in each condition. Applicants then examined how the 50 genes that most influenced IC varied, exposing both synergistic and antagonistic interactions between progression through G1 and PERK activation. (F) Epistatic interactions among the three branches of the UPR. Applicants isolated 104 genes that strongly varied in our large-scale perturb-seq experiment, and clustered them by their expression pattern within the population. The heatmap shows average expression profiles for each perturbation and chemical treatment. Patterns of induction determine the branch specificity of each gene. The bottom panel shows an unbiased decomposition of the total response into three components obtained via ICA, showing that many ATF6/IRE1α targets have some overlapping regulation. See also FIG. 89.

FIG. 84A-G Genome-scale CRISPRi screening for genetic stresses that perturb the IRE1 branch of the unfolded protein response. (A) Schematic of UPRE (mCh) and constitutive EF1α (GFP) reporter cassettes. (B) K562 reporter cells (cBA011) were transduced with the indicated sgRNAs and treated with 2 μg/mL tunicamycin or DMSO after 4 days. Approximately, 12 hours later these cells were evaluated by flow cytometry. Data is representative of two independent experiments. (C) Schematic of sgRNA screen. K562 cells stably expressing the mCh/GFP reporter cassettes and a dCas9-BFP-KRAB fusion protein were transduced with pooled genome-scale hCRISPRi libraries. Transduced cells were selected, sorted for high and low mCh/GFP ratio, and processed for sequencing of the sgRNA-containing DNA cassettes. (D) Volcano plots of UPRE reporter gene phenotypes and p-values from hCRISPRi-v2 reporter screen. Data generated from negative control sgRNAs are indicated in gray. Screen hits and select genes are indicated in pink and red, respectively. (E) Gene UPRE reporter phenotypes from replicates of hCRISPRi-v2 screen in K562 cells (cBA011). Phenotypes generated from negative control sgRNAs are indicated in gray. (F) UPRE reporter gene phenotypes from hCRISPRi-v2 reporter screen by functional category. Red indicates screen hits. (G) Comparison of mCherry UPRE reporter signal to EF1α driven GFP in cBA011 cells transduced with 257 sgRNAs targeting 152 hit genes from the hCRISPRi-v2 screen and 3 distinct negative controls. Data represent log 2 averages of median fluorescence signals (normalized to untransduced cells) across four possible experiments (n=2-7 technical or experimental replicates), normalized medians from all four experiments are included in the log 2 averages for each of the control sgRNAs. See also FIG. 90.

FIG. 85A-D A large-scale perturb-seq experiment interrogating ER homeostasis (A) Functional clustering of hits from perturb-seq analysis of ER homeostasis. Applicants picked ~100 guides from our genome-wide screen and subjected them to perturb-seq analysis, totaling ~65,000 single cells. Average expression profiles were created from all cells bearing guides targeting the same gene and hierarchically clustered. The figure shows a heatmap of correlations between expression profiles for all perturbations along with functional annotations. (B) Cell cycle analysis of perturb-seq hits. For each perturbation, the fraction of cells in each cell cycle stage was computationally identified. The figure shows the change in composition induced by each perturbation relative to control cells (containing the NegCtrl-2 guide). (C) Target knockdown efficiency. Average depletion of the sgRNA target was assessed within each subpopulation. Genes targeted by multiple guides have multiple possibly overlapping dots. Error bars are 95% confidence intervals estimated by bootstrapping. (D) Average phenotypes of perturb-seq hits. The UPRE score from the primary genome-wide screen is compared to three computationally derived scores measuring activation of the three branches of the UPR for each perturbation. The final panel is the $\log_{10}$ number of genes differentially expressed relative to control cells (containing the NegCtrl-2 guide) measured by the Kolmogorov-Smirnov test at P<0.01. Genes targeted by multiple guides have multiple possibly overlapping dots. See also FIG. 91.

FIG. 86A-L Single-cell information reveals a bifurcated UPR within a population and allows unbiased discovery of UPR-controlled genes (A) Single-cell analysis of HSPA5-perturbed cells. The figure shows t-sne plots of guide identity, cell cycle position, and UMI count per cell in HSPA5-perturbed cells and control cells (containing the NegCtrl3 guide). (B) Low rank ICA analysis of HSPA5-perturbed cells identifies two subpopulation-defining independent components. The right panel shows a discretized breakdown of the cells based on applying a threshold to IC1. (C) Branch activation scores in HSPA5-perturbed cells. (D) Expression of UPR genes in HSPA5-perturbed cells. The figure shows the normalized expression matrix of all HSPA5-perturbed cells. Each row is a cell, and each column is a gene in the same order as FIG. 83F. The cells have been ordered by increasing value of IC1. (E) Cell cycle composition of HSPA5-perturbed cells. (F) Mean expression of HSPA5 across subpopulations. Error bars are 95% confidence intervals. (G) Strategy for using correlated expression to identify functionally related genes. (H) Unbiased identification of induced gene expression programs in perturb-seq experiment. 200 example genes induced by perturbation of ER homeostasis were identified computationally, and clustered based on their co-expression across the 65,000 cells in the perturb-seq experiment. Top part of figure shows normalized expression across all of the perturbations in the perturb-seq experiment. Bottom part shows normalized expression in epistasis experiment, to assess UPR dependence. Full-size version of figure in FIG. 92A. (I) Implicit correlation information in perturb-seq orders the three branches of the UPR. UPR-responsive genes (from FIG. 83F) whose expression were altered in the perturb-seq experiment were clustered using single-cell co-expression data from the epistasis experiment, the perturb-seq experiment, and unperturbed control cells. The figure shows the cophenetic correlation coefficients between dendrogram orderings, measuring how similarly genes cluster, along with a visual guide to the movement of major groups. Full version of figure in FIG. 92B. (J) Strategy for enriching cells perturbed for a trait of interest. E.g., a group of genes of interest may be induced in only a fraction of the population across many different perturbations. (K) Enriching cells strengthens correlations and identifies related genes. Cells enriched for a set of bait cholesterol biosynthesis genes were identified. Within the enriched population, a group of genes clustered with the bait genes and showed stronger correlated expression than in unperturbed control cells. Right panel shows Reactome annotations and SREBP binding data for the group. (L) Combining correlation information with other types of data. An identical analysis to the previous panel was applied to heat shock genes. The figure shows the correlation matrix among the top hits, and compares this to the most enriched transcription factor binding sites measured by Encode. See also FIG. 92.

FIG. 87A-F Translocon loss-of-function preferentially activates IRE1 UPR signaling. (A) Single-cell analysis of cells depleted for SEC61B in perturb-seq experiment. Panels show the sgRNA identity and IRE1 activation score for each cell. (B) Identical analysis for SEC61A1. (C) RT-PCR probing for XBP1 splicing. (D) K562 cells (cBA011) transduced and sorted for expression of the indicated sgRNAs were collected on the indicated days post transduction for analysis of XBP1 mRNA splicing (top) and expression of SSR2 and CHOP mRNA (bottom). Data represent means relative to ACTB mRNA and normalized to cells transfected with a negative control sgRNA (dotted lines)±standard error of technical replicates (n=3). (E) K562 cells (cBA010) transduced with the indicated sgRNAs and selected with puromycin were treated with 0.5 μM thapsigargin for 1.5 hours or left untreated 6 days post transduction. Cells were then collected for analysis of XBP1 mRNA splicing and expression of CHOP mRNA. Data represent means relative to ACTB mRNA and normalized to cells transfected with NegCtrl-3±standard error of technical replicates (n=3). (F) A model in which IRE1α actively monitors the function and number of translocons and acts to increase them as needed. See also FIG. 93.

FIG. 88A-F Design and characterization of three-guide vector (related to FIG. 82). (A) Characterization of initial three-guide vector by GFP knockdown. GFP+K562 cells with dCas9-KRAB were transduced with either the single perturb-seq vector expressing a GFP-targeting guide RNA, initial three-guide vectors expressing a GFP-targeting guide RNA from the promoter indicated in parentheses and negative control guide RNAs from the other two promoters, or a single vector expressing a negative control guide RNA. GFP levels were measured by flow cytometry 10 d after transduction. Plotted are kernel density estimates of normalized flow cytometry counts for infected (BFP+) cells. Traces for the single perturb-seq construct and the negative control are the same as in FIG. 82E. (B) Characterization of h7SK promoter in the context of the perturb-seq vector. Experiment was conducted as described in (A). Traces for the single perturb-seq construct and the negative control are the same as in FIG. 82E. (C) Characterization of GFP+K562 cells with increased dCas9-KRAB levels. BFP levels report on expression level of the dCas9-BFP-KRAB construct. Increase in dCas9-KRAB is measured by change in BFP fluorescence relative to WT K562 cells. Plotted are kernel density estimates of normalized flow cytometry counts. (D) Crystal structure of Cas9 bound to guide RNA and target DNA (PDB ID code 4008 (Nishimasu et al. 2014)), highlighting location of constant region mutations. Cas9 is shown in gray, target ssDNA in yellow, and the guide RNA in orange (targeting region) and cyan (constant region). Constant region bases that were mutated are highlighted in red. (E) Characterization of RNA polymerase III promoters from different mammalian species by GFP knockdown. GFP+K562 cells with dCas9-KRAB were transduced with vectors expressing a GFP-targeting guide RNA from the different promoters, in the context of the perturb-seq vector. GFP levels were measured by flow cytometry either 9 d (experiment 1) or 8 d after transduction (experiment 2). % knockdown was calculated after subtracting GFP levels of WT K562 and calculating GFP levels relative to GFP+K562 cells transduced with a negative control vector. Abbreviations: bU6, bovine U6; sU6, sheep U6; buU6, buffalo U6; pU6, pig U6. (F) Cloning strategy for final three-guide vector. In step 1, protospacers are ligated into the individual backbones. In step 2, three guide RNA expression cassettes are amplified by PCR and inserted into the perturb-seq backbone in a single reaction by four-piece Gibson assembly to obtain the final barcoded three-guide vector.

Figure 83D:
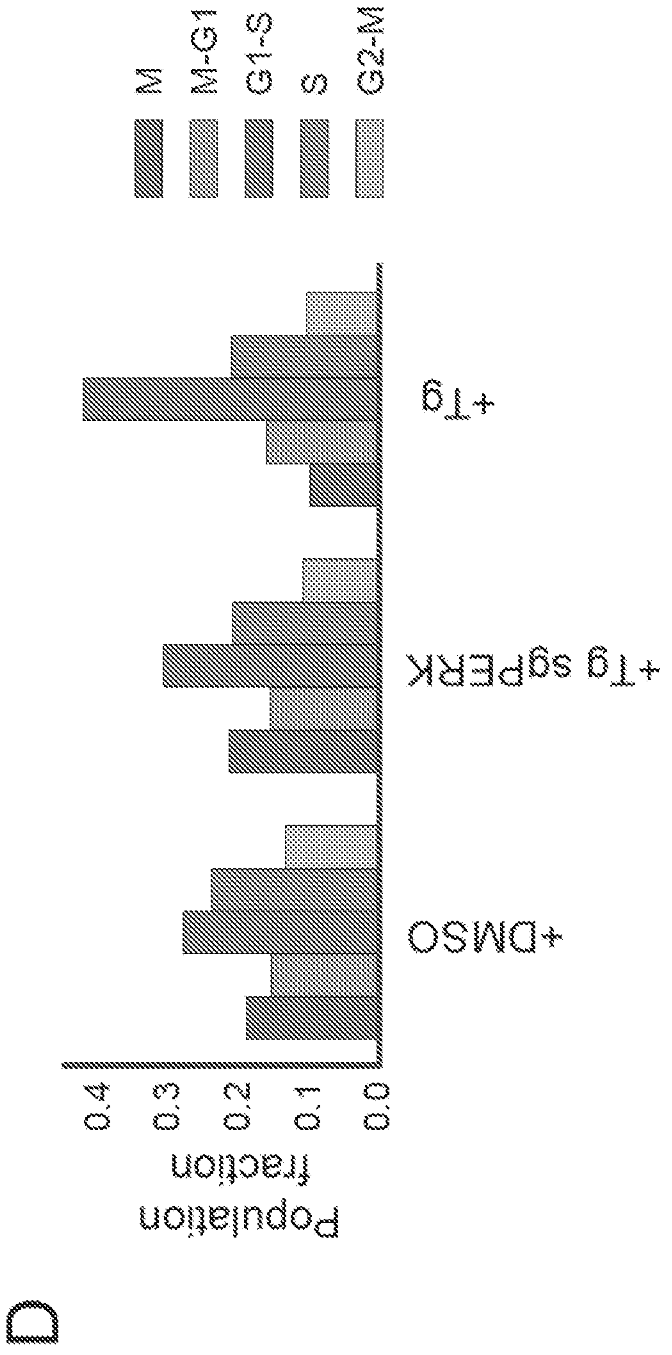
Figure 89A:
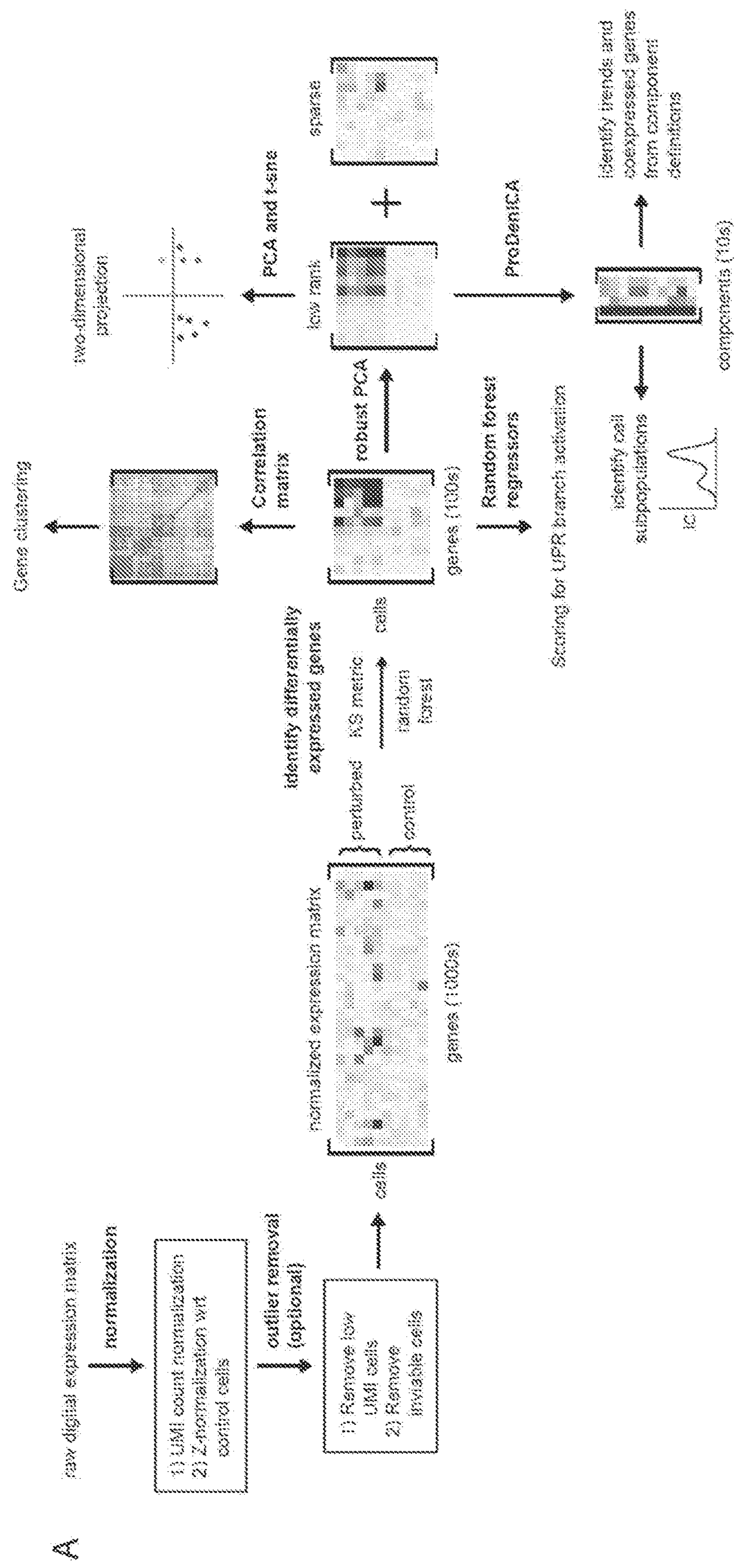
Figure 89B:
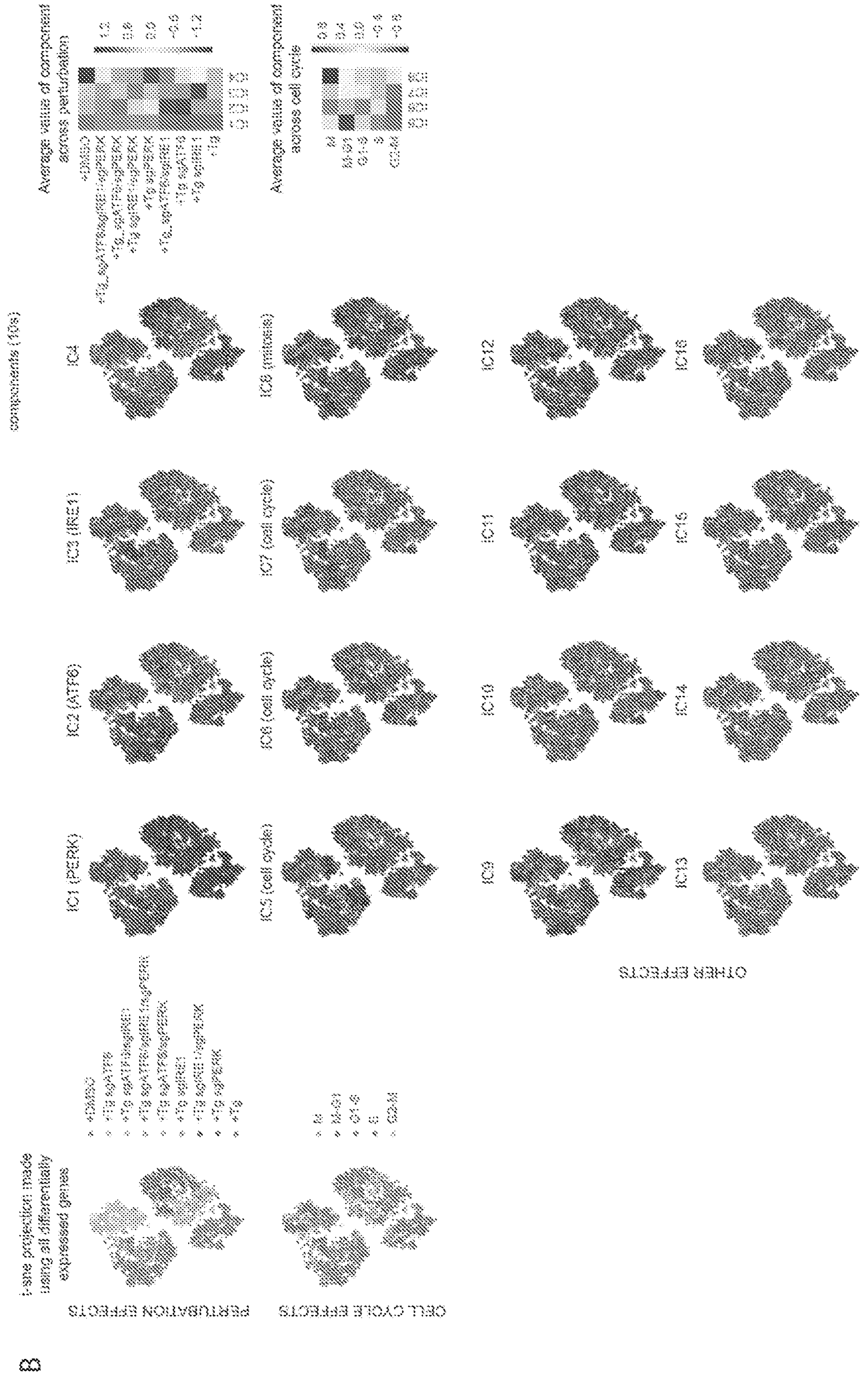

FIG. 89A-B Perturb-seq analytical pipeline (related to FIG. 83). (A) Schematic of the analytical pipeline used in the paper. Each step is explained in the Methods, and each single-cell figure has a dedicated section in the Methods describing its construction. (B) Example analysis of thapsigargin-treated cells, related to FIG. 83B. The left panels show t-sne projections of the whole population derived using all differentially expressed genes, as described in the Methods. The middle panels show the 16 independent components found by low rank ICA overlaid on the t-sne plot. The right panels show the average values of the four components identified as varying by perturbation within each of the subpopulations, and the average values of the four components identified as varying through the cell cycle in each cell cycle phase. Further details are in the Methods.

FIG. 90A-D CRISPRi screens used to select UPR-modulating sgRNAs for perturb-seq (related to FIG. 84). (A) K562 cells (cBA011) were treated with indicated concentrations of tunicamycin in 0.16% DMSO or DMSO alone. Cells were evaluated by flow cytometry or collected for analysis of XBP1 mRNA splicing at indicated times. Data represent average median fluorescence±SD (n=3) normalized to DMSO. (B) Comparison of gene phenotypes from the hCRISPRi-v1 and hCRISPRi-v2 screens. Genes chosen for analysis on the perturb-seq platform (83) are indicated in red. (C) Comparison of UPRE reporter gene phenotypes from the hCRISPRi-v2 with gene growth phenotypes from a previously reported genome-scale hCRISPRi-v2 screen (27661255). Select hits are indicated in red. (D) Top eleven annotated functional clusters from DAVID enrichment analysis. Representative names were chosen for each cluster.

FIG. 91A-F Perturb-seq screen performance (related to FIG. 85). (A) Similarity of phenotypes between guides targeting the same gene. Average expression profiles were created for each sgRNA-containing subpopulation, and hierarchically clustered. Guides targeting a common gene are indicated by color. (B) Shift in sgRNA target expression upon depletion. The distribution of expression of each targeted gene is compared between control cells (containing the NegCtrl2 guide) and each sgRNA-containing subpopulation. sgRNAs are ordered by target expression. (C) Homogeneity of knockdown. Applicants computationally separated each sgRNA-containing subpopulation into top- and bottom-third most perturbed cells based on the deviation of their RNA-seq profiles from the distribution of expression seen in control cells (Methods). The plot shows the average difference in percentage knockdown between these two subpopulations for each sgRNA (gray dot), along with a kernel density estimate of the distribution (black). (D) Expression of UPR genes in perturb-seq experiment. The plot shows the average normalized expression within each perturbed subpopulation of all of the genes identified as UPR-responsive in FIG. 83F. The thapsigargin data from that figure is repeated to the right for comparison. (E) Alternate scoring system for branch activation. An alternative method of scoring branch activation was developed using independent component analysis. For comparison with FIG. 85D. See Methods for details. (F) Performance of random forest scoring system for branch activation. To cross-validate branch activation scores, three alternative scoring systems were prototyped in the epistasis experiment of FIG. 83, where branch activation can be inferred from perturbation identity: (1) group score, based on expression of defined gene lists, (2) ICA score, seen in FIG. 91E, (3) random forest score, seen in FIG. 85D. Cells were defined as "active" for a given branch if they were treated with tunicamycin or thapsigargin, and that branch of the UPR was not depleted. The plots show the distributions of scores in active and inactive cells for each of the three branches and each of the three scoring systems. See Methods for details.

Figure 92A:
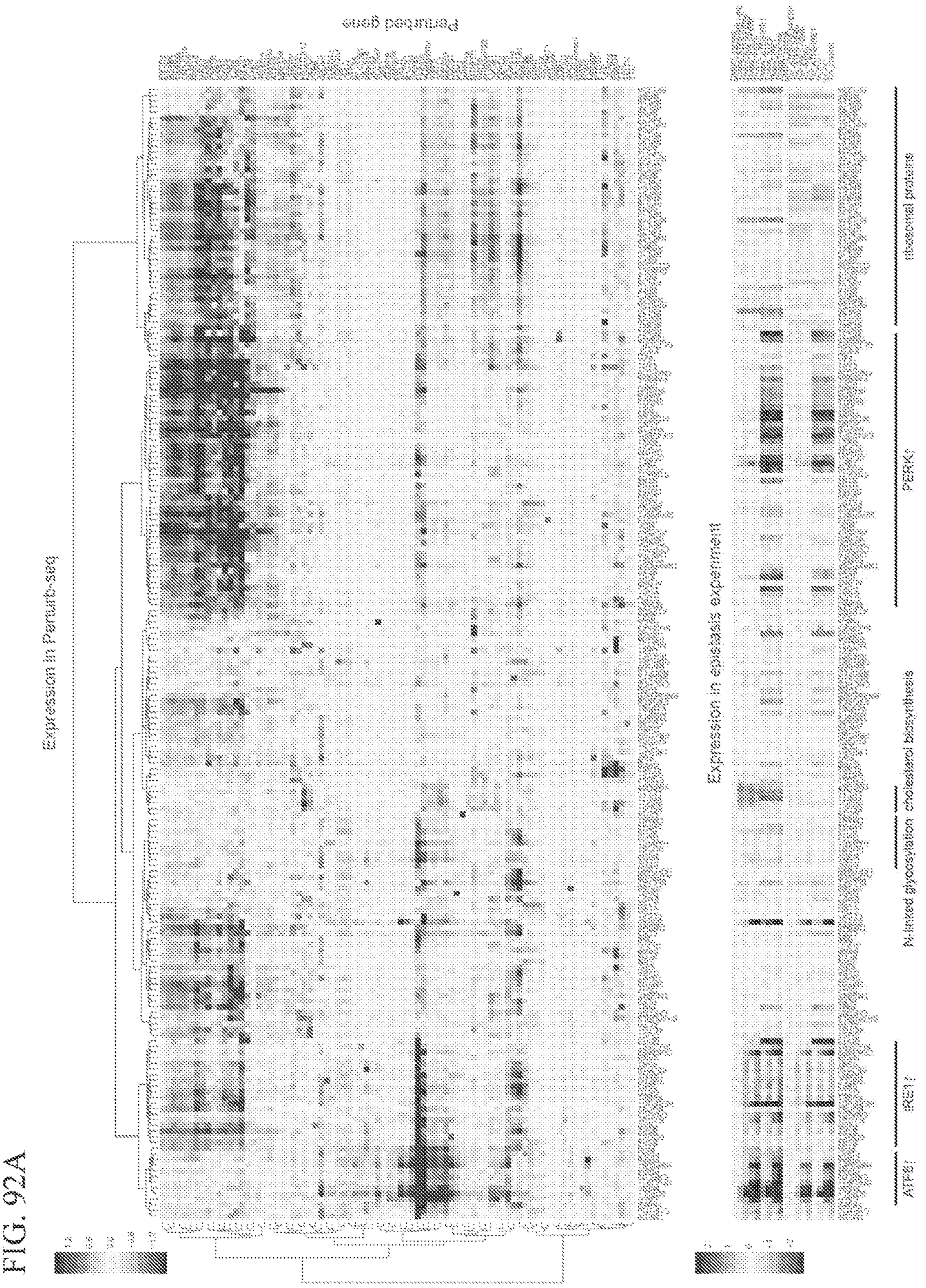
Figure 92B:
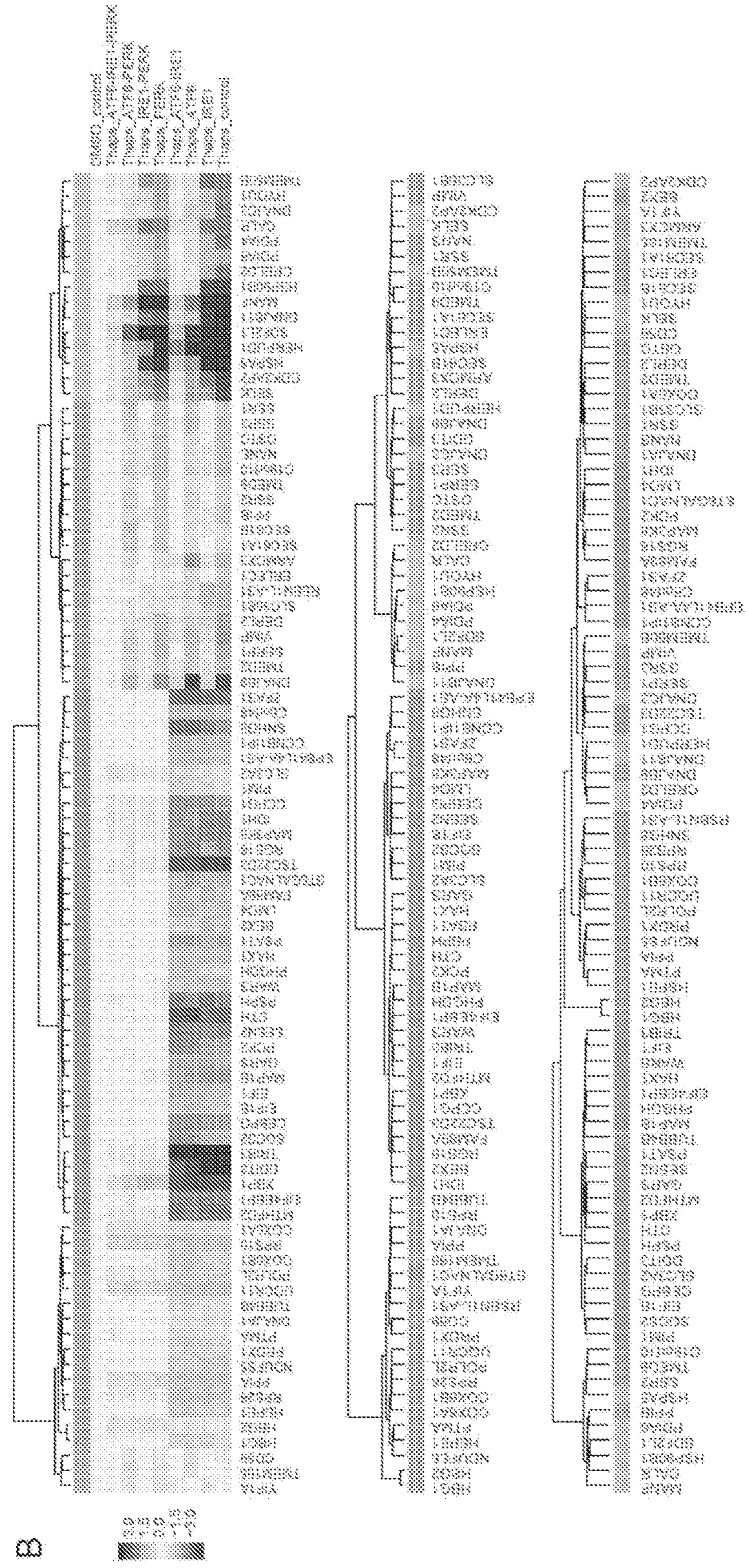

FIG. 92A-B Functionally clustering genes using single-cell correlation information (related to FIG. 86). (A) Full-size version of FIG. 86H. (B) Full-size version of FIG. 86I.

FIG. 93A-C Depletion of individual translocon components SEC61A1, SEC61B, or SEC61G upregulate expression of complex partner genes but have distinct growth phenotypes (related to FIG. 87). (A) ATF6 and PERK branch activation scores for SEC61B- and SEC61A1-perturbed subpopulations. For comparison with FIG. 87A. (B) K562 cells (cBA011) transduced and sorted for expression of the indicated sgRNAs were collected 6 days post transduction for analysis of SEC61A1, SEC61B, SEC61G, and ALG2 expression. Data represent means relative to ACTB mRNA and normalized to cells transfected with NegCtrl-3±standard error of technical replicates (n=3). Data from the cells with NegCtrl-1, SEC61A1-2, and SEC61B-2 sgRNAs are represented here and in FIG. 87D. (C) Phenotypes for individual sgRNAs targeting SEC61A1, SEC61B, and SEC61G from two growth screens, one reported elsewhere (27661255) and the other conducted in parallel to the first with essentially the same conditions. Data for 10 library negative control sgRNAs were randomly chosen for inclusion. Guides used separately elsewhere are numbered.

Figure 94A:
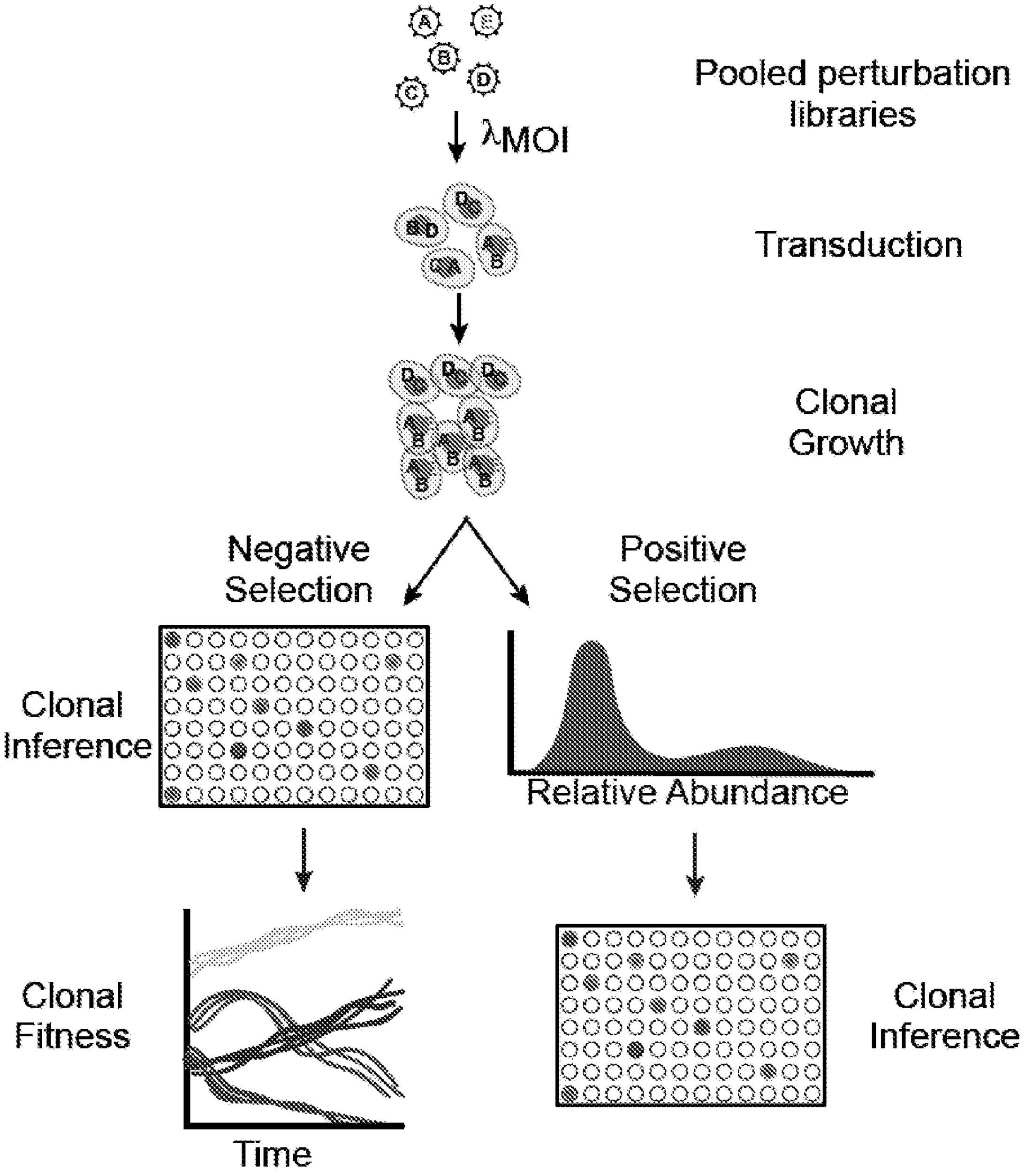
Figure 94B:
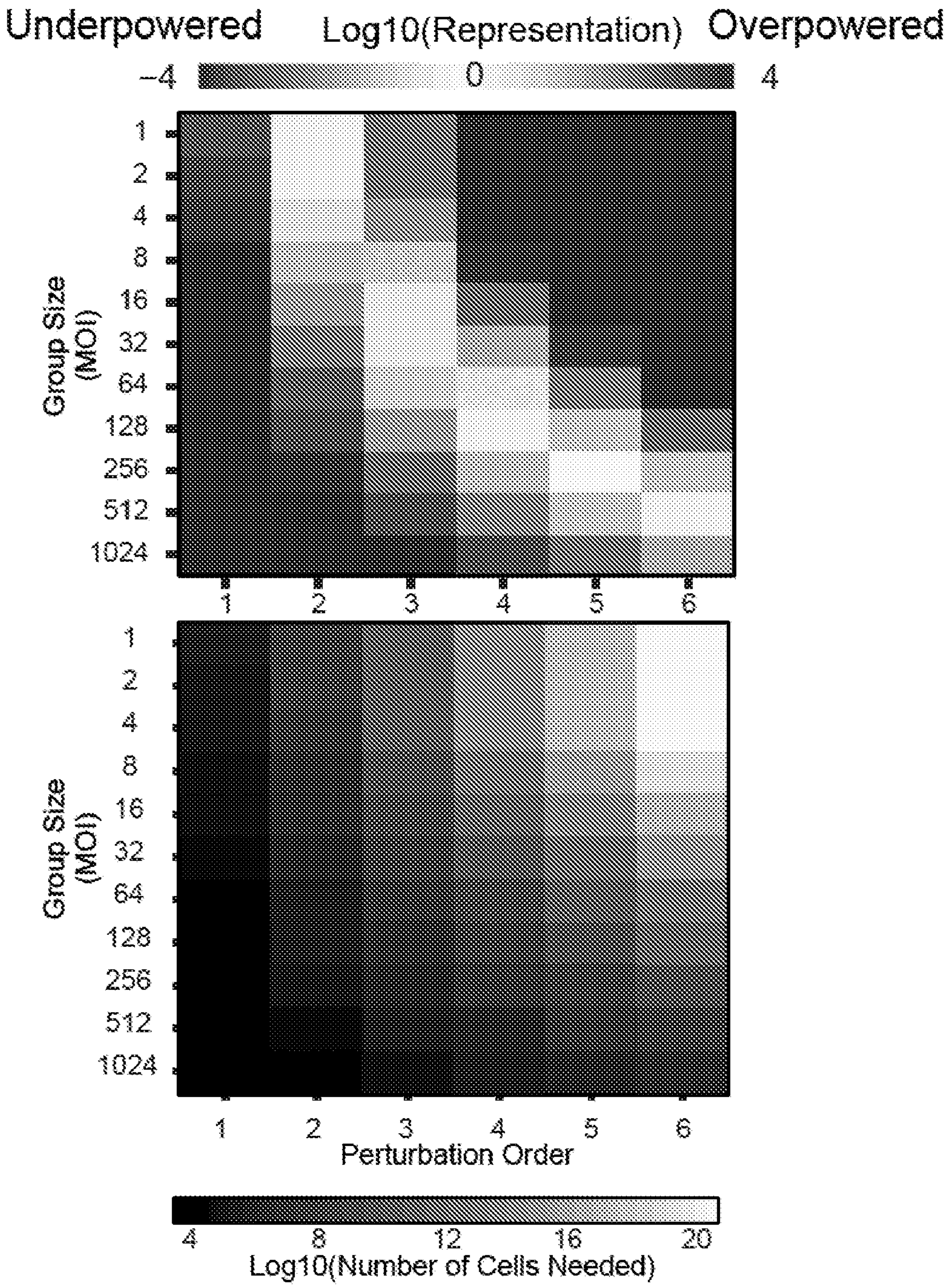

FIGS. 94A-94B An overview of approach and potential of group testing. FIG. 94A: The Shuffle-seq approach for measuring the effects of combinatorial perturbations at screening scale. Cells were transduced such that most cells had more than 1 perturbation and allowed to clonally expand. After being subjected to a screening assay, the cells were sorted into a multiwell plate with thousands of cells per well. Correlated patterns of perturbation identities across wells strongly implicated clonal origin. FIG. 94B: Statistical power to detect signal as a function of MOI and perturbation order assuming sparsity of effects assuming 10,000 genes with 100 million cells. (top) The log 10 number of cells that would be needed to perform a combinatorial screen for various MOI's assuming sparsity of effects. (bottom)

Figure 95A:
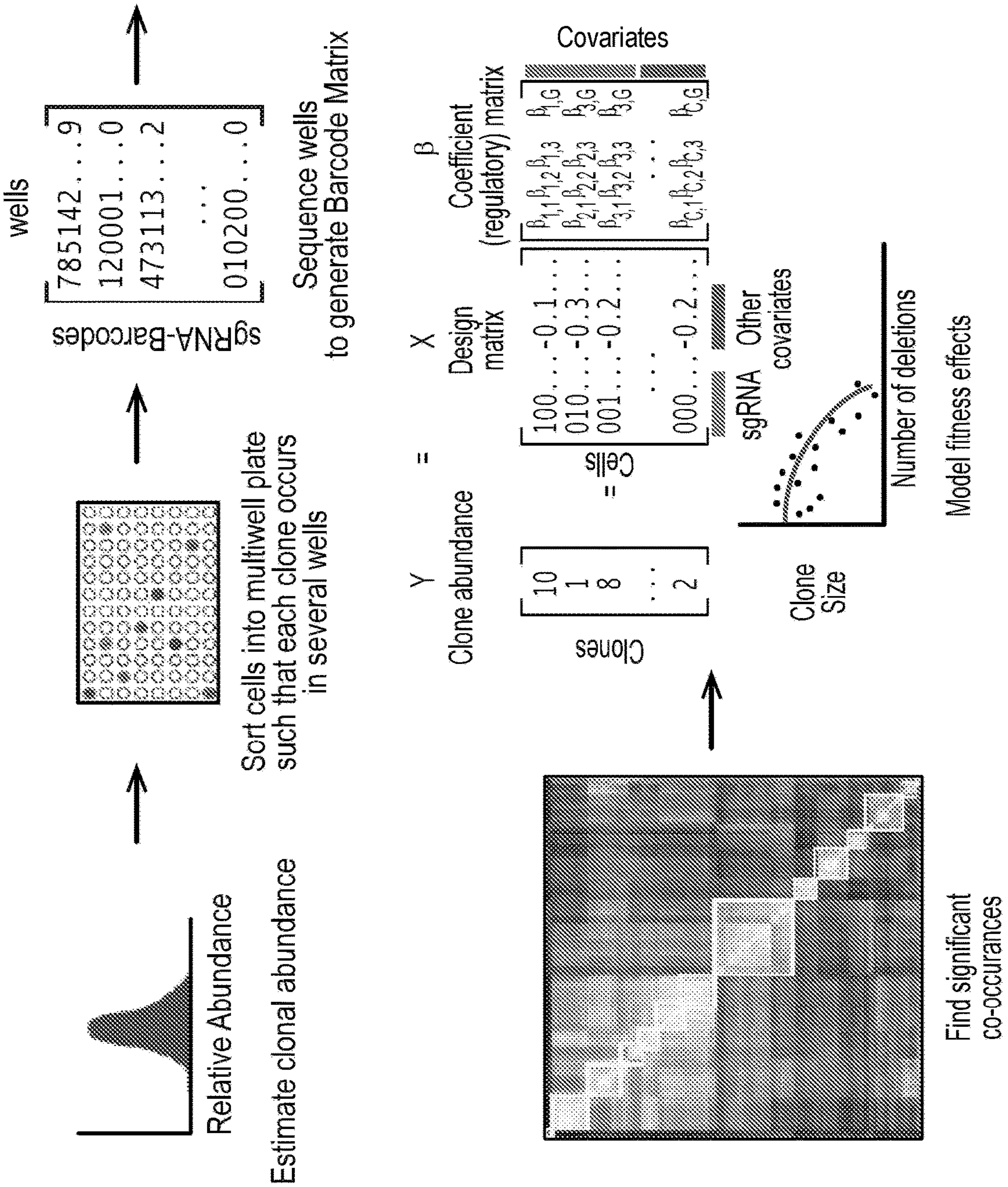
Figure 95B:
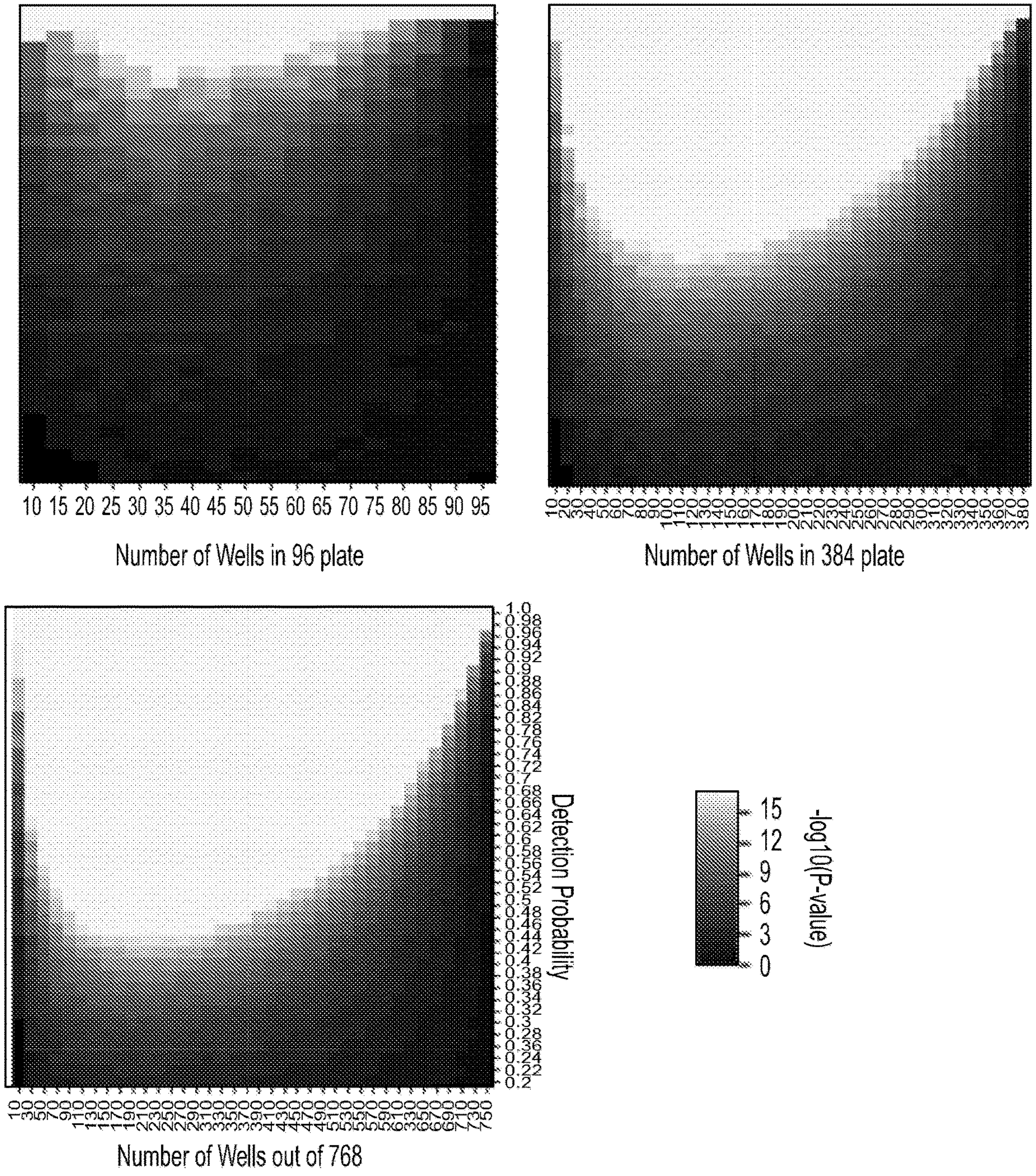
Figure 95C:
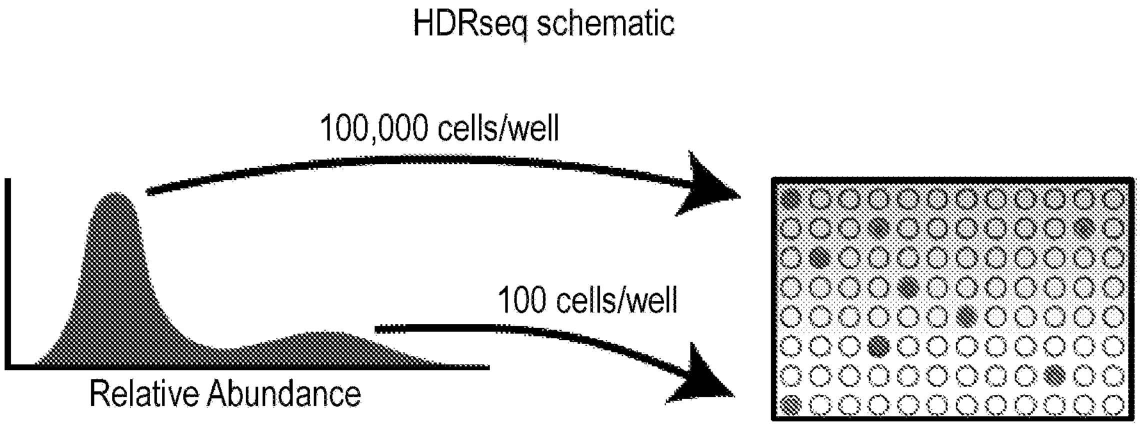
Figure 95D:
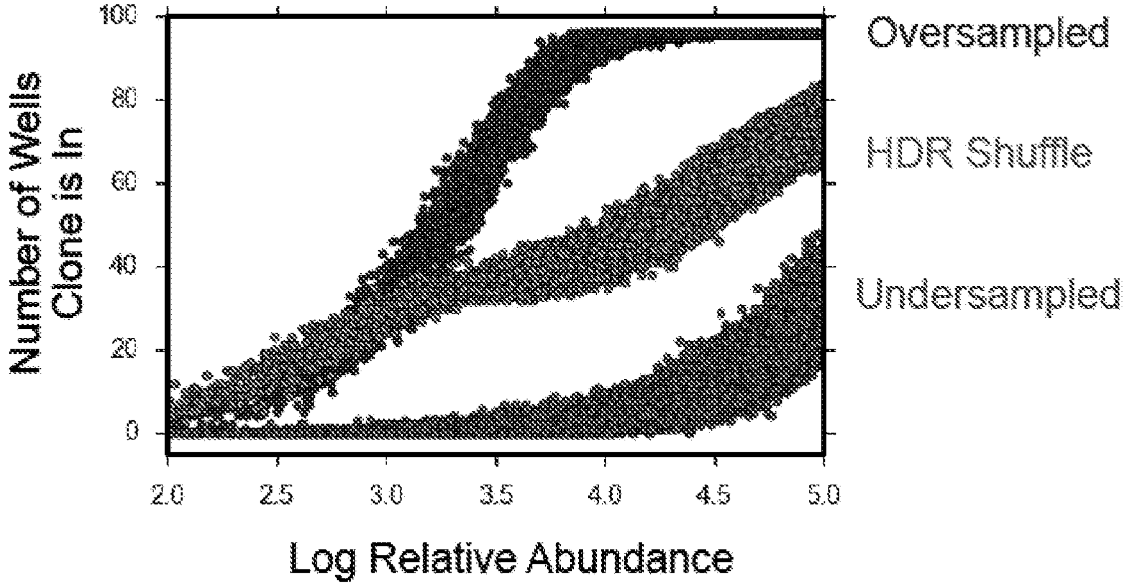
Figure 95E:
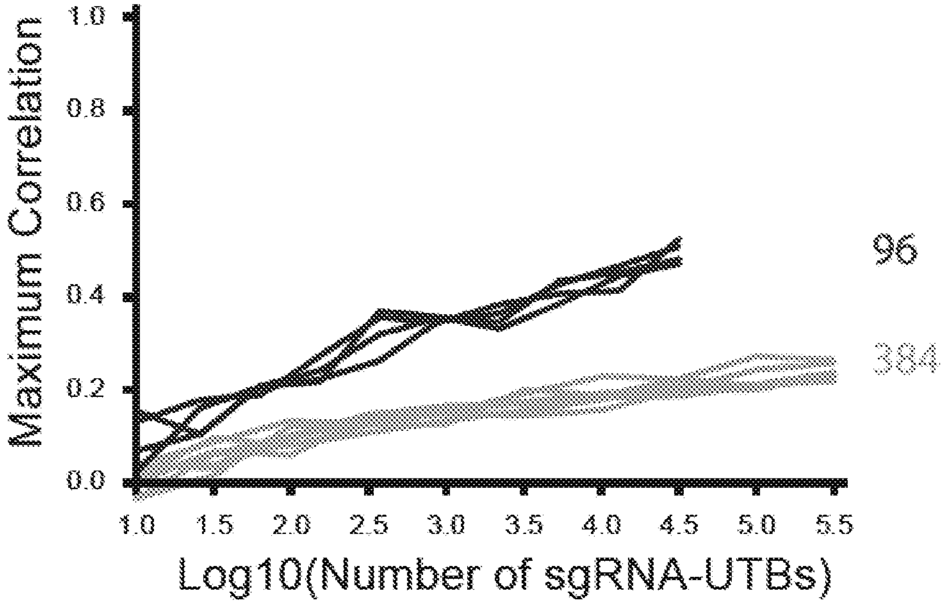
Figure 95F:
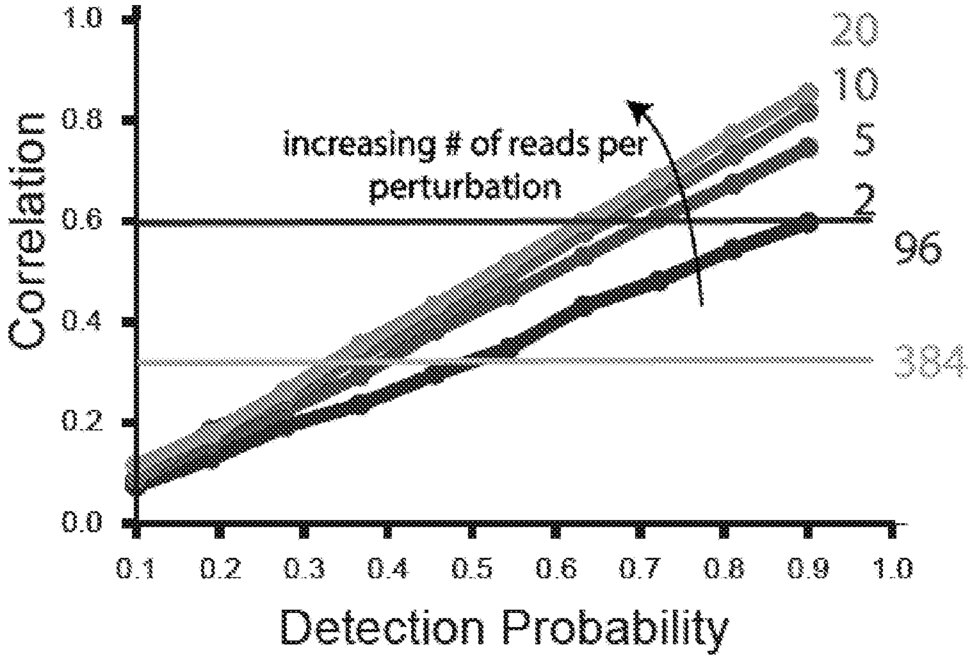

FIGS. 95A-95F An overview of the clonal inference approach. FIG. 95A: The relative clonal abundance was estimated based on bulk sequencing results. Cells were sorted into a multiwell plate such that each clone is represented in at least 10 wells. Reverse transcription and PCR was used to identify which sgRNA-BC combinations occur in which wells. Significant correlations in which barcode pairs co-occur was used to infer clonal identity. The relationship between clonal abundance (fitness) and sgRNA perturbation identity was determined. FIG. 95B: The number of wells a clone were represented in for accurate detection was a function of the size of the plate and the detection probability. FIG. 95C: In cases in which the clonal abundances were highly skewed (as in the case of positive selection screens) a high dynamic range (HDR) sorting strategy can improve resolution by sorting different numbers of cells per well. FIG. 95D: In an example screen, where the clonal abundances were biased, an oversampled clone might be present in all 96 wells, while an undersampled clone would be present in few or no wells. For the same distribution, the HDR approach was able to represent each clone in an intermediate number of wells. FIG. 95E: Assuming a quantitative rather than binary measure of sgRNA-UTB abundance per well, the LSH maximum correlation between two Poisson distributed vectors across a 96 and 384 well plate respectively as a function of the total number of sgRNA-UTBs present. FIG. 95F: The correlation between two sgRNA-UTB pairs that were derived from the same cells as a function of detection probability and sequencing depth.

Figure 96A:
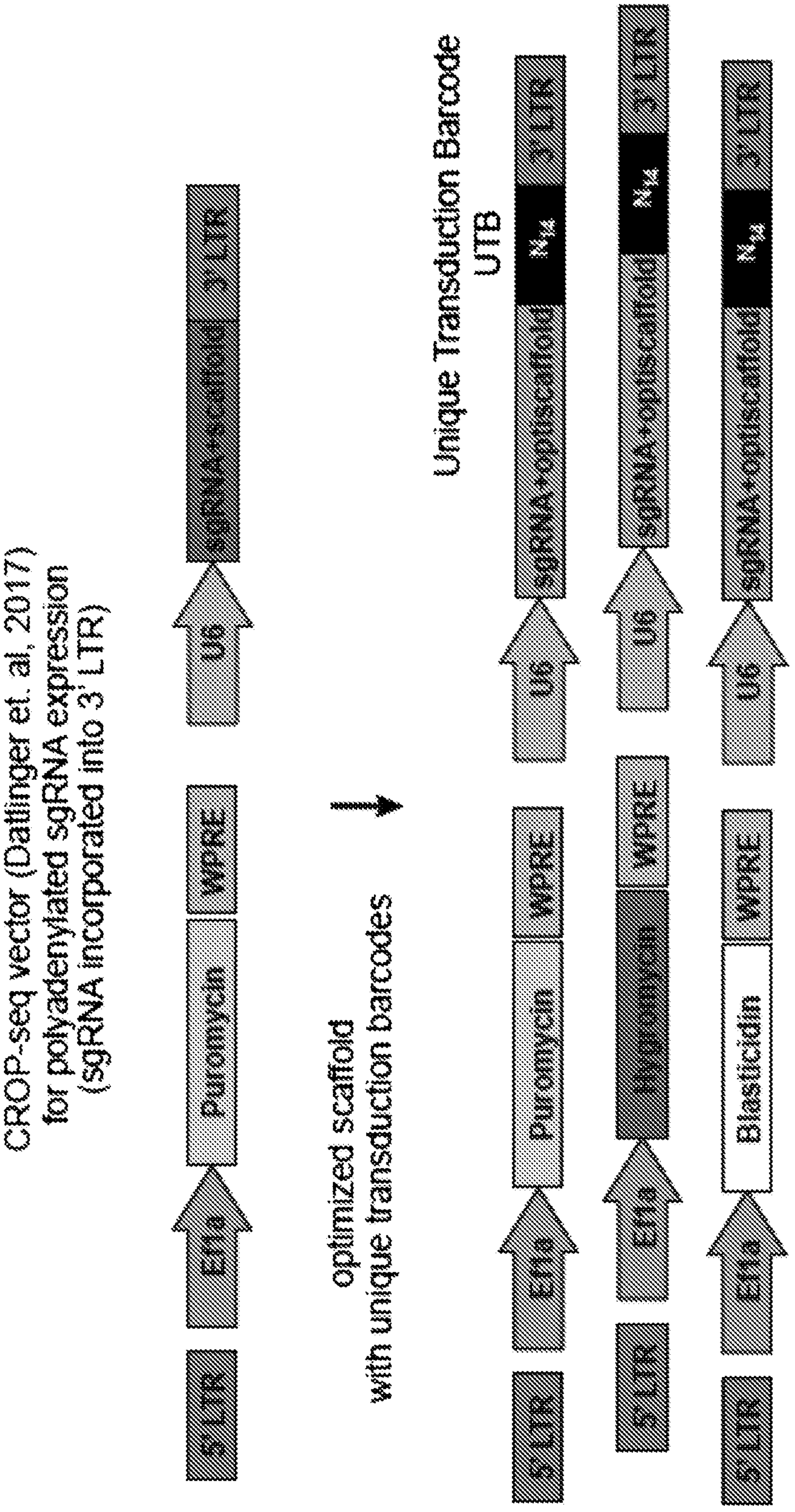

FIGS. 96A-96E. Creating an sgRNA-barcode library of sufficient complexity. FIG. 96A: The CROP-seq vector developed in Datlinger et al. (2017) was modified to include the optimized scaffold as described in Chen et al. (2013) as well as a 3' 14 bp random barcode.

Figure 96B:
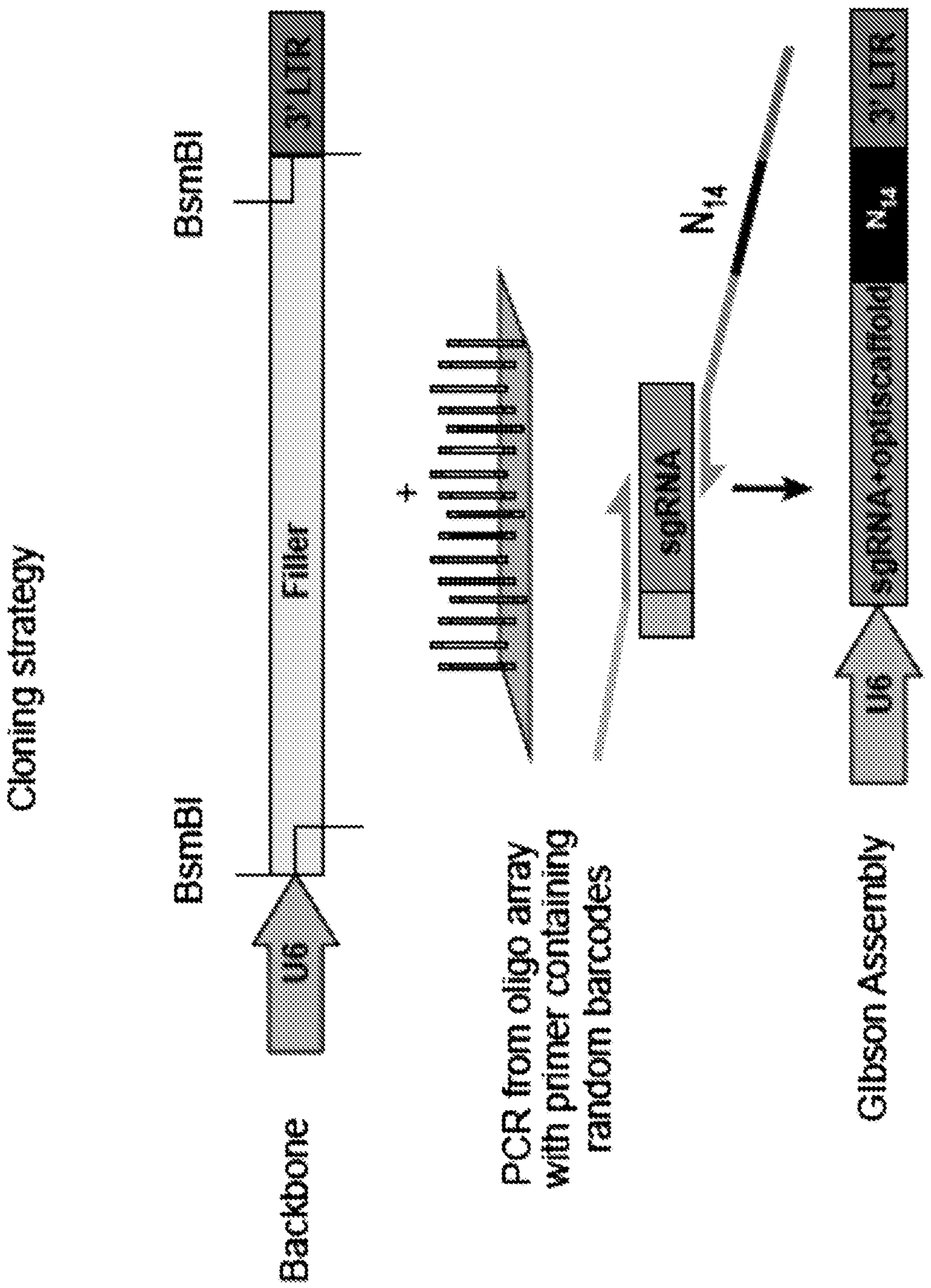
Figure 96C:
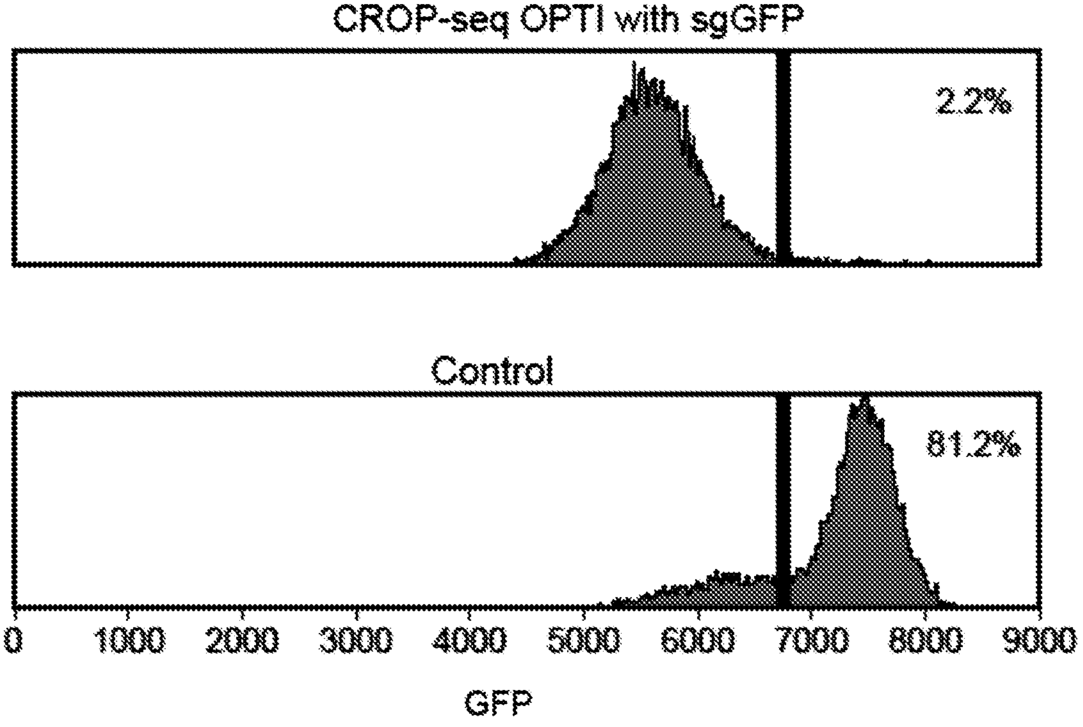
Figure 96D:
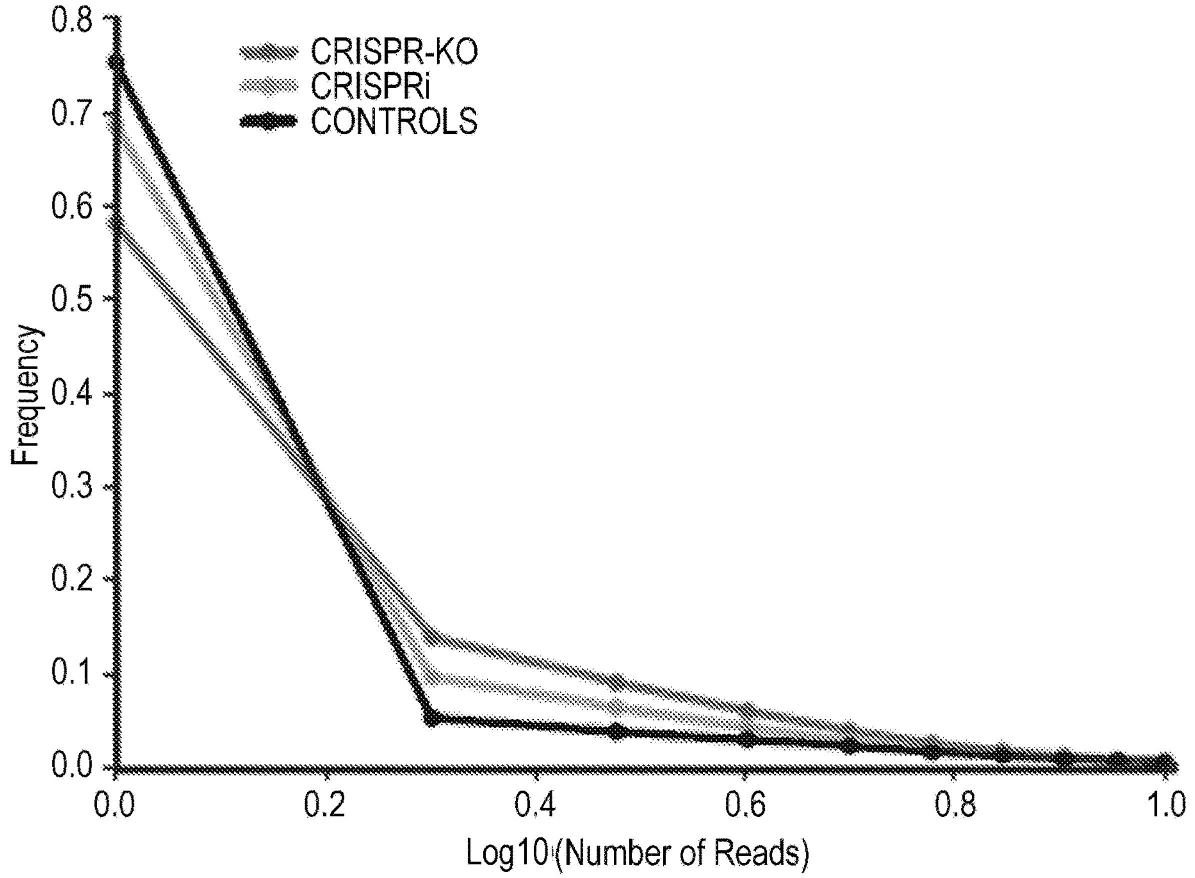
Figure 96E:
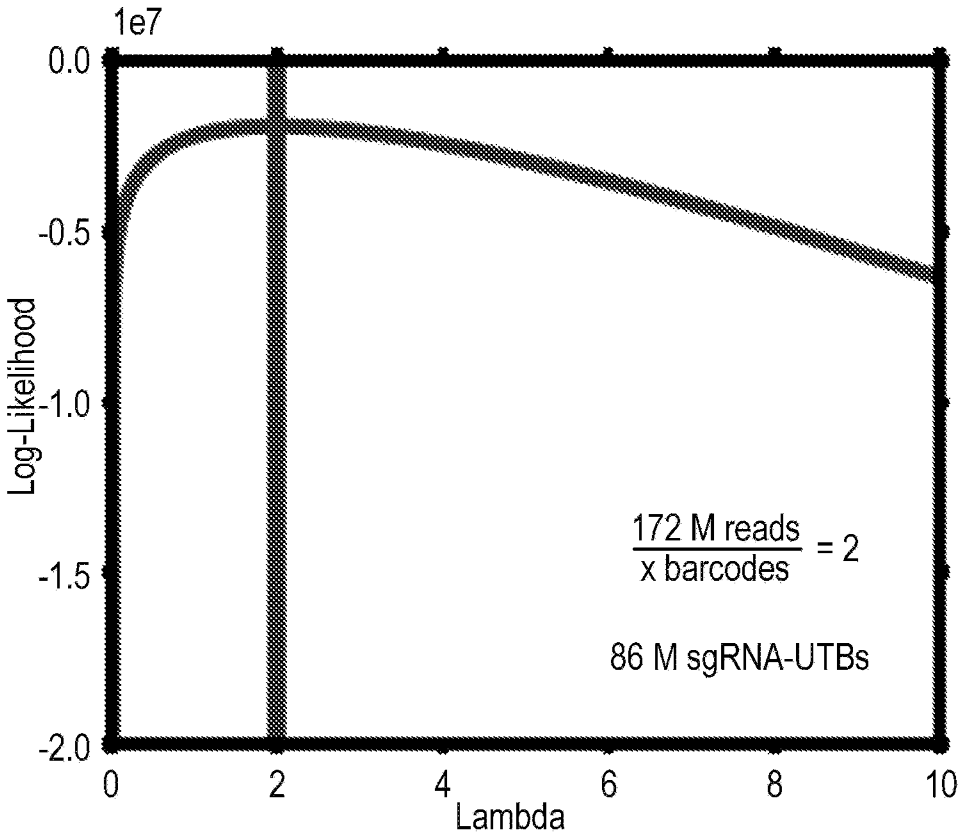

FIG. 96B: The scaffold and barcode were added onto an oligo array of an sgRNA library during a PCR stem. FIG. 96C: The modified vector created a 97% GFP knockdown in a Cas9-P2A-GFP K562 cells. FIG. 96D: The distribution of number of reads per sgRNA-barcode pair after deep sequencing of initial libraries. FIG. 96E: Log-likelihood fit of observed distribution of reads to a poisson distribution. At least 86 million barcodes were inferred to be present in the CRISPR-KO library.

Figure 97A:
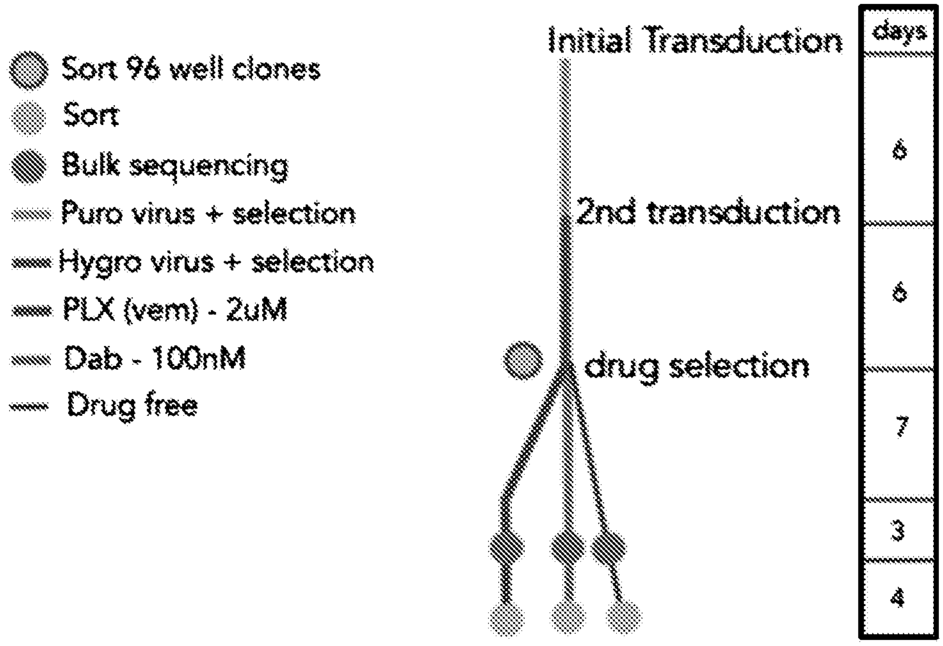
Figure 97B:
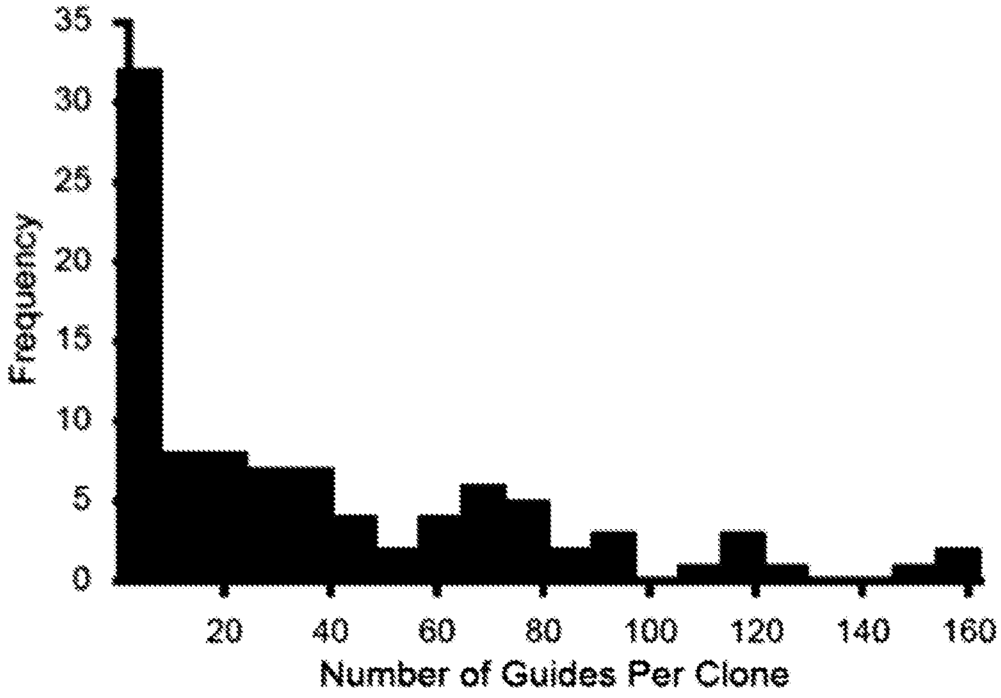
Figure 97C:
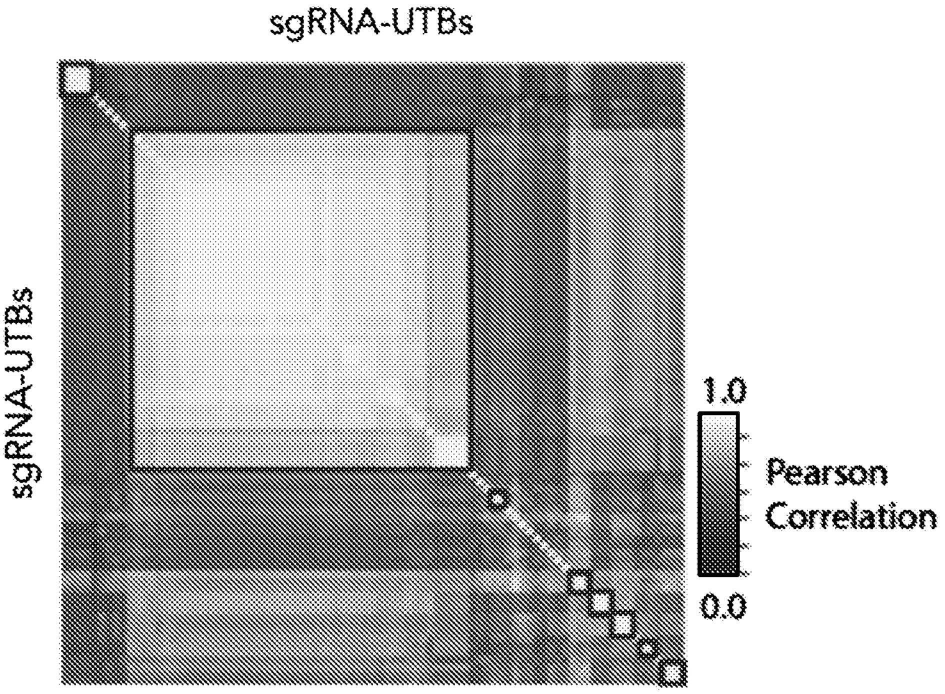

FIGS. 97A-97C. A melanoma screen to identify mechanisms of resistance. FIG. 97A: An overview of the screen timeline. FIG. 97B: Average number of sgRNAs per cell as determined by sequencing individual clones from the screen population. FIG. 97C: Correlation matrix between the most abundant sgRNA-UTBs. 60% of clonal blocks, highlighted in black, contain sgRNAs that targets genes that were hits in a previous study.

Figure 98:
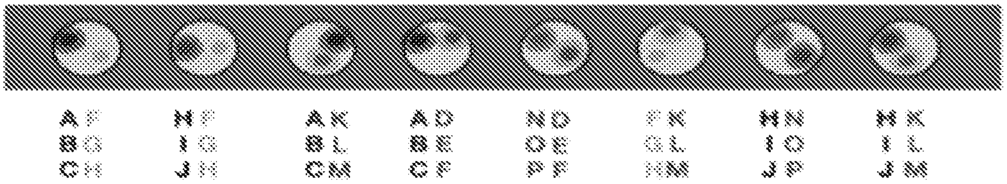

FIG. 98. Spatially encoded barcodes can be used to infer clonal effects associated with millions of genetic perturbations.

The figures herein are for illustrative purposes only and are not necessarily drawn to scale.

DETAILED DESCRIPTION OF THE EXAMPLE EMBODIMENTS

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology $2^{nd}$ ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms “a”, “an”, and “the” include both singular and plural referents unless the context clearly dictates otherwise.

The term “optional” or “optionally” means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms “about” or “approximately” as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier “about” or “approximately” refers is itself also specifically, and preferably, disclosed.

It is noted that in this disclosure and particularly in the claims and/or paragraphs, terms such as “comprises”, “comprised”, “comprising” and the like can have the meaning attributed to it in U.S. Patent law; e.g., they can mean “includes”, “included”, “including”, and the like; and that terms such as “consisting essentially of” and “consists essentially of” have the meaning ascribed to them in U.S. Patent law, e.g., they allow for elements not explicitly recited, but exclude elements that are found in the prior art or that affect a basic or novel characteristic of the invention.

As used herein, a “biological sample” may contain whole cells and/or live cells and/or cell debris. The biological sample may contain (or be derived from) a “bodily fluid”. The present invention encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

The terms “subject,” “individual,” and “patient” are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

Reference is made to International Patent numbers PCT/US16/059233, filed Oct. 27, 2016, PCT/US2016/059195, filed Oct. 27, 2016, and PCT/US16/059230 filed Oct. 27, 2016. Reference is also made to U.S. provisional application Ser. No. 62/247,630 filed Oct. 28, 2015, 62/247,656 filed Oct. 28, 2015, 62/372,393 filed Aug. 9, 2016, 62/247,729 filed Oct. 28, 2015, 62/394,721 filed Sep. 14, 2016, 62/395,273 filed Sep. 15, 2016, and 62/500,784 filed May 3, 2017.

All publications, published patent documents, and patent applications cited herein are hereby incorporated by reference to the same extent as though each individual publication, published patent document, or patent application was specifically and individually indicated as being incorporated by reference.

Overview

Functional genomics has transformed our ability to identify the components of molecular circuits in cells. However, despite over a decade of intensive research, Applicants are still incredibly limited in our ability to predict how perturbing one or more components will affect the cell's phenotype. For example, the recent explosion in studies on the genetic basis of human disease, from genome-wide association studies (Manolio et al., 2009; Shendure and Akey, 2015; Visscher et al., 2012) to rare Mendelian disease (Altshuler et al., 2008; Bamshad et al., 2011; Botstein and Risch, 2003) to cancer genetics (Melnikov et al., 2012) (Lawrence et al., 2014; Martincorena and Campbell, 2015), have identified many disease-associated genes, but the mechanisms by which they contribute to pathogenesis remain largely obscure. It is increasingly clear that a lack of biological understanding of the complex nature of molecular networks severely constrains our progress towards therapeutic intervention (Sawyers, 2004).

Genomic research on dissecting molecular systems in mammalian cells has proceeded along two main paths. Observational studies use global analysis of molecular profiles in different cells to draw correlational hypotheses that relate regulators to their targets. Conversely, genetic perturbation screens, with RNAi, and more recently CRISPR/Cas9-based genome editing, have opened the way for comprehensive analysis of gene function in mammalian cells in vitro and in vivo. Such screens are designed in either: (1) an individual ("arrayed") format, where each perturbation is delivered and its effect is measured separately, or in (2) a pooled format, where the effects of perturbations are measured en masse. Pooled phenotypic readouts rely on measuring cell autonomous effects, such growth, drug resistance (Bandyopadhyay et al., 2010; Bassik et al., 2013a; Kampmann et al., 2014; Shalem et al., 2014; Wang et al., 2014), or the expression of a single gene (Melnikov et al., 2012; Parnas et al., 2015; Rajagopal et al., 2016; Smith et al., 2013). In general, pooled screens are more efficient, scalable, and less prone to batch effects than arrayed screens, but have thus far been limited to lower-content readouts. As a result, they are unable to discern between multiple molecular mechanisms that result in similar downstream phenotypes. Such distinctions require a more comprehensive readout, such as the transcriptional profile of a cell. Typically, detailed profiling of 'hits' from screens requires individual testing, in a time and labor intensive manner (Parnas et al., 2015).

Transcriptional profiles are a rich readout of the cell's molecular state, but have been challenging to assess in a screening scale. A few studies tested the transcriptional profiles in a hundred or more individual perturbation experiments, in either follow up studies of pre-validated hits, or in model organisms, such as yeast, where the most recent effort assessed ~1,500 KO strains individually. Indeed, even signature assays (Amit et al., Science. 2009 9; 326(5950):257-63) were only measured in large screens in the context of highly resourced centralized efforts (LINCS program). This "readout barrier" is common to all genetic screening, in vitro or in vivo, from unicellular model organisms to mice or human cells.

Indeed, it has been challenging to bridge the gap between the use of transcriptional or other rich profiles and the scale of pooled screens. In mammalian cells, a few studies tested transcriptional profiles in a hundred or more individual perturbation experiments, in either follow up studies of pre-validated hits (Berger et al., 2016; Parnas et al., 2015), or in model organisms, such as yeast (Hughes et al., 2000), where a recent effort assessed ~1,500 knock out (KO) strains individually (Kemmeren et al., 2014). Indeed, even signature assays (Amit et al., 2009) were only performed in large screens in the context of highly resourced centralized efforts (Duan et al., 2014; Lamb et al., 2006). This "readout barrier" is common to all genetic screening, in vitro or in vivo, from unicellular model organisms to mice or human cells.

Notably, a rich readout-such as a genomic profile-would be particularly important to understand the combined effect of multiple factors, in systems where this effect cannot simply be predicted by the sum of their individual effects. Comprehensive analysis of the effects of pairs of genes on cell viability ("synthetic lethality") has been performed in yeast (Boone et al., 2007; Costanzo et al., 2010; Tong, 2004). In mammals, the effects of interactions on cell viability (Bassik et al., 2013b; Wong et al., 2016) or cell morphology characteristics (Laufer et al., 2013) were assessed for a small number of selected pairs of genes. Few studies have examined the relationship between a high dimensional phenotype, like gene expression, and pairwise interactions. One study in yeast that explored the marginal transcriptional effect associated with double knockouts of a few transcription factors compared to their respective single knockouts (Capaldi et al., 2008), highlighted the potential power of the approach to determine how a regulatory circuit is wired and functions. Very few studies have examined higher order interactions beyond a limited handful (Haber et al., 2013; Tsumura et al., 2006). To the best of our knowledge, there have been few if any studies coupling a high content readout with scalable generation of cells containing multiple perturbations.

It has been suggested, by the Applicants (Macosko et al., 2015) and others (Liberali et al., 2014; Macosko et al., 2015; Shendure and Fields, 2016) that scalable methods of transcriptionally assaying perturbations using single cell profiling, if developed, could provide an important new tool in the understanding the functions of genes and circuits.

Here, applicants addressed the challenge of scaling the phenotypic measurements in genetic screens by developing Perturb-Seq and provide this ability by developing Perturb-seq, which combines pooled CRISPR screening with a massively parallel single cell RNA-seq readout. Applicants leverage the modularity of sgRNAs in the CRISPR/Cas9 system to perform pooled, multi-locus gene perturbation in mammalian cells (Chen et al., 2015; Cong et al., 2013; Gilbert et al., 2014, 2013; Konermann et al., 2014; Qi et al., 2013; Ran et al., 2015; Zalatan et al., 2015), including in primary cells (Platt et al., 2014). Applicants rely on the scale and single cell nature of massively parallel single cell RNA-seq (Fan et al., 2015; Klein et al., 2015; Macosko et al., 2015) to provide a rich, genome-scale cell autonomous readout for up to millions of cells in a day's work (with appropriate parallelization (Joensson and Andersson Svahn, 2012)). Perturb-Seq uses a CRISPR lentiviral vector, which both delivers an sgRNA to a cell, and reports on the identity of the delivered sgRNA by an expressed barcode on a polyadenylated transcript, captured efficiently by scRNA-seq. Perturb-Seq can be used to assess the effect of single gene perturbations. By increasing the multiplicity of infection, a greater fraction of cells possesses more than one guide, and the approach is more powered to test for epistatic effects. Applicants further developed an integrated computational framework to decipher the effect of individual perturbations and the marginal contributions of pairwise interactions on the level of each expressed gene, gene modules, and global cell states and types.

Applicants demonstrated the power of Perturb-seq in the context of two distinct biological systems: perturbing key transcription factors (TFs) implicated in cell differentiation and the immune response in bone marrow derived dendritic cells (BMDCs), post-mitotic primary innate immune cells responding to the pathogen component lipopolysaccharide (LPS); and perturbing TFs or (MOI) cell cycle regulators in K562 cells, a rapidly dividing erythroleukemia cell line. Applicants further developed an integrated computational framework to decipher the effect of individual perturbations and the marginal contributions of pairwise interactions on the level of each transcript, transcriptional module, and global cell states. This framework can be extended to include other high dimensional molecular phenotypes as they become available, as well as incorporate a variety of cell metadata such as lineage information.

The present invention provides tools and methods for the systematic analysis of genetic interactions, including higher order interactions.

The present invention provides tools and methods for combinatorial probing of cellular circuits, for dissecting cellular circuitry, for delineating molecular pathways, and/or for identifying relevant targets for therapeutics development.

The present invention provides tools and methods for pooled screening of perturbations and genome scale readouts in single cells, thus allowing relevant phenotypes to be correlated to specific perturbations.

In one aspect, the invention provides a method for determining genetic interactions. This method involves causing a set of P genetic perturbations in cells, wherein the method may comprise: determining, based upon random sampling, a subset of $\pi$ genetic perturbations from the set of P genetic perturbations; performing said subset of $\pi$ genetic perturbations in a population of cells; performing single-cell molecular profiling of the population of genetically perturbed cells of step; inferring single-cell molecular profiles for the set of P genetic perturbations in cells.

The population of cells with a plurality of genomic sequence or perturbation conditions involves a plurality of cells and perturbations to be tested and measurements sampled to obtain meaningful data and to infer appropriate circuits. The number of genes perturbed, and how many are perturbed simultaneously (the order of the perturbation, pairs, triplets, etc.) varies. In a tissue with n cell types, the rarest present in m %, how many cells X do you need to sequence so that you have at least Y of the rarest subtype.

Figure 34:
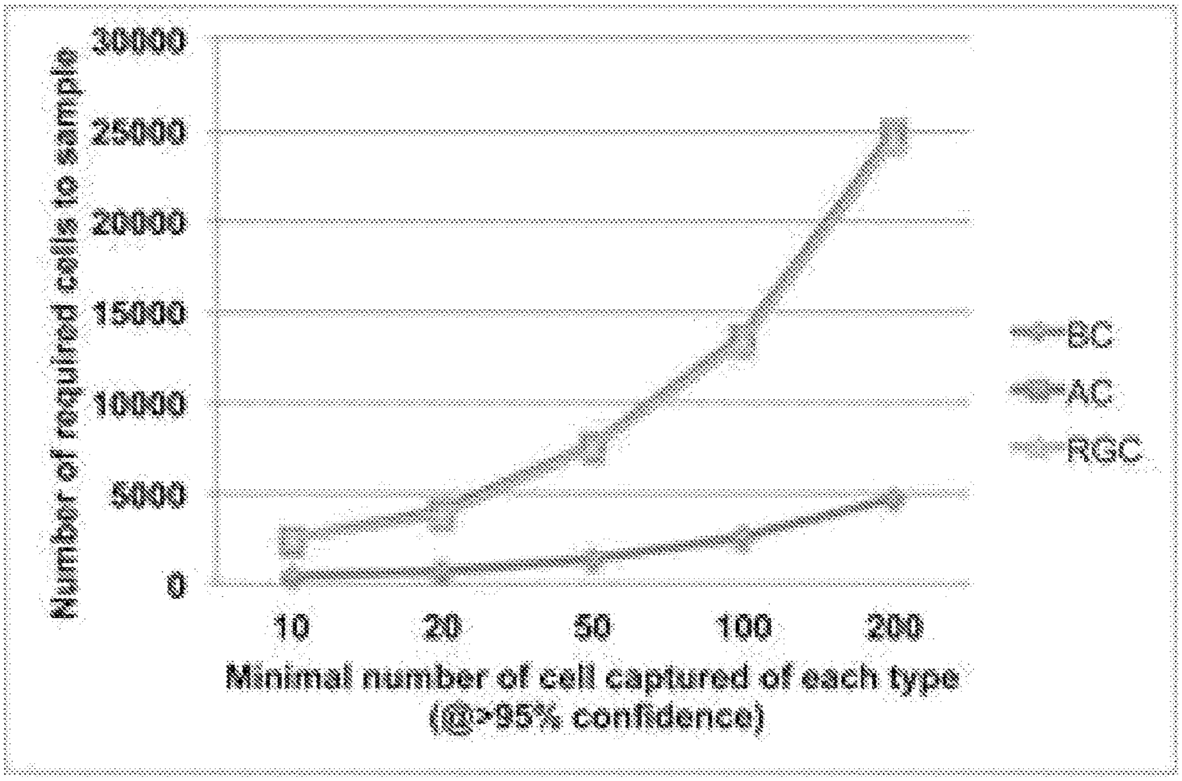
FIG. 34 illustrates an estimate number of cells (Y axis) needed to capture a given minimal number of cells per subtype (X axis) for BCs (rarest subtype ~5%), AC, and RGCs (rarest subtype ~1%).
Figure 35:
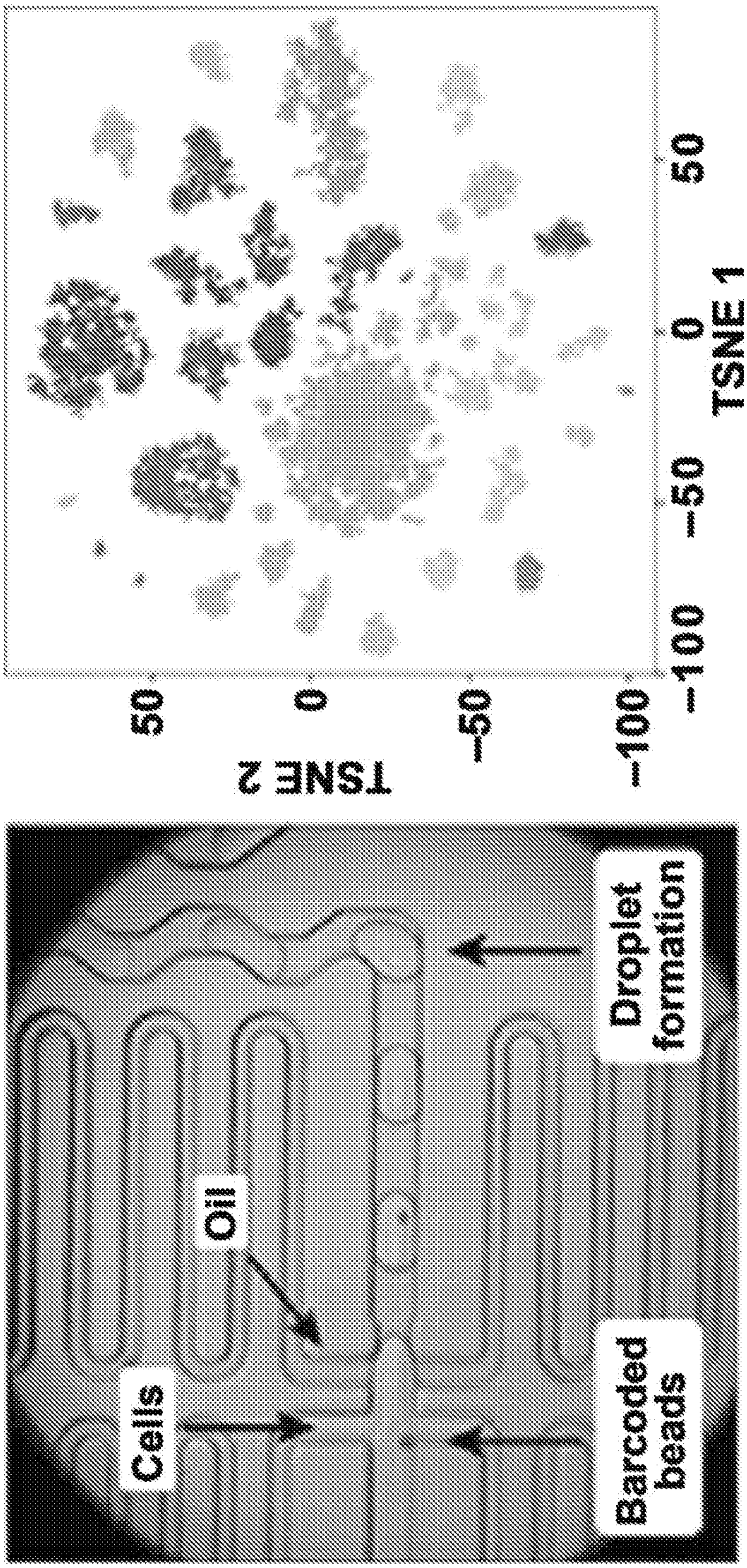
FIG. 35 illustrates a Drop-Seq. From left: Device; clear separation of a mixture of mouse and human cells; and t-SNE of 44,808 single cells from a mouse retina, distinguishing 39 subpopulations (colors).
Figure 36:
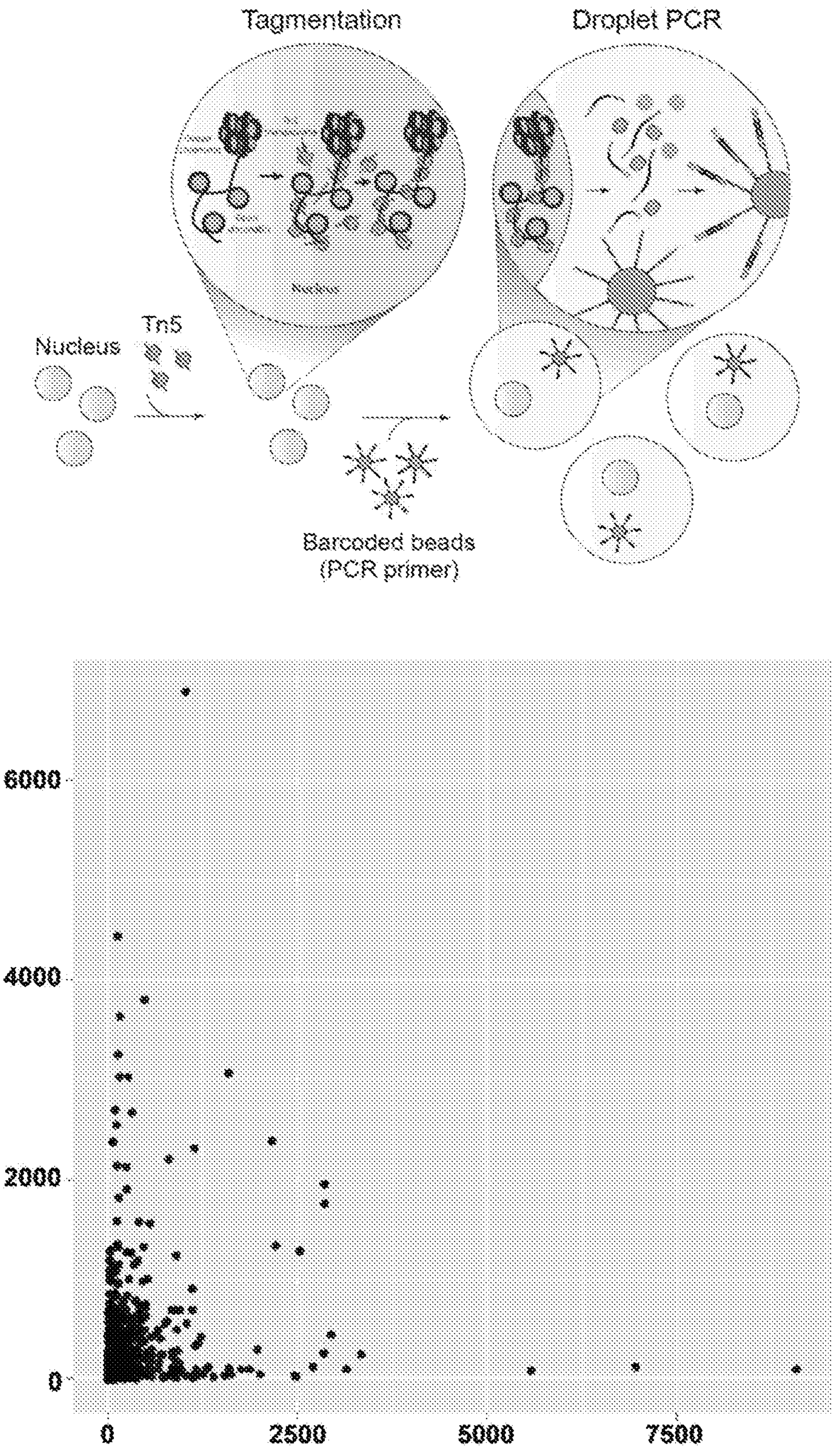
FIG. 36 illustrates a Drop-ATAC. Left: schematic. Right: Number of human (x-axis) vs. mouse (y-axis) reads in each barcode in a species cell mixing experiment.
Figure 37:
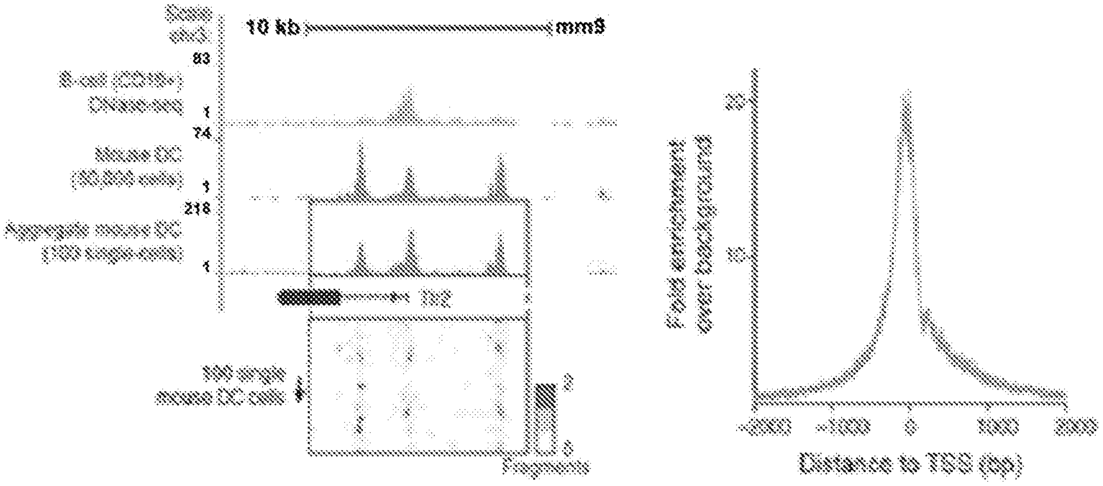
FIG. 37 illustrates a Single cell ATAC-Seq in DCs.
Figure 38:
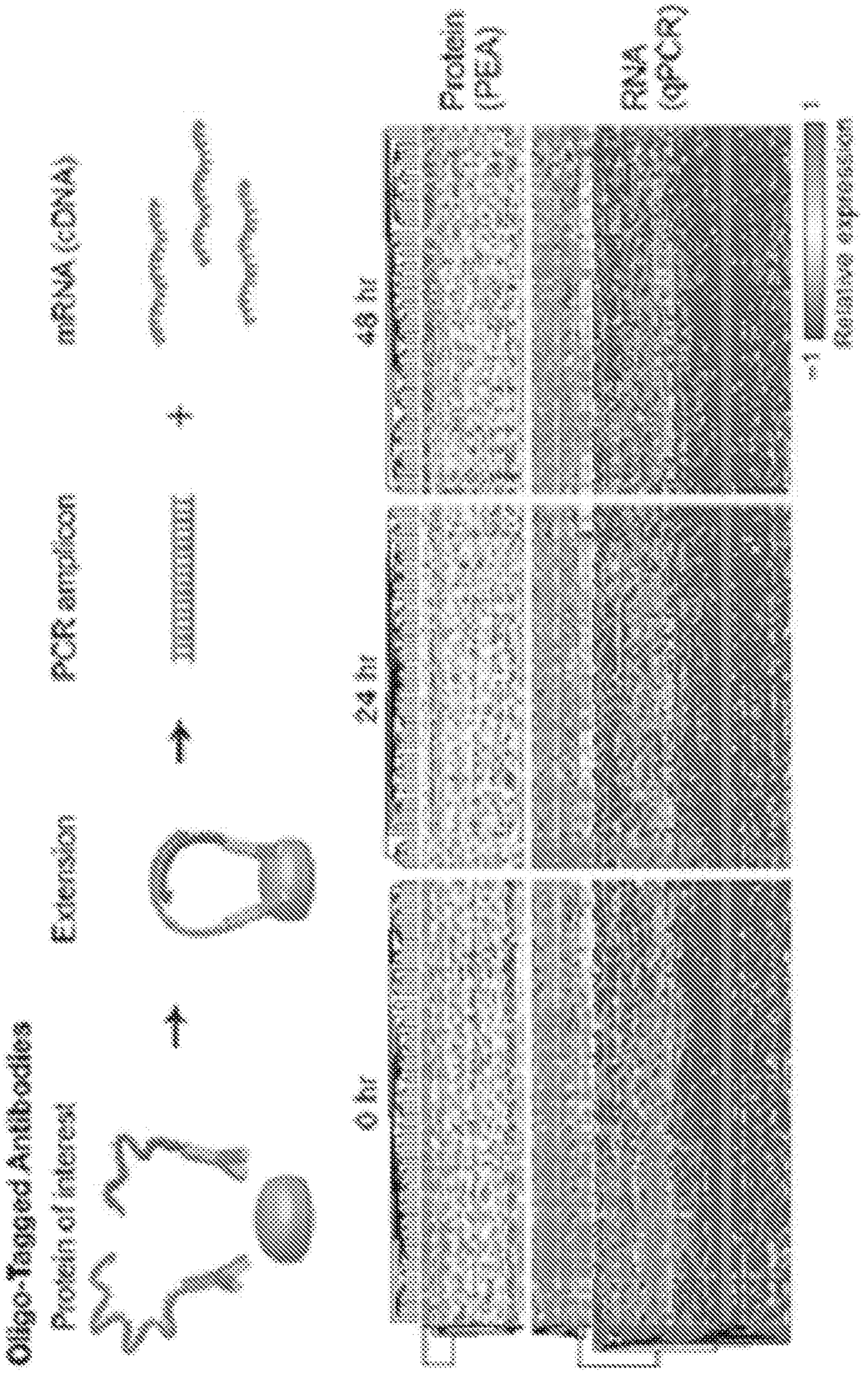
FIG. 38 illustrates a Single cell protein+RNA by PEA. Top: PEA: Bottom: PEA distinguishes single THP-1 and K562 cells.
Figure 39:
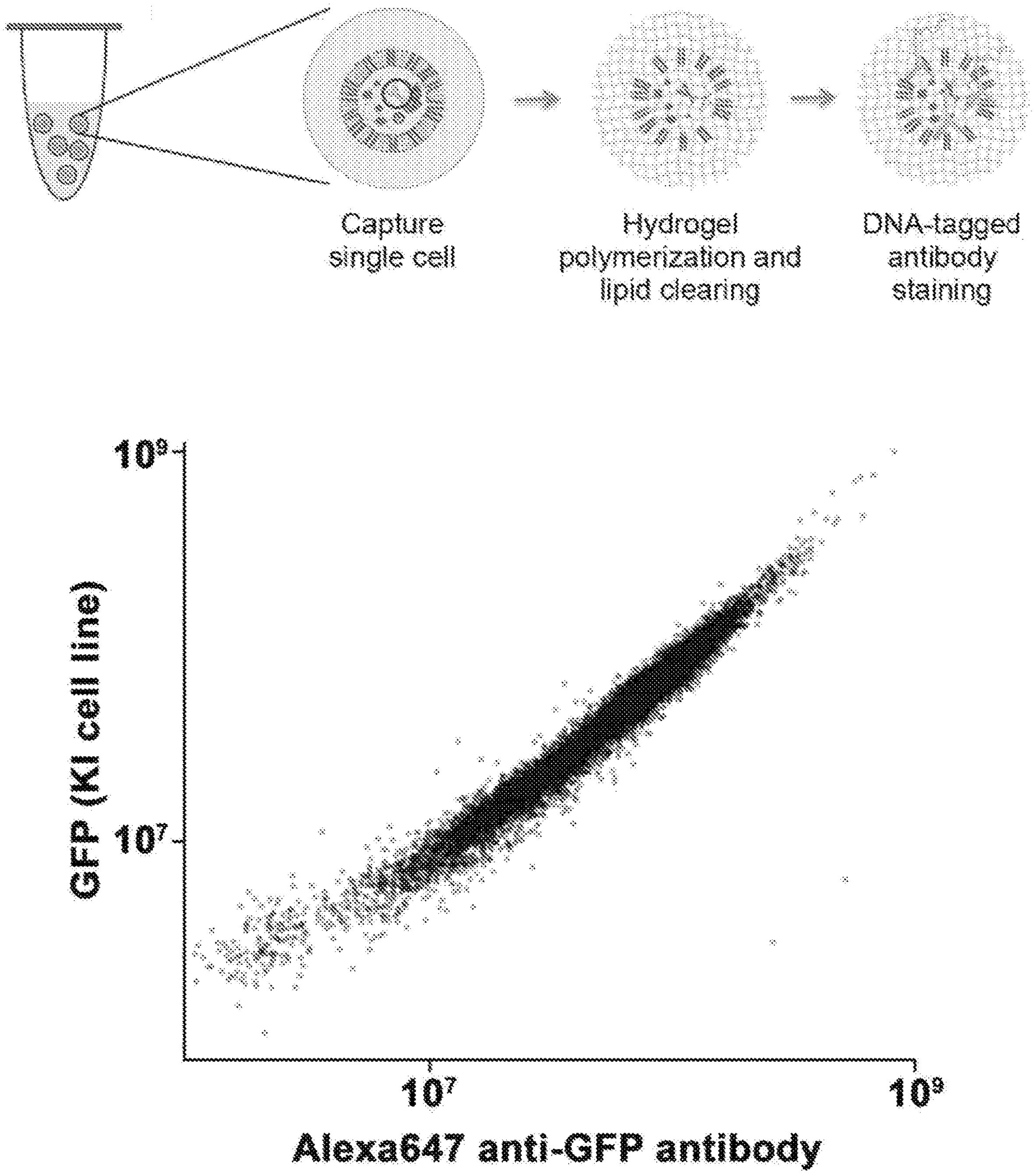
FIG. 39 illustrates a NGS proteomics in hydrogel droplets.
Figure 40:
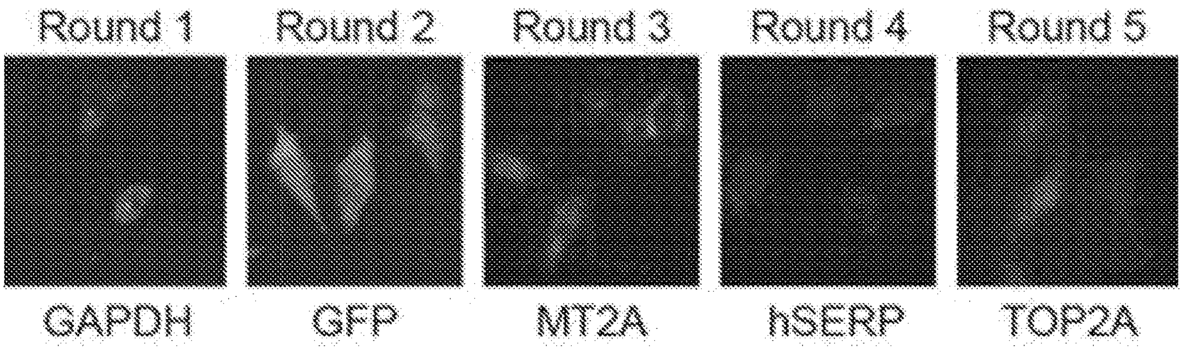
FIG. 40 illustrates a Rapid sequential FISH of 5 genes using five sequential rounds.
Figure 41:
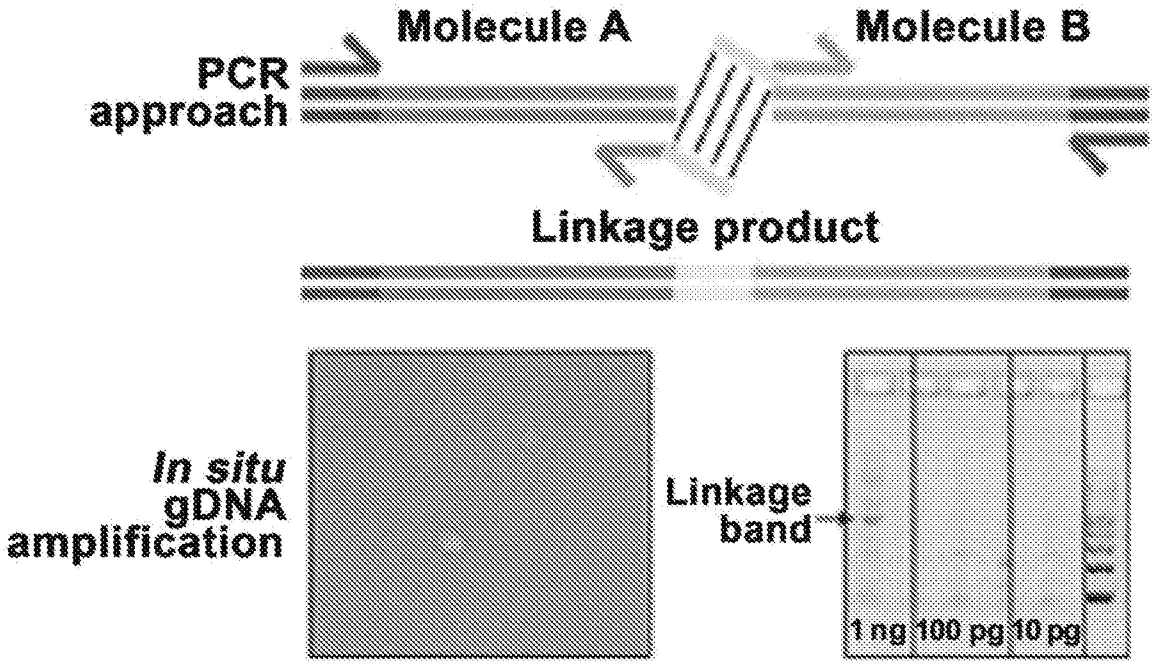
FIG. 41 illustrates a Linkage PCR in gel droplets of two CRISPR barcodes.
Figure 42:
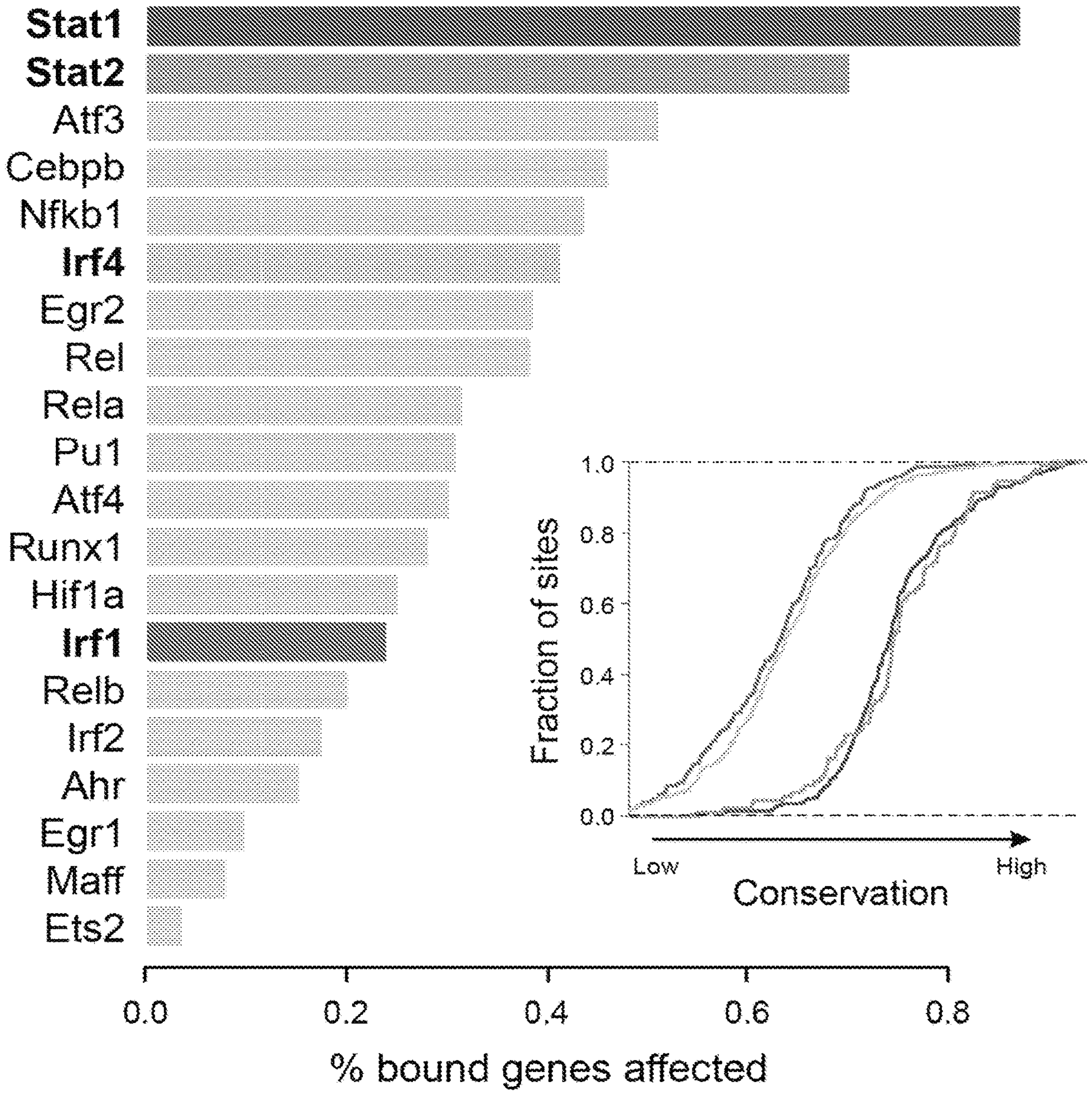
FIG. 42 illustrates a Proportion of sites (x-axis) where perturbation of bound TF (y-axis) affects target's expression.
Figure 43:
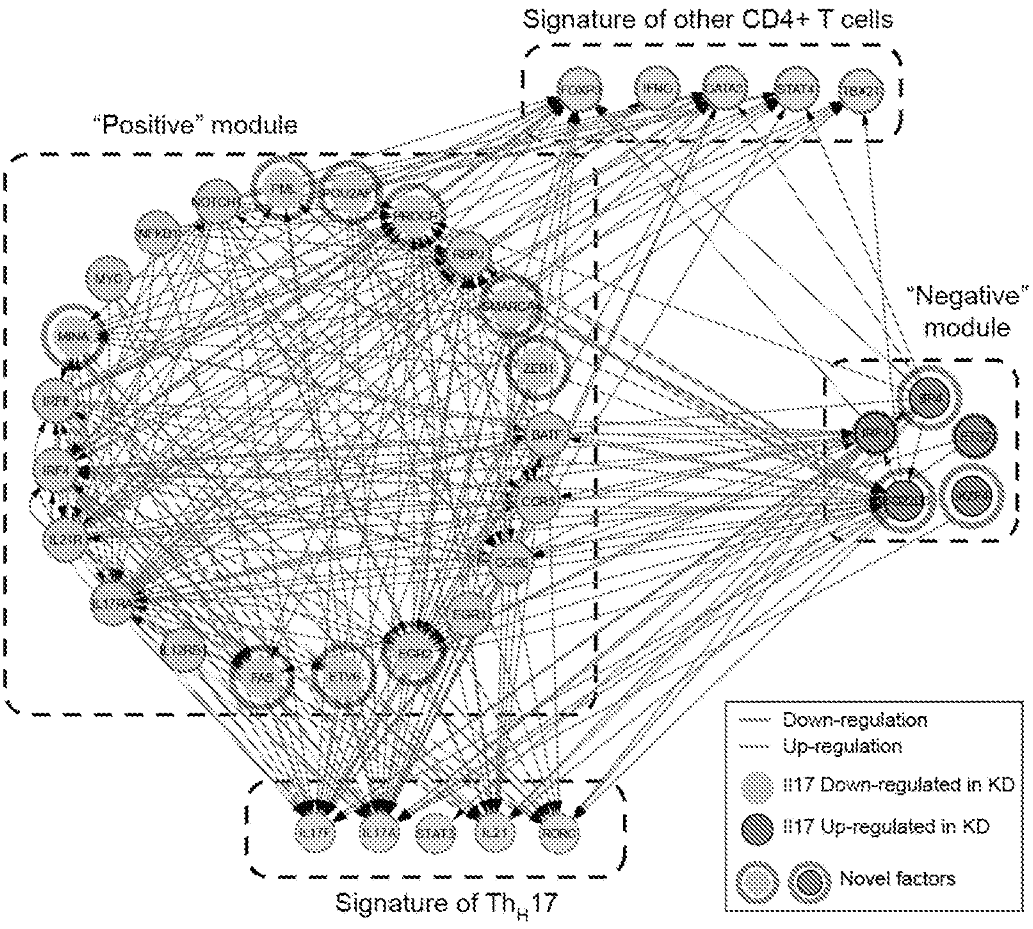
FIG. 43 illustrates a Perturbation model of Th17 cell differentiation.
Figure 44:
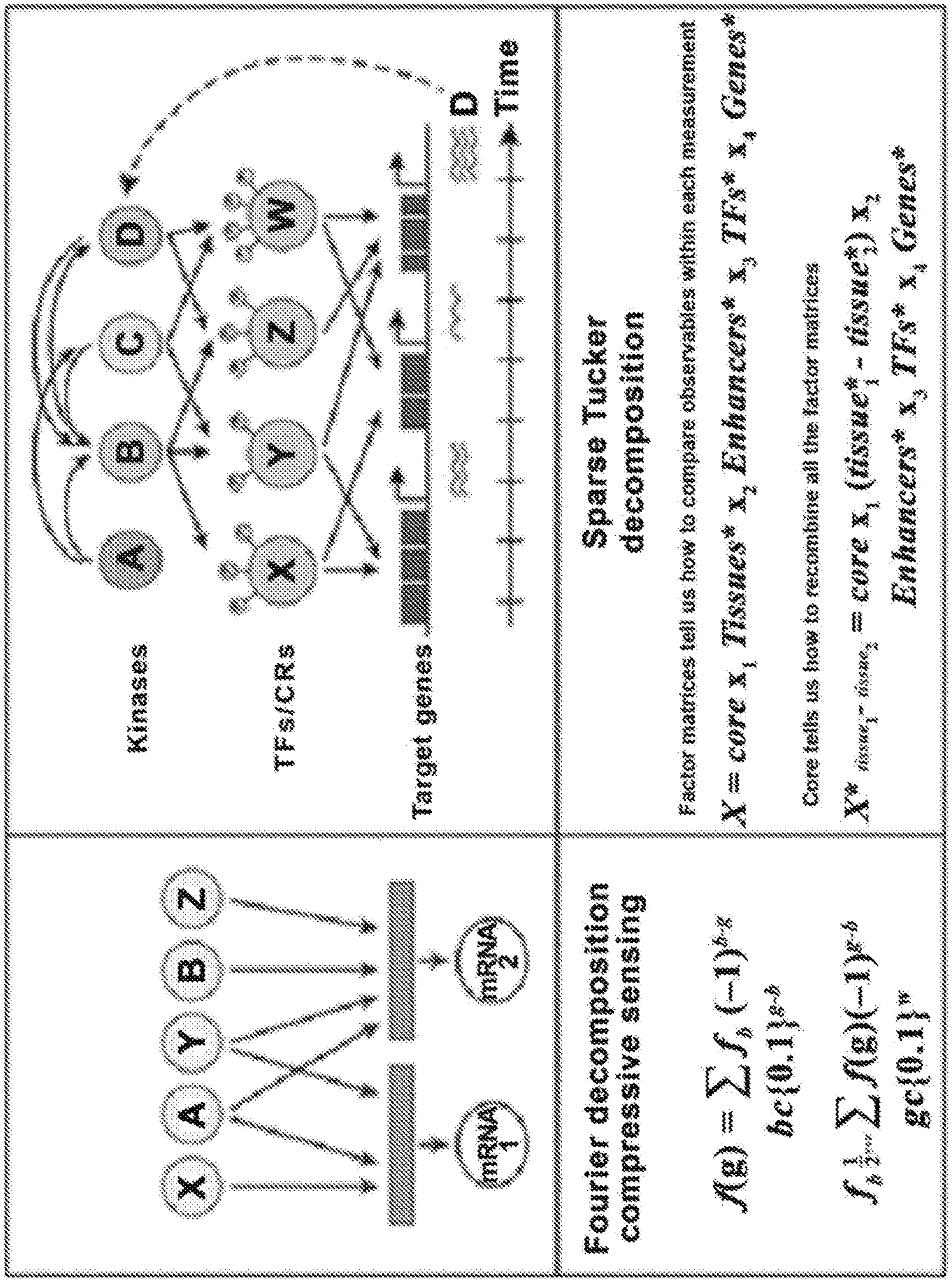
FIG. 44 illustrates a Genetic (left) vs. molecular (right) models.
Figure 45:
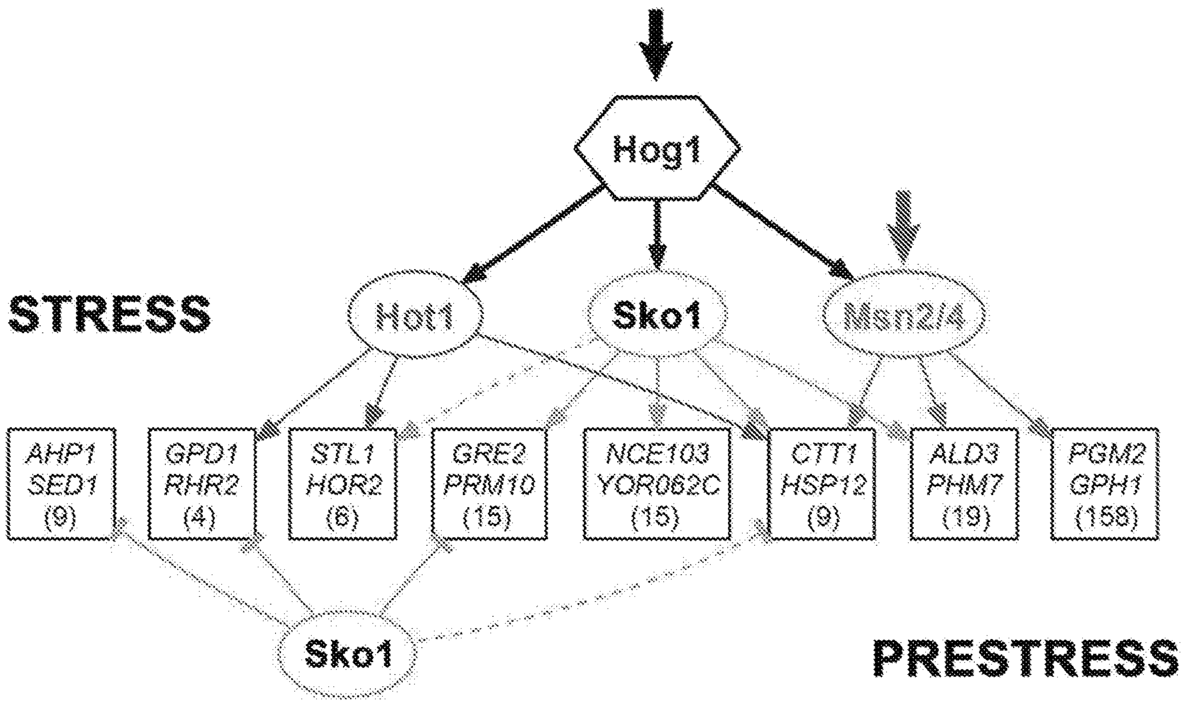
FIG. 45 illustrates a Hog network. Each set of incoming edges is quantified for each 1-5-way contribution (not shown).
Figure 46:
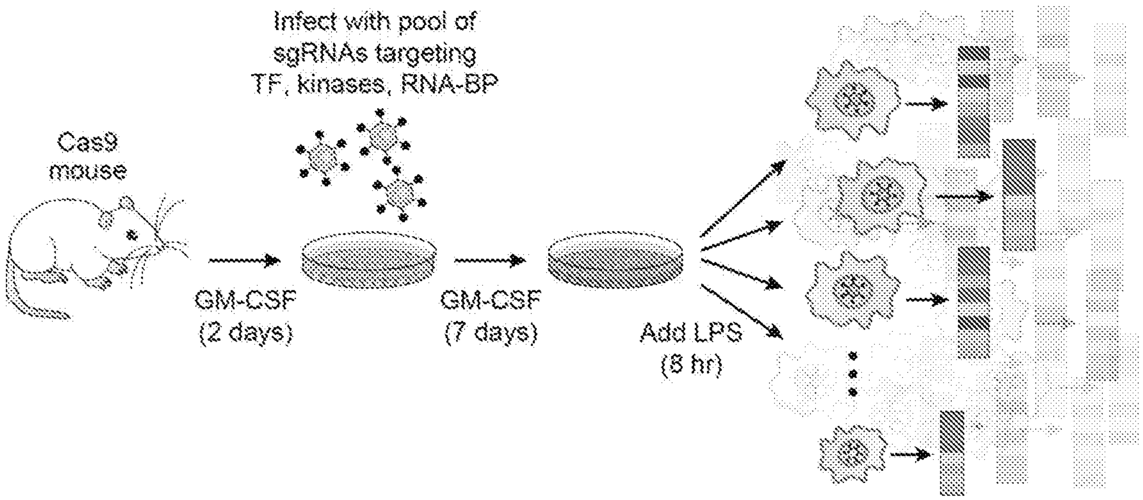
FIG. 46 illustrates MCPP assays in Cas9-expressing DCs. Cells are infected with a library of sgRNA-expressing lentiviruses that target regulators; DCs are stimulated with LPS; finally, millions of cells are profiled by scRNA-seq or NGS proteomics to monitor changes in gene or protein expression by one or multiple sgRNAs per cell.
Figure 47:
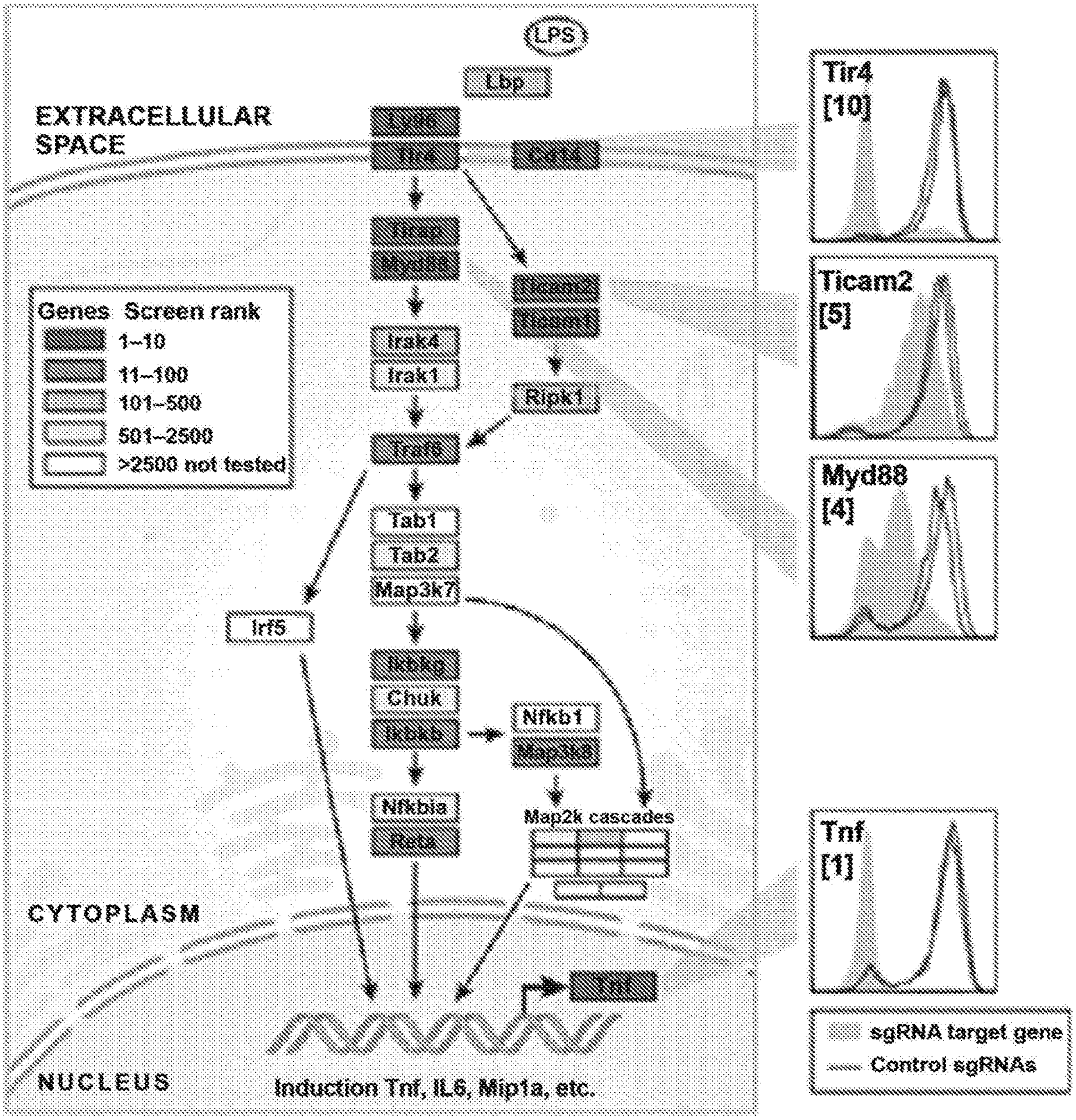
FIG. 47 illustrates a CRISPR screen. TLR pathway with screen hits marked (blue). Illustrative flow cytometry staining of Tnf for (shaded) vs. sgRNA controls (empty).

For example, ~500 cells ensures ≥95% chance of including ≥10 of each cell type, based on the following calculation (FIG. 34). Assume the most conservative scenario that of M cell subtypes (for example, 12), all but one having the lowest predicted proportion (for example, $p_{min}$=5%). Assuming that the Central Limit Theorem holds (a reasonable assumption when solving to detect at least 10 cells of each type) the number of cells of each type i, termed $T_i$, will distribute as $E[T_i]=N*p_{min}$, $STDV[T_i]=\sqrt{(N*p_{min}*(1-p_{min})}$. The minimal N (total number of cells to profile) can be solved such that all (m−1) subtypes have at least n cells (the last, majority, subtype easily clears this threshold since its proportion is much higher). Applicants confirmed with simulation that the strategy conservatively holds in practice even for n<10, and take a margin of additional (conservative) error, to allow for subsequent failed RNA-Seq experiments (<20-30%, depending on protocol).

Screening of Combinatorial Perturbations

In another aspect, the present disclosure provides for methods of screening combinatorial perturbations that provide a certain phenotype (e.g., shuffle-seq). In some embodiments, the methods comprise introducing a plurality of perturbations to a plurality of cells. Each of the plurality of cells may receive at least 1, 2, 3, 4, 5, 10, 20, 30, 40, 50, 60, 70, 80, 90, 100, 11, 120, 130, 140, 150, 160, 170, 180, 190, or 200 perturbations. In some cases, the plurality of perturbations may be pooled before introducing to the plurality of cells.

In some embodiments, the perturbations may comprise polynucleotides. In these cases, the perturbations may be introduced to the cells using methods for delivering nucleotides to cells, e.g., transduction, transformation, transfection, infection, or a combination thereof.

The cells for screening the combinatorial perturbations may be cells that exhibit one or more phenotypes of interest. In some cases, the cells may be derived from a patient or a disease model. For example, the cells may be tumor cells.

The perturbations may comprise polynucleotides. In some cases, the perturbations may be CRISPR-Cas-based and may comprise guide RNAs. For example, the plurality of perturbations comprise a genome-wide library of sgRNA.

In some cases, each perturbation may comprise one or more barcodes. The barcodes may provide identity for the perturbation and the corresponding guide RNAs. In some cases, each perturbation may comprise a unique barcode. Alternatively or additionally, a plurality of perturbations may comprise a common barcode, e.g., barcode indicating the sample source of the plurality of perturbations. In one example, the barcodes may be unique transduction barcodes.

The method for screening combinatorial perturbations may further comprise expanding the plurality of cells introduced with the plurality of perturbations. The expanding results a plurality of clonal populations. Each of the clonal populations may result from expanding one cell comprising one or more introduced perturbations.

The method for screening combinatorial perturbations may further comprise selecting a subpopulation from the clonal cell population. Cells in the subpopulation may have one or more common phenotypes. In some cases, selecting the subpopulation may be performed by selecting cells based on the phenotype, e.g., cell sorting techniques based on viability, fluorescence, radioactivity, magnetic features. For example, the cells may be selected by flow cytometry. The cells may be sorted to different containers, e.g., different wells in a multi-well plate.

The common phenotypes among the cells in the subpopulations may result from the perturbations introduced in the cells. For example, the phenotypes may result from disruption and/or additions of genes by perturbations. In some cases, the phenotype may be the cells' response to a drug, e.g., a drug for treating cancer.

The method for screening combinatorial perturbations may further comprise identifying the combinatorial perturbations introduced in the cells of the subpopulation. In some cases, the identification may be performed by sequencing, e.g., deep sequencing. The identification of combinatorial perturbations may include identifying perturbation correlating to a barcode.

In certain embodiments, combinations of perturbations provided to a cell having a phenotype are determined by splitting a pool of cells provided with the perturbations and having the phenotype into smaller pools and determining the perturbations present in each smaller pool. Based on the probability of having the same perturbations identified in the same individual pools more than once indicates that the perturbations were present in the same cell.

Modelling Genetic Interactions

The method of the invention may be used for determining genetic interactions, including modelling and/or analyzing such interactions. Such genetic interactions form part of cellular circuitry, in that the interactions reflect connections of components within one or more cellular pathways. Such pathways may be intracellular pathways or intercellular pathways.

In some embodiments, the method of the invention may further comprise determining genetic interactions.

In some embodiments, the method of the invention may further comprise confirming genetic interactions with additional genetic manipulations.

The method may further comprise a validation step, wherein additional manipulations are performed in order to confirm previously identified genetic interactions. Such validation step may include in vivo or in vitro experiments, such as gene inactivation, gene deletion, gene activation or overexpression, and combinations thereof. Such genetic manipulations may be performed with any genetic tool available in the art, comprising but not limited to RNAi, CRISPR-Cas based gene editing, nucleic acid transfection, etc.

Genetic Perturbations

In one aspect, said set of P genetic perturbations or said subset of $\pi$ genetic perturbations may comprise single-order genetic perturbations. Within the meaning of the present invention, single-order genetic perturbation means that a given cell undergoes a single genetic perturbation (one perturbation per cell).

In one aspect, said set of P genetic perturbations or said subset of $\pi$ genetic perturbations may comprise combinatorial genetic perturbations. Within the meaning of the present invention, combinatorial or higher-order genetic perturbation means that a given cell undergoes a combination of k single-order genetic perturbations (k perturbations per cell), with $k>1$. In some embodiments, k is an integer ranging from 2 to 15. In some embodiments, k=2, 3, 4, 5, 6, 7, 8, 9 or 10.

Within the meaning of the present invention, said genetic perturbation may comprise gene knock-down (gene repression or gene inactivation), gene knock-out (gene deletion), gene activation, gene insertion, or regulatory element deletion.

Combinations of different types of genetic perturbations are also envisioned within the meaning of the present invention. For example, a combination of genetic perturbations may comprise a knock-down for a first gene, combined to an activation of a second gene, etc.

In one aspect, said set of P genetic perturbations or said subset of $\pi$ genetic perturbations may comprise genome-wide perturbations. Genome-wide perturbations are genetic perturbations that affect loci across the entire genome. Genome-wide perturbation may include single perturbations of >100, >200, >500, >1,000, >2,500, >5,000, >10,000, >15,000 or >20,000 single genomic loci. The present invention encompasses k-order combinations of genome-wide perturbation.

In some embodiments, the method may comprise determining k-order genetic interactions.

In some embodiments, said set of P genetic perturbations may comprise combinatorial genetic perturbations, such as k-order combinations of single-order genetic perturbations, wherein k is an integer ranging from 2 to 15, and step (e) may comprise determining j-order genetic interactions, with $j<k$. Such embodiments rely on sampling higher-order interactions in order to more efficiently infer lower order ones. Given a limited number of possible assays, one is more powered to determine lower order interactions (e.g., 2-, 3-way) from measuring higher order interactions (e.g., 5-way) than from allotting all assays to the lower order, because any higher order interaction carries some information about all interaction terms up to that order (e.g., in compressed sensing, it informs in convolved form on additional Fourier coefficients). Thus, even if most interactions are low order (2- or 3-way) these embodiments are more powered to detect them.

CRISPR-Cas Systems

In some embodiments, RNAi- or CRISPR-Cas-based perturbation may be performed. Said perturbation may be performed (e.g. "delivered") in an array-format or pool-format. Some embodiments may comprise pooled single or combinatorial CRISPR-Cas-based perturbation with a genome-wide library of sgRNAs, wherein each sgRNA comprises a unique molecular identifier. In some embodiments, a step may comprise pooled combinatorial CRISPR-Cas-based perturbation with a genome-wide library of sgRNAs, wherein each sgRNA comprises a unique molecular identifier and is co-delivered with a reporter mRNA.

CRISPR-Cas systems, including CRISPR-Cas9 systems, as used herein, refer to non-naturally occurring systems derived from bacterial Clustered Regularly Interspaced Short Palindromic Repeats loci. These systems generally comprise an enzyme (Cas protein, such as Cas9 protein) and one or more RNAs. Said RNA is a CRISPR RNA and may be an sgRNA. Said RNA and/or said enzyme may be engineered, for example for optimal use in mammalian cells, for optimal delivery therein, for optimal activity therein, for specific uses in gene editing, etc.

sgRNA refers to a CRISPR single-guide RNA. This RNA is a component of a CRISPR-Cas system. The sequence of the sgRNA determines the target sequence for gene editing, knock-down, knock-out, insertion, etc. For genome-wide approaches, it is possible to design and construct suitable sgRNA libraries. Such sgRNAs may be delivered to cells using vector delivery such as viral vector delivery. Combination of CRISPR-Cas-mediated perturbations may be obtained by delivering multiple sgRNAs within a single cell. This may be achieved in pooled format. In the case of sgRNA viral vector delivery, combined perturbation may be obtained by delivering several sgRNA vectors to the same cell. This may also be achieved in pooled format, and number of combined perturbations in a cell then corresponds to the MOI (multiplicity of infection). Using CRISPR-Cas systems, one may generally implement MOI values of up to 10, 12 or 15.

The CRISPR-Cas system may be implemented in order to cause massively combinatorial molecular perturbations (MCMP), including single-order and combinatorial genome-wide genetic perturbations.

CRISPR-Cas-based gene editing allows to perform pooled genome-scale screens with expression readouts in primary cells (A Genome-wide CRISPR Screen in Primary Immune Cells to Dissect Regulatory Networks. Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. Cell July 15. (2015) 2015 Jul. 30; 162(3):675-86. doi:10.1016/j.cell.2015.06.059. Epub 2015 Jul. 16).

In some embodiments, the present invention involves combinatorial perturbations by way of CRISPR-Cas (such as CRISPR-Cas9) assays. In accordance with the present invention, sampling a far-from-exhaustive number of higher order perturbations, when coupled with complex genomic readouts, may suffice to resolve most non-linear relations. Accordingly, in some aspects, the present invention relies on pooled, combinatorial perturbations with genomic readout into Massively Combinatorial Perturbation Profiling (MCPP).

In some embodiments, the method of the invention may comprise one or more CRISPR-Cas-based assays. Such CRISPR-Cas assays are advantageous for implementing a precise perturbation of genes and their expression levels.

In some embodiments, CRISPR-Cas systems may be used to knockout protein-coding genes by frameshifts (indels). Embodiments include efficient and specific CRISPR-Cas9 mediated knockout (Gilbert, L. A., Horlbeck, M. A., Adamson, B., Villalta, J. E., Chen, Y., Whitehead, E. H., Guimaraes, C., Panning, B., Ploegh, H. L., Bassik, M. C., Qi, L. S., Kampmann, M. & Weissman, J. S. Genome-Scale CRISPR-Mediated Control of Gene Repression and Activation. *Cell.* 159, 647-661, doi:10.1016/j.cell.2014.09.029 (2014). PMCID:4253859; Ran, F. A., Cong, L., Yan, W. X., Scott, D. A., Gootenberg, J. S., Kriz, A. J., Zetsche, B., Shalem, O., Wu, X., Makarova, K. S., Koonin, E. V., Sharp, P. A. & Zhang, F. In vivo genome editing using *Staphylococcus aureus* Cas9. *Nature.* 520, 186-191, doi:10.1038/nature14299 (2015). PMCID:4393360), including a CRISPR mediated double-nicking to efficiently modify both alleles of a target gene or multiple target loci (Ran, F. A., Hsu, P. D., Lin, C. Y., Gootenberg, J. S., Konermann, S., Trevino, A. E., Scott, D. A., Inoue, A., Matoba, S., Zhang, Y. & Zhang, F. Double nicking by RNA-guided CRISPR Cas9 for enhanced genome editing specificity. *Cell.* 154, 1380-1389, doi:10.1016/j.cell.2013.08.021 (2013). PMCID: 3856256; Wang, H., Yang, H., Shivalila, C. S., Dawlaty, M. M., Cheng, A. W., Zhang, F. & Jaenisch, R. One-step generation of mice carrying mutations in multiple genes by CRISPR-Cas-mediated genome engineering. *Cell.* 153, 910-918, doi:10.1016/j.cell.2013.04.025 (2013). PMCID: 3969854) and implementation of a smaller Cas9 protein for delivery on smaller vectors (Ran, F. A., Cong, L., Yan, W. X., Scott, D. A., Gootenberg, J. S., Kriz, A. J., Zetsche, B., Shalem, O., Wu, X., Makarova, K. S., Koonin, E. V., Sharp, P. A. & Zhang, F. In vivo genome editing using *Staphylococcus aureus* Cas9. Nature. 520, 186-191, doi:10.1038/nature14299 (2015). PMCID:4393360).

CRISPR-mediated activation or inactivation (CRISPRa/i) systems may be used to activate or inactivate gene transcription. Briefly, a nuclease-dead (deactivated) Cas9 RNA-guided DNA binding domain (dCas9) (Qi, L. S., Larson, M. H., Gilbert, L. A., Doudna, J. A., Weissman, J. S., Arkin, A. P. & Lim, W. A. Repurposing CRISPR as an RNA-guided platform for sequence-specific control of gene expression. Cell. 152, 1173-1183, doi:10.1016/j.cell.2013.02.022 (2013). PMCID:3664290) tethered to transcriptional repressor domains that promote epigenetic silencing (e.g., KRAB) forms a "CRISPRi" (Gilbert, L. A., Larson, M. H., Morsut, L., Liu, Z., Brar, G. A., Torres, S. E., Stern-Ginossar, N., Brandman, O., Whitehead, E. H., Doudna, J. A., Lim, W. A., Weissman, J. S. & Qi, L. S. CRISPR-mediated modular RNA-guided regulation of transcription in eukaryotes. Cell. 154, 442-451, doi:10.1016/j.cell.2013.06.044 (2013). PMCID:3770145; Konermann, S., Brigham, M. D., Trevino, A. E., Hsu, P. D., Heidenreich, M., Cong, L., Platt, R. J., Scott, D. A., Church, G. M. & Zhang, F. Optical control of mammalian endogenous transcription and epigenetic states. Nature. 500, 472-476, doi:10.1038/nature12466 (2013). PMCID:3856241) that represses transcription. To use dCas9 as an activator (CRISPRa), a guide RNA may be engineered to carry RNA binding motifs (e.g., MS2) that recruit effector domains fused to RNA-motif binding proteins, increasing transcription (Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. Nature. 517, 583-588, doi:10.1038/nature14136 (2015). PMCID:4420636).

Perturb-seq combines emerging technologies in the field of genome engineering, single-cell analysis and immunology, in particular the CRISPR-Cas9 system and droplet single-cell sequencing analysis. In certain embodiments, a CRISPR system is used to create an INDEL at a target gene. In other embodiments, epigenetic screening is performed by applying CRISPRa/i/x technology (see, e.g., Konermann et al. "Genome-scale transcriptional activation by an engineered CRISPR-Cas9 complex" Nature. 2014 Dec. 10. doi:10.1038/nature14136; Qi, L. S., et al. (2013). "Repurposing CRISPR as an RNA-guided platform for sequence-specific control of gene expression". Cell. 152 (5): 1173-83; Gilbert, L. A., et al., (2013). "CRISPR-mediated modular RNA-guided regulation of transcription in eukaryotes". Cell. 154 (2): 442-51; Komor et al., 2016, Programmable editing of a target base in genomic DNA without double-stranded DNA cleavage, Nature 533, 420-424; Nishida et al., 2016, Targeted nucleotide editing using hybrid prokaryotic and vertebrate adaptive immune systems, Science 353 (6305); Yang et al., 2016, Engineering and optimising deaminase fusions for genome editing, Nat Commun. 7:13330; Hess et al., 2016, Directed evolution using dCas9-targeted somatic hypermutation in mammalian cells, Nature Methods 13, 1036-1042; and Ma et al., 2016, Targeted AID-mediated mutagenesis (TAM) enables efficient genomic diversification in mammalian cells, Nature Methods 13, 1029-1035). Numerous genetic variants associated with disease phenotypes are found to be in non-coding region of the genome, and frequently coincide with transcription factor (TF) binding sites and non-coding RNA genes. Not being bound by a theory, CRISPRa/i/x approaches may be used to achieve a more thorough and precise understanding of the implication of epigenetic regulation. In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In certain embodiments, other CRISPR-based perturbations are readily compatible with Perturb-seq, including alternative editors such as CRISPR/Cpf1. In certain embodiments, Perturb-seq uses Cpf1 as the CRISPR enzyme for introducing perturbations. Not being bound by a theory, Cpf1 does not require Tracr RNA and is a smaller enzyme, thus allowing higher combinatorial perturbations to be tested.

CRISPR-Cas systems may also be used for the deletion of regulatory elements. To target non-coding elements, pairs of guides may be designed and used to delete regions of a defined size, and tile deletions covering sets of regions in pools. The delivery of two sgRNAs may mediate efficient excision of 500 bp genomic fragments.

CRISPR-Cas systems may also be used for gene editing, e.g. by RNA-templated homologous recombination. Keskin, H., Shen, Y., Huang, F., Patel, M., Yang, T., Ashley, K., Mazin, A. V. & Storici, F. Transcript-RNA-templated DNA recombination and repair. Nature. 515, 436-439, doi: 10.1038/nature13682 (2014).

CRISPR transgenic mice may be used to derive 'CRISPR-ready' cells. 'CRISPR-mice' are mice where the mouse germ line is engineered to harbor key elements of a CRISPR system, and cells require only the programmable (sgRNA) element to activate the CRISPR-Cas system. CRISPR mice include Cas9-transgenic mice (Platt, R. J., Chen, S., Zhou, Y., Yim, M. J., Swiech, L., Kempton, H. R., Dahlman, J. E., Parnas, O., Eisenhaure, T. M., Jovanovic, M., Graham, D. B., Jhunjhunwala, S., Heidenreich, M., Xavier, R. J., Langer, R., Anderson, D. G., Hacohen, N., Regev, A., Feng, G., Sharp, P. A. & Zhang, F. CRISPR-Cas9 knockin mice for genome editing and cancer modeling. *Cell.* 159, 440-455, doi:10.1016/j.cell.2014.09.014 (2014). PMCID:4265475; Parnas O., Jovanovic M., Eisenhaure T M., Herbst R H., Dixit A., Ye C J., Przybylski D., Platt R J. rosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3): 675-86. doi:10.1016/j.cell.2015.06.059. Epub 2015 Jul. 16).

CRISPR-Cas based perturbations, including single order or higher order perturbations, may be implemented in pooled format. The perturbation (screen) may be performed with expression readouts or reporter expression readout (genome-wide reporter-based pooled screens).

CRISPR-Cas functional genomics assays that may be used to cause sets of genetic perturbations are described in Shalem O., Sanjana N E., Zhang F. High-throughput functional genomics using CRISPR-Cas9. *Nat Rev Genet*. May; 16(5):299-311. (2015). doi: 10.1038/nrg3899. Epub 2015 Apr. 9.

sgRNA libraries, including genome-wide libraries of sgRNAs, may be designed as described in Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/j.cell.2015.06.059. Epub 2015 Jul. 16; Sanjana, N. E., Shalem, O. & Zhang, F. Improved vectors and genome-wide libraries for CRISPR screening. *Nat Methods.* 11, 783-784, doi:10.1038/nmeth.3047 (2014); Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout in human screening cells. *Science.* 343, 84-87, doi:10.1126/science.1247005 (2014). PMCID:4089965; Shalem, O., Sanjana, N. E. & Zhang, F. High-throughput functional genomics using CRISPR-Cas9. *Nat Rev Genet.* 16, 299-311, doi:10.1038/nrg3899 (2015).

A pooled genome-wide screen for CRISPR-mediated KO (knock-out) may be performed as in Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout screening in human cells. *Science.* 343, 84-87, doi:10.1126/science.1247005 (2014). PMCID:4089965.

An expression marker-based genome-wide CRISPR screen may be performed as in Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi: 10.1016/j.cell.2015.06.059. Epub 2015 Jul. 16.

A pooled, genome-scale, CRISPRa screen may be performed as in Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. *Nature.* 517, 583-588, doi:10.1038/nature14136 (2015). PMCID:4420636.

Pooled combinatorial perturbations may be performed, where the delivered perturbations and impact (molecular profiling) are determined post hoc, in either a conventional readout (e.g., sorting followed by sequencing) or with high-content single cell genomics.

In some embodiment, the CRISPR-Cas screen is performed by co-delivering multiple sgRNA using viral vector delivery (eg, sgRNA encoding vectors at a relatively high MOI) into cells pre-expressing the Cas9 enzyme to obtain as many higher order combinations as possible. For small sets of ~5 genes one may generate a combinatorially complete ascertained set of all 32 perturbations.

To detect which perturbations were co-delivered in pooled bins, several strategies are envisioned: (1) Combining two or more guide barcodes using in situ PCR in PEG hydrogel that restricts the diffusion of double stranded DNA; (2) Split-pool tagging of guide barcodes in hydrogels, such that only guides from the same cell are tagged with the same sequence; (3) FISH of expressed guides for imaging readouts. In each case it is possible to use an error-correction scheme in the barcodes.

To detect which perturbations were co-delivered with a single cell genomics readout, it is possible to report the (combinatorial) perturbation in a manner compatible with the full genomic readout. For example one may use an sgRNA vector that also highly expresses a synthetic poly-adenylated RNA reporter of the sgRNA barcode. This RNA will be captured along with the cellular mRNA in the transcriptome profiling, eg scRNA-seq (Drop-Seq, see below), or reported by FISH hybridization, such that the same assay ascertains the sgRNAs and their impact on expression (Parnas O., Jovanovic M., Eisenhaure T M., Herbst R H., Dixit A., Ye C J., Przybylski D., Platt R J., Tirosh I., Sanjana N E., Shalem O., Satija R., Raychowdhury R., Mertins P., Carr S A., Zhang F., Hacohen N., Regev A. A Genome-wide CRISPR Screen in Primary Immune Cells to Dissect Regulatory Networks. *Cell* July 15. (2015) 2015 Jul. 30; 162(3):675-86. doi:10.1016/j.cell.2015.06.059. Epub 2015 Jul. 16).

In general, a CRISPR-Cas or CRISPR system as used in herein and in documents, such as WO 2014/093622 (PCT/US2013/074667), refers collectively to transcripts and other elements involved in the expression of or directing the activity of CRISPR-associated ("Cas") genes, including sequences encoding a Cas gene, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), or "RNA(s)" as that term is herein used (e.g., RNA(s) to guide Cas, such as Cas9, e.g. CRISPR RNA and transactivating (tracr) RNA or a single guide RNA (sgRNA) (chimeric RNA)) or other sequences and transcripts from a CRISPR locus. In general, a CRISPR system is characterized by elements that promote the formation of a CRISPR complex at the site of a target sequence (also referred to as a protospacer in the context of an endogenous CRISPR system). See, e.g, Shmakov et al. (2015) "Discovery and Functional Characterization of Diverse Class 2 CRISPR-Cas Systems", Molecular Cell, DOI: dx.doi.org/10.1016/j.molcel.2015.10.008.

In certain embodiments, a protospacer adjacent motif (PAM) or PAM-like motif directs binding of the effector protein complex as disclosed herein to the target locus of interest. In some embodiments, the PAM may be a 5' PAM (i.e., located upstream of the 5' end of the protospacer). In other embodiments, the PAM may be a 3' PAM (i.e., located downstream of the 5' end of the protospacer). The term "PAM" may be used interchangeably with the term "PFS" or "protospacer flanking site" or "protospacer flanking sequence".

In a preferred embodiment, the CRISPR effector protein may recognize a 3' PAM. In certain embodiments, the CRISPR effector protein may recognize a 3' PAM which is 5'H, wherein H is A, C or U.

In the context of formation of a CRISPR complex, "target sequence" refers to a sequence to which a guide sequence is designed to have complementarity, where hybridization between a target sequence and a guide sequence promotes the formation of a CRISPR complex. A target sequence may comprise RNA polynucleotides. The term "target RNA" refers to a RNA polynucleotide being or comprising the target sequence. In other words, the target RNA may be a RNA polynucleotide or a part of a RNA polynucleotide to which a part of the gRNA, i.e. the guide sequence, is designed to have complementarity and to which the effector function mediated by the complex comprising CRISPR effector protein and a gRNA is to be directed. In some embodiments, a target sequence is located in the nucleus or cytoplasm of a cell.

In certain example embodiments, the CRISPR effector protein may be delivered using a nucleic acid molecule encoding the CRISPR effector protein. The nucleic acid molecule encoding a CRISPR effector protein, may advantageously be a codon optimized CRISPR effector protein. An example of a codon optimized sequence, is in this instance a sequence optimized for expression in eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a CRISPR effector protein is a codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at kazusa.or.jp/codon/and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid.

In certain embodiments, the methods as described herein may comprise providing a Cas transgenic cell in which one or more nucleic acids encoding one or more guide RNAs are provided or introduced operably connected in the cell with a regulatory element comprising a promoter of one or more gene of interest. As used herein, the term "Cas transgenic cell" refers to a cell, such as a eukaryotic cell, in which a Cas gene has been genomically integrated. The nature, type, or origin of the cell are not particularly limiting according to the present invention. Also the way the Cas transgene is introduced in the cell may vary and can be any method as is known in the art. In certain embodiments, the Cas transgenic cell is obtained by introducing the Cas transgene in an isolated cell. In certain other embodiments, the Cas transgenic cell is obtained by isolating cells from a Cas transgenic organism. By means of example, and without limitation, the Cas transgenic cell as referred to herein may be derived from a Cas transgenic eukaryote, such as a Cas knock-in eukaryote. Reference is made to WO 2014/093622 (PCT/US13/74667), incorporated herein by reference. Methods of US Patent Publication Nos. 20120017290 and 20110265198 assigned to Sangamo BioSciences, Inc. directed to targeting the Rosa locus may be modified to utilize the CRISPR-Cas system of the present invention. Methods of US Patent Publication No. 20130236946 assigned to Cellectis directed to targeting the Rosa locus may also be modified to utilize the CRISPR-Cas system of the present invention. By means of further example reference is made to Platt et. al. (Cell; 159(2):440-455 (2014)), describing a Cas9 knock-in mouse, which is incorporated herein by reference. The Cas transgene can further comprise a Lox-Stop-polyA-Lox(LSL) cassette thereby rendering Cas expression inducible by Cre recombinase. Alternatively, the Cas transgenic cell may be obtained by introducing the Cas transgene in an isolated cell. Delivery systems for transgenes are well known in the art. By means of example, the Cas transgene may be delivered in for instance eukaryotic cell by means of vector (e.g., AAV, adenovirus, lentivirus) and/or particle and/or nanoparticle delivery, as also described herein elsewhere.

It will be understood by the skilled person that the cell, such as the Cas transgenic cell, as referred to herein may comprise further genomic alterations besides having an integrated Cas gene or the mutations arising from the sequence specific action of Cas when complexed with RNA capable of guiding Cas to a target locus.

In certain aspects the invention involves vectors, e.g. for delivering or introducing in a cell Cas and/or RNA capable of guiding Cas to a target locus (i.e. guide RNA), but also for propagating these components (e.g. in prokaryotic cells). A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety. Thus, the embodiments disclosed herein may also comprise transgenic cells comprising the CRISPR effector system. In certain example embodiments, the transgenic cell may function as an individual discrete volume. In other words samples comprising a masking construct may be delivered to a cell, for example in a suitable delivery vesicle and if the target is present in the delivery vesicle the CRISPR effector is activated and a detectable signal generated.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s); and, when a single vector provides for more than 16 RNA(s), one or more promoter(s) can drive expression of more than one of the RNA(s), e.g., when there are 32 RNA(s), each promoter can drive expression of two RNA(s), and when there are 48 RNA(s), each promoter can drive expression of three RNA(s). By simple arithmetic and well established cloning protocols and the teachings in this disclosure one skilled in the art can readily practice the invention as to the RNA(s) for a suitable exemplary vector such as AAV, and a suitable promoter such as the U6 promoter. For example, the packaging limit of AAV is ~4.7 kb. The length of a single U6-gRNA (plus restriction sites for cloning) is 361 bp. Therefore, the skilled person can readily fit about 12-16, e.g., 13 U6-gRNA cassettes in a single vector. This can be assembled by any suitable means, such as a golden gate strategy used for TALE assembly (genome-engineering.org/taleffectors/). The skilled person can also use a tandem guide strategy to increase the number of U6-gRNAs by approximately 1.5 times, e.g., to increase from 12-16, e.g., 13 to approximately 18-24, e.g., about 19 U6-gRNAs. Therefore, one skilled in the art can readily reach approximately 18-24, e.g., about 19 promoter-RNAs, e.g., U6-gRNAs in a single vector, e.g., an AAV vector. A further means for increasing the number of promoters and RNAs in a vector is to use a single promoter (e.g., U6) to express an array of RNAs separated by cleavable sequences. And an even further means for increasing the number of promoter-RNAs in a vector, is to express an array of promoter-RNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short and nature.com/mt/journal/v16/n9/abs/mt2008144a.html). In an advantageous embodiment, AAV may package U6 tandem gRNA targeting up to about 50 genes. Accordingly, from the knowledge in the art and the teachings in this disclosure the skilled person can readily make and use vector(s), e.g., a single vector, expressing multiple RNAs or guides under the control or operatively or functionally linked to one or more promoters-especially as to the numbers of RNAs or guides discussed herein, without any undue experimentation.

The guide RNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Additional effectors for use according to the invention can be identified by their proximity to cas1 genes, for example, though not limited to, within the region 20 kb from the start of the cas1 gene and 20 kb from the end of the cas1 gene. In certain embodiments, the effector protein comprises at least one HEPN domain and at least 500 amino acids, and wherein the C2c2 effector protein is naturally present in a prokaryotic genome within 20 kb upstream or downstream of a Cas gene or a CRISPR array. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. In certain example embodiments, the C2c2 effector protein is naturally present in a prokaryotic genome within 20 kb upstream or downstream of a Cas 1 gene. The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of. Orthologous proteins may but need not be structurally related, or are only partially structurally related.

Guide Molecules

The methods described herein may be used to screen inhibition of CRISPR systems employing different types of guide molecules. As used herein, the term "guide sequence" and "guide molecule" in the context of a CRISPR-Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. The guide sequences made using the methods disclosed herein may be a full-length guide sequence, a truncated guide sequence, a full-length sgRNA sequence, a truncated sgRNA sequence, or an E+F sgRNA sequence. In some embodiments, the degree of complementarity of the guide sequence to a given target sequence, when optimally aligned using a suitable alignment algorithm, is about or more than about 50%, 60%, 75%, 80%, 85%, 90%, 95%, 97.5%, 99%, or more. In certain example embodiments, the guide molecule comprises a guide sequence that may be designed to have at least one mismatch with the target sequence, such that a RNA duplex formed between the guide sequence and the target sequence. Accordingly, the degree of complementarity is preferably less than 99%. For instance, where the guide sequence consists of 24 nucleotides, the degree of complementarity is more particularly about 96% or less. In particular embodiments, the guide sequence is designed to have a stretch of two or more adjacent mismatching nucleotides, such that the degree of complementarity over the entire guide sequence is further reduced. For instance, where the guide sequence consists of 24 nucleotides, the degree of complementarity is more particularly about 96% or less, more particularly, about 92% or less, more particularly about 88% or less, more particularly about 84% or less, more particularly about 80% or less, more particularly about 76% or less, more particularly about 72% or less, depending on whether the stretch of two or more mismatching nucleotides encompasses 2, 3, 4, 5, 6 or 7 nucleotides, etc. In some embodiments, aside from the stretch of one or more mismatching nucleotides, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), Clustal W, Clustal X, BLAT, Novoalign (Novocraft Technologies; available at www.novocraft.com), ELAND (Illumina, San Diego, CA), SOAP (available at soap.genomics.org.com), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay. For example, the components of a nucleic acid-targeting CRISPR system sufficient to form a nucleic acid-targeting complex, including the guide sequence to be tested, may be provided to a host cell having the corresponding target nucleic acid sequence, such as by transfection with vectors encoding the components of the nucleic acid-targeting complex, followed by an assessment of preferential targeting (e.g., cleavage) within the target nucleic acid sequence, such as by Surveyor assay as described herein. Similarly, cleavage of a target nucleic acid sequence (or a sequence in the vicinity thereof) may be evaluated in a test tube by providing the target nucleic acid sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art. A guide sequence, and hence a nucleic acid-targeting guide RNA may be selected to target any target nucleic acid sequence.

In certain embodiments, the guide sequence or spacer length of the guide molecules is from 15 to 50 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In certain example embodiment, the guide sequence is 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nt.

In some embodiments, the guide sequence is an RNA sequence of between 10 to 50 nt in length, but more particularly of about 20-30 nt advantageously about 20 nt, 23-25 nt or 24 nt. The guide sequence is selected so as to ensure that it hybridizes to the target sequence. This is described more in detail below. Selection can encompass further steps which increase efficacy and specificity.

In some embodiments, the guide sequence has a canonical length (e.g., about 15-30 nt) is used to hybridize with the target RNA or DNA. In some embodiments, a guide molecule is longer than the canonical length (e.g., >30 nt) is used to hybridize with the target RNA or DNA, such that a region of the guide sequence hybridizes with a region of the RNA or DNA strand outside of the Cas-guide target complex. This can be of interest where additional modifications, such deamination of nucleotides is of interest. In alternative embodiments, it is of interest to maintain the limitation of the canonical guide sequence length.

In some embodiments, the sequence of the guide molecule (direct repeat and/or spacer) is selected to reduce the degree secondary structure within the guide molecule. In some embodiments, about or less than about 75%, 50%, 40%, 30%, 25%, 20%, 15%, 10%, 5%, 1%, or fewer of the nucleotides of the nucleic acid-targeting guide RNA participate in self-complementary base pairing when optimally folded. Optimal folding may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g., A. R. Gruber et al., 2008, Cell 106(1): 23-24; and P A Carr and G M Church, 2009, Nature Biotechnology 27(12): 1151-62).

In some embodiments, it is of interest to reduce the susceptibility of the guide molecule to RNA cleavage, such as to cleavage by Cas13. Accordingly, in particular embodiments, the guide molecule is adjusted to avoid cleavage by Cas13 or other RNA-cleaving enzymes.

In certain embodiments, the guide molecule comprises non-naturally occurring nucleic acids and/or non-naturally occurring nucleotides and/or nucleotide analogs, and/or chemically modifications. Preferably, these non-naturally occurring nucleic acids and non-naturally occurring nucleotides are located outside the guide sequence. Non-naturally occurring nucleic acids can include, for example, mixtures of naturally and non-naturally occurring nucleotides. Non-naturally occurring nucleotides and/or nucleotide analogs may be modified at the ribose, phosphate, and/or base moiety. In an embodiment of the invention, a guide nucleic acid comprises ribonucleotides and non-ribonucleotides. In one such embodiment, a guide comprises one or more ribonucleotides and one or more deoxyribonucleotides. In an embodiment of the invention, the guide comprises one or more non-naturally occurring nucleotide or nucleotide analog such as a nucleotide with phosphorothioate linkage, a locked nucleic acid (LNA) nucleotides comprising a methylene bridge between the 2' and 4' carbons of the ribose ring, or bridged nucleic acids (BNA). Other examples of modified nucleotides include 2'-O-methyl analogs, 2'-deoxy analogs, or 2'-fluoro analogs. Further examples of modified bases include, but are not limited to, 2-aminopurine, 5-bromo-uridine, pseudouridine, inosine, 7-methylguanosine. Examples of guide RNA chemical modifications include, without limitation, incorporation of 2'-O-methyl (M), 2'-O-methyl 3'phosphorothioate (MS), S-constrained ethyl (cEt), or 2'-O-methyl 3'thioPACE (MSP) at one or more terminal nucleotides. Such chemically modified guides can comprise increased stability and increased activity as compared to unmodified guides, though on-target vs. off-target specificity is not predictable. (See, Hendel, 2015, Nat Biotechnol. 33(9):985-9, doi:10.1038/nbt.3290, published online 29 Jun. 2015 Ragdarm et al., 0215, *PNAS*, E7110-E7111; Allerson et al., *J. Med. Chem.* 2005, 48:901-904; Bramsen et al., *Front. Genet.*, 2012, 3:154; Deng et al., *PNAS*, 2015, 112:11870-11875; Sharma et al., *MedChemComm.*, 2014, 5:1454-1471; Hendel et al., *Nat. Biotechnol.* (2015) 33(9): 985-989; Li et al., *Nature Biomedical Engineering*, 2017, 1, 0066 DOI: 10.1038/s41551-017-0066). In some embodiments, the 5' and/or 3' end of a guide RNA is modified by a variety of functional moieties including fluorescent dyes, polyethylene glycol, cholesterol, proteins, or detection tags. (See Kelly et al., 2016, *J. Biotech.* 233:74-83). In certain embodiments, a guide comprises ribonucleotides in a region that binds to a target RNA and one or more deoxyribonucleotides and/or nucleotide analogs in a region that binds to Cas13. In an embodiment of the invention, deoxyribonucleotides and/or nucleotide analogs are incorporated in engineered guide structures, such as, without limitation, stem-loop regions, and the seed region. For Cas13 guide, in certain embodiments, the modification is not in the 5'-handle of the stem-loop regions. Chemical modification in the 5'-handle of the stem-loop region of a guide may abolish its function (see Li, et al., *Nature Biomedical Engineering*, 2017, 1:0066). In certain embodiments, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, or 75 nucleotides of a guide is chemically modified. In some embodiments, 3-5 nucleotides at either the 3' or the 5' end of a guide is chemically modified. In some embodiments, only minor modifications are introduced in the seed region, such as 2'-F modifications. In some embodiments, 2'-F modification is introduced at the 3' end of a guide. In certain embodiments, three to five nucleotides at the 5' and/or the 3' end of the guide are chemically modified with 2'-O-methyl (M), 2'-O-methyl 3' phosphorothioate (MS), S-constrained ethyl (cEt), or 2'-O-methyl 3' thioPACE (MSP). Such modification can enhance genome editing efficiency (see Hendel et al., *Nat. Biotech-*

*nol.* (2015) 33 (9): 985-989). In certain embodiments, all of the phosphodiester bonds of a guide are substituted with phosphorothioates (PS) for enhancing levels of gene disruption. In certain embodiments, more than five nucleotides at the 5' and/or the 3' end of the guide are chemicially modified with 2'-O-Me, 2'-F or S-constrained ethyl(cEt). Such chemically modified guide can mediate enhanced levels of gene disruption (see Ragdarm et al., 0215, PNAS, E7110-E7111). In an embodiment of the invention, a guide is modified to comprise a chemical moiety at its 3' and/or 5' end. Such moieties include, but are not limited to amine, azide, alkyne, thio, dibenzocyclooctyne (DBCO), or Rhodamine. In certain embodiment, the chemical moiety is conjugated to the guide by a linker, such as an alkyl chain. In certain embodiments, the chemical moiety of the modified guide can be used to attach the guide to another molecule, such as DNA, RNA, protein, or nanoparticles. Such chemically modified guide can be used to identify or enrich cells generically edited by a CRISPR system (see Lee et al., *eLife,* 2017, 6: e25312, DOI:10.7554).

In some embodiments, the modification to the guide is a chemical modification, an insertion, a deletion or a split. In some embodiments, the chemical modification includes, but is not limited to, incorporation of 2'-O-methyl (M) analogs, 2'-deoxy analogs, 2-thiouridine analogs, N6-methyladenosine analogs, 2'-fluoro analogs, 2-aminopurine, 5-bromo-uridine, pseudouridine (Ψ), N1-methylpseudouridine (me1Ψ), 5-methoxyuridine (5moU), inosine, 7-methylguanosine, 2'-O-methyl 3'phosphorothioate (MS), S-constrained ethyl (cEt), phosphorothioate (PS), or 2'-O-methyl 3'thioPACE (MSP). In some embodiments, the guide comprises one or more of phosphorothioate modifications. In certain embodiments, at least 1, 2, 3, 4, 5, 6, 7, 8, 9, 10, 11, 12, 13, 14, 15, 16, 17, 18, 19, 20, or 25 nucleotides of the guide are chemically modified. In certain embodiments, one or more nucleotides in the seed region are chemically modified. In certain embodiments, one or more nucleotides in the 3'-terminus are chemically modified. In certain embodiments, none of the nucleotides in the 5'-handle is chemically modified. In some embodiments, the chemical modification in the seed region is a minor modification, such as incorporation of a 2'-fluoro analog. In a specific embodiment, one nucleotide of the seed region is replaced with a 2'-fluoro analog. In some embodiments, 5 to 10 nucleotides in the 3'-terminus are chemically modified. Such chemical modifications at the 3'-terminus of the Cas13 CrRNA may improve Cas13 activity. In a specific embodiment, 1, 2, 3, 4, 5, 6, 7, 8, 9 or 10 nucleotides in the 3'-terminus are replaced with 2'-fluoro analogues. In a specific embodiment, 1, 2, 3, 4, 5, 6, 7, 8, 9 or 10 nucleotides in the 3'-terminus are replaced with 2'-O-methyl (M) analogs.

In some embodiments, the loop of the 5'-handle of the guide is modified. In some embodiments, the loop of the 5'-handle of the guide is modified to have a deletion, an insertion, a split, or chemical modifications. In certain embodiments, the modified loop comprises 3, 4, or 5 nucleotides. In certain embodiments, the loop comprises the sequence of UCUU, UUUU, UAUU, or UGUU.

In some embodiments, the guide molecule forms a stem-loop with a separate non-covalently linked sequence, which can be DNA or RNA. In particular embodiments, the sequences forming the guide are first synthesized using the standard phosphoramidite synthetic protocol (Herdewijn, P., ed., Methods in Molecular Biology Col 288, Oligonucleotide Synthesis: Methods and Applications, Humana Press, New Jersey (2012)). In some embodiments, these sequences can be functionalized to contain an appropriate functional group for ligation using the standard protocol known in the art (Hermanson, G. T., Bioconjugate Techniques, Academic Press (2013)). Examples of functional groups include, but are not limited to, hydroxyl, amine, carboxylic acid, carboxylic acid halide, carboxylic acid active ester, aldehyde, carbonyl, chlorocarbonyl, imidazolylcarbonyl, hydrazide, semicarbazide, thiosemicarbazide, thiol, maleimide, haloalkyl, sufonyl, ally, propargyl, diene, alkyne, and azide. Once this sequence is functionalized, a covalent chemical bond or linkage can be formed between this sequence and the direct repeat sequence. Examples of chemical bonds include, but are not limited to, those based on carbamates, ethers, esters, amides, imines, amidines, aminotriazines, hydrazine, disulfides, thioethers, thioesters, phosphorothioates, phosphorodithioates, sulfonamides, sulfonates, sulfones, sulfoxides, ureas, thioureas, hydrazide, oxime, triazole, photolabile linkages, C—C bond forming groups such as Diels-Alder cyclo-addition pairs or ring-closing metathesis pairs, and Michael reaction pairs.

In some embodiments, these stem-loop forming sequences can be chemically synthesized. In some embodiments, the chemical synthesis uses automated, solid-phase oligonucleotide synthesis machines with 2'-acetoxyethyl orthoester (2'-ACE) (Scaringe et al., J. Am. Chem. Soc. (1998) 120: 11820-11821; Scaringe, Methods Enzymol. (2000) 317: 3-18) or 2'-thionocarbamate (2'-TC) chemistry (Dellinger et al., J. Am. Chem. Soc. (2011) 133: 11540-11546; Hendel et al., Nat. Biotechnol. (2015) 33:985-989).

In certain embodiments, the guide molecule comprises (1) a guide sequence capable of hybridizing to a target locus and (2) a tracr mate or direct repeat sequence whereby the direct repeat sequence is located upstream (i.e., 5') from the guide sequence. In a particular embodiment the seed sequence (i.e. the sequence essential critical for recognition and/or hybridization to the sequence at the target locus) of the guide sequence is approximately within the first 10 nucleotides of the guide sequence.

In a particular embodiment the guide molecule comprises a guide sequence linked to a direct repeat sequence, wherein the direct repeat sequence comprises one or more stem loops or optimized secondary structures. In particular embodiments, the direct repeat has a minimum length of 16 nts and a single stem loop. In further embodiments the direct repeat has a length longer than 16 nts, preferably more than 17 nts, and has more than one stem loops or optimized secondary structures. In particular embodiments the guide molecule comprises or consists of the guide sequence linked to all or part of the natural direct repeat sequence. A typical Type V or Type VI CRISPR-cas guide molecule comprises (in 3' to 5' direction or in 5' to 3' direction): a guide sequence a first complimentary stretch (the “repeat”), a loop (which is typically 4 or 5 nucleotides long), a second complimentary stretch (the “anti-repeat” being complimentary to the repeat), and a poly A (often poly U in RNA) tail (terminator). In certain embodiments, the direct repeat sequence retains its natural architecture and forms a single stem loop. In particular embodiments, certain aspects of the guide architecture can be modified, for example by addition, subtraction, or substitution of features, whereas certain other aspects of guide architecture are maintained. Preferred locations for engineered guide molecule modifications, including but not limited to insertions, deletions, and substitutions include guide termini and regions of the guide molecule that are exposed when complexed with the CRISPR-Cas protein and/or target, for example the stemloop of the direct repeat sequence.

In particular embodiments, the stem comprises at least about 4 bp comprising complementary X and Y sequences, although stems of more, e.g., 5, 6, 7, 8, 9, 10, 11 or 12 or fewer, e.g., 3, 2, base pairs are also contemplated. Thus, for example X2-10 and Y2-10 (wherein X and Y represent any complementary set of nucleotides) may be contemplated. In one aspect, the stem made of the X and Y nucleotides, together with the loop will form a complete hairpin in the overall secondary structure; and, this may be advantageous and the amount of base pairs can be any amount that forms a complete hairpin. In one aspect, any complementary X: Y basepairing sequence (e.g., as to length) is tolerated, so long as the secondary structure of the entire guide molecule is preserved. In one aspect, the loop that connects the stem made of X: Y basepairs can be any sequence of the same length (e.g., 4 or 5 nucleotides) or longer that does not interrupt the overall secondary structure of the guide molecule. In one aspect, the stemloop can further comprise, e.g. an MS2 aptamer. In one aspect, the stem comprises about 5-7 bp comprising complementary X and Y sequences, although stems of more or fewer basepairs are also contemplated. In one aspect, non-Watson Crick basepairing is contemplated, where such pairing otherwise generally preserves the architecture of the stemloop at that position.

In particular embodiments the natural hairpin or stemloop structure of the guide molecule is extended or replaced by an extended stemloop. It has been demonstrated that extension of the stem can enhance the assembly of the guide molecule with the CRISPR-Cas protein (Chen et al. Cell. (2013); 155(7): 1479-1491). In particular embodiments the stem of the stemloop is extended by at least 1, 2, 3, 4, 5 or more complementary basepairs (i.e. corresponding to the addition of 2, 4, 6, 8, 10 or more nucleotides in the guide molecule). In particular embodiments these are located at the end of the stem, adjacent to the loop of the stemloop.

In particular embodiments, the susceptibility of the guide molecule to RNAses or to decreased expression can be reduced by slight modifications of the sequence of the guide molecule which do not affect its function. For instance, in particular embodiments, premature termination of transcription, such as premature transcription of U6 Pol-III, can be removed by modifying a putative Pol-III terminator (4 consecutive U's) in the guide molecules sequence. Where such sequence modification is required in the stemloop of the guide molecule, it is preferably ensured by a basepair flip.

In a particular embodiment, the direct repeat may be modified to comprise one or more protein-binding RNA aptamers. In a particular embodiment, one or more aptamers may be included such as part of optimized secondary structure. Such aptamers may be capable of binding a bacteriophage coat protein as detailed further herein.

In some embodiments, the guide molecule forms a duplex with a target RNA comprising at least one target cytosine residue to be edited. Upon hybridization of the guide RNA molecule to the target RNA, the cytidine deaminase binds to the single strand RNA in the duplex made accessible by the mismatch in the guide sequence and catalyzes deamination of one or more target cytosine residues comprised within the stretch of mismatching nucleotides.

A guide sequence, and hence a nucleic acid-targeting guide RNA may be selected to target any target nucleic acid sequence. The target sequence may be mRNA.

In certain embodiments, the target sequence should be associated with a PAM (protospacer adjacent motif) or PFS (protospacer flanking sequence or site); that is, a short sequence recognized by the CRISPR complex. Depending on the nature of the CRISPR-Cas protein, the target sequence should be selected such that its complementary sequence in the DNA duplex (also referred to herein as the non-target sequence) is upstream or downstream of the PAM. In the embodiments of the present invention where the CRISPR-Cas protein is a Cas13 protein, the compelementary sequence of the target sequence is downstream or 3' of the PAM or upstream or 5' of the PAM. The precise sequence and length requirements for the PAM differ depending on the Cas13 protein used, but PAMs are typically 2-5 base pair sequences adjacent the protospacer (that is, the target sequence). Examples of the natural PAM sequences for different Cas13 orthologues are provided herein below and the skilled person will be able to identify further PAM sequences for use with a given Cas13 protein.

Further, engineering of the PAM Interacting (PI) domain may allow programing of PAM specificity, improve target site recognition fidelity, and increase the versatility of the CRISPR-Cas protein, for example as described for Cas9 in Kleinstiver B P et al. Engineered CRISPR-Cas9 nucleases with altered PAM specificities. Nature. 2015 Jul. 23; 523 (7561):481-5. doi:10.1038/nature14592. As further detailed herein, the skilled person will understand that Cas13 proteins may be modified analogously.

In particular embodiment, the guide is an escorted guide. By "escorted" is meant that the CRISPR-Cas system or complex or guide is delivered to a selected time or place within a cell, so that activity of the CRISPR-Cas system or complex or guide is spatially or temporally controlled. For example, the activity and destination of the 3 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time.

The escorted CRISPR-Cas systems or complexes have a guide molecule with a functional structure designed to improve guide molecule structure, architecture, stability, genetic expression, or any combination thereof. Such a structure can include an aptamer.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R.

Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

Accordingly, in particular embodiments, the guide molecule is modified, e.g., by one or more aptamer(s) designed to improve guide molecule delivery, including delivery across the cellular membrane, to intracellular compartments, or into the nucleus. Such a structure can include, either in addition to the one or more aptamer(s) or without such one or more aptamer(s), moiety(ies) so as to render the guide molecule deliverable, inducible or responsive to a selected effector. The invention accordingly comprehends an guide molecule that responds to normal or pathological physiological conditions, including without limitation pH, hypoxia, $O_2$ concentration, temperature, protein concentration, enzymatic concentration, lipid structure, light exposure, mechanical disruption (e.g. ultrasound waves), magnetic fields, electric fields, or electromagnetic radiation.

Light responsiveness of an inducible system may be achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

The invention contemplates energy sources such as electromagnetic radiation, sound energy or thermal energy to induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 $mW/cm^2$. In a preferred embodiment, a stimulation paradigm of as low as 0.25 sec every 15 sec should result in maximal activation.

The chemical or energy sensitive guide may undergo a conformational change upon induction by the binding of a chemical source or by the energy allowing it act as a guide and have the Cas13 CRISPR-Cas system or complex function. The invention can involve applying the chemical source or energy so as to have the guide function and the Cas13 CRISPR-Cas system or complex function; and optionally further determining that the expression of the genomic locus is altered.

There are several different designs of this chemical inducible system: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html).

A chemical inducible system can be an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cas13 CRISPR-Cas complex or system, and the binding will induce the change of sub-cellular localization of the polypeptide, leading to the entire polypeptide entering the nucleus of cells. Once inside the nucleus, the guide protein and the other components of the Cas13 CRISPR-Cas complex will be active and modulating target gene expression in cells.

While light activation may be an advantageous embodiment, sometimes it may be disadvantageous especially for in vivo applications in which the light may not penetrate the skin or other organs. In this instance, other methods of energy activation are contemplated, in particular, electric field energy and/or ultrasound which have a similar effect.

Electric field energy is preferably administered substantially as described in the art, using one or more electric pulses of from about 1 Volt/cm to about 10 kVolts/cm under in vivo conditions. Instead of or in addition to the pulses, the electric field may be delivered in a continuous manner. The electric pulse may be applied for between 1 μs and 500 milliseconds, preferably between 1 μs and 100 milliseconds. The electric field may be applied continuously or in a pulsed manner for 5 about minutes.

As used herein, 'electric field energy' is the electrical energy to which a cell is exposed. Preferably the electric field has a strength of from about 1 Volt/cm to about 10 kVolts/cm or more under in vivo conditions (see WO97/49450).

As used herein, the term "electric field" includes one or more pulses at variable capacitance and voltage and including exponential and/or square wave and/or modulated wave and/or modulated square wave forms. References to electric fields and electricity should be taken to include reference the presence of an electric potential difference in the environment of a cell. Such an environment may be set up by way of static electricity, alternating current (AC), direct current (DC), etc, as known in the art. The electric field may be uniform, non-uniform or otherwise, and may vary in strength and/or direction in a time dependent manner.

Single or multiple applications of electric field, as well as single or multiple applications of ultrasound are also possible, in any order and in any combination. The ultrasound and/or the electric field may be delivered as single or multiple continuous applications, or as pulses (pulsatile delivery).

Electroporation has been used in both in vitro and in vivo procedures to introduce foreign material into living cells. With in vitro applications, a sample of live cells is first mixed with the agent of interest and placed between electrodes such as parallel plates. Then, the electrodes apply an electrical field to the cell/implant mixture. Examples of systems that perform in vitro electroporation include the Electro Cell Manipulator ECM600 product, and the Electro Square Porator T820, both made by the BTX Division of Genetronics, Inc (see U.S. Pat. No. 5,869,326).

The known electroporation techniques (both in vitro and in vivo) function by applying a brief high voltage pulse to electrodes positioned around the treatment region. The electric field generated between the electrodes causes the cell membranes to temporarily become porous, whereupon molecules of the agent of interest enter the cells. In known electroporation applications, this electric field comprises a single square wave pulse on the order of 1000 V/cm, of about 100.mu.s duration. Such a pulse may be generated, for example, in known applications of the Electro Square Porator T820.

Preferably, the electric field has a strength of from about 1 V/cm to about 10 kV/cm under in vitro conditions. Thus, the electric field may have a strength of 1 V/cm, 2 V/cm, 3 V/cm, 4 V/cm, 5 V/cm, 6 V/cm, 7 V/cm, 8 V/cm, 9 V/cm, 10 V/cm, 20 V/cm, 50 V/cm, 100 V/cm, 200 V/cm, 300 V/cm, 400 V/cm, 500 V/cm, 600 V/cm, 700 V/cm, 800 V/cm, 900 V/cm, 1 kV/cm, 2 kV/cm, 5 kV/cm, 10 kV/cm, 20 kV/cm, 50 kV/cm or more. More preferably from about 0.5 kV/cm to about 4.0 kV/cm under in vitro conditions. Preferably the electric field has a strength of from about 1 V/cm to about 10 kV/cm under in vivo conditions. However, the electric field strengths may be lowered where the number of pulses delivered to the target site are increased. Thus, pulsatile delivery of electric fields at lower field strengths is envisaged.

Preferably the application of the electric field is in the form of multiple pulses such as double pulses of the same strength and capacitance or sequential pulses of varying strength and/or capacitance. As used herein, the term "pulse" includes one or more electric pulses at variable capacitance and voltage and including exponential and/or square wave and/or modulated wave/square wave forms:

Preferably the electric pulse is delivered as a waveform selected from an exponential wave form, a square wave form, a modulated wave form and a modulated square wave form.

A preferred embodiment employs direct current at low voltage. Thus, Applicants disclose the use of an electric field which is applied to the cell, tissue or tissue mass at a field strength of between 1V/cm and 20V/cm, for a period of 100 milliseconds or more, preferably 15 minutes or more.

Ultrasound is advantageously administered at a power level of from about 0.05 W/cm2 to about 100 W/cm$^2$. Diagnostic or therapeutic ultrasound may be used, or combinations thereof.

As used herein, the term "ultrasound" refers to a form of energy which consists of mechanical vibrations the frequencies of which are so high they are above the range of human hearing. Lower frequency limit of the ultrasonic spectrum may generally be taken as about 20 kHz. Most diagnostic applications of ultrasound employ frequencies in the range 1 and 15 MHz' (From Ultrasonics in Clinical Diagnosis, P. N. T. Wells, ed., 2nd. Edition, Publ. Churchill Livingstone [Edinburgh, London & NY, 1977]).

Ultrasound has been used in both diagnostic and therapeutic applications. When used as a diagnostic tool ("diagnostic ultrasound"), ultrasound is typically used in an energy density range of up to about 100 mW/cm$^2$ (FDA recommendation), although energy densities of up to 750 mW/cm$^2$ have been used. In physiotherapy, ultrasound is typically used as an energy source in a range up to about 3 to 4 W/cm$^2$ (WHO recommendation). In other therapeutic applications, higher intensities of ultrasound may be employed, for example, HIFU at 100 W/cm up to 1 kW/cm2 (or even higher) for short periods of time. The term "ultrasound" as used in this specification is intended to encompass diagnostic, therapeutic and focused ultrasound.

Focused ultrasound (FUS) allows thermal energy to be delivered without an invasive probe (see Morocz et al 1998 Journal of Magnetic Resonance Imaging Vol. 8, No. 1, pp. 136-142). Another form of focused ultrasound is high intensity focused ultrasound (HIFU) which is reviewed by Moussatov et al in Ultrasonics (1998) Vol. 36, No. 8, pp. 893-900 and TranHuuHue et al in Acustica (1997) Vol. 83, No. 6, pp. 1103-1106.

Preferably, a combination of diagnostic ultrasound and a therapeutic ultrasound is employed. This combination is not intended to be limiting, however, and the skilled reader will appreciate that any variety of combinations of ultrasound may be used. Additionally, the energy density, frequency of ultrasound, and period of exposure may be varied.

Preferably the exposure to an ultrasound energy source is at a power density of from about 0.05 to about 100 Wcm-2. Even more preferably, the exposure to an ultrasound energy source is at a power density of from about 1 to about 15 Wcm-2.

Preferably the exposure to an ultrasound energy source is at a frequency of from about 0.015 to about 10.0 MHz. More preferably the exposure to an ultrasound energy source is at a frequency of from about 0.02 to about 5.0 MHz or about 6.0 MHz. Most preferably, the ultrasound is applied at a frequency of 3 MHz.

Preferably the exposure is for periods of from about 10 milliseconds to about 60 minutes. Preferably the exposure is for periods of from about 1 second to about 5 minutes. More preferably, the ultrasound is applied for about 2 minutes. Depending on the particular target cell to be disrupted, however, the exposure may be for a longer duration, for example, for 15 minutes.

Advantageously, the target tissue is exposed to an ultrasound energy source at an acoustic power density of from about 0.05 Wcm-2 to about 10 Wcm-2 with a frequency ranging from about 0.015 to about 10 MHz (see WO 98/52609). However, alternatives are also possible, for example, exposure to an ultrasound energy source at an acoustic power density of above 100 Wcm-2, but for reduced periods of time, for example, 1000 Wcm-2 for periods in the millisecond range or less.

Preferably the application of the ultrasound is in the form of multiple pulses; thus, both continuous wave and pulsed wave (pulsatile delivery of ultrasound) may be employed in any combination. For example, continuous wave ultrasound may be applied, followed by pulsed wave ultrasound, or vice versa. This may be repeated any number of times, in any order and combination. The pulsed wave ultrasound may be applied against a background of continuous wave ultrasound, and any number of pulses may be used in any number of groups.

Preferably, the ultrasound may comprise pulsed wave ultrasound. In a highly preferred embodiment, the ultrasound is applied at a power density of 0.7 Wcm-2 or 1.25 Wcm-2 as a continuous wave. Higher power densities may be employed if pulsed wave ultrasound is used.

Use of ultrasound is advantageous as, like light, it may be focused accurately on a target. Moreover, ultrasound is advantageous as it may be focused more deeply into tissues unlike light. It is therefore better suited to whole-tissue penetration (such as but not limited to a lobe of the liver) or whole organ (such as but not limited to the entire liver or an entire muscle, such as the heart) therapy. Another important advantage is that ultrasound is a non-invasive stimulus which is used in a wide variety of diagnostic and therapeutic applications. By way of example, ultrasound is well known in medical imaging techniques and, additionally, in orthopedic therapy. Furthermore, instruments suitable for the application of ultrasound to a subject vertebrate are widely available and their use is well known in the art.

In particular embodiments, the guide molecule is modified by a secondary structure to increase the specificity of the CRISPR-Cas system and the secondary structure can protect against exonuclease activity and allow for 5' additions to the guide sequence also referred to herein as a protected guide molecule.

In one aspect, the invention provides for hybridizing a “protector RNA” to a sequence of the guide molecule, wherein the “protector RNA” is an RNA strand complementary to the 3' end of the guide molecule to thereby generate a partially double-stranded guide RNA. In an embodiment of the invention, protecting mismatched bases (i.e. the bases of the guide molecule which do not form part of the guide sequence) with a perfectly complementary protector sequence decreases the likelihood of target RNA binding to the mismatched basepairs at the 3' end. In particular embodiments of the invention, additional sequences comprising an extended length may also be present within the guide molecule such that the guide comprises a protector sequence within the guide molecule. This “protector sequence” ensures that the guide molecule comprises a “protected sequence” in addition to an “exposed sequence” (comprising the part of the guide sequence hybridizing to the target sequence). In particular embodiments, the guide molecule is modified by the presence of the protector guide to comprise a secondary structure such as a hairpin. Advantageously there are three or four to thirty or more, e.g., about 10 or more, contiguous base pairs having complementarity to the protected sequence, the guide sequence or both. It is advantageous that the protected portion does not impede thermodynamics of the CRISPR-Cas system interacting with its target. By providing such an extension including a partially double stranded guide molecule, the guide molecule is considered protected and results in improved specific binding of the CRISPR-Cas complex, while maintaining specific activity.

In particular embodiments, use is made of a truncated guide (tru-guide), i.e. a guide molecule which comprises a guide sequence which is truncated in length with respect to the canonical guide sequence length. As described by Nowak et al. (Nucleic Acids Res (2016) 44 (20): 9555-9564), such guides may allow catalytically active CRISPR-Cas enzyme to bind its target without cleaving the target RNA. In particular embodiments, a truncated guide is used which allows the binding of the target but retains only nickase activity of the CRISPR-Cas enzyme.

CRISPR RNA-Targeting Effector Proteins

In one example embodiment, the CRISPR system effector protein is an RNA-targeting effector protein. In certain embodiments, the CRISPR system effector protein is a Type VI CRISPR system targeting RNA (e.g., Cas13a, Cas13b, Cas13c or Cas13 d). Example RNA-targeting effector proteins include Cas13b and C2c2 (now known as Cas13a). It will be understood that the term “C2c2” herein is used interchangeably with “Cas13a”. “C2c2” is now referred to as “Cas13a”, and the terms are used interchangeably herein unless indicated otherwise. As used herein, the term “Cas13” refers to any Type VI CRISPR system targeting RNA (e.g., Cas13a, Cas13b, Cas13c or Cas13 d). When the CRISPR protein is a C2c2 protein, a tracrRNA is not required. C2c2 has been described in Abudayyeh et al. (2016) “C2c2 is a single-component programmable RNA-guided RNA-targeting CRISPR effector”; Science; DOI: 10.1126/science.aaf5573; and Shmakov et al. (2015) “Discovery and Functional Characterization of Diverse Class 2 CRISPR-Cas Systems”, Molecular Cell, DOI: dx.doi.org/10.1016/j.molcel.2015.10.008; which are incorporated herein in their entirety by reference. Cas13b has been described in Smargon et al. (2017) “Cas13b Is a Type VI-B CRISPR-Associated RNA-Guided RNases Differentially Regulated by Accessory Proteins Csx27 and Csx28,” Molecular Cell. 65, 1-13; dx.doi.org/10.1016/j.molcel.2016.12.023., which is incorporated herein in its entirety by reference. 1

In some embodiments, one or more elements of a nucleic acid-targeting system is derived from a particular organism comprising an endogenous CRISPR RNA-targeting system. In certain example embodiments, the effector protein CRISPR RNA-targeting system comprises at least one HEPN domain, including but not limited to the HEPN domains described herein, HEPN domains known in the art, and domains recognized to be HEPN domains by comparison to consensus sequence motifs. Several such domains are provided herein. In one non-limiting example, a consensus sequence can be derived from the sequences of C2c2 or Cas13b orthologs provided herein. In certain example embodiments, the effector protein comprises a single HEPN domain. In certain other example embodiments, the effector protein comprises two HEPN domains.

In one example embodiment, the effector protein comprise one or more HEPN domains comprising a RxxxxH motif sequence. The RxxxxH motif sequence can be, without limitation, from a HEPN domain described herein or a HEPN domain known in the art. RxxxxH motif sequences further include motif sequences created by combining portions of two or more HEPN domains. As noted, consensus sequences can be derived from the sequences of the orthologs disclosed in U.S. Provisional Patent Application 62/432,240 entitled “Novel CRISPR Enzymes and Systems,” U.S. Provisional Patent Application 62/471,710 entitled “Novel Type VI CRISPR Orthologs and Systems” filed on Mar. 15, 2017, and U.S. Provisional Patent Application 62/484,786 entitled “Novel Type VI CRISPR Orthologs and Systems,” filed on Apr. 12, 2017.

In certain other example embodiments, the CRISPR system effector protein is a C2c2 nuclease. The activity of C2c2 may depend on the presence of two HEPN domains. These have been shown to be RNase domains, i.e. nuclease (in particular an endonuclease) cutting RNA. C2c2 HEPN may also target DNA, or potentially DNA and/or RNA. On the basis that the HEPN domains of C2c2 are at least capable of binding to and, in their wild type form, cutting RNA, then it is preferred that the C2c2 effector protein has RNase function. Regarding C2c2 CRISPR systems, reference is made to U.S. Provisional 62/351,662 filed on Jun. 17, 2016 and U.S. Provisional 62/376,377 filed on Aug. 17, 2016. Reference is also made to U.S. Provisional 62/351,803 filed on Jun. 17, 2016. Reference is also made to U.S. Provisional Application No. 62/432,240 entitled "Novel Crispr Enzymes and Systems" filed Dec. 9, 2016. Reference is further made to East-Seletsky et al. "Two distinct RNase activities of CRISPR-C2c2 enable guide-RNA processing and RNA detection" Nature doi:10/1038/nature19802 and Abudayyeh et al. "C2c2 is a single-component programmable RNA-guided RNA targeting CRISPR effector" bioRxiv doi: 10.1101/054742.

In certain embodiments, the C2c2 effector protein is from an organism of a genus selected from the group consisting of: Leptotrichia, *Listeria, Corynebacterium, Sutterella, Legionella, Treponema, Filifactor, Eubacterium, Streptococcus, Lactobacillus, Mycoplasma, Bacteroides, Fluviicola, Flavobacterium*, Sphaerochaeta, Azospirillum, *Gluconacetobacter, Neisseria, Roseburia, Parvibaculum, Staphylococcus, Nitratifractor, Mycoplasma, Campylobacter*, and Lachnospira, or the C2c2 effector protein is an organism selected from the group consisting of: Leptotrichia shahii, Leptotrichia *wadei, Listeria seeligeri, Clostridium aminophilum, Carnobacterium gallinarum, Paludibacter propionicigenes, Listeria* weihenstephanensis, or the C2c2 effector protein is a *L. wadei* F0279 or L. *wadei* F0279 (Lw2) C2C2 effector protein. In another embodiment, the one or more guide RNAs are designed to detect a single nucleotide polymorphism, splice variant of a transcript, or a frameshift mutation in a target RNA or DNA.

In certain example embodiments, the RNA-targeting effector protein is a Type VI-B effector protein, such as Cas13b and Group 29 or Group 30 proteins. In certain example embodiments, the RNA-targeting effector protein comprises one or more HEPN domains. In certain example embodiments, the RNA-targeting effector protein comprises a C-terminal HEPN domain, a N-terminal HEPN domain, or both. Regarding example Type VI-B effector proteins that may be used in the context of this invention, reference is made to U.S. application Ser. No. 15/331,792 entitled "Novel CRISPR Enzymes and Systems" and filed Oct. 21, 2016, International Patent Application No. PCT/US2016/058302 entitled "Novel CRISPR Enzymes and Systems", and filed Oct. 21, 2016, and Smargon et al. "Cas13b is a Type VI-B CRISPR-associated RNA-Guided RNase differentially regulated by accessory proteins Csx27 and Csx28" Molecular Cell, 65, 1-13 (2017); dx.doi.org/10.1016/j.molcel.2016.12.023, and U.S. Provisional Application No. to be assigned, entitled "Novel Cas13b Orthologues CRISPR Enzymes and System" filed Mar. 15, 2017. In particular embodiments, the Cas13b enzyme is derived from *Bergeyella zoohelcum.*

In certain example embodiments, the RNA-targeting effector protein is a Cas13c effector protein as disclosed in U.S. Provisional Patent Application No. 62/525,165 filed Jun. 26, 2017, and PCT Application No. US 2017/047193 filed Aug. 16, 2017.

In some embodiments, one or more elements of a nucleic acid-targeting system is derived from a particular organism comprising an endogenous CRISPR RNA-targeting system. In certain embodiments, the CRISPR RNA-targeting system is found in *Eubacterium* and Ruminococcus. In certain embodiments, the effector protein comprises targeted and collateral ssRNA cleavage activity. In certain embodiments, the effector protein comprises dual HEPN domains. In certain embodiments, the effector protein lacks a counterpart to the Helical-1 domain of Cas13a. In certain embodiments, the effector protein is smaller than previously characterized class 2 CRISPR effectors, with a median size of 928 aa. This median size is 190 aa (17%) less than that of Cas13c, more than 200 aa (18%) less than that of Cas13b, and more than 300 aa (26%) less than that of Cas13a. In certain embodiments, the effector protein has no requirement for a flanking sequence (e.g., PFS, PAM).

In certain embodiments, the effector protein locus structures include a WYL domain containing accessory protein (so denoted after three amino acids that were conserved in the originally identified group of these domains; see, e.g., WYL domain IPR026881). In certain embodiments, the WYL domain accessory protein comprises at least one helix-turn-helix (HTH) or ribbon-helix-helix (RHH) DNA-binding domain. In certain embodiments, the WYL domain containing accessory protein increases both the targeted and the collateral ssRNA cleavage activity of the RNA-targeting effector protein. In certain embodiments, the WYL domain containing accessory protein comprises an N-terminal RHH domain, as well as a pattern of primarily hydrophobic conserved residues, including an invariant tyrosine-leucine doublet corresponding to the original WYL motif. In certain embodiments, the WYL domain containing accessory protein is WYL1. WYL1 is a single WYL-domain protein associated primarily with Ruminococcus.

In other example embodiments, the Type VI RNA-targeting Cas enzyme is Cas13 d. In certain embodiments, Cas13 d is *Eubacterium* siraeum DSM 15702 (EsCas13 d) or *Ruminococcus* sp. N15.MGS-57 (RspCas13 d) (see, e.g., Yan et al., Cas13 d Is a Compact. RNA-Targeting Type VI CRISPR Effector Positively Modulated by a WYL-Domain-Containing Accessory Protein, Molecular Cell (2018), doi.org/10.1016/j.molcel.2018.02.028). RspCas13 d and EsCas13 d have no flanking sequence requirements (e.g., PFS, PAM).

Cas13 RNA Editing

In one aspect, the invention provides a method of modifying or editing a target transcript in a eukaryotic cell. In some embodiments, the method comprises allowing a CRISPR-Cas effector module complex to bind to the target polynucleotide to effect RNA base editing, wherein the CRISPR-Cas effector module complex comprises a Cas effector module complexed with a guide sequence hybridized to a target sequence within said target polynucleotide, wherein said guide sequence is linked to a direct repeat sequence. In some embodiments, the Cas effector module comprises a catalytically inactive CRISPR-Cas protein. In some embodiments, the guide sequence is designed to introduce one or more mismatches to the RNA/RNA duplex formed between the target sequence and the guide sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

The present application relates to modifying a target RNA sequence of interest (see, e.g, Cox et al., Science. 2017 Nov. 24; 358(6366):1019-1027). Using RNA-targeting rather than DNA targeting offers several advantages relevant for therapeutic development. First, there are substantial safety benefits to targeting RNA: there will be fewer off-target events because the available sequence space in the transcriptome is significantly smaller than the genome, and if an off-target event does occur, it will be transient and less likely to induce negative side effects. Second, RNA-targeting therapeutics will be more efficient because they are cell-type independent and not have to enter the nucleus, making them easier to deliver.

The present invention may also use a Cas12 CRISPR enzyme. Cas12 enzymes include Cas12a (Cpf1), Cas12b (C2c1), and Cas12c (C2c3), described further herein.

A further aspect of the invention relates to the method and composition as envisaged herein for use in prophylactic or therapeutic treatment, preferably wherein said target locus of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors. In particular embodiments, the invention thus comprises compositions for use in therapy. This implies that the methods can be performed in vivo, ex vivo or in vitro. In particular embodiments, when the target is a human or animal target, the method is carried out ex vivo or in vitro.

A further aspect of the invention relates to the method as envisaged herein for use in prophylactic or therapeutic treatment, preferably wherein said target of interest is within a human or animal and to methods of modifying an Adenine or Cytidine in a target RNA sequence of interest, comprising delivering to said target RNA, the composition as described herein. In particular embodiments, the CRISPR system and the adenosine deaminase, or catalytic domain thereof, are delivered as one or more polynucleotide molecules, as a ribonucleoprotein complex, optionally via particles, vesicles, or one or more viral vectors.

In one aspect, the invention provides a method of generating a eukaryotic cell comprising a modified or edited gene. In some embodiments, the method comprises (a) introducing one or more vectors into a eukaryotic cell, wherein the one or more vectors drive expression of one or more of: Cas effector module, and a guide sequence linked to a direct repeat sequence, wherein the Cas effector module associate one or more effector domains that mediate base editing, and (b) allowing a CRISPR-Cas effector module complex to bind to a target polynucleotide to effect base editing of the target polynucleotide within said disease gene, wherein the CRISPR-Cas effector module complex comprises a Cas effector module complexed with the guide sequence that is hybridized to the target sequence within the target polynucleotide, wherein the guide sequence may be designed to introduce one or more mismatches between the RNA/RNA duplex formed between the guide sequence and the target sequence. In particular embodiments, the mismatch is an A-C mismatch. In some embodiments, the Cas effector may associate with one or more functional domains (e.g. via fusion protein or suitable linkers). In some embodiments, the effector domain comprises one or more cytidine or adenosine deaminases that mediate endogenous editing of via hydrolytic deamination. In particular embodiments, the effector domain comprises the adenosine deaminase acting on RNA (ADAR) family of enzymes. In particular embodiments, the adenosine deaminase protein or catalytic domain thereof capable of deaminating adenosine or cytidine in RNA or is an RNA specific adenosine deaminase and/or is a bacterial, human, cephalopod, or *Drosophila* adenosine deaminase protein or catalytic domain thereof, preferably TadA, more preferably ADAR, optionally huADAR, optionally (hu)ADAR1 or (hu)ADAR2, preferably huADAR2 or catalytic domain thereof.

A further aspect relates to an isolated cell obtained or obtainable from the methods described herein comprising the composition described herein or progeny of said modified cell, preferably wherein said cell comprises a hypoxanthine or a guanine in replace of said Adenine in said target RNA of interest compared to a corresponding cell not subjected to the method. In particular embodiments, the cell is a eukaryotic cell, preferably a human or non-human animal cell, optionally a therapeutic T cell or an antibody-producing B-cell.

In some embodiments, the modified cell is a therapeutic T cell, such as a T cell suitable for adoptive cell transfer therapies (e.g., CAR-T therapies). The modification may result in one or more desirable traits in the therapeutic T cell, as described further herein.

The invention further relates to a method for cell therapy, comprising administering to a patient in need thereof the modified cell described herein, wherein the presence of the modified cell remedies a disease in the patient.

The present invention may be further illustrated and extended based on aspects of CRISPR-Cas development and use as set forth in the following articles and particularly as relates to delivery of a CRISPR protein complex and uses of an RNA guided endonuclease in cells and organisms:

Multiplex genome engineering using CRISPR-Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463):472-6. doi: 10.1038/Nature12466. Epub 2013 Aug. 23 (2013);

Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B); Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013);

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR-Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 February. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260 Mar. 12, 2015 (multiplex screen in mouse), and In vivo genome editing using *Staphylococcus aureus* Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520 (7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR-Cas9 cleavage of viral DNA efficiently suppresses hepatitis B virus," Scientific Reports 5:10833. doi: 10.1038/srep10833 (Jun. 2, 2015).

Nishimasu et al., Crystal Structure of *Staphylococcus aureus* Cas9," Cell 162, 1113-1126 (Aug. 27, 2015).

BCL11A enhancer dissection by Cas9-mediated in situ saturating mutagenesis, Canver et al., Nature 527 (7577):192-7 (Nov. 12, 2015) doi: 10.1038/nature15521. Epub 2015 Sep. 16.

*Cpf1 Is a Single RNA-Guided Endonuclease of a Class* 2 *CRISPR-Cas System*, Zetsche et al., Cell 163, 759-71 (Sep. 25, 2015).

*Discovery and Functional Characterization of Diverse Class* 2 *CRISPR-Cas Systems*, Shmakov et al., Molecular Cell, 60 (3), 385-397 doi:10.1016/j.molcel.2015.10.008 Epub Oct. 22, 2015.

*Rationally engineered Cas*9 *nucleases with improved specificity*, Slaymaker et al., Science 2016 Jan. 1 351 (6268): 84-88 doi:10.1126/science.aad5227. Epub 2015 Dec. 1.

Gao et al, "Engineered Cpf1 Enzymes with Altered PAM Specificities," bioRxiv 091611; doi: http://dx.doi.org/10.1101/091611 (Dec. 4, 2016).

Cox et al., "RNA editing with CRISPR-Cas13," Science. 2017 Nov. 24; 358(6366):1019-1027. Doi: 10.1126/science.aaq0180. Epub 2017 Oct. 25.

Gaudelli et al. "Programmable base editing of A-T to G-C in genomic DNA without DNA cleavage" Nature 464 (551); 464-471 (2017).

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA: Cas9-directed cleavage at the targeted genomic site to kill unmutated cells and circumvents the need for selectable markers or counter-selection systems. The study reported reprogramming dual-RNA: Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli,* 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR Cas9 enzyme and also Transcriptional Activator Like Effectors.

Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and guide RNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA: DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR-Cas9 knockout and nucleotide preference at the cleavage site. The authors also found that the sequence preference for CRISPRi/a is substantially different from that for CRISPR-Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of Tlr4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

Cox et al., (2017) reported the use of catalytically inactive Cas13 (dCas13) to direct adenosine-to-inosine deaminase activity by ADAR2 (adenosine deaminase acting on RNA type 2) to transcripts in mammalian cells. The system, referred to as RNA Editing for Programmable A to I Replacement (REPAIR), has no strict sequence constraints and can be used to edit full-length transcripts. The authors further engineered the system to create a high-specificity variant and minimized the system to facilitate viral delivery.

The methods and tools provided herein are may be designed for use with or Cas13, a type II nuclease that does not make use of tracrRNA. Orthologs of Cas13 have been identified in different bacterial species as described herein. Further type II nucleases with similar properties can be identified using methods described in the art (Shmakov et al. 2015, 60:385-397; Abudayeh et al. 2016, Science, 5; 353 (6299)). In particular embodiments, such methods for identifying novel CRISPR effector proteins may comprise the steps of selecting sequences from the database encoding a seed which identifies the presence of a CRISPR-Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

Also, “Dimeric CRISPR RNA-guided FokI nucleases for highly specific genome editing”, Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells. Also, Harrington et al. “Programmed DNA destruction by miniature CRISPR-Cas14 enzymes” Science 2018 doi:10/1126/science.aav4293, relates to Cas14.

With respect to general information on CRISPR/Cas Systems, components thereof, and delivery of such components, including methods, materials, delivery vehicles, vectors, particles, and making and using thereof, including as to amounts and formulations, as well as CRISPR-Cas-expressing eukaryotic cells, CRISPR-Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, and 8,945,839; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO2014/093661 (PCT/US2013/074743), WO2014/093694 (PCT/US2013/074790), WO2014/093595 (PCT/US2013/074611), WO2014/093718 (PCT/US2013/074825), WO2014/093709 (PCT/US2013/074812), WO2014/093622 (PCT/US2013/074667), WO2014/093635 (PCT/US2013/074691), WO2014/093655 (PCT/US2013/074736), WO2014/093712 (PCT/US2013/074819), WO2014/093701 (PCT/US2013/074800), WO2014/018423 (PCT/US2013/051418), WO2014/204723 (PCT/US2014/041790), WO2014/204724 (PCT/US2014/041800), WO2014/204725 (PCT/US2014/041803), WO2014/204726 (PCT/US2014/041804), WO2014/204727 (PCT/US2014/041806), WO2014/204728 (PCT/US2014/041808), WO2014/204729 (PCT/US2014/041809), WO2015/089351 (PCT/US2014/069897), WO2015/089354 (PCT/US2014/069902), WO2015/089364 (PCT/US2014/069925), WO2015/089427 (PCT/US2014/070068), WO2015/089462 (PCT/US2014/070127), WO2015/089419 (PCT/US2014/070057), WO2015/089465 (PCT/US2014/070135), WO2015/089486 (PCT/US2014/070175), WO2015/058052 (PCT/US2014/061077), WO2015/070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO2016/049258 (PCT/US2015/051830), WO2016/094867 (PCT/US2015/065385), WO2016/094872 (PCT/US2015/065393), WO2016/094874 (PCT/US2015/065396), WO2016/106244 (PCT/US2015/067177).

Mention is also made of U.S. application 62/180,709, 17 Jun. 2015, PROTECTED GUIDE RNAS (PGRNAS); U.S. application 62/091,455, filed, 12 Dec. 2014, PROTECTED GUIDE RNAS (PGRNAS); U.S. application 62/096,708, 24 Dec. 2014, PROTECTED GUIDE RNAS (PGRNAS); U.S. applications 62/091,462, 12 Dec. 2014, 62/096,324, 23 Dec. 2014, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 2014 and 62/180,692, 17 Jun. 2015, ESCORTED AND FUNCTIONALIZED GUIDES FOR CRISPR-CAS SYSTEMS; U.S. application 62/091,461, 12 Dec. 2014, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 2014, UNBIASED IDENTIFICATION OF DOUBLE-STRAND BREAKS AND GENOMIC REARRANGEMENT BY GENOME-WISE INSERT CAPTURE SEQUENCING; U.S. application 62/096,761, 24 Dec. 2014, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 2014, 62/181,641, 18 Jun. 2015, and 62/181,667, 18 Jun. 2015, RNA-TARGETING SYSTEM; U.S. application 62/096,656, 24 Dec. 2014 and 62/181,151, 17 Jun. 2015, CRISPR HAVING OR ASSOCIATED WITH DESTABILIZATION DOMAINS; U.S. application 62/096,697, 24 Dec. 2014, CRISPR HAVING OR ASSOCIATED WITH AAV; U.S. application 62/098,158, 30 Dec. 2014, ENGINEERED CRISPR COMPLEX INSERTIONAL TARGETING SYSTEMS; U.S. application 62/151,052, 22 Apr. 2015, CELLULAR TARGETING FOR EXTRACELLULAR EXOSOMAL REPORTING; U.S. application 62/054,490, 24 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 2014, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 2014, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 2014 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 2014, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 2014, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 2014, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 2014 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 2014, FUNCTIONAL SCREENING WITH OPTIMIZED FUNCTIONAL CRISPR-CAS SYSTEMS; U.S. application 62/087,546, 4 Dec. 2014 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 2014, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

In particular embodiments, pre-complexed guide RNA and CRISPR effector protein, (optionally, adenosine deaminase fused to a CRISPR protein or an adaptor) are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4):910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Other Perturbations

The invention also involves perturbing by subjecting the cell to an increase or decrease in temperature. The temperature may range from about 0 °C to about 100 °C, advantageously about 10 °C, 15 °C, 20 °C, 25 °C, 30 °C, 35 °C, 40 °C, 45 °C, 50 °C, 55 °C, 60 °C, 65 °C, 70 °C, 75 °C, 80 °C, 85 °C, 90 °C, 95 °C or 100 °C. In another embodiment, the temperature may be closer to a physiological temperature, e.g., about 30 °C, 31 °C, 32 °C, 33 °C, 34 °C, 35 °C, 36 °C, 37 °C, 38 °C, 39 °C or 40 °C.

The invention also involves perturbing by subjecting the cell to a chemical agent. Samples of chemical agents include, but are not limited to, an antibiotic, a small molecule, a hormone, a hormone derivative, a steroid or a steroid derivative.

The invention also involves perturbing by subjecting the cell to a biological agent. Examples of biological agents may be, but are not limited to cytokines and Toll-like receptor agonists (Amit et al., Science. 2009 9; 326(5950):257-63, Chevrier et al., Cell. 2011 Nov. 11; 147(4):853-67); Wang et al., Cell. 2015 Dec. 3; 163(6):1413-27; and Gaublomme et al., Cell. 2015 Dec. 3; 163(6):1400-12).

In one aspect of the invention the perturbing may be with an energy source such as electromagnetic energy or ultrasound. The electromagnetic energy may be a component of visible light having a wavelength in the range of 450 nm-700 nm. In a preferred embodiment the component of visible light may have a wavelength in the range of 450 nm-500 nm and may be blue light. The blue light may have an intensity of at least 0.2 mW/cm2, or more preferably at least 4 mW/cm2. In another embodiment, the component of visible light may have a wavelength in the range of 620-700 nm and is red light.

The invention also involves perturbing by subjecting the cell to a chemical agent and/or temperature is across a gradient. A biomolecular gradient may be formed, for example, as reviewed in Keenan and Folch, Lab Chip. 2008 January; 8(1): doi:10.1039/b711887b. Biomolecule gradients have been shown to play roles in a wide range of biological processes including development, inflammation, wound healing, and cancer metastasis. Elucidation of these phenomena requires the ability to expose cells to biomolecule gradients that are quantifiable, controllable, and mimic those that are present in vivo.

A chemical gradient may be formed without requiring fluid flow (see, e.g., Abhyankar et al., Lab Chip, 2006, 6, 389-393). This device consists of a membrane-covered source region and a large volume sink region connected by a microfluidic channel. The high fluidic resistance of the membrane limits fluid flow caused by pressure differences in the system, but allows diffusive transport of a chemical species through the membrane and into the channel. The large volume sink region at the end of the microfluidic channel helps to maintain spatial and temporal stability of the gradient. The chemical gradient in a 0.5 mm region near the sink region experiences a maximum of 10 percent change between the 6 and 24 h data points. Abhyankar et al., Lab Chip, 2006, 6, 389-393 present the theory, design, and characterization of this device and provide an example of neutrophil chemotaxis as proof of concept for future quantitative cell-signaling applications.

In another embodiment, a gradient may also be introduced with nanowires. In this embodiment, the nanowires do not necessarily introduce a gradient but may introduce other things into the system. A generalized platform for introducing a diverse range of biomolecules into living cells in high-throughput could transform how complex cellular processes are probed and analyzed. Shalek et al., PNAS | Feb. 2, 2010 | vol. 107 | no. 5 demonstrate spatially localized, efficient, and universal delivery of biomolecules into immortalized and primary mammalian cells using surface-modified vertical silicon nanowires. The method relies on the ability of the silicon nanowires to penetrate a cell's membrane and subsequently release surface-bound molecules directly into the cell's cytosol, thus allowing highly efficient delivery of biomolecules without chemical modification or viral packaging. This modality enables one to assess the phenotypic consequences of introducing a broad range of biological effectors (DNAs, RNAs, peptides, proteins, and small molecules) into almost any cell type. Shalek et al., PNAS | Feb. 2, 2010 | vol. 107 | no. 5 show that this platform can be used to guide neuronal progenitor growth with small molecules, knock down transcript levels by delivering siRNAs, inhibit apoptosis using peptides, and introduce targeted proteins to specific organelles. Shalek et al., PNAS | Feb. 2, 2010 | vol. 107 | no. 5 further demonstrate codelivery of siRNAs and proteins on a single substrate in a microarray format, highlighting this technology's potential as a robust, monolithic platform for high-throughput, miniaturized bioassays.

A gradient may be established, for example, in a fluidic device, such as a microfluidic device (see, e.g., Tehranirokh et al., BIOMICROFLUIDICS 7, 051502 (2013)). Microfluidic technology allows dynamic cell culture in microperfusion systems to deliver continuous nutrient supplies for long term cell culture. It offers many opportunities to mimic the cell-cell and cell-extracellular matrix interactions of tissues by creating gradient concentrations of biochemical signals such as growth factors, chemokines, and hormones. Other applications of cell cultivation in microfluidic systems include high resolution cell patterning on a modified substrate with adhesive patterns and the reconstruction of complicated tissue architectures. In the review of Tehranirokh et al., BIOMICROFLUIDICS 7, 051502 (2013), recent advances in microfluidic platforms for cell culturing and proliferation, for both simple monolayer (2D) cell seeding processes and 3D configurations as accurate models of in vivo conditions, are examined. In another embodiment, the fluidic device may be a controlled fluidic device as described below.

Device for Establishing a Gradient

The invention provides a controlled fluidic device for establishing a gradient, particularly a concentration gradient, which may comprise a closed chamber comprising one or more inlet port(s) that deliver two or more different fluids via separate inlet channels and at least one outlet port wherein the location of the one or more inlet port(s) and the at least one outlet port are located so that the flow of fluids can be controlled within the closed chamber and a gradient of the mixture of the two or more fluids from the two or more inlet ports is established.

In a related aspect, the invention provides a controlled fluidic device wherein the controlled fluidic device is a polygonal plate having an upper surface and a lower surface and a peripheral plate edge having a pre-determined depth. In an embodiment of the invention, the controlled fluidic device may comprise a device wherein at least one of the two fluids includes at least one component for which a gradient could be established.

In a related aspect, the invention provides a controlled fluidic device which may comprise at least component which includes at least two subcomponents. In an embodiment of the invention, the controlled fluidic device may comprise a closed chamber comprising a chip.

The invention provides a method of identifying altered chemical resistance in a bacterial population in the controlled fluidic device as described above, the method which may comprise synthesizing a mutant bacterial strain to express fluorescent proteins; introducing a known concentration of the bacterial strain into the closed chamber; administering the two or more different fluids into the closed chamber via the two more inlet ports; isolating DNA from a single cell; purifying DNA from bacteria; sequencing DNA from bacteria; preparing and sequencing a single composite sequence library; wherein identification of alteration in level of expression compared to a baseline gene expression measurement of at least one biomarker is indicative of chemical resistance, and wherein the baseline gene expression measurement is the gene expression measured in the microfluidic well prior to administration of the two or more different fluids.

The present invention also provides a method of evaluating response in a cell population in the controlled fluidic device as described, the method which may comprise introducing a cell population into the closed chamber; administering the two or more different fluids into the closed chamber via the two more inlet ports such that a concentration gradient is established in the closed chamber; and, measuring the response of the cell population at various concentrations across the concentration gradient.

In another aspect, the invention provides a method of identifying altered bacterial populations according to the method of evaluating a response, the method comprising: a microfluidic device having a closed chamber having an upper surface and a lower surface and a peripheral plate edge having a predetermined depth; a plurality of microfluidic wells extending from the upper surface of the closed chamber, each well connected to adjacent ones of the plurality of wells by microchannels extending from the upper surface of the plate and extending from a first well to a second well such that the first well is in fluid communication with the second well; wherein the microfluidic device and plurality of wells connected by microchannels creates a chemical concentration gradient in adjacent microfluidic wells wherein one microfluidic well has a different chemical concentration than an adjacent microfluidic well; providing a chemical dye via an inlet port of the closed chamber; providing a chemical via an inlet port of the closed chamber; optionally providing a second chemical via an inlet port of the closed chamber; an outlet port of the closed chamber; and, a peripheral flow channel adjacent a portion of the peripheral plate edge and extending from the inlet port to the outlet port.

The present invention provides a method of identifying a compound associated with an altered bacterial population as described above, the method comprising: designing a combinatorial library wherein each member of the library comprises at least one pharmacophore associated with the altered gene expression; wherein alteration in level of expression compared to a baseline gene expression measurement of at least one biomarker is indicative of an altered bacterial population; synthesizing a plurality of compounds from said combinatorial library; and, screening said compounds for candidates associated with the altered bacterial population.

The invention provides an array of controlled microfluidic devices, comprising a plurality of controlled microfluidic devices according to the controlled fluidic device for establishing a gradient, comprising a closed chamber comprising one or more inlet port(s) that deliver two or more different fluids via separate inlet channels and at least one outlet port wherein the location of the one or more inlet port(s) and the at least one outlet port are located so that the flow of fluids can be controlled within the closed chamber and a gradient of the mixture of the two or more fluids from the two or more inlet ports is established.

Labeling

Methods of international patent publication no. WO2014047561 and US patent publication no. 2015/0259674 are contemplated in the present invention.

The invention also contemplates a labeling ligand which may comprise a unique perturbation identifier (UPI) sequence attached to a perturbation-sequence-capture sequence, and sequencing includes isolating via microbeads comprising a perturbation-sequence-capture-binding-sequence having specific binding affinity for the perturbation-sequence-capture sequence attached to the UPI sequence.

The UPI sequence may be attached to a universal ligation handle sequence, whereby a unique source identifier USI may be generated by split-pool ligation. The labeling ligand may comprise an oligonucleotide label which may comprise a regulatory sequence configured for amplification by T7 polymerase. The labeling ligands may comprise oligonucleotide sequences configured to hybridize to a transcript specific region. The labeling ligand may comprise an oligonucleotide label, wherein the oligonucleotide label may further comprise a photocleavable linker.

The oligonucleotide label may further comprise a restriction enzyme site between the labeling ligand and unique constituent identifier (UCI).

The method may comprise forming discrete unique-identifier-transfer compositions, each of which may comprise the cell and a transfer particle, wherein: (a) an oligonucleotide label further may comprise a capture sequence, and unique constituent identifier (UCI) and capture sequence are together releasably attached to the labeling ligand; the labelling ligand is bound to the target cellular constituent; and, (ca transfer particle may comprise: (i) a capture-binding-sequence having specific binding affinity for the capture sequence attached to the UCI, and, (ii) a unique source identifier (USI) sequence that is unique to each transfer particle.

In one embodiment, the USI may comprise 4-15 nucleotides.

In another embodiment, the invention may further comprise releasing the UCI from the labeled ligand, under conditions within the unique-identifier-transfer composition so that the released capture sequence binds to the capture-binding-sequence on the transfer particle, thereby transferring the UCI to the transfer particle.

In another embodiment, the ligation handle may comprise a restriction site for producing an overhang complementary with a first index sequence overhang, and wherein the method further comprises digestion with a restriction enzyme. In another embodiment, the ligation handle may comprise a nucleotide sequence complementary with a ligation primer sequence and wherein the overhang complementary with a first index sequence overhang is produced by hybridization of the ligation primer to the ligation handle.

In another embodiment, the invention may further comprise quantitating relative amount of UCI sequence associated with a first cell to the amount of the same UCI sequence associated with a second cell, whereby the relative differences of a cellular constituent between cell(s) are determined.

In another embodiment, the labeling ligand may comprise an antibody or an antibody fragment, such as but not limited to, a nanobody, Fab, Fab', (Fab')2, Fv, ScFv, diabody, triabody, tetrabody, Bis-scFv, minibody, Fab2, or Fab3 fragment.

In another embodiment, the labeling ligand may comprise an aptamer.

In another embodiment, the labeling ligand may comprise a nucleotide sequence complementary to a target sequence.

In another embodiment, the cell or a population includes wherein the cell(s) are a member of a cell population, and the method further comprises transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct. The genomic sequence-perturbation construct may comprises sequence encoding a guide RNA sequence of a CRISPR-Cas targeting system. The method may further comprise multiplex transformation of the population of cells with a plurality of genomic sequence-perturbation constructs. The method may further comprise a UPI sequence attached to a perturbation-sequence-capture sequence, and the transfer particle may comprise a perturbation-sequence-capture-binding-sequence having specific binding affinity for the perturbation-sequence-capture sequence attached to the UPI sequence. The UPI sequence is attached to a universal ligation handle sequence, whereby a USI is generated by split-pool ligation.

In an advantageous embodiment, agents may be uniquely labeled in a dynamic manner (see, e.g., U.S. provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, one or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

Single Cell Sequence Methods

Cells come in different types, sub-types and activity states, which are classify based on their shape, location, function, or molecular profiles, such as the set of RNAs that they express. RNA profiling is in principle particularly informative, as cells express thousands of different RNAs. Approaches that measure for example the level of every type of RNA have until recently been applied to “homogenized” samples—in which the contents of all the cells are mixed together. Methods to profile the RNA content of tens and hundreds of thousands of individual human cells have been recently developed, including from brain tissues, quickly and inexpensively. To do so, special microfluidic devices have been developed to encapsulate each cell in an individual drop, associate the RNA of each cell with a ‘cell barcode’ unique to that cell/drop, measure the expression level of each RNA with sequencing, and then use the cell barcodes to determine which cell each RNA molecule came from.

In certain embodiments, the invention involves high-throughput single-cell RNA-seq and/or targeted nucleic acid profiling (for example, sequencing, quantitative reverse transcription polymerase chain reaction, and the like).

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq: Single-Cell RNA-Seq by Multiplexed Linear Amplification. Cell Reports, Cell Reports, Volume 2, Issue 3, p 666-673, 2012).

In certain embodiments, the invention involves plate based single cell RNA sequencing (see, e.g., Picelli, S. et al., 2014, “Full-length RNA-seq from single cells using Smart-seq2” Nature protocols 9, 171-181, doi:10.1038/nprot.2014.006).

In certain embodiments, the invention involves high-throughput single-cell RNA-seq. In this regard reference is made to Macosko et al., 2015, “Highly Parallel Genome-wide Expression Profiling of Individual Cells Using Nanoliter Droplets” Cell 161, 1202-1214; International patent application number PCT/US2015/049178, published as WO2016/040476 on Mar. 17, 2016; Klein et al., 2015, “Droplet Barcoding for Single-Cell Transcriptomics Applied to Embryonic Stem Cells” Cell 161, 1187-1201; International patent application number PCT/US2016/027734, published as WO2016168584A1 on Oct. 20, 2016; Zheng, et al., 2016, “Haplotyping germline and cancer genomes with high-throughput linked-read sequencing” Nature Biotechnology 34, 303-311; Zheng, et al., 2017, “Massively parallel digital transcriptional profiling of single cells” Nat. Commun. 8, 14049 doi:10.1038/ncomms14049; International patent publication number WO2014210353A2; Zilionis, et al., 2017, “Single-cell barcoding and sequencing using droplet microfluidics” Nat Protoc. January; 12(1):44-73; Cao et al., 2017, “Comprehensive single cell transcriptional profiling of a multicellular organism by combinatorial indexing” bioRxiv preprint first posted online Feb. 2, 2017, doi: dx.doi.org/10.1101/104844; Rosenberg et al., 2017, “Scaling single cell transcriptomics through split pool barcoding” bioRxiv preprint first posted online Feb. 2, 2017, doi: dx.doi.org/10.1101/105163; Rosenberg et al., “Single-cell profiling of the developing mouse brain and spinal cord with split-pool barcoding” Science 15 Mar. 2018; Vitak, et al., “Sequencing thousands of single-cell genomes with combinatorial indexing” Nature Methods, 14(3):302-308, 2017; Cao, et al., Comprehensive single-cell transcriptional profiling of a multicellular organism. Science, 357(6352):661-667, 2017; and Gierahn et al., “Seq-Well: portable, low-cost RNA sequencing of single cells at high throughput” Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, “In vivo interrogation of gene function in the mammalian brain using CRISPR-Cas9” Nature Biotechnology Vol. 33, pp. 102-106; Habib et al., 2016, “Div-Seq: Single-nucleus RNA-Seq reveals dynamics of rare adult newborn neurons” Science, Vol. 353, Issue 6302, pp. 925-928; Habib et al., 2017, “Massively parallel single-nucleus RNA-seq with DroNc-seq” Nat Methods. 2017 October; 14(10):955-958; and International patent application number PCT/US2016/059239, published as WO2017164936 on Sep. 28, 2017, which are herein incorporated by reference in their entirety.

Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947. See also international patent application serial no. PCT/US2014/058637 for disclosure regarding a microfluidic laboratory on a chip.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Drop-Sequence methods and apparatus provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

The invention provides a method for creating a single-cell sequencing library comprising: merging one uniquely barcoded mRNA capture microbead with a single-cell in an emulsion droplet having a diameter of 75-125 μm; lysing the cell to make its RNA accessible for capturing by hybridization onto RNA capture microbead; performing a reverse transcription either inside or outside the emulsion droplet to convert the cell's mRNA to a first strand cDNA that is covalently linked to the mRNA capture microbead; pooling the cDNA-attached microbeads from all cells; and preparing and sequencing a single composite RNA-Seq library.

The invention provides a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A) or unique oligonucleotides of length two or more bases; 2) repeating this process a large number of times, at least two, and optimally more than twelve, such that, in the latter, there are more than 16 million unique barcodes on the surface of each bead in the pool. (See www.ncbi.nlm.nih.gov/pmc/articles/PMC206447)

Generally, the invention provides a method for preparing a large number of beads, particles, microbeads, nanoparticles, or the like with unique nucleic acid barcodes comprising performing polynucleotide synthesis on the surface of the beads in a pool-and-split fashion such that in each cycle of synthesis the beads are split into subsets that are subjected to different chemical reactions; and then repeating this split-pool process in two or more cycles, to produce a combinatorially large number of distinct nucleic acid barcodes. Invention further provides performing a polynucleotide synthesis wherein the synthesis may be any type of synthesis known to one of skill in the art for "building" polynucleotide sequences in a step-wise fashion. Examples include, but are not limited to, reverse direction synthesis with phosphoramidite chemistry or forward direction synthesis with phosphoramidite chemistry. Previous and well-known methods synthesize the oligonucleotides separately then "glue" the entire desired sequence onto the bead enzymatically. Applicants present a complexed bead and a novel process for producing these beads where nucleotides are chemically built onto the bead material in a high-throughput manner. Moreover, Applicants generally describe delivering a "packet" of beads which allows one to deliver millions of sequences into separate compartments and then screen all at once.

The invention further provides an apparatus for creating a single-cell sequencing library via a microfluidic system, comprising: a oil-surfactant inlet comprising a filter and a carrier fluid channel, wherein said carrier fluid channel further comprises a resistor; an inlet for an analyte comprising a filter and a carrier fluid channel, wherein said carrier fluid channel further comprises a resistor; an inlet for mRNA capture microbeads and lysis reagent comprising a filter and a carrier fluid channel, wherein said carrier fluid channel further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops.

A mixture comprising a plurality of microbeads adorned with combinations of the following elements: bead-specific oligonucleotide barcodes created by the described methods; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, B-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-(vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5'5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosine and derivatives; erythrosine B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

The invention described herein enables high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organelles or single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 μL to 10 nL work as individual reactors. Disclosed embodiments provide 104 to 105 single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as described herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell per droplet with only a few droplets containing more than one cell when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, small molecules, DNA, primers, antibodies. Smaller droplets may be in the order of femtoliter (fL) volume drops, which are especially contemplated with the droplet dispensors. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that 1011 or 1015 different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 μm droplets were made at 10 kHz per second. Formation of these libraries rely on limiting dilutions.

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41, 780) and European publication number EP2047910 to Raindance Technologies Inc. The content of each of which is incorporated by reference herein in its entirety.

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioninformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provides an ability to create a library of emulsion droplets on demand with the further capability of manipulating the droplets through the disclosed process(es). Disclosed embodiments may, thereby, provide dynamic tracking of the droplets and create a history of droplet deployment and application in a single cell based environment.

Droplet generation and deployment is produced via a dynamic indexing strategy and in a controlled fashion in accordance with disclosed embodiments of the present invention. Disclosed embodiments of the microfluidic device described herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

Undersampling—A Sampling Based Framework for Genetic Interactions

According to the invention, random sampling may comprise matrix completion, tensor completion, compressed sensing, or kernel learning.

In some aspects, where random sampling comprises matrix completion, tensor completion, or compressed sensing, I may be of the order of log P.

The invention relies on a random sampling assumption, e.g. that the combinatorial space is sparse and/or of low rank. This assumption is generic and advantageously does not rely on the pre-determination of a (known) set of genetic interactions. This assumption constrains the range or complexity of models, and thus can be used to restrict sampling size (undersampling). Further, as detailed below, the invention relies on the following: (1) Given a limited number of assays, if one wishes to infer interactions up to an order j, it is advantageous to randomly sample interactions at a higher order $k>j$, because higher order perturbations maximize the information that can be recovered; and (2) in such a method, one may use a model that accounts for higher order interactions when analyzing lower order ones. For example, it is possible to aim for each perturbation to target $k\sim5$-7 genes at once to estimate/model interactions at lower order $j\sim3$-5.

Although some experimental methods open the way to test non-linear interactions by high order combinatorial genetic perturbations, exhaustive combinatorial exploration is intractable for anything but 2- or 3-way interactions for a few genes.

According to the invention, random matrix theory and compressive sensing may be used to re-formulate this as a random sampling problem, developing a new framework from experimental design to model inference, testing and refinement.

To infer combinatorial models from a dramatic undersampling of the full high-order combinatorial space with massively combinatorial molecular perturbations (MCPP), one may rely on random matrix theory, compressive sensing and kernel learning.

According to the invention, it is made possible to model non-linear regulatory functions from genetic manipulations (perturbations).

One may learn models of higher-order genetic interactions from combinatorial perturbations with single cell profiling. Although the learning problem is underdetermined due to combinatorial explosion (2" possible interaction terms among m genes), it can become tractable in the presence of additional structure, including sparsity and smoothness, that constrains the range or complexity of models. One may thus rely on the following: (1) Given a limited number of assays, if one wishes to infer interactions up to an order j, it is advantageous to randomly sample interactions at a higher order k>j, because higher order perturbations maximize the information that can be recovered; and (2) in such a design, one can use a model that accounts for higher order interactions when analyzing lower order ones. One may for example aim for each perturbation to target k~5-7 genes at once to estimate interactions at j~3-5.

Thus the present invention relies on a learning approach that takes multiplex perturbations at a high order n and a complex readout data (e.g., RNA profile) and infers a model of genetic interactions at a lower order (m<n), as well as strategies for experimental design, model testing and refinement.

If one assumes that genetic interactions are low rank, sparse, or both, then the true number of degrees of freedom is small relative to the complete combinatorial expansion, so that one can infer the full nonlinear landscape with a relatively small random sampling of high-order perturbations, without specific knowledge of which genes are likely to interact. Analysis of prior studies supports the sparsity assumption in yeast (for fitness: Costanzo, M., Baryshnikova, A., Bellay, J., Kim, Y., Spear, E. D., Sevier, C. S., Ding, H., Koh, J. L., Toufighi, K., Mostafavi, S., Prinz, J., St Onge, R. P., VanderSluis, B., Makhnevych, T., Vizeacoumar, F. J., Alizadeh, S., Bahr, S., Brost, R. L., Chen, Y., Cokol, M., Deshpande, R., Li, Z., Lin, Z. Y., Liang, W., Marback, M., Paw, J., San Luis, B. J., Shuteriqi, E., Tong, A. H., van Dyk, N., Wallace, I. M., Whitney, J. A., Weirauch, M. T., Zhong, G., Zhu, H., Houry, W. A., Brudno, M., Ragibizadeh, S., Papp, B., Pal, C., Roth, F. P., Giaever, G., Nislow, C., Troyanskaya, O. G., Bussey, H., Bader, G. D., Gingras, A. C., Morris, Q. D., Kim, P. M., Kaiser, C. A., Myers, C. L., Andrews, B. J. & Boone, C. The genetic landscape of a cell. Science. 327, 425-431, doi:10.1126/science.1180823 (2010)), and fly (for 11 imaging phenotypes: Laufer, C., Fischer, B., Billmann, M., Huber, W. & Boutros, M. Mapping genetic interactions in human cancer cells with RNAi and multiparametric phenotyping. Nat Methods. 10, 427-431, doi:10.1038/nmeth.2436 (2013)), and to the limited tested extent, mammals (for 60 genes: Bassik, M. C., Kampmann, M., Lebbink, R. J., Wang, S., Hein, M. Y., Poser, I., Weibezahn, J., Horlbeck, M. A., Chen, S., Mann, M., Hyman, A. A., Leproust, E. M., McManus, M. T. & Weissman, J. S. A systematic mammalian genetic interaction map reveals pathways underlying ricin susceptibility. *Cell.* 152, 909-922, doi:10.1016/j.cell.2013.01.030 (2013). PMCID:3652613).

Matrix (Tensor) Completion.

All the values of a matrix (tensor) are filled in using a small collection of sampled entries. Applicants hypothesize that the rank of a tensor of higher-order interactions is a fraction of the number of tested genes which is tested by calculating the rank from a dense sampling of second or third order knockouts from a small collection of genes. If the rank of interactions is limited, then Applicants randomly sample sets of genes to knockout from a larger collection, and fill in the remaining values via nuclear norm regularized least-squares optimization (Candes, E. J. & Plan, Y. Matrix Completion With Noise. *Proceedings of the IEEE.* 98, 925-936, doi: Doi 10.1109/Jproc.2009.2035722 (2010)). Provable guarantees suggest that if the rank, r, is small relative to the number of genes, n, then m≥O ($n^{6/5}$ r log n) sampled entries are sufficient. However, since these guarantees assume rough uniformity in the loadings of interaction singular vectors, this assumption is unlikely to hold if the interaction matrix is very sparse. In this case, Applicants perform the same random sampling, and simultaneously regularize over both the nuclear norm and the L1 norm of the matrix (Richard, E., Savalle, P. & Vayatis, N. Estimation of Simultaneously Sparse and Low Rank Matrices. *arXiv.* doi:arXiv:1206.6474).

Compressed Sensing

Here, instead of working with a tensor of interaction terms, Applicants work with a basis that spans all higher order interactions. Each single quantitative phenotype is a real-valued function $f(g)$ on possible genotypes g (the $2^m$ possible allelic or knockout states), represented as binary strings of length m. Applicants analyze such Boolean functions using Fourier decomposition (O'Donnell, R. Analysis of boolean functions. (Cambridge University Press, 2014)) $f(g)=\Sigma_{sbe\text{-}f(2,1)}m\hat{f}_b(-1)^{dg}$, $$\hat{f}_b = \frac{1}{2^m}\sum\nolimits_{g\in\{0,1\}^m} f(g)(-1)^{g\cdot b},$$

where $f$ is an orthogonal basis indexed by binary strings b, and each Fourier coefficient $\hat{f}_b$ precisely quantifies the effect of one possible multi-gene interaction. For example with m=2, $\hat{f}_{oo}$ is the average phenotype; $\hat{f}_{10}$ is the effect of the first gene KO, marginalized over the genetic background of the second; similarly for $\hat{f}_{01}$; and $\hat{f}_{11}$ quantifies the two-way interaction (the extent to which the double KO phenotype differs from that predicted by the sum of the effects of the single KOs). Applicants hypothesize that such genotype-phenotype maps are approximately sparse in the Fourier basis, such that there is a small number, s, of nonzero Fourier coefficients (not known a priori). With perturbations generated only up to a limited order, Applicants obtain a truncated Fourier model, which is a general linear model: the genetic interactions are in the basis functions (encoded into a design matrix), and the response is linear in the unknown Fourier coefficients. Applicants assume most truncated coefficients are negligible. Assuming that the genotype-phenotype maps are approximately sparse in the Fourier basis, Applicants use L1-penalized regression to learn the coefficients of the map from paired genotype-phenotype observations $g_i$, $f(g_i)$ (with uncertainty or noise in both).

Compressed sensing posits that if Applicants' perturbations are de-coherent under the given basis, then exact recovery is possible with dramatic under-sampling (in the noiseless case) (Candes, E. Compressive sampling. *Proceedings of the International Congress of Mathematicians Madrid, Aug.* 22-30, 2006. 3, 19, doi:10.4171/022 (2006)), such that a sample size n=C's log p will suffice, where s is the number of effectively nonzero coefficients, p is the magnitude of combinatorial expansion and C depends on noise and experimental design (how the $g_i$ are sampled) (Candes, E. Mathematics of sparsity (and few other things). *ICM* 2014 *Proceedings, to appear*. (2014)). By varying the penalization parameter, Applicants learn sparse structures at different levels of thresholding, and find the level below which the data become insufficient to capture the signal (Hastie, T., Friedman, J. & Tibshirani, R. *The elements of statistical learning*. Vol. 2 (Springer, 2009)). Applicants explore using a larger penalization parameter on the higher order interaction coefficients, and, with good estimates of single perturbations, even no penalty on the linear terms, or regressing those out first. If each experiment is a Poisson random sampling of KOs, Applicants expect the measurements to have good de-coherence under the Fourier basis, provided the mean number of KO experiments per gene is not too low. If Applicants' assumptions are correct, a soft phase transition in performance as the number of observations crosses a threshold should be observed. Applicants use a small complete dataset or downsampling of a larger more random dataset, to assess if the appropriate transition is observed.

Kernel Learning.

If there is no strict sparsity in the rank or in the coefficients, Applicants build predictive functions of the effects of combinatorial perturbations, using a kernel of experimental similarity. Given m experiments, Applicants define an m×m polynomial kernel, for example, based on the overlap in knockouts between any pair of experiments. Applicants learn a weighted combination of kernel vectors that fits a collection of training data, and use the coefficients to predict the outcome of new experiments. Here, the density of nonlinear interaction terms can be much greater, since Applicants do not directly learn any particular interaction coefficient, but rather a kernelized version of the entire polynomial. Indeed, if the interaction terms are too sparse, kernel learning is unlikely to be successful with under-sampling.

Applicants analyzed 3-way interaction data measured by overexpression of every 3-way combination of 39 miRNAs and a phenotype of drug resistance, and confirmed substantial sparsity in the data. Applicants analyzed the 5-way interactions affecting expression profiles in response to salt in yeast between the MAPK Hog1 (p38 ortholog) and 4 TFs (1, 2, 3, 4, and 5 KO: 32 perturbations). Using a (non-regularized) linear model, Applicants quantified 1- and 2-way interactions, finding diverse non-linearities.

Analyzing a Cell Population at the Single Cell Level

The method according to the invention may comprise a step for single-cell molecular profiling. In some embodiments the step may comprise processing said cell population in order to physically separate cells. In some embodiments the step may comprise single-cell manipulation, e.g. using microfluidics based techniques. In some embodiments the step may comprise reverse emulsion droplet-based single-cell analysis or hydrogel droplet-based single-cell analysis.

The method of the invention may use microfluidics, e.g. to culture cells in specific combinations, control the spatiotemporal signals they receive, and/or trace and sample them as desired.

Molecular Profiling at the Single Cell Level

The method according to the invention may comprise a step for single-cell molecular profiling. This step may involve analyzing biomolecules quantitatively or semi-quantitatively. The biomolecules may include RNA, mRNA, pre-mRNA, proteins, chromatin or DNA. Said analysis may be performed genome-wide. Said analysis may be coupled (dual or sequential analysis of two or more types of biomolecules).

In some embodiments the step may comprise single-cell genomic profiling, single-cell RNA profiling, single-cell DNA profiling, single-cell epigenomic profiling, single-cell protein profiling, or single-cell reporter gene expression profiling. Proteins that may be used to alter genomic and epigenomic state are described in Shmakov et al., 2015, Molecular Cell 60, 1-13 and Zetsche et al., 2015, Cell 163, 759-771.

In some embodiments the step may comprise single-cell RNA abundance analysis, single-cell transcriptome analysis, single-cell exome analysis, single-cell transcription rate analysis, or single-cell RNA degradation rate analysis.

In some embodiments the step may comprise single-cell DNA abundance analysis, single-cell DNA methylation profiling, single-cell chromatin profiling, single-cell chromatin accessibility profiling, single-cell histone modification profiling, or single-cell chromatin indexing.

In some embodiments the step may comprise single-cell protein abundance analysis, single-cell post-translational protein modification analysis, or single-cell proteome analysis.

In some embodiments the step may comprise single-cell mRNA reporter analysis, detection or quantification.

In some embodiments the step may comprise single-cell dual molecular profiling, such any combination of two amongst single-cell RNA profiling, single-cell DNA profiling, single-cell protein profiling, mRNA reporter analysis.

The method of the invention may include at the step determining single cell RNA levels. For single cell RNA-Seq (scRNA-Seq), one may use Drop-Seq (Macosko, E. Z., Basu, A., Satija, R., Nemesh, J., Goldman, M., Tirosh, I., Bialas, A. R., Kamitaki, N., Sanes, J. R., Weitz, D. A., Shalek, A. K., Regev, A. & McCarroll, S. A. Highly Parallel Genome-wide Expression Profiling of Individual Cells Using Nanoliter Droplets. Cell. 2015 May 21; 161(5):1202-14. doi: 10.1016/j.cell.2015.05.002. PMCID:4481139) and variants thereof. This technique relies on reverse-emulsion, early barcoding for analyzing $10^4$-$10^6$ cells/experiment at very low cost. Drop-Seq enables to co-encapsulate individual cells with uniquely barcoded mRNA capture beads in reverse emulsion droplets. After lysis and mRNA capture, the emulsion is broken and all beads/cells are processed (RT, library prep) together, deconvolving each cell's profile from bead barcodes. In some embodiments, droplets can compartmentalize hundreds of cells/sec, are stable over time and to heat, and can serve as micro-vessels to add reagents; after RT, barcoded beads are stable and can be sorted or subselected. Sampling noise from shallow read depth is substantially lower than the technical variability between cells (Shalek, A. K., Satija, R., Shuga, J., Trombetta, J. J., Gennert, D., Lu, D., Chen, P., Gertner, R. S., Gaublomme, J. T., Yosef, N., Schwartz, S., Fowler, B., Weaver, S., Wang, J., Wang, X., Ding, R., Raychowdhury, R., Friedman, N., Hacohen, N., Park, H., May, A. P. & Regev, A. Single-cell RNA-seq reveals dynamic paracrine control of cellular variation. Nature. 510, 363-369, doi:10.1038/nature13437 (2014). PMCID:4193940.), so one may sufficiently estimate expression with ~100,000 reads per cell for many applications (especially with a 5' or 3'-end protocol, Satija, R., Farrell, J. A., Gennert, D., Schier, A. F. & Regev, A. Spatial reconstruction of single-cell gene expression data. *Nature biotechnology*. 33, 495-502, doi:10.1038/nbt.3192 (2015)).

Single cell RNA may also be analyzed as described in Klein, A. M., Mazutis, L., Akartuna, I., Tallapragada, N., Veres, A., Li, V., Peshkin, L., Weitz, D. A., Kirschner, M. W. Droplet barcoding for single-cell transcriptomics applied to embryonic stem cells. Cell. 2015 May 21; 161(5):1187-201. doi:10.1016/j.cell.2015.04.044. PMCID:4441768.

The method of the invention may include determining RNA transcription and degradation rates. One may use RNA metabolically labeled with 4-thiouridine, to measure RNA transcription and degradation rates (Rabani, M., Raychowdhury, R., Jovanovic, M., Rooney, M., Stumpo, D. J., Pauli, A., Hacohen, N., Schier, A. F., Blackshear, P. J., Friedman, N., Amit, I. & Regev, A. High-resolution sequencing and modeling identifies distinct dynamic RNA regulatory strategies. *Cell*. 159, 1698-1710, doi:10.1016/j.cell.2014.11.015 (2014). PMCID:4272607; Rabani, M., Levin, J. Z., Fan, L., Adiconis, X., Raychowdhury, R., Garber, M., Gnirke, A., Nusbaum, C., Hacohen, N., Friedman, N., Amit, I. & Regev, A. Metabolic labeling of RNA uncovers principles of RNA production and degradation dynamics in mammalian cells. *Nature biotechnology*. 29, 436-442, doi:10.1038/nbt.1861 (2011). PMCID:3114636).

The method of the invention may include a step of determining DNA methylation. One may apply methods for reduced representation (RRBS), targeted capture, and whole genome bisulfite sequencing of DNA methylation from bulk to ultra-low inputs (Chan, M. M., Smith, Z. D., Egli, D., Regev, A. & Meissner, A. Mouse ooplasm confers context-specific reprogramming capacity. Nature genetics. 44, 978-980, doi:10.1038/ng.2382 (2012). PMCID:3432711; Smith, Z. D., Chan, M. M., Humm, K. C., Karnik, R., Mekhoubad, S., Regev, A., Eggan, K. & Meissner, A. DNA methylation dynamics of the human preimplantation embryo. Nature. 511, 611-615, doi:10.1038/nature13581 (2014). PMCID: 4178976; Smith, Z. D., Chan, M. M., Mikkelsen, T. S., Gu, H., Gnirke, A., Regev, A. & Meissner, A. A unique regulatory phase of DNA methylation in the early mammalian embryo. Nature. 484, 339-344, doi:10.1038/nature10960 (2012). PMCID:3331945) to single cells.

The method of the invention may include a step determining Chromatin accessibility. This may be performed by ATAC-Seq. For massively parallel single cell ATAC-Seq one may implement a droplet-based assay. First, in-tube, one may use Tn5 transposase to fragment chromatin inside isolated intact nuclei and add universal primers at cutting sites. Next, in-drop, one may use a high diversity library of barcoded primers to uniquely tag all DNA that originated from the same single cell. Alternatively, one may perform all steps in drop. One may also use a strategy that relies on split pooled nuclei barcoding in plates (Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. Science. 2015 May 22; 348(6237): 910-4. doi:10.1126/science.aab1601. Epub 2015 May 7). Applicants have optimized key steps in a mixture of human and mouse cells, with specificity that exceeds the initial performance of mRNA Drop-Seq. Applicants have also used a Fluidigm C1 protocol (see www.fluidigm.com/products/c1-system) to analyze ~100 single DCs, closely reproducing ensemble measures, high enrichment in TSSs, and nucleosome-like periodicity.

ATAC-seq (assay for transposase-accessible chromatin) identifies regions of open chromatin using a hyperactive prokaryotic Tn5-transposase, which preferentially inserts into accessible chromatin and tags the sites with sequencing adaptors (Pott and Lieb Genome Biology (2015) 16:172 DOI 10.1186/s13059-015-0737-7 and Buenrostro J D, Giresi P G, Zaba L C, Chang H Y, Greenleaf W J. Transposition of native chromatin for fast and sensitive epigenomic profiling of open chromatin, DNA-binding proteins and nucleosome position. Nat Methods. 2013; 10:1213-128). Two very different approaches were used: one relied on physical isolation of single cells (Buenrostro J D, Wu B, Litzenburger U M, Ruff D, Gonzales M L, Snyder M P, et al. Single-cell chromatin accessibility reveals principles of regulatory variation. Nature. 2015; 523:486-90), and the other avoided single-cell reaction volumes by using a two-step combinatorial indexing strategy (Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4).

In the indexing scheme, Cusanovich et al. [Cusanovich D A, Daza R, Adey A, Pliner H A, Christiansen L, Gunderson K L, et al. Epigenetics. Multiplex single-cell profiling of chromatin accessibility by combinatorial cellular indexing. Science. 2015; 348:910-4] lysed cells, and 2500 nuclei were placed into each well of a 96-well plate. Transposases loaded with unique adaptors were added to each well, creating 96 pools of approximately 2500 nuclei, each pool with distinct barcodes. Nuclei from all of the transposition reactions were mixed, and using a fluorescence-activated cell sorter (FACS) 15-25 nuclei were deposited into each well of a second 96-well plate. Nuclei in each well of this second plate were lysed, and the DNA was amplified using a primer containing a second barcode. The low number of nuclei per well ensured that about 90% of the resulting barcode combinations were unique to a single cell. This combinatorial indexing strategy enabled the recovery of 500-1500 cells with unique tags per experiment. Overall Cusanovich et al. obtained scATAC-seq data from over 15,000 individual cells from mixtures of GM12878 lymphoblastoid cells with HEK293, HL-60, or mouse Patski cells. The number of reads associated with any single cell was very low, varying from 500 to about 70,000 with a median of fewer than 3000 reads per cell.

Buenrostro et al. [Buenrostro J D, Wu B, Litzenburger U M, Ruff D, Gonzales M L, Snyder M P, et al. Single-cell chromatin accessibility reveals principles of regulatory variation. Nature. 2015; 523:486-90] used a programmable microfluidic device (C1, Fluidigm) to isolate single cells and perform ATAC-seq on them in nanoliter reaction chambers. Each nanochamber was analyzed under a microscope to ensure that a single viable cell had been captured. This approach is simple and has the significant advantage of a carefully monitored reaction environment for each individual cell, although the throughput was limited to processing 96 cells in parallel. Buenrostro et al. sampled 1632 cells from eight different cell lines, including GM12878, K562, and H1 cells, and obtained an average of 73,000 reads per cell, about 20 times the number of reads per cell obtained using the barcoding strategy.

The method of the invention may include a step of determining histone modifications and protein-DNA interactions. One may apply tools that use genomic barcoding to index chromatin prior to immunoprecipitation to enable multiplexed analysis of limited samples and individual cells in a single reaction. For single-cell chromatin profiling, one may use Drop-ChIP where the chromatin of individual cells is barcoded in droplets. Based on the Drop-Seq technique, one may encapsulate single cells, lyse and MNase-digest chromatin, then fuse a second droplet with barcoded oligos, ligate them to the fragmented chromatin, break the emulsion, add carrier chromatin, and carry out ChIP-Seq. this may be performed using a protocol with split-pool barcoding to collect $10^4$-$10^5$ single cells/assay.

ChIP-sequencing, also known as ChIP-seq, is a method used to analyze protein interactions with DNA which may be used with perturbation. ChIP-seq combines chromatin immunoprecipitation (ChIP) with massively parallel DNA sequencing to identify the binding sites of DNA-associated proteins. It can be used to map global binding sites precisely for any protein of interest. ChIP-seq is used primarily to determine how transcription factors and other chromatin-associated proteins influence phenotype-affecting mechanisms. Determining how proteins interact with DNA to regulate gene expression is for understanding many biological processes and disease states. This epigenetic information is complementary to genotype and expression analysis. ChIP-seq technology is as an alternative to ChIP-chip which requires a hybridization array. Specific DNA sites in direct physical interaction with transcription factors and other proteins can be isolated by chromatin immunoprecipitation. ChIP produces a library of target DNA sites bound to a protein of interest in vivo. Massively parallel sequence analyses are used in conjunction with whole-genome sequence databases to analyze the interaction pattern of any protein with DNA, see, e.g., Johnson D S, Mortazavi A et al. (2007) Genome-wide mapping of in vivo protein-DNA interactions. Science 316: 1497-1502, or the pattern of any epigenetic chromatin modifications. This can be applied to the set of ChIP-able proteins and modifications, such as transcription factors, polymerases and transcriptional machinery, structural proteins, protein modifications, and DNA modifications. See, e.g., "Whole Genome Chromatin IP Sequencing," Illumina, Inc (2010), available at www.illumina.com/Documents/products/datasheets/datasheet_chip_sequence.pdf (Chromatin Immunoprecipitation with massively parallel sequencing).

For multiplex analysis of (limited) bulk samples, one may rely on chromatin indexing (MINT-ChIP; iChIP), where MNase-fragmented chromatin is indexed by ligation to a uniquely barcoded adaptor and then pooled and processed in multiplex through all subsequent phases, either with (MINT-ChIP) or without (ichIP: Lara-Astiaso, D., Weiner, A., Lorenzo-Vivas, E., Zaretsky, I., Jaitin, D. A., David, E., Keren-Shaul, H., Mildner, A., Winter, D., Jung, S., Friedman, N. & Amit, I. Immunogenetics. Chromatin state dynamics during blood formation. Science. 345, 943-949, doi:10.1126/science.1256271 (2014). PMCID:4412442) carrier chromatin (without adaptors).

The method of the invention may include a step of determining proteins. Recently developed assays (e.g., CyTOF: Bendall, S. C., Simonds, E. F., Qiu, P., Amir el, A. D., Krutzik, P. O., Finck, R., Bruggner, R. V., Melamed, R., Trejo, A., Ornatsky, O. I., Balderas, R. S., Plevritis, S. K., Sachs, K., Pe'er, D., Tanner, S. D. & Nolan, G. P. Single-cell mass cytometry of differential immune and drug responses across a human hematopoietic continuum. Science. 332, 687-696, doi:10.1126/science.1198704 (2011). PMCID: 3273988), allow multiplexed, single cell detection of dozens of proteins in millions of cells, but rely on antibodies and cannot yet be combined with DNA readout. Conversely, mass spectrometry (LC-MS/MS) allows quantitative analysis of entire proteomes, but deep analysis requires large amounts of protein/cells. To measure single cell protein levels and post-translational modifications (PTMs), one may use one of three complementary antibody-based assays: (1) standard flow cytometry with a few proteins/PTMs, >106 single cells); (2) CyTOF (Bendall, S. C., Simonds, E. F., Qiu, P., Amir el, A. D., Krutzik, P. O., Finck, R., Bruggner, R. V., Melamed, R., Trejo, A., Ornatsky, O. I., Balderas, R. S., Plevritis, S. K., Sachs, K., Pe'er, D., Tanner, S. D. & Nolan, G. P. Single-cell mass cytometry of differential immune and drug responses across a human hematopoietic continuum. *Science.* 332, 687-696, doi:10.1126/science.1198704 (2011). PMCID:3273988) (heavy metal labeling with multiplex barcoding; ~30-50 proteins/PTMs, 105-106 single cells); and (3) novel, highly multiplexed, DNA sequencing-based readouts of protein levels (100s proteins/PTMs; $10^6$ cells). For sequencing based readouts, one may use one of two approaches, geared at detecting hundreds of proteins in single cells: Immuno-Seq (when antibodies can be washed out: Niemeyer, C. M., Adler, M. & Wacker, R. Detecting antigens by quantitative immuno-PCR. *Nat Protoc.* 2, 1918-1930, doi:10.1038/nprot.2007.267 (2007)) and proximity extension assays (PEA, when antibodies cannot be washed away: Hammond, M., Nong, R. Y., Ericsson, O., Pardali, K. & Landegren, U. Profiling cellular protein complexes by proximity ligation with dual tag microarray readout. *PLoS One.* 7, e40405, doi:10.1371/journal.pone.0040405 (2012). PMCID:3393744; Nong, R. Y., Wu, D., Yan, J., Hammond, M., Gu, G. J., Kamali-Moghaddam, M., Landegren, U. & Darmanis, S. Solid-phase proximity ligation assays for individual or parallel protein analyses with readout via real-time PCR or sequencing. *Nat Protoc.* 8, 1234-1248, doi:10.1038/nprot.2013.070 (2013); Stahlberg, A., Thomsen, C., Ruff, D. & Aman, P. Quantitative PCR analysis of DNA, RNAs, and proteins in the same single cell. *Clin Chem.* 58, 1682-1691, doi:10.1373/clinchem.2012.191445 (2012).) These use DNA-sequence based encoding, and are compatible with other genomic readouts (e.g., sgRNA barcodes). DNA-sequence tags can be conjugated to antibodies (Janssen, K. P., Knez, K., Spasic, D. & Lammertyn, J. Nucleic acids for ultra-sensitive protein detection. Sensors (Basel). 13, 1353-1384, doi:10.3390/s130101353 (2013). PMCID:3574740), nanobodies (Pardon, E., Laeremans, T., Triest, S., Rasmussen, S. G., Wohlkonig, A., Ruf, A., Muyldermans, S., Hol, W. G., Kobilka, B. K. & Steyaert, J. A general protocol for the generation of Nanobodies for structural biology. *Nat Protoc.* 9, 674-693, doi:10.1038/nprot.2014.039 (2014). PMCID: 4297639; Theile, C. S., Witte, M. D., Blom, A. E., Kundrat, L., Ploegh, H. L. & Guimaraes, C. P. Site-specific N-terminal labeling of proteins using sortase-mediated reactions. *Nat Protoc.* 8, 1800-1807, doi:10.1038/nprot.2013.102 (2013). PMCID:3941705) or aptamers (Janssen, K. P., Knez, K., Spasic, D. & Lammertyn, J. Nucleic acids for ultra-sensitive protein detection. *Sensors* (Basel). 13, 1353-1384, doi:10.3390/s130101353 (2013). PMCID:3574740.). Detection of specific transcripts and proteins in single cells may be performed as well (Frei et al., Highly multiplexed simultaneous detection of RNAs and proteins in single cells. *Nat Methods.* 2016 March; 13(3):269-75.)

In certain embodiments of the present invention, quantitative measurements of both the copy number and spatial distribution of large fractions of the transcriptome in single cells is measured by multiplexed error-robust fluorescence in situ hybridization (MERFISH) (Moffitt and Zhuang, Chapter One-RNA Imaging with Multiplexed Error-Robust Fluorescence In Situ Hybridization (MERFISH), *Methods in Enzymology*. Volume 572, 2016, Pages 1-49).

Multiplex Analysis of Single Cell Constituents

It is an object of the present invention to provide a method for the high multiplex analysis of cellular constituents by linking nucleic acids tags to existing ligand binding and/or antibody technologies to enable proteomic or cellular constituent detection and relative quantification by next-generation sequencing (NGS) in single cells or isolated aggregations of cellular constituents. The present invention may combine perturbation of single cells followed by protein analysis in the single cells, Thus, protein expression may be linked to a perturbation.

It is a further object of the present invention to provide for comparing high multiplex protein data variation between single cells or isolated aggregation of cellular constituents and between different biological conditions (e.g. healthy vs. diseased states; one genetic perturbation vs. another, different genetic backgrounds).

It is a further object of the present invention to provide massively parallel profiling of all circuit aspects in single cells or isolated aggregations of cellular constituents: from RNA to chromatin organization to protein levels.

In a first aspect, the present invention provides a method of assaying segregated cellular constituents, comprising: admixing at least one isolated aggregation of cellular constituents with monomers of a polymerizable gel; polymerizing the gel, to embed the cellular constituents in discrete polymer matrices; incubating the cellular constituents embedded in the polymer matrices with one or more labeling ligands with specific binding affinity for one or more target cellular constituents to produce one or more labeled cellular constituents in the polymer matrices, wherein each of the one or more labeling ligand comprises a bound oligonucleotide label comprising a unique constituent identifier (UCI) sequence, and wherein the incubation comprises binding conditions under which the labeling ligand will bind to the cellular constituent within the polymer matrix, and the incubation further comprises washing conditions under which unbound labeling ligands will be washed out of the polymer matrix; and sequencing the oligonucleotide label, whereby detecting the UCI by sequencing indicates the presence of the target cellular constituent.

Cellular constituents may include any molecule within a cell; i.e. proteins, nucleic acids, or post translational modifications (PTM). The cellular constituent may be a protein, RNA transcript, metabolite, or a DNA molecule. Specific cellular constituents may be proteins, modified proteins, hormones, cytokines, cellular metabolites, or carbohydrates. The isolated aggregation of cellular constituents may be a cell, an extracellular vesicle, an organelle, or an organized subcomponent thereof, including molecular complexes. Isolated aggregations of cellular constituents may include separate organelles of a single cell or separate organelles isolated from a population of cells. Organelles may be for example, mitochondria, nuclei, or cellular vesicles. In one embodiment, a specific type of single cells may be isolated. In one embodiment, immune cells are isolated from a population of cells. Not being bound by a theory, single mitochondria can be purified from a population of cells and the relative amounts of constituents present in each individual mitochondrion may be analyzed. Not being bound by a theory, immune cells may be isolated by a method such as cell sorting and the relative representation of cellular constituents may be determined for each individual cell.

The step of admixing the isolated aggregation of cellular constituents with monomers may be carried out in an aqueous solution, or in an aqueous aliquot or droplet present in an oil emulsion. The polymer matrix may be a hydrogel. The polymer matrix may be any hydrogel capable of polymerization to create a solid matrix that fixes the cellular constituents and provides a porosity capable of allowing labeling ligands to freely diffuse through the network of pores. The cellular constituents may be further fixed by treating with an aldehyde. The aldehyde may be formaldehyde, paraformaldehyde, or glutaraldehyde. Not being bound by a theory the fixation in a solid matrix prevents the mixing of the cellular constituents between the isolated aggregations of cellular constituents. Not being bound by a theory, capturing cellular constituents in a solid polymer mesh insures that they are physical units that can be ligand and/or antibody stained as a pool and isolated as single cells or isolated aggregates of cellular constituents subsequently. Not being bound by a theory, the fixing of cellular constituents in the polymer matrix allows access to the labeling ligands to intracellular constituents.

The physical units formed by the polymer matrix may be particles, droplets, or a continuous polymer matrix with discrete regions comprising the isolated aggregates of cellular constituents. Therefore, the polymer matrix may include more than one isolated aggregate of cellular constituents. The polymer matrix may be divided such that isolated aggregates of cellular constituents are separable. The polymer matrix may be separable in that individual particles, droplets, or sections can be isolated. They may be isolated by physical manipulation using a sorting device. The sorting device may use microfluidics. They may be separated by use of dilution or manual manipulation by a user. They may be separated by use any kind of (micro) dissection. The cellular constituents within the polymer matrix may be stained with a dye, or a dye-conjugated ligand indicating the location of individual cellular constituents or cells. The polymer matrix may be punched to isolate a core, wherein each core from the polymer matrix contains a single isolated aggregate of cellular constituents. Not being bound by a theory, the fixation of isolated aggregates of cellular constituents in a matrix allows each isolated aggregate of cellular constituents to be compartmentalized wherein the separate compartments can be treated in a single experimental vessel or container and separated subsequently.

The labeling ligands are linked with an oligonucleotide label that can be used to determine the identity of the ligand. Each oligonucleotide label may comprise a unique constituent identifier (UCI) that can be used to determine the presence of a cellular constituent. Not being bound by a theory, the availability of unique sequences allows the labeling and detection of a plurality of ligands each for a specific constituent. Not being bound by a theory, the UCI allows a DNA readout for detection of a cellular constituent. The DNA readout may be by any sequencing method or method of amplification, such as by PCR or next generation sequencing. The oligonucleotide label may additionally include a promoter for amplification by an RNA polymerase, such as T7 polymerase. Not being bound by a theory, amplification by T7 polymerase allows amplification of low represented sequences, whereas such sequences may be diluted out by domination of a higher represented sequence during PCR. Not being bound by a theory, the labeling of each labeling ligand with a unique UCI allows the identification of more than ten, or hundred, or thousands of cellular constituents in an isolated aggregation of cellular constituents.

The method may further comprise segregating the discrete polymer matrices comprising the labeled constituents before the step of sequencing. Segregating the discrete polymer matrices may be by sorting single discrete matrices into separate reaction vessels. Segregating the discrete polymer matrices may be by forming discrete unique-identifier-transfer compositions, each comprising the cellular constituents embedded in a discrete polymer matrix and a transfer particle, wherein: the ligand oligonucleotide label further comprises a capture sequence, and the UCI and capture sequence are together releasably attached to the labeling ligand; the labelling ligand is bound to the target cellular constituent; and, the transfer particle comprises: a capture-binding-sequence having specific binding affinity for the capture sequence attached to the UCI, and, a unique source identifier (USI) sequence that is unique to each transfer particle. The USI of each transfer particle preferably comprises 4-15 nucleotides. The method may further comprise releasing the UCI from the labeled ligand, under conditions within the unique-identifier-transfer composition so that the released capture sequence binds to the capture-binding-sequence on the transfer particle, thereby transferring the UCI to the transfer particle. The transfer particle may be a solid bead. The transfer particle may be a hydrogel bead. The transfer particle may also be used to capture nucleic acids present in a discrete polymer matrix. The nucleic acids may be RNA and/or DNA. Not being bound by a theory the transfer particle may be used to capture both the UCI and the nucleic acids, whereby the source of the bound cellular constituents and nucleic acids can be determined after sequencing.

The method may further comprise, before the sequencing step, generating a USI for each discrete polymer matrix by a split pool ligation method, wherein the oligonucleotide label further comprises a universal ligation handle (ULH) sequence configured to produce a DNA overhang capable of hybridization to a complementary over hang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence.

The split pool ligation method may comprise: splitting the pool of discrete polymer matrices into separate pools of polymer matrices, each containing a unique first index sequence; ligating the first index sequence to the ligation handle; pooling the discrete polymer matrices; optionally, splitting the pool of discrete polymer matrices into separate pools each containing a unique middle index sequence; ligating the middle index sequence to the first index sequence; and pooling the discrete polymer matrices; optionally, repeating the steps with another middle index sequence; splitting the pool of discrete polymer matrices into pools containing a unique final index sequence; and ligating the final index sequence to the preceding index sequence, whereby each discrete polymer matrix comprises a USI. The USI may have no middle index sequence, one middle index sequence, two middle index sequences, preferably the USI has a first, middle, and final index sequence. Not being bound by a theory, the size of the unique sequences in each index determines the amount included. Not being bound by a theory, the number of indices selected is the amount necessary such that the probability of having identical USI sequences on spate polymer matrices is approaching zero. In an exemplary embodiment, each index includes 192 unique sequences.

The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle. Additionally, the ULH may comprise a dsDNA part that already includes the overhang needed for index ligation.

The UCI may comprise 4 to 30 nucleotides or 7 to 30 nucleotides, preferably about 21 nucleotides. The oligonucleotide label may further comprise a unique molecular identifier (UMI) sequence. The first, middle, or final index sequence may further comprises a unique molecular identifier (UMI) sequence. The UMI may comprise 4-20 nucleotides. The UMI may comprise 8 to 16 nucleotides.

The isolated aggregation of cellular constituents may be a cell, an extracellular vesicle, an organelle, or an organized subcomponent thereof.

The sequencing may comprise combining a primer having a unique source identifier (USI) sequence with UCI, so that the USI and UCI sequences are sequenced together, and the USI preferably comprises 20 to 120 nucleotides.

The step of admixing, the isolated aggregation of cellular constituents with monomers may be carried out in an aqueous aliquot or in a droplet formed by an aqueous solution in oil emulsion. The aqueous aliquot may be a separate reaction vessel such as a well in a plate. The droplet may be formed by a microfluidic device. The polymer matrix may be a hydrogel. The method may be a multiplex assay with a plurality of labeling ligands, each labeling ligand have a distinct UCI. The labeling ligand may be non-covalently bound to the target cellular constituent.

The method may further comprise pooling the oligonucleotide labels comprising a USI from a plurality of polymer matrices and sequencing the pooled UCI sequences and USI sequences. The method may further comprise pooling the oligonucleotide labels comprising a USI and UMI from a plurality of polymer matrices and sequencing the pooled UCI sequences, USI sequences, and UMI sequences.

The method may further comprise washing the cellular constituents embedded in the polymer matrices to remove selected cellular components from the polymer matrices before incubating the cellular constituents with the labeling ligand. The washing may comprise treating the cellular constituents embedded in the polymer matrices with a detergent so as to remove lipids from the polymer matrices before incubating the cellular constituents with the labeling ligand. The detergent may be an anionic detergent or non-ionic detergent. The detergent may be SDS, NP-40, triton X-100, or any other detergent known in the art capable of removing lipids.

The method may further comprise quantitating the relative amount of the UCI sequence associated with a first aggregation of cellular constituents to the amount of the same UCI sequence associated with a second aggregation of cellular constituents, whereby the relative differences of a cellular constituent between aggregations of cellular constituents are determined. The relative amount may be compared to a control sample. The control sample may have predetermined amounts of cellular constituents. There may be more than one control sample. There may be at least three control samples. The at least three control samples can be used to generate a standard curve upon which all of the other cellular constituents within discrete polymer matrices are compared. The control sample may comprise isolated aggregations of cellular constituents that were untreated as compared relative to isolated aggregations of cellular constituents that were treated with a different condition. Cells may be treated with drugs, small molecules, pathogens, hormones, cytokines, proteins, nucleic acids, virus particles, or grown in different cellular environments. Cells may be isolated from a diseased tissue. The cells from the diseased tissue may be compared to cells from non-diseased tissue. Cells may be treated with systems that knockout, decrease or increase expression of a gene. Cells may be treated with systems that knockout functional elements of a genome. Functional elements include, but are not limited to promoters, enhancers, repressors, centromeres, or telomeres. CRISPR systems may be used.

The labeling ligand may be an antibody or an antibody fragment. The antibody fragment may be a nanobody, Fab, Fab', (Fab')2, Fv, ScFv, diabody, triabody, tetrabody, Bis-scFv, minibody, Fab2, or Fab3 fragment. The labeling ligand may be an aptamer. The labeling ligand may be a nucleotide sequence complementary to a target sequence.

The method may comprise multiplex binding of two or more labeling ligands to each aggregation of cellular constituents. The two or more distinct labeling ligands may comprise complementary oligonucleotide sequences, so that binding of the labeling ligands to respective target cellular constituents that are in proximity permits the complementary sequences of the distinct ligands to hybridize, forming an amplifiable polynucleotide duplex. The method may further comprise amplifying the polynucleotide duplex to provide an amplified sequence that is a detectable signal that target cellular constituents are in proximity. The complementary oligonucleotide sequences, which serve as a start site for polymerase extension, can either be designed to query proximity of two specific cellular constituents, or it can be designed to be universal, thereby querying interactions between all members of the labeling ligand panel.

In one embodiment, at least two distinct labeling ligands comprise oligonucleotide sequences configured to be ligated, so that binding of the labeling ligands to respective target cellular constituents that are in proximity permits the oligonucleotide sequences of the distinct ligands to ligate, forming an amplifiable polynucleotide duplex. The method may further comprise amplifying the polynucleotide duplex to provide an amplified sequence that is a detectable signal that target cellular constituents are in proximity.

One of the labeling ligands may comprise an oligonucleotide label with a restriction enzyme site between the labeling ligand and the UCI, and wherein the method may further comprise treating with a restriction enzyme, whereby the UCI from the labeling ligand is transferred to the oligonucleotide label of the labeling ligand in proximity.

The method may further comprise labeling the aggregation of cellular constituents by fluorescent in situ hybridization.

The aggregation of cellular constituents may be a cell that is a member of a cell population. The cell may be transformed or transduced with one or more genomic sequence-perturbation constructs that perturb a genomic sequence in the cells, wherein each distinct genomic sequence-perturbation construct comprises a unique-perturbation-identifier (UPI) sequence unique to that construct. The genomic sequence-perturbation construct may comprise a sequence encoding a guide RNA sequence of a CRISPR-Cas targeting system. The method may further comprise multiplex transformation of the population of cells with a plurality of genomic sequence-perturbation constructs. The UPI sequence may be attached to a perturbation-sequence-capture sequence, and the microbeads may comprise a perturbation-sequence-capture-binding-sequence having specific binding affinity for the perturbation-sequence-capture sequence attached to the UPI sequence. The UPI sequence may be attached to a universal ligation handle sequence, whereby a USI may be generated by split-pool ligation. The method may further comprise multiplex sequencing of the pooled UCI sequences, USI sequences, and UPI sequences.

The oligonucleotide label may comprise a regulatory sequence configured for amplification by an RNA polymerase, such as T7 polymerase. The labeling ligands may comprise oligonucleotide sequences configured to hybridize to a transcript specific region. The oligonucleotide label may further comprise attachment chemistry, such as an acrylic phosphoramidite modification, whereby the modification allows for incorporation into the polymer matrices upon polymerization. The acrylic phosphoramidite may be Acrydite™ (Eurofins Scientific, Luxembourg). The method may further comprise amplification of the oligonucleotide label and USI by PCR or T7 amplification before sequencing. T7 amplification may be followed by cDNA generation and optionally amplification by PCR. The oligonucleotide label may further comprise at least one spacer sequence, preferably two spacer sequences. The oligonucleotide label may further comprise a photocleavable linker. The oligonucleotide label may further comprise a restriction enzyme site between the labeling ligand and UCI.

The discrete polymer matrices may be labeled and washed more than once. Discrete polymer matrices may be labeled with a marker specific for a cell type or cell cycle marker or developmental marker, or differentiation marker, or disease marker. The label may be a fluorescent label. The fluorescent label may be used to separate the discrete polymer matrices into distinct groups. The label may be used to identify a certain cell type prior to embedding it into a discrete polymer matrix. The discrete polymer matrices of a distinct group may then be labeled again with labeling ligands that contain an oligonucleotide label of the present invention. After novel information is obtained from the multiplex assay of the present invention, a 'banked' population of polymer matrices can be stained for newly identified markers and the population of interest can be sorted (enriched) for, and investigated more deeply.

In another aspect, the present invention provides a method of determining open chromatin in individual cells comprising: isolating single cells into droplets formed by an aqueous solution in oil emulsions, wherein the droplets further comprise Tn5-transposase loaded with two tagmentation adapters, wherein one adapter is configured for incorporation into a polymer matrix and the second adapter is configured with a ligation handle for generating a USI; incubating the droplets to allow cell lysis and tagmentation of open chromatin; infusing monomers of a polymerizable gel into the droplets; polymerizing the gel, to embed the cellular constituents in discrete polymer matrices; optionally incubating the polymer matrices with one or more labeling ligands with specific binding affinity for one or more target cellular constituents to produce one or more labeled cellular constituents in the polymer matrices, wherein each of the one or more labeling ligand comprises a bound oligonucleotide label comprising a unique constituent identifier (UCI) sequence and a sequence capable of hybridization to the tagmentation adapter configured for incorporation into a polymer matrix, and wherein the incubation comprises binding conditions under which the labeling ligand will bind to the cellular constituent within the polymer matrix and the oligonucleotide label will hybridize to said tagmentation adapter, and wherein the incubation further comprises washing conditions under which unbound labeling ligands will be washed out of the polymer matrix; and extending the genomic DNA and adapter DNA, whereby a continuous DNA strand is generated comprising the adapters, genomic DNA, and DNA overhang; optionally the oligonucleotide label bound to a labeling ligand; generating a USI at the DNA overhang by split-pool ligation; sequencing the continuous DNA strand, whereby open chromatin is determined and optionally the presence of a cellular constituent at a site of open chromatin is determined.

In another aspect, the present invention provides a method of measuring RNA levels in individual cells comprising: isolating single cells into droplets formed by an aqueous solution in oil emulsions, wherein the droplets comprise at least one labeling ligands specific for binding at one or more target RNA transcripts, wherein the labeling ligands are configured for incorporation into a polymer matrix and comprise a ligation handle for generating a USI; lysing the cells in the droplets under conditions wherein the labeling ligands will bind to the target RNA transcripts; injecting monomers of a polymerizable gel into the droplets; polymerizing the gel, to embed the labeling ligands in discrete polymer matrices; optionally, staining the discrete polymer matrices with at least one additional labeling ligand; generating a USI by split-pool ligation; and sequencing the resulting DNA, whereby RNA levels and optionally protein levels are determined in single cells. The droplets may comprise at least one pair of labeling ligands specific for binding at adjacent sites of one or more target RNA transcripts, wherein each pair of labeling ligands comprises one labeling ligand configured for incorporation into a polymer matrix and one labeling ligand comprising a ligation handle for generating a USI, and wherein the method may further comprise injecting a ligation reaction buffer comprising a ligase that is configured to allow ligation of the pair of labeling ligands if they are hybridized adjacently with single nucleotide resolution on the target RNA transcript, such that off target binding of labeling ligand does not get ligated, and will not be amplified in subsequent steps.

In another aspect, the present invention provides a method of assaying segregated cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence, and wherein the incubation comprises binding conditions under which the labeling ligand will bind to the cellular constituent within the cell(s), and the incubation further comprises washing conditions under which unbound labeling ligands will be washed from the cell(s); admixing the cell(s) with monomers of a polymerizable gel; isolating single cells into droplets formed by an aqueous solution in oil emulsions; polymerizing the gel, to embed the labeling ligands and other cellular constituents in discrete polymer matrices; optionally, staining the discrete polymer matrices with at least one additional labeling ligand; generating a USI by split-pool ligation; and sequencing the oligonucleotide label, whereby detecting the UCI by sequencing indicates the presence of the target cellular constituent. The labeling ligands in step (b) may comprise at least one pair of labeling ligands specific for binding at adjacent sites of one or more target RNA transcripts, wherein each pair of labeling ligands comprises one labeling ligand configured for incorporation into a polymer matrix and one labeling ligand comprising a ligation handle for generating a USI, and wherein the method further comprises ligating the pair of labeling ligands if they are within proximity after binding to the target RNA transcripts. Any of the preceding methods may comprise polymer matrices wherein they further comprise magnetic particles. In one embodiment, any hydrogel droplet encapsulated aggregations of cellular constituents may further comprise magnetic particles embedded into the droplets. Not being bound by a theory, magnetic particles enable magnetic separation, aiding in clean up and washing steps in multiple reactions. Not being bound by a theory, the use of magnetic particles greatly enhances automation and therefore throughput.

In another aspect, the present invention provides a method of assaying segregated cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence, and wherein the incubation comprises binding conditions under which the labeling ligand will bind to the cellular constituent within the cell(s), and the incubation further comprises washing conditions under which unbound labeling ligands will be washed from the cell(s); and sequencing the oligonucleotide label, whereby detecting the UCI by sequencing indicates the presence of the target cellular constituent. The cellular constituent may comprise a protein, RNA transcript, or a DNA molecule. The method may further comprise segregating the cell(s) before sequencing. The segregating the cell(s) may comprise sorting the single cell(s) into a separate reaction vessel(s). The segregating the cell(s) may comprise forming discrete unique-identifier-transfer compositions, each comprising a cell and a transfer particle, wherein: the oligonucleotide label further comprises a capture sequence, and the UCI and capture sequence are together releasably attached to the labeling ligand; the labelling ligand is bound to the target cellular constituent; and, the transfer particle comprises: a capture-binding-sequence having specific binding affinity for the capture sequence attached to the UCI, and, a unique source identifier (USI) sequence that is unique to each transfer particle, and the USI preferably comprises 4-15 nucleotides. The method may further comprise releasing the UCI from the labeled ligand, under conditions within the unique-identifier-transfer composition so that the released capture sequence binds to the capture-binding-sequence on the transfer particle, thereby transferring the UCI to the transfer particle. The method may further comprise, before sequencing in step, generating a USI for each cell(s) by a split pool ligation method, wherein the oligonucleotide label further comprises a universal ligation handle (ULH) sequence configured to produce a DNA overhang capable of hybridization to a complementary over hang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of cell(s) into separate pools of cell(s), each containing a unique first index sequence; ligating the first index sequence to the ligation handle; pooling the cell(s); optionally, splitting the pool of cell(s) into separate pools each containing a unique middle index sequence; ligating the middle index sequence to the first index sequence; and pooling the cell(s); optionally, repeating with another middle index sequence; splitting the pool of cell(s) into pools containing a unique final index sequence; and ligating the final index sequence to the preceding index sequence, whereby each cell comprises a USI.

The ligation handle may comprise a restriction site for producing an overhang complementary with a first index sequence overhang, and wherein the method further comprises digestion with a restriction enzyme. The ligation handle may comprise a nucleotide sequence complementary with a ligation primer sequence and wherein the overhang complementary with a first index sequence overhang is produced by hybridization of the ligation primer to the ligation handle.

The UCI may comprise 4 to 30 nucleotides, or 7 to 30 nucleotides, or about 21 nucleotides. The oligonucleotide label may further comprise a unique molecular identifier (UMI) sequence. The first, middle, or final index sequence may further comprise a unique molecular identifier (UMI) sequence. The UMI may be 4-20 nucleotides. The UMI may be 8 to 16 nucleotides.

The sequencing may comprise combining a primer having a unique source identifier (USI) sequence with UCI, so that the USI and UCI sequences are sequenced together, and the USI preferably comprises 20 to 120 nucleotides.

The method may comprise a multiplex assay with a plurality of labeling ligands, each labeling ligand have a distinct UCI. The labeling ligand may be non-covalently bound to the target cellular constituent. The method may further comprise pooling the oligonucleotide labels comprising a USI from a plurality of cells and sequencing the pooled UCI sequences and USI sequences. The method may further comprise pooling the oligonucleotide labels comprising a USI and UMI from a plurality of cells and sequencing the pooled UCI sequences, USI sequences, and UMI sequences. The method may further comprise quantitating the relative amount of the UCI sequence associated with a first cell to the amount of the same UCI sequence associated with a second cell, whereby the relative differences of a cellular constituent between cell(s) are determined.

The labeling ligand may be an antibody or an antibody fragment. The antibody fragment may be a nanobody, Fab, Fab', (Fab')2, Fv, ScFv, diabody, triabody, tetrabody, Bis-scFv, minibody, Fab2, or Fab3 fragment. The labeling ligand may be an aptamer. The labeling ligand may be a nucleotide sequence complementary to a target sequence.

The method may comprise multiplex binding of two or more labeling ligands to the cellular constituents. At least two distinct labeling ligands may comprise complementary oligonucleotide sequences, so that binding of the labeling ligands to respective target cellular constituents that are in proximity permits the complementary sequences of the distinct ligands to hybridize, forming an amplifiable polynucleotide duplex. The method may further comprise amplifying the polynucleotide duplex to provide an amplified sequence that is a detectable signal that target cellular constituents are in proximity. At least two distinct labeling ligands may comprise oligonucleotide sequences configured to be ligated, so that binding of the labeling ligands to respective target cellular constituents that are in proximity permits the oligonucleotide sequences of the distinct ligands to ligate, forming an amplifiable polynucleotide duplex. The method may further comprise amplifying the polynucleotide duplex to provide an amplified sequence that is a detectable signal that target cellular constituents are in proximity. One of the labeling ligands may comprise a restriction enzyme site between the labeling ligand and the oligonucleotide label, and wherein the method further comprises treating with a restriction enzyme, whereby the UCI from said labeling ligand is transferred to the oligonucleotide label of the labeling ligand in proximity.

The method may further comprise labeling the cell(s) by fluorescent in situ hybridization.

The cell(s) may be a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct. The genomic sequence-perturbation construct may comprise a sequence encoding a guide RNA sequence of a CRISPR-Cas targeting system. The method may further comprise multiplex transformation of the population of cells with a plurality of genomic sequence-perturbation constructs. The UPI sequence may be attached to a perturbation-sequence-capture sequence, and the transfer particle may comprise a perturbation-sequence-capture-binding-sequence having specific binding affinity for the perturbation-sequence-capture sequence attached to the UPI sequence. The UPI sequence may be attached to a universal ligation handle sequence, whereby a USI may be generated by split-pool ligation. The method may further comprise multiplex sequencing of the pooled UCI sequences, USI sequences, and UPI sequences.

In another aspect, the present invention provides a method of determining interactions between 2 or more cellular constituents, comprising: admixing at least one isolated aggregation of cellular constituents with monomers of a polymerizable gel; polymerizing the gel, to embed the cellular constituents in discrete polymer matrices; incubating the cellular constituents embedded in the polymer matrices with one or more labeling ligands with specific binding affinity for one or more target cellular constituents to produce one or more labeled cellular constituents in the polymer matrices, wherein each of the one or more labeling ligands comprise a bound oligonucleotide label comprising a unique constituent identifier (UCI) sequence and a universal hybridization nucleotide sequence, and wherein the incubation comprises binding conditions under which the labeling ligand will bind to the cellular constituent within the polymer matrix, and the incubation further comprises washing conditions under which unbound labeling ligands will be washed out of the polymer matrix; incubating the polymer matrices with at least one Unique Location Index probe, wherein the probe comprises at least two repeating nucleotide sequences, each repeat comprising a restriction enzyme site, a Unique Location Index (ULI) sequence, and a complementary universal hybridization nucleotide sequence, and wherein the incubation comprises binding conditions under which the universal hybridization sequence will hybridize the complementary universal hybridization sequence; extending the oligonucleotide label hybridized to the probe such that the oligo bound to the affinity ligand incorporates the ULI sequence that is unique to that Unique Location Index probe; digestion with a restriction enzyme specific for the site on the probe, sequencing the oligonucleotide label, whereby detecting the same ULI with two or more UCI's indicates that the cellular constituents were interacting. The ULI sequence may be randomly generated, such that no two ULI sequences are the same. Methods of generating a barcode sequence described herein may be used to generate a ULI. The ULI will be detected with the UCI, such that when multiple cellular constituents are in proximity oligonucleotide labels comprising each UCI and the ULI from a single probe will be generated. Not being bound by a theory, using a plurality of labeling ligands with specificity for a plurality of cellular constituents will allow novel interactions to be determined. The use of polymer matrices allows a stable platform for washing out the unbound labeling ligands before staining with the ULI probes. The cellular constituent may comprise a protein, RNA transcript, or a DNA molecule. The ULI may be 4-30 nucleotides. The ULI may be 8-20 nucleotides.

The method may further comprise segregating the discrete polymer matrices comprising the labeled constituents before sequencing. The segregating of the discrete polymer matrices may comprise sorting single discrete matrices into separate reaction vessels.

The method may further comprise, before sequencing, generating a USI for each discrete polymer matrix by a split pool ligation method, wherein the restriction site on the ULI probe is a universal ligation handle (ULH) sequence configured to produce a DNA overhang capable of hybridization to a complementary over hang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of discrete polymer matrices into separate pools of polymer matrices, each containing a unique first index sequence; ligating the first index sequence to the ligation handle; pooling the discrete polymer matrices; optionally, splitting the pool of discrete polymer matrices into separate pools each containing a unique middle index sequence; ligating the middle index sequence to the first index sequence; and pooling the discrete polymer matrices; optionally, repeating step (d) with another middle index sequence; splitting the pool of discrete polymer matrices into pools containing a unique final index sequence; and ligating the final index sequence to the preceding index sequence, whereby each discrete polymer matrix comprises a USI.

The oligonucleotide label may further comprise a unique molecular identifier (UMI) sequence. The first, middle, or final index sequence may further comprise a unique molecular identifier (UMI) sequence. The method may further comprise pooling the oligonucleotide labels comprising a USI, ULI and UMI from a plurality of polymer matrices and sequencing the pooled UCI sequences, USI sequences, ULI sequences, and UMI sequences.

The aggregation of cellular constituents may be a cell that is a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct.

In another aspect, the present invention provides a method of determining interactions between 2 or more cellular constituents, comprising: fixing and permeabilizing at least one cell; incubating the fixed and permeabilized cell(s) with one or more labeling ligands with specific binding affinity for one or more target cellular constituents to produce one or more labeled cell(s), wherein each of the one or more labeling ligands comprise a bound oligonucleotide label comprising a unique constituent identifier (UCI) sequence and a universal hybridization nucleotide sequence, and wherein the incubation comprises binding conditions under which the labeling ligand will bind to the cellular constituent within the cell(s), and the incubation further comprises washing conditions under which unbound labeling ligands will be washed from the polymer cell(s); incubating the cell(s) with at least one Unique Location Index probe, wherein the probe comprises at least two repeating nucleotide sequences, each repeat comprising a restriction enzyme site, a Unique Location Index (ULI) sequence, and a complementary universal hybridization nucleotide sequence, and wherein the incubation comprises binding conditions under which the universal hybridization sequence will hybridize to the complementary universal hybridization sequence; extending the oligonucleotide label hybridized to the probe; digesting with a restriction enzyme specific for the site on the probe; and sequencing the oligonucleotide label, whereby detecting the same ULI with two or more UCI's indicates that the cellular constituents were interacting. The cellular constituent may comprise a protein, RNA transcript, or a DNA molecule. The ULI may be 4-30 nucleotides. The ULI may be 8-20 nucleotides.

The method may further comprise segregating the cell(s) comprising the labeled constituents before sequencing. The segregating of the cell(s) may comprise sorting single discrete matrices into separate reaction vessels. The method may further comprise, before sequencing, generating a USI for each cell by a split pool ligation method, wherein the restriction site on the ULI probe is a universal ligation handle (ULH) sequence configured to produce a DNA overhang capable of hybridization to a complementary over hang on a first index nucleotide sequence, wherein the first index nucleotide sequence comprises an overhang complementary to a final index sequence or optionally a middle index sequence, wherein the middle index sequence comprises overhangs complementary to the first index sequence and to the final index sequence or optionally to another middle index sequence and final index sequence, wherein the final index sequence has a single overhang complementary to the preceding index sequence, and wherein the first, middle, and final index sequences are selected from a plurality of unique sequences comprising compatible DNA overhangs and 10 to 30 base pairs of unique sequence. The split pool ligation method may comprise: splitting the pool of cells into separate pools of cells, each containing a unique first index sequence; ligating the first index sequence to the ligation handle; pooling the cells; optionally, splitting the pool of cells into separate pools each containing a unique middle index sequence; ligating the middle index sequence to the first index sequence; and pooling the cells; optionally, repeating with another middle index sequence; splitting the pool of cells into pools containing a unique final index sequence; and ligating the final index sequence to the preceding index sequence, whereby each cell comprises a USI.

The oligonucleotide label may further comprise a unique molecular identifier (UMI) sequence. The first, middle, or final index sequence may further comprise a unique molecular identifier (UMI) sequence. The method may further comprise pooling the oligonucleotide labels comprising a USI, ULI and UMI from a plurality of polymer matrices and sequencing the pooled UCI sequences, USI sequences, ULI sequences, and UMI sequences.

The cells may be a member of a cell population, further comprising transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct. The perturbation constructs may be any as described herein.

The oligonucleotide label may comprise a regulatory sequence configured for amplification by T7 polymerase.

The labeling ligands may comprise oligonucleotide sequences configured to hybridize to a transcript specific region.

Before sequencing, the method may further comprise: amplification of the oligonucleotide label by PCR; or T7 amplification of the oligonucleotide label followed by subsequent cDNA generation, and optionally amplification by PCR.

The oligonucleotide label may further comprise at least one spacer sequence. The oligonucleotide label may further comprise a photocleavable linker. The oligonucleotide label may further comprise a restriction enzyme site between the labeling ligand and UCI.

The oligonucleotide label may comprise one or more iso-dG and/or iso-dC nucleotides. The oligonucleotide labels for hybridization in a proximity assay may comprise one or more iso-dG and/or iso-dC nucleotides. The universal hybridization sequences may comprise one or more iso-dG and/or iso-dC nucleotides. Not being bound by a theory the one or more iso-dG and/or iso-dC nucleotides will increase specificity of hybridization.

In one embodiment, the oligonucleotide label of any of the methods described herein may comprise one or more iso-dG and/or iso-dC nucleotides. Two complementary sequences may comprise one sequence with iso-dG and the other complementary sequence with iso-dC, whereby the two sequences are capable of hybridizing with each other, but not with sequences containing only dG, dC, dA, and/or dT. The sequence of the oligonucleotide labels for hybridization in a proximity assay may advantageously comprise one or more iso-dG and/or iso-dC nucleotides.

Any of the methods of the present invention may advantageously be combined for determining any combination of protein detection, RNA detection, open chromatin detection, protein-protein interactions, protein-RNA interactions, or protein-DNA interactions.

The terms "isolated aggregation of cellular constituents" or "single aggregations of cellular constituents" or "aggregations of cellular constituents" or "aggregations of biologically connected cellular constituents" are used interchangeably and refer to any group of cellular constituents that originate from the same source, that are functionally connected biologically, and that can be isolated individually. Examples may be a cell, an extracellular vesicle, an organelle, or an organized subcomponent thereof. Specific examples may be a nucleus or a mitochondria.

The term "cellular constituent" refers to any cellular molecule, including but not limited to a protein, nucleic acid, RNA molecule, DNA molecule, or carbohydrate.

The term "unique molecular identifiers" (UMI) refers to a sequencing linker used in a method that uses molecular tags to detect and quantify unique amplified products. A UMI is used to distinguish effects through a single clone from multiple clones. In preferred embodiments, the amplification is by PCR. A sequencer linker with a random sequence of between 4 and 20 basepairs and an index sequence is added to the 5' end of the template, which is amplified and sequenced. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI and UCI's are designed such that assignment to the original can take place despite up to 4-7 errors during amplification or sequencing.

The term "unique constituent identifier" (UCI) refers to any unique nucleotide sequence linked to a labeling ligand, such that the presence of the sequence indicates the presence of the cellular constituent that the labeling ligand specifically binds. In an exemplary embodiment, the UCI is linked to an antibody for a specific cellular constituent. If the cellular constituent is present in a sample, the antibody will bind and the UCI can be detected. If the cellular constituent is not present in a sample, the antibody will not bind and the UCI will not be detected above background. In another exemplary embodiment, the labeling ligand is an oligonucleotide probe and the cellular constituent is an RNA transcript molecule complementary to the sequence of the oligonucleotide probe. The sequence of the oligonucleotide probe may be the UCI or may comprise an additional UCI sequence to identify the RNA transcript.

The term "unique source identifier" (USI) refers to a unique nucleotide sequence that is associated with the nucleic acids from a single cell or single isolated aggregation of cellular constituents (source), such that upon sequencing a pool of nucleic acid sequences from more than one cell or isolated aggregation of cellular constituents, the presence of a USI in the sequenced product indicates that a product originated from a single source. USI may be used interchangeably with the term "barcode."

The term "unique-amplification-identifier" (UAI) refers to a nucleotide sequence that is only formed only when two or more nucleotide sequences are in close proximity to each other such that they can be ligated. The UAI can be generated using methods described for the proximity ligation assay (PLA) or proximity extension assay (PEA) (Fredriksson S, et al. (2002) Protein detection using proximity-dependent DNA ligation assays. Nature biotechnology 20: 473-477; Gullberg M, et al. (2004) Cytokine detection by antibody-based proximity ligation. Proceedings of the National Academy of Sciences of the United States of America 101:8420-8424; and Lundberg M, et al. (2011)

Homogeneous antibody-based proximity extension assays provide sensitive and specific detection of low-abundant proteins in human blood. Nucleic acids research 39(15): e102). PEA is based on pairs of antibodies that are linked to oligonucleotides having slight affinity to one another (PEA probes). Upon target binding the probes are brought in proximity, and the two oligonucleotides are extended by a DNA polymerase forming the UAI that now acts as a unique surrogate marker for the specific antigen.

The terms "sticky end," "overhang" and "DNA overhang" refer to a double stranded DNA having either a 3' or 5' single stranded DNA overhang capable of hybridization to another complementary sticky end or DNA overhang.

The term "hydrogel" refers to any network of polymer chains that are hydrophilic, and sometimes found as a colloidal gel, in which water is the dispersion medium. Hydrogels are highly absorbent (they can contain over 90% water) natural or synthetic polymeric networks. Hydrogels also possess a degree of flexibility very similar to natural tissue, due to their significant water content. Hydrogel may include polyvinyl alcohol, sodium polyacrylate, acrylate polymers, copolymers with an abundance of hydrophilic groups, agarose, methylcellulose, hyaluronan, and other naturally derived polymers.

The term "tagmentation" refers to a step in the Assay for Transposase Accessible Chromatin using sequencing (ATAC-seq) as described. (See, Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218). Specifically, a hyperactive Tn5 transposase loaded in vitro with adapters for high-throughput DNA sequencing, can simultaneously fragment and tag a genome with sequencing adapters. In one embodiment, the adapters are compatible with the methods described herein.

The present invention may also include barcoding. Barcoding may be performed based on any of the compositions or methods disclosed in patent publication WO 2014047561 A1, Compositions and methods for labeling of agents, incorporated herein in its entirety. In one embodiment each labeling ligand has a barcode (UCI). In one embodiment, a sgRNA has a barcode. In one embodiment the UCI is captured on a bead that includes a barcode sequence (USI). Not being bound by a theory, amplified sequences from single cells or isolated aggregations of cellular constituents can be sequenced together and resolved based on the barcode associated with each USI. Not being bound by a theory, the presence of a labeling ligand can be determined by sequencing of the UCI.

In certain embodiments barcoding uses an error correcting scheme (T. K. Moon, Error Correction Coding: Mathematical Methods and Algorithms (Wiley, New York, ed. 1, 2005)). Not being bound by a theory, amplified sequences from single cells can be sequenced together and resolved based on the barcode associated with each cell.

The term "barcode" as used herein, refers to any unique, non-naturally occurring, nucleic acid sequence that may be used to identify the originating source of a nucleic acid fragment. Such barcodes may be sequences including but not limited to about 20 base pair sequences. Although it is not necessary to understand the mechanism of an invention, it is believed that the barcode sequence provides a high-quality individual read of a barcode associated with a viral vector, labeling ligand, shRNA, sgRNA or cDNA such that multiple species can be sequenced together.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a *crocus*?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94).

In certain embodiments, sequencing is performed using unique molecular identifiers (UMI). The term "unique molecular identifiers" (UMI) refers to a sequencing linker used in a method that uses molecular tags to detect and quantify unique amplified products. A UMI is used to distinguish effects through a single clone from multiple clones. In preferred embodiments, the amplification is by PCR. A sequencer linker with a random sequence of between 4 and 20 base pairs is added to the 5' end of the template, which is amplified and sequenced. Sequencing allows for high resolution reads, enabling accurate detection of true variants. As used herein, a "true variant" will be present in every amplified product originating from the original clone as identified by aligning all products with a UMI. Each clone amplified will have a different random UMI that will indicate that the amplified product originated from that clone. Background caused by the fidelity of the amplification process can be eliminated because true variants will be present in all amplified products and background representing random error will only be present in single amplification products (See e.g., Islam S. et al., 2014. Nature Methods No: 11, 163-166). Not being bound by a theory, the UMI's are designed such that assignment to the original can take place despite up to 4-7 errors during amplification or sequencing.

Unique molecular identifiers are a subtype of nucleic acid barcode that can be used, for example, to normalize samples for variable amplification efficiency. For example, in various embodiments, featuring a solid or semisolid support (for example a hydrogel bead), to which nucleic acid barcodes (for example a plurality of barcode sharing the same sequence) are attached, each of the barcodes may be further coupled to a unique molecular identifier, such that every barcode on the particular solid or semisolid support receives a distinct unique molecule identifier. A unique molecular identifier can then be, for example, transferred to a target molecule with the associated barcode, such that the target molecule receives not only a nucleic acid barcode, but also an identifier unique among the identifiers originating from that solid or semisolid support.

In certain embodiments, multiple displacement amplification (MDA) is used. Multiple displacement amplification (MDA, is a non-PCR-based isothermal method based on the annealing of random hexamers to denatured DNA, followed by strand-displacement synthesis at constant temperature (Blanco et al. J. Biol. Chem. 1989, 264, 8935-8940). It has been applied to samples with small quantities of genomic DNA, leading to the synthesis of high molecular weight DNA with limited sequence representation bias (Lizardi et al. Nature Genetics 1998, 19, 225-232; Dean et al., Proc. Natl. Acad. Sci. U.S.A 2002, 99, 5261-5266). As DNA is synthesized by strand displacement, a gradually increasing number of priming events occur, forming a network of hyper-branched DNA structures. The reaction can be catalyzed by enzymes such as the Phi29 DNA polymerase or the large fragment of the Bst DNA polymerase. The Phi29 DNA polymerase possesses a proofreading activity resulting in error rates 100 times lower than Taq polymerase (Lasken et al. Trends Biotech. 2003, 21, 531-535).

The invention provides a method for preparing uniquely barcoded particles. Unique barcode sequences may be generated by a split pool method. The split pool method may include sticky end ligation. Sticky end ligation may include a sticky end ligation handle and separate indexes containing unique sequences capable of hybridizing to a sticky end (see examples). The sticky end may comprise a ssDNA overhang. The over-hang may be 2, 3, 4, 5, 6, 7, 8, preferably 4 bases. The overhang may be generated by a restriction enzyme. Each index may contain a plurality of unique sequences. Each index may contain 10, 20, 30, 40, 50, 60, 70, 80, 90, 100, 200, preferably 192 sequences. In one embodiment there are 2, 3, 4, preferably 3 indexes. A unique barcode sequence is generated by ligation of the first index to the ligation handle, splitting and pooling of the ligated samples, and then addition of the next index also containing sticky ends. The last index preferably has a sticky end for ligation to the previous index. The last index may advantageously include a primer sequence for priming of PCR. Methods of split pooling have been described. In one embodiment the ligation handle is digested with a restriction enzyme to produce a four base overhang. In another embodiment, a ligation primer is hybridized to the ligation handle to generate an at least 4 base overhang that is complementary to an index in the split pool method.

In one exemplary embodiment, the hydrogel particles or polymer matrices are split into pools, each pool containing a unique index A and each ligation handle is ligated to a sequence in index A. All particles are then pooled and re-split into new pools containing a unique index B. After ligation, all of the particles are pooled again and re-split into new pools containing a unique index C. If each index has 100 unique sequences and for each cycle the particles are split into 100 pools each containing a unique sequence, then after 3 cycles of split and pool ligation, the barcode on any given particle possess the same one of 1003=1,000,000 possible barcodes, but different particles have different sequences.

In another embodiment, single cell or single isolated aggregation of cellular constituent analysis is performed by digital polymerase chain reactions (PCR), e.g., Fluidigm C. Digital polymerase chain reaction (digital PCR, DigitalPCR, dPCR, or dePCR) is a refinement of conventional polymerase chain reaction methods that can be used to directly quantify and clonally amplify nucleic acids including DNA, cDNA or RNA. The key difference between dPCR and traditional PCR lies in that PCR carries out one reaction per single sample and dPCR carries out a single reaction within samples separated into a large number of partitions wherein the reactions are carried out in each partition individually. A sample is partitioned so that individual nucleic acid molecules within the sample are localized and concentrated within many separate regions. The capture or isolation of individual nucleic acid molecules may be effected in micro well plates, capillaries, the dispersed phase of an emulsion, and arrays of miniaturized chambers, as well as on nucleic acid binding surfaces.

In a preferred embodiment, single cell or single aggregation of cellular constituent analysis is performed using microfluidics. Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology. reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947 and PCT publication No.WO2014085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment single cell analysis is performed in droplets using methods according to WO 2014085802. Each of these patents and publications is herein incorporated by reference in their entireties for all purposes.

Single cells or isolated aggregations of cellular constituents may be sorted into separate vessels by dilution of the sample and physical movement, such as pipetting. A machine can control the pipetting and separation. The machine may be a computer controlled robot.

Microfluidics may also be used to separate the single cells and/or isolated aggregations of cellular constituents. Single cells and/or isolated aggregations of cellular constituents can be separated using microfluidic devices. Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. The small volume of microfluidics technology improves amplification and construction of DNA libraries made from single cells and single isolated aggregations of cellular constituents. Furthermore, incorporation of microfluidics technology enhances system integration and automation.

Single cells and/or single isolated aggregations of cellular constituents of the present invention may be divided into single droplets using a microfluidic device. The single cells and/or single isolated aggregations of cellular constituents in such droplets may be further labeled with a barcode. In this regard reference is made to Macosko et al., 2015, "Highly Parallel Genome-wide Expression Profiling of Individual Cells Using Nanoliter Droplets" Cell 161, 1202-1214 and Klein et al., 2015, "Droplet Barcoding for Single-Cell Transcriptomics Applied to Embryonic Stem Cells" Cell 161, 1187-120, 1 all the contents and disclosure of each of which are herein incorporated by reference in their entirety. Not being bound by a theory, the volume size of an aliquot within a droplet may be as small as 1 fL.

Single cells and/or single aggregations of cellular constituents may be diluted into a physical multi-well plate or a plate free environment. The multi-well assay modules (e.g., plates) may have any number of wells and/or chambers of any size or shape, arranged in any pattern or configuration, and be composed of a variety of different materials. Preferred embodiments of the invention are multi-well assay plates that use industry standard multi-well plate formats for the number, size, shape and configuration of the plate and wells. Examples of standard formats include 96-, 384-, 1536- and 9600-well plates, with the wells configured in two-dimensional arrays. Other formats include single well, two well, six well and twenty-four well and 6144 well plates. Plate free environments of the present invention utilize a single polymerizable gel containing compartmentalized cells and/or isolated aggregations of cellular constituents. In one embodiment, extraction of single cells and/or single isolated aggregations of cellular constituents may be by a mechanical punch. Single cells and/or single isolated aggregations of cellular constituents may be visualized in the gel before a punch.

In one embodiment, a DNA tag including a protein specific barcode (UCI) is conjugated to detection biomolecules or labeling ligands with high target affinity and low unspecific binding, such as antibodies (Janssen et al., 2013) or nanobodies (Pardon et al., 2014; Theile et al., 2013) or aptamers (Janssen et al., 2013).

In one embodiment, to ensure proper staining of intracellular and cell surface proteins with, for instance, DNA-tagged antibodies, single cells are embedded in hydrogel droplets. Not being bound by a theory, the hydrogel mesh provides a physical framework, chemically incorporates biomolecules and is permeable to macromolecules such as antibodies (Chung et al., 2013). In one embodiment, to further improve permeability and staining efficiency, lipids are cleared (Chung et al., 2013). Not being bound by a theory, the clearance of the lipids and the porosity of the hydrogel allow for more efficient washing and removal of unspecific antibodies. This higher accuracy of measurement is important for the high multiplex measurements and computational inference of regulatory mechanisms.

In one embodiment, cells embedded in a hydrogel mesh can be stained with the DNA-tagged antibodies and washed in bulk before isolating the single cells. Once isolated, a cell specific oligonucleotide barcode (USI) can be introduced before subsequent DNA amplification and library preparation steps. Isolating single cells into individual reaction chambers to perform PCR amplification or a proximity ligation/extension assay (Assarsson et al., 2014) can be achieved at modest throughput either by FACS sorting into multi-well plates or microfluidic capture using the Fluidigm C1 (Shalek et al., 2014).

In one embodiment, for more high throughput processing, a microfluidic chip can be used to capture the hydrogel embedded cells or cellular constituents in nanoliter-sized aqueous droplets (Macosko et al., 2015, "Highly Parallel Genome-wide Expression Profiling of Individual Cells Using Nanoliter Droplets" Cell 161, 1202-1214). In one embodiment, the hydrogel embedded cells or cellular constituents are poisson loaded into microwells (Fan et al., 2015). The aqueous droplets or microwells may be simultaneously loaded with barcoded beads, each of which has oligonucleotides including; a "cell barcode" that is the same across all the primers on the surface of any one bead, but different from the cell barcodes on all other beads; a Unique Molecular Identifier (UMI), different on each primer, that enables sequence reads derived from the same original DNA tag (amplification and PCR duplicates) to be identified computationally (Kivioja et al., 2012); and a capture sequence to bind the oligos (either amplified PCR products or original DNA tags released by proteinase K treatment, or enzymatic/photonic oligo cleavage). Once the beads are loaded, they can be pooled for amplification and library preparation, and sequencing. These beads can take multiple forms, the preferred drop-seq beads are polystyrene, oligo functionalized beads, but alternative beads are possible, such as soft beads (polymer gel based beads), that allow for one on one pairing with cells, as to avoid the poisson loading needed in the described drop-seq scheme. This reduces the amount of cells one needs, and makes it possible to analyze rare cell types or clinical samples only available in low amounts of cells.

In one embodiment, the present invention provides for the simultaneous detection of proteins and nucleic acids. Nucleic acids can be reverse cross-linked after separation of discrete polymer matrices into separate wells or droplets. The contents of individual wells or droplets may then be sequenced. In one embodiment, crosslinking is reversed by incubating the cross-linked sample in high salt (approximately 200 mM NaCl) at 65 °C for at least 4 h.

In one embodiment, Drop-Seq (Macosko et al., 2015) is used to analyze RNA or DNA in single cells in parallel to the detection of cellular constituents. Drop-Seq is a reverse emulsion, early barcoding method for analyzing 104-$10^6$ cells/experiment at very low cost ($0.06/cell). The Drop-seq method may be used to encapsulate discrete hydrogel matrices in a droplet. The RNA and/or DNA can be reverse cross-linked and the oligonucleotide labels can be removed from the labelling ligand. Capture of RNA, DNA, and oligonucleotide labels on barcoded beads, library preparation, and sequencing is performed as described previously.

In one embodiment, the detection of proteins or post translational modifications (PTM) is determined by sequencing based readouts. In some embodiments, Immuno-Seq is used when antibodies can be washed out (Niemeyer, C. M., et al., Nat Protoc. 2, 1918-1930 (2007)) and proximity extension assays (PEA) is used when antibodies cannot be washed away (Hammond, M., et al. PLoS One. 7, e40405, (2012); and Stahlberg, A., et al. Clin Chem. 58, 1682-1691 (2012)). These methods use DNA-sequence based encoding, and are compatible with other genomic readouts (e.g., sgRNA barcodes).

In another embodiment, the detection of proteins embedded in a hydrogel matrix is determined by FACS. Not being bound by a theory, the encapsulation of cellular constituents in a hydrogel matrix and removing lipids provides for improved binding of antibodies to intracellular targets as compared to regular fixation and permeabilization protocols for FACS alone.

In one embodiment, PEA methods are used for profiling protein-protein or protein-nucleic acid interactions by, respectively, using antibodies against two protein targets (Leuchowius, K. J., et al. Cytometry A. 75, 833-839 (2009)). or replacing one antibody with an oligonucleotide complementary to a sequence of interest (Gustafsdottir, S. M., et al. Proceedings of the National Academy of Sciences of the United States of America. 104, 3067-3072, (2007)).

In another aspect, the present invention provides screening methods to determine the effect on protein, post translational modifications and cellular constituents of single cells or isolated aggregations of cellular constituents in response to the perturbation of genes or cellular circuits. Perturbation may be knocking down a gene, increasing expression of a gene, mutating a gene, mutating a regulatory sequence, or deleting non-protein-coding DNA.

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). A genome-wide sgRNA mouse library (10 sgRNAs/gene) may also be used in a mouse that expresses a Cas9 protein. The cells of the mouse can then be analyzed using the methods of the present invention.

In one embodiment, a CRISPR system may be used to activate gene transcription. A nuclease-dead RNA-guided DNA binding domain, dCas9, tethered to transcriptional repressor domains that promote epigenetic silencing (e.g., KRAB) may be used for "CRISPRi" that represses transcription. To use dCas9 as an activator (CRISPRa), a guide RNA is engineered to carry RNA binding motifs (e.g., MS2) that recruit effector domains fused to RNA-motif binding proteins, increasing transcription. A key dendritic cell molecule, p65, may be used as a signal amplifier, but is not required.

In one embodiment, perturbation is by deletion of regulatory elements. Non-coding elements may be targeted by using pairs of guide RNAs to delete regions of a defined size, and by tiling deletions covering sets of regions in pools.

In one embodiment, perturbation of genes is by RNAi. The RNAi may be shRNA's targeting genes. The shRNA's may be delivered by any methods known in the art. In one embodiment, the shRNA's may be delivered by a viral vector. The viral vector may be a lentivirus.

In one embodiment, a CRISPR based pooled screen is used. Perturbation may rely on sgRNA expression cassettes that are stably integrated into the genome. The expressed sgRNA may serve as a molecular barcode, reporting the loss of function of the target in a cell. Alternatively, optimized separate barcodes may be co-expressed with the sgRNA, should sgRNAs not be ideal as barcodes. Transduction of cells at a higher multiplicity of infection (MOI) or delivering vectors by transfection at a higher MOI would result in any given cell receiving multiple sgRNA's and allow combinatorial perturbations. In one embodiment, 2, or 3, or 4, or 5, or up to 10 genes, preferably 5-7 genes are perturbed in a single cell.

In one embodiment, recombinant Cas9 protein and sgRNA is delivered simultaneously to cells with nanowires or the recently developed 'CellSqueeze' (Sharei, A., et al. Proceedings of the National Academy of Sciences of the United States of America. 110, 2082-2087, (2013)). Applicants have shown that nanowires can deliver functional proteins, RNA and small molecules alone and in combinations into the cell's cytoplasm, and do not cause toxicity or inappropriate activation and allow the cells to respond normally to signals (Shalek, A. K., et al. Nano Lett. 12, 6498-6504, (2012); Yosef, N., et al. Nature. 496, 461-468, (2013); and Shalek, A. K., et al. Proceedings of the National Academy of Sciences of the United States of America. 107, 1870-1875, (2010)).

In one embodiment, hybrid measurements or alternative readouts are measured. The alternative readouts may either be stand alone, or hybrid measurements. One alternative readout may be epigenetic measurements. Not being bound by a theory, when biomolecules with functional groups are formaldehyde fixed and bound to the polymer mesh, and membrane and nuclear lipids are cleared, chromosomal DNA is preserved and is accessible for further interrogation. Epigenetic assays that have been applied to single cells may be combined with a perturbation and protein level readout. Not being bound by a theory, the new layers of information aid in understanding of the regulatory mechanisms underpinning cellular behavior. Histone modifications have been measured at specific gene loci at the single cell level (Gomez et al., 2013). This publication uses ISH-PLA (in situ hybridization (ISH), proximity ligation assay (PLA)). They use a biotin modified ISH probe, by binding with streptavidin and an oligo bound anti-streptavidin antibody. As antibodies against multiple histone modifications are readily available, the PLA scheme is applicable to the present invention. Not being bound by a theory, a histone code based on the combination of a plurality of histone modifications determines gene expression at a given locus. Many histone modifications at many genetic loci can be determined simultaneously by replacing the biotin-streptavidin construct by an ISH probe conjugated to a linker (peptide, DNA or nanoparticles, . . . ), followed by another DNA barcode reporting on the genetic locus, and including a binding sequence to the oligo conjugated to the histone modification antibody.

In one embodiment, chromatin accessibility is determined using a single cell ATAC-seq assay. ATAC-seq offers genome-wide chromatin accessibility of regulatory elements, transcription factor binding and nucleosome positioning.

In one embodiment, DNA methylation analysis is determined. Cytosine methylation analysis has been analyzed at the single cell level (Kantlehner et al., 2011), as has adenine methylation (Lorthongpanich et al., 2013).

In one embodiment, the spatial organization of chromosomes is determined. The spatial organization of chromosomes has been found to have fundamental effects on gene expression and cellular function. Single cell measurements (Hi-C) have revealed extensive cell-to-cell heterogeneity in chromosome structure (Nagano et al., 2013). This method can be incorporated into the present invention.

In one embodiment, protein-protein interactions are measured. In addition to assessing presence and abundance of individual proteins, assays such as Proximity Extension Assay (PEA) allow for assaying the proximity of two proteins. In particular, the present invention allows for probing protein-protein interactions by designing pairs of antibodies for the interacting proteins of interest, such that the oligos conjugated to these antibodies have a binding region, which only bind when the two proteins are in near proximity, and therefore only PCR amplify in this case.

In one embodiment, protein-DNA interaction measurements are determined. Similar to the modified ISH-PLA described herein, instead of probing histone modifications, one could probe protein (transcription factor) proximity to many specific genetic loci, in a multiplex fashion.

In one embodiment, fluorescent in situ hybridization methods are used in the present invention. The present invention allows a combined approach where cells can be fluorescently labeled by methods known in the art, and cells of interest can be selected for downstream profiling of cellular constituents. In addition, the assays of the present invention can be combined with in situ hybridization methods such as RNA and DNA FISH.

In another embodiment, the gelled, and cleared cells offer a platform in which any biological agent that is able to be detected by a high affinity and specific counterpart or ligand that can directly or indirectly be conjugated to a DNA molecule could be detected and quantified using the methods of the present invention.

Releasing the oligo's to be sequenced from their antibody can take a multitude of forms; i.e. in one embodiment, oligo's could be released from their antibodies by digesting all proteins (for instance proteinase K), alternatively, photocleavable linkers could be used, or restriction sites could be included in the oligo sequence to allow for enzymatic restriction and release. In another embodiment, the oligo can stay bound to the antibody, and in situ amplified (i.e. either by PCR, rolling circle amplification or T7 polymerase amplification) and the products of this reaction could be captured and sequenced.

Similarly, capturing the released oligo's could take a number of forms: in a drop based approach, beads can be loaded with capture oligo's as described herein. Microwells could either be loaded with beads, or their surface could be functionalized with capture oligos from which further amplification could take place. Alternatively, in the scenario where drops are sorted. into multiwell plates, or microfluidic reaction chambers such as the Fluidigm Cl system, oligos can be amplified linearly or exponentially, and cellular barcodes and library adapters can be added on during these amplification steps.

Many different assays have been developed for oligo-barcode based detection of proteins (Janssen et al., 2013) and may be used in the present invention.

In one embodiment, cells are fixed and monomer infused before capturing them in a droplet. Alternatively, cells or aggregations of constituents are co-flowed with a lysis/monomer solution into a larger diameter drop. In this embodiment, biomolecules from a single cell or isolated aggregation of constituents are spread over a larger volume, which with similar polymer density could increase accessibility for staining.

The present invention also provides for cell handling before hydrogel polymerization. In one embodiment, cells are fixed and infused with polymer monomers in bulk. Cells may then be segregated and polymerization initiated. Segregation can be by any means described herein. In preferred embodiments, segregation is performed by making single cell drops.

In another embodiment, biochemical, thermal, or optical treatment on chip of individual cells in reverse emulsion droplets is performed. In this embodiment, polymer monomers may be spiked in microfluidically and optionally fixation reagents. Polymerization of the monomers may then be performed. This allows biochemical, thermal, or optical treatments at the single-cell level. Examples include, but are not limited to: lysis, DNA/RNA fragmentation/tagmentation, dosing with drugs, enzymatic reactions, or any perturbation of the sample before fixation and/or anchoring biomolecules to the polymer mesh upon polymerization.

In one embodiment, the oligonucleotide label may comprise Iso-deoxyguanosine (iso-dG) and 5-methyl iso-dC (iso-dC). Iso-deoxyguanosine forms a Watson-Crick base pair with 5-methyl iso-dC, but has a different type of hydrogen bonding pattern than those observed for the natural base pairs A: T and C: G. Substitution of a iso-dG: 5-Me-iso-dC base pair for a C: G pair increases the Tm of the resulting duplex by ~2 deg C per base pair substitution (Switzer, C., et al., Enzymatic incorporation of a new base pair into DNA and RNA. J. Am Chem. Soc. (1989), 111: 8322-8323; and Horn, T., et al., Hybridization properties of the 5-methyl-isocytidine/isoguanosine base pair in synthetic oligodeoxynucleotides. Tetrahedron Lett. (1995), 36:2033-2036). Furthermore, since iso-dG does not pair with dC, iso-dG: 5-Me-iso-dC can function as a stable unnatural base pair that can be used to expand the genetic code. The combination of iso-dG's high selectivity for 5-Me-iso-dC, and the resulting base pair's high thermodynamic stability, make this modified base particular attractive in embodiments of the present invention.

In one embodiment, iso-dG: 5-Me-iso-dC base pairing is used for molecular recognition. The 5-Me-iso-dC: iso-dG base pair may be incorporated into hybridization assays to enhance probe-target specificity and reduce spurious hybridization to non-target sequences. For example, Collins and co-workers significantly improved the sensitivity of a branched DNA quantitative hybridization assay for detecting the HIV POL sequence by incorporating ~30% 5-Me-iso-dC and iso-dG into the pre-amplifier, branched DNA (bDNA) amplifier and alkaline phosphate probe sequences used in the assay (Collins, M. L, et al. A branched DNA signal amplification assay for quantification of nucleic acid targets below 100 molecules/ml.Nucleic Acids Res. (1997), 25:2979-2984). Use of this strategy resulted in a significant reduction in non-specific hybridization of the above three sequence types to non-target nucleic acid sequences, and thus less amplification of background. The limits of detection of the assay were improved 10-fold, from <500 HIV molecules/mL to <50 molecules/mL. In preferred embodiments, the present invention utilizes the 5-Me-iso-dC: iso-dG base pair to ensure the correct sequences base pair during hybridization of ligation handle primers and during hybridization of two oligonucleotide labels in proximity assays.

In another embodiment, iso-dG: 5-Me-iso-dC base pairing is used for qPCR and artificially expanded genetic systems. A number of research groups have been working on optimizing PCR amplification on templates containing 5-Me-iso-dC. Such optimization is necessary to enable the full development of artificially expanded genetic systems utilizing an expanded genetic code, thereby allowing for the site-specific incorporation of novel functional components (such as unnatural amino acids) into proteins. In 2004, Johnson and co-workers observed that, by using the Klenow fragment of Taq polymerase (KF-Taq) in PCR, the fidelity of the 5-Me-iso-dC: iso-dG base pair was about 96% per amplification cycle (Johnson, S. C., et al., A third base pair for the polymerase chain reaction: inserting isoC and isoG. Nucleic Acids Resl. (2004), 32:1937-1941). The limit in fidelity is chiefly due to the ability of iso-dG's 1,2 tautomer to mis-pair with dT. More recently, Sismour and Benner solved this problem by using 2-thio-dT (dT*) in place of dT. dT*pairs with dA, but not with iso-dG (Sismour, A. M.; Benner, S. A. The use of thymidine analogs to improve the replication of an extra DNA base pair: a synthetic biological system. Nucleic Acids Resl. (2005), 33:5640-5646). Using this artificial base pair system (5-Me-iso-dC: iso-dG, dA: dT*, dC: dG) with KF-Taq, the fidelity in PCR was increased to about 98% per amplification cycle.

The present invention also provides methods applicable to the study of bulk cells and is not limited to single cells. Moreover, the assays described herein are also amenable to regularly fixed and permeabilized cells (i.e. not using polymerization). The proximity assays described herein may be performed on cells without generating discrete polymer matrices. Additionally, detection of cellular constituents utilizing labeling ligands and a sequencing readout may be used to detect low abundant cellular constituents. Not being bound by a theory, the oligonucleotide label may be amplified and increase the signal as compared to antibody readouts known in the art. Moreover, determination of proteins in relation to open chromatin need not be performed in a polymer matrix.

The present inventions provide advantages over prior assays for detecting proteins and post translation modifications (PTM) in single cells or isolated aggregations of cellular constituents. Standard flow cytometry can be used to detect a few proteins/PTMs in greater than 106 single cells; and CyTOF (heavy metal labeling with multiplex barcoding) can be used to detect ~30-50 proteins/PTMs in 105-106 single cells. The present invention provides highly multiplexed, DNA sequencing-based readouts of protein/PTM levels of greater than 100's of proteins/PTMs in greater than $10^6$ cells.

The present invention advantageously provides a Massively Combinatorial Perturbation Profiling (MCPP) approach. Applicants can perturb vast numbers of combinations of genes, each targeting many circuit components at once. Applicants can use massively-parallel single cell genomics to measure genomic profiles and single cell proteomics to measure protein profiles after each perturbation. Applicants can infer the individual and combinatorial effects at each order, relying on random matrix theory, compressive sensing and kernel learning.

Biological systems are not linear: the combined effect of multiple factors is not simply the sum of their individual effects. This is a direct outcome of the biochemistry underlying molecular biology, from allosteric protein changes to cooperative binding, and is essential for cells to process complex signals. However, it has remained an insurmountable stumbling block to achieving a quantitative and predictive understanding of circuits on a genomic scale, with far-reaching implications for basic and translational science. Thus, the present invention provides a powerful combination by being able to measure transcriptional chromatin, epigenetic and proteomic changes as a function of genetic perturbation at the single cell level.

Combinatorial perturbation analyses have measured important genetic interactions, mainly from growth phenotypes in yeast. Mammalian studies have used ricin susceptibility and cell count phenotypes, but none combined large-scale, combinatorial genetic manipulation with complex, quantitative phenotypes, such as proteomic profiles. The single cell resolution readout of both response and perturbation, across many cells, serves as an improved starting point to unravel the function and interaction of the perturbed genes.

Sparse Coding

Mammalian genomes contain approximately 20,000 genes, and mammalian expression profiles are frequently studied as vectors with 20,000 entries corresponding to the abundance of each gene. It is often assumed that studying gene expression profiles requires measuring and analyzing these 20,000 dimensional vectors, but some mathematical results show that it is often possible to study high-dimensional data in low dimensional space without losing much of the pertinent information. In one embodiment of the present invention, less than 20,000 aptamers are used to detect protein expression in single cells. Not being bound by a theory, working in low dimensional space offers several advantages with respect to computation, data acquisition and fundamental insights about biological systems.

In one embodiment, aptamers are chosen for protein targets that are generally part of gene modules or programs, whereby detection of a protein allows for the ability to infer expression of other proteins present in a module or gene program. Samples are directly compared based only on the measurements of these signature genes.

In alternative embodiments, sparse coding or compressed sensing methods can be used to infer large amounts of data with a limited set of target proteins. Not being bound by a theory, the abundance of each of the 20,000 genes can be recovered from random composite measurements. In this regard, reference is made to Cleary et al., "Composite measurements and molecular compressed sensing for highly efficient transcriptomics" posted on Jan. 2, 2017 at biorxiv.org/content/early/2017/01/02/091926, doi.org/10:1101/091926, incorporated herein by reference in its entirety.

A simple, flexible, and cost-effective, transcriptome-wide gene-expression profiling solution that does not require measuring individual genes or single cell profiling is desired. This would greatly accelerate the rate of discovery of medically-relevant connections encoded therein by leveraging knowledge of relative abundances of genes to extrapolate underlying cell circuitry.

The present invention relates to genomic informatics and gene-expression profiling. Gene-expression profiles provide complex molecular fingerprints regarding the relative state of a cell or tissue. Similarities in gene-expression profiles between organic states (i.e., for example, normal and diseased cells and/or tissues) provide molecular taxonomies, classification, and diagnostics. Similarities in gene-expression profiles resulting from various external perturbations (i.e., for example, ablation or enforced expression of specific genes, and/or small molecules, and/or environmental changes) reveal functional similarities between these perturbagens, of value in pathway and mechanism-of-action elucidation. Similarities in gene-expression profiles between organic (e.g. disease) and induced (e.g. by small molecule) states may identify clinically-effective therapies.

To achieve these and other advances and in accordance with the purpose of the present invention, as embodied and broadly described, in one aspect of the present invention, a probe set comprising 100 or more molecules assembled according to a set of random measurement values forming at least one measurement vector, where each molecule comprises a tag for the at least one measurement vector operably linked to a probe for one type of transcript of a plurality of types of transcripts.

In an aspect of the present invention, the probe set corresponds to a Design Matrix comprising m×n measurement values, where m is a number of measurement vectors and n is the number of types of transcripts. In another aspect, the tag uniquely corresponds to one of the measurement vectors. In an aspect, the molecules of the probe set are single-stranded DNA. In an aspect, the tag is a barcode. In another aspect, the transcript is a gene.

In an aspect, the number of measurement vectors is approximately 100-30,000. In an aspect, the number of measurement vectors is based on an estimate of system sparsity. In an aspect, the number of measurement vectors is based on the log of the number of types of transcripts. In an aspect the number of measurement vectors is approximately k log (n), where k is an estimate of sparsity. In an aspect, the Design Matrix may be adjusted according to a basis. In an aspect, k is approximately equal to 10. In another aspect, m is less than n. In another aspect, n is greater than 10.

In another aspect of the invention, a method of measuring relative abundances of transcripts in a pool of samples, comprises generating a Design Matrix comprising m×n measurement values, where m is a number of measurement vectors and n is the number of types of transcripts; generating a probe library corresponding to the Design Matrix, wherein the probe library comprises a collection of molecules assembled according to the measurement values, where each molecule has a tag for one of the measurement vectors operably linked to a probe for one of the types of transcripts; contacting the probe library to the pool of samples, resulting in m measurement results for each sample of the pool of samples; generating an Observed Measurement Matrix M comprising the measurement results for each sample of the pool of samples; and applying a sparse coding solving process to the Observed Measurement Matrix M to learn system matrix S as indicative of relative abundance of the transcripts in each of the samples.

In another aspect of the present invention, the measurement values in the Design Matrix are independent. In another aspect, the measurement values in the Design Matrix are random.

In an aspect, the number of measurement vectors is approximately 100-30,000. In an aspect, the number of measurement vectors is based on an estimate of system sparsity. In an aspect, the number of measurement vectors is based on the log of the number of types of transcripts. In an aspect the number of measurement vectors is approximately k log (n), where k is an estimate of sparsity. In an aspect, the Design Matrix may be adjusted according to a basis. In an aspect, k is approximately equal to 10. In another aspect, m is less than n. In another aspect, n is greater than 10.

In another aspect of the present invention, the tag uniquely corresponds to one of the measurement vectors. In an aspect, the tag is a barcode.

In another aspect of the present invention, the molecules of the probe library are single-stranded DNA. In an aspect, each molecule in the probe library further comprises a tag for one of the samples.

In another aspect of the present invention, the contacting includes binding and the contacting may, in some aspects, include hybridization.

In another aspect of the present invention, the sample is a cell.

In another aspect of the present invention, generating the Observed Measurement Matrix include hybrid selection and tag quantification. In an aspect, tag quantification includes sequencing.

In another aspect of the present invention, a method for measuring relative abundances of n biomolecules in a pool of samples, comprises generating a Design Matrix comprising m×n measurement values, where m is a number of measurement vectors and n is the number of types of biomolecules; generating a probe library corresponding to the Design Matrix, wherein the probe library comprises a collection of molecules assembled according to the measurement values, where each molecule has a tag for one of the measurement vectors operably linked to a probe for one of the types of biomolecules; contacting the probe library to the pool of samples, resulting in m measurement results for each sample of the pool of samples; generating an Observed Measurement Matrix M comprising the measurements results for each sample in the pool of samples; and applying a sparse coding solving process to the Observed Measurement Matrix to learn system matrix S as indicative of relative abundance of the biomolecules in each of the samples.

In another aspect of the present invention, the measurement values in the Design Matrix are independent. In another aspect, the measurement values in the Design Matrix are random.

In an aspect of the present invention, the biomolecule is a transcript, protein, DNA, non-naturally occurring nucleic acid, peptide. In an aspect of the present invention, the samples include cells, blood, hair, nails, mucus, tissue, feces or urine. In an aspect of the present invention, the probe is a molecule that binds to the biomolecule. In an aspect, the probe is a complex of molecules. In another aspect, the probe comprises an antibody or binding fragment thereof.

In another aspect of the present invention, the molecules of the probe library are single-stranded DNA. In an aspect, each molecule in the probe library further comprises a tag for one of the samples.

In another aspect of the present invention, the contacting includes binding and the contacting may, in some aspects, include hybridization.

In another aspect of the present invention, the tag uniquely corresponds to one of the measurement vectors. In an aspect, the tag is a barcode. In an aspect, each molecule in the probe library further comprises a tag for one of the samples.

In an aspect, the number of measurement vectors is approximately 1-30,000. In an aspect, the number of measurement vectors is based on an estimate of system sparsity. In an aspect, the number of measurement vectors is based on the log of the number of types of biomolecules. In an aspect the number of measurement vectors is approximately k log (n), where k is an estimate of sparsity. In an aspect, the Design Matrix may be adjusted according to a basis. In an aspect, k is approximately equal to 10. In another aspect, m is less than n. In another aspect, n is greater than 10.

In another aspect of the present invention, generating the Observed Measurement Matrix include tag quantification. In an aspect, tag quantification includes sequencing.

The term "device" as used herein, refers to any composition capable of measuring expression levels of transcripts. For example, a device may comprise a solid planar substrate capable of attaching nucleic acids (i.e., an oligonucleotide microarray). Alternatively, a device may comprise a solution-based bead array, wherein nucleic acids are attached to beads and detected using a flow cytometer. Alternatively, a device may comprise a nucleic-acid sequencer.

The term "probe" as used herein, refers to any molecule capable of attaching and/or binding to a nucleic acid (i.e., for example, a barcode nucleic acid). For example, a capture probe may be an oligonucleotide attached to a bead, wherein the oligonucleotide is at least partially complementary to another oligonucleotide. Alternatively, a capture probe may comprise a polyethylene glycol linker, an antibody, a polyclonal antibody, a monoclonal antibody, an Fab fragment, a biological receptor complex, an enzyme, a hormone, an antigen, and/or a fragment or portion thereof. A probe may be a nucleic acid sequence, the nucleic acid being for example deoxyribonucleic acid (DNA), ribonucleic acid (RNA), peptide nucleic acid (PNA) or other non-naturally occurring nucleic acid.

The term "Design Matrix" as used herein, refers to a collection of the relative number of times up to which a type of transcript can be counted for a specific type of measurement. The collection may be described as a table and will be so in the following for the sake of the description. However, it is understood that the collection need not be generated as a table but can also be generated in any other form suitable for the measuring relative abundances of transcripts, e.g. a string of data. Each entry in the table is intended to be a randomly generated number, at least initially. In general, each row in the matrix corresponds to a specific type of measurement, while each column in the matrix corresponds to a type of transcripts in the sample pool. Thus, the number of rows in the Design Matrix corresponds to the number of specific types of measurements, while the number of columns in the Design Matrix corresponds to the number of types of transcripts in the sample pool. Of course, one of skill may choose to adjust the Design Matrix to reflect fewer than all available types of measurement and fewer than all types of transcripts in the sample pool. Further, one of skill in the art will appreciate that the Design Matrix itself may be transposed such that the number of rows indicates the number of types of transcripts, while the number of columns indicates the number of types of measurement.

The term "relative number of times" as used herein, means that if for a type of measurements, the relative number is $a_1$ for type of transcripts 1, $a_2$ for type of transcripts 2, . . . an for type of transcripts n, then type of transcripts 1 can be counted up to $k.a_1$ times, type of transcripts 2 up to $k.a_2$ times, . . . type of transcripts n up to $k.a_n$ times; k being an integer.

The term "count" and its derivatives as used in the definitions, encompasses any method that yield a measured value indicative of the count.

The term "Observed Measurement Matrix" as used herein, refers to a collection of measured values of a specific type of measurement for a specific type of sample in the sample pool or portion of sample (such as a cell, or a type of cell). The collection may be described as a table and will be so in the following for the sake of the description. However, it is understood that the collection need not be generated as a table but can also be generated in any other form suitable for the measuring relative abundances of transcripts, e.g. a string of data. In general, each row in the matrix corresponds to a specific type of measurement, while each column in the matrix corresponds to a type of samples in the sample pool or portion of sample. Thus, the number of rows in the Observed Measurement Matrix corresponds to the number of specific types of measurements, while the number of columns in the Observed Measurement Matrix corresponds to the number of types of samples in the sample pool. Of course, one of skill may choose to adjust the Observed Measurement Matrix to reflect fewer than all available types of measurement and fewer than all types of samples in the sample pool. Further, one of skill in the art will appreciate that the Observed Measurement Matrix itself may be transposed such that the number of rows indicates the number of types of sample, while the number of columns indicates the number of types of measurement.

Correspondingly, any reference to a Matrix used herein, refers to a collection of values, which may be described as a table and will be so in the following for the sake of the description. However, it is understood that the collection need not be generated as a table but can also be generated in any other form suitable for the measuring relative abundances of transcripts, e.g. a string of data. Any reference to a vector (in the mathematical sense) used herein, refers to a collection of values which may be described as row or a column, in some instances row or column of a table, and will be so in the following for the sake of the description. However, it is understood that the collection need not be generated as a row or a column but can also be generated in any other form suitable for the measuring relative abundances of transcripts.

The term "Connectivity Map" as used herein, refers to a public database of transcriptome-wide gene-expression profiles derived from cultured human cells treated with a plurality of perturbagens, and pattern-matching algorithms for the scoring and identification of significant similarities between those profiles and external gene-expression data, as described by Lamb et al., "The Connectivity Map: using gene-expression signatures to connect small molecules, genes and disease". Science 313:1929 (2006). Build02 of the Connectivity Map contains 7,056 full-transcriptome gene-expression profiles generated with Affymetrix high-density oligonucleotide microarrays representing the biological effects of 1,309 small-molecule perturbagens, and is available at broadinstitute.org/cmap.

The term "query signature" as used herein, refers to any set of up- and down-regulated genes between two cellular states (e.g., cells treated with a small molecule versus cells treated with the vehicle in which the small molecule is dissolved) derived from a gene-expression profile that is suitable to query Connectivity Map. For example, a 'query signature' may comprise a list of genes differentially expressed in a distinction of interest; (e.g., disease versus normal), as opposed to an 'expression profile' that illustrates all genes with their respective expression levels.

The term "connectivity score" as used herein, refers to a relative measure of the similarity of the biological effects of a perturbagen used to generate a query signature with those of a perturbagen represented in the Connectivity Map based upon the gene-expression profile of a single treatment with that perturbagen. For example, one would expect every treatment instances with vorinostat, a known histone deacetylase (HDAC) inhibitor, to have a high connectivity score with a query signature generated from the effects of treatments with a panel of HDAC inhibitors.

The term "enrichment score" as used herein, refers to a measure of the similarity of the biological effects of a perturbagen used to generate a query signature with those of a perturbagen represented in the Connectivity Map based upon the gene-expression profiles of multiple independent treatments with that perturbagen.

The term "small organic molecule" as used herein, refers to any molecule of a size comparable to those organic molecules generally used in pharmaceuticals. The term excludes biological macromolecules (e.g., proteins, nucleic acids, etc.). Preferred small organic molecules range in size from approximately 10 Da up to about 5000 Da, more preferably up to 2000 Da, and most preferably up to about 1000 Da.

The sample may be a biological sample, for example a blood, buccal, cell, cerebrospinal fluid, mucus, saliva, semen, tissue, tumor, feces, urine, and vaginal sample. It may be obtained from an animal, a plant or a fungus. The animal may be a mammal. The mammal may be a primate. The primate may be a human. In other embodiments, the sample may be an environmental sample, such as water or soil.

As used herein, the term "sample template" refers to nucleic acid originating from a sample which is analyzed for the presence of a target sequence of interest. In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

"Target sequence" is intended to designate either one target sequence or more than one target sequence, i.e. any sequence of interest at which the analysis is aimed. Thus, the sample may comprise more than one target sequence and preferably a plurality of target sequences, the number of which may be 2, 3, 4, 5, 6, 7, 8, 9, 10, 11, 12, 13, 14, 15, 16, 17, 18, 19, 20 and above.

The present invention is related to the field of genomic informatics and gene-expression profiling. Gene-expression profiles provide complex molecular fingerprints regarding the relative state of a cell or tissue. Similarities in gene-expression profiles between organic states (i.e., for example, normal and diseased cells and/or tissues) provide molecular taxonomies, classification, and diagnostics. Similarities in gene-expression profiles resulting from various external perturbations (i.e., for example, ablation or enforced expression of specific genes, and/or small molecules, and/or environmental changes) reveal functional similarities between these perturbagens, of value in pathway and mechanism-of-action elucidation. Similarities in gene-expression profiles between organic (e.g. disease) and induced (e.g. by small molecule) states may identify clinically-effective therapies. Improvements described herein allow for the efficient and economical generation of full-transcriptome gene-expression profiles by identifying cluster centroid landmark transcripts that predict the expression levels of other transcripts within the same cluster.

Some embodiments of the present invention contemplate measuring relative gene abundances of transcripts in a pool of samples to allow genome-wide transcriptional profiling for applications including, but not limited to, disease classification and diagnosis without resort to expensive and laborious microarray technology (i.e., for example, Affymetrix GeneChip microarrays). Other uses include, but are not limited to, generating gene-expression data for use in and with information databases (i.e., for example, connectivity maps). A connectivity map typically may comprise a collection of a large number of gene-expression profiles together with allied pattern-matching software. The collection of profiles is searched with the pattern-matching algorithm for profiles that are similar to gene-expression data derived from a biological state of interest. The utility of this searching and pattern-matching exercise resides in the belief that similar biological states may be identified through the transitory feature of common gene-expression changes. The gene-expression profiles in a connectivity map may be derived from known cellular states, or cells or tissues treated with known chemical or genetic perturbagens. In this mode, the connectivity map is a tool for the functional annotation of the biological state of interest. Alternatively, the connectivity map is populated with gene-expression profiles from cells or tissues treated with previously uncharacterized or novel perturbagens. In this mode, the connectivity map functions as a screening tool. Most often, a connectivity map is populated with profiles of both types. Connectivity maps, in general, establish biologically-relevant connections between disease states, gene-product function, and small-molecule action. In particular, connectivity maps have wide-ranging applications including, but not limited to, functional annotation of unknown genes and biological states, identification of the mode of action or functional class of a small molecule, and the identification of perturbagens that modulate or reverse a disease state towards therapeutic advantage as potential drugs. See Lamb et al, "The Connectivity Map: using gene-expression signatures to connect small molecules, genes and disease" Science 313:1929-1935 (2006), and Lamb, "The Connectivity Map: a new tool for biomedical research" Nature Reviews Cancer 7:54-60 (2007). However, the high cost of generating gene-expression profiles severely limits the size and scope of connectivity maps. A connectivity map populated with gene-expression profiles derived from every member of an industrial small-molecule drug-screening library, a saturated combinatorial or diversity-orientated chemical library, a comprehensive collection of crude or purified plant or animal extracts, or from the genetic ablation or forced expression of every gene in a mammalian genome, for example, would be expected to facilitate more, and more profound, biological discoveries than those of existing connectivity maps.

The present invention contemplates compositions and methods for making and using a transcriptome-wide gene-expression profiling platform that "under samples" the total number of transcripts. Because gene expression is believed to be highly correlated, direct measurement of a small number allows the expression levels of the remainder to be inferred. The present invention, therefore, has the potential to reduce the cost and increase the throughput of full-transcriptome gene-expression profiling relative to the well-known conventional approaches that require all transcripts to be measured.

Gene expression data are highly structured, such that the expression level of some genes is predictive of the expression level of others. Knowledge that gene expression data are highly structured allows for the assumption that the number of degrees of freedom in the system are small, which allows for assuming that the basis for computation of the relative gene abundances is sparse.

It is possible to make several biologically motivated assumptions that allow Applicants to recover the nonlinear interaction terms while under-sampling without having any specific knowledge of which genes are likely to interact. In particular, if Applicants assume that genetic interactions are low rank, sparse, or a combination of these, then the true number of degrees of freedom is small relative to the complete combinatorial expansion, which enables Applicants to infer the full nonlinear landscape with a relatively small number of perturbations. Working around these assumptions, analytical theories of matrix completion and compressed sensing may be used to design under-sampled combinatorial perturbation experiments. In addition, a kernel-learning framework may be used to employ under-sampling by building predictive functions of combinatorial perturbations without directly learning any individual interaction coefficient.

In the framework of matrix completion, or more generally tensor completion, the goal is to fill in all the values of a matrix using a small collection of sampled entries. Applicants hypothesize that the rank of a matrix of second-order interactions, or tensor of higher-order interactions, is a fraction of the number of genes being tested. Applicants can test this idea by explicitly calculating the rank from a dense sampling of second or third order knockouts from a small collection of genes. If the rank of interactions is indeed limited, then Applicants can randomly sample pairs of genes to knockout from a larger collection (in the second order case), and then fill in the remaining values via nuclear norm regularized least-squares optimization [Matrix Completion with Noise. E. Candes and Y. Plan]. Provable guarantees for this recovery suggest that if the rank, r, is small relative to the number of genes, n, then m samples such that $$m \geq O\left(\frac{6}{5} nr \log(n)\right)$$

are sufficient. However, these guarantees assume rough uniformity in the loadings of interaction singular vectors, and this assumption is unlikely to hold up if the interaction matrix itself is very sparse. In this case, Applicants can perform the same random sampling scheme, and then simultaneously regularize over both the nuclear norm, and L1 norm of the interaction matrix [Estimation of Simultaneously Sparse and Low Rank Matrices. Richard et. Al.]. As may be appreciated by one of skill in the art, the "sparsity" of a matrix is a measure of the non-zero elements of a matrix relative to the total number of elements of a matrix. A sparse matrix is a matrix in which most of the elements are zero, which is indicative of loose correlation between systems.

As may be appreciated by one of skill in the art, the "rank" of a matrix is the maximum number of linearly independent row vectors in the matrix or the maximum number of linearly independent column vectors in the matrix. The rank of a matrix denotes the "information content of the matrix. The lower the rank, the lower is the information content. A basis for a vector space is a collection of vectors that form a set that is linearly independent and that spans the space.

In the related setting of compressed sensing Applicants can directly leverage the sparse nature of interactions. In this case, instead of working with a tensor of interaction terms, Applicants work with a basis that spans all higher order interactions. This can be, for example, the Fourier basis of higher-order polynomials, in which case Applicants assume that there is a small number, s, of nonzero Fourier coefficients, which are not known a priori, but can accurately capture the effects of any combinatorial perturbation. Then, if Applicants make m random combinatorial knockouts, where m≥O (s log f) and f is the magnitude of combinatorial $$\left(\text{e.g. } f = \binom{100}{3} = \text{"100 choose 3"} = 161700\right),$$

expansion Applicants can recover the nonzero coefficients, and, thus, the set of nonlinear interaction terms, through L1 regularized regression. Compressed sensing tells Applicants that if the perturbations are de-coherent under the given basis, then exact recovery is possible with dramatic under-sampling (in the noiseless case) [Compressive sampling. E. Candes.]. Applicants use this measure of de-coherence, then, as a guide in designing combinatorial perturbations. In particular, if each of m experiments includes a Poisson random sampling of knockouts, then Applicants expect the measurements to have good de-coherence under the Fourier basis, provided the mean number of knockouts is not too low (e.g. >1).

The formulations for matrix completion and compressed sensing each rely on a degree of sparsity—either in the rank or in the coefficients—to achieve recovery with under-sampling. For each of these Applicants can estimate the level of sparsity by performing dense combinatorial perturbations on a small collection of genes, or, in the case of compressed sensing, simply randomly sampling higher-order knockouts. However, Applicants also consider the alternative formulation of kernel learning, which does not have such strict demands on sparsity. In this case Applicants build predictive functions of the effects of combinatorial perturbations using a kernel of experimental similarity. More specifically, assume m experiments with Poisson random sampling of knockouts for each measurement. Then, Applicants can define an m-by-m polynomial kernel, for example, based on the overlap in knockouts between any pair of experiments. If Applicants build such a kernel, and learn the weighted combination of kernel vectors that fits a collection of training data, Applicants can then use these coefficients to predict the outcome of new experiments. In this case the density of nonlinear interaction terms can be much greater, since Applicants do not directly learn any particular interaction coefficient, but rather a kernelized version of the entire polynomial. In fact, if the interaction terms are too sparse, the kernel learning framework is unlikely to be successful with any significant under-sampling. However, together, kernel learning, matrix completion, and compressed sensing represent a complimentary range of approaches for inferring the effects of higher-order, combinatorial perturbations, with different assumptions on the underlying structure of the data for each framework.

The overall sparsity level of biological networks has been estimated in several ways. By comparing colony sizes between single and double mutants, the genetic landscape of *S. cerevisiae* has been mapped revealing that <5% of 5.4 million gene pairs interact significantly with respect to fitness. [Costanzo*, Baryshnikova* et. Al., 2011] In mammalian cells, a systematic screen for ricin toxicity using a hierarchical approach revealed that among 60 genes with significant individual effects, interactions broadly divided genes into functional complexes and were of a relatively higher density [Bassik et. Al., 2013]. A higher dimensional phenotype using imaging between 282 target genes, 20 query genes, and 11 phenotypes found approximately 5,000 significant interactions [Laufer et. Al., 2013]. Sparsity with respect to gene expression phenotypes has not been well studied.

The empirical limits on the number of DSB that might be tenable for an individual cell to survive vary, but rough estimates using imaging of phosphorylation of H2AX and 53BP1 suggest this number could be in the 10-50 range.

According to embodiments of the present invention, each measurement integrates signal across many genes (for example, all 29k genes). Thus, the measurements are not sensitive to the stochastic capture of any single gene, but rather to the average signal across a broad range of genes. In this sense the present scheme is robust to technical noise. In addition, probe sets according to the present invention can be designed independently from any existing data. The probes are, in this sense, universally appropriate for any system desired to be measured. This method recognizes that there may be many different signature gene networks across many cell types/tissues, but that these are used to a sparse degree in any single cell. That is, in a single cell the number of active gene networks is small relative to the total number of all existing gene networks. This assumption can be used to under sample the transcriptome, such that a computational analysis is designed to recover signal from sparse systems. It is assumed that the gene networks (or their abstracted analogs) are sparsely used in any single cell, and specific knowledge of when the networks are active, or even the definitions of the networks themselves, are not required. Every gene is represented in every measurement, even If exact correlations between measurements, genes or expressions are not known. By analyzing transcriptomic measurements across many cells or tissues, it is possible to identify structures in the data that reflect the underlying cell circuitry. These same structures can be exploited to recover gene abundances, while dramatically under-sampling the full signal. In particular, if a given cell or tissue has a sparse representation in some basis, then Applicants can use the theories of compressive sensing and sparse coding to guide the design of RNA probe libraries that Applicants believe reduces sequencing requirements nearly 1000-fold.

To design compressive measurements, Applicants first consider the canonical basis described by Principle Component Analysis (PCA) as an example of an embedding for RNA-Seq data. Suppose, for the sake of argument, that Applicants knew of a universal set of 100 PCs, and that a linear combination of these could be used to describe the gene abundances in any system. By building molecular probes for each PC, Applicants could measure the response along each component in a given sample, and then take the linear combination of these 100 measurements to recover the abundance of every gene. Generally speaking, a basis that is universally appropriate for all systems (in a sense, this is an ultimate goal of biology) is not known. However, there is a surprising result which tells Applicants that making random measurements is universally appropriate for any basis that Applicants are likely to encounter [Compressive sampling. In Proc. Int. Congress of Math., Madrid, Spain, August 2006.]. After making random measurements, and using methods of sparse coding [Efficient sparse coding algorithms. In NIPS, 2006.], Applicants can simultaneously infer the basis and its sparse contributions to the samples in question, and recover the desired signal.

Measurements may be made via hybridization with targeted gene probes, which are barcoded and sequenced to count hybridization events. In such case, each measurement uses a given collection of probes, and there may be multiple probes per gene. For one of m measurements, a random library may be constructed from a barcode pool, and a pool of gene-specific oligos. Each oligo in the barcode pool may contain a universal adapter, a cell/experiment ID, a molecular ID, a measurement ID (one of m total), and a linker region. Gene specific oligos may contain a complimentary linker region, and a target sequence for the given gene. The final probe pool may be created by annealing and extension reactions.

The choice of probe sets may be a random design. Random probe sets have several advantages. Two random measurements are orthogonal (not correlated) with high probability, which means that each random measurement is effectively measuring something “new.” This is difficult, if not impossible, to ensure when each measurement consists of a single gene, and, thus, random probes do a better job of maximizing the information content of a small number of measurements. Existence of a gene correlation structure is assumed without knowing what it is. The probe sets are substantially universally appropriate. By randomly scattering measurements throughout the transcriptome, it can be ensured that Applicants sample from the relevant structures with high probability. Applicants then employ computational methods of Sparse Coding to learn the basis, or gene expression structure which is appropriate for the sample at hand. Importantly, the learning is integrated into the same process for inferring the full gene expression profile, and does not require a separate set of measurements. The number of types of measurements can be approximated by k log (n), where k is an estimated value of sparsity.

At least two methods for randomizing the amount of probe for each gene in each library are considered. First, the molecular IDs are synthesized randomly. Each of these IDs are assigned to +1/−1, such that when counting hybridization events for a given measurement Applicants either increment or decrement the total depending on the molecular ID. Thus, Applicants could have the same number of probes for every gene in each measurement, but the sum across molecular IDs for a given gene is a binomial random variable. Alternatively, a Liquid Handling Robot may be used to mix the barcode and gene pools according to a randomly generated matrix. In either case, the probe library is sequenced after construction to determine its composition.

In the present system, measurements are read out via sequencing, after hybrid selection and amplification. The number of types of measurements is contemplated to be between approximately 100 and 30,000 different types of measurements. The number of types of measurements can be based on an estimate of system sparsity. The number of types of measurements per sample can be, for example, 100. To the extent that there is any knowledge of assumptions about certain measurements or between genes, the number and type of measurements may be adjusted. For each measurement barcode within a cell, Applicants can have gene specific probes for each of ~29k genes. However, the number of probes for a given gene will vary across each of the 100 measurements, according to random design. Once types of measurements are established, and the number or transcripts to be measured are determined, a Design Matrix having a number of rows corresponding to the number of types of measurements (measurement vectors) and the number of column corresponding to the number of transcripts can be generated. The Design Matrix is populated by "measurement values," which are random numbers of measurements such that for each type of measurement each transcript can be counted up to a relative number of times that is random and independent of other elements/entries in the Design Matrix. In other words, the relative number of times up to which a certain measurement type can count each respective transcript is random and independent of the relative number of times up to which that certain measurement type can count other transcripts in the sample and the relative number of times up to which a certain transcript can be counted for a certain type of measurement is random and independent of the relative number of times up to which that certain transcript can be counted for other types of measurement. While the measurements may be random and independent, such is not required. Knowledge of some relationships between measurements may allow manipulation of the measurement values to improve calculations. For example, steps according to the present application may be iterated multiple times to refine results by incorporating knowledge gained through a first round of measurements. Similarly, knowledge of relationships between genes, measurements and transcripts may be used to inform and select some measurement values for the Design Matrix, although this is not required. For example, the Design Matrix can be adjusted according to a known basis.

A probe library corresponding to the Design Matrix may be generated. For example, a probe library comprises 100 or more molecules assembled according to a set of random measurement values forming at least one measurement vector, where each molecule comprises a tag for the at least one measurement vector operably linked to a probe for one type of transcript of a plurality of types of transcripts. The probe library includes a collection of molecules assembled according to the measurement values, where each molecule has a tag, e.g., a barcode, for one of the measurement types operably linked to a probe for one of the types of transcripts. The tag may uniquely correspond to a measurement type/vector. Probes contemplated according to the present invention may be single-stranded DNA, transcript, protein, DNA, non-naturally occurring nucleic acid, peptide, or the like. That is, each amount of probe can thus be adjusted based on the random measurement values in the Design Matrix such that the amount of a specific probe is known relative to the amounts of the other probes based on the Design Matrix.

While the present example describes cells as the sample for measurement, the sample may include cells, blood, hair, nails, mucus, tissue, feces, urine, body secretion or the like.

For one application, measurements may be made in single cells, and probe sets may be held as oligos on beads. For example, in one aspect each oligo may hold at least one of a sequencing adapter, a cellular barcode, a measurement barcode, a molecular barcode, and a primary gene-specific probe. cDNA targets may be captured on the primary probes, and then secondary probes, which target sequences immediately adjacent to the primary probes, may be introduced. Ligation of the primary and secondary probes produces a full-length fragment that can be amplified via universal sequences on the 5' end of the bead-attached oligo, and 3' end of the free-floating secondary probe. After amplification, Applicants sequence the barcode-containing regions to count the number of molecular events for each cell/measurement barcode combination. Contacting the probe library to the pool of samples thus results in a number of measurement results for each cell of the pool of cells.

The sample types are not limited to cells and may be any of numerous types of biomolecules. A biomolecule is any molecule that is present in living organisms, such as large macromolecules such as proteins, polysaccharides, lipids, and nucleic acids, as well as small molecules such as primary metabolites, secondary metabolites, and natural products. In an advantage embodiment, the biomolecule is a nucleic acid, such as but not limited to, deoxyribonucleic acid (DNA), ribonucleic acid (RNA), peptide nucleic acid (PNA) or other non-naturally occurring nucleic acid. In another advantageous embodiment, the biomolecule is a protein, such as but not limited to, peptides, antibodies, immunogenic molecules or enzymes.

An Observed Measurement Matrix may thus be constructed using the measurement results for each cell/sample to populate the elements/entries of the Observed Measurement Matrix. Construction of the Observed Measurement Matrix can include tag quantification, and tag quantification can include sequencing. For example, a relative count is conducted of the tags such that the relative number of times a certain tag is counted per cell is entered into an appropriate element of the Observed Measurement Matrix M. A sparse coding solving process may then be applied to the Observed Measurement Matrix M to learn system matrix S as indicative of relative abundance of the transcripts in each of the samples.

An example of a sparse coding process can be exemplified by $$\underset{m\times c}{M} = \underset{m\times n}{DM} \cdot \underset{n\times c}{S}$$

where m is the number of measurement vectors, c is the number of cell vectors, and n is the number of gene vectors. S is a System Matrix, which can be determined once M and DM are populated (M with actual measurements/counts and DM with random measurement values). S is thus indicative of the relative gene abundances.

Moreover, once S is known, a Basis Matrix B, can be determined based on knowledge of X, a matrix populated by known contributions of genes n and cells c to the sample.

$$\underset{n\times c}{S} = \underset{n\times n}{B} \cdot \underset{n\times c}{X}$$

Knowledge of the Basis can then be used to generate new measurement values of the Design Matrix to refine calculation of a new System Matrix S'.

Testing for linearity of hybrid selection is contemplated, along with dynamic range, by, for example, splitting bulk cDNA prepared from a population of K562 cells. In one split, qRT-PCR is performed for a collection of 25 genes that range from the highest abundance, to being absent. In a second split, hybrid selection is tested on a collection of 24 random probe libraries (3 experimental IDs, each with 8 measurement indices). The goal is to optimize the hybridization conditions for maximal dynamic range, while ensuring that the readout from sequencing after hybridization is linear with regards to qPCR controls, and the amount of probe for a given gene in a given library. The size of the probe library is then be successively increased to 100 genes, then 1000, and finally to the set of all genes. The measurements are more robust with larger panels of genes, since Applicants' readout is effectively the sum of hybridization events across all probes for a given measurement index. In other words, since only barcodes are sequenced the barcodes and not the gene specific regions, the process is not sensitive to the stochastic capture of transcripts for any single gene, but rather to the average capture across all genes. Finally, this design is compatible with single cell technologies, and has indeed been designed with this application in mind. In particular, random probe libraries held on beads in place of barcoded poly-dT oligos are contemplated, but this is just one of many possible constructions.

In a first round of experiments, Applicants have constructed the random probe sets as follows. One pool of oligos is synthesized to contain a universal sequence, a cellular barcode, a measurement barcode, a molecular barcode, and a linker region. A second pool is synthesized to contain a complimentary linker region, and a gene-specific target. Oligos from the two pools can be annealed, and then extended in the 3' direction on the barcoded fragment with the Klenow fragment, or T4 DNA polymerase. These can be treated with lambda exonuclease, and purified by size selection for the full-length fragment. This can be done for each gene, and then the fragments can be mixed and pooled according to random design. Alternatively, fragments for each gene in each measurement can be pooled in equal amounts. In this case, Applicants achieve random measurements by assigning each molecular identifier (which was synthesized randomly) to a +1/−1. When integrating the counts for a given measurement, Applicants then increment or decrement the count according to this assignment. Since the molecular barcodes and assignments are made randomly, the sum of +1/−1 assignments for a given gene behave as a random variable across the different measurements. Secondary gene probes can be synthesized independently.

It is anticipated that probe libraries may be constructed and provided and present methods applied to provide cost-effective gene-expression profiling. Accordingly a product comprising completed probe libraries, or a kit for making the libraries according to principles of the present invention are possible. For some applications it may make sense to focus on a subset of genes, in which case the kit would be particularly appropriate.

In addition, random probes and sparse coding could be applied as a service. That is, a customer may provide a sample or sample pools to an entity for constructing a probe library according to customer objectives and sample, applying the steps of the methods according to principles of the present invention and providing as its result a report of the relative gene-abundances or gene-expression profile or the like. This could be particularly useful for applications that require the analysis of tens to hundreds of thousands of transcriptional profiles, since Applicants estimate that methods according to principles of the present invention reduce sequencing requirements by 100-1000 fold. For example, when screening for combinatorial effects of small molecules, or when testing for the presence of very rare cell types (such as cancer stem cells), a large number of profiles need to be generated.

Rapidly advancing experimental methods are opening new ground for the exploration of higher-order genetic interactions. These methods include the CRISPR-Cas system for knockouts, which enables greater degrees of combinatorial perturbations, as well as high-throughput readout techniques such as single-cell RNA-Seq. The ability to sequence the transcriptomes of tens of thousands of cells using droplet microfluidics has recently been demonstrated [Macosko et. al., 2015]. By constructing a polyadenylated RNA barcode that is associated with a CRISPR sgRNA, Applicants was able to couple the experimental scale of microfluidic technologies with perturbation experiments in mammalian cells.

However, even with these advances, Applicants are limited to full combinatorial samplings of second- or third-order interactions for a small number of genes. For example, for a collection of 30 genes, performing all third-order knockouts is at the boundary of experimental feasibility (30 choose 3=4060 experiments), while a dense sampling of fourth-order terms for the same size collection (30 choose 4=27405), or third-order terms for a larger collection (100 choose 3=161700) is intractable. Therefore, Applicants are motivated to identify schemes that leverage Applicants' ability to perform combinatorial perturbations, while also dramatically under-sampling the full combinatorial space.

Compressive Sensing the Transcriptome

1$^{st}$ Trial Run-Analysis

Probe Library Creation

The new protocols generated a much higher percentage of fragments of the correct size (eg 70-99% stitched) as compared with the original L1000 protocol (19-42% stitched). Having larger cDNA input also resulted in a greater percentage of stitched fragments.

UMI Counting

Correlations of individual gene counts with expectation based on RPKM from ENCODE were generally positive, but not stunning. Results with gene counts from qPCR were largely unchanged. For the new ligation protocols, correlations were generally positive, except for row1 which generally has low (negative) values. For the L1000 ligation protocol correlations were more consistently positive, except for condition 21, which shows negative correlations for many rows/conditions.

Applicants also considered UMIs aggregated across genes, with randomly chosen rows. This mimics the intended setting. In this case correlations were generally much higher (range 47-79%). The best condition by this measure was 26_27 (new protocol with low ligation, low L/R ratio with undiluted cDNA).

The normalization strategy used in initial trials is based on sequenced barcode counts from direct ligation of probes, without cDNA targets. Quantifying barcode counts in this way gives an overall estimate of the abundance of each member of the library. In future experiments, applicants will compare the results of this normalization strategy to a normalization based on ligation to a pool of genomic DNA.

X18 Samples (3 FBC Vs 6 RBC)

<P5 barcoding>

Original L1000: P5-30

New protocol (high ligation 5ul mix input for R1, see notes below): P5-25

New protocol (low ligation 1 ul mix input for R1, see notes below): P5-26

<P7 barcoding>

1. High L/R ratio probe mix+5 μL cDNA input (~50 ng/μL): P7-14
2. High L/R ratio probe mix+5 μL (1/8 diluted) cDNA input (~6 ng/μL): P7-21
3. Low L/R ratio probe mix+5 μL cDNA input (~50 ng/μL): P7-27
4. Low L/R ratio probe mix+5 μL (1/8 diluted) cDNA input (~6 ng/μL): P7-28
5. High L/R ratio probe mix direct ligation with T7: P7-15
6. Low L/R ratio probe mix direct ligation with T7: P7-20

Read Counts

| F | R | Total Fragments | Stitched | % Stitched |
|---|---|---|---|---|
| 26 | 27 | 799365 | 795574 | 99.5% |
| 25 | 27 | 890612 | 881037 | 98.9% |
| 26 | 20 | 839036 | 825118 | 98.3% |
| 26 | 14 | 401287 | 383828 | 95.6% |
| 26 | 28 | 628901 | 589907 | 93.8% |
| 26 | 21 | 237079 | 217109 | 91.6% |
| 25 | 14 | 124932 | 109626 | 87.7% |
| 26 | 15 | 1067299 | 906534 | 84.9% |
| 25 | 15 | 1033888 | 838764 | 81.1% |
| 25 | 28 | 726668 | 570421 | 78.5% |
| 25 | 20 | 849166 | 628951 | 74.1% |
| 25 | 21 | 65325 | 46374 | 71.0% |
| 30 | 20 | 437882 | 186679 | 42.6% |
| 30 | 14 | 774238 | 257647 | 33.3% |
| 30 | 15 | 938377 | 268906 | 28.7% |
| 30 | 21 | 745495 | 144001 | 19.3% |
| 30 | 28 | 1066525 | 189338 | 17.8% |
| 30 | 27 | 966163 | 149402 | 15.5% |

Correlation with RPKM

For each read Applicants parse barcodes into structures such as:

cell1 AGGTCGTA row1 ACTB ACTB

Stitched reads that do not fit this format are discarded. For direct ligation (no cDNA), Applicants allow the left and right gene barcodes to differ, but for all others Applicants require that the gene barcodes are identical.

Once parsed, Applicants count the number of UMIs for every gene in each condition and row (8 rows per condition). After normalizing by the number of UMIs in the corresponding direct ligation condition, Applicants can compare the normalized UMI count with actual RPKM for each gene.

Figure 3:
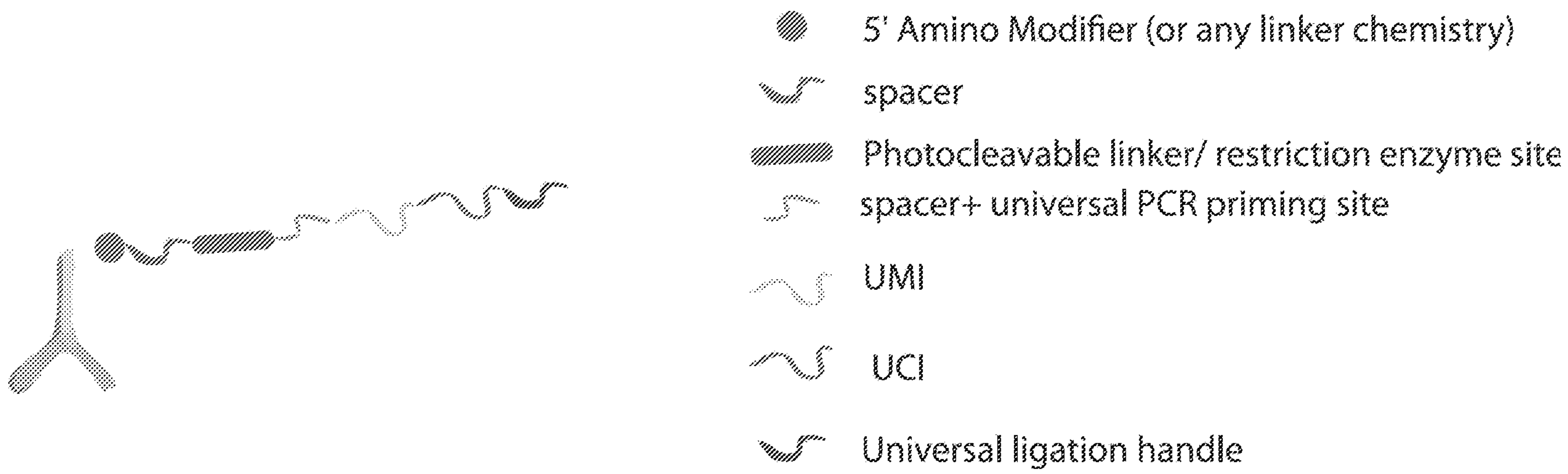
FIG. 3 illustrates measuring protein levels by staining of aggregations of cellular constituents with high affinity reagents (antibodies) linked to an oligonucleotide with the structure [5' Amino Modifier]-[~6 bp spacer]-[PhotoCleavable linker]-[~4 bp spacer]-[Illumina PCR primer]-[~8-16 bp UMI]-[~21 bp UCI]-[~20 bp universal ligation handle]. Note: UMI may be omitted in case of incorporation of a UMI in a split and pool index.

For a given experimental condition, probes were included at 8 dilution levels (rows 1-8). In row 1, probes for all targets were included at approximately the same concentration. In each successive dilution level (rows 2-8) the overall concentration of probes was serially diluted so that the probe concentration in row 8 was approximately 100-fold lower than the concentration in row 1. Thus, correlations of observed versus expected counts within each of the 8 dilution levels of a given experiment reflect the sensitivity of each assay across a 100-fold change in probe concentration. Correlations from these results are included at the end of this document. In FIG. 3 the results for one example condition (24_26) are depicted in a scatter plot.

Figure 4:
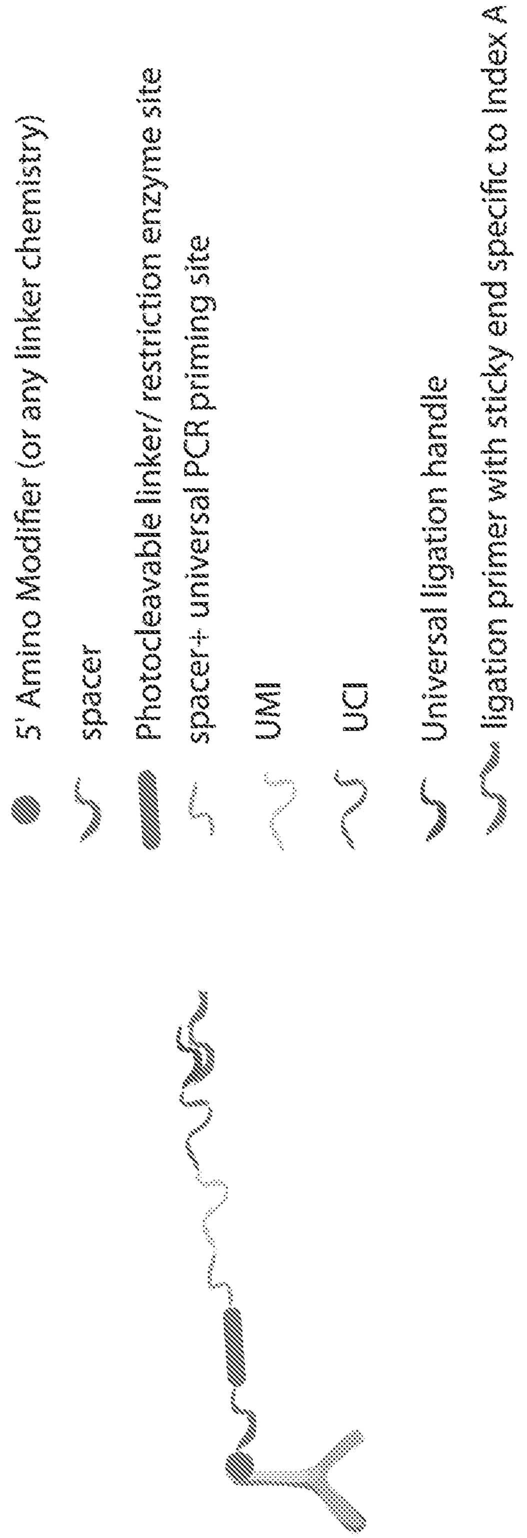
FIG. 4 illustrates hybridization of a ligation primer that binds to the universal ligation handle on oligonucleotide label with a sticky end needed for ligation of index A is produced.

Applicants can also ask how each condition would perform in the random setting where Applicants aggregate counts across all genes. To do this Applicants begin with a single gene, and choose a random row from the given condition. Applicants increment the "observed" count by the number of UMIs for that gene in that row, and increment the "expected" count by the product of the direct ligation UMI count for that gene/row with the RPKM of the gene. This is repeated for every gene such that Applicants have "observed" and "expected" sums across all genes with randomly chosen rows. This was repeated 8 times to generate a vector of random observations and expectations. Below Applicants report the correlation of these vectors for each condition, averaged across 50 random trials. In FIG. 4 the simulation results for one example condition (24_26) are depicted in a scatter plot.

| condition | correlation |
|---|---|
| 25_21 | 46.6% |
| 25_14 | 49.0% |
| 26_21 | 52.9% |
| 30_14 | 57.8% |
| 30_27 | 63.4% |
| 30_21 | 65.0% |
| 30_28 | 68.9% |
| 25_27 | 69.7% |
| 26_14 | 70.2% |
| 25_28 | 74.1% |
| 26_28 | 76.6% |
| 26_27 | 79.3% |

Results for individual genes in each condition (condition IDs offset by 1):

norm.24_13.row1.txt:correlation: 0.101860
norm.24_13.row2.txt:correlation: 0.198498
norm.24_13.row3.txt:correlation: 0.125971
norm.24_13.row5.txt:correlation: 0.184587
norm.24_13.row6.txt:correlation: −0.065662
norm.24_13.row7.txt:correlation: 0.548366
norm.24_13.row8.txt:correlation: 0.188612
norm.24_20.row1.txt:correlation: 0.018865
norm.24_20.row2.txt:correlation: 0.011796
norm.24_20.row3.txt:correlation: −0.067194
norm.24_20.row5.txt:correlation: −0.220015
norm.24_20.row6.txt:correlation: −0.157439
norm.24_20.row7.txt:correlation: 0.364206
norm.24_20.row8.txt:correlation: 0.080670
norm.24_26.row1.txt:correlation: 0.372970
norm.24_26.row2.txt:correlation: 0.778385
norm.24_26.row3.txt:correlation: 0.794532
norm.24_26.row5.txt:correlation: 0.501830
norm.24_26.row6.txt:correlation: 0.340869
norm.24_26.row7.txt:correlation: 0.562235
norm.24_26.row8.txt:correlation: 0.576566
norm.24_27.row1.txt:correlation: 0.381881
norm.24_27.row2.txt:correlation: 0.771273
norm.24_27.row3.txt:correlation: 0.684149
norm.24_27.row5.txt:correlation: 0.445928
norm.24_27.row6.txt:correlation: 0.170683 norm.24_27.row7.txt:correlation: 0.543163
norm.24_27.row8.txt:correlation: 0.530076
norm.25_13.row1.txt:correlation: 0.309518
norm.25_13.row2.txt:correlation: 0.490934
norm.25_13.row3.txt:correlation: 0.349481
norm.25_13.row5.txt:correlation: 0.397947
norm.25_13.row6.txt:correlation: 0.272807
norm.25_13.row7.txt:correlation: −0.158994
norm.25_13.row8.txt:correlation: 0.256215
norm.25_20.row1.txt:correlation: 0.141412
norm.25_20.row2.txt:correlation: 0.275601
norm.25_20.row3.txt:correlation: −0.170215
norm.25_20.row5.txt:correlation: −0.115663
norm.25_20.row6.txt:correlation: −0.306711
norm.25_20.row7.txt:correlation: −0.590045
norm.25_20.row8.txt:correlation: −0.327281
norm.25_26.row1.txt:correlation: 0.513396
norm.25_26.row2.txt:correlation: 0.135664
norm.25_26.row3.txt:correlation: 0.493248
norm.25_26: row5.txt:correlation: 0.592195
norm.25_26.row6.txt:correlation: 0.649929
norm.25_26.row7.txt:correlation: 0.638488
norm.25_26.row8.txt:correlation: 0.592366
norm.25_27.row1.txt:correlation: 0.435686
norm.25_27.row2.txt:correlation: −0.043748
norm.25_27.row3.txt:correlation: 0.249897
norm.25_27.row5.txt:correlation: 0.615696
norm.25_27.row6.txt:correlation: 0.591814
norm.25_27.row7.txt:correlation: 0.550319
norm.25_27.row8.txt:correlation: 0.433558
norm.29_13.row1.txt:correlation: −0.351870
norm.29_13.row2.txt:correlation: 0.144392
norm.29_13.row3.txt:correlation: 0.057765
norm.29_13.row5.txt:correlation: 0.393736
norm.29_13.row6.txt:correlation: 0.031146
norm.29_13.row7.txt:correlation: 0.043738
norm.29_13.row8.txt:correlation: 0.382760
norm.29_20.row1.txt:correlation: −0.092086
norm.29_20.row2.txt:correlation: 0.040947
norm.29_20.row3.txt:correlation: 0.265565
norm.29_20.row5.txt:correlation: 0.589432
norm.29_20.row6.txt:correlation: 0.117522
norm.29_20.row7.txt:correlation: 0.386742
norm.29_20.row8.txt:correlation: 0.557595
norm.29_26.row1.txt:correlation: −0.218187
norm.29_26.row2.txt:correlation: 0.578199
norm.29_26.row3.txt:correlation: 0.549576
norm.29_26.row5.txt:correlation: 0.131541
norm.29_26.row6.txt:correlation: 0.271451
norm.29_26.row7.txt:correlation: 0.429337
norm.29_26.row8.txt:correlation: 0.189393
norm.29_27.row1.txt:correlation: −0.246045
norm.29_27.row2.txt:correlation: 0.449658
norm.29_27.row3.txt:correlation: 0.425474
norm.29_27.row5.txt:correlation: 0.376062
norm.29_27.row6.txt:correlation: −0.444794
norm.29_27.row7.txt:correlation: −0.125790
norm.29_27.row8.txt:correlation: 0.399004

Figure 5:
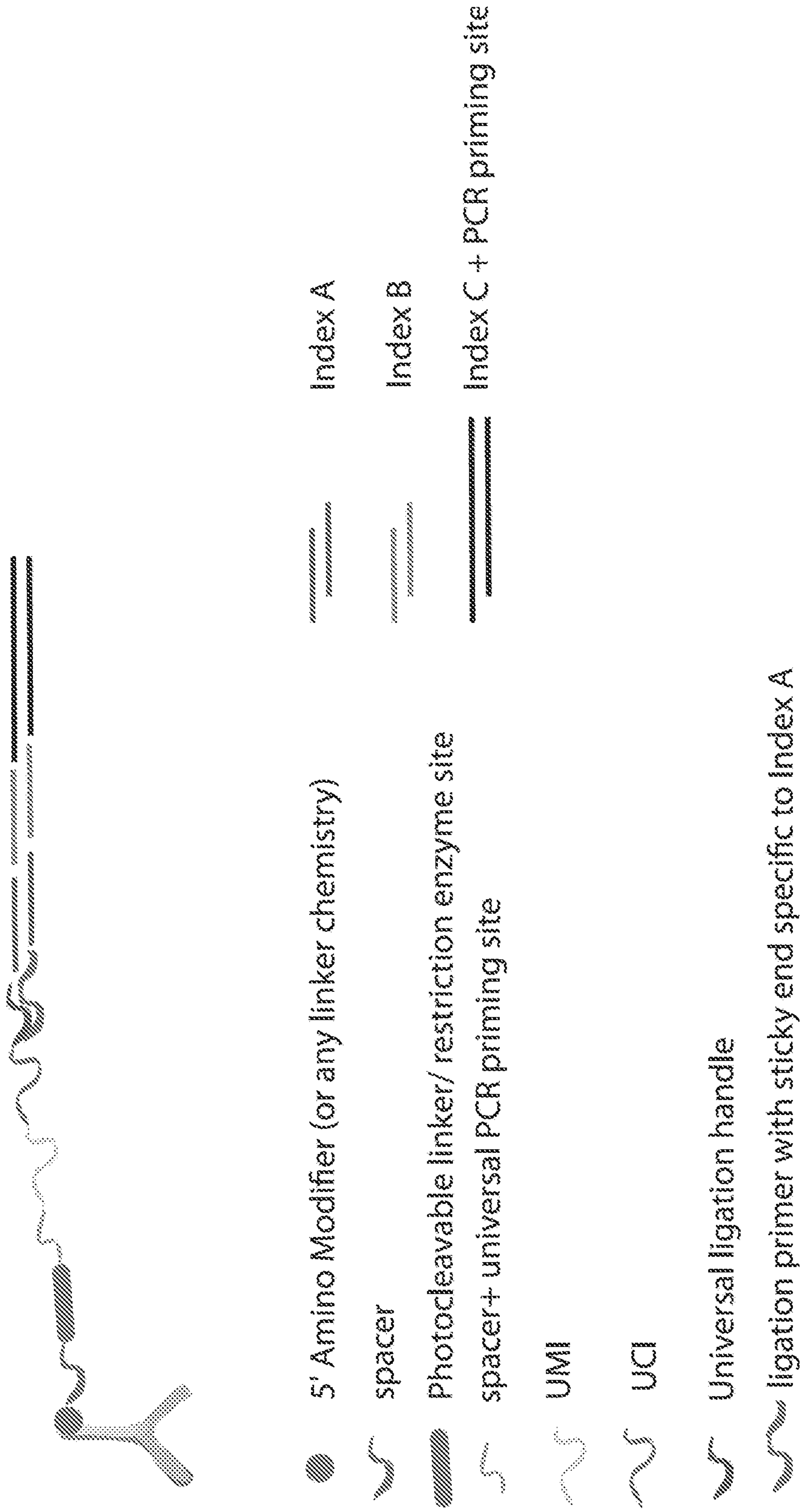
FIG. 5 illustrates split-pool ligation using single-cell hydrogel drops as the basic unit and ligation of Index A, B and [C+PCR primer].
Figure 6:
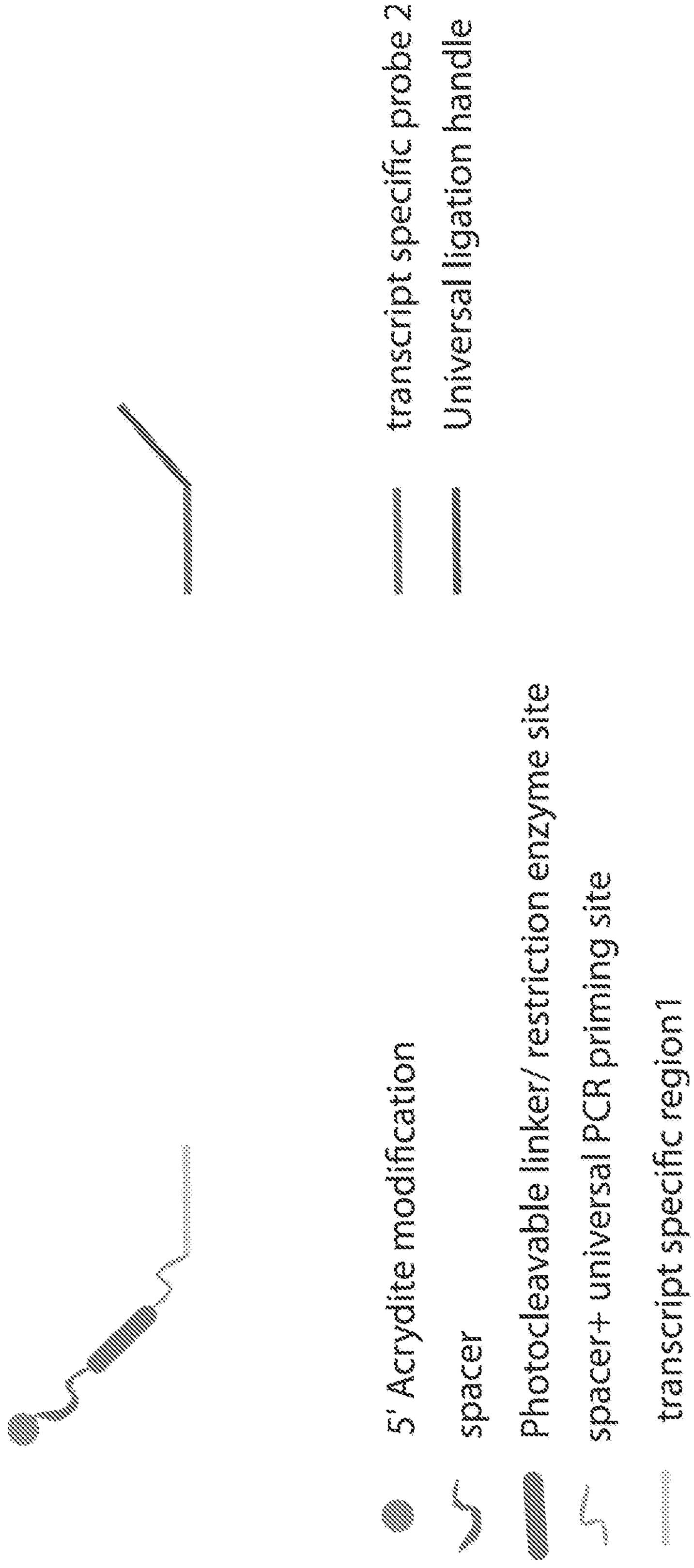
FIG. 6 illustrates staining in bulk with adjacent oligo's that hybridize to an RNA transcript or single guide RNA (sgRNA) at sites adjacent to each other.
Figure 7:
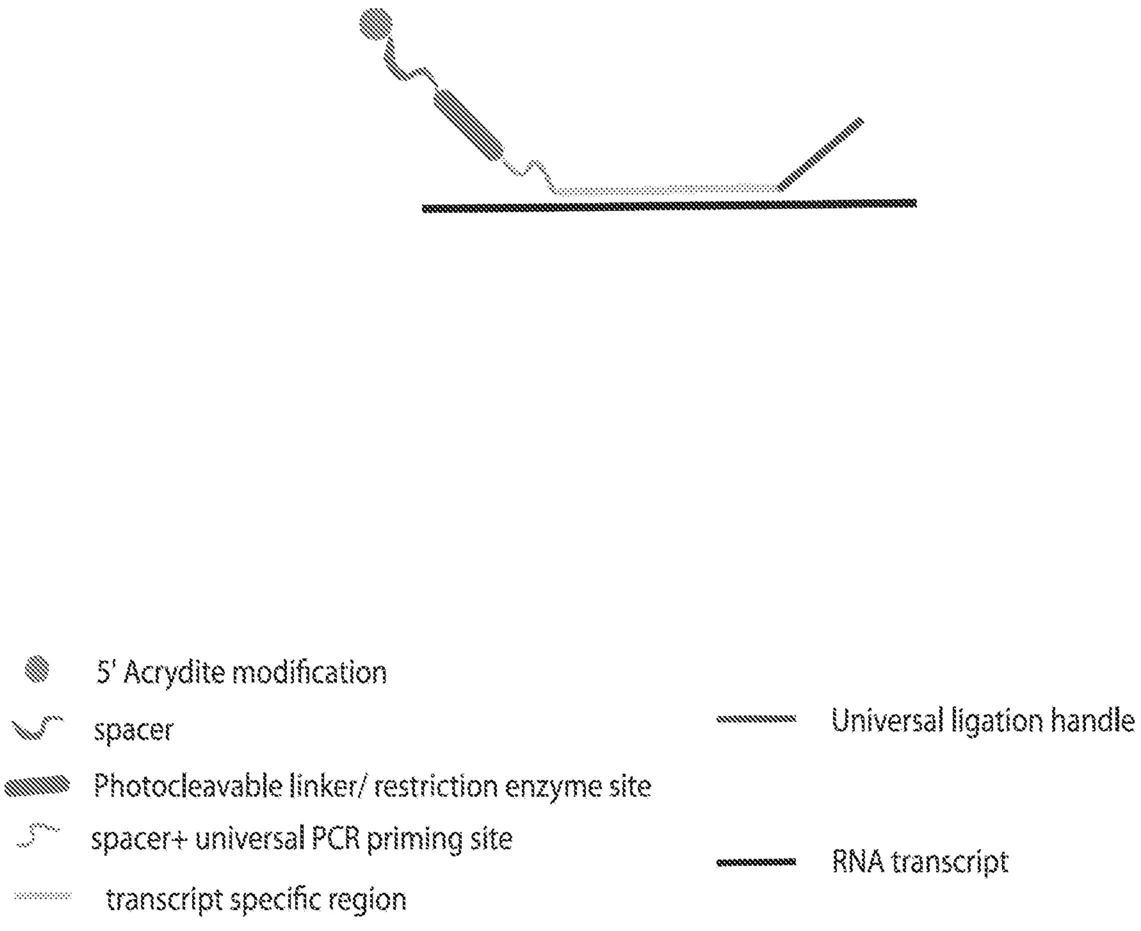
FIG. 7 illustrates single probe detection of an RNA transcript or sgRNA using a single DNA probe that specifically binds to the target transcript.
Figure 8:
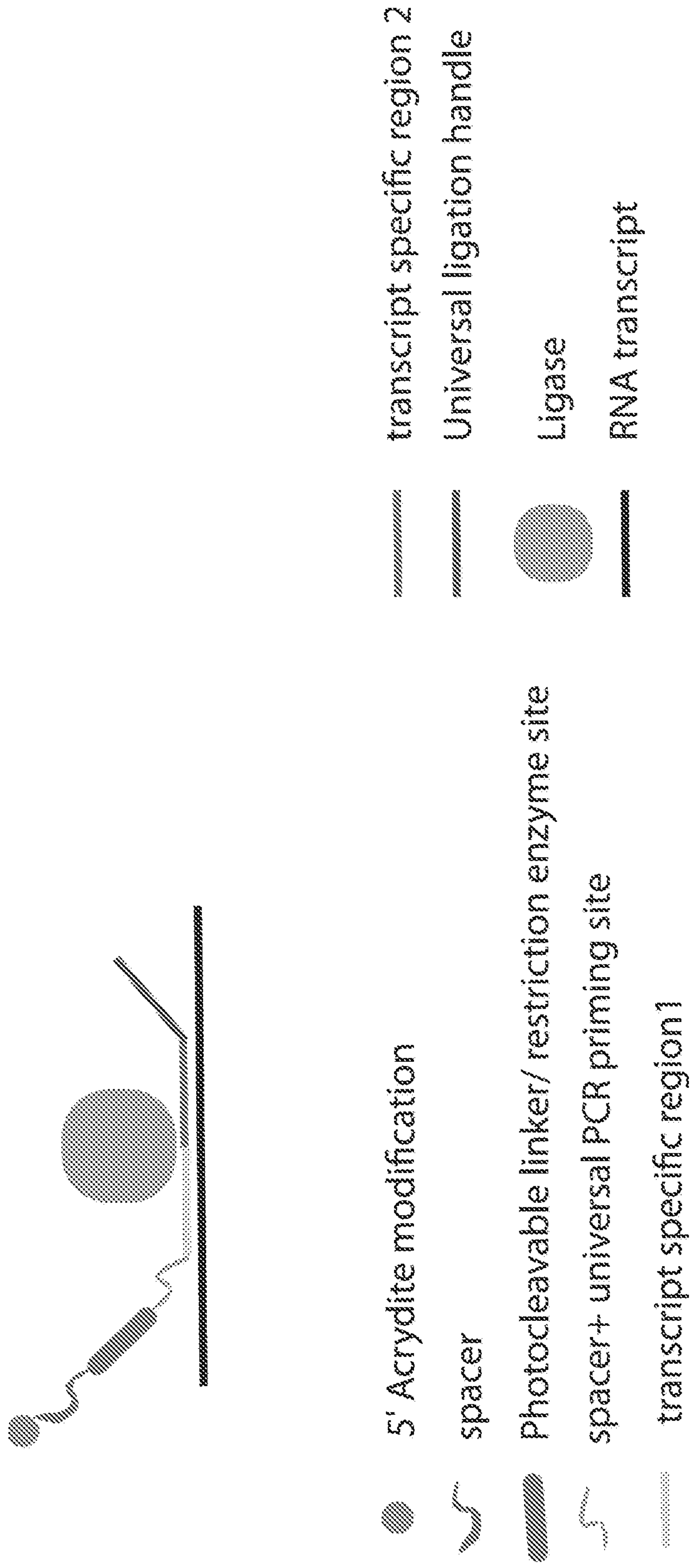
FIG. 8 illustrates dual probe detection of an RNA transcript or sgRNA using adjacently binding probes that are ligated, such that only dually detection events are amplified.
Figure 9:
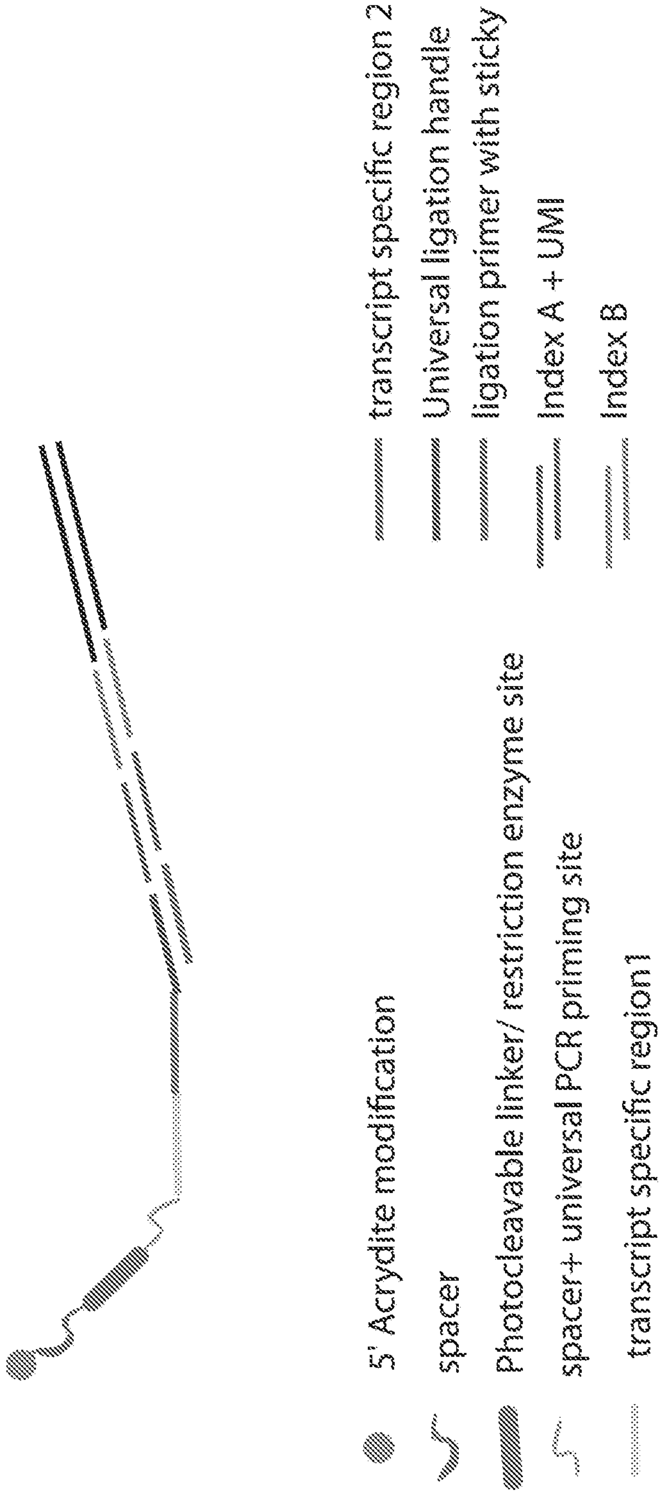
FIG. 9 illustrates staining with the ligation primer and performing split-pool ligation with an Index A containing a UMI in index C such that sequencing starts with a random region (improves cluster detection) and ligation primer is no longer separately added, but pre hybridized before staining.
Figure 11:
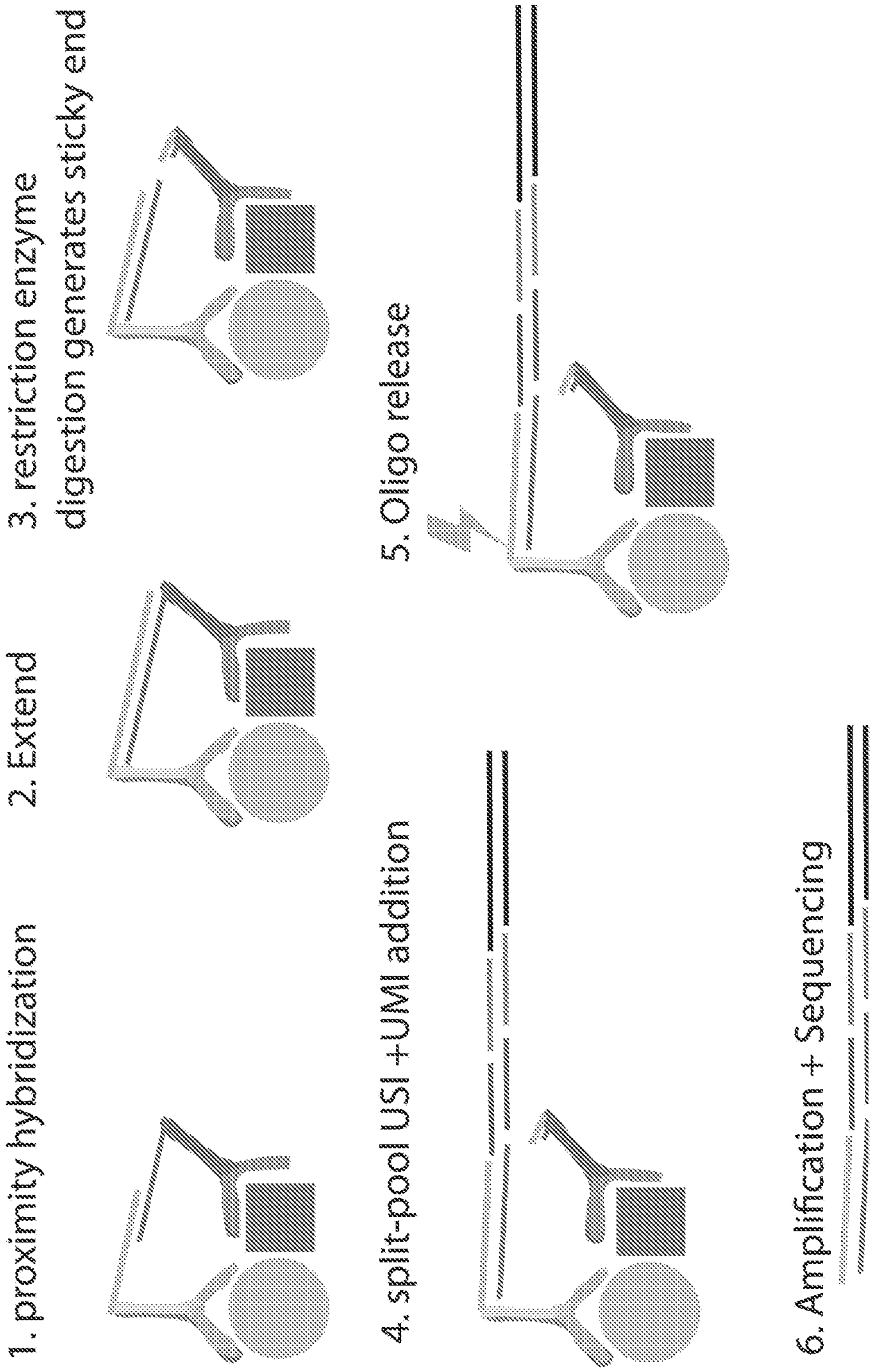
FIG. 11 illustrates measuring protein-protein complexes by performing a restriction enzyme digestion to generate an oligonucleotide containing two UCI and a compatible end for ligation to an index A for split-pool ligation.
Figure 12:
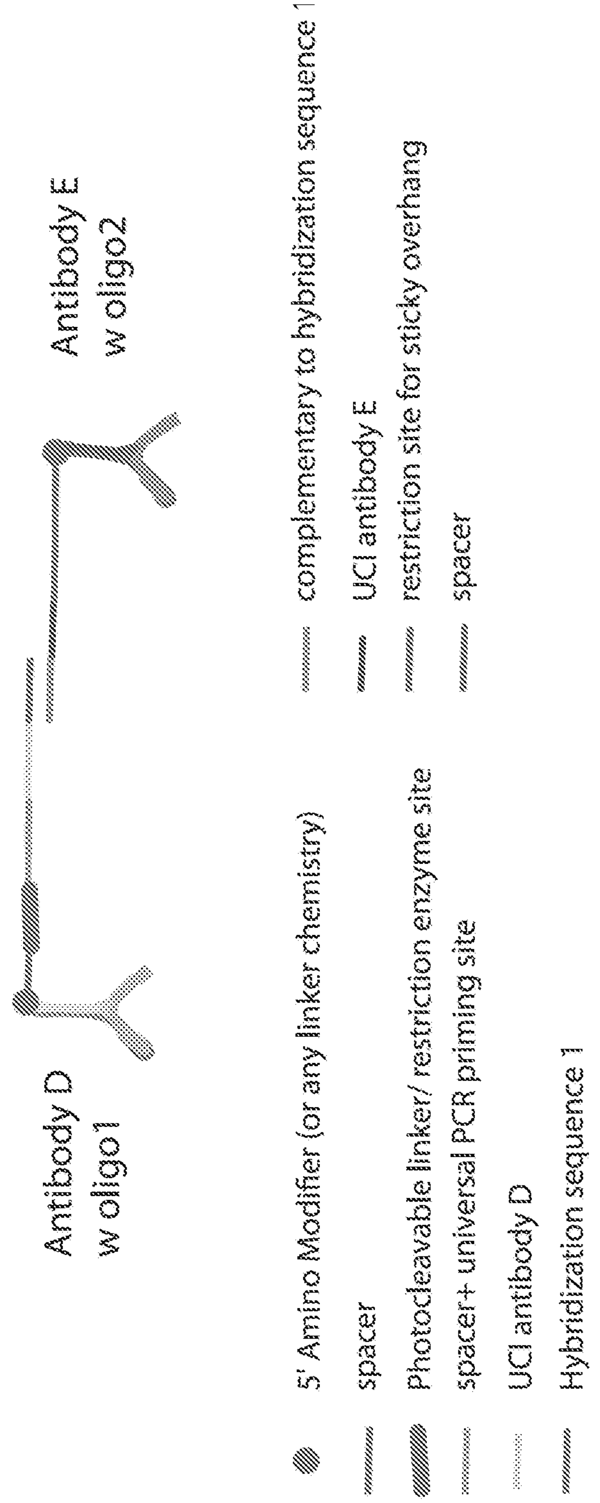
FIG. 12 illustrates oligonucleotide structures for measuring protein-protein complexes. Oligo 1: [5' Amino Modifier]-[~6 bp spacer]-[PhotoCleavable linker]-[~4 bp spacer]-[Illumina PCR primer]-[~21 bp UCI]-[~11 bp Hybridization sequence 1]. Oligo 2: [5' Amino Modifier]-[~6 bp spacer]-[RE site for sticky overhang]-[~21 bp UCI]-[~11 bp Hybridization sequence 1 complement].

In a second round of optimizations, the probe library was expanded to target 24 genes that range from the most abundant, to non-abundant in the sample. As illustrated in the plots exemplified in FIGS. 5-8, correlation values for individual dilution levels (rows 1-8) were significantly higher than initial experiments. Correlation levels may be determined for a probe library and various dilution conditions of that probe library. For example, FIG. 5 is plot of expected counts versus observed counts for a predetermined set of probes under a range of dilution criteria for the protocol Purified cDNA High. In the experiment exemplified, 24 different genes from most abundant to not present were measured and correlation values determined within a dilution level, where a correlation of closer to 1 indicates a higher degree of correlation. In the first dilution level (row 1), probes for each of 24 genes were included at approximately equal abundance. In the second dilution level (row 2) the overall concentration of probes was reduced by a factor of 2. Each row down to row 8 was successively diluted, so that the concentration of probes in row 8 was approximately 100-fold lower than in row 1. Thus, the 8 correlation values in FIG. 5 represent the sensitivity of the assay across a 100-fold change in the concentration of gene probes.

Figure 27:
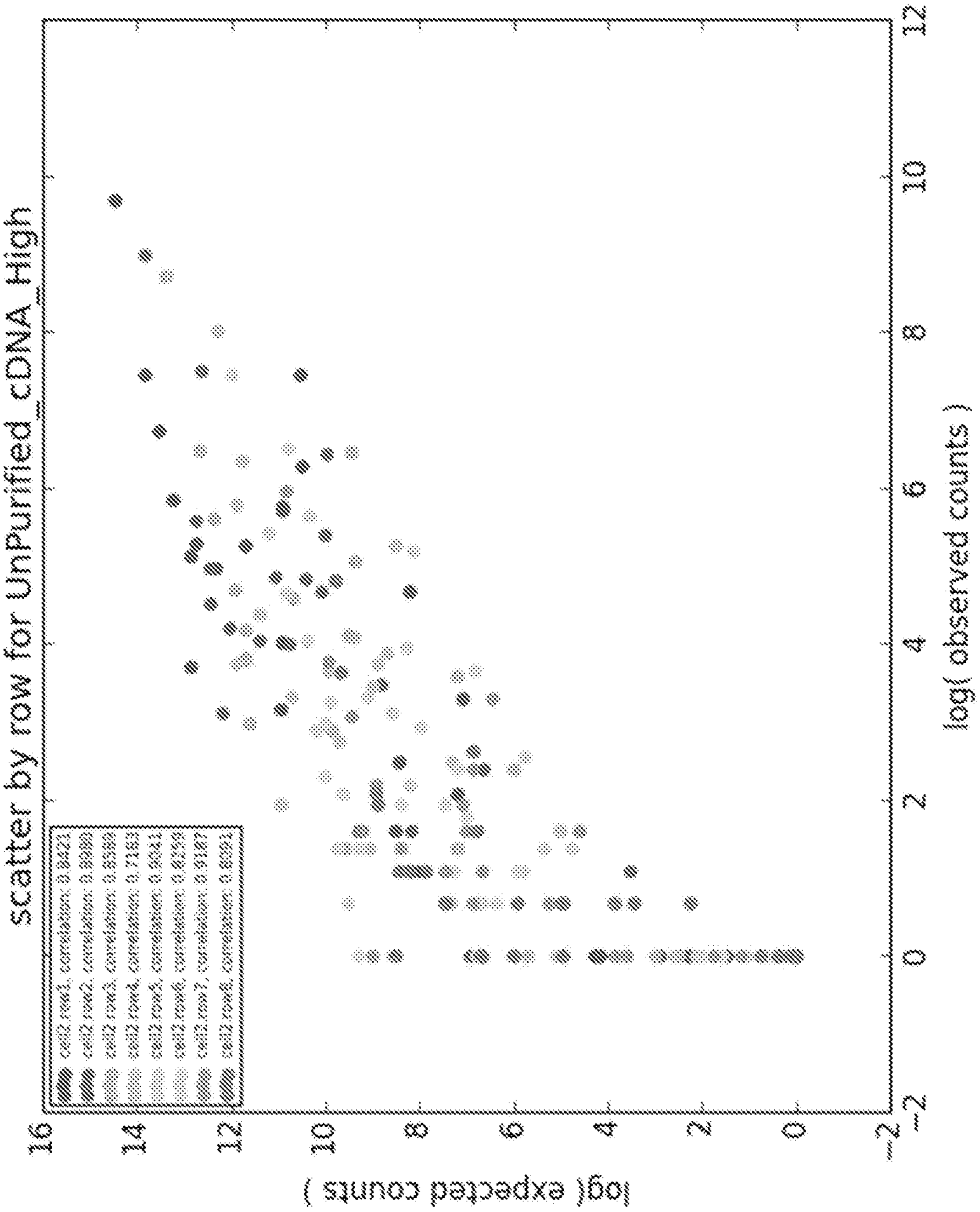
FIG. 27 is plot of expected counts versus observed counts for a predetermined set of probes under certain dilution criteria for unPurified cDNA High.

Similarly, FIG. 27 is plot of expected counts versus observed counts for a predetermined set of probes under a range of dilution criteria for unPurified cDNA High.

Figure 28:
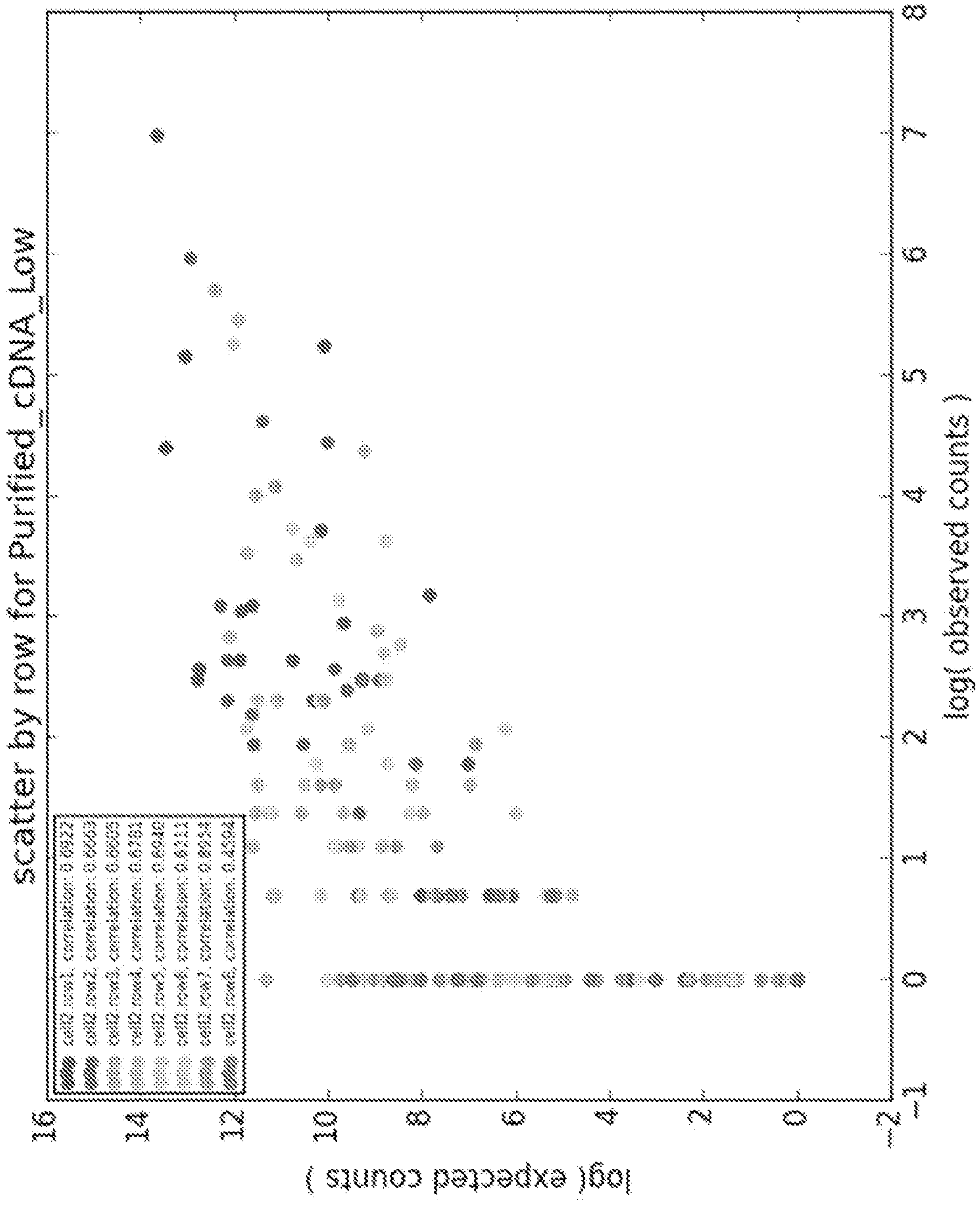
FIG. 28 is plot of expected counts versus observed counts for a predetermined set of probes under certain dilution criteria for Purified cDNA Low.

FIG. 28 is plot of expected counts versus observed counts for a predetermined set of probes under a range of dilution criteria for Purified cDNA Low.

Figure 29:
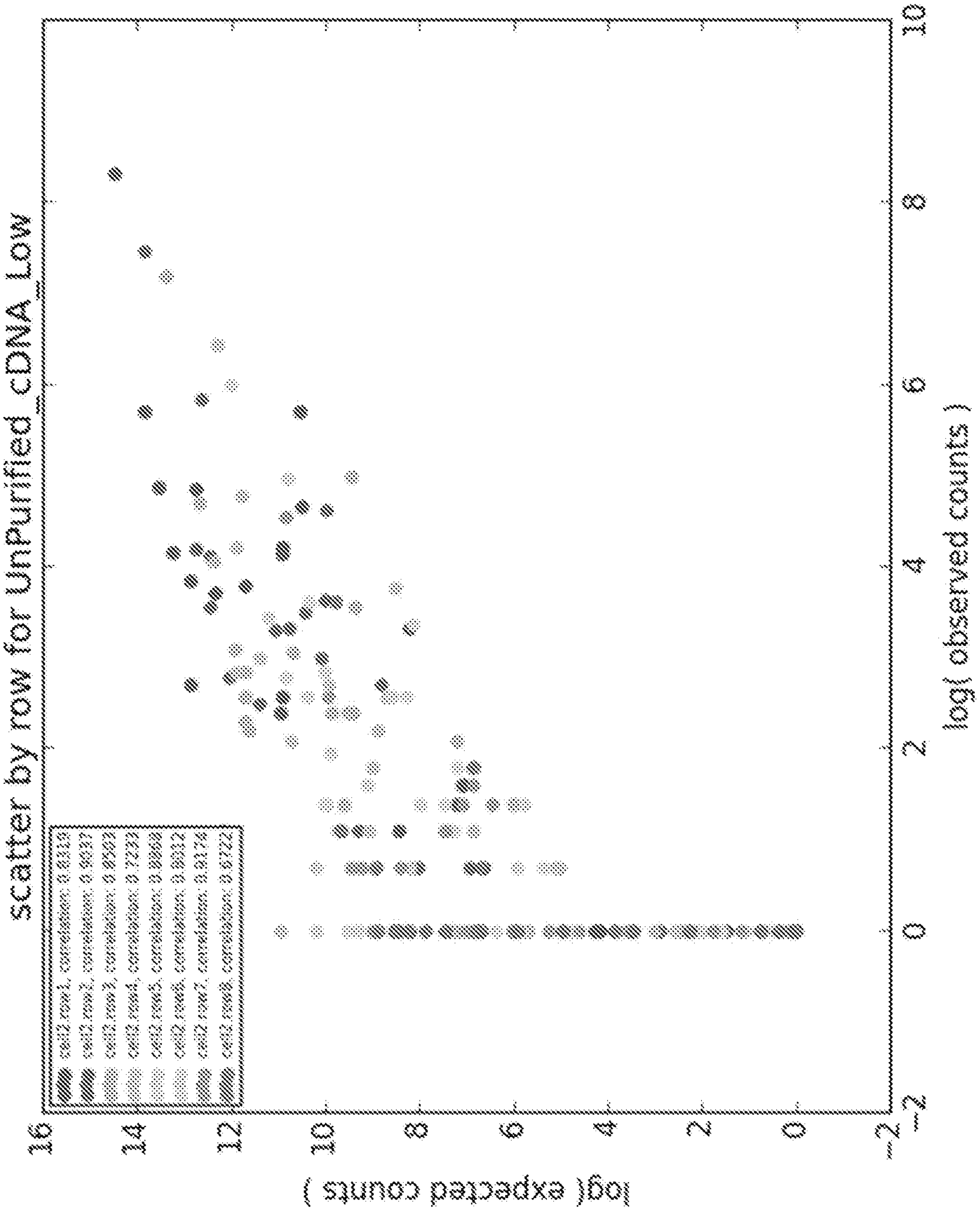
FIG. 29 is plot of expected counts versus observed counts for a predetermined set of probes under certain dilution criteria for unPurified cDNA Low.
Figure 30:
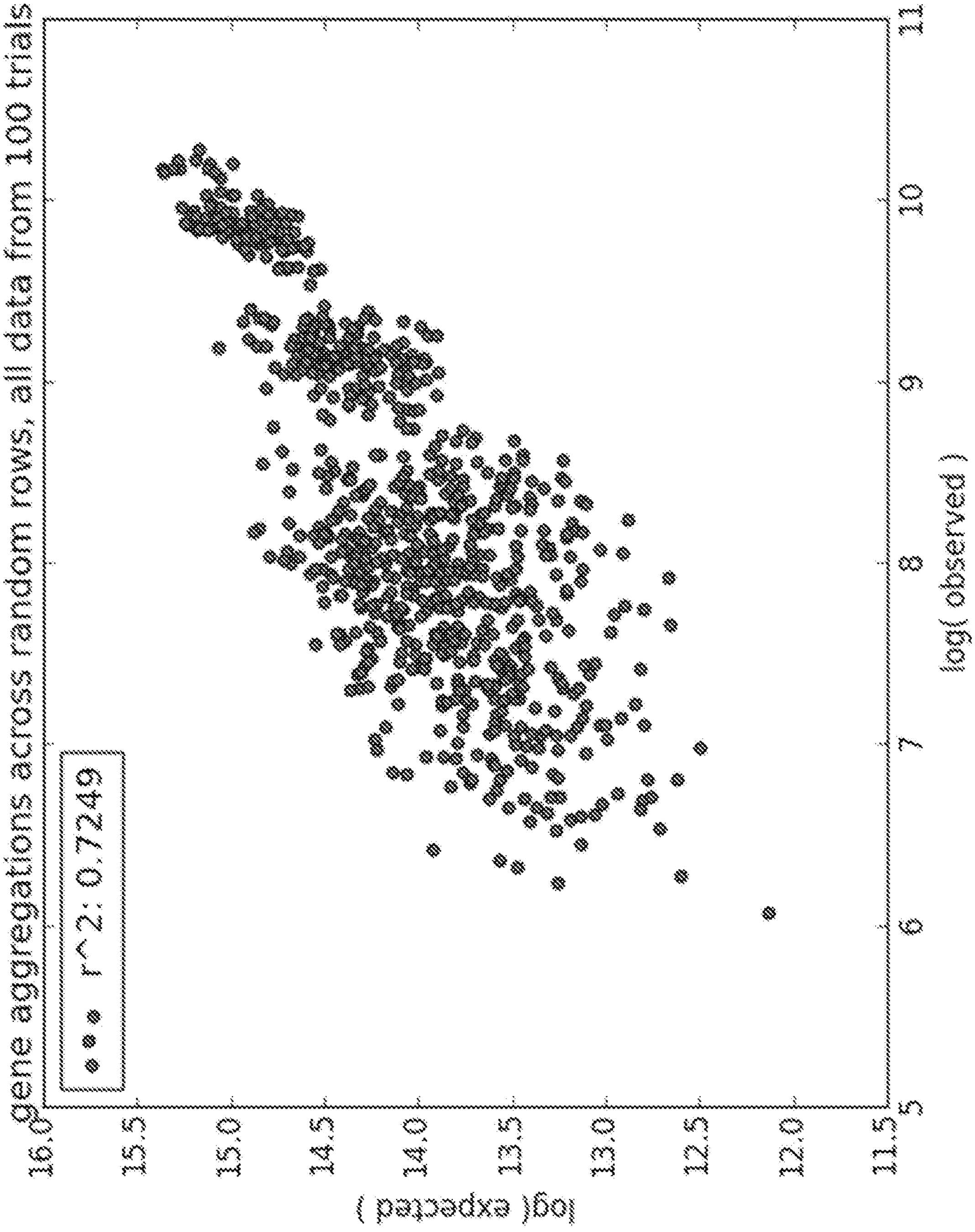
FIGS. 30-33 illustrate results of computational simulations where counts are aggregated across all genes from randomly chosen rows.
Figure 31:
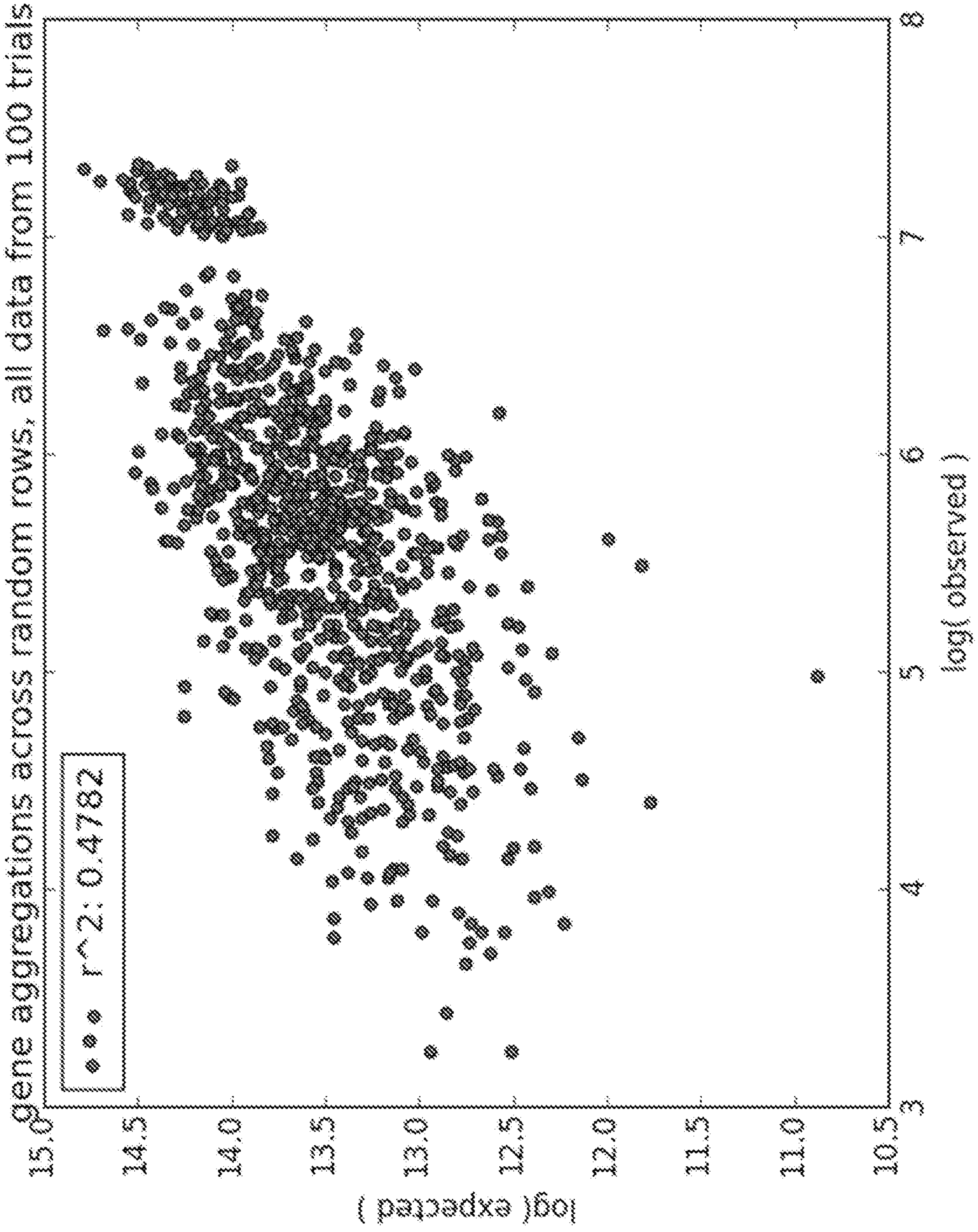
Figure 32:
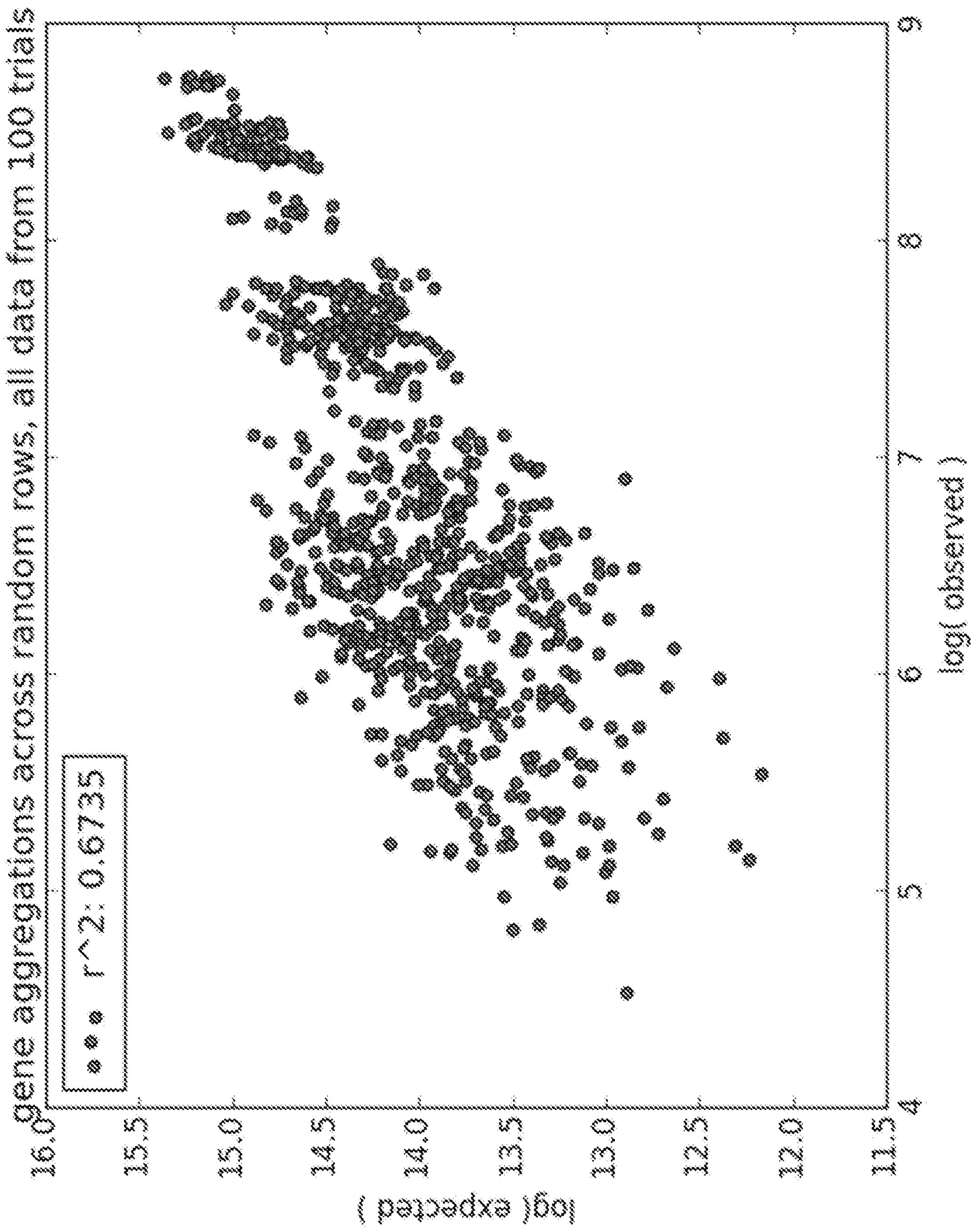
Figure 33:
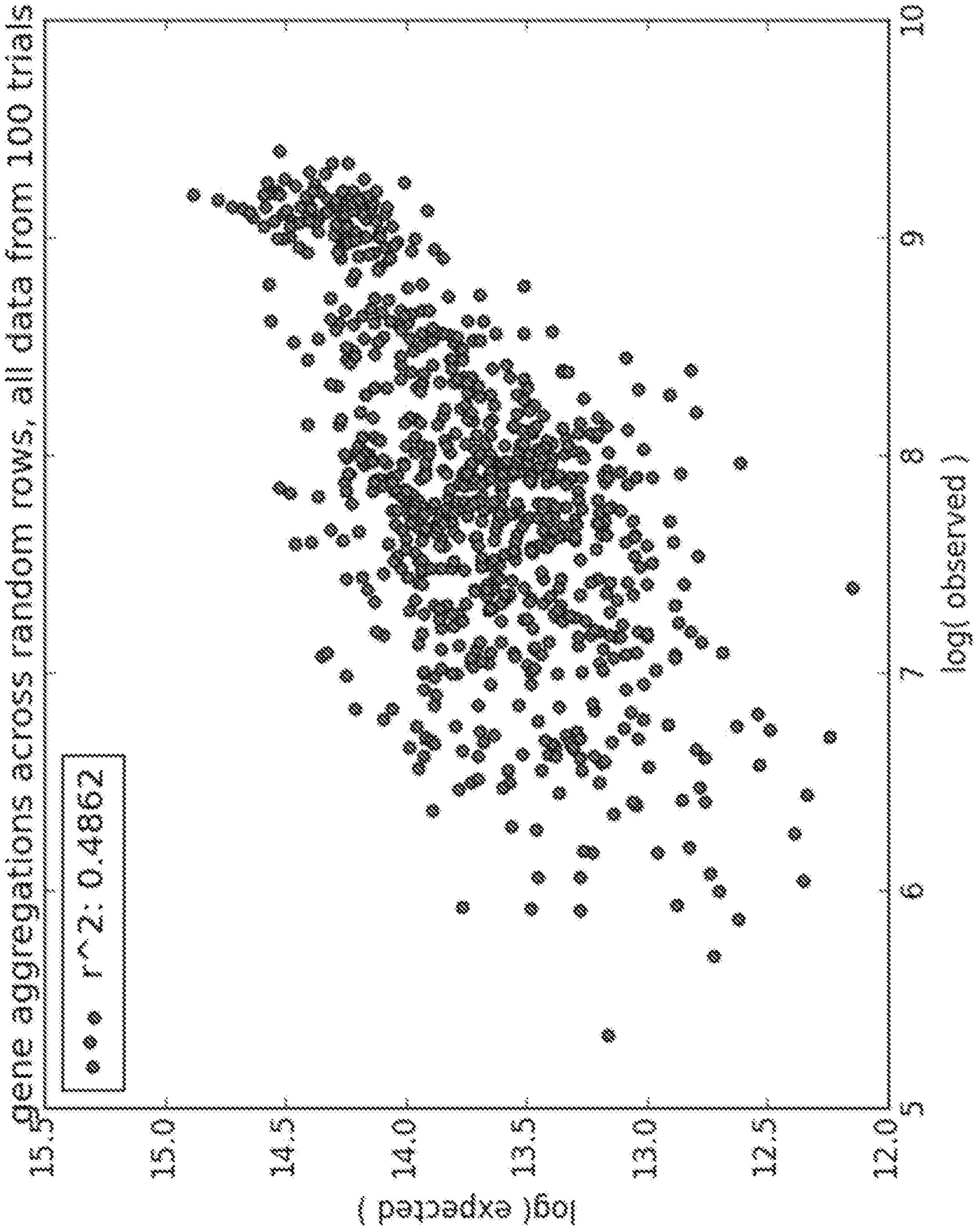

FIG. 29 is plot of expected counts versus observed counts for a predetermined set of probes under a range of dilution criteria for unPurified cDNA Low.

The same data can be used to computationally simulate the random setting, where counts are aggregated across all genes from randomly chosen rows, as described above for initial optimizations. Results for these simulations are presented in FIGS. 30-33.

The population of cells with a plurality of genomic sequence or perturbation conditions involves a plurality of cells and perturbations to be tested and measurements sampled to obtain meaningful data and to infer appropriate circuits. The number of genes perturbed, and how many are perturbed simultaneously (the order of the perturbation, pairs, triplets, etc.) varies. In a tissue with n cell types, the rarest present in m %, how many cells X do you need to sequence so that you have at least Y of the rarest subtype.

For example, ~500 cells ensures ≥95% chance of including ≥10 of each type, based on the following calculation (FIG. 34). Assume the most conservative scenario that of M cell subtypes (for example, 12), all but one having the lowest predicted proportion (for example, $p_{min}$=5%). Assuming that the Central Limit Theorem holds (a reasonable assumption when solving to detect at least 10 cells of each type) the number of cells of each type i, termed $T_i$, will distribute as $E[T_i]=N*p_{min}$, $STDV[T_i]=\sqrt{(N*p_{min}*(1-p_{min}))}$. The minimal N (total number of cells to profile) can be solved such that all (m−1) subtypes have at least n cells (the last, majority, subtype easily clears this threshold since its proportion is much higher). Applicants confirmed with simulation that the strategy conservatively holds in practice even for n<10, and take a. margin of additional (conservative) error, to allow for subsequent failed RNA-Seq experiments (<20-30%, depending on protocol).

Amplification may involve thermocycling or isothermal amplification (such as through the methods RPA or LAMP). Cross-linking may involve overlap-extension PCR or use of ligase to associate multiple amplification products with each other.

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of *E. coli* DNA polymerase, and reverse transcriptase. A preferred amplification method is PCR. In particular, the isolated RNA can be subjected to a reverse transcription assay that is coupled with a quantitative polymerase chain reaction (RT-PCR) in order to quantify the expression level of a sequence associated with a signaling biochemical pathway.

Detection of the gene expression level can be conducted in real time in an amplification assay. In one aspect, the amplified products can be directly visualized with fluorescent DNA-binding agents including but not limited to DNA intercalators and DNA groove binders. Because the amount of the intercalators incorporated into the double-stranded DNA molecules is typically proportional to the amount of the amplified DNA products, one can conveniently determine the amount of the amplified products by quantifying the fluorescence of the intercalated dye using conventional optical systems in the art. DNA-binding dye suitable for this application include SYBR green, SYBR blue, DAPI, propidium iodine, Hoechst, SYBR gold, ethidium bromide, acridines, proflavine, acridine orange, acriflavine, fluorcoumarin, ellipticine, daunomycin, chloroquine, distamycin D, chromomycin, homidium, mithramycin, ruthenium polypyridyls, anthramycin, and the like.

In another aspect, other fluorescent labels such as sequence specific probes can be employed in the amplification reaction to facilitate the detection and quantification of the amplified products. Probe-based quantitative amplification relies on the sequence-specific detection of a desired amplified product. It utilizes fluorescent, target-specific probes (e.g., TaqMan® probes) resulting in increased specificity and sensitivity. Methods for performing probe-based quantitative amplification are well established in the art and are taught in U.S. Pat. No. 5,210,015.

Sequencing may be performed on any high-throughput platform with read-length (either single- or paired-end) sufficient to cover both template and cross-linking event UID's. Methods of sequencing oligonucleotides and nucleic acids are well known in the art (see, e.g., WO93/23564, WO98/28440 and WO98/13523; U.S. Pat. Nos. 5,525,464; 5,202,231; 5,695,940; 4,971,903; 5,902,723; 5,795,782; 5,547,839 and 5,403,708; Sanger et al., Proc. Natl. Acad. Sci. USA 74:5463 (1977); Drmanac et al., Genomics 4:114 (1989); Koster et al., Nature Biotechnology 14:1123 (1996); Hyman, Anal. Biochem. 174:423 (1988); Rosenthal, International Patent Application Publication 761107 (1989); Metzker et al., Nucl. Acids Res. 22:4259 (1994); Jones, Biotechniques 22:938 (1997); Ronaghi et al., Anal. Biochem. 242:84 (1996); Ronaghi et al., Science 281:363 (1998); Nyren et al., Anal. Biochem. 151:504 (1985); Canard and Arzumanov, Gene 11:1 (1994); Dyatkina and Arzumanov, Nucleic Acids Symp Ser 18:117 (1987); Johnson et al., Anal. Biochem. 136:192 (1984); and Elgen and Rigler, Proc. Natl. Acad. Sci. USA 91(13):5740 (1994), all of which are expressly incorporated by reference).

The present invention may be applied to (1) single-cell transcriptomics: cDNA synthesized from mRNA is barcoded and cross-linked during in situ amplification, (2) single-cell proteomics: cDNA or DNA synthesized from RNA- or DNA-tagged antibodies of one or multiple specificities maps the abundance and distributions of different protein-antigens and (3) whole-tissue transcriptomic/proteomic mapping (molecular microscopy or VIPUR microscopy): using the frequency of cross-contamination between cells to determine their physical proximity, and via applications (1) single-cell transcriptomics and (2) single-cell proteomics, determining the global spatial distribution of mRNA, protein, or other biomolecules in a biological sample. This may be used, for example, to screen for anti-cancer/pathogen immunoglobulins (by analyzing co-localization of B cells and T cells within affected tissue) for immunotherapy.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO. 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

As used herein the term "variant" should be taken to mean the exhibition of qualities that differ, such as, but not limited to, genetic variations including SNPs, insertion deletion events, and the like.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid sequence by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y.

"Hybridization" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence.

As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. % homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p387). Examples of other software than may perform sequence comparisons include, but are not limited to, the BLAST package (see Ausubel et al., 1999 Short Protocols in Molecular Biology, 4th Ed.—Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174(2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result.

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine.

Hybridization can be performed under conditions of various stringency. Suitable hybridization conditions for the practice of the present invention are such that the recognition interaction between the probe and sequences associated with a signaling biochemical pathway is both sufficiently specific and sufficiently stable. Conditions that increase the stringency of a hybridization reaction are widely known and published in the art. See, for example, (Sambrook, et al., (1989); Nonradioactive In Situ Hybridization Application Manual, Boehringer Mannheim, second edition). The hybridization assay can be formed using probes immobilized on any solid support, including but are not limited to nitrocellulose, glass, silicon, and a variety of gene arrays. A preferred hybridization assay is conducted on high-density gene chips as described in U.S. Pat. No. 5,445,934.

For a convenient detection of the probe-target complexes formed during the hybridization assay, the nucleotide probes are conjugated to a detectable label. Detectable labels suitable for use in the present invention include any composition detectable by photochemical, biochemical, spectroscopic, immunochemical, electrical, optical or chemical means. A wide variety of appropriate detectable labels are known in the art, which include fluorescent or chemiluminescent labels, radioactive isotope labels, enzymatic or other ligands. In preferred embodiments, one will likely desire to employ a fluorescent label or an enzyme tag, such as digoxigenin, β-galactosidase, urease, alkaline phosphatase or peroxidase, avidin/biotin complex.

The detection methods used to detect or quantify the hybridization intensity will typically depend upon the label selected above. For example, radiolabels may be detected using photographic film or a phosphoimager. Fluorescent markers may be detected and quantified using a photodetector to detect emitted light. Enzymatic labels are typically detected by providing the enzyme with a substrate and measuring the reaction product produced by the action of the enzyme on the substrate; and finally colorimetric labels are detected by simply visualizing the colored label.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-(vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumarin 151); cyanine dyes; cyanosine; 4',6-diaminidino-2-phenylindole (DAPI); 5'5''-dibromopyrogallol-sulfonephthalein (Bromopyrogallol 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosine and derivatives; erythrosin B, erythrosine, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolla Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colorimetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., international patent application serial no. PCT/US2013/61182 filed Sep. 23, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, a detectable oligonucleotide tag may comprise one or more non-oligonucleotide detectable moieties. Examples of detectable moieties include, but are not limited to, fluorophores, microparticles including quantum dots (Empodocles, et al., Nature 399:126-130, 1999), gold nanoparticles (Reichert et al., Anal. Chem. 72:6025-6029, 2000), biotin, DNP (dinitrophenyl), fucose, digoxigenin, haptens, and other detectable moieties known to those skilled in the art. In some embodiments, the detectable moieties are quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique nucleotide sequence may be a nucleotide sequence that is different (and thus distinguishable) from the sequence of each detectable oligonucleotide tag in a plurality of detectable oligonucleotide tags. A unique nucleotide sequence may also be a nucleotide sequence that is different (and thus distinguishable) from the sequence of each detectable oligonucleotide tag in a first plurality of detectable oligonucleotide tags but identical to the sequence of at least one detectable oligonucleotide tag in a second plurality of detectable oligonucleotide tags. A unique sequence may differ from other sequences by multiple bases (or base pairs). The multiple bases may be contiguous or non-contiguous. Methods for obtaining nucleotide sequences (e.g., sequencing methods) are described herein and/or are known in the art.

In some embodiments, detectable oligonucleotide tags comprise one or more of a ligation sequence, a priming sequence, a capture sequence, and a unique sequence (optionally referred to herein as an index sequence). A ligation sequence is a sequence complementary to a second nucleotide sequence which allows for ligation of the detectable oligonucleotide tag to another entity which may comprise the second nucleotide sequence, e.g., another detectable oligonucleotide tag or an oligonucleotide adapter. A priming sequence is a sequence complementary to a primer, e.g., an oligonucleotide primer used for an amplification reaction such as but not limited to PCR. A capture sequence is a sequence capable of being bound by a capture entity. A capture entity may be an oligonucleotide which may comprise a nucleotide sequence complementary to a capture sequence, e.g. a second detectable oligonucleotide tag. A capture entity may also be any other entity capable of binding to the capture sequence, e.g. an antibody, hapten or peptide. An index sequence is a sequence which may comprise a unique nucleotide sequence and/or a detectable moiety as described above.

"Complementary" is a term which is used to indicate a sufficient degree of complementarity between two nucleotide sequences such that stable and specific binding occurs between one and preferably more bases (or nucleotides, as the terms are used interchangeably herein) of the two sequences. For example, if a nucleotide in a first nucleotide sequence is capable of hydrogen bonding with a nucleotide in second nucleotide sequence, then the bases are considered to be complementary to each other. Complete (i.e., 100%) complementarity between a first nucleotide sequence and a second nucleotide is preferable, but not required for ligation, priming, or capture sequences.

The present invention also relates to a computer system involved in carrying out the methods of the invention relating to both computations and sequencing.

A computer system (or digital device) may be used to receive, transmit, display and/or store results, analyze the results, and/or produce a report of the results and analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers).

In some embodiments, the computer system may comprise one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc.

A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users.

A machine readable medium which may comprise computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The subject computer-executable code can be executed on any suitable device which may comprise a processor, including a server, a PC, or a mobile device such as a smartphone or tablet. Any controller or computer optionally includes a monitor, which can be a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard, mouse, or touch-sensitive screen, optionally provide for input from a user. The computer can include appropriate software for receiving user instructions, either in the form of user input into a set of parameter fields, e.g., in a GUI, or in the form of preprogrammed instructions, e.g., preprogrammed for a variety of different specific operations.

The present invention also contemplates multiplex assays. The present invention is especially well suited for multiplex assays. For example, the invention encompasses use of a SureSelect$^{XT}$, SureSelect$^{XT2}$ and SureSelect$^{QXT}$ Target Enrichment System for Illumina Multiplexed Sequencing developed by Agilent Technologies (see, e.g., www.agilent.com/genomics/protocolvideos), a SeqCap EZ kit developed by Roche NimbleGen, a TruSeq® Enrichment Kit developed by Illumina and other hybridization-based target enrichment methods and kits that add sample-specific sequence tags either before or after the enrichment step a well as Illumina HiSeq, MiSeq and NexSeq, Life Technology Ion Torrent. Pacific Biosciences PacBio RSII, Oxford Nanopore MinIon, PromethIon and GridIon and other massively parallel Multiplexed Sequencing Platforms.

Although the present invention and its advantages have been described in detail, it should be understood that various changes, substitutions and alterations can be made herein without departing from the spirit and scope of the invention as defined in the appended claims.

Protocol

Description of Basic Protocol

Probe Library Generation

Each probe library has two groups of probes. One group is called "left probe," and the other "right probe." Each of the probes bind a short sequence on the target transcript (or cDNA, or target molecule) and the two binding sites are exactly right next to each other (juxtaposition probe set), so that once bound to target they can be ligated to given a single ligation product.

Figure 13:
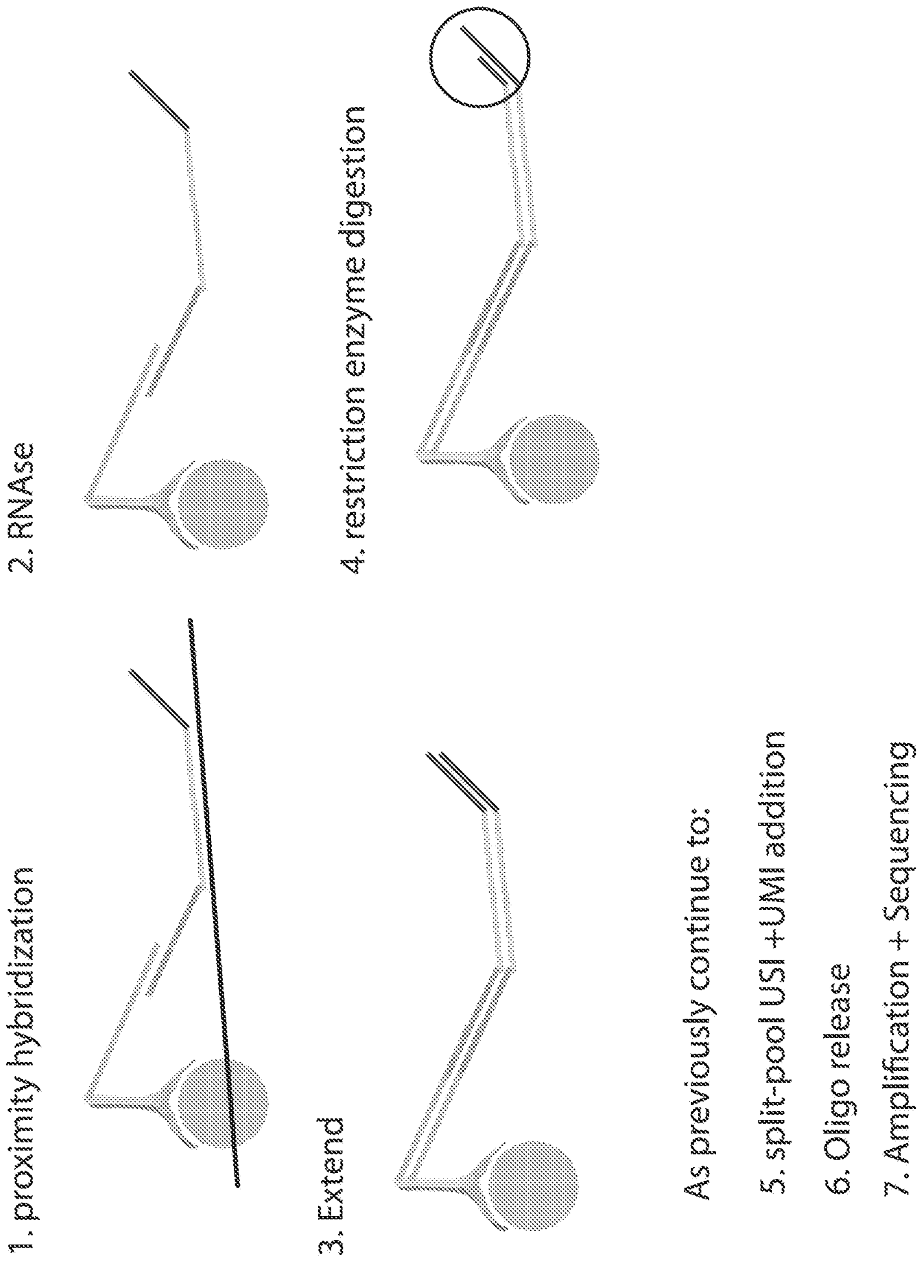
FIG. 13 illustrates measuring protein-RNA complexes using proximity hybridization. The Final oligonucleotide to sequence contains the UCI protein, UCI RNA and UMI+USI via split-pool ligation protocol.

Applicants synthesized the two groups probe separately, and one of the probes will have the measurement barcode, the random molecular index (UMI), and optionally the cell barcodes for single-cell experiments, as shown in FIG. 13.

The probe design in FIG. 13 is just one group of the probe, in the figure it will be the left side probe, given the 5'-3' direction. Applicants generate the probe through performing Klenow extension synthesis followed by lamda exonuclease digestion. In detail, Oligo 1 is first synthesized, containing the Universal adapter, Cell label, UMI, SMRI, and a LK (linker) region, followed by the synthesis of Oligo 2, the complementary sequence.

Figure 14:
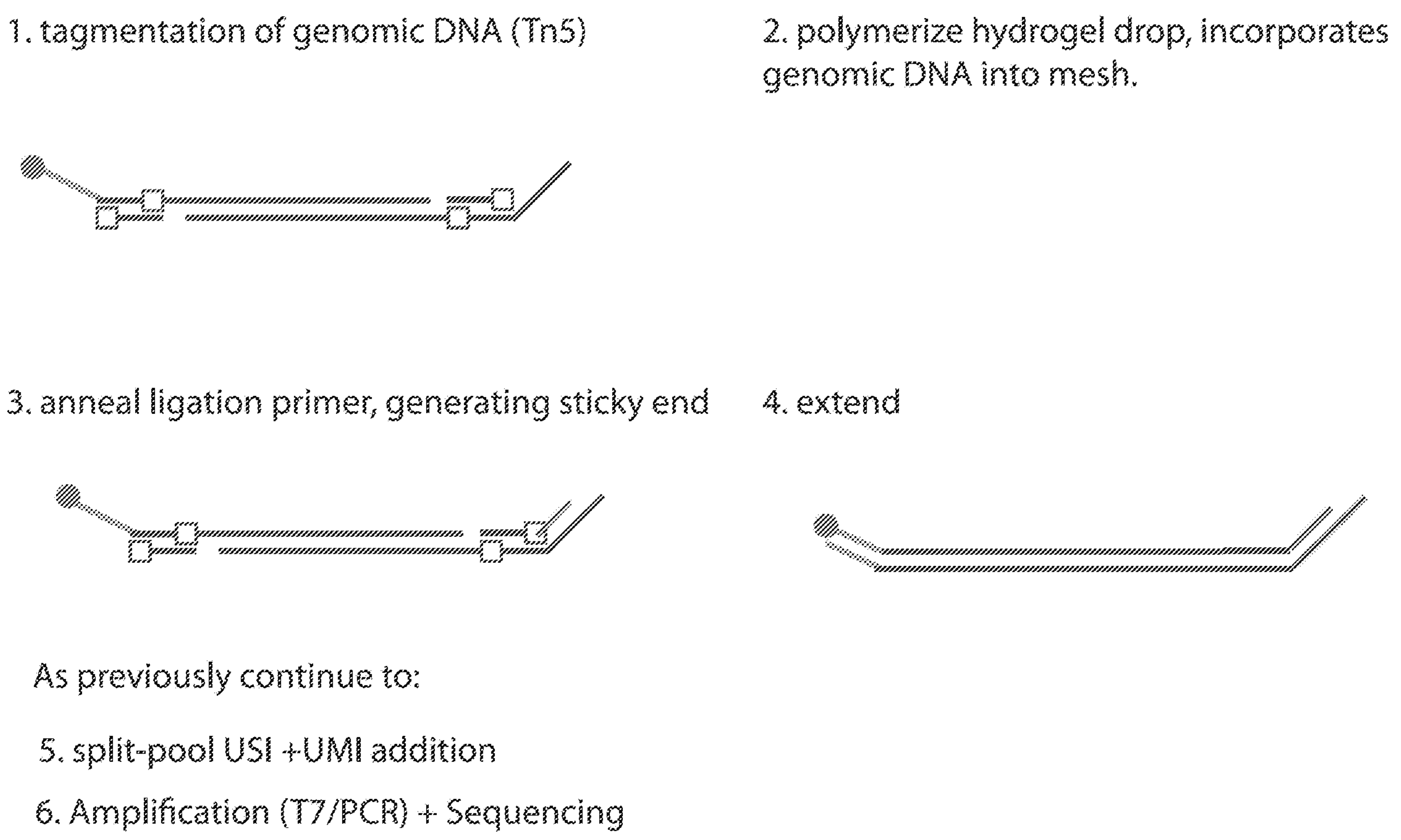
FIG. 14 illustrates high throughput single-cell ATAC-seq.
Figure 15:
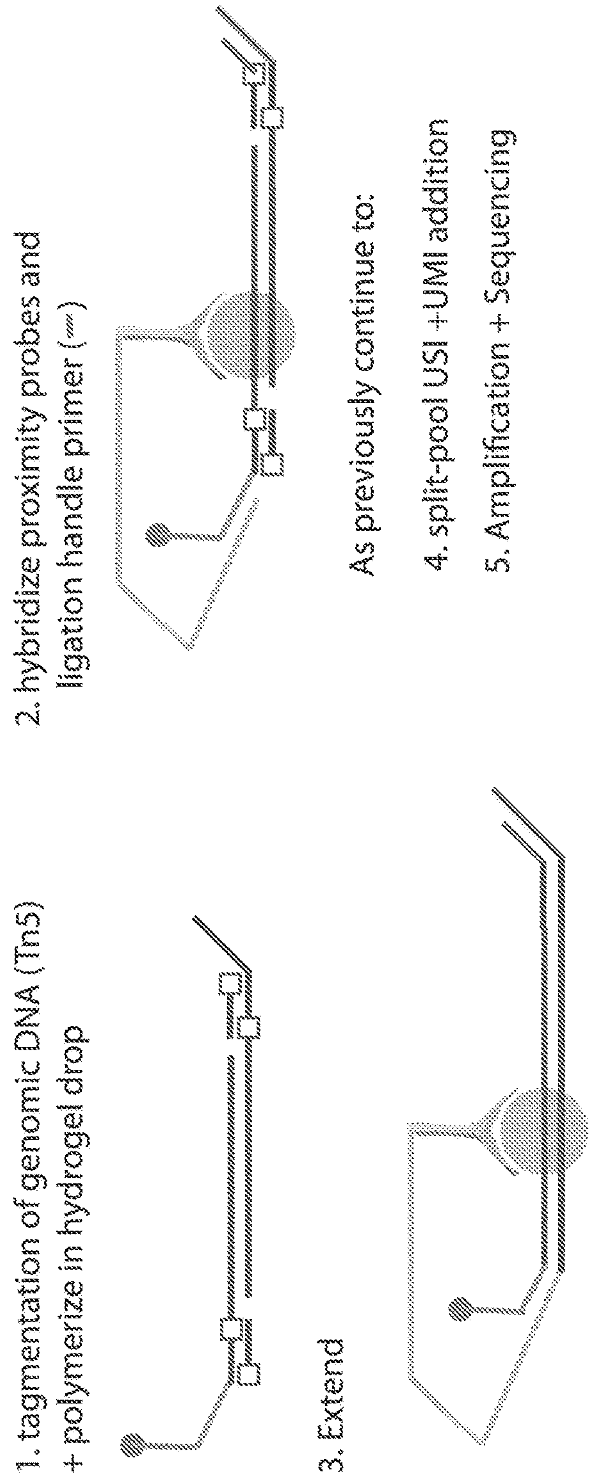
FIG. 15 illustrates high throughput single-cell measuring protein-DNA complexes.
Figure 16:
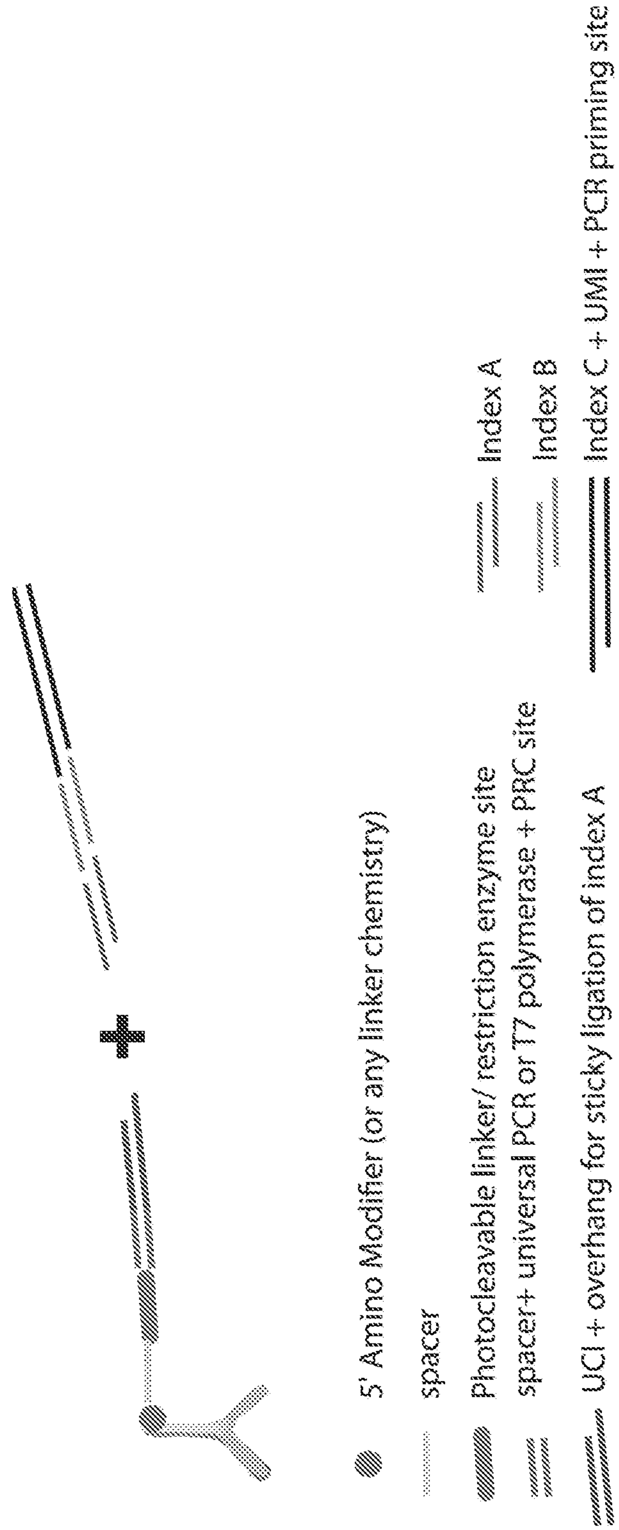
FIG. 16 illustrates staining with an antibody bound to an oligonucleotide label and performing split-pool ligation with an Index C containing a UMI in index C such that sequencing starts with a random region (improves cluster detection) and ligation primer is no longer separately added, but pre hybridized before staining.
Figure 17:
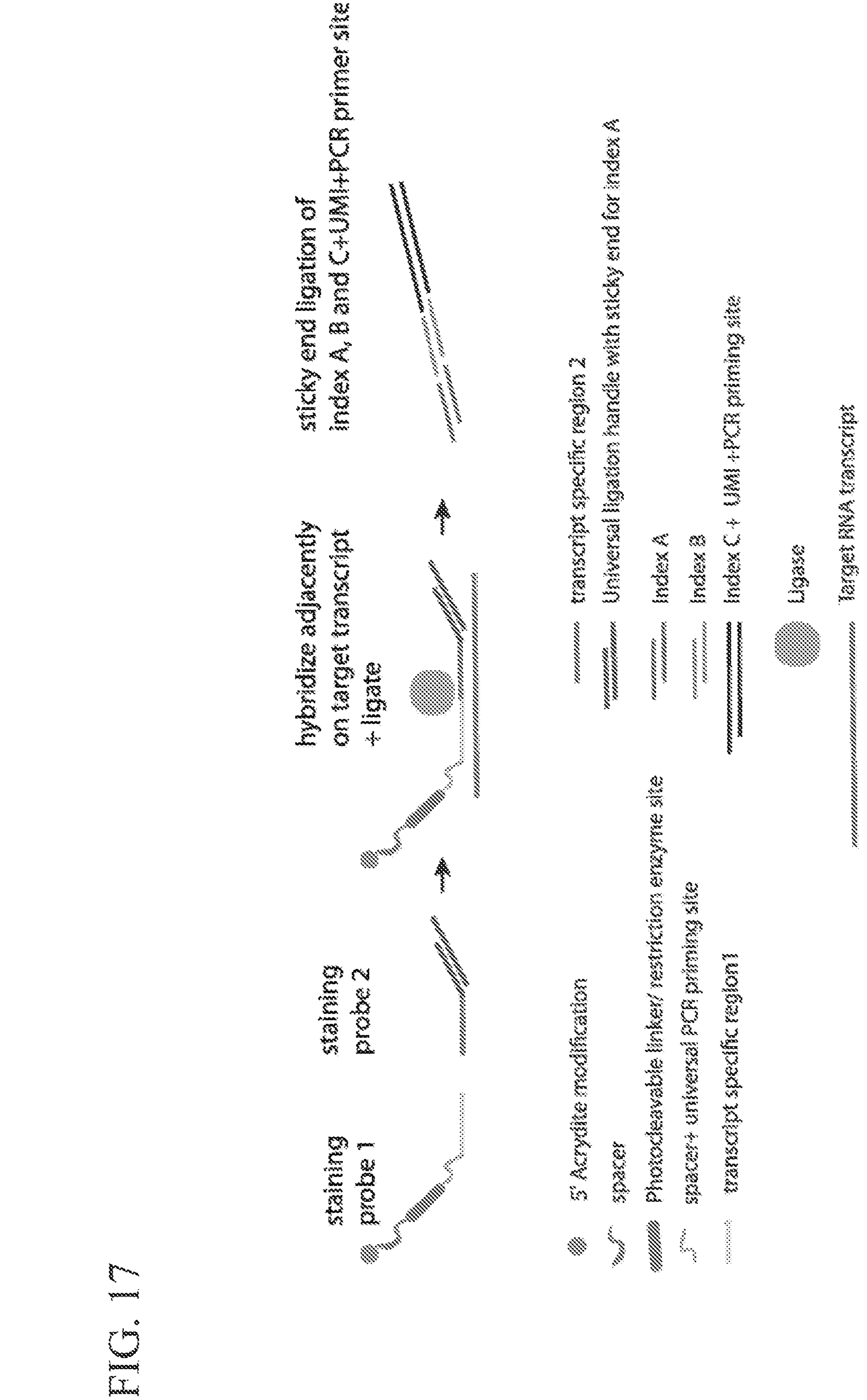
FIG. 17 illustrates alternative embodiments of measuring RNA levels.
Figure 19:
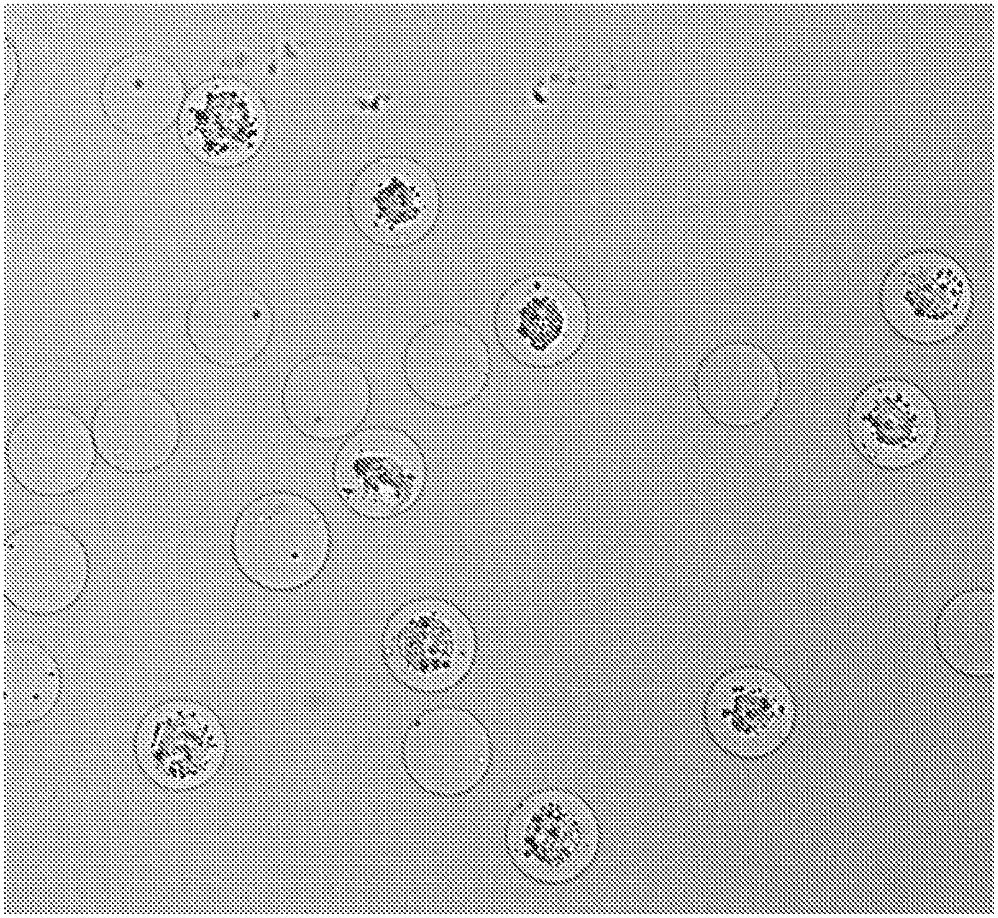
FIG. 19 illustrates a brightfield microscopy image showing hydrogel droplet encapsulated cells with magnetic particles embedded into the droplets to enable magnetic separation, aiding in clean up and washing steps in multiple reactions. Greatly enhances automation and therefore throughput.
Figure 20:
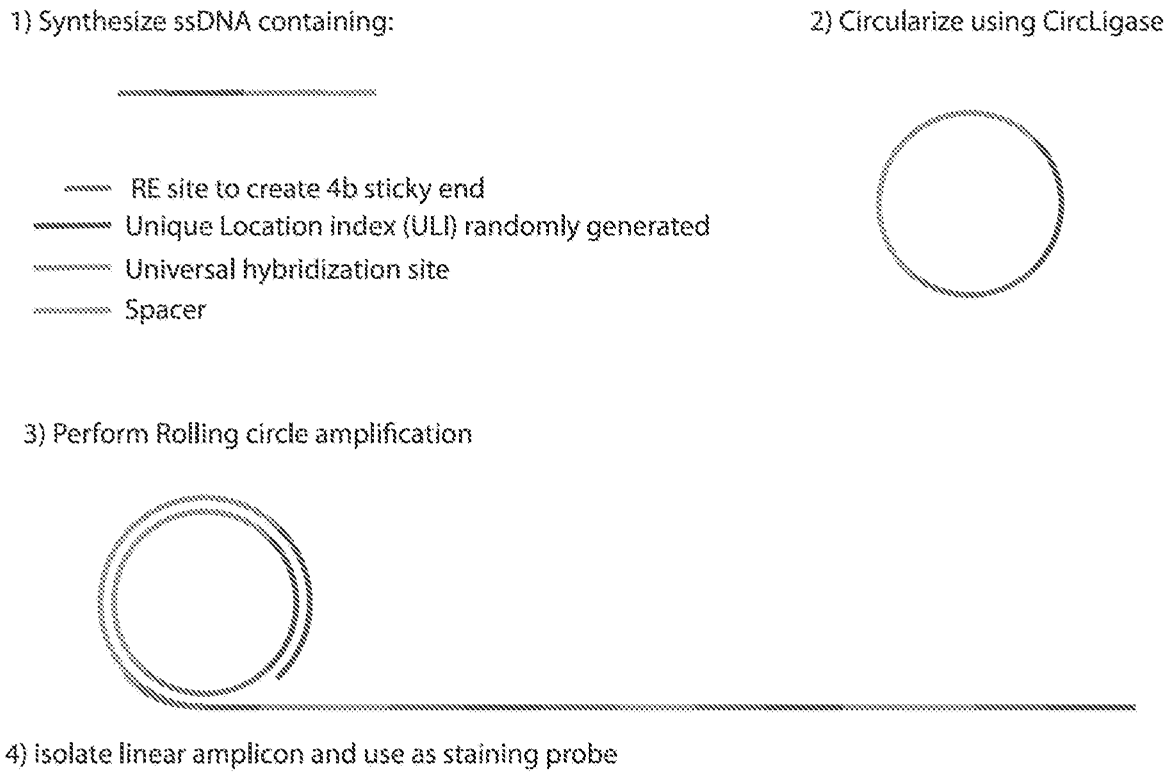
FIG. 20 illustrates a novel probe for detection of complexes consisting of more than 2 cellular constituents at the same time. The probe includes a Unique Location Identifier (ULI). It can be constructed by rolling circle amplification.
Figure 21:
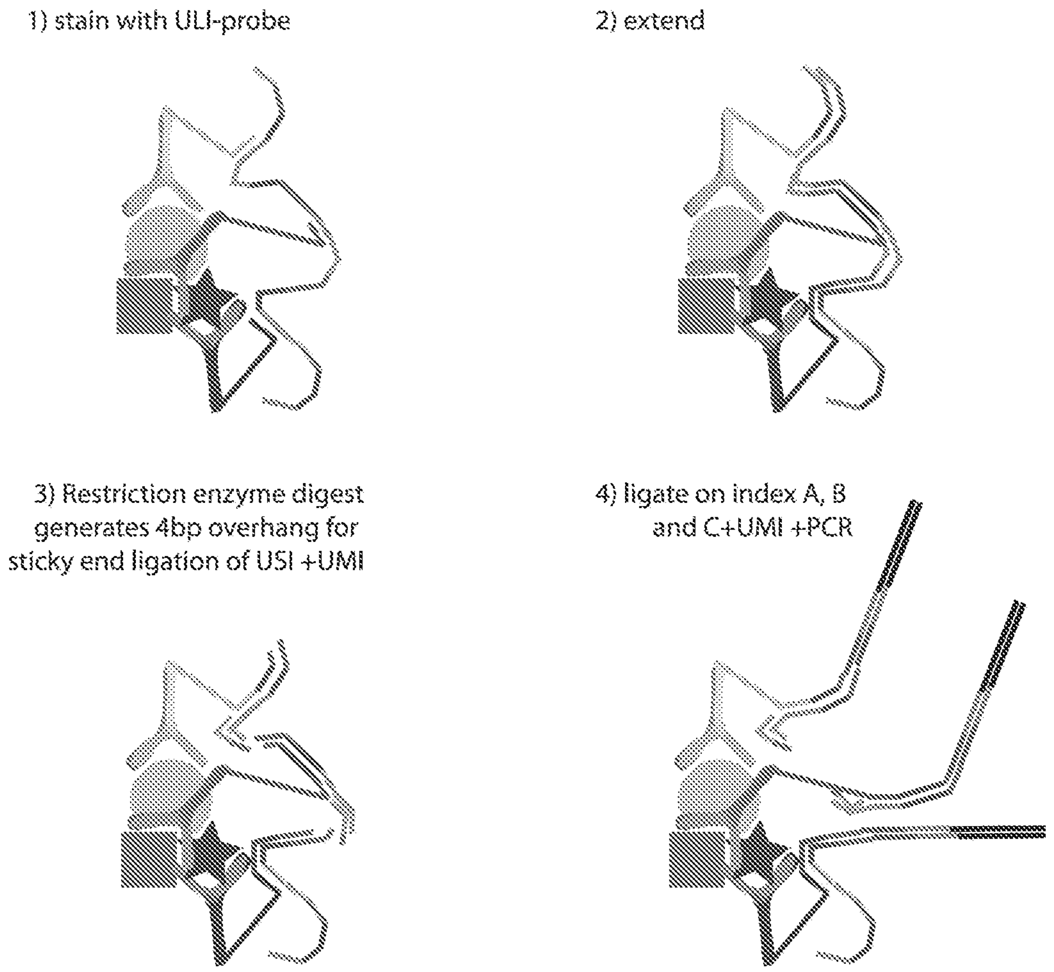
FIG. 21 illustrates the overall scheme to measure the proximity of 3 or more proteins, RNA or DNA molecules. The hybridization sequence of the ligand bound oligo binds to the complementary hybridization site on the ULI probe. By extension, each ligand bound oligo incorporates the same ULI. Restriction enzyme digestion generates a 4 bp overhang. Sticky end ligation is used to attach a USI+UMI.
Figure 22:
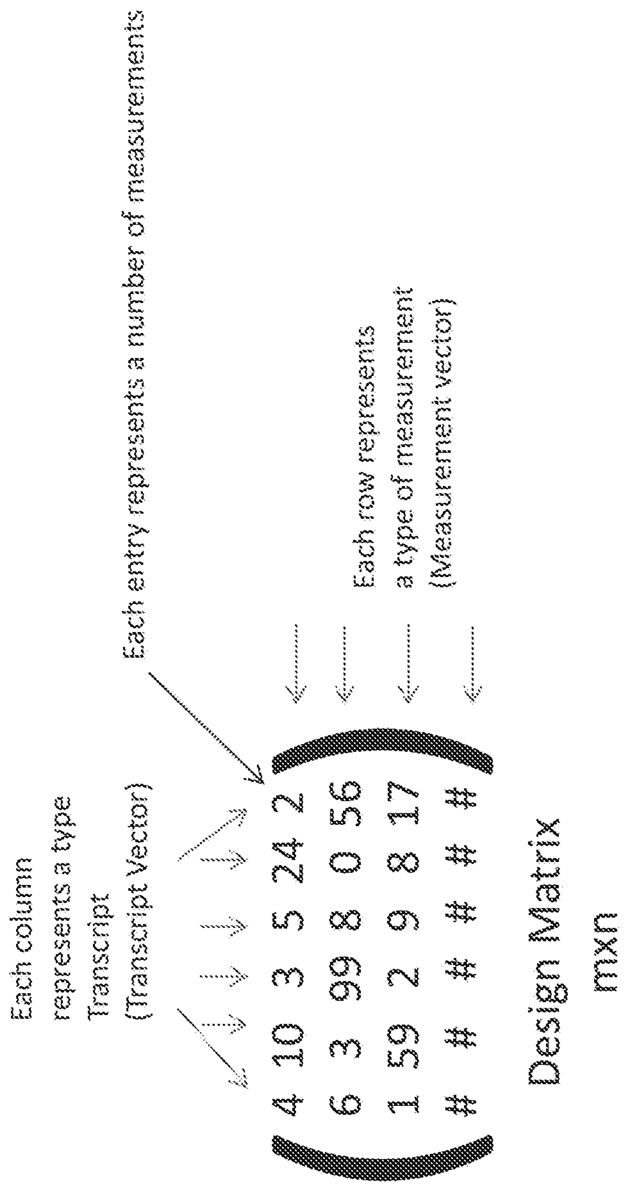
FIG. 22 is an illustrative example of a Design Matrix according to aspects of the present invention.
Figure 23:
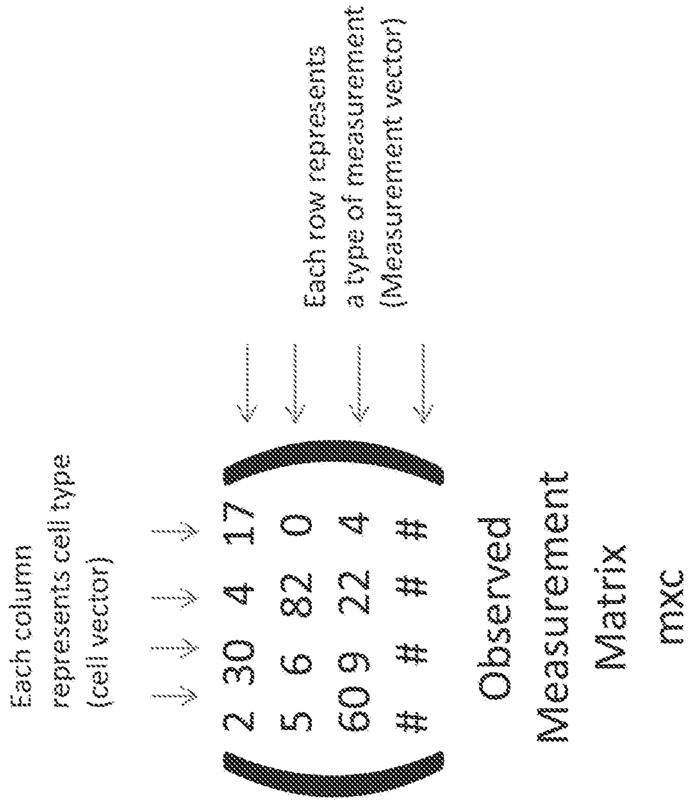
FIG. 23 is an illustrative example of an Observed Measurement Matrix according to aspects of the present invention.
Figure 24:
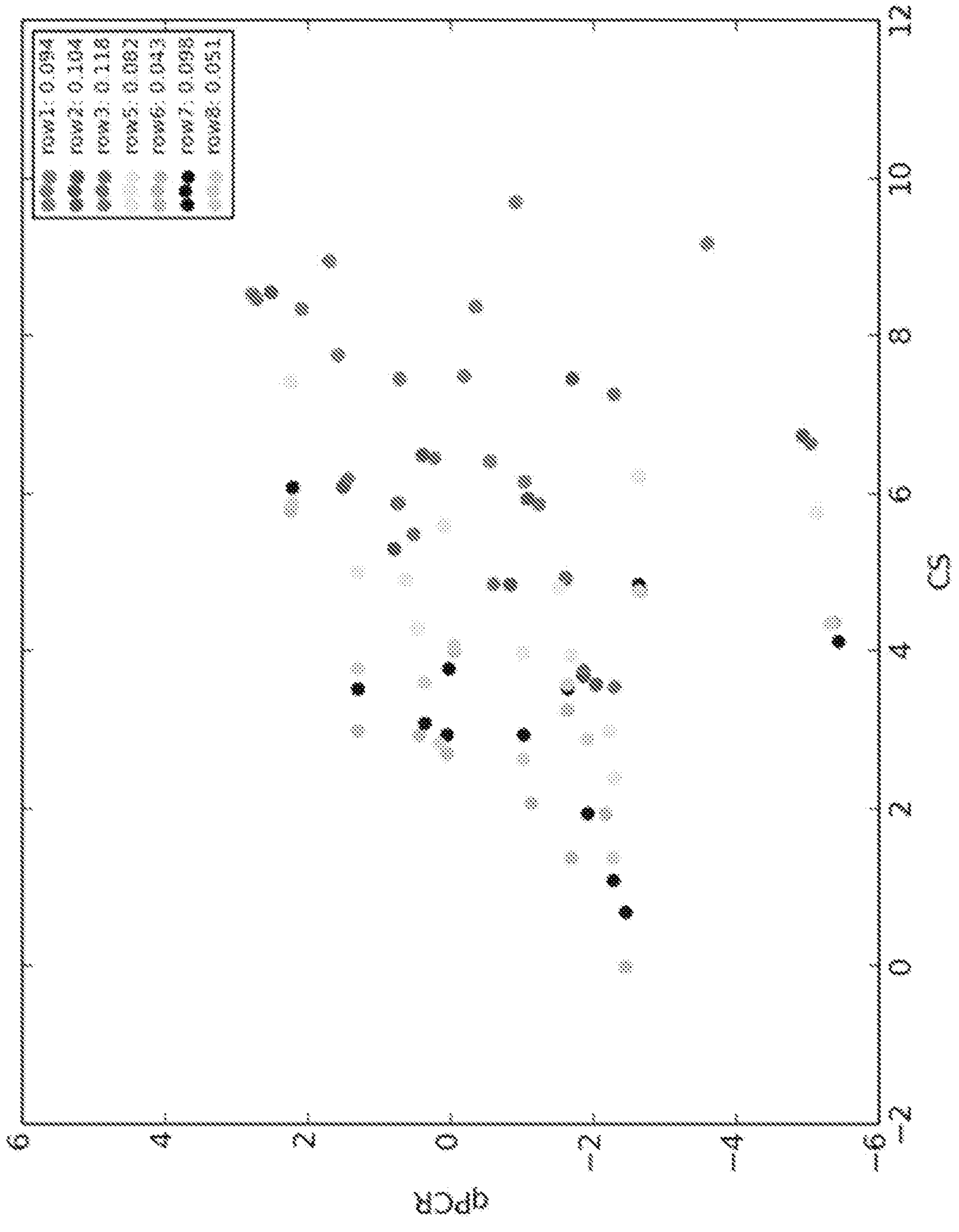
FIG. 24 is a plot of expected counts versus observed counts for a predetermined set of probes under certain dilution criteria.
Figure 25:
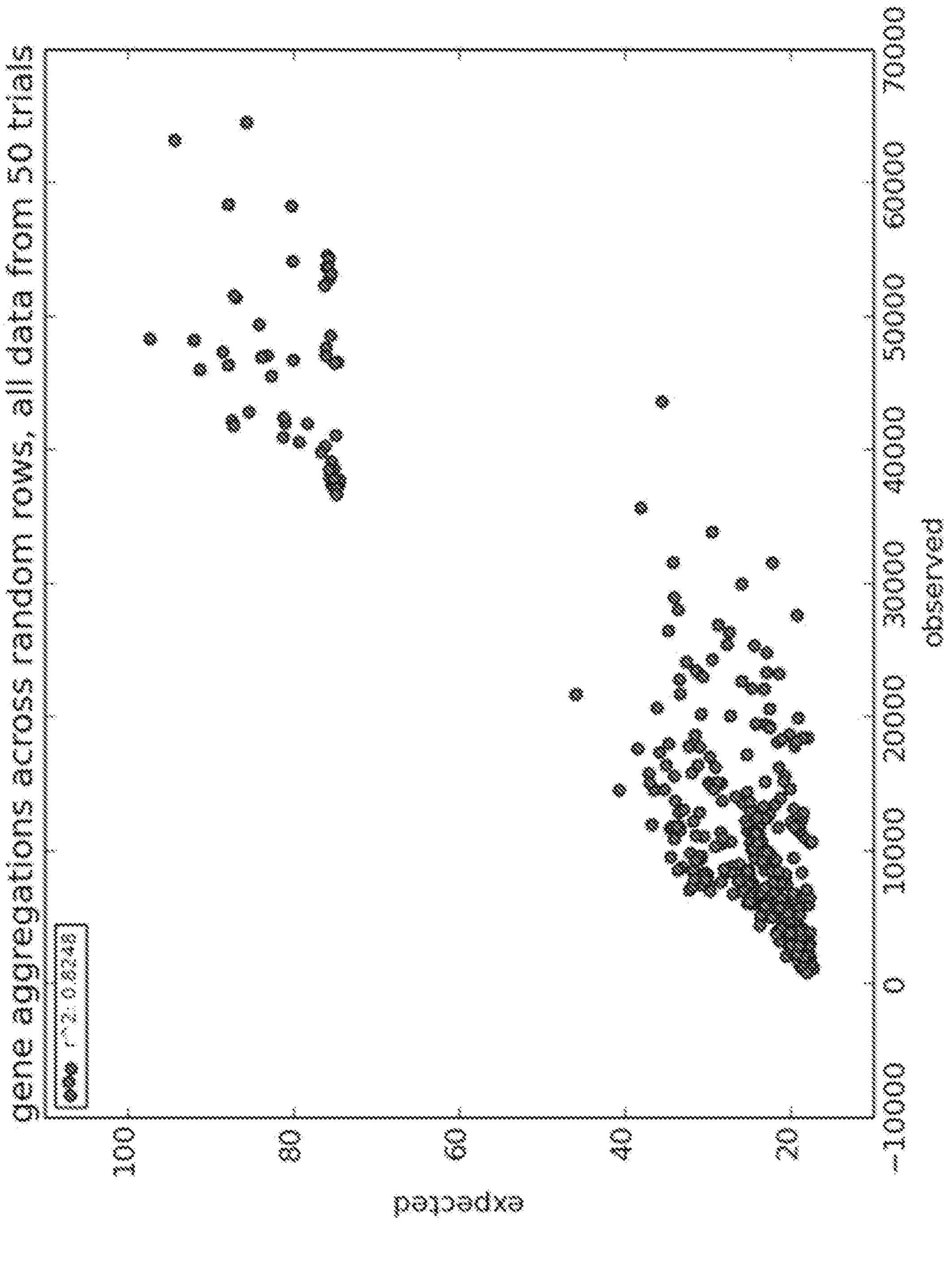
FIG. 25 is a plot of gene aggregations (observed versus expected) across random rows of a measurement vector for a 50 trial-experiment.
Figure 26:
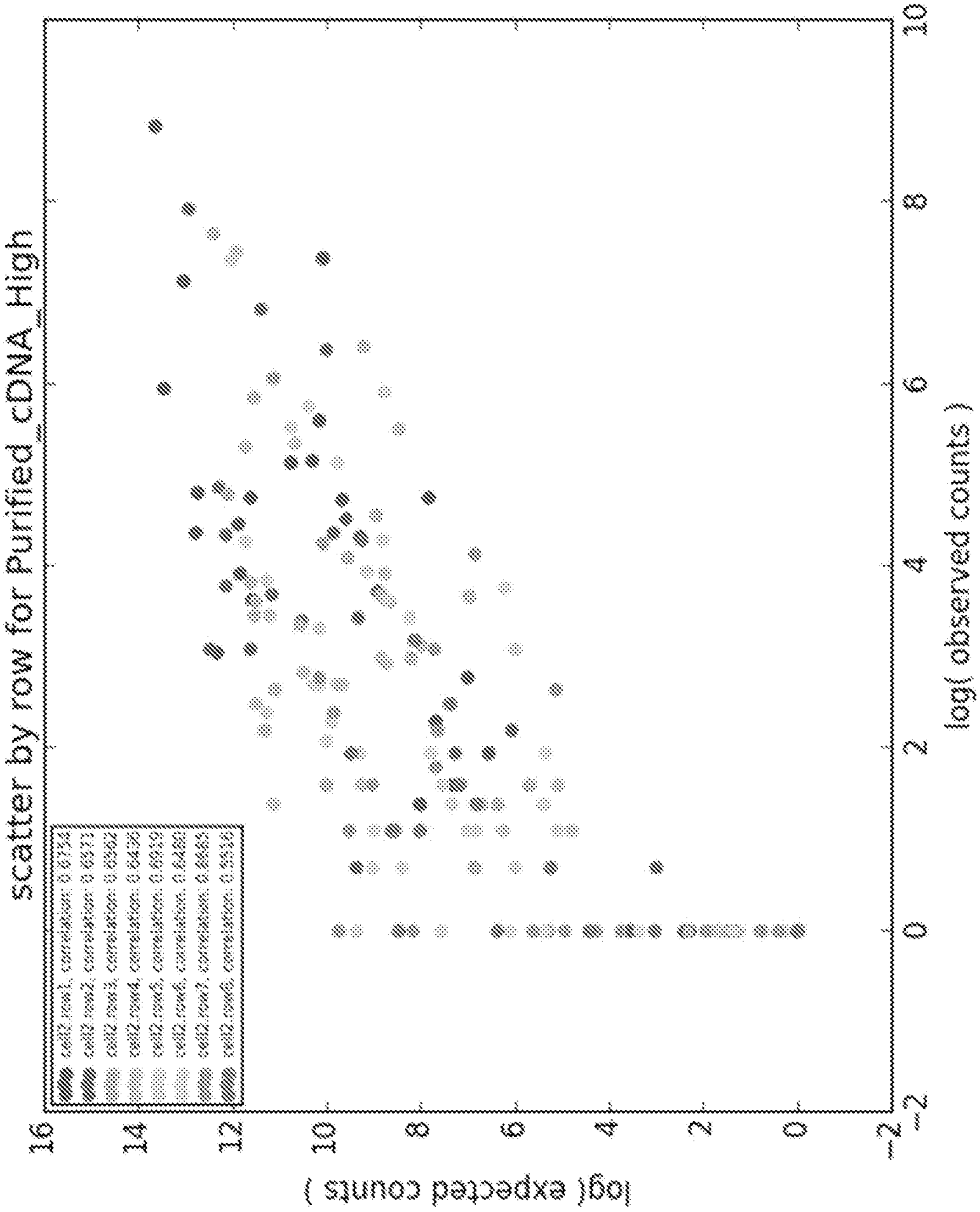
FIG. 26 is plot of expected counts versus observed counts for a predetermined set of probes under certain dilution criteria for Purified cDNA High.

The left probe combined with the right side probe will be able to bind specifically to the designed location in the target transcript. Applicants then ligate the two probes to form amplification-ready product. This is followed by amplification to add on sequencing adapter. The amplified probes are then purified, quantified, and subjected to next-generation sequencing and analysis, as shown in FIG. 14.

Detailed Experimental Implementation for Bulk RNA

1. Extract RNA from K562 cells (K562 is a human immortalised myelogenous leukemia cell line)
2. Prepare cDNA by synthesis, using the RNA as template
3. Split part for qPCR and RNA-seq (as a reference control)
4. Split part for probe binding/ligation in the compressive sensing experiment
5. Synthesize Left and Right Probe and Generate Probe Library Mix (1) Synthesize Oligo 1 with the adapter and barcode, and linker region (2) Synthesize Oligo 2 with the complementary sequence to the linker region and gene-specific probe (3) Anneal Oligo 1 and Oligo 2, and perform Klenow extension to synthesize the complete left side probe. The left side of the probe is either purified by column or used directly without further purification.

(4) Synthesize Oligo 3 with the right side gene-specific probe sequence, and then phosphorylate the right side probe with T4 Polynucleotide Kinase to phosphorylate the 5' end of the oligo to render it ligation-ready (5) Mix probes according to the design matrix to generate a probe library mix with both left and right probe.

6. Hybridize the probe library to the cDNA sample using a slow ramping protocol, where the mix is incubated at 95 °C for 5 minutes, then gradually cooled down to room temperature (25 °C). The annealed mixture containing left and right probes bound to the cDNA molecules are then ligated using Taq ligase to generate the ligation products at 45 °C for 2 hours, and the enzymatic activity is heat-inactivated at 65 °C for 20 minutes.

A control reaction where the probe library mixture is directly ligated with T7 DNA ligase without the addition of cDNA is also performed to obtain the abundance of the probe sets within the library. The ligation step is performed in a similar set-up except cDNA input is substituted with water, and ligation reaction is carried out at room temperature (25 °C) for 2 hours.

7. Amplify the ligation product using the library-amplification primer, which will also add the next-generation sequencer adapter to complete sequencing-ready library construction. The amplified is purified and size-selected between 200-300 bp and quantified.

Experimental Design for Implementation for Single Cell Sample

Each cell is captured and encapsulated in hydrogel droplet, which contains one side of the probe. These single-cell containing droplets are then lysed to allow initial hybridization, barcoded uniquely. Then, the other side of the probe will be added to the system to allow hybridization, ligation, and amplification. The final product are then purified and sequenced (or quantified/detected in other means), and subject to data analysis.

From Genetic Interactions to Molecular Interactions

Analyzing and determining genetic interactions can be used for dissection cellular circuitry. Results obtained using the method of the invention may be combined with further methods in order to probe molecular pathways. This may be achieved by using further perturbation assays (e.g. for validation purposes), by combining with complementary experiments in animal models (e.g. a Cas9 mouse or cell lines derived therefrom), including further genetic, biochemical or cellular testing. The systematic, sparsity-based approach may also be combined with 'knowledge-based' (informed) approaches, based on previously identified molecular interactions, such as known components of a given metabolic pathway.

The method of the invention may also be used to identify groups of cells based on their molecular profiling. The method of the invention may be used to identify possible target for therapeutics efforts.

The method of the invention may also be used to dissect cellular circuitry in relation with a spatial and/or temporal approach. For examples, the cells in the population may be synchronized with respect to their cell cycling.

Screening Methods

The present invention also envisions screening methods involving the herein described embodiments.

In one embodiment, the screening involves a pooled, loss-of-function genetic screening approach suitable for both positive and negative selection that uses a genome-scale lentiviral single-guide RNA (sgRNA) library (see, e.g., Wang et al., Science. 2014 Jan. 3; 343(6166):80-4. doi: 10.1126/science.1246981. Epub 2013 Dec. 12). Briefly, sgRNA expression cassettes were stably integrated into the genome, which enabled a complex mutant pool to be tracked by massively parallel sequencing. A library containing 73,000 sgRNAs was used to generate knockout collections and performed screens in two human cell lines. A screen for resistance to the nucleotide analog 6-thioguanine identified all expected members of the DNA mismatch repair pathway, whereas another for the DNA topoisomerase II (TOP2A) poison etoposide identified TOP2A, as expected, and also cyclin-dependent kinase 6, CDK6. A negative selection screen for essential genes identified numerous gene sets corresponding to fundamental processes. sgRNA efficiency is associated with specific sequence motifs, enabling the prediction of more effective sgRNAs. See also Chen et al., Genome-wide CRISPR Screen in a Mouse Model of Tumor Growth and Metastasis, Cell (2015). DOI: 10.1016/j.cell.2015.02.038.

The activator screen method of Konermann et al., Nature (2014) doi:10.1038/nature14136 may be applied to the present invention. Systematic interrogation of gene function requires the ability to perturb gene expression in a robust and generalizable manner. Konermann et al. describes structure-guided engineering of a CRISPR-Cas9 complex to mediate efficient transcriptional activation at endogenous genomic loci. Konermann et al. used these engineered Cas9 activation complexes to investigate single-guide RNA (sgRNA) targeting rules for effective transcriptional activation, to demonstrate multiplexed activation of ten genes simultaneously, and to upregulate long intergenic non-coding RNA (lincRNA) transcripts. Konermann et al. also synthesized a library consisting of 70,290 guides targeting all human RefSeq coding isoforms to screen for genes that, upon activation, confer resistance to a BRAF inhibitor. The top hits included genes previously shown to be able to confer resistance, and novel candidates were validated using individual sgRNA and complementary DNA overexpression. A gene signature based on the top screening hits correlated with a gene expression signature of BRAF inhibitor resistance in cell lines and patient-derived samples. These results collectively demonstrate the potential of Cas9-based activators as a powerful genetic perturbation technology.

The mouse of Platt et al., Cell. 2014 Oct. 9; 159(2):440-55. doi: 10.1016/j.cell.2014.09.014. Epub 2014 Sep. 25 may also be contemplated in the present invention. Platt et al. established a Cre-dependent Cas9 knockin mouse and demonstrated in vivo as well as ex vivo genome editing using adeno-associated virus (AAV)-, lentivirus-, or particle-mediated delivery of guide RNA in neurons, immune cells, and endothelial cells. Using these mice, Platt et al. simultaneously modeled the dynamics of KRAS, p53, and LKB1, the top three significantly mutated genes in lung adenocarcinoma. Delivery of a single AAV vector in the lung generated loss-of-function mutations in p53 and Lkb1, as well as homology-directed repair-mediated Kras(G12D) mutations, leading to macroscopic tumors of adenocarcinoma pathology. In certain embodiments, Cre-dependent Cas9 knockin mice or any Cre-dependent CRISPR enzyme mouse (e.g., Cpf1) may be crossed with tissue-specific Cre transgenic mice as described herein.

Genetic screens infer gene function in mammalian cells, but it has remained difficult to assay complex phenotypes—such as transcriptional profiles—in large screens. Applicants have developed Perturb-seq. Perturb-seq advantageously combines single cell RNA-seq and CRISPR based perturbations identified by unique polyadenylated barcodes to perform many such assays in a pooled experiment. Applicants demonstrate Perturb-seq by analyzing 200,000 cells across three screens: transcription factors involved in the response of dendritic cells to LPS, transcription factors bound in K562 cells, and cell cycle regulators in the same cell line. Perturb-seq accurately identifies individual gene targets, gene signatures, and cell states affected by each perturbation and their genetic interactions. The individual gene target predictions were validated by their known functions and ChIP-Seq. Applicants advantageously posit new functions for regulators affecting cell differentiation, the anti-viral response, and mitochondrial function during immune activation. Perturb-seq can be flexibly applied to diverse cell metadata, to customize design and scope of pooled genomic assays.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1: Combinatorial Genetic Perturbations in Mouse Cells Using CRISPR-Cas Mediated Multiple Gene Activation A pooled perturbation assay is performed in mouse cells, using a CRISPR-Cas system, as described in Shalem O., Sanjana N E., Zhang F. High-throughput functional genomics using CRISPR-Cas9. Nat Rev Genet. May; 16(5):299-311. (2015). doi:10.1038/nrg3899. Epub 2015 Apr. 9. The pooled assay is designed to reach MOI values of 3-4, corresponding to orders 3-4 of genetic perturbations, concerning a total of 7,000 target genomic loci.

An sgRNA library is designed as described in Sanjana, N. E., Shalem, O. & Zhang, F. Improved vectors and genome-wide libraries for CRISPR screening. *Nat Methods.* 11, 783-784, doi:10.1038/nmeth.3047 (2014); Konermann, S., Brigham, M. D., Trevino, A. E., Joung, J., Abudayyeh, O. O., Barcena, C., Hsu, P. D., Habib, N., Gootenberg, J. S., Nishimasu, H., Nureki, O. & Zhang, F. Genome-scale transcriptional activation by an engineered CRISPR-Cas9 complex. *Nature.* 517, 583-588, doi:10.1038/nature14136 (2015). PMCID:4420636.

Effects of the genetic perturbations are determined in terms of single-cell RNA profiling. Said RNA profiling is carried out using droplet technology (Drop-Seq technique, as described in Macosko, E. Z., Basu, A., Satija, R., Nemesh, J., Goldman, M., Tirosh, I., Bialas, A. R., Kamitaki, N., Sanes, J. R., Weitz, D. A., Shalek, A. K., Regev, A. & McCarroll, S. A. Highly Parallel Genome-wide Expression Profiling of Individual Cells Using Nanoliter Droplets. Cell. 2015 May 21; 161(5):1202-14. doi:10.1016/j.cell.2015.05.002. PMCID:4481139; or Klein, A. M., Mazutis, L., Akartuna, I., Tallapragada, N., Veres, A., Li, V., Peshkin, L., Weitz, D. A., Kirschner, M. W. Droplet barcoding for single-cell transcriptomics applied to embryonic stem cells. Cell. 2015 May 21; 161(5):1187-201. doi:10.1016/j.cell.2015.04.044. PMCID:4441768).

Example 2: Combinatorial Genetic Perturbations in Human Cells Using CRISPR-Cas Mediated Multiple Gene Knock-Outs A pooled perturbation assay is performed in a human using a CRISPR-Cas system, as described in Shalem O., Sanjana N E., Zhang F. High-throughput functional genomics using CRISPR-Cas9. Nat Rev Genet. May; 16(5):299-311. (2015). doi: 10.1038/nrg3899. Epub 2015 Apr. 9. The pooled assay is designed to reach MOI values of 2-3, corresponding to orders 2-3 of genetic perturbations regarding a total of 10,000 target genomic loci.

An sgRNA library is designed as described in Sanjana, N. E., Shalem, O. & Zhang, F. Improved vectors and genome-wide libraries for CRISPR screening. *Nat Methods.* 11, 783-784, doi:10.1038/nmeth.3047 (2014); Shalem, O., Sanjana, N. E., Hartenian, E., Shi, X., Scott, D. A., Mikkelsen, T. S., Heckl, D., Ebert, B. L., Root, D. E., Doench, J. G. & Zhang, F. Genome-scale CRISPR-Cas9 knockout screening in human cells. Science. 343, 84-87, doi:10.1126/science.1247005 (2014). PMCID:4089965; Shalem, O., Sanjana, N. E. & Zhang, F. High-throughput functional genomics using CRISPR-Cas9. Nat Rev Genet. 16, 299-311, doi:10.1038/nrg3899 (2015).

Effects of the genetic perturbations are determined in terms of single-cell RNA profiling. Said RNA profiling is carried out using droplet technology (Drop-Seq technique, as described in Macosko, E. Z., Basu, A., Satija, R., Nemesh, J., Goldman, M., Tirosh, I., Bialas, A. R., Kamitaki, N., Sanes, J. R., Weitz, D. A., Shalek, A. K., Regev, A. & McCarroll, S. A. Highly Parallel Genome-wide Expression Profiling of Individual Cells Using Nanoliter Droplets. Cell. 2015 May 21; 161(5):1202-14. doi: 10.1016/j.cell.2015.05.002. PMCID:4481139; or Klein, A. M., Mazutis, L., Akartuna, I., Tallapragada, N., Veres, A., Li, V., Peshkin, L., Weitz, D. A., Kirschner, M. W. Droplet barcoding for single-cell transcriptomics applied to embryonic stem cells. Cell. 2015 May 21; 161(5):1187-201. doi: 10.1016/j.cell.2015.04.044. PMCID:4441768).

Example 3: Perturb-Seq: Pooled CRISPR Screens with Single Cell RNA-Seq Readout

Applicants devised Perturb-seq by combining the design of a pooled CRISPR screen, where the identity of each perturbation is reported by a unique barcode for each guide that is assayed by sequencing, with massively-parallel, droplet-based scRNA-seq, as a rich genomic phenotype for each cell (FIG. 48A). In Perturb-seq, the sgRNA barcode is reported by a polyadenylated RNA, which is captured by single cell RNA-seq. Perturb-seq uses a CRISPR lentiviral vector that both delivers an sgRNA to a cell and reports on the identity of the delivered sgRNA by an expressed Poly-Adenylated Perturbation Index (PAPI) (FIG. 48B). As in a typical pooled genetic screen, applicants first infect cells with a pool of lentiviruses, each carrying a construct for a particular guide. Depending on the multiplicity of infection (MOI), applicants expect a different distribution of the number of lentivirus genomic insertions (and hence sgRNAs) in each cell. At low MOI, the vast majority of cells would have one or no guides. In such a case, Perturb-seq can be used to assess the effect of single gene perturbations. By increasing the multiplicity of infection (At higher MOI), a greater fraction of cells possesses more than one guide. Thus, the MOI is a tunable parameter that, for a given number of cells, determines how powered tests will be to study epistatic effects.

Next, following growth, differentiation, and/or stimulation, Applicants collect the cells and process them through massively parallel scRNA-seq. This process tags the mRNA of each cell, including the synthetic PAPI, with a unique cell barcode (CBC) and a unique molecular identifier (UMI). The CBC associates the cell's transcriptional profile with the genetic perturbation(s) delivered to this cell, as encoded by the PAPI. Applicants perform Whole Transcriptome Amplification (WTA), library preparation, and sequencing in a single pool. In our current implementation, Applicants rely on a droplet method, which is now commercially available (Zheng et al., 2016) (Methods and Resources), but our design is compatible with additional single-cell RNA-seq methods (Fan et al., 2015; Klein et al., 2015; Macosko et al., 2015), and Applicants have tested it successfully with Drop-seq (Macosko et al., 2015) in both K562 cells and BMDCs, albeit with different gene targets than in the rest of this study (AD, OP, BL, and AR, unpublished data).

Applicants demonstrate Perturb-seq, in two complementary biological systems: K562 cells, a rapidly growing human erythroleukemia cell line, and bone marrow derived mouse dendritic cells (BMDCs), a post-mitotic, short-lived primary cell, which Applicants analyzed pre-stimulation (0 h) and three hours following stimulation with LPS. Applicants have previously established both systems for genome-wide CRISPR screens, with a readout of either cell viability (in K562 cells (Wang et al., 2015)), or an expression marker (TNF, in BMDCs (Parnas et al., 2015)). In both systems, the Cas9 protein is stably knocked into the cell either in vitro (K562: cells) or in the germline of a transgenic mouse from which the cells are derived (Parnas et al., 2015; Platt et al., 2014).

Altogether, Applicants performed six Perturb-seq experiments, analyzing 200,000 cells in total (FIG. 48C). In K562 cells, Applicants targeted either 14 TFs or 10 cell cycle regulators, in separate pooled experiments (Table S1). For TFs, Applicants performed experiments in both lower and higher MOI, and at two time points (7 and 13 days post infection). In BMDCs, Applicants targeted 24 TFs (Table S1) important for either BMDC cell differentiation or the response to LPS (Amit et al., 2009; Garber et al., 2012), and measured their effects at both pre-stimulation (0 h) and three hours (3 h) post-stimulation. Finally, in each case, Applicants collected reference single cell RNA-seq data from unperturbed cells in separate experiments: 5,400 K562 cells; 2,700 unstimulated BMDCs; and 1,300 BMDCs stimulated with LPS for 3 h (Table S1).

Example 4: Perturb-Seq Efficiently Detects Expressed RNA Barcodes, Gene Expression Profiles, and Impact on Targeted Genes To couple massively parallel scRNA-seq with a pooled CRISPR/Cas9 screen, applicants developed a lentiviral vector in which a polyadenylated random barcode is associated with an sgRNA and reports on its identity (FIG. 48C, Methods and Resources). Applicants first matched each sgRNAs with the identity of its corresponding RNA barcode, by either Sanger or next-generation sequencing (Methods and Resources), and then converted it into lentivirus for pooled transduction. The guide barcode follows the ORF for BFP, allowing us to sort only infected cells. Finally, because accurate detection of sgRNA from single cells is critical for the accuracy of the pooled approach, applicants designed a dial-out PCR approach, which applicants applied following WTA, to further amplify and sequence the barcode (Methods).

Applicants also developed an enrichment protocol to optimize our ability to detect the sgRNA(s) delivered to each cell. First, Applicants associated each sgRNA with the identity of its corresponding PAPI, by either Sanger or next-generation sequencing (Methods and Resources). Applicants next converted the plasmids into lentiviruses for pooled transduction. The plasmid construct included an ORF encoding a BFP-T2A-Puromycin (FIG. 48B), allowing us to select for transduced cells by FACS sorting or by antibiotic selection. Finally, to increase the accuracy of detection of sgRNA from single cells, Applicants designed a dial-out PCR approach, to enrich for the PAPI following WTA (Methods and Resources). Applicants observed low levels of many PAPIs present in many cells (due to cross talk caused by PCR chimeras and ambient RNA) (FIG. 55F), and account for it by normalizing the observed number of PAPIs within a cell, and setting a threshold (Methods and Resources).

Applicants estimated the probability of detection of the PAPI by considering two factors: (1) the initial MOI and (2) the transcript capture efficiency of our scRNA-seq protocol. Applicants reasoned that these should be described well by a generative model, where applicants assume a zero-truncated Poisson distribution for infection with a guide-carrying lentivirus (zeros are truncated by BFP+ selection), convolved with a binomial process (for the probability of detection) (Methods). Indeed, the predicted fit was indistinguishable from the observed frequencies of number of guides per cell (FIG. 55A-C, bottom panels, KS-test). Using this approach, applicants estimated 94% (92-96%) detection probability with an approximate initial MOI of 0.63 in the K562 TF pool, a 98% probability with an MOI of 0.35 in the cell cycle pool, and a 60% detection probability with an approximate initial MOI of 1.4 in BMDCs at 3 h (FIG. 55A-E). The lower detection probability in BMDCs reflects overall lower complexity of these single cell profiles (Table S1), and is an additional source of noise, which Applicants handle in downstream computational analysis. Nevertheless, even in BMDCs, Applicants were able to detect cells with multiple guides per cell (FIG. 48D).

TABLE S1

| Pool | Number of Cells | Number of sgRNAs | Cells/ sgRNA | Average PAPI detected/cell | Median Genes Detected | Median Transcripts Detected |
|---|---|---|---|---|---|---|
| PBMDC 3 hr | 37369 | 57 | 655.5964912 | 1.1 | 1537 | 5074 |
| PBMDC unstim | 32624 | 57 | 572.3508772 | 1.1 | 988 | 2187 |
| K562 TFs low MOI 7 days | 33104 | 30 | 1103.466667 | 1.3 | 3015 | 11610 |
| K562 TFs low MOI 13 days | 19268 | 30 | 642.2666667 | 1.1 | 2952 | 12303 |
| K562 TFs high MOI | 51898 | 30 | 1729.933333 | 1.9 | 3080 | 13974 |
| K562 cell cycle regulators | 26020 | 33 | 788.4848485 | 1.2 | 3764 | 11716 |
| Wildtype PBMDC 3 hr | 1310 | NA | NA | NA | 728 | 2162 |
| Wildtype PBMDC unstim | 2713 | NA | NA | NA | 585 | 1450 |
| Wildtype K562 | 5409 | NA | NA | NA | 1284 | 3285 |
| TOTALS | 209715 | 237 | 5492.098884 | 7.7 | 17933 | 63761 |
| AVERAGES | 23301.66667 | 39.5 | 915.3498139 | 1.283333333 | 1992.555556 | 7084.555556 |

Single cell RNA-seq profiles typically represent only a fraction of the molecular complexity of the measured cell's transcriptome (estimated at 2-26% for droplet based approaches (Klein et al., 2015; Macosko et al., 2015; Zheng et al., 2016)). In both systems, averages of approximately 100 single cell droplet profiles recovered the population complexity (FIG. 55J,K). (Applicants do note a bias in capture efficiency of small transcripts (<500 nts; FIG. 55L), which may be associated with the 3' library preparation protocol.)

Finally, Applicants showed that a reduction of the targeted gene's expression is typically associated with the corresponding perturbation (FIG. 48E,F, FIG. 55G-I). In general, this measure should be a proxy for cutting efficiency, although it is possible that regulatory mechanisms can in some cases cause overexpression of a transcript in the absence of a functional protein. Indeed, the expression of sgRNA targets was significantly reduced from zero (e.g., in BMDCs: FIG. 48F, p-value$<10^{-4}$, one-sample t-test). Notably, our ability to determine a reduction in expression is strongly related to the expression level of the target in the wild type cells (FIG. 551).

Figure 56H:
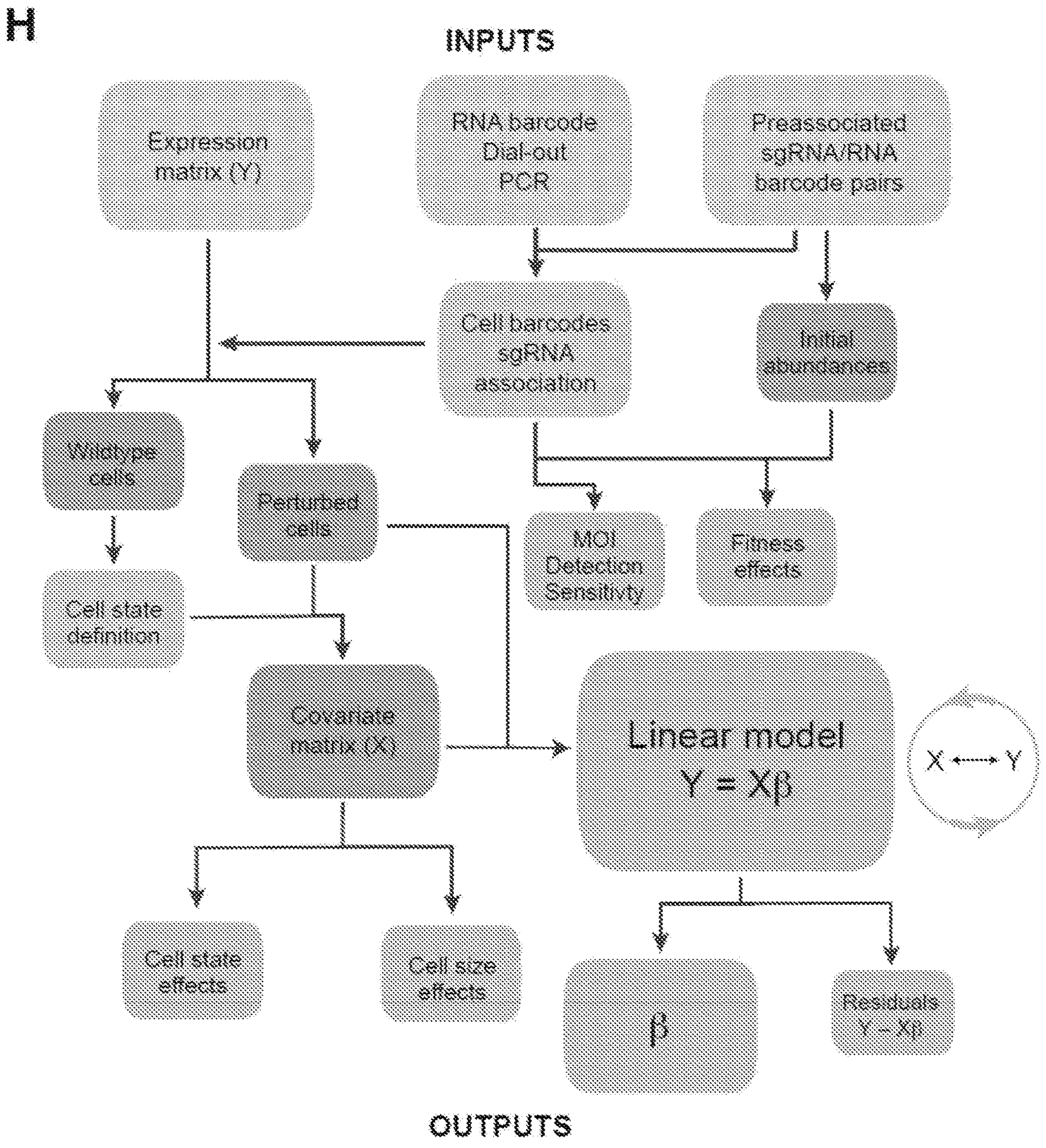

Example 5: A Computational Model to Predict the Effect of Perturbations on the Expression of Individual Genes and on Global Cell States Applicants next devised a computational framework, based on a linear model, to estimate the impact of perturbations on gene expression (FIG. 48G, FIG. 49 and FIG. 56) (FIG. 49). In the basic linear model (FIG. 49) (FIGS. 48G and 49A) the logarithm of, the expression of each gene in a cell is explained as a linear (weighted) combination of the effects of individual sgRNAs on the gene. Thus, the log expression level of each gene in each cell (expression matrix Y, observed) is a product of two matrices: one describing cell attributes-which guides are present in each cell (design matrix X, observed), and the other represents the regulatory effect of each attribute on each gene (coefficient matrix B). This basic model assumes no interactions: that is, the combined effect of two perturbations is simply their weighted sum. The perturb-seq measurements provide matrix Y (expression levels in each cell) and X (guides in each cell; based on analysis of dial-out PCR measurements of PAPIs; Methods and Resources), with good fidelity (FIG. 48) (FIGS. 48 and 55). Thus, Applicants can fit matrix β to determine the effect of each guide on each gene.

To fit the coefficient matrix β (effect of each guide on each gene) given the observations, Applicants used elastic net regularization, which contains both $L_1$ penalty, to reduce the number of hypotheses tested, and an $L_2$ penalty on the magnitude of the coefficients (Methods and Resources). The second regularization is especially important in the case of correlated covariates and noisy data. Notably, Applicants did not provide any other prior knowledge when learning the model: in particular, Applicants did not include which gene is targeted by which guide. After the model is fit, Applicants evaluate the significance of the fit coefficients using a permutation-based approach to calculate significance (Methods and Resources, FIGS. 56D-G).

Next, applicants considered how to handle key confounders that are observed in the data. Applicants account for three key classes of covariates that represent either core biological phenomena or expected confounders (FIG. 49A-G): (1) the number of observed UMIs in a cell ("cell quality"); (2) the probability that a perturbation successfully affected the cell; and (3) the presence of distinct subpopulations, of either different cell types or states, in the same sample. Below Applicants describe how each of these aspects manifests in the original data, and how it is handled by our model.

First, as typical in scRNA-seq experiments (Kharchenko et al., 2014; Shalek et al., 2014; Stegle et al., 2015), scRNA-seq profiles from individual cells in the same experiment can vary substantially in their quality, for example as reflected here by the number of UMIs (RNA barcode) (FIG. 49). assigned to the cell. Applicants ability to detect the expression of a given transcript in any given cell depends on both technical and biological factors relating to the total number of transcripts Applicants captured in that cell and the transcript's original expression level in that cell (FIG. 49B). To address this confounder in the basic linear model, Applicants added a covariate to our model that represents the sum of the total number of UMIs detected per cell as well the square of this feature (FIG. 49C).

Next, Applicants considered effect of a perturbation (FIG. 49F) as well as the possibility that in some cells even when a guide is confidently detected, it may not have had any phenotypic effect in that specific cell. This could happen, for example, because the CRISPR system produced no mutations, a heterozygous cell for a fully or partially haplosufficient gene, an in-frame mutation, or even if the editing event was too recent to have had a phenotypic impact. Indeed, for most guides, while cells carrying the guide are distinguishable on average from those that do not, there are still cells with reliably detected guides, but with profiles that are similar to those of cells without the guide (e.g., FIG. 49H, FIG. 56I).

When profiling RNA from a population of perturbed cells in bulk, this mixture would dilute the true perturbation phenotype. If perturbation effects are strong, it should be possible to distinguish true perturbed cells from unperturbed cells leveraging the single cell nature of our data. The regulatory matrix (β) derived from the observed guide-to-cell assignment, provides an initial assessment of the effects of perturbations. Applicants use this model to revisit each cell and predict whether each of the observed guides had perturbed the cell (FIG. 49H, right). Applicants can then re-estimate the model with the corrected perturbation-to-cell assignment. This one iteration can be thought of as approximate Expectation-Minimization applied to the linear model.

Third, Applicants reasoned that the cells in each of our experiments might belong to one of several states or types, and that those global states can be affected by the perturbations (FIG. 49E). For example, in K562 cells Applicants expected (Macosko et al., 2015) cells in different phases of the cell cycle, as well as apoptotic cells. In BMDCs, unsupervised clustering shows several distinct subpopulations, including overlap with those previously reported (Helft et al., 2015). Indeed, even after accounting for cell complexity, many transcripts still show two distinct modes of expression (e.g., FIG. 49C). Thus, Applicants may want to distinguish between a global impact of a perturbation on cell proportions and a more specific impact within a cell state. To model sub-populations, Applicants first define them using the profiles of the matched, genetically unperturbed, experiments (Methods and Resources), and then incorporate this classification as a set of covariates in our model. Applicants fit the model either with or without these sub-populations covariates. When cell states are fit as covariates, the two modes of expression are no longer observed in the residuals (e.g., FIG. 49D), and some of the sgRNA's effect are accounted for (compare FIGS. 49F and G), suggesting that those perturbations may have primarily affected the proportions of cell types.

After the model is fit, Applicants can evaluate the significance of the observed coefficients using a permutation based approach to calculate significance (Materials and Methods, FIGS. 56D-G).

Applicants framework, MIMOSCA (FIG. 49H), can be readily extended to incorporate non-linear interactions between covariates. In principle, gene perturbations may interact in nonlinear ways with one another ("genetic interactions"), with cell states (cell state specific gene expression changes), or with our quality measures (e.g., changes in cell size). Applicants describe an extension for interactions between perturbations below.

Example 6: The Linear Model is Robust, Reproducible and Predictive

Applicants assessed the quality of the linear model by its robustness, fit, and biological coherence. Applicants determined the contribution of the four core components of the model (cell complexity, batch, phenotypic effects of perturbations, and cell state), by analyzing the proportion of the variance in the data each explains (FIG. 49I, FIG. 56A-C). For example, for stimulated BMDCs, the perturbations themselves explain 5% of the variance in the data, 17% is explained when adding covariates associated with number of transcripts detected, and up to 20% with cell state covariates (FIG. 49I). Applicants obtain similar results with the other datasets (FIG. 56A-C). This highlights the importance of accounting for covariates to ensure sensitive detection of the relevant perturbation signal (FIG. 54). Furthermore, gene-gene correlations in the residuals were significantly reduced as covariates were added (FIG. 49J), This suggests that much of the global correlation is mediated through transcripts detected and cell states.

Figure 56I:
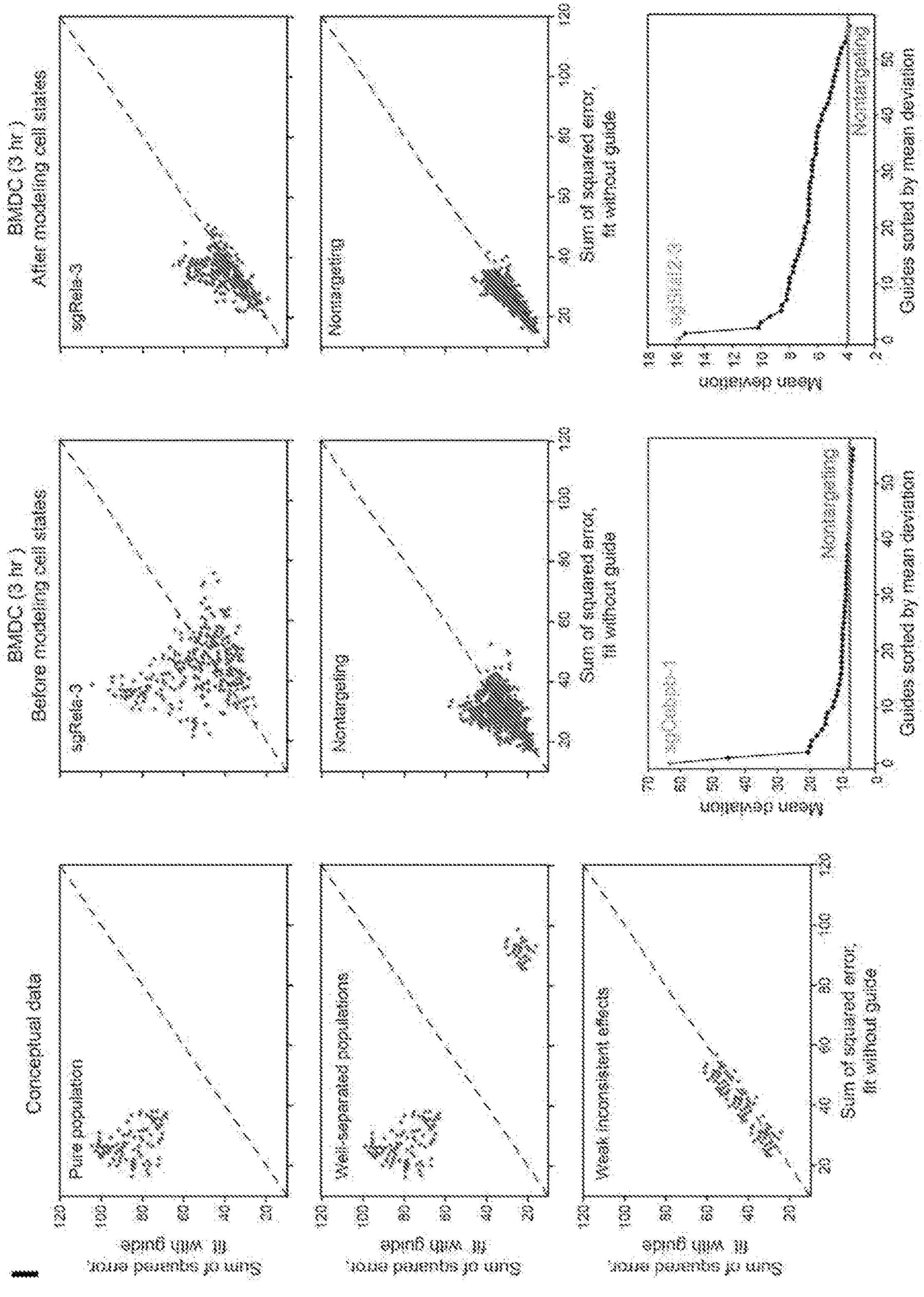

Considering the multivariate nature of gene expression measurements, Applicants also analyzed the consistency in the effects on genes across cells that all contain a particular perturbation (FIG. 56I). Overall, guides targeting genes have stronger and more consistent effects than the non-targeting control guides.

Example 7: Perturb-Seq Dissects the Transcriptional Program in the LPS Response in BMDC Applicants next analyzed the effect of each of 24 TFs on the transcriptional response in BMDCs to LPS. Briefly, when DCs are stimulated with LPS they activate the expression of ~2,000 genes (Amit et al., 2009; Parnas et al., 2015), organized into several key response modules (Parnas et al., 2015; Shalek et al., 2014). Previously, Applicants have implicated dozens of factors in the response, and validated some of their roles by genetic perturbations (Amit et al., 2009; Parnas et al., 2015). In addition, ChIP-seq analysis of 29 transcription factors (19 of them among the 24 Applicants perturbed) at 4 time points during the response (Garber et al., 2012) showed that factors can be distinguished into three categories: (1) pioneer factors that commit the cells to their lineage (CEBPB and Spil/Pu.1); (2) broad binders that prime lineage specific genes, before their stimulus-induced expression (e.g., JunB, Irf4, Atf3); and (3) dynamic factors that activate response-specific genes (e.g., Stat2). Knockdown of some factors, but not all, affect the expression of the genes they bind, suggesting buffering genetic interactions for at least some factors (Garber et al., 2012). The response is not perfectly synchronous, such that at different time points, there is bi-modality across the cell population in the expression of specific modules (Shalek et al., 2013, 2014). Finally, Applicants showed that the cells in a BMDC population may consist of at least two sub-types, and that their relative proportions may shift between experiments (Shalek et al., 2013, 2014). Applicants reasoned that this extensive prior knowledge would help benchmark our results, and that the single cell nature of our screen and computational model would directly address the challenges of heterogeneity.

Applicants performed Perturb-seq at two time points. Applicants obtained precursor cells from the bone marrow of Cas9 transgenic mice (Platt et al., 2014), and after two days of culturing in GM-CSF, Applicants infected the cells with a pool of lentivirus carrying the Perturb-seq vector with 1-4 guide RNAs targeting each of 24 factors (total of 67 guides) and a non-targeting control. After another seven days, Applicants stimulated the cells with LPS, and collected cells for scRNA-seq at 0 and 3 h, profiling 32,624 and 37,369 cells, respectively (Table S1).

Figure 51A:
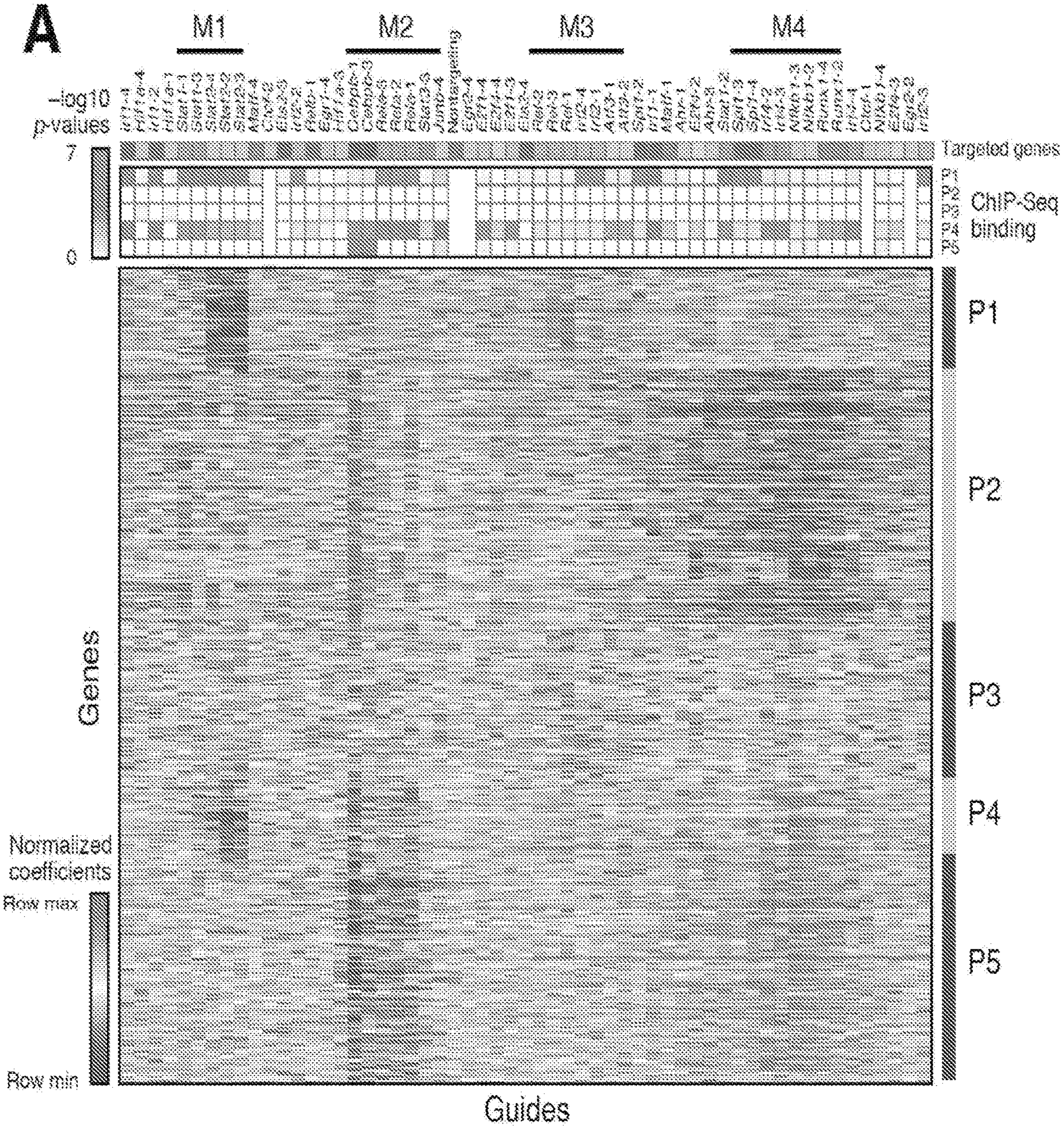
FIG. 51A-G illustrates Perturb-Seq recovers a gene regulatory circuit for BMDCs balancing cell states and immune responses. (A,B) Four TF modules control five transcriptional programs in BMDCs at 3 h post-LPS. (A) Shown is the regulatory coefficient of each guide (labeled and color coded columns) on each gene (rows) based on a model that does not account for cell states as co-variates. Guides and genes are clustered by the similarity of their profiles. Four TF modules (M1-4) and five target programs (P1-5) are marked. Green-white heatmap shows the enrichment in bound targets of each TF based on ChIP-Seq (Garber et al., 2012) in each program (rows). (B) Bi-partite graph, based on (A) of association of TF modules (top) to target programs (bottom). Blue (red) arrows: TF in module activates (inhibits) program (perturbation has the opposite effect). Bottom: TFs from modules that are members of the regulated program (blue: activator of the program; red: repressor of the program). (C,D) TF-TF circuit in BMDCs at 3 h post-LPS. (C) Heatmap as in (A) but only showing genes (rows) that encode the TFs targeted by the guides. (D) TF-TF circuit based on the associations in (C). TFs are shown as nodes. TF modules are shadowed in grey. Blue (red) arrows: TF in module activates (inhibits) program (perturbation has the opposite effect). (E-F) ChIP-Seq support for genetic network. (E) Expected effects of perturbation of a TF (green) on a target gene when the factor does not regulate (or bind) the gene (top); directly binds and represses it (middle) or directly binds and activates it (bottom). (F) Regulatory effect of each guide (rows) on its bound target (colorbar) as defined by ChIP-Seq in BMDCs at four time points (columns, 0, 0.5, 1, and 2 h post-LPS). (G) The proportion of bound targets at 120 min post-LPS for the TF targeted by each guide (rows) that are repressed (blue), activated (red) or unaffected (grey) by the perturbation. Asterisks denote significant enrichments (as in F). See also FIG. 58.
Figure 51B:
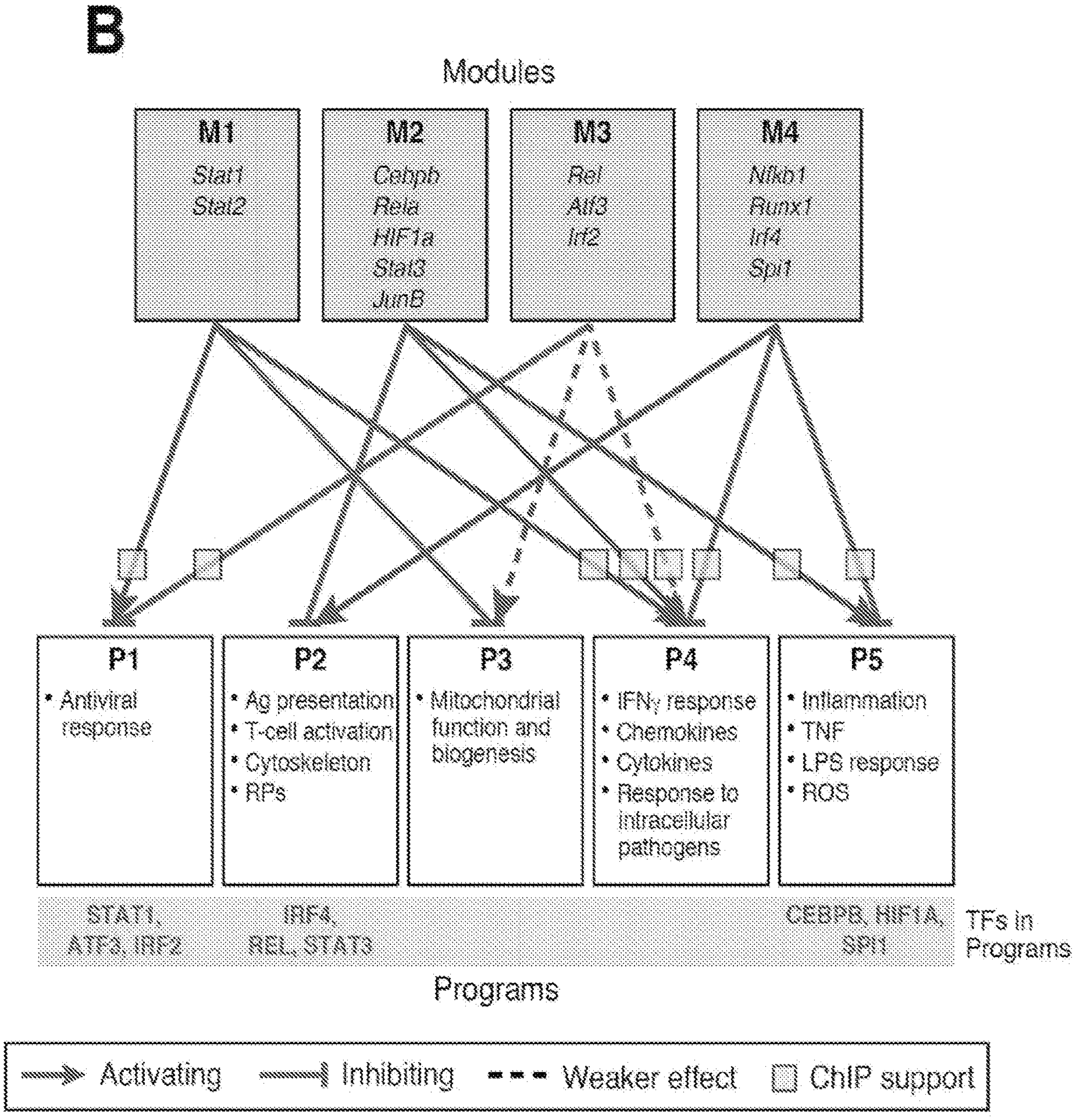

Fitting our regulatory model without considering subpopulations or genetic interactions (FIGS. 50 and 51, Methods and Resources), the key predictions—the regulatory effects of guides on genes—were coherent in the sense that guides targeting the same gene typically grouped together by their similar impact on genes in the model (i.e., by the regulatory coefficients, β, in matrix B; FIG. 51A), Thus, the correlation in regulatory profiles (β) between guides targeting the same gene is significantly higher than between those targeting different genes (FIG. 50B, $P<10^{-9}$, Wilcoxon signed-rank test), even though the model had no knowledge which guides target the same gene. The model also typically shows the repressive effect of guides on the expression of their direct target, although no information was provided to the model on the identity of the gene that it is designed for (FIG. 50A, separate column on left).

Applicants uncovered four key modules of transcription factors (M1-M4), based on the overall regulatory effects of the different guides as inferred in the regulatory matrix, consistent with their known function (FIG. 50) (FIG. 50A yellow squares, and 51A): (1) the anti-viral TFs (Stat1, 2; M1); (2) the pioneer factor Cebpb along with the broad binder JunB and the dynamic binders Rela, Stat3 and Hif1a (M2); (3) The dynamic binders Rel and Irf2, along with the broad binder Atf3 (M3); and (4) The pioneer factor Spi1/Pu.1, broad binders. Runx1 and Irf4, and the dynamic binder Nfkb1 (M4). While each TF module consists of guides targeting different TFs, the correlation in the regulatory effects of guides targeting the same gene is especially high (e.g., Stat1, Stat2, Cebpb, Rela, Rel, Irf2, Atf3, Spi1/Pu.1, Irf4, Nfkb1, Runx1 etc.; FIGS. 51A, 50B), supporting the specificity of Perturb-seq and suggesting TF specific effects within the context of shared overall programs.

The four TF modules regulate five major biological programs (P1-5; FIGS. 51A and B): an anti-viral response (P1), a program of antigen presentation, cytoskeleton and ribosomal protein (RP) expression, including some markers of DC maturation and of "cluster disrupted" cells (e.g., SerpinB6) (P2), mitochondrial function and biogenesis (P3), an interferon gamma program, with chemokines and cytokines important in the response to intracellular pathogens (viruses, bacteria or parasites) (P4), and an inflammatory TNF response (P5). For example, perturbation of Stat1 and Stat2 (M1 module) represses both the anti-viral (P1) program and the interferon gamma program (P4). Perturbation of the M2 module (Cebpb, Rela, and other factors) represses both the inflammatory and IFN gamma modules, consistent with their roles of activators of inflammation, and activates the P2 program of antigen presentation, cytoskeleton and RPs. The M4 module (Spi1, Nfkb1, Runx1, etc.) has an opposite effect to that of M2. The Rel module (M3) has a partially opposing effect to that of the Stat (M1) module, for example inhibiting the antiviral program.

These results highlight both known functional associations and novel predictions. For example, Stat1 and Stat2 are well known activators of the anti-viral program (Shalek et al., 2013). The predicted repression of the antiviral program by the Rel module, including Irf2 and Atf3, is supported by a recent report in macrophages (Labzin et al., 2015) that Atf3 can act as a direct transcriptional repressor of the interferon beta (IFN-β) gene, that it further modulates the expression of other genes downstream of IFN signaling, and that Atf3-null macrophages have an enhanced clearing of virus.

Our model also predicted that Stat1 and 2 are repressors of a program of mitochondrial function and biogenesis in BMDCs (FIGS. 51A and B). BMDCs undergo a shift from mitochondrial to glycolytic metabolism during the LPS response, including mitophagy (Cohen and Sheva, 1998) (Jovanovic et al., 2015). Recent studies showed that Stat1 inhibits mitochondrial biogenesis in mouse liver (Sisler et al., 2015), and reported Stat2 deficiency in two children as a novel disorder of mitochondrial fission (Shahni et al., 2015). Stat1 and 2 were also reported as physically present in the mitochondria, where they may provide both sensing and signaling functions (Meier and Larner, 2014).

The comprehensive model, predicting the effects of each factor on each gene, also provides a detailed view into the way in which DCs control different processes. For example, Gbp2,2b,3,4,5 and 7, a set of IFNγ regulated genes important for the response for intracellular infections by bacteria or parasites, are all positively regulated by Stat1 and 2, and negatively regulated by Rel and Irf2. Stat1 has been reported as an activator of GBPs (Ramsauer et al., 2007) and Rel is reported to bind the Gbp2 promoter (Wei et al., 2008). However, Gbp3,4,5, and 7 are also repressed by M2 (CEBPB, Rela and others), and hence are members of P4, whereas Gbp2 and 2b are not (and are members of P1). This may reflect the distinct roles of different GBPs in infections with different parasites [REF]. Moreover, perturbation of the M1 and M3 TF modules affects not only these effector genes, but also Irf8 and Batf, key transcription factors that control the GBPs (Tussiwand et al., 2012). Irf8 expression is repressed under Stat2 perturbation, suggesting that the impact on the effector genes may be at least partially indirectly mediated through Irf8 perturbation. Moreover, the TF Batf is induced during Stat2 perturbation, which may reflect the cell's attempt at compensation, since Batf can act in a compensatory capacity in the response to intracellular parasites and *Leishmania* (Tussiwand et al., 2012). Although both IRF8 and BATF regulate differentiation, this is unlikely to be the case here, as the regulatory effect of Stat2 on GBPs, IRF8 and is maintained—and even strengthened—in a model that accounts for cell states and controls for other differentiation effects (below).

Example 8: Opposing Programs of BMDC Differentiation Controlled by Two Modules Each with a Distinct Pioneer Factor Two of the TF modules-M2 (Cebpb, JunB, Rela, Stat3 and Hif1a) and M4 (Spi1, Runx1, Irf4, and Nfkb1) had diametrically opposed effects on broad programs: P2 was repressed by factors in M2 and induced by those in M4, whereas P4 and P5 were both induced by M2 factors and repressed by M4 factors. (P4 is regulated by Stats whereas P5 is not, as Applicants discuss below.) The P4 and P5 programs each reflect key aspects of the DC response to LPS and pathogens. Conversely, the P2 program is less expected: in addition to genes for antigen presentation (MHC II system) and cytoskeleton proteins (important for DC migration after maturation), it is also enriched for ribosomal proteins. P2 also includes SerpinB6 and CD86: Applicants have previously associated SerpinB6 with "cluster disrupted cells" (Shalek et al., 2014), a sub-population in BMDCs that appears to express some maturation genes even prior to stimulation (Shalek et al., 2014) and refs within]; CD86 is known to be associated with DC maturation (Helft et al., 2015). The expression of ribosomal, cytoskeletal and MHC II proteins has been previously reported to be induced in pre-DCs along DC differentiation from progenitors [REF: PMID 26054720 and Biorxiv: biorxiv.org/content/biorxiv/early/2016/10/07/079509.full.pdf]. Several genes expressed by these pre-DCs, but not earlier progenitors are members of P2, including genes associated with early pre-DCs (lglas3, Itgax), actin polymerization (Crip1), and late-pre-DCs (Cd74, H2-Ab1,H2-AA, H2-Eb1). Furthermore, a recent study showed that protein synthesis is reduced upon full differentiation [Biorxiv: biorxiv.org/content/biorxiv/early/2016/10/07/079509.full.pdf]. Thus, P2 may reflect a distinct cell state or type, for example, maybe cells that are either less differentiated or abortive or arrested in their differentiation ex vivo.

Applicants reasoned these effects may thus be best interpreted by a global impact of some of the perturbed TFs on set of possible BMDC-like cell types or states, such that an increase at one cell type under a given perturbation, would come at the proportional decrease of others. Indeed, the BMDCs population Applicants study do have substantial heterogeneity, including the presence of distinct sub-types, such as "cluster-disrupted" cells among the Cd11c$^+$ cells (Shalek et al., 2013, 2014) as well as ~10% of the cells that are Cd11c (Amit 2009, Garber) 2012]). For example, if a perturbation is detrimental to proper derivation of BMDCs ex vivo, it would lead to an increase in the number of cells with the active P2 program, over those that assume P4 and/or P5.

Figure 58A:
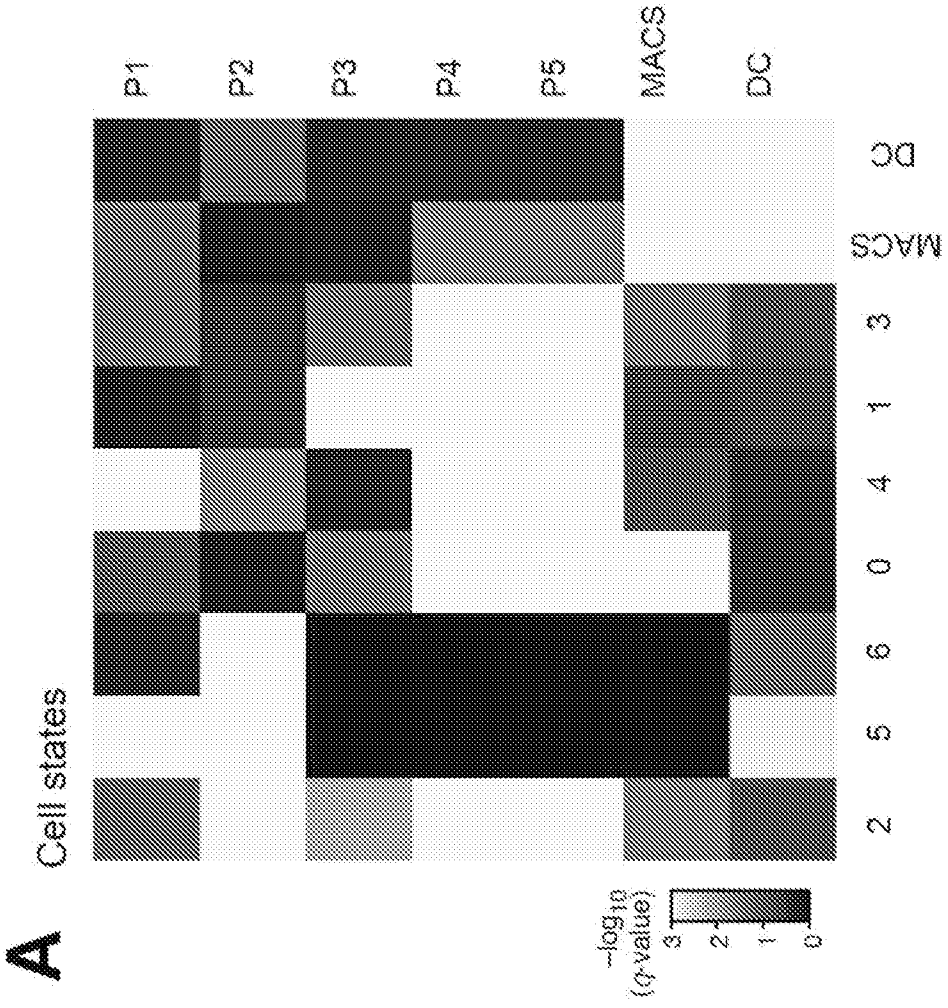
FIG. 58A-D illustrates additional aspects of the regulatory circuitry of BMDCs. (A) Relation between cell states and regulatory programs. Shown is the significance ($-\log_{10}$ (P-value) of the hypergeometric test) of the overlap between the genes in each of the programs P1-P5 (as in FIG. 51A) and the genes induced in each of the seven transcriptional states of genetically unperturbed DCs at 3 h post-LPS (as in FIG. 50C). (B) TF control of transcriptional programs in BMDCs at pre-stimulation (0 h). Shown is the regulatory coefficient of each guide (labeled columns) on each gene (rows) based on a model that does not account for cell states as co-variates. Guides and genes are clustered by the similarity of their profiles. Four target programs (P1-4) are marked. Green-white heatmap shows the enrichment in bound targets of each TF based on ChIP-Seq (Garber et al., 2012) in each program (rows) based on either a lenient, genome-wide background (top) or a strict background (bottom) restricted only to the genes in the four programs. (C) Enrichment in bound genes based on a lenient background. Green-white heatmap shows the enrichment in bound targets of each TF based on ChIP-Seq (Garber et al., 2012) in each program (rows) based on either a lenient, genome-wide background for the same model as in FIG. 51. (D) Relation between TFs and transcriptional programs in BMDCs at 3 h post-LPS after accounting for cell states. Shown is the regulatory coefficient of each guide (labeled columns) on each gene (rows) based on a model that accounts for cell states as co-variates. Guides and genes are clustered by the similarity of their profiles. Five target programs (P1-5) are marked (distinct from the programs of FIG. 51A).

To test for this possibility, Applicants first used unsupervised analysis to identify a set of seven cell clusters present in 1,310 wild type cells stimulated with LPS (FIG. 50C, Methods and Resources). The clusters are significantly associated with the five programs identified by genetic perturbations, with distinct enrichments for P2 (cluster 2, 5 and 6), P3 (cluster 1) and P4/5 (clusters 0, 1, 3, 4) (FIG. 58A). This supports the hypothesis that P2 and P4/5 are states that exist in different cells in the somewhat heterogeneous BMDC population, absent perturbation, but the probability that a cell assumes any of these states over the other options may be impacted by at least some of the TF perturbations. Applicants next tested the association of each guide or targeted gene with each state by either predicting the probability that a guide associates with a state, or assigning cells to states and testing for their enrichment in the state (FIG. 50D, Methods and Resources).

Both methods show that cells perturbed for specific TFs are significantly associated with one or more of the cell state clusters, compared to the expected proportion of cells in that state when considering their frequencies in the WT cells?/non-targeted cells? in the same pool. In particular, cells perturbed for Cebpb, and to a lesser extent Rela or JunB, all from M2, are enriched in one or more cell clusters matching P2 and concomitantly depleted in cell clusters matching P5, whereas those perturbed for Spi1, Irf4, Nfkb1, or (to a lesser extent) Runx1, have the opposite pattern (FIG. 50D).

Figure 57C:
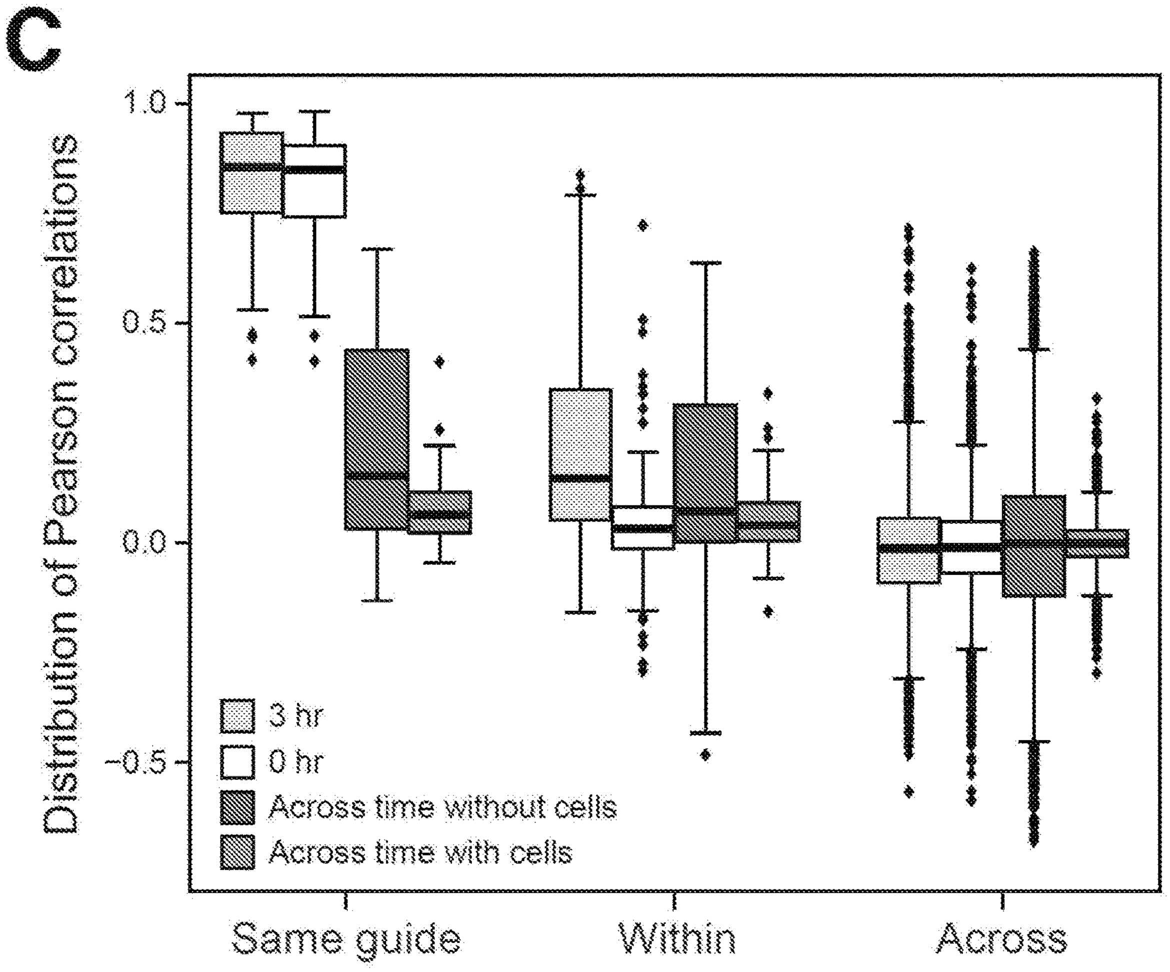
Figure 57D:
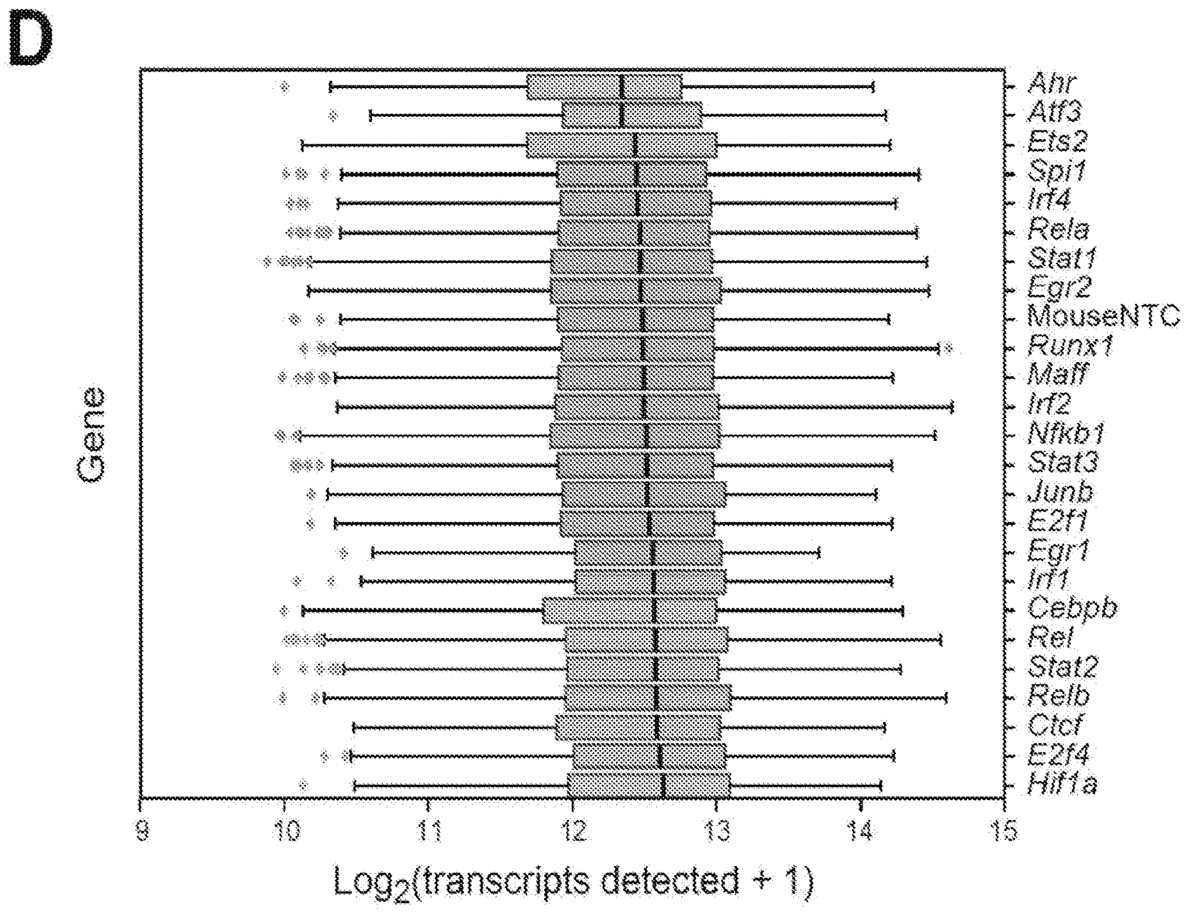
Figure 57E:
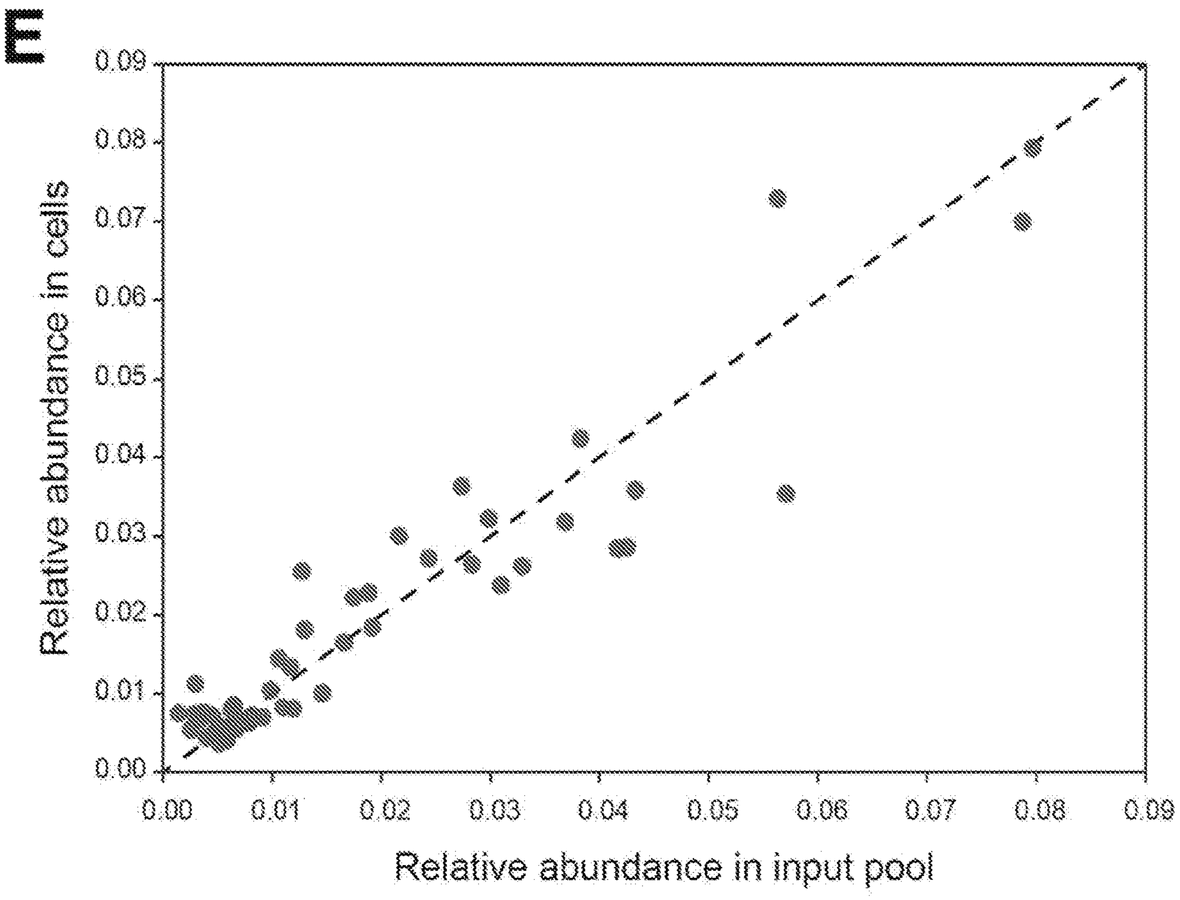
Figure 57F:
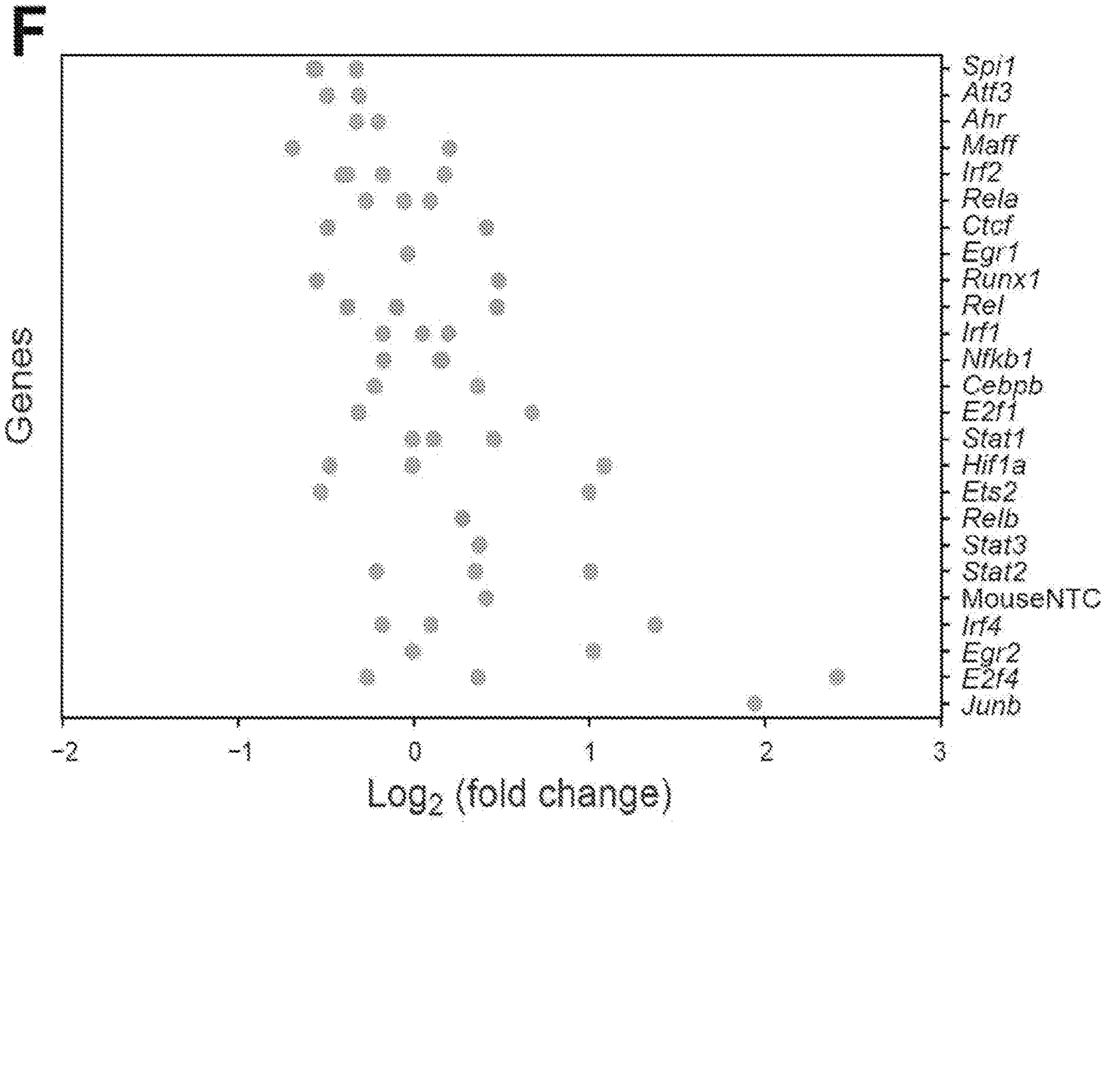

This suggests a model where factors in M2 and M4—each involving a different pioneer factor (Garber et al., 2012)—CEBPB and Spi1, respectively—have mutually opposing effects on DC differentiation programs. In this model, M2 promotes differentiation, leading to LPS-responsive programs (P4 and P5), whereas M4 promotes a mutually exclusive cell state that is either less differentiated, or less productive (P2). Importantly, the two states are present in different cells in a BMDC population absent genetic perturbation. Furthermore, consistent with this model, Applicants observed the two TF modules and their effects with the same pattern prior to stimulation with LPS, when the other programs are largely not detected (FIG. 57A,B and 58B).

Example 9: Diametrically Opposed Programs are Generated by a Regulatory Circuit with Self-Reinforcing and Mutually Inhibitory Transcriptional Modules Applicants next asked how is the transcriptional circuit wired to control these mutually exclusive states or types. Examining the genes in the key transcriptional programs P2 and P5 Applicants noted that they include as members their key positive and negative regulators (FIG. 51B, bottom, blue and red gene names, respectively). This would lead to both positive (reinforcing) and negative (inhibiting) feedback loops that can support the diametrically opposed, mutually exclusive behavior of M2 and M4 (FIG. 51B) and could explain how disrupting one of the factors in a TF module would 'flip' the cell to the other state. Specifically, IRF4, a TF in M4 is a target gene in P2, a program that M2 positively controls, generating a positive feedback loop. Conversely, Stat3, another target genes in P2, is a member of M2, generating a negative feedback loop. Similarly, Cebpb and Hif1a of M2 are members of its positive target program M5, but so is Spi1, a member of its negative regulator module, M4. The same organizational principle is present in P1, the antiviral program controlled by M1 (positively) and M3 (negatively): Stat1 is a member of the program (based on its positive regulation by Stat2; by definition, our genetic experiment cannot ascertain its auto-regulation), but so are Irf2 and Atf3, members of M3. This architecture—observed in other immune cell systems (Yosef et al., 2013); reviewed in (Yosef and Regev, 2016) may be a general principle in the DC network, resulting in balanced regulation of the cell's diverse functions, for example based on functional demands (Okabe and Medzhitov, 2014).

Figure 51C:
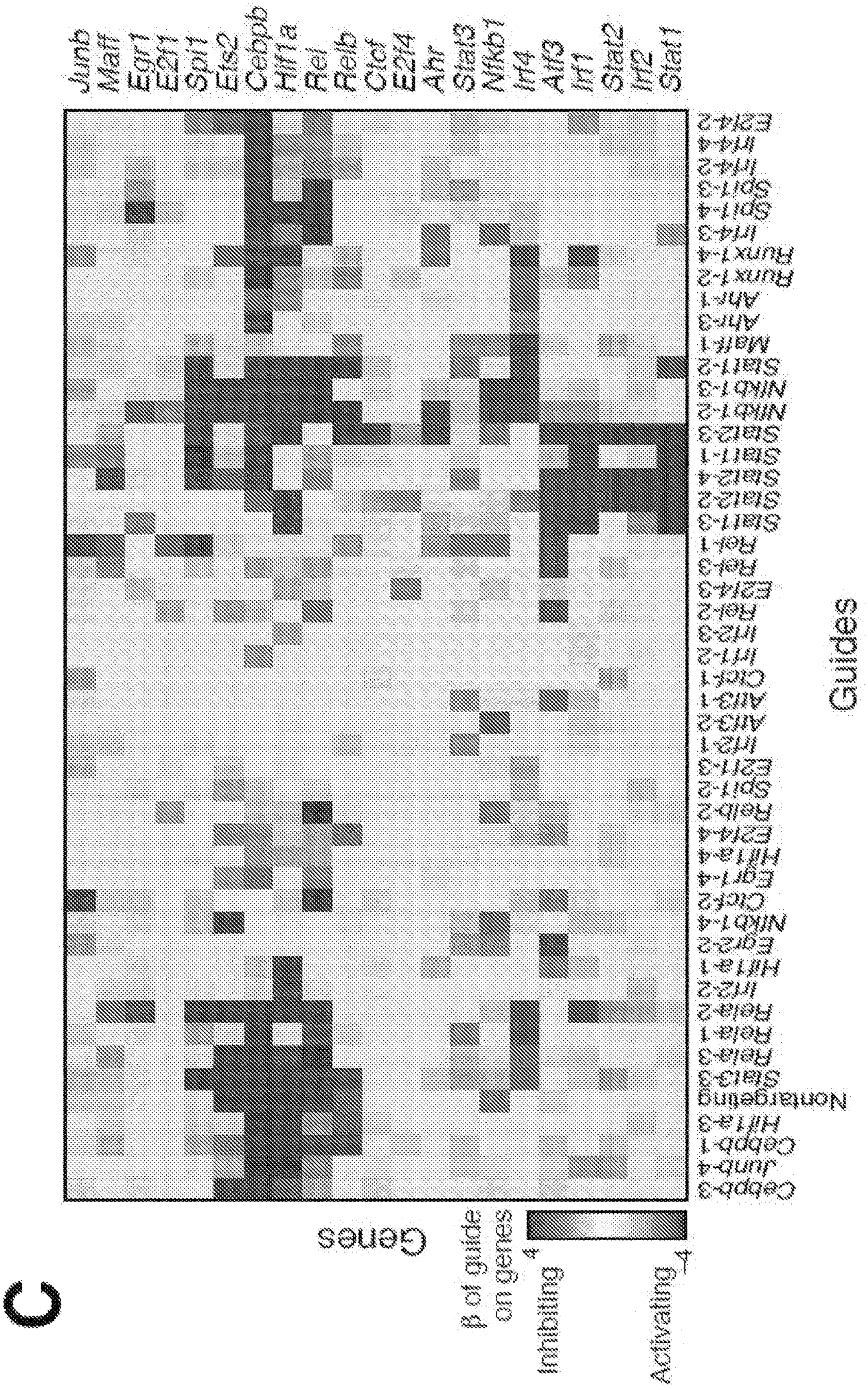

Applicants further sharpened the details of this balanced architecture by constructing a gene level genetic circuit based on the individual significant effects of the key transcription factors on each other (FIGS. 51C and D). Most of the TF modules (FIG. 51D, shaded areas), have internally reinforcing positive regulation of one module TF by another (e.g., Hif1a and Cebpb by each other and by JunB, Stat3, Rela (M2); Stat1 and Stat2 (M1); Spi1 by Irf4 and Irf4 by NfKB1 and Runx1 (M4)), and negative regulation between modules (e.g., Cebpb and HIF1a in M2 negatively regulated by Runx1 and NFKB1 in M4; Rela in M4 negatively regulates Irf2 in M2; Stat3 and Rela in M4 repress Rel in M3). Importantly, there is a regulatory asymmetry in the network: some factors (e.g., Nfkb1, Rela, Runx1) regulate many others, but are not regulated themselves, whereas a few factors-Cebpb, Hif1A, Spi1, Irf4, Rel, Atf3—are particularly highly regulated by many others (~6 incoming edges compared to ~1 for the other factors). These latter factors are typically themselves members of key transcriptional programs, as noted above, and thus would account for broad-impact feedback loops.

Figure 51D:
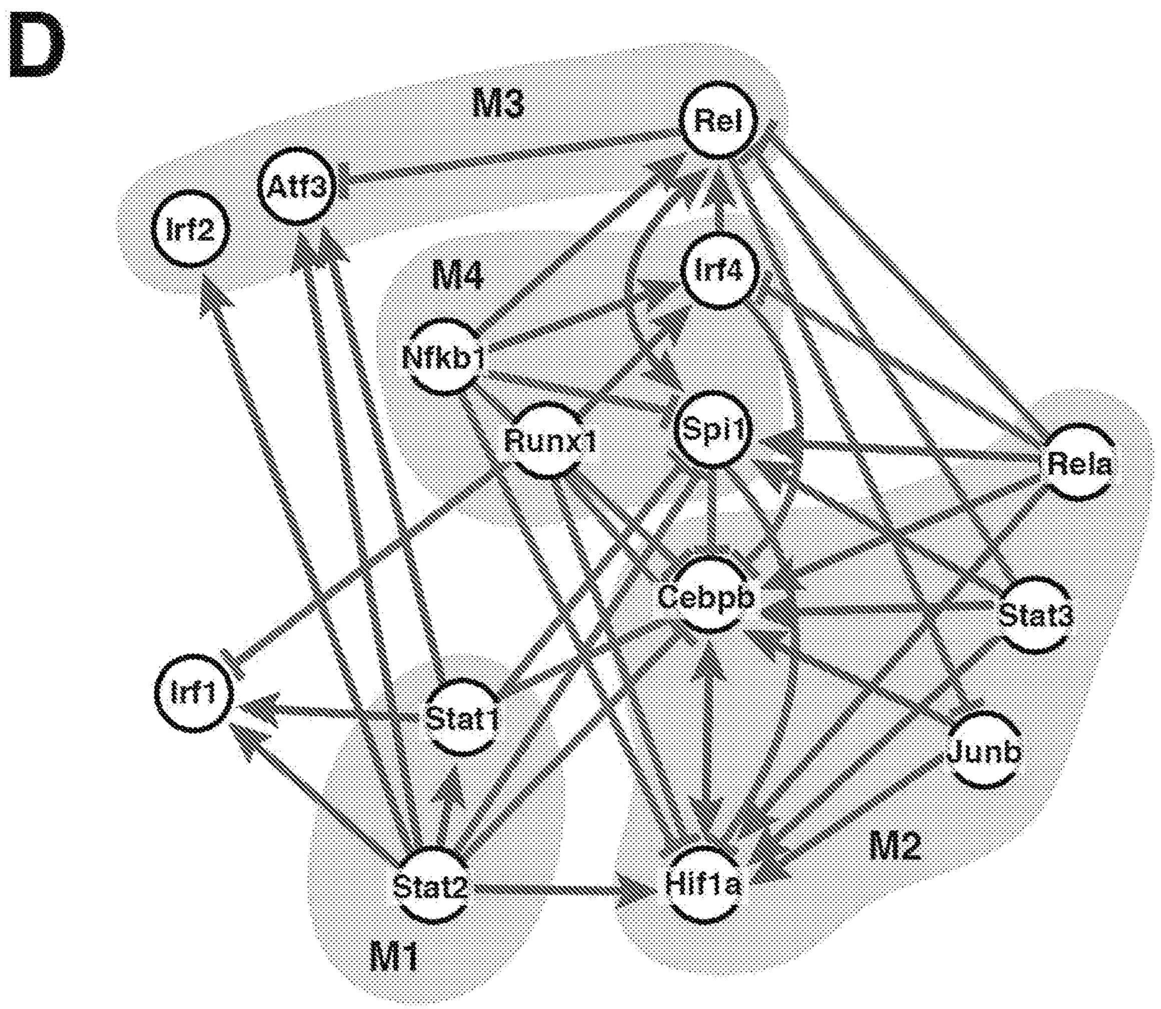
Figure 51E:
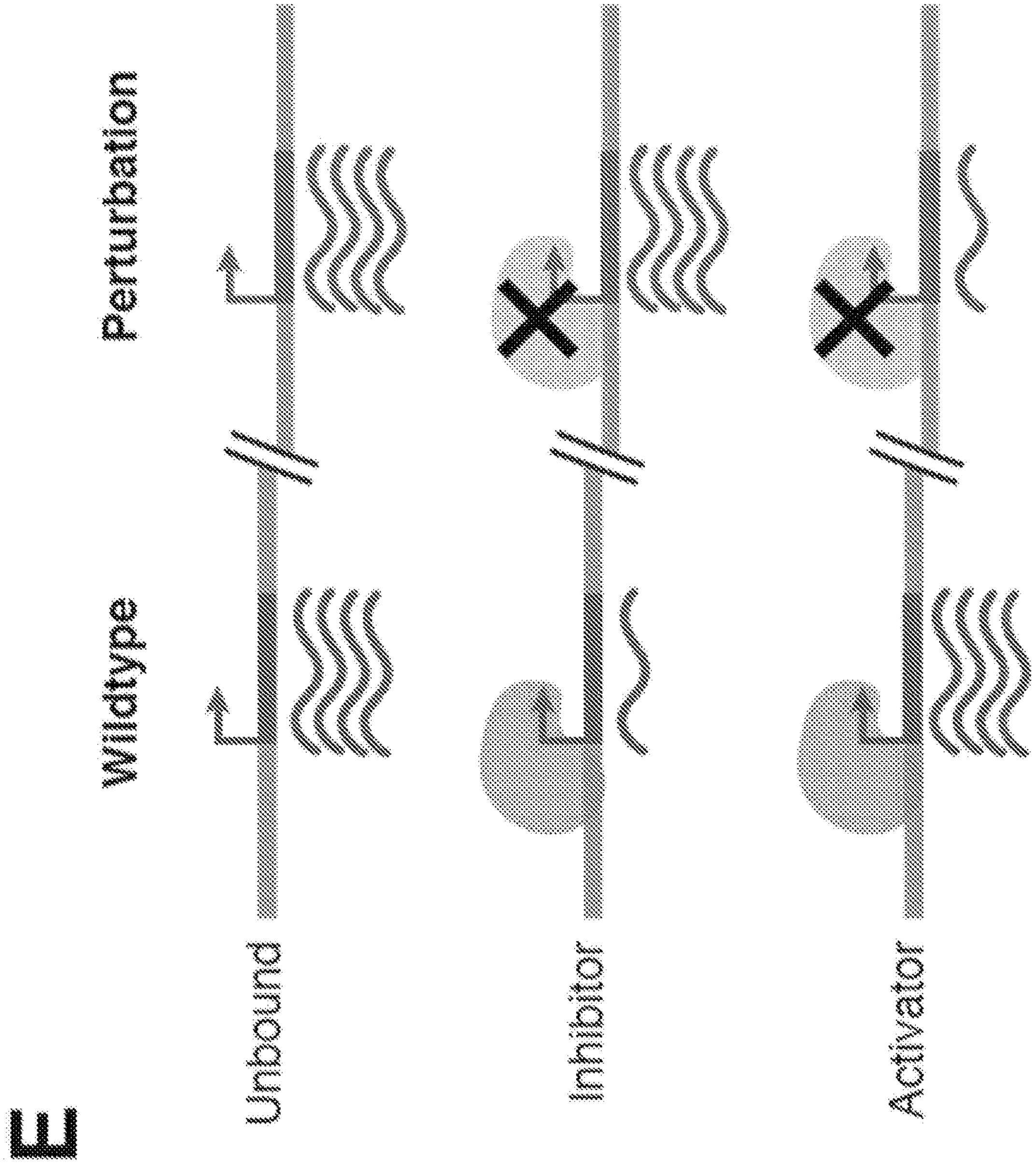

Example 10: The Genetic Circuit is Strongly Supported by the Binding Patterns of Transcription Factors To support the genetic model and relate it to underlying mechanisms, Applicants compared the effects of the individual factors to their binding patterns, which Applicants previously measured for 22 of the 24 TFs by ChIP-Seq at bulk populations of BMDCs at 0, 30, 60, and 120 min following stimulation with LPS (Garber et al., 2012). Applicants tested whether the bound targets of each individual TF (by ChIP-Seq) are more likely to be negatively or positively regulated by the TF in our model than genes that are not bound by the factor (FIG. 51E, Methods and Resources).

Figure 51F:
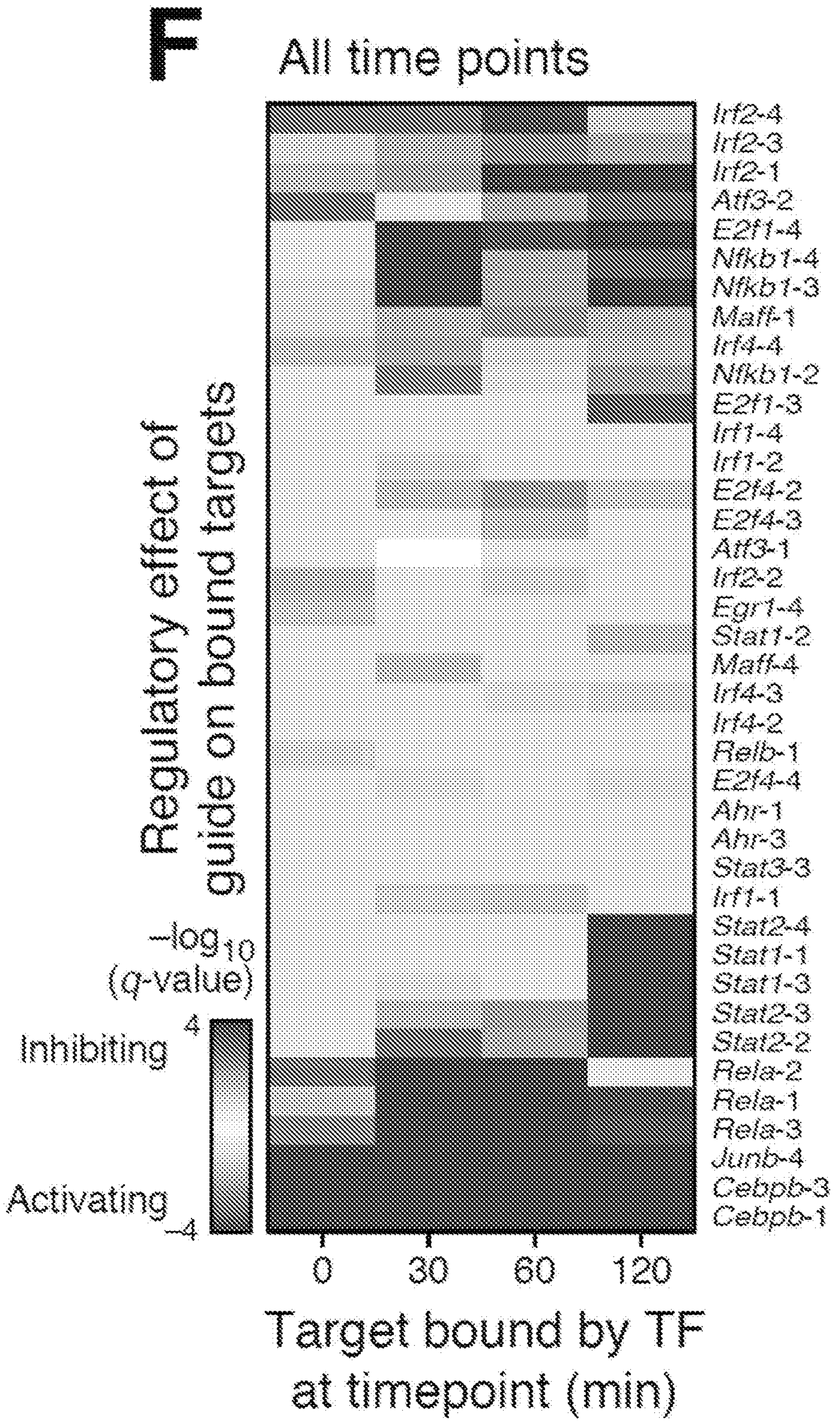

The negative effects of a TF perturbation on individual genes are strongly supported by corresponding binding of the TF to these genes' regulatory regions, and consistent with the TF's known role as an activator (FIG. 51F,G). In particular, genes bound by Rela and Cebpb, both prior to LPS stimulation and at each subsequent time point, are enriched for negative regulatory effects of the guides perturbing these factors. This effect on targets bound across the time course is consistent with the role of these factors as transcriptional activators and with the strong effect perturbing Cebpb and Rela on cell sub-populations at both unstimulated cells (FIG. 57B) and at 3 h post LPS (FIG. 50D). Furthermore, genes bound by Stat1 and Stat2 at 2 h post LPS, but not earlier, are enriched for negative regulatory effects of the guides perturbing these factors. This is consistent with the role of Stat1 and 2 as activators and with the fact that they only bind most of their targets later in the response (Garber et al., 2012).

Figure 58B:
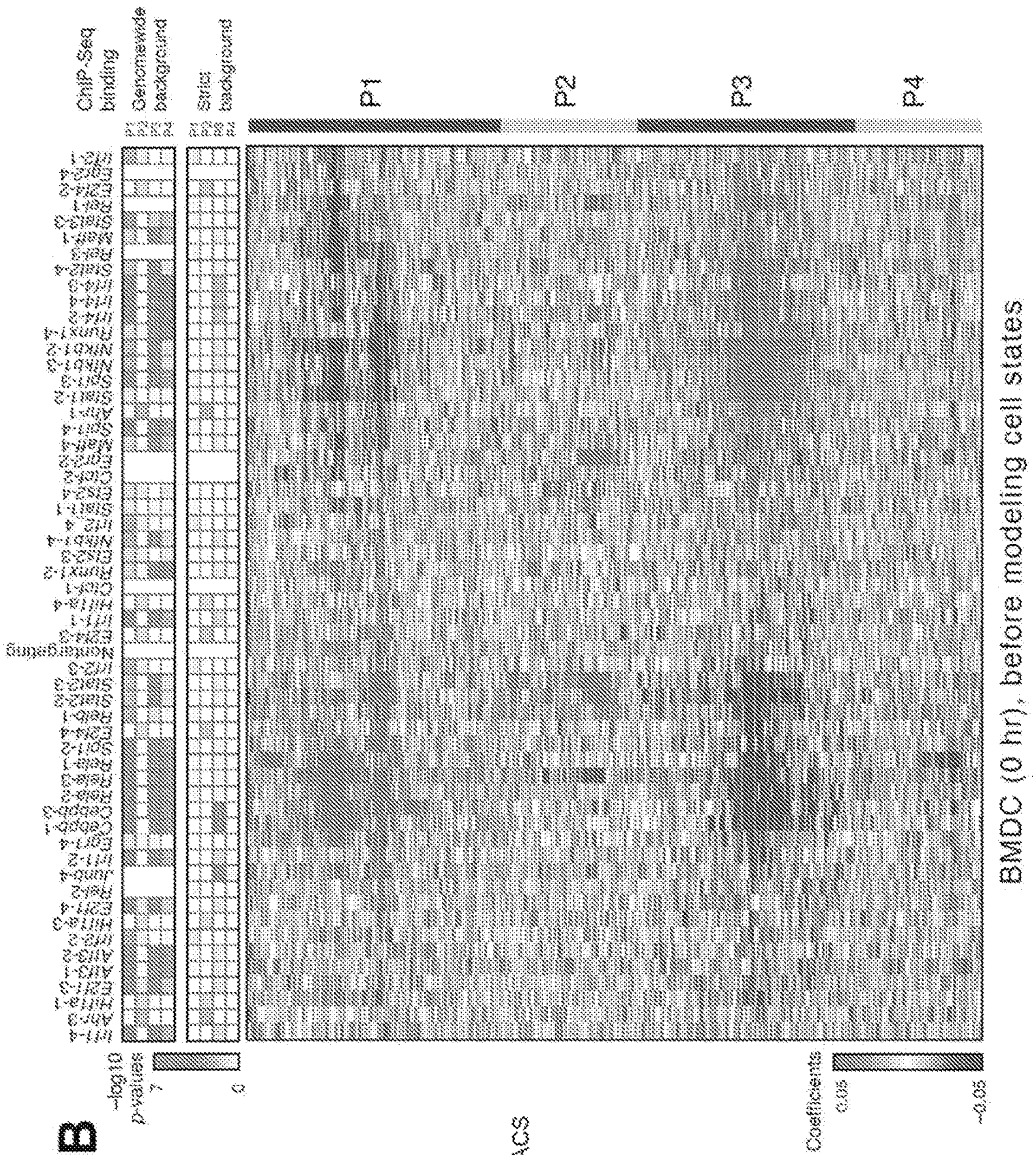

Similarly, the analysis strongly supports the role of factors as repressors, as the genes that they bind are enriched for positive regulatory effects of the perturbing guides (FIG. 51F,G). These include Irf2, Atf3, and Nfkb1. Irf2 is bound to its targets both pre- and post-LPS stimulation, and its perturbation indeed induces their expression even at time 0 (FIG. 58B), both in our current study and in an earlier one using RNAi (Garber et al., 2012). The targets bound by Atf3 and preferentially induced by its perturbation are enriched for anti-viral genes (e.g., $P<1.32\times10^{-6}$), directly supporting our model's prediction that Atf3 is a repressor of the antiviral response, and related observations in macrophages (Labzin et al., 2015), as discussed above. Finally, Nfkb1 (encoding p50) acts as a repressor for its known bound targets, suggesting that its major impact might be as a p50-p50 homodimer, a known transcriptional repressor that recruits HDAC-1 (Cartwright et al., 2016; Elsharkawy et al., 2010), rather than as part of the p65 (Rela)-p50 heterodimer, which is a transcriptional activator (Rela perturbation represses its bound target, consistent with p65's role in activating NFkB complexes.) Applicants return to the relationship between Nfkb1 and Rela when Applicants address genetic interactions below.

The distinct binding patterns of many of the TFs support their specific and direct associations with three of the regulatory programs: P1, P4 and P5 (FIG. 51A,B). Compared to a stringent background of only those genes in any of the programs (rather than a genome-wide background), genes bound by the M1 factors, Stat1 and 2, are enriched in P1 and P4 (both positively regulated by M1); genes bound by Atf3 and Irf2 (from M3) are enriched in P1 (negatively regulated by M3, and consistent with the role of the two factors as repressors; above); genes bound by Atf3 are also enriched in P4 (including key targets such as IL-6, where Atf3 is known to act as a repressor in the TLR4/LPS response in macrophages [PMID: 16688168]); Stat3 and Rela targets are enriched in P4, and Cebpb targets are enriched in P5, both programs positively regulated by their module M2. M4 factors Irf4 and Runx1, and to a lesser extent NFKB1, are enriched for bound targets in P4, and NFKB1 targets are also weakly enriched in its repressed target program P5.

Figure 51G:
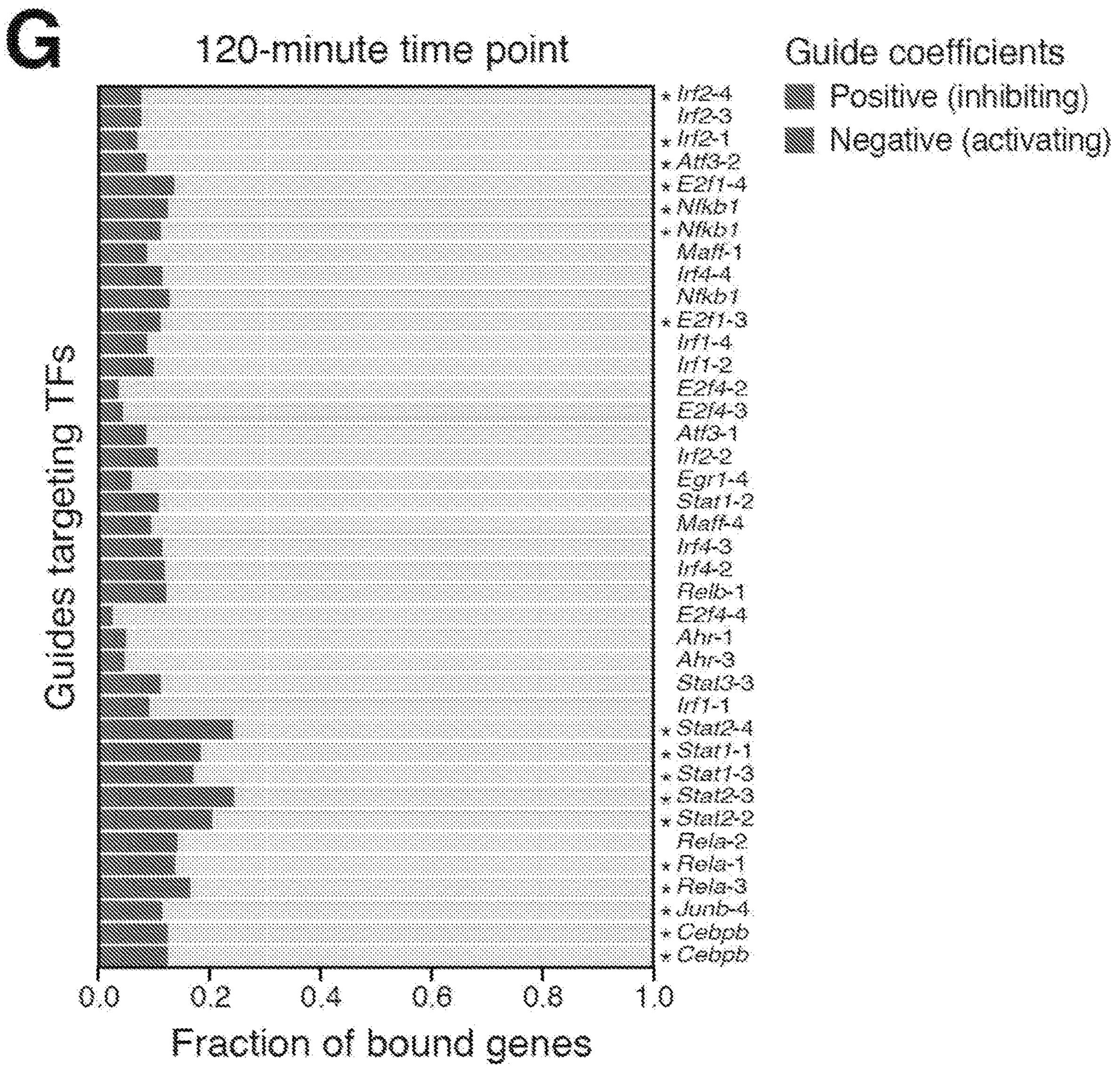
Figure 58C:
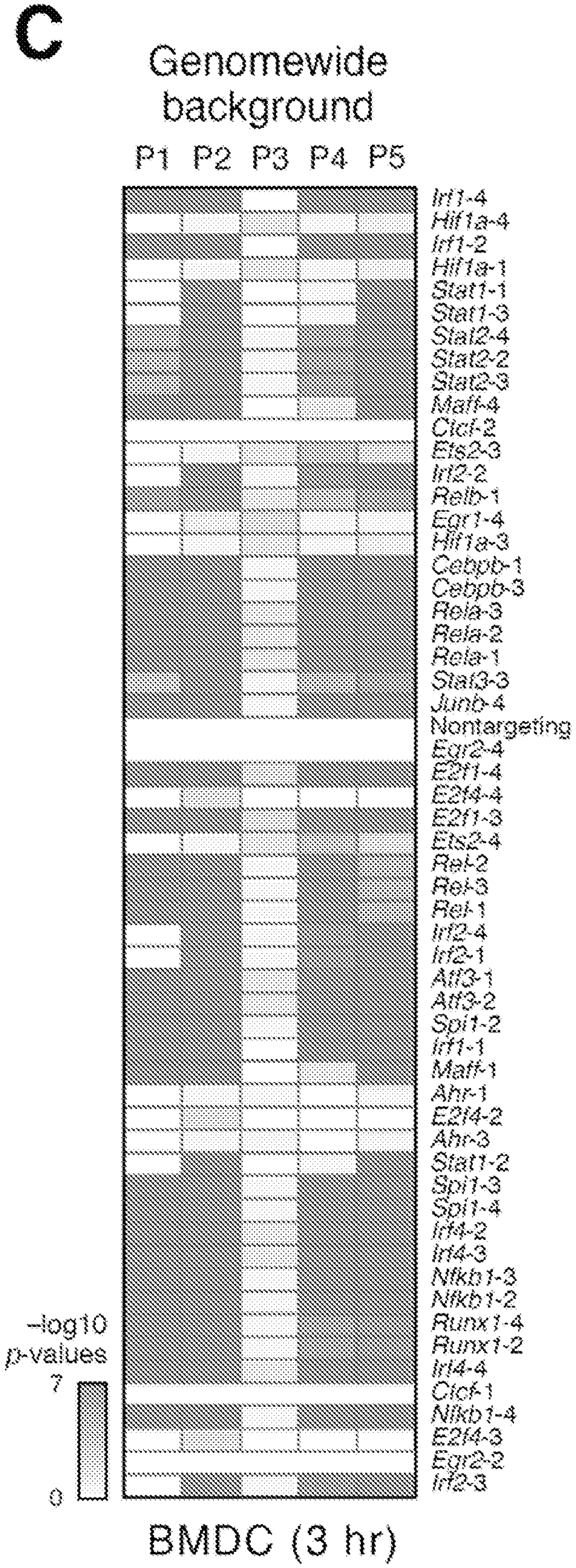

The remaining two programs do not show such enrichments for bound TF targets. The mitochondrial P3 program is not enriched for targets bound by any of the factors, even when comparing to a more lenient, genome-wide background (FIG. 58C). This supports a model where Stat1 and 2 do not regulate these genes directly, but possibly through another function, such as mitochondrial signals (Meier and Larner, 2014). This is further consistent with the fact that Stat1 and 2 perturbation affects the mitochondrial module even pre-stimulation, when Stat1 and 2 are not bound to promoters (Garber et al., 2012) and that they repress the module (while act as transcriptional activators). The P2 genes, however, are enriched for binding by many key factors when comparing to a genome-wide background genes (FIG. 58C). These include Cebpb and Spi1, but also many other factors that do not regulate the program. One possibility is that binding by some of these factors (e.g., Spi1 in M4) does directly activate this module. Another is that the P2 program and associated cell state/type are the outcome of the competing positive and negative effects of M2 and M4 on P4/P5, such that it is an alternative default or arrested state taken by the cell instead of the differentiated or responsive state P4/5. Finally, in some cases the bound targets of TFs (e.g., Rela, SPI1) are enriched (relative to the stringent background) in programs (e.g., P1) where their perturbation does not appear to have a substantial effect on the target genes (FIGS. 51A and 51G).

Figure 58D:
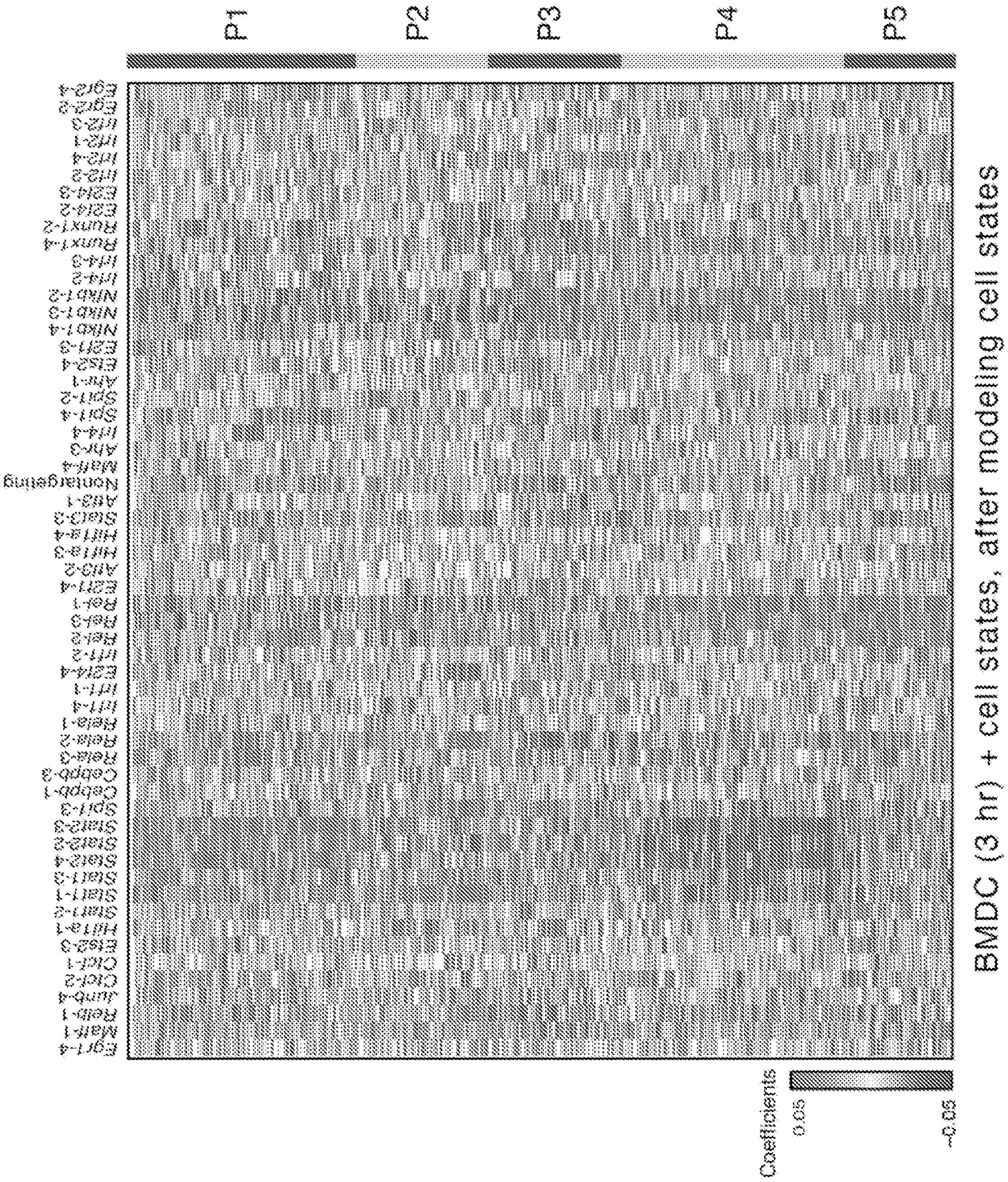

Example 11: TF-Specific Programs are Revealed Once Accounting for the Global Effects on Sub-Populations The presence of a small number of TF modules that share global effects on the one hand, and of factor-specific effects on the other hand, motivated us to distinguish global effects on the relative proportions of sub-populations, from effects of TFs that are independent of the context of a cell type or its global state. Applicants also reasoned that absent such distinction, the unique contribution of individual TFs may be masked by entire TF modules with similar global effects. Applicants therefore introduced the assignment of the perturbed cells into the seven states (subpopulations, FIG. 50C) as covariates in the model. Once Applicants explicitly modeled these global cell states, guides targeting the same TF grouped particularly tightly together (Stat2, Stat1; Irf2, NFkB and Irf4; Rel; Rela; Irf1; and Irf2 and Egr2; FIG. 50E,F and FIG. 58D), compared to their membership in larger modules of guides with similar global profiles observed when global states were not explicitly modeled (FIG. 50A,B).

Rather than emphasizing the regulatory system controlling the two major cell types/states (which were now reflected in the covariates), the resulting model (FIG. 58D) highlighted subtler effects unique to one or a few factors. For example, in this model, Applicants distinguished a positive regulatory effect of Runx1 and Ctcf, and a negative effect of Rel, on the expression of the antigen presentation (MHCII) system, which was not detectable before. Similarly, Applicants found a strong repressive effect of Irf2 (consistent with its role as a repressor) on the IFN gamma response. Importantly, the two models are complementary: the first emphasized global phenomena, and uncovered a densely interconnected transcriptional circuit that controls the mutually exclusive choice between two global states or types and allows to maintain both in a mixed population. The second controlled for this major phenomenon, and thus uncovered additional, more specific effects that are independent of (and may be masked by) global cell states.

Example 12: Genetic Interactions Between TFs Affect Gene Expression and Global Cell States The network Applicants infer from observing the impact of single gene perturbations is densely interconnected. Multiple TFs often impact the same gene and program (FIGS. 50 and 51), but can either have the same, opposite, or no effect on transcription when perturbed individually. These effects can be direct when the two transcription factors bind the target gene Applicants leveraged the fact that in each pooled Perturb-Seq experiment Applicants obtained cells containing more than one guide (e.g., FIG. 48D), to analyze the extent to which the observed transcriptional defect. (on individual gene targets or on global cell states) in cells where two genes are perturbed deviates from what Applicants would expect based on a linear supposition (FIG. 52).

Figure 52A:
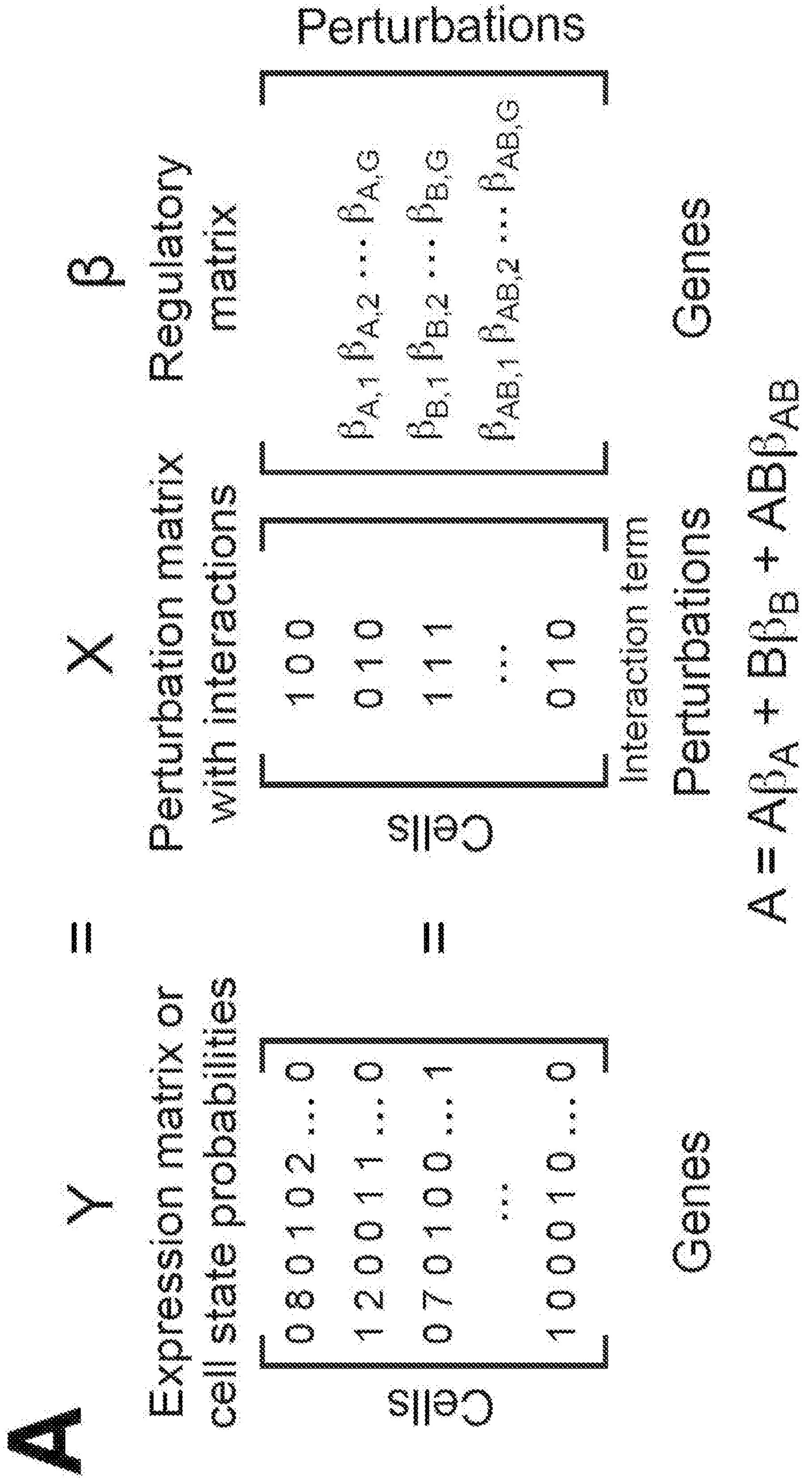
FIG. 52A-F illustrates dissecting genetic interactions between perturbations using Perturb-seq. (A) Extending the linear model framework to include higher order polynomial functions as the product of single covariates. (B) Interaction analysis on cell states for BMDCs at 3 h post-LPS. Heatmap shows the enrichment (red) or depletion (blue) of single, pair and triplets of guides (rows) in cells in each of seven states (as in FIG. 50C). (C) A three-way genetic interaction enhances cell state 2. Box plot shows the distribution of probabilities of assignment to cell state 2 marginally contributed by the individual perturbation of each of NFKB1, Stat2, and Rel, their pair wise interaction and three-way interaction. (D) Genetic interaction categories. A schematic illustrating the 27 possible schemes of genetic interaction between two genes (A,B), when considering all permutations of significantly positive (red), negative (blue) or no (white) regulatory coefficients marginally associated with each of the two individual guides or their combination. The four key categories of relationships (buffering, synergistic, dominant, and additive) are color coded on left. (E) The distribution genes in each of the 27 categories (rows) for every pair of perturbations assayed for interaction (columns). Key examples are marked on bottom. (F) Genetic interaction between Rela and Nfkb1 associated with co-binding. Shown are the marginal regulatory coefficients for Rela, Nfkb1 and their interaction term for each gene (rows) with at least one non-zero coefficient, sorted by the four key categories (color code, left). ChIP-Seq enrichment of individually bound and co-bound targets is shown for each of the groups (right). See also FIG. 59.
Figure 52B:
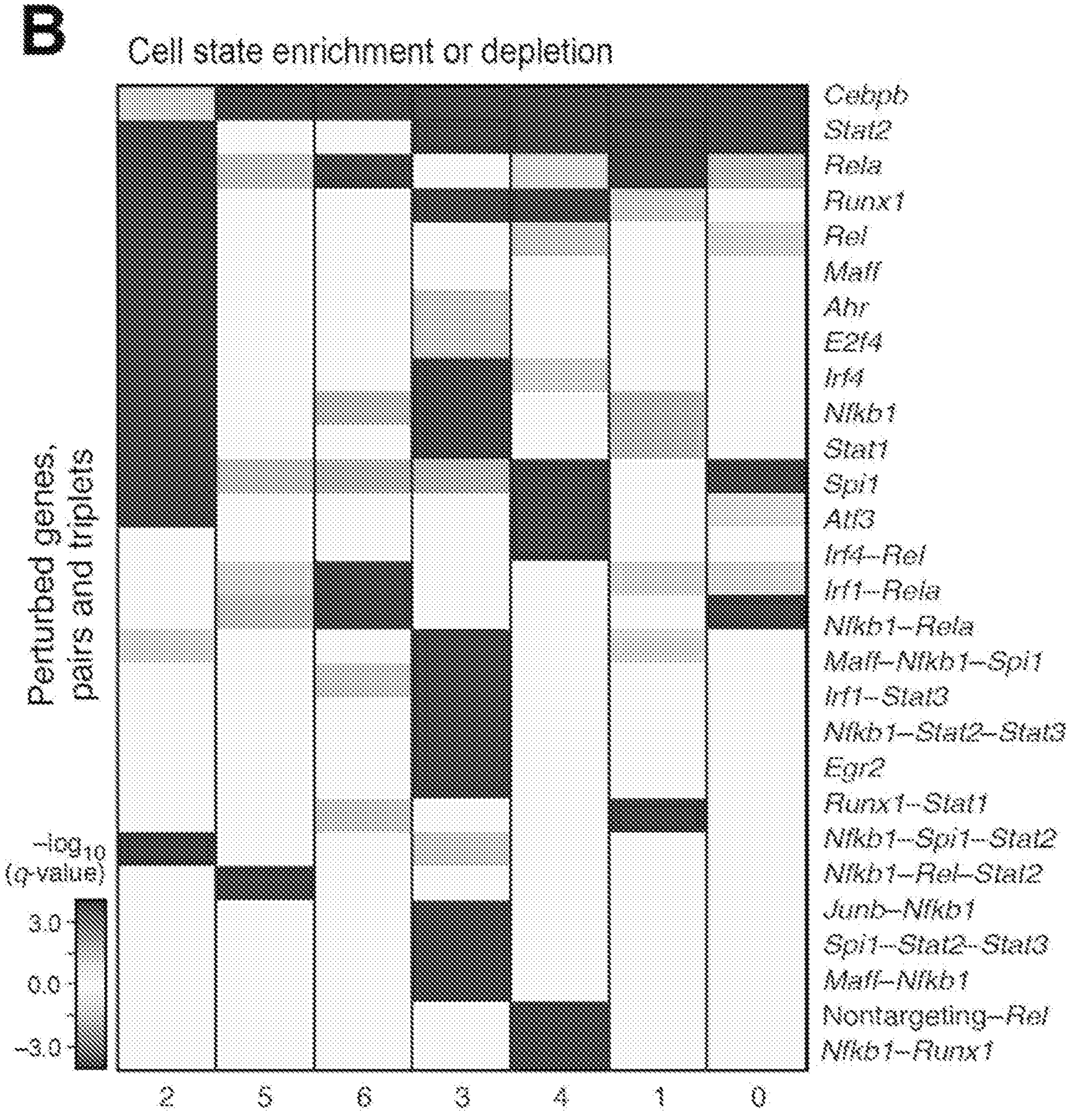

First, Applicants found several significant (non-additive) interaction terms for the extent to which perturbing more than one gene affected the probability of being in one of our seven cell states: that is the proportion of cells observed with the combination of guides was higher or lower than expected given the proportion of cells observed with the individual guides (FIG. 52B). For example (FIG. 52C), Runx1-NFKB1 are depleted from cells in state 4 (related to P4/5), even though each alone is either enriched (Runx1) or unchanged (NFKB1) in proportion in this state. This may be consistent with a recent report that co-expression of NFKB1 (p50) and Runx1 in macrophages enhances the expression of inflammatory genes (such as I11b from P5) [PMID 27573239]. Applicants even uncovered three-way genetic interactions, such as one between Nfkb1, Rel, and Stat2 (FIG. 52C), where cells with a 3-way perturbation have a higher probability of assuming cell state 2 (partially corresponding to the P2 program), even though neither cells carrying single nor double perturbations show a related effect. Two other 3-way combinations involving NFKB1 and Stat2 are each enriched in a different cell state: NFKB1-Stat2-Spi1 is enriched in cell state 1 (corresponding to P3, mitochondrial biogenesis), and NFKB1-Stat2-Stat3 is enriched in cell state 3 (corresponding to P5, the inflammatory response).

Figure 52C:
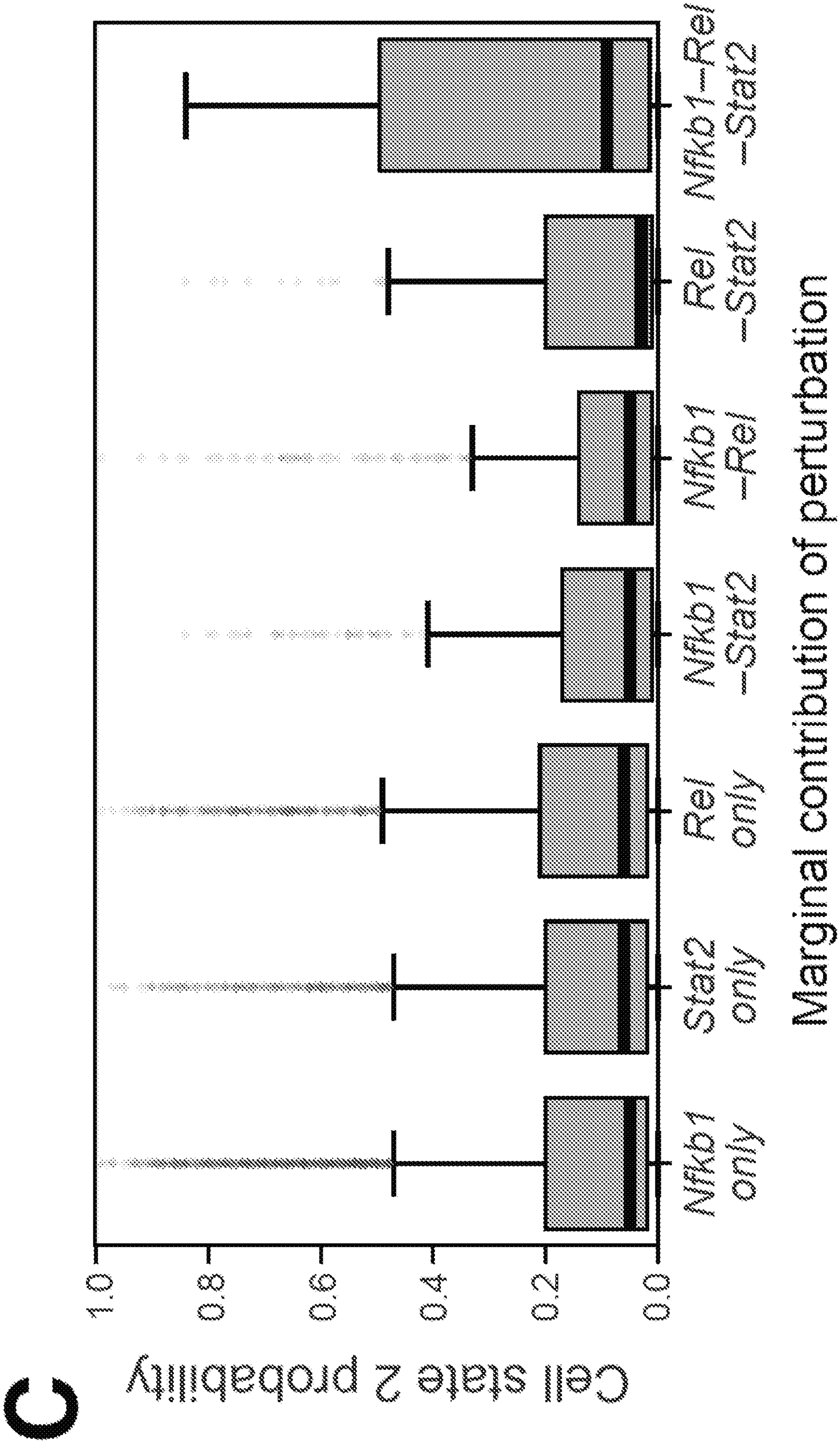
Figure 52D:
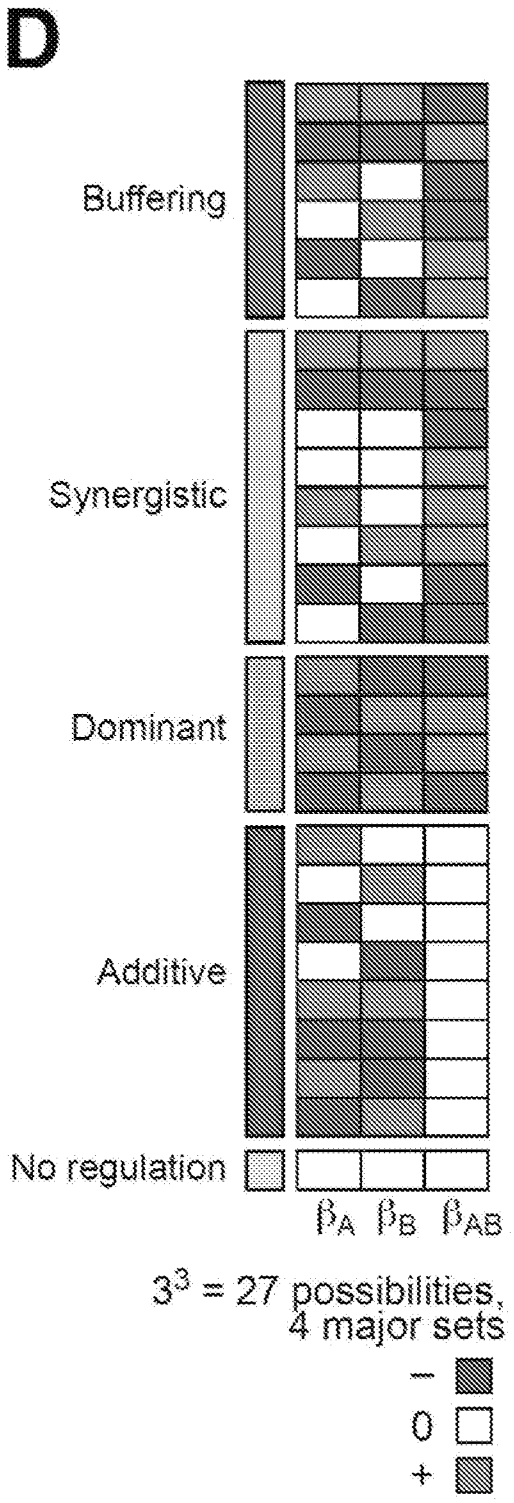
Figure 52E:
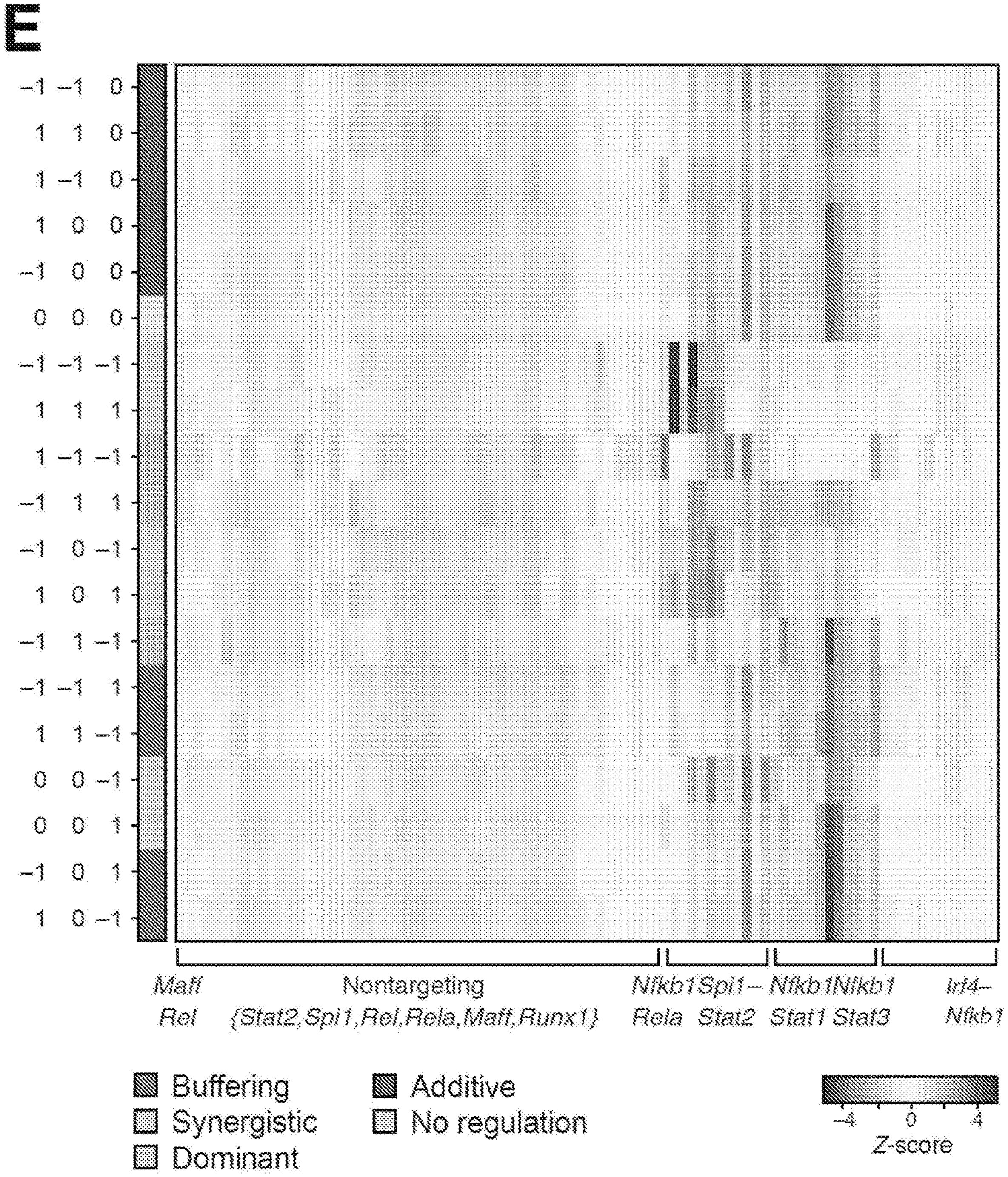

Next, Applicants assessed the effect of genetic interactions on the expression of each gene, by learning a new model, expanding the original one to include interaction terms with two genes per term (FIG. 52A, Methods and Resources). Then, Applicants stratified the genes by each of the 27 possible categories when considering the negative, positive, or no effect of each member of the pair and their interaction (FIG. 52D,E). The 27 categories in turn belong to four major classes: additive (no interaction), synergistic, buffering, or dominant (when the two factors have opposing effects, and the interaction term enhances one of them). Finally, Applicants assessed for each pair of TFs the relative proportion of target genes that are in each of the 27 categories (FIG. 52E).

While some TFs participate in genetic interactions that impact many target of genes, others mostly have additive effects. In particular, most TF pairs involving one of Runx1, Irf1, Irf2, or Irf4 has mostly additive effects. In contrast, interactions that include combinations of Stat1, Stat2, Stat3, Rela, Nfkb1 and Spi1 tend to be highly enriched for interactions: they had non-additive effects on a large proportion of their targets. Surprisingly, only a subset of these, all involving Nfkb1 (Stat1-Nfkb1, Stat3-Nfkb1, Rel-Nfkb1, Spi1-Nfkb1) contain buffering interactions (FIG. 52E).

Figure 52F:
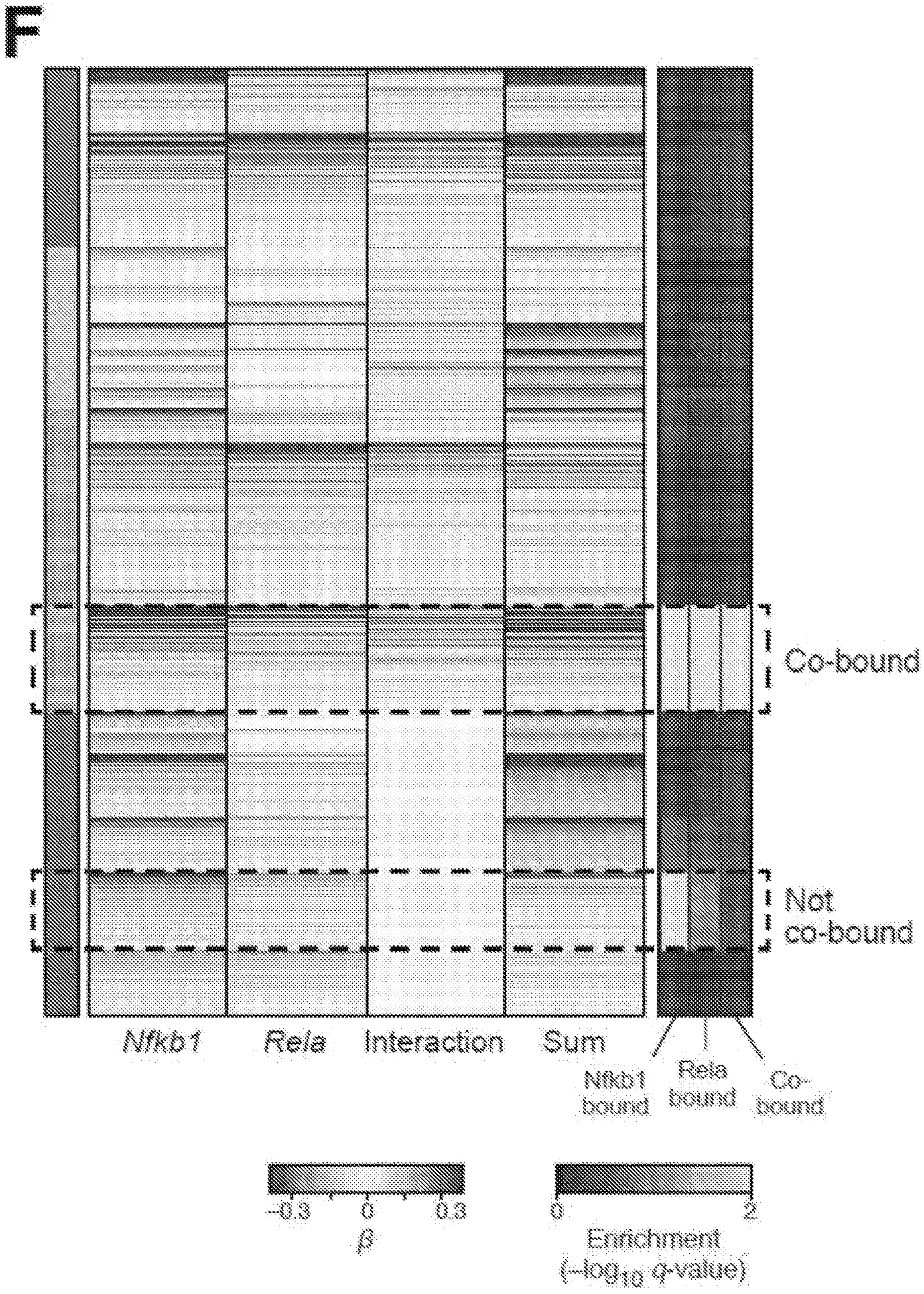
Figure 59:
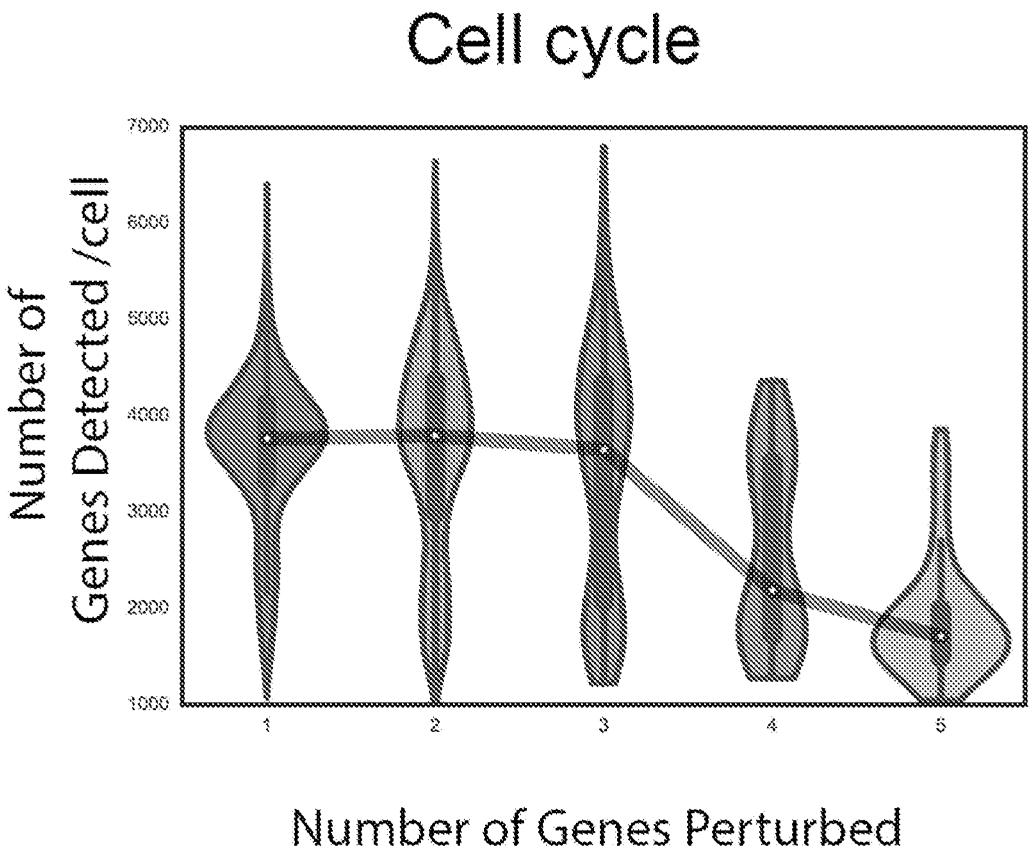
FIG. 59 illustrates the genetic interactions for K562 TFs.

The gene-level analysis of genetic interactions allows us to relate the presence (or absence) of interactions to the molecular mechanisms by which TFs act on their targets, as is illustrated in the case of NFKB1 and Rela (FIG. 52F). As noted herein, NFKB1 and Rela individually have opposing effects on the genes in both P4 and P5 (the programs reflecting the response to intracellular parasites and the inflammatory response): NFKB1 acts as a repressor, and Rela as an activator, ChIP-Seq profiles indicates that these affected genes are directly bound by the respective factors. The model with interaction terms shows that this group of genes (FIG. 52F, hatched boxes) splits in two: in some genes, the joint perturbation of Rela and NFKB1 leads to an additive effect (no interaction: final gene expression is a sum of the two opposing effects), in the others, there is a dominant interaction, such that the observed expression reflects the effect of NFKB1 over that of Rela. While both sets belong to the same broad programs (FIG. 52F, hatched boxes), and both are enriched for ChIP targets of both NFKB1 and Rela (FIG. 52F, right panel), only the set with the dominant interaction are co-bound by both factors (FIG. 52F, right panel). Applicants observed a very similar phenomenon—where genetic interactions between two TFs is present only in those genes that they co-bind (but not in other genes from the same program, despite their similar individual effects)—for additional pairs of TFs (e.g., buffering interactions for Runx1-Rel and Irf4-Nfkb1 for P4 and P5 targets) (FIG. 59).

Example 13: Global Transcriptional Modules and Specific Effects of TFs in K562 Cells To explore the generality of our approach, Applicants also performed Perturb-seq targeting TFs in K562 cells, a rapidly proliferating cell line that is not synchronized by a stimulus. The TFs were chosen to be not essential for cell viability, but are known to bind targets in K562 cells. Fitting a linear model without cell state co-variates, the TFs partition into two global modules by the correlations in their coefficients: one including EGR1, CREB1, and ETS1, and the other including GABPA, NR2C2, and ELF1, as well as a distinct response to YY1 (FIG. 53A and FIG. 60). Although some guides partitioned inconsistently between the two modules, there was an overall significant consistency between guides to the same gene, both within an experiment (FIG. 60), and across experiments conducted at different time points (FIG. 53E), as tested by growing a subset of the cells used for the promoter experiments an additional six days (FIG. 53E). (Such a later time point is not possible to study in BMDCs, a primary short-lived cell culture.)

Figure 53C:
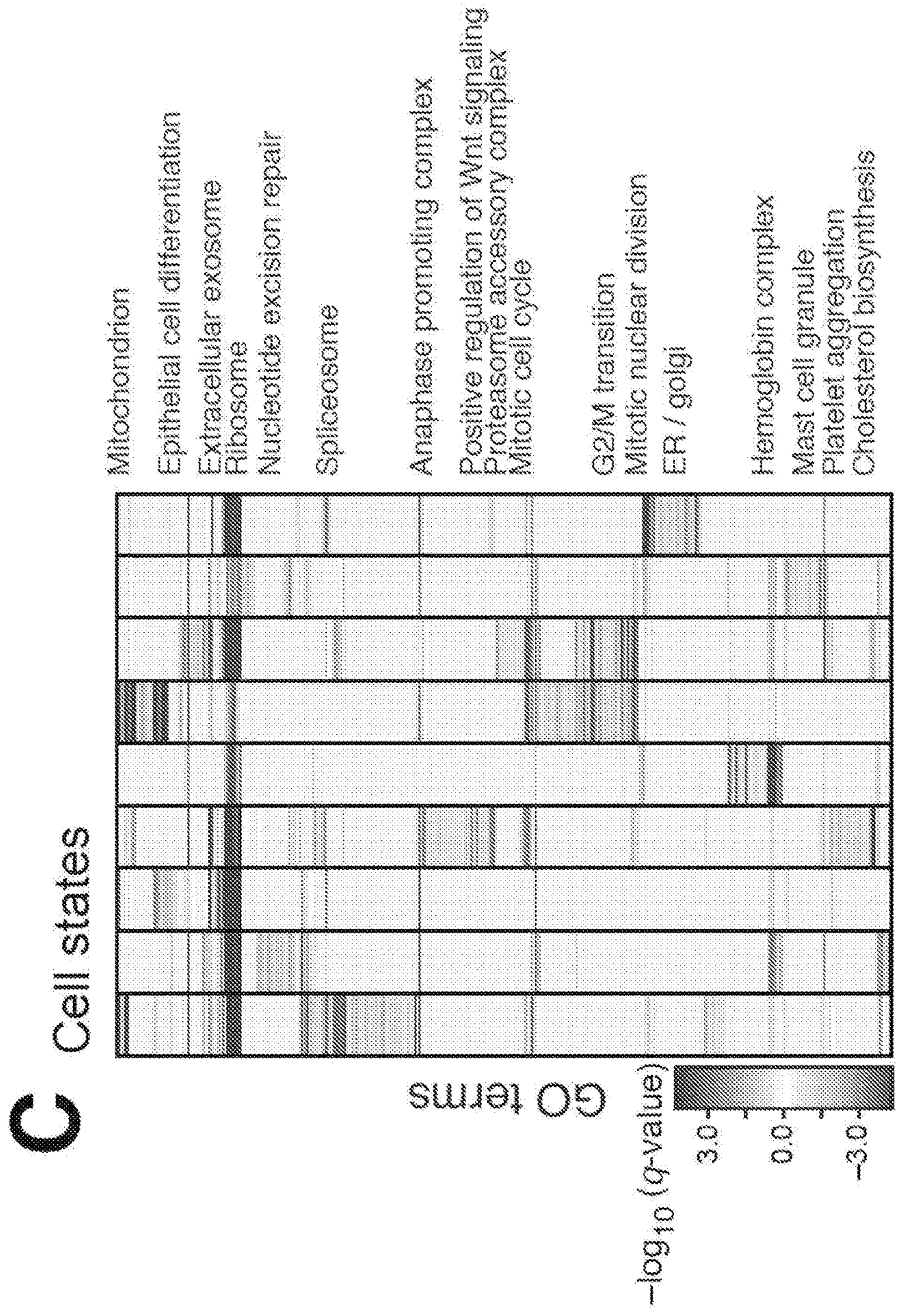
Figure 53D:
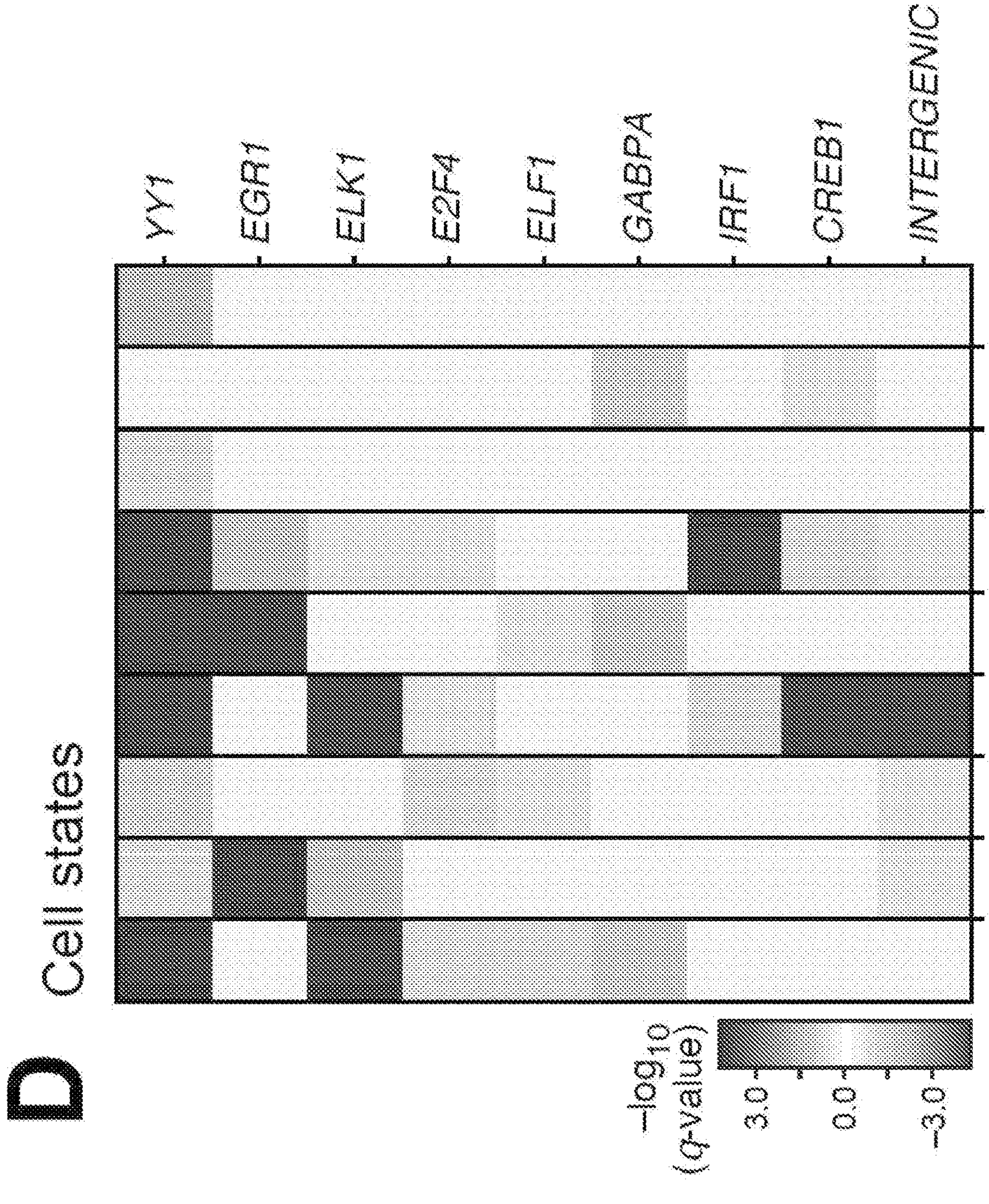
Figure 53G:
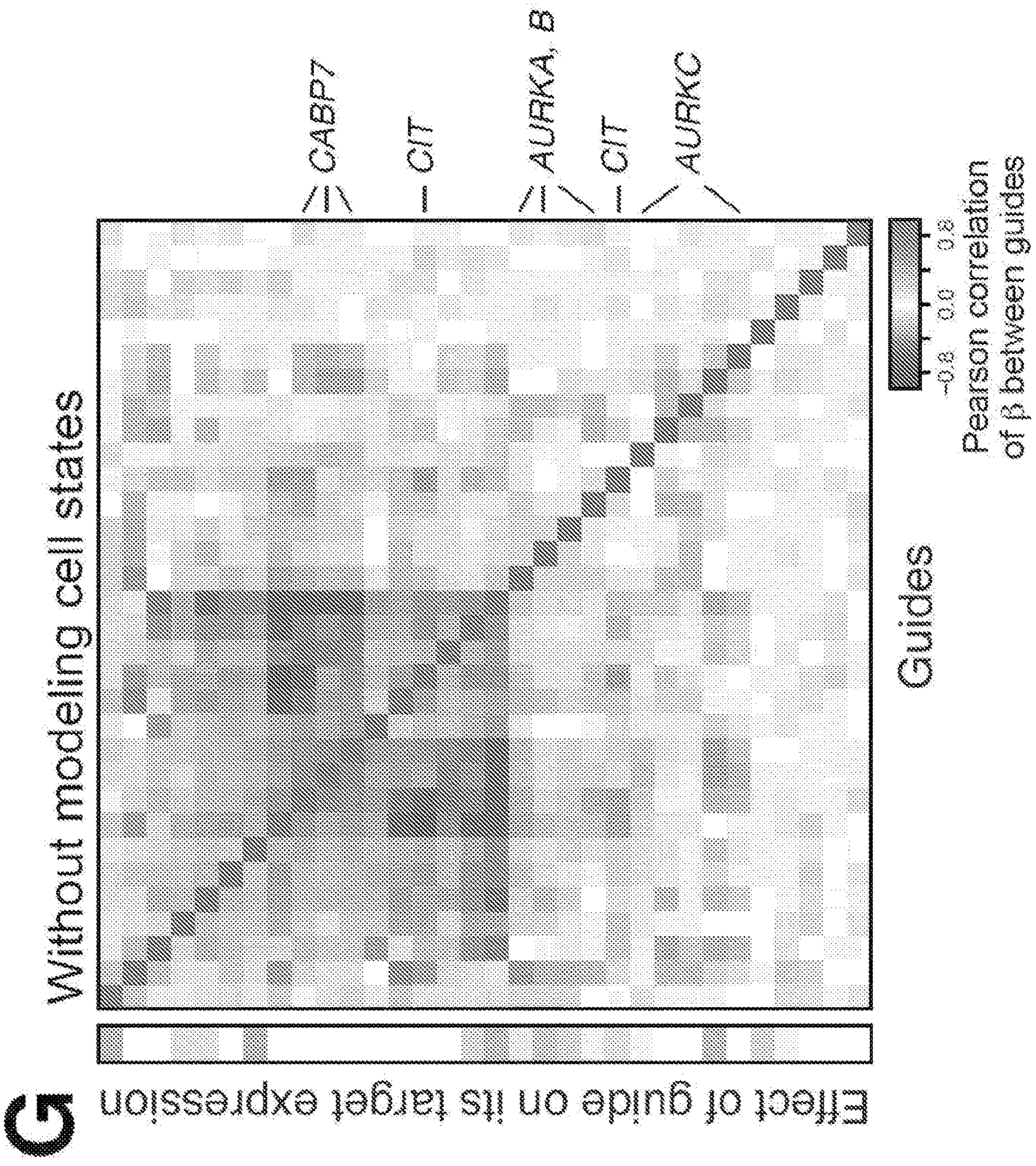

As in BMDCs, Applicants explored the role of global cell states. Initial unsupervised clustering partitioned the cells to 9 "states", reflecting biological processes such as G2/M transition, mitotic cell cycle, anaphase promoting complex, the ribosome, cholesterol biosynthesis, and hemoglobin complex (FIG. 53C). Applicants tested each perturbation for enrichment in each state (FIG. 53D) and found significant associations. For example, cells perturbed in EGR1 are depleted from State 6, enriched for hemoglobin, consistent with EGR1's known role in this process (PMID 19597182). In another example, cells perturbed in YY1 are enriched from State 5 (enriched for cholesterol biosynthesis genes), consistent with the role of YY1 as a repressor of key genes in this process (PMID: 17925399, 26310456, 11145566).

Next, Applicants fitted a model that accounted for cell states. Applicants reasoned that, unlike BMDCs, many of the states are in fact continuous (e.g., phase in the cell cycle) rather than discrete (e.g., cell types). Applicants therefore performed PCA on the unperturbed dataset, scored the cells from the Perturb-Seq experiment against those principle component (PC) scores, and introduced these state PC scores as covariates to the linear model. In the resulting model (FIG. 53B) the two global modules are far less correlated, but individual guides to the same gene are much more consistent in their effects (FIGS. 53B,F), suggesting Applicants have controlled for the shared program. This higher consistency is also observed when comparing across experiments and time points (FIG. 53F), suggesting that TF-specific effects can be reproducibly identified even if global states and cell proportions change over time.

Applicants used the model that accounts for cell states to explore the individual functions of TFs. For example, Applicants find a distinctive repression of mitochondrial functions upon perturbation of GABPA (FIG. 60Y) consistent with its role as a required regulator of mitochondrial biogenesis ($P<2.05\times10^{-9}$) (PMID 24958105) and weakly supported by ChIP-Seq binding [REF]. YY1 perturbation represses oxidative phosphorylation ($P<1.11\times10^{-11}$) (known to be regulated by YY1; PMID 12525853, and enriched for its binding by ChIP-Seq [REF]) and induces an NFkB innate immune response ($P<2.82\times10^{-11}$) (PMID 22065573).

Example 14: Perturbations of Cell Cycle Regulators Reveal Distinct Profiles Associated with Similar Fitness Effects and Mitotic Arrest Individual cells in a rapidly dividing cell line, such as K562 cells, naturally vary in their cell cycle state. This continuous spectrum is readily detected in scRNA-seq profiles (Buettner et al., 2015; Kowalczyk et al., 2015; Macosko et al., 2015). Factors that impact the cell cycle can be discovered by their impact on morphological features or key marker genes, but the fact that perturbation of two genes has the same overall phenotypic endpoint (e.g., arrest at a particular phase) does not necessarily reflect identical underlying mechanisms.

To address this question, Applicants targeted in K562 cells 13 genes (with 33 guides) that were previously identified by a mitotic arrest phenotype in a genome-wide arrayed imaging screen in HeLa cells (Neumann et al., 2010) (Table S1). The genes were associated with diverse phenotypes, ranging from a reduction in migration speed to “grape-like” cells with clusters of micronuclei (FIG. 60, reproduced from (Neumann et al., 2010)).

First, Applicants used the preponderance of cells with each PAPI to determine the fitness effects of each gene. Unlike BMDCs, where fitness effects are mild, K562 cells are rapidly proliferating and our cell cycle targets are known to affect proliferation (Neumann et al., 2010). Applicants assessed the number of cells carrying each PAPI relative to their expected frequency given the input pool with either of two complementary Bayesian probabilistic models that compute the expected probability of each guide in the resulting cell population (Methods and Resources). Applicants identified a strong proliferative advantage conferred by targeting PTGER2, CABP7 and CIT, while a subset of guides targeting genes such as AURKA, TORIAIP1, and RACGAP1 show proliferative disadvantage (FIG. 53I). (Similar analysis of the TFs in K562 cells showed a proliferative disadvantage of ELK1 and EGR1, whereas—as expected—there were few fitness effects in DCs). Surviving cells may be enriched for in-frame mutations or off target (yet compensatory) effects.

Applicants next asked whether these fitness effects can be explained by the genes and processes regulated by the perturbation of each gene. Applicants collapsed all guides for a given gene into a single covariate to increase our ability to discern the true impact of a gene. Applicants found distinct processes affected by those factors with positive and negative effects on fitness, but also two different routes to increased fitness. First, supervised analysis using signature gene sets for the cell cycle phases (Macosko et al., 2015), showed that perturbation of the three Aurora Kinase genes (A, B, and C) and of TORIAIP1 (which decrease fitness) are all associated with an increase in G2/M and M signature expression (FIG. 53H). Conversely, perturbation of CABP7 and PTGER2-which increase fitness—are associated with a strong opposite effect: decrease in G2/M and M signature expression and increase in the M/G1 signature (FIG. 53H). Notably, perturbation of CIT, which also increases fitness, has an increase in G1/S and S cell cycle states, highlighting a different route to an overall phenotype of increased fitness.

Furthermore, signature-free analysis of our perturbation by our gene-level model (FIG. 60) shows that perturbation of CABP7 strongly induces a program of mitochondrial respiration and biogenesis ($P<1.59\times10^{-11}$), NFkB signaling ($P<2.45\times10^{-6}$), and mitotic division ($P<2.45\times10^{-9}$), consistent with the fitness advantage. Perturbation of CIT and PTGER2 repressed these global programs and instead induced the expression of genes of other phases, especially 11 histone genes induced by CIT.

Notably, the overall partitioning of factors based on their global effects on gene expression also mostly followed their previous reported groupings based on cell biological features in HeLa cells (FIG. 60, reproduced from (Neumann et al., 2010)): (1) CIT, PTGER2 and RACGAP1 (binuclear phenotype); (2) Cenpe and Arhgef17 (grape-like phenotype and mitotic delay); and (3) Aurorak kinases A, B, and C (proliferation and migration defects). A notable exception is CABP7, which despite a similar binuclear phenotype to that of CIT, PTGER2 and RACGAP1 has a distinct transcriptional phenotype, as described above (FIG. 60).

Figure 60A:
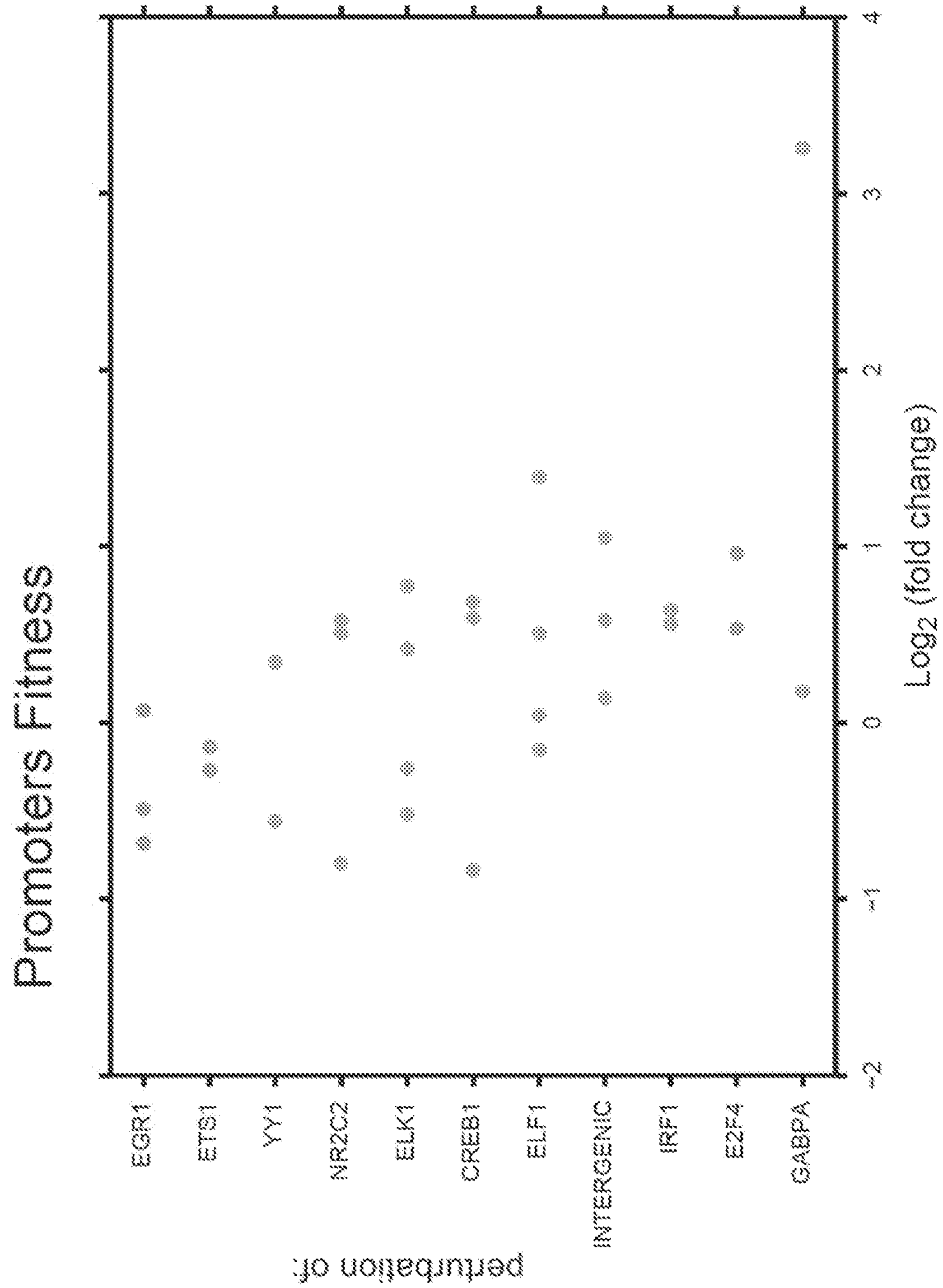
FIG. 60A-D illustrates additional analysis of the role TFs and cell cycle regulators in K562 cells. (A) Assessing potential fitness effects of TF perturbations in K562 cells. Shown is the distribution of fold changes of sgRNA abundance compared to the input abundance (X axis) for the guides (dots) targeting each gene (Y axis). (B) TF control of transcriptional programs in K562 cells. Shown is the regulatory coefficient of each guide (labeled columns) on each gene (rows) based on a model that either does not (B) or does (C) account for cell states as co-variates. Guides and genes are clustered by the similarity of their profiles. Target programs are marked with key enriched annotations. Green-white heatmap shows the enrichment in bound targets of each TF based on ChIP-Seq in each program (rows) based on either a lenient, genome-wide background (top) or a strict background (bottom) restricted only to the genes in the programs. (C) Cell cycle genes in our screen. Shown is the cell biological classification of our genes (Figure reproduced from Neumann et al). (D) Effects of perturbing cell cycle genes on transcriptional programs in K562 cells. Plot as in (B) but for the cell cycle regulators.
Figure 60B:
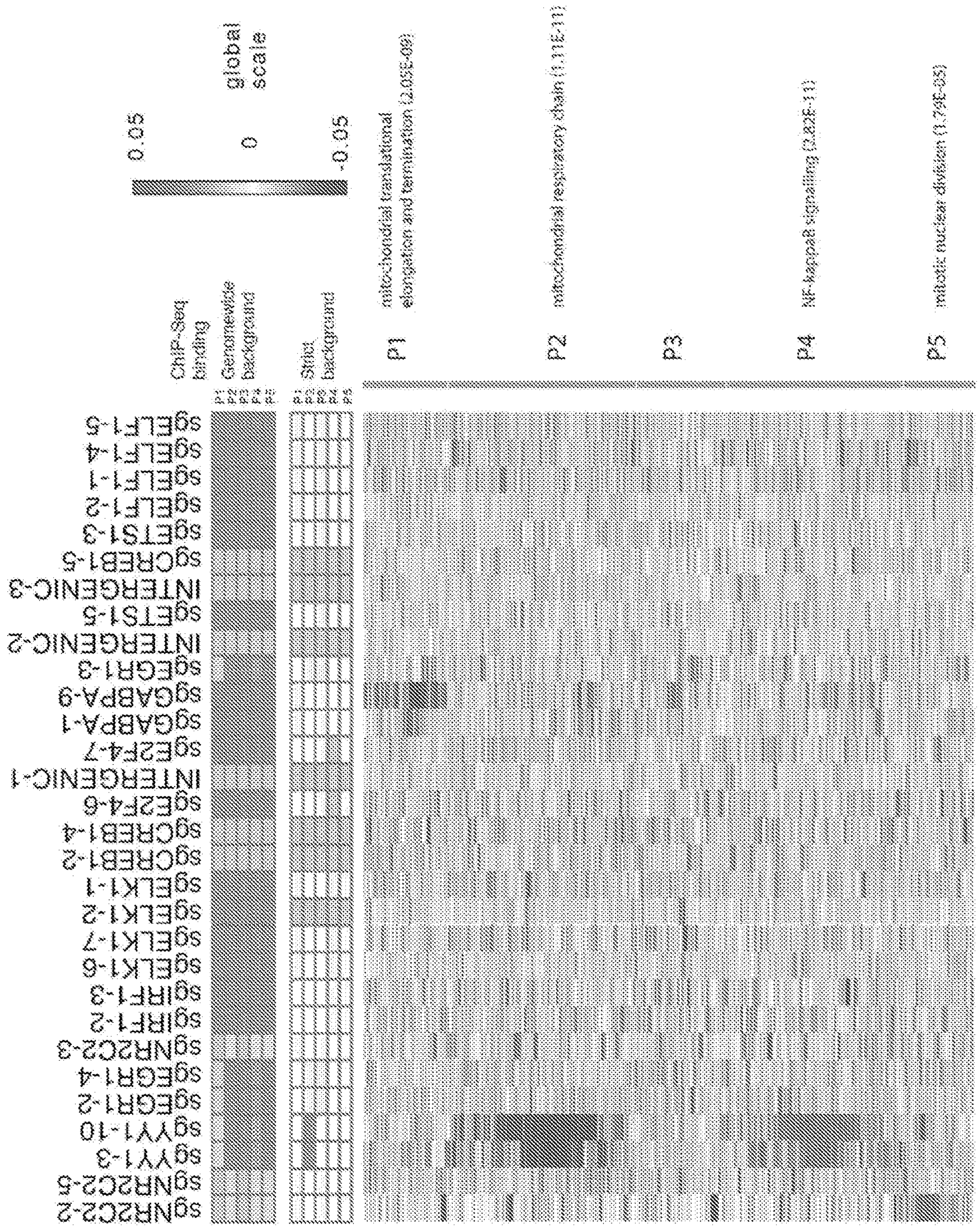
Figure 60C:
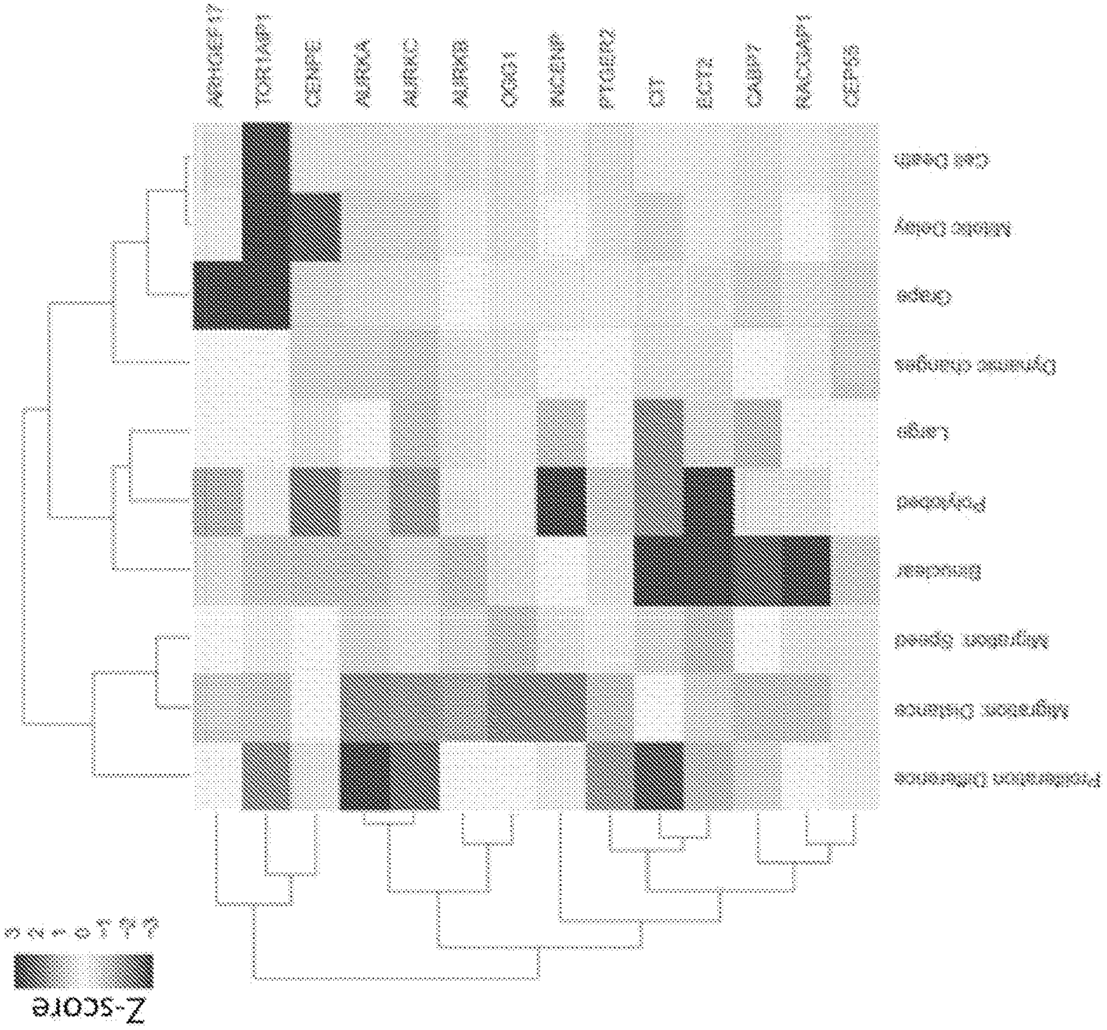
Figure 60D:
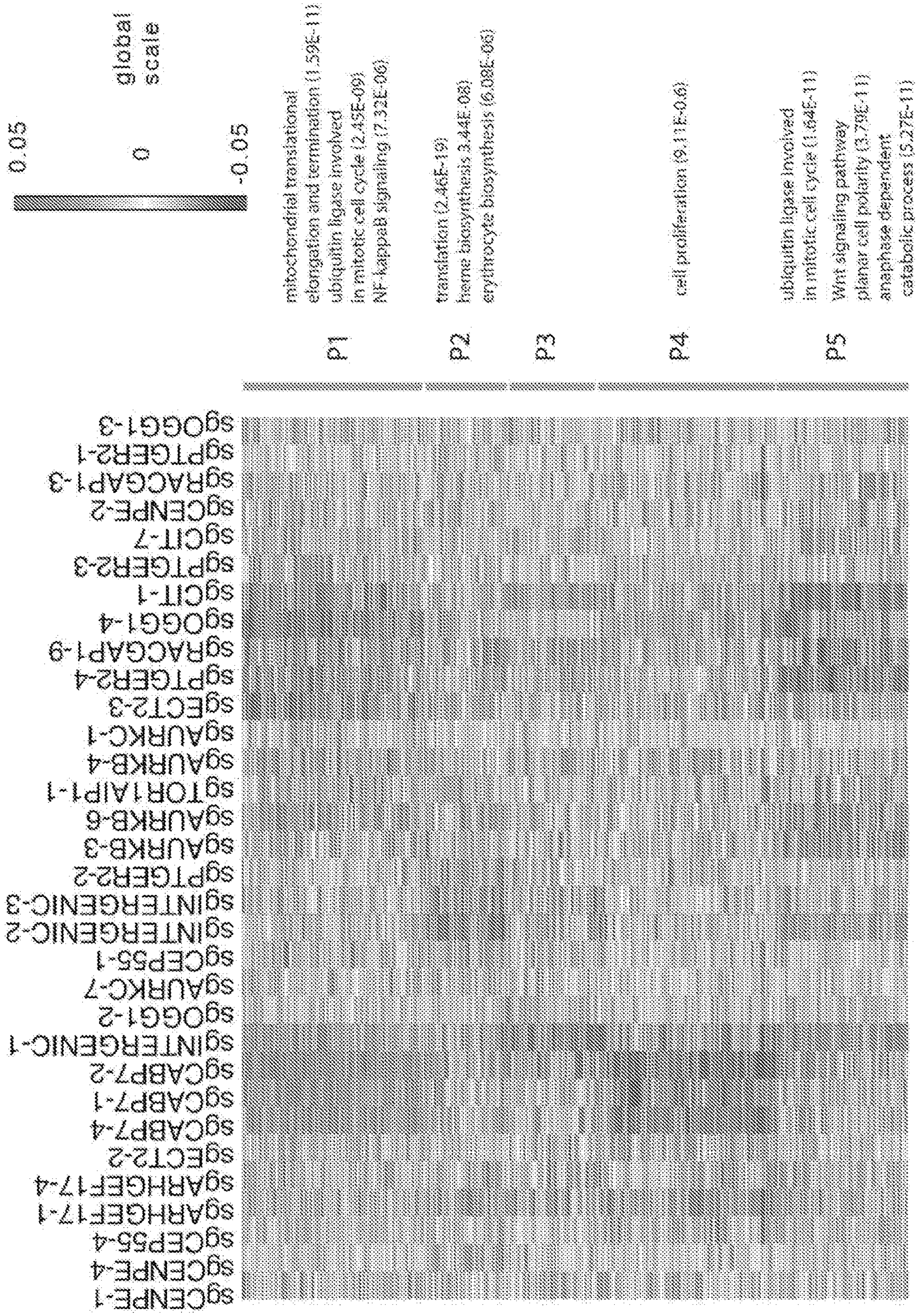

Finally, when examining the nonlinear effects associated with multiple perturbations, Applicants found several significant interactions (FIG. 60), and noted a significant nonlinear decrease in genes detected when more than three cell cycle genes are perturbed (FIG. 60D).

Fitness considers individual guides and synthetic lethality (Livnat model). The effect on G1/S, G2/M cell states is shown (FIG. 51C), “virtual FACS” plus Livnat model. FIG. 51D shows the underlying transcriptional patterns, such that there is a correlation between imaging phenotype and transcription phenotype, such that there is a different expression signature with same imaging phenotype.

Example 15: A Brief Guide to the Miserly: The Effects of Perturbations on Gene Signatures and PC Scores can be Recovered with Substantially Lower Numbers of Cells and Reads The regulatory coefficients associated with the perturbations are highly structured in each of the studied systems (FIGS. 50-53), consistent with the modular organization of genes regulatory systems (Heimberg et al., 2016; Kemmeren et al., 2014; Sokolov et al., 2016). Thus, sets of target genes are affected in coherent ways across sets of perturbations. Satisfyingly, these gene sets are enriched for members of coherent biological pathways (FIGS. 50-53).

Applicants thus reasoned that recovery of effects at a pathway level should be more robust—and could be detected even if a substantially smaller number of cells is analyzed and/or a smaller number of reads is sequenced per cell. Such a scenario would be highly favorable for researchers who may often desire to employ Perturb-seq to determine key phenotypes (as assayed by their signatures) over fine regulatory connections (such as the targets of each TF, or the wiring and logic of a TF circuit). Applicants thus quantified our ability to detect gene level regulation (FIG. 54A) vs. signature or state level regulation (FIG. 54B), when Applicants down-sample cells and reads/cell across our dataset (Applicants had sequenced each library to near-saturation to permit such analysis; Methods and Resources). In particular, Applicants considered signatures quantified in two ways: (1) cell state changes, as defined by our clusters on unperturbed cells; and (2) previously described pathways, such as the antiviral response in BMDCs (Shalek et al., 2014) (Methods and Resources).

Applicants found that the number of cells and reads needed to detect signature level effects (FIGS. 54B, 61B-H) is indeed substantially lower than that needed to detect individual effects on target genes (FIG. 54A, and FIG. 61I-L). In fact, there is almost no change in the observed effects on signatures as Applicants down-sample to approximately half the transcripts and cells in our full dataset (148 cells/perturbation (32-671); 780 transcripts); and a Spearman correlation of 0.5 between the effects is still discernable with just 10% of the cells and 25% of the transcripts (30 cells/perturbation (6-134), 390 transcripts). In contrast, the scale required to reach confident estimates in transcriptional effects on individual target genes is higher (~100-200 cells, 500+ transcripts). These estimates—approximately consistent across our three systems (primary cell and cell lines; TFs and cell cycle regulators)—should provide helpful guidelines for future researchers using Perturb-seq.

Example 16

Figure 66:
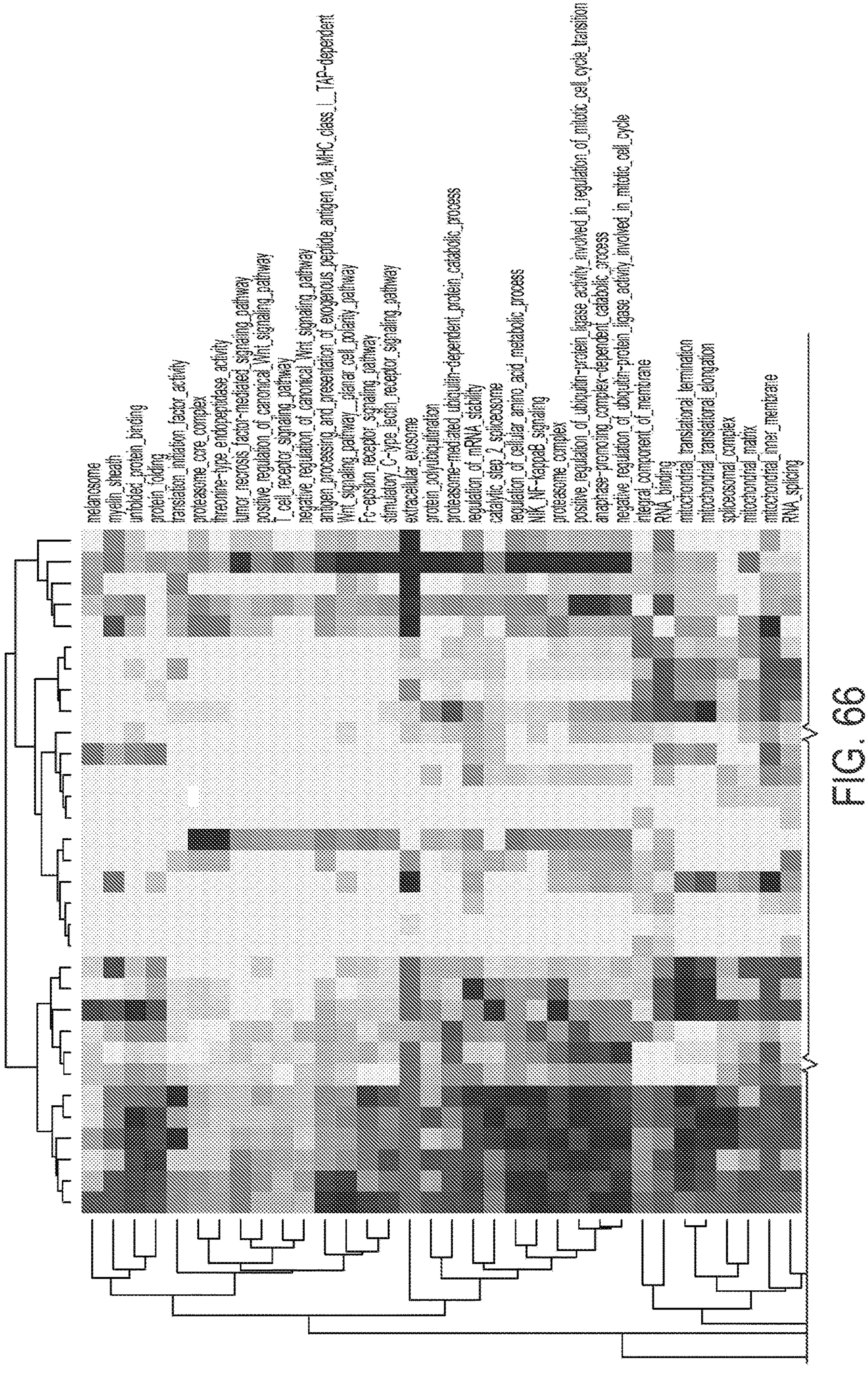
FIG. 66 illustrates GO terms associated with the following sgRNAs.
Figure 66:
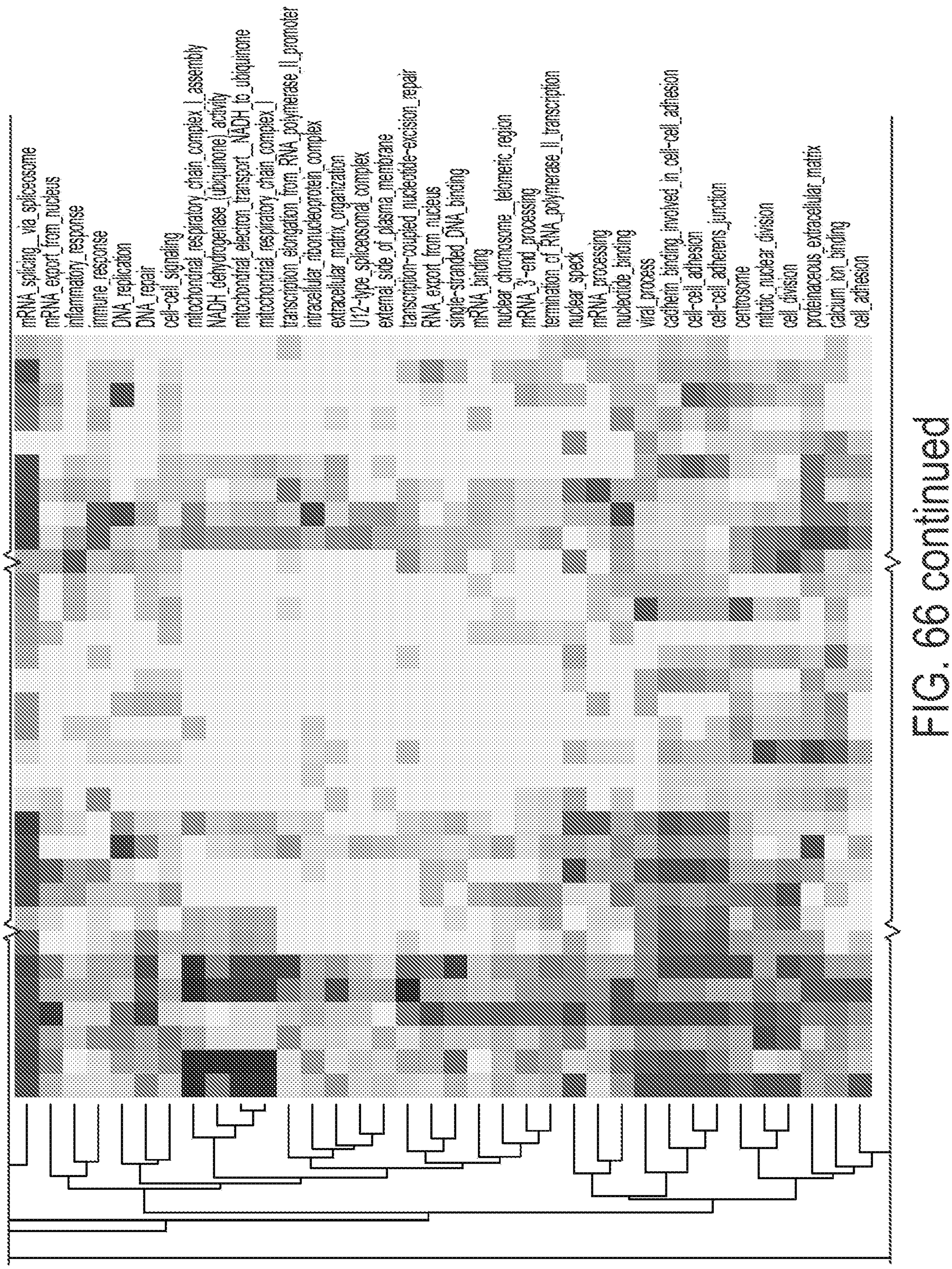
Figure 66:
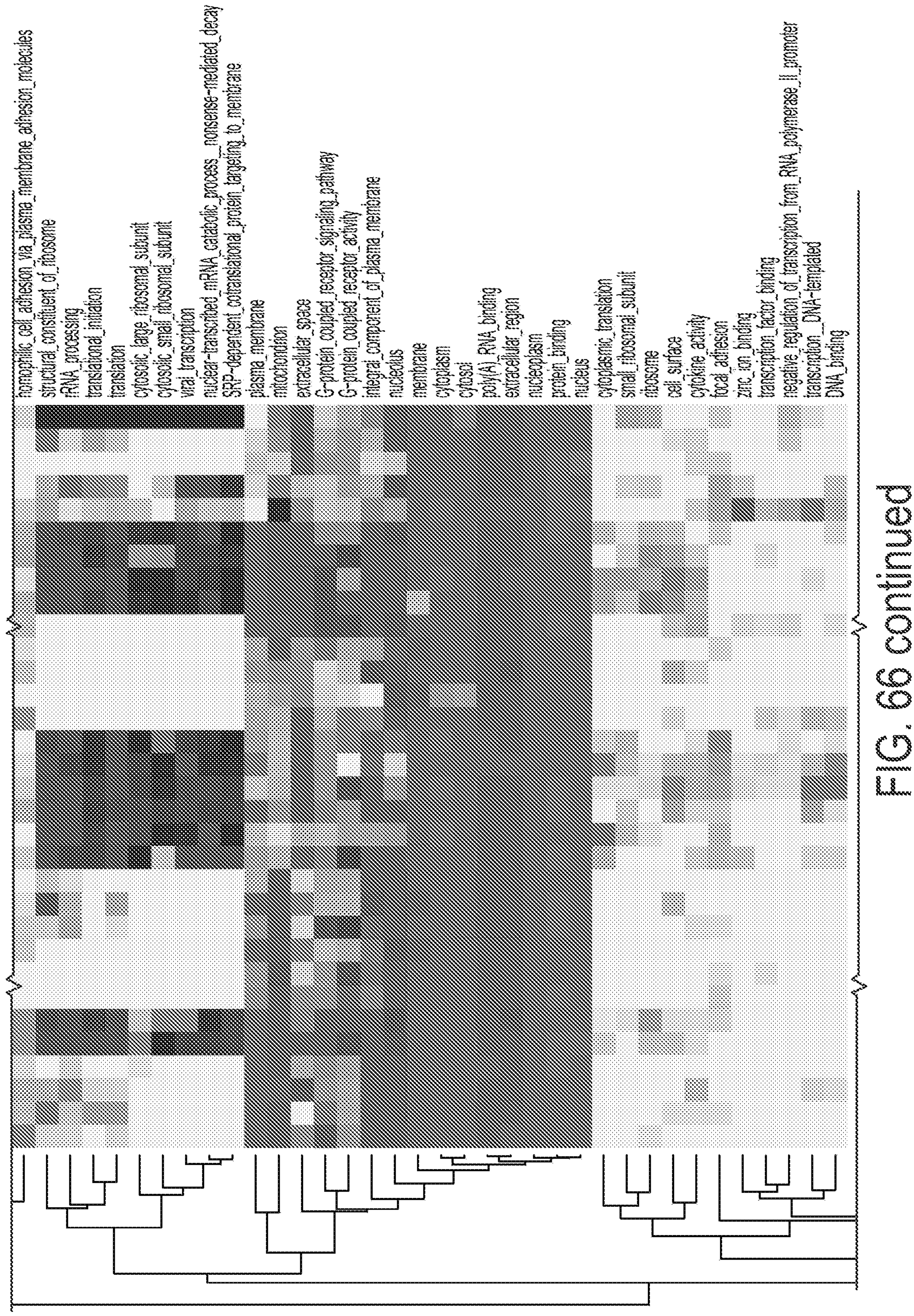
Figure 66:
Figure 66:
Figure 66:
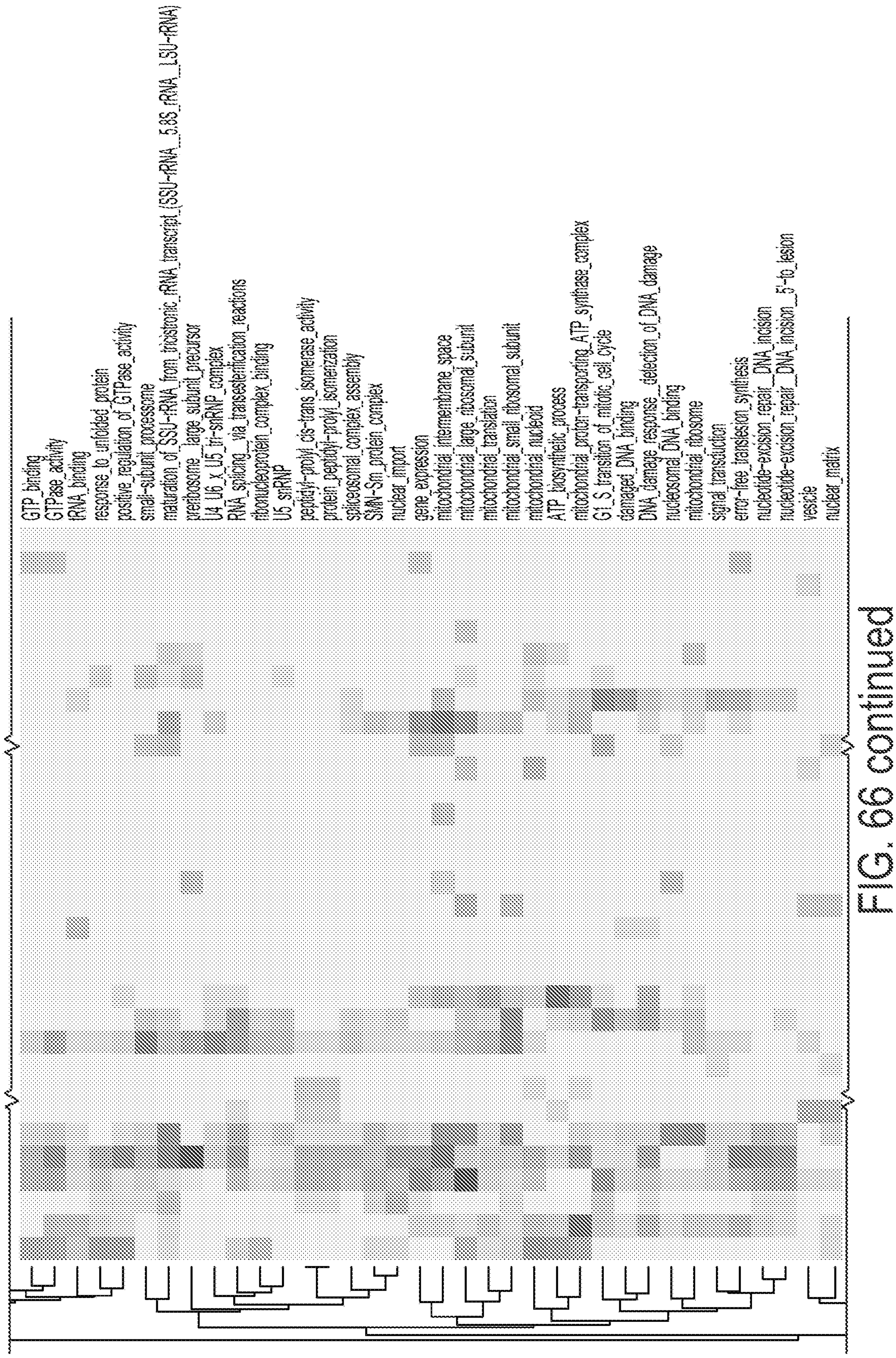
Figure 66:
Figure 66:
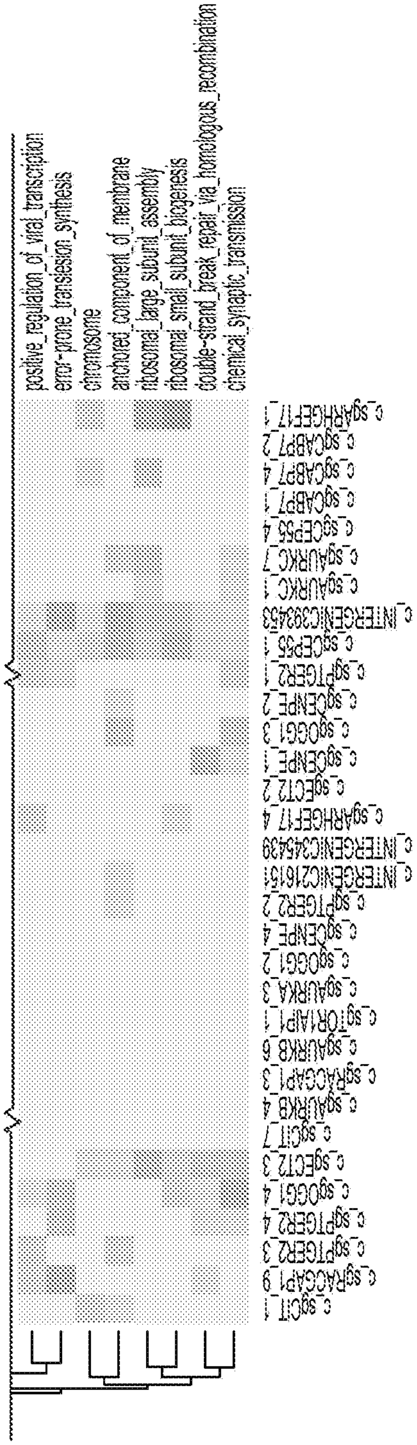
Figure 67:
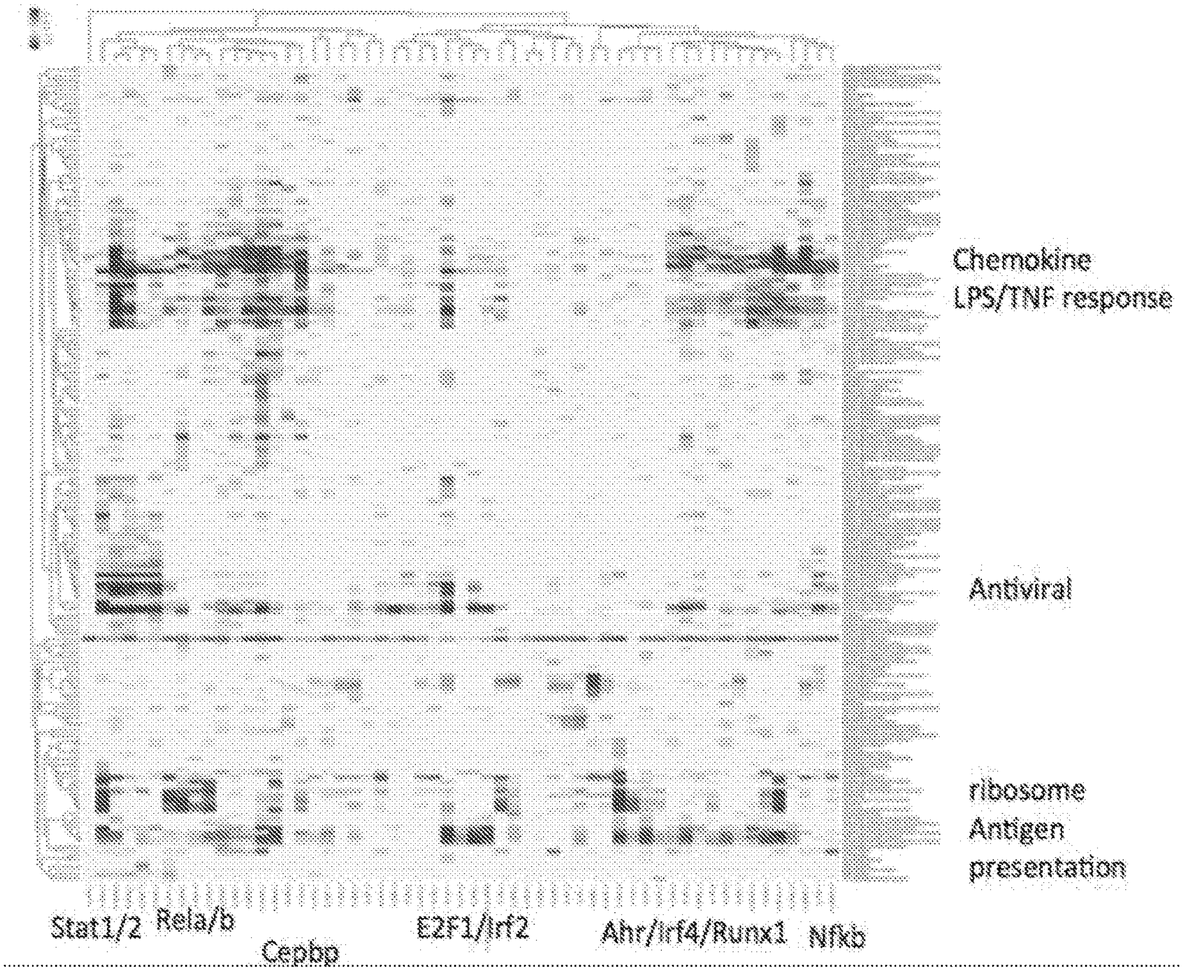
FIG. 67 illustrates Gene set (GO/MSigDB) analysis.

Turning to FIG. 66, GO terms associated with the following sgRNAs: c_sgCIT_1, c_sgRACGAP1_9, c_sgPTGER2_3, c_sgPTGER2_4, c_sgOGG1_4, c_sgECT2_3, c_sgCIT_7, c_sgAURKB_4, c_sgRACGAP1_3, c_sgAURKB_6, c_sgTORIAIP1_1, c_sgAURKA_3, c_sgOGG1_2, c_sgCENPE_4, c_sgPTGER2_2, c_INTERGENIC216151, c_INTERGENIC345439, c_sgARHGEF17_4, c_sgECT2_2, c_sgCENPE_1, c_sgOGG1_3, c_sgCENPE_2, c_sgPTGER2_1, c_sgCEP55_1, c_INTERGENIC393453, c_sgAURKC_1, c_sgAURKC_7, c_sgCEP55_4, c_sgCABP7_1, c_sgCABP7_4, c_sgCABP7_2, c_sgARHGEF17_1 are shown. The Table below describes the labeling of the figure.

| X-axis left to right | y-axis bottom to top |
|---|---|
| c_sgCIT_1 | chemical_synaptic_transmission |
| c_sgRACGAP1_9 | double-strand_break_repair_via_homologous_recombination |
| c_sgPTGER2_3 | ribosomal_small_subunit_biogenesis |
| c_sgPTGER2_4 | ribosomal_large_subunit_assembly |
| c_sgOGG1_4 | anchored_component_of_membrane |
| c_sgECT2_3 | chromosome |
| c_sgCIT_7 | error-prone_translesion_synthesis |
| c_sgAURKB_4 | positive_regulation_of_viral_transcription |
| c_sgRACGAP1_3 | transmembrane_signaling_receptor_activity |
| c_sgAURKB_6 | oxidative_phosphorylation |
| c_sgTOR1AIP1_1 | ribosomal_large_subunit_biogenesis |
| c_sgAURKA_3 | exon-exon_junction_complex |
| c_sgOGG1_2 | serine-type_endopeptidase_activity |
| c_sgCENPE_4 | heparin_binding |
| c_sgPTGER2_2 | hemoglobin_complex |
| c_INTERGENIC216151 | regulation_of_ion_transmembrane_transport |
| c_INTERGENIC345439 | visual_perception |
| c_sgARHGEF17_4 | potassium_ion_transmembrane_transport |
| c_sgECT2_2 | growth_factor_activity |
| c_sgCENPE_1 | 7-methylguanosine_mRNA_capping |
| c_sgOGG1_3 | snRNA_transcription_from_RNA_polymerase_II_promoter |
| c_sgCENPE_2 | chromosome_centromeric_region |
| c_sgPTGER2_1 | chromosome_segregation |
| c_sgCEP55_1 | endosomal_transport |
| c_INTERGENIC393453 | mitotic_metaphase_plate_congression |
| c_sgAURKC_1 | aerobic_respiration |
| c_sgAURKC_7 | viral_life_cycle |
| c_sgCEP55_4 | mitochondrion_organization |
| c_sgCABP7_1 | DNA_duplex_unwinding |
| c_sgCABP7_4 | postsynaptic_membrane |
| c_sgCABP7_2 | small_nuclear_ribonucleoprotein_complex |
| c_sgARHGEF17_1 | telomere_maintenance_via_recombination |
| | DNA_replication_initiation |
| | cell_proliferation |
| | cell_cycle |
| | proteasome_regulatory_particle |
| | proteasome_regulatory_particle base_subcomplex |
| | COPII_vesicle_coating |
| | formation_of_translation_preinitiation_complex |
| | thioredoxin_peroxidase_activity |
| | double-stranded_RNA_binding |
| | intracellular_protein_transport |
| | toxin_transport |
| | nuclear_matrix |
| | vesicle |
| | nucleotide-excision_repair__DNA_incision__5'-to_lesion |
| | nucleotide-excision_repair__DNA_incision |
| | error-free_translesion_synthesis |
| | signal_transduction |
| | mitochondrial_ribosome |
| | nucleosomal_DNA_binding |
| | DNA_damage_response__detection_of_DNA_damage |
| | damaged_DNA_binding |
| | G1_S_transition_of_mitotic_cell_cycle |
| | mitochondrial_proton-transporting_ATP_synthase_complex |
| | ATP_biosynthetic_process |

-continued

| X-axis left to right | y-axis bottom to top |
|---|---|
| | mitochondrial_nucleoid<br>mitochondrial_small_ribosomal_subunit<br>mitochondrial_translation<br>mitochondrial_large_ribosomal_subunit<br>mitochondrial_intermembrane_space<br>gene_expression<br>nuclear_import<br>SMN-Sm_protein_complex<br>spliceosomal_complex_assembly<br>protein_peptidyl-prolyl_isomerization<br>peptidyl-prolyl_cis-trans_isomerase_activity<br>U5_snRNP<br>ribonucleoprotein_complex_binding<br>RNA_splicing_via_transesterification_reactions<br>U4_U6_x_U5_tri-snRNP_complex<br>preribosome__large_subunit_precursor<br>maturation_of_SSU-rRNA_from_tricistronic_rRNA_transcript_(SSU-rRNA__5.8S_small-subunit_processome)<br>positive_regulation_of_GTPase_activity<br>response_to_unfolded_protein<br>tRNA_binding<br>GTPase_activity<br>GTP_binding<br>GDP_binding<br>receptor_complex<br>tricarboxylic_acid_cycle<br>cell_redox_homeostasis<br>NAD_binding<br>electron_carrier_activity<br>regulation_of_translational_initiation<br>nucleotide-excision_repair__DNA_damage_recognition<br>spliceosomal_snRNP_assembly<br>U2_snRNP<br>precatalytic_spliceosome<br>chromatin<br>methylosome<br>U1_snRNP<br>proteasome_assembly<br>DNA_recombination<br>telomere_maintenance<br>proteasome_core_complex__alpha-subunit_complex<br>positive_regulation_of_protein_localization_to_Cajal_body<br>chaperonin-containing_T-complex<br>zona_pellucida_receptor_complex<br>positive_regulation_of_telomere_maintenance_via_telomerase<br>positive_regulation_of_establishment_of_protein_localization_to_telomere<br>positive_regulation_of_telomerase_RNA_localization_to_Cajal_body<br>tRNA_aminoacylation_for_protein_translation<br>negatiye_regulation_of_apoptotic_process<br>proteasome_accessory_complex<br>ATPase_actiyity<br>ubiquitin-dependent_protein_catabolic_process<br>identical_protein_binding<br>endoplasmic_reticulum-Golgi_intermediate_compartment<br>protein_stabilization<br>sister_chromatid_cohesion<br>condensed_chromosome_kinetochore<br>protein_transport<br>spindle_pole<br>kinetochore<br>DNA_damage_response_signal_transduction_by_p53_class_mediator_resulting_retrograde_vesicle-mediated_transport_Golgi_to_ER<br>ER_to_Golgi_vesicle-mediated_transport<br>transcription_coactivator_activity<br>protein_complex_binding<br>intracellular_membrane-bounded_organelle<br>regulation_of_signal_transduction_by_p53_class_mediator<br>regulation_of_cellular_response_to_heat<br>mitotic_nuclear_envelope_disassembly<br>intracellular_transport_of_virus<br>protein_sumoylation<br>RNA_processing<br>ER-associated_ubiquitin-dependent_protein_catabolic_process<br>nuclear_envelope<br>covalent_chromatin_modification<br>nuclear_membrane<br>protein_complex<br>nuclear_chromatin |

-continued

| X-axis left to right | y-axis bottom to top |
|---|---|
| | spindle |
| | G2_M_transition_of_mitotic_cell_cycle |
| | ubiquitin_protein_ligase_binding |
| | midbody |
| | endoplasmic_reticulum_membrane |
| | endoplasmic_reticulum |
| | ATP_binding |
| | chromatin_binding |
| | protein_kinase_binding |
| | regulation_of_transcription_from_RNA_polymerase_II_promoter |
| | ligase_activity |
| | enzyme_binding |
| | Golgi_apparatus |
| | ubiquitin_protein_ligase_activity |
| | ubiquitin-protein_transferase_activity |
| | transcription_initiation_from_RNA_polymerase_II_promoter |
| | cellular_response_to_DNA_damage_stimulus |
| | DNA_binding |
| | transcription__DNA-templated |
| | negative_regulation_of_transcription_from_RNA_polymerase_II_promoter |
| | transcription_factor_binding |
| | zinc_ion_binding |
| | focal_adhesion |
| | cytokine_activity |
| | cell_surface |
| | ribosome |
| | small_ribosomal_subunit |
| | cytoplasmic_translation |
| | nucleus |
| | protein_binding |
| | nucleoplasm |
| | extracellular_region |
| | poly(A)_RNA_binding |
| | cytosol |
| | cytoplasm |
| | membrane |
| | nucleolus |
| | integral_component_of_plasma_membrane |
| | G-protein_coupled_receptor_activity |
| | G-protein_coupled_receptor_signaling_pathway |
| | extracellular_space |
| | mitochondrion |
| | plasma_membrane |
| | SRP-dependent_cotranslational_protein_targeting_to_membrane |
| | nuclear-transcribed_mRNA_catabolic_process__nonsense-mediated_decay |
| | viral_transcription |
| | cytosolic_small_ribosomal_subunit |
| | cytosolic_large_ribosomal_subunit |
| | translation |
| | translational_initiation |
| | rRNA_processing |
| | structural_constituent_of_ribosome |
| | homophilic_cell_adhesion_via_plasma_membrane_adhesion_molecules |
| | cell_adhesion |
| | calcium_ion_binding |
| | proteinaceous_extracellular_matrix |
| | cell_division |
| | mitotic_nuclear_division |
| | centrosome |
| | cell-cell_adherens_junction |
| | cell-cell_adhesion |
| | cadherin_binding_involved_in_cell-cell_adhesion |
| | viral_process |
| | nucleotide_binding |
| | mRNA_processing |
| | nuclear_speck |
| | termination_of_RNA_polymerase_II_transcription |
| | mRNA_3'-end_processing |
| | nuclear_chromosome_telomeric_region |
| | mRNA_binding |
| | single-stranded_DNA_binding |
| | RNA_export_from_nucleus |
| | transcription-coupled_nucleotide-excision_repair |
| | external_side_of_plasma_membrane |
| | U12-type_spliceosomal_complex |
| | extracellular_matrix_organization |
| | intracellular_ribonucleoprotein_complex |

-continued

| X-axis left to right | y-axis bottom to top |
|---|---|
| | transcription_elongation_from_RNA_polymerase_II_promoter |
| | mitochondrial_respiratory_chain_complex_I |
| | mitochondrial_electron_transport_NADH_to_ubiquinone |
| | NADH_dehydrogenase_(ubiquinone)_activity |
| | mitochondrial_respiratory_chain_complex_I_assembly |
| | cell-cell_signaling |
| | DNA_repair |
| | DNA_replication |
| | immune_response |
| | inflammatory_response |
| | mRNA_export_from_nucleus |
| | mRNA_splicing via_spliceosome |
| | RNA_splicing |
| | mitochondrial_inner_membrane |
| | mitochondrial_matrix |
| | spliceosomal_complex |
| | mitochondrial_translational_elongation |
| | mitochondrial_translational_termination |
| | RNA_binding |
| | integral_component_of_membrane |
| | negative_regulation_of_ubiquitin-protein_ligase_activity_involved_in_mitotic_cell_anaphase-promoting_complex-dependent_catabolic_process |
| | positive_regulation_of_ubiquitin-protein_ligase_activity_involved_in_regulation_of_proteasome_complex |
| | NIK_NF-kappaB_signaling |
| | regulation_of_cellular_amino_acid_metabolic_process |
| | catalytic_step_2_spliceosome |
| | regulation_of_mRNA_stability |
| | proteasome-mediated_ubiquitin-dependent_protein_catabolic_process |
| | protein_polyubiquitination |
| | extracellular_exosome |
| | stimulatory_C-type_lectin_receptor_signaling_pathway |
| | Fc-epsilon_receptor_signaling_pathway |
| | Wnt_signaling_pathway__planar_cell_polarity_pathway |
| | antigen_processing_and_presentation_of_exogenous_peptide_antigen_via_MHC_negative_regulation_of_canonical_Wnt_signaling_pathway |
| | T_cell_receptor_signaling_pathway |
| | positive_regulation_of_canonical_Wnt_signaling_pathway |
| | tumor_necrosis_factor-mediated_signaling_pathway |
| | threonine-type_endopepticlase_activity |
| | proteasome_core_complex |
| | translation_initiation_factor_activity |
| | protein_folding |
| | unfolded_protein_binding |
| | myelin_sheath |
| | melanosome |

Whereas the nature of the experimental system minimizes batch effects when comparing perturbations, as all cells are grown in one pool, applicants sought to determine to what extent the effects observed are reproducible across when compared to a later time point. A subset of the cells used for the promoter experiments were grown for seven more days, and then assayed for expression in the same manner.

Reports suggest that CRISPRi uniformly reduces expression of a gene across all cells, while the CRISPR-KO system creates an assortment of heterogeneous indel mutations. In order to compare these two systems, applicants perturbed three of the same genes using four sgRNAs per gene with the CRISPRi system.

Example of Cost for Conditions and Cells:

| Cells | Conditions-low (800 cells/condition) | Conditions-high (80 cells/condition) | Cost ($)-low (1000 reads/cell) | Cost-high (5,000 reads/cell) |
|---|---|---|---|---|
| 10,000 | 12.5 | XXX | 250 | 1,250 |
| 50,000 | 62.5 | 625* | 1,250 | 6,250 |
| 100,000 | 125 | 1,250* | 2,500 | 12,000 |
| 500,000 | 625* | 6,250* | 12,500 | 62,500 |

-continued

| Cells | Conditions-low (800 cells/condition) | Conditions-high (80 cells/condition) | Cost ($)-low (1000 reads/cell) | Cost-high (5,000 reads/cell) |
|---|---|---|---|---|
| 1,000,000 | 1,250* | 12,500* | 25,000 | 125,000 |
| 10,000,000 | 12,500* | 125,000* | 250,000 | 1.25 million |

*significantly more than previously feasible (100's of conditons)

Figure 68:
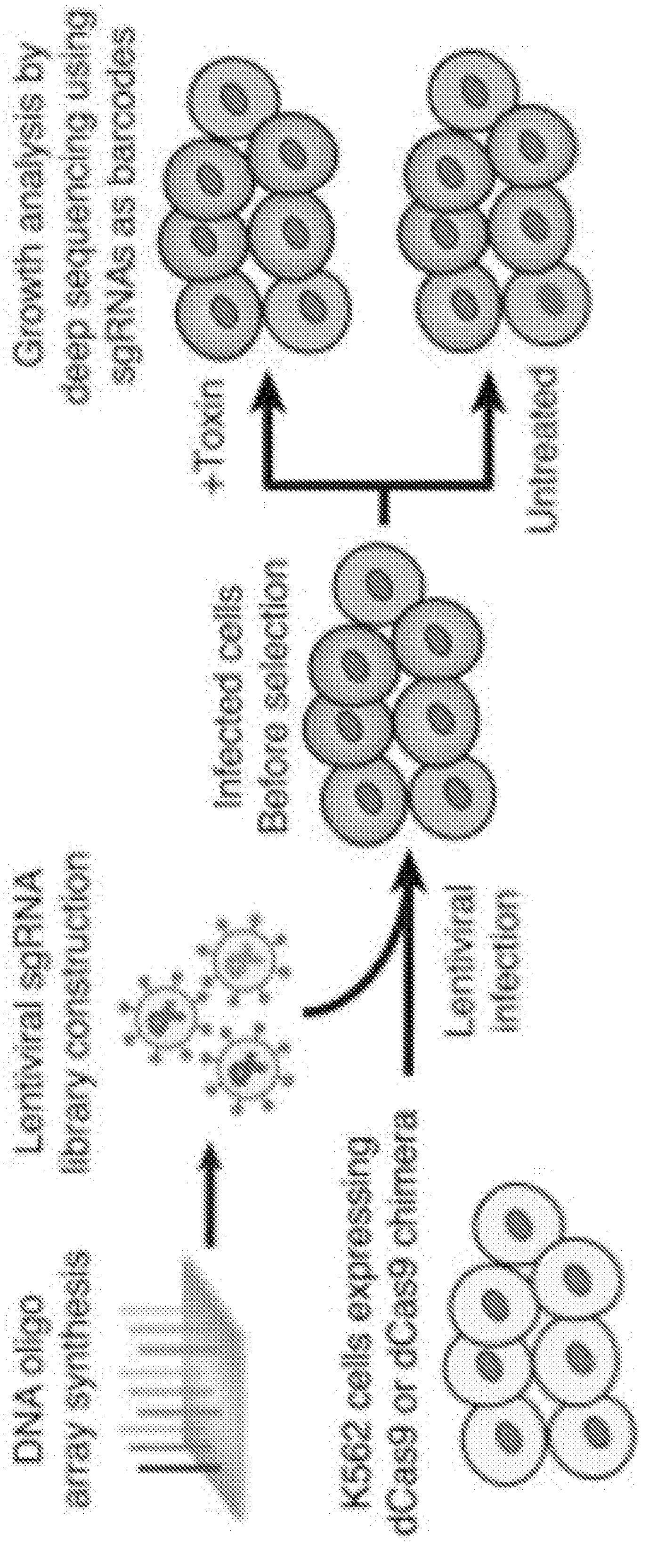
FIG. 68 illustrates a graphical embodiment of a perturb-Seq experiment.
Figure 69:
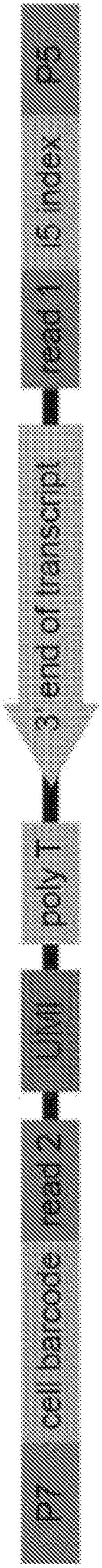
FIG. 69 illustrates RT primers that are used to tag the 3' ends of transcripts.
Figure 70:
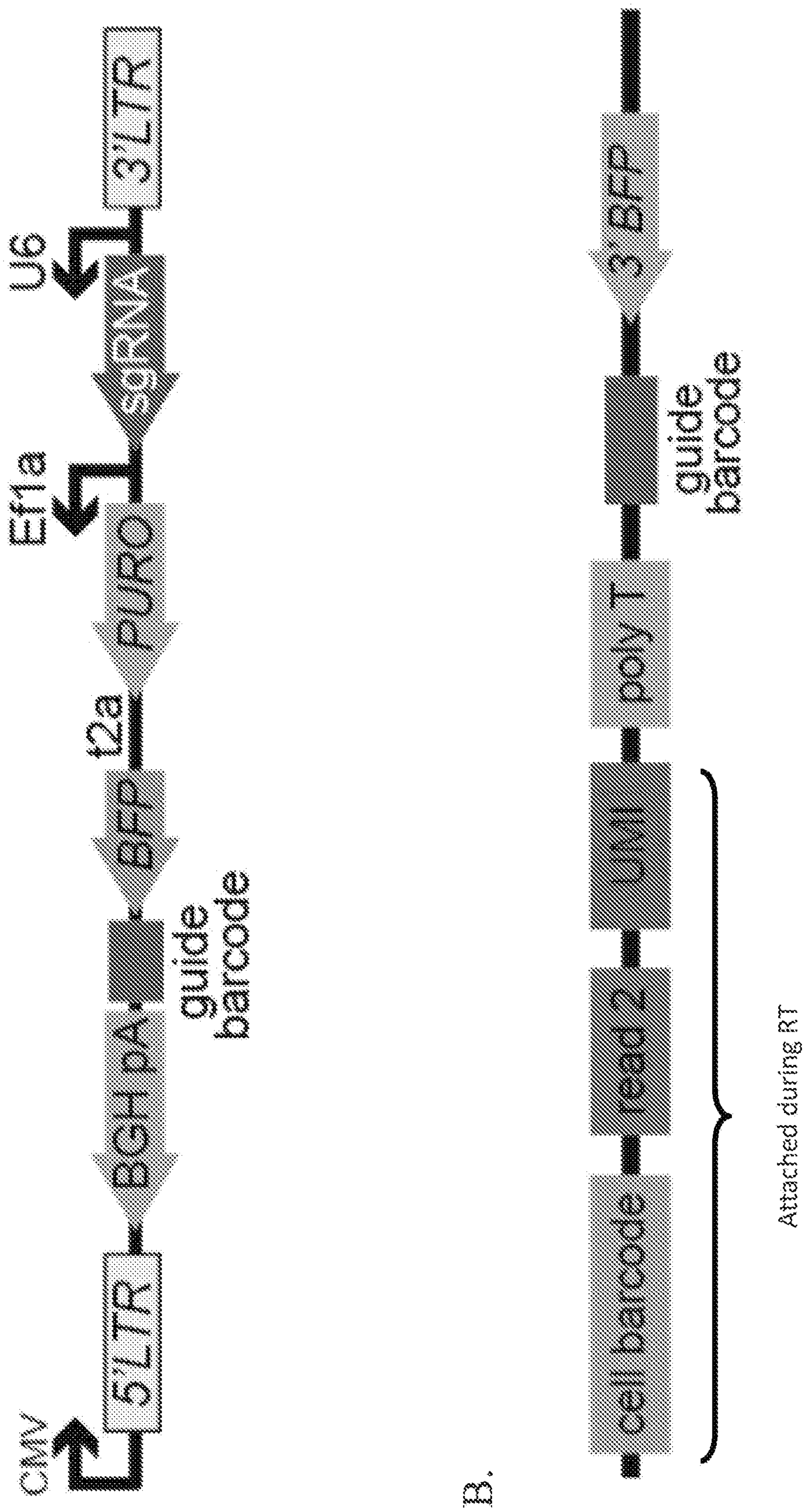
FIG. 70 illustrates a vector for introducing a guide RNA and the actual transcript insert after capture.
Figure 71:
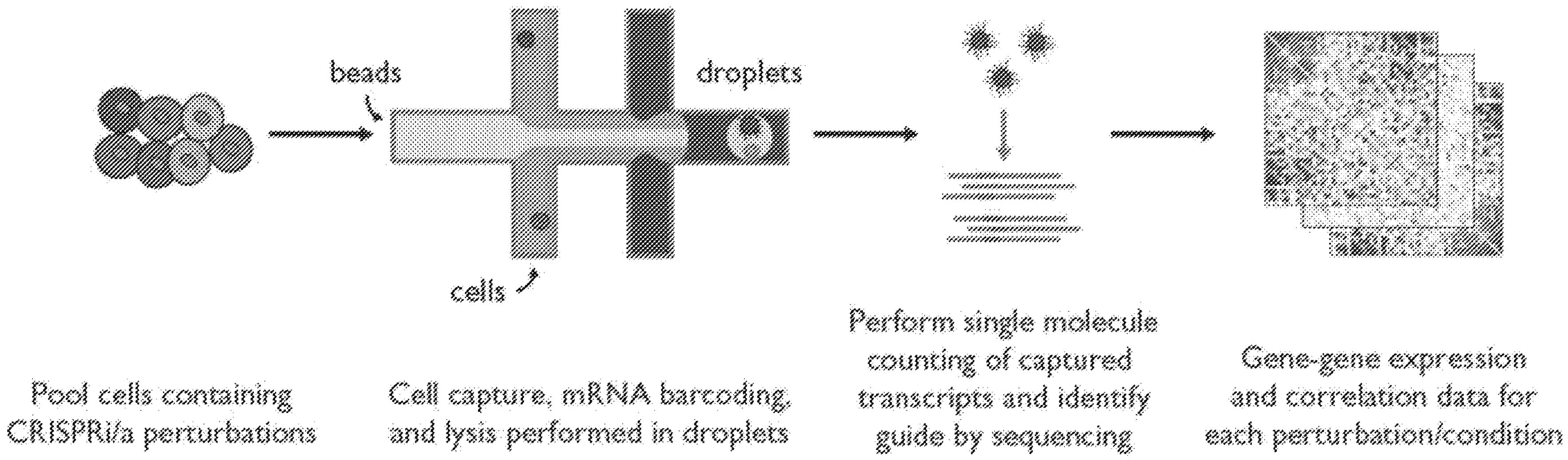
FIG. 71 illustrates a graphical embodiment of a perturb-Seq experiment.

Example 17: Vectors for Capturing Guide RNAs in Single Cells and RT Primers for Labelling Transcripts Assays typically measure either a great number of cells, or a great number of genes. RNA-seq allows for the measuring of the expression of every gene in the genome, but can only get average behavior. High content microscopy/flow cytometry allows for the measuring of many individual cells, but only a handful of reporters. Single-cell resolution exposes new phenotypes and the present invention allows for determining rich phenotypes for each perturbation, thus enabling mechanistic understanding and functional clustering (FIG. 68). Before the present invention guide RNAs could not be easily captured. Applicants developed a novel vector for measuring the guide RNA in a single cell that may be distinguished from guide RNAs present in the pool of cells of the present invention. The vector relies on the capture of a reporter transcript having a unique guide RNA specific barcode (FIG. 70).

Figure 81A:
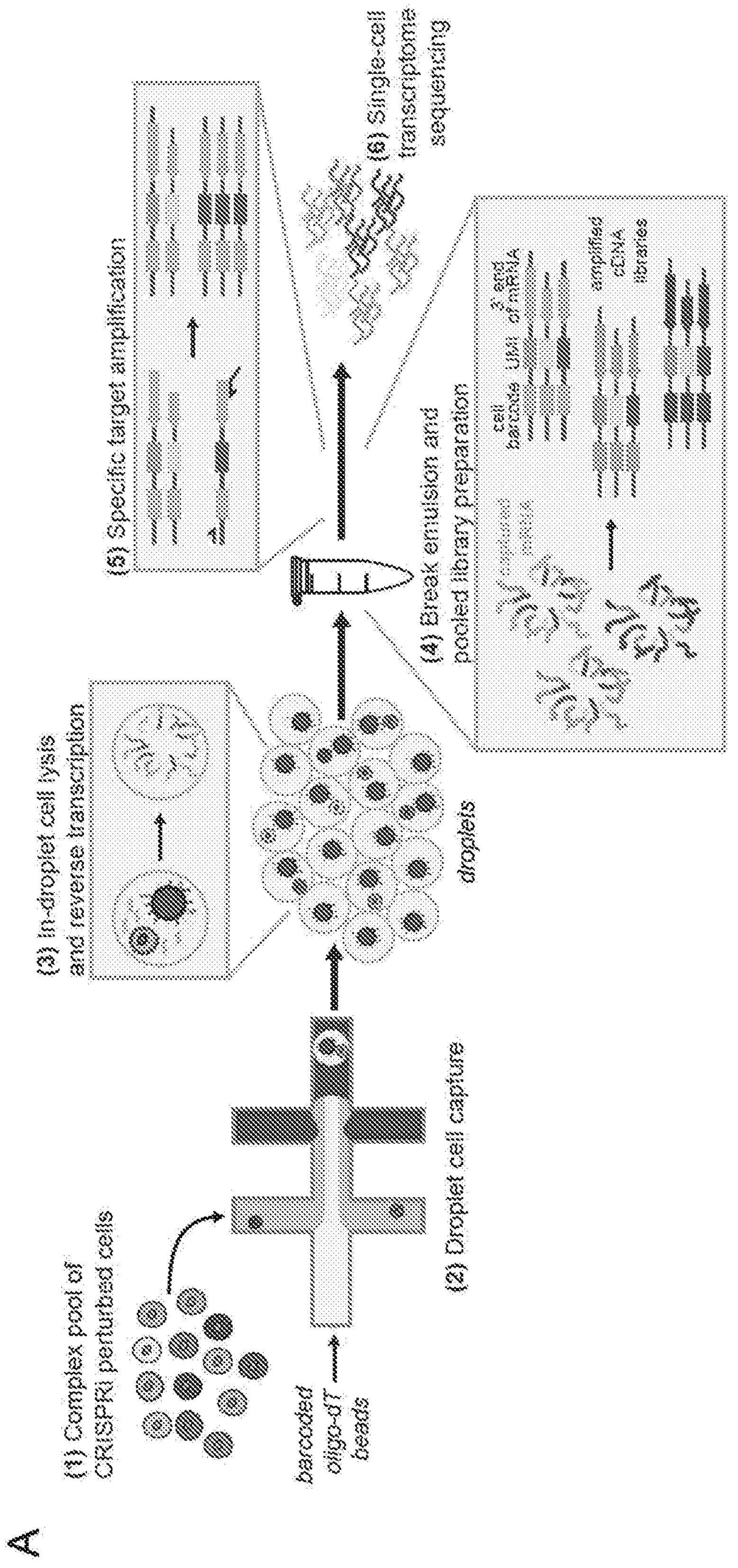
Figure 81B:
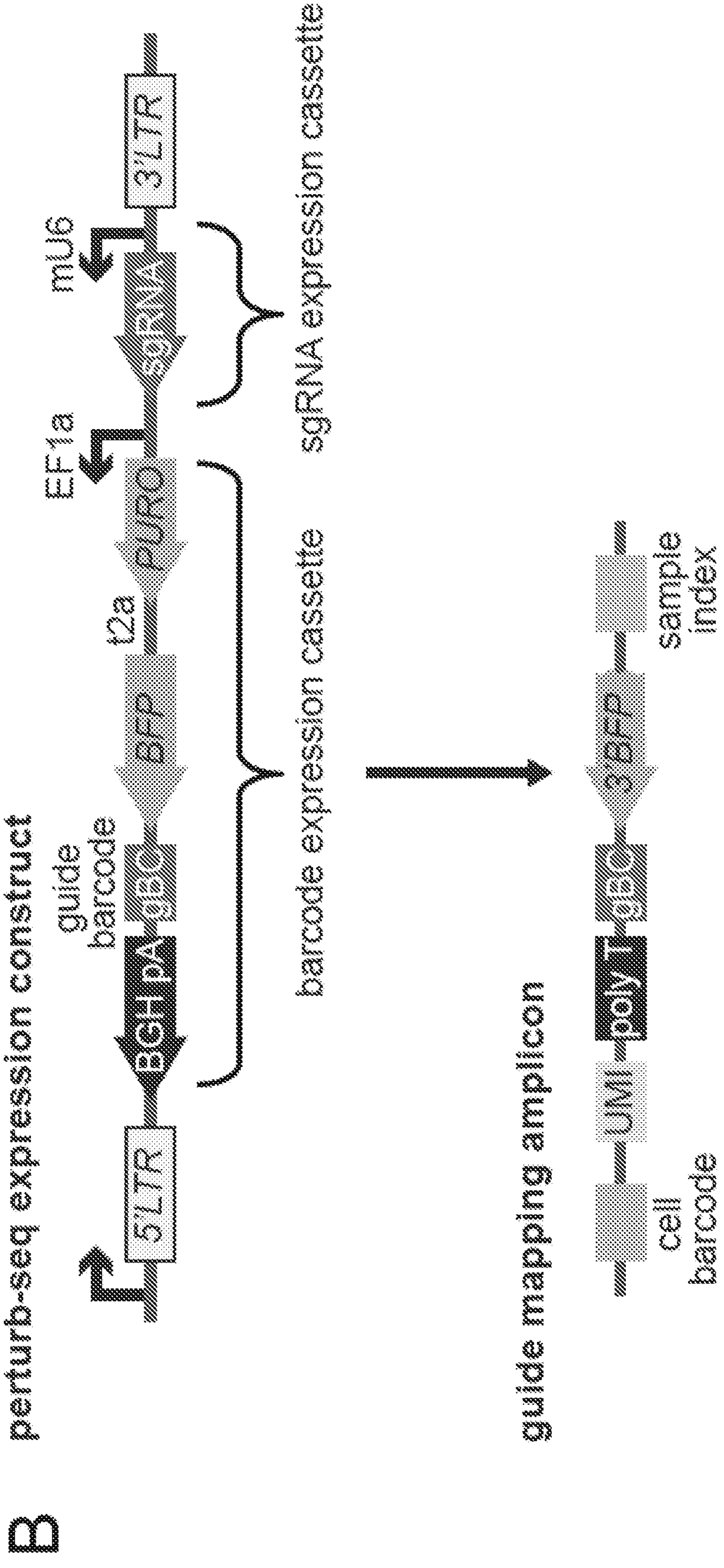

To build a highly parallel platform for conducting functional genetic studies with complex phenotypes (defined by single cell expression profiling), Applicants developed a simple method for encoding the identity of genetic perturbations into the DNA of individual cells (FIG. 81A-B). These DNA "barcodes" can be expressed as mRNAs and, therefore, captured during single-cell RNA-sequencing library preparation (FIG. 81A-B). This strategy is broadly applicable because our barcode design allows the encoding of different pieces of information; however, here Applicants focus on the case where the barcode encodes the identity of a perturbation made using CRISPRi/a (23849981, 25307932). In this system, CRISPR guide RNAs (sgRNAs) are delivered to cells using a lentiviral delivery vector, called the perturb-seq vector, that carries tandem expression cassettes: one encoding an sgRNA under control of a polymerase III-driven promoter and the other encoding a polymerase II-driven mRNA (FIG. 81B). This mRNA carries a guide-mapping barcode, or "guide barcode," that uniquely identifies the sgRNA in the former expression cassette, as well as two cell selection markers, blue fluorescent protein (BFP) and puromycin (PURO). Because the majority of single cell RNA sequencing platforms rely on polyadenylation-mediated priming for reverse transcription and capture only the 3' end of message RNAs in sequencing amplicons, Applicants engineered our barcode expression transcript to terminate with a strong polyadenylation signal sequence (BGH polyadenylation signal cloned from pcDNA3.1(+)) and placed the sgRNA-mapping barcode adjacent to this sequence. To incorporate this design into a functional lentiviral delivery system and prevent the BGH polyadenylation sequence from disrupting provirus expression, both the guide and barcode expression cassettes were encoded in reverse orientation with respect to the lentiviral genome. After incorporation into a target cell genome, the expressed barcode transcript can be captured by any oligo-dT-based protocol for cDNA construction. Specific amplification of the barcode transcript can then be used to enrich this important mapping information within RNA-sequencing libraries.

Figure 72:
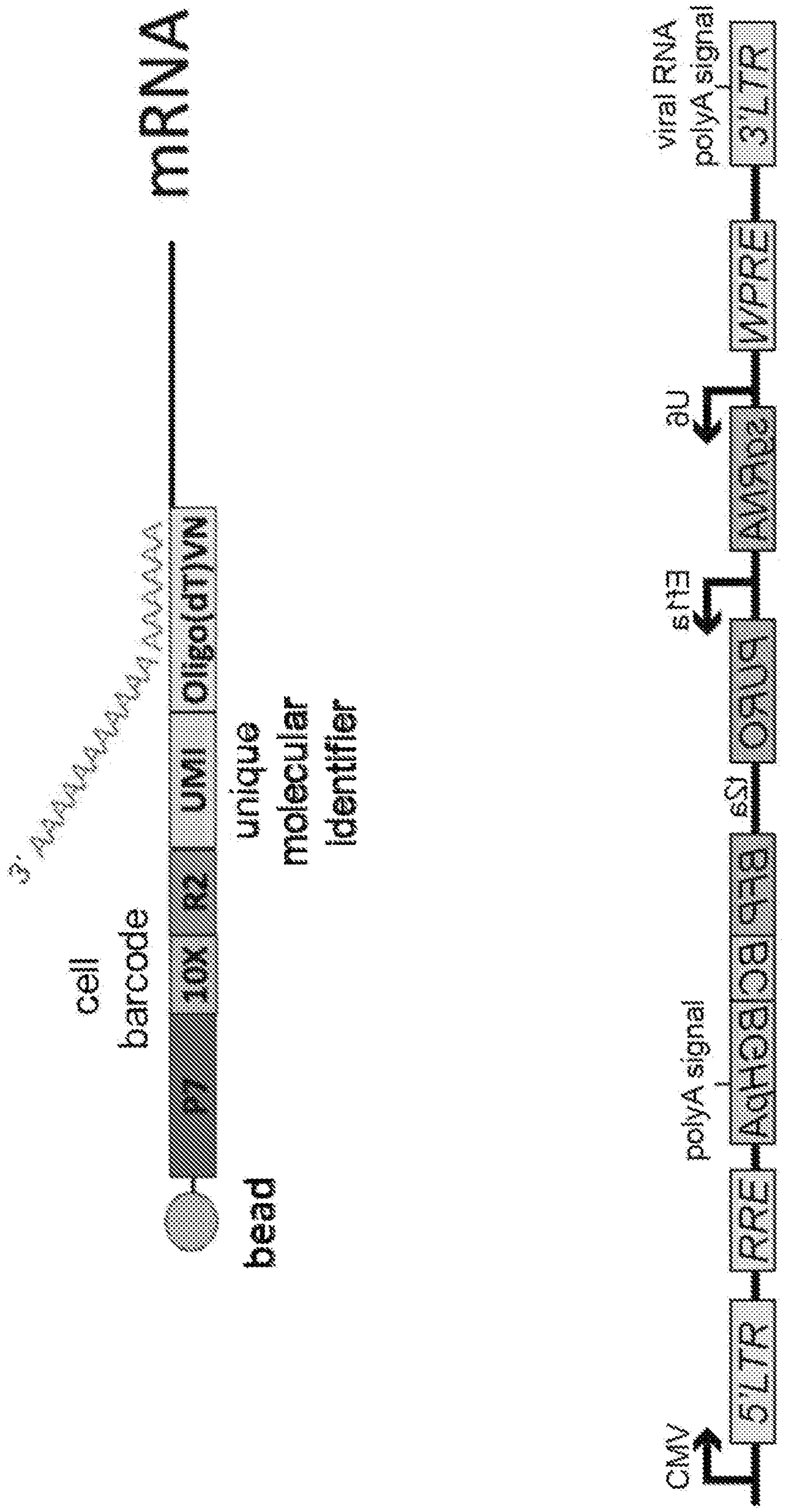
FIG. 72 illustrates that capture primers contain two barcodes specifying cell and molecule identity. Recover guide information is measured by co-expressing a polyadenylated guide barcode from a guide RNA vector.
Figure 73:
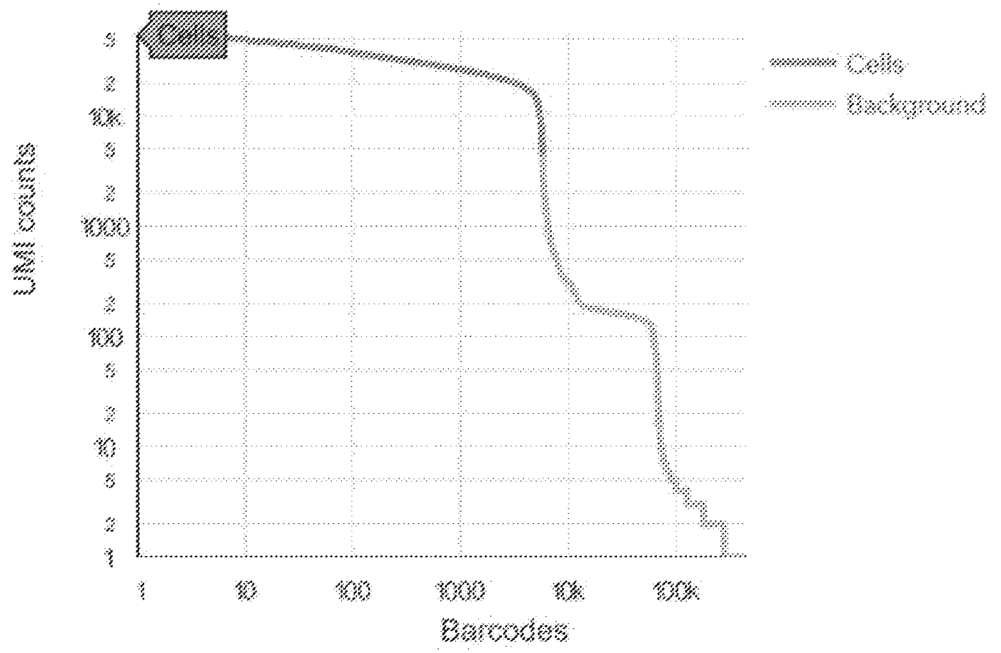
FIG. 73 illustrates read statistics per cell.
Figure 78:
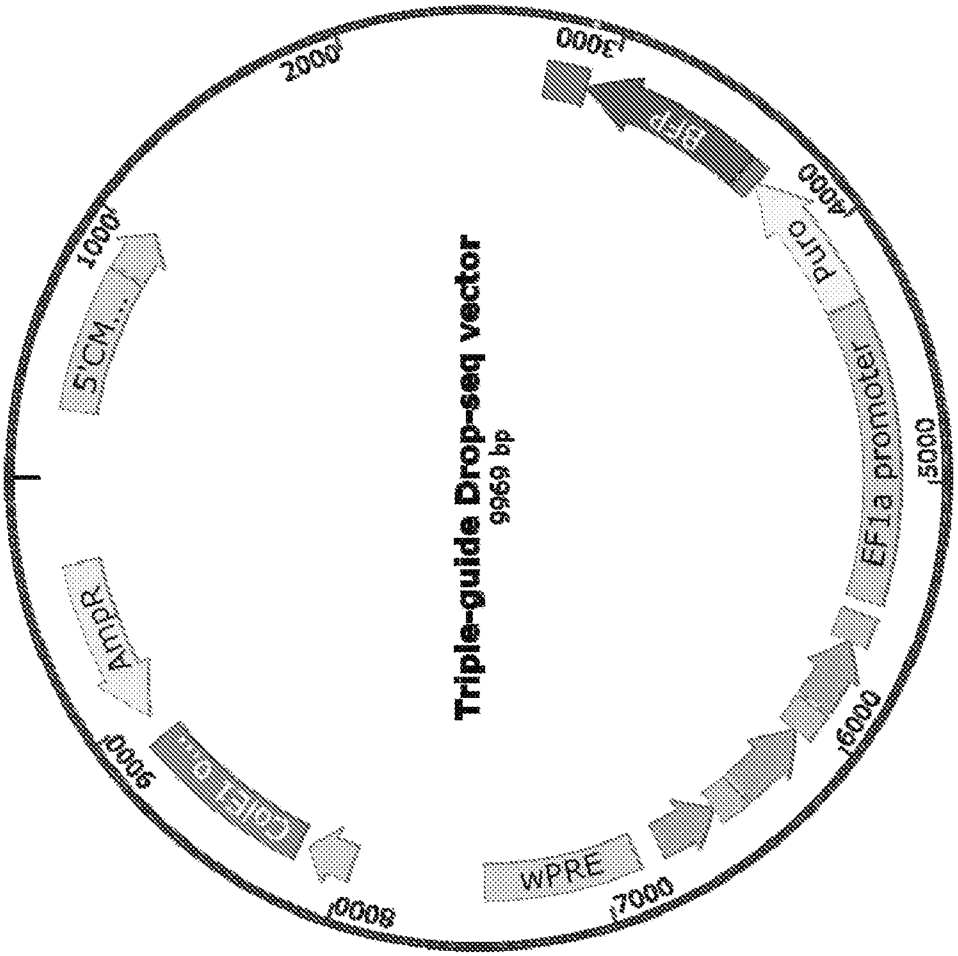
FIG. 78 illustrates a triple guide Drop-Seq vector.
Figure 79:
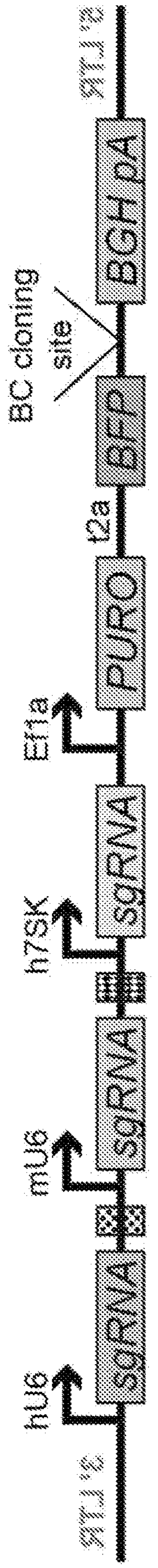
FIG. 79 illustrates a triple guide Drop-Seq vector.

In the Drop-seq method beads are used to deliver RT primers (FIG. 70), which are used to tag the 3' ends of transcripts with: (1) Cell barcode, a sequence common to all primers on that bead, used to group transcripts after sequencing; and (2) UMI (Unique Molecular Identifier), a random sequence used to identify duplicates introduced during PCR amplification. Therefore, all of the transcripts in a cell, including the reporter transcript are tagged. The method allows one to introduce diverse perturbations using CRISPRi/a into single cells, pool, and profile responses by droplet RNAseq. Perturb-seq in droplets relies on 3 barcodes to map single cell transcriptomes and analyze expression (FIG. 72). Vectors can also be used having multiple guide RNAs. In one embodiment, three guides are expressed from a single vector (FIGS. 78, 79).

Applicants performed pilot experiments with eight cell lines containing transcription factor knockdowns by CRISPRi, ~6,000 cells total. The targets had minimal growth defects, but still showed phenotypes in some screens. One control guide at 3-fold higher representation was used in addition to guides for seven transcription factors: EP300, BHLHE40, CREB1, DDIT3, ZNF326, SNAI1, SPI1. Two sequencing runs were performed on the same library. A HiSeq 2500 rapid run resulted in 132 million reads total, ~22,900 reads per cell, ~10,000 UMIs per cell, and had 2.29X coverage. A HiSeq 4000 lane run resulted in 300 million reads, ~52,000 reads per cell, ~17,000 UMIs per cell, and had 3X coverage. The merged data set resulted in 75,000 reads per cell, ~20,700 UMIs per cell, and 3.6X coverage.

Figure 74:
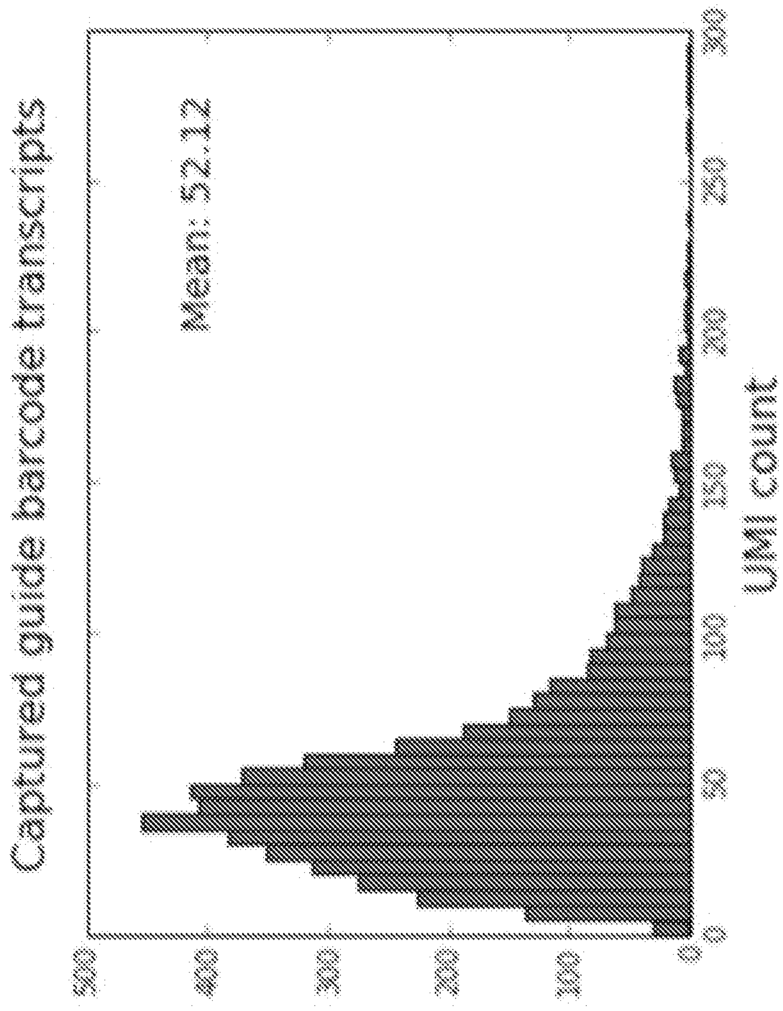
FIG. 74 illustrates guide identification.
Figure 75:
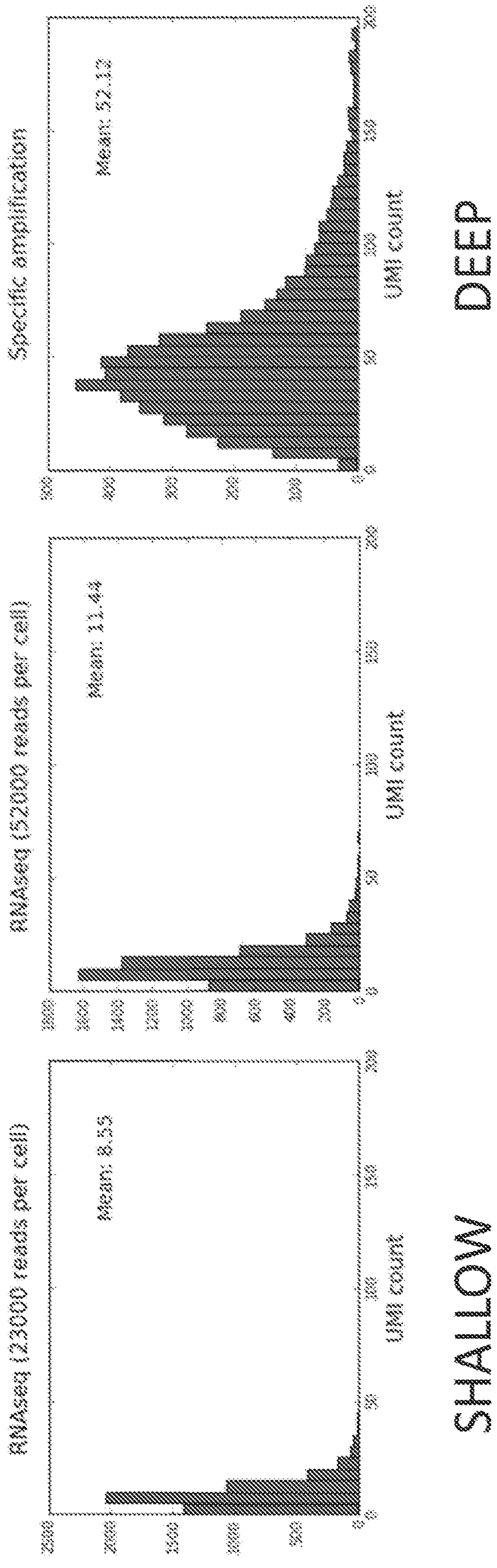
FIG. 75 illustrates capture of the guide barcode transcripts during RNAseq and specific amplification.

A dial-out PCR approach was designed for guide identification (FIG. 81). Transcripts containing guide barcodes are specifically amplified by PCR and prepared as separate sequencing libraries. Sequencing coverage is high (16.5 reads/UMI), so almost every molecule is detected (FIG. 74). Applicants also capture the guide barcode transcripts during RNAseq and the identities agree, but are less certain (FIG. 75).

Guide identification is done by consensus because most cells have a clearly dominant guide. When two guides show similar abundance, that cell barcode is ignored as a cell doublet.

| cell BC | guide identity | read count | UMI count | coverage | good coverage |
|---|---|---|---|---|---|
| AGCCTCAC | * | 132 | 86 | 1.534884 | False |
| AGGCGA-1 | EP300_pDS268 | 3888 | 243 | 16.000000 | True |
| | ZNF326_pDS262 | 629 | 37 | 17.0000 | True |
| ATAGCGTG | * | 87 | 67 | 1.298507 | False |
| CAACCA-1 | 62(mod)_pBA581 | 3906 | 213 | 18.338028 | True |

(cell BC - Seq. I.D. Nos. 1 and 2)

Guide identification is illustrated the following in test experiment.

| rank | guide identity | number of cells | percentage |
|---|---|---|---|
| 1 | 62(mod)_pBA581 | 1552 | 28.22 |
| 2 | SPI1_pDS255 | 600 | 10.91 |
| 3 | EP300_pDS268 | 525 | 9.55 |
| 4 | ZNF326_pDS262 | 492 | 8.95 |
| 5 | SNAI1_pDS266 | 477 | 8.67 |
| 6 | BHLHE40_pDS258 | 472 | 8.58 |
| 7 | CREB1_pDS269 | 436 | 7.93 |
| 8 | DDIT3_pDS263 | 410 | 7.45 |
| | * | 4 | 0.07 |
| | Multiplets | 353 | 6.42 |
| | Total uniquely identified | 4964 | 90.25 |
| | Total unidentifiable | 183 | 3.33 |
| | Total number of cells | 5500 | 100.00 |

Figure 76:
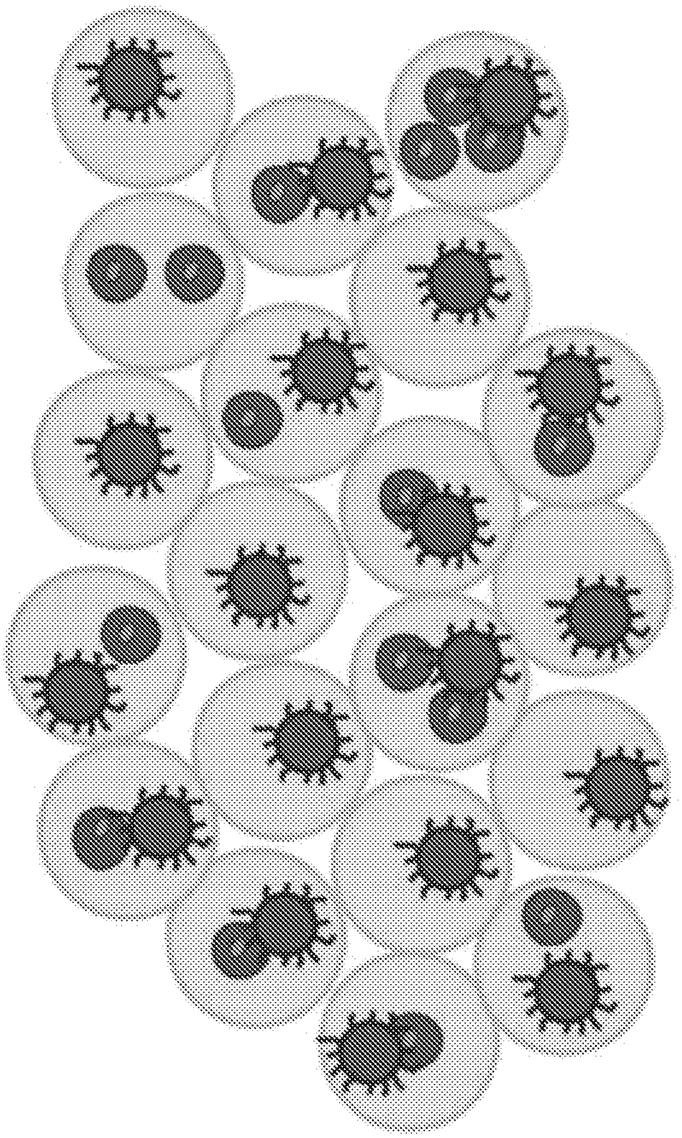
FIG. 76 illustrates singles, doubles and triplets during droplet sequencing.
Figure 77:
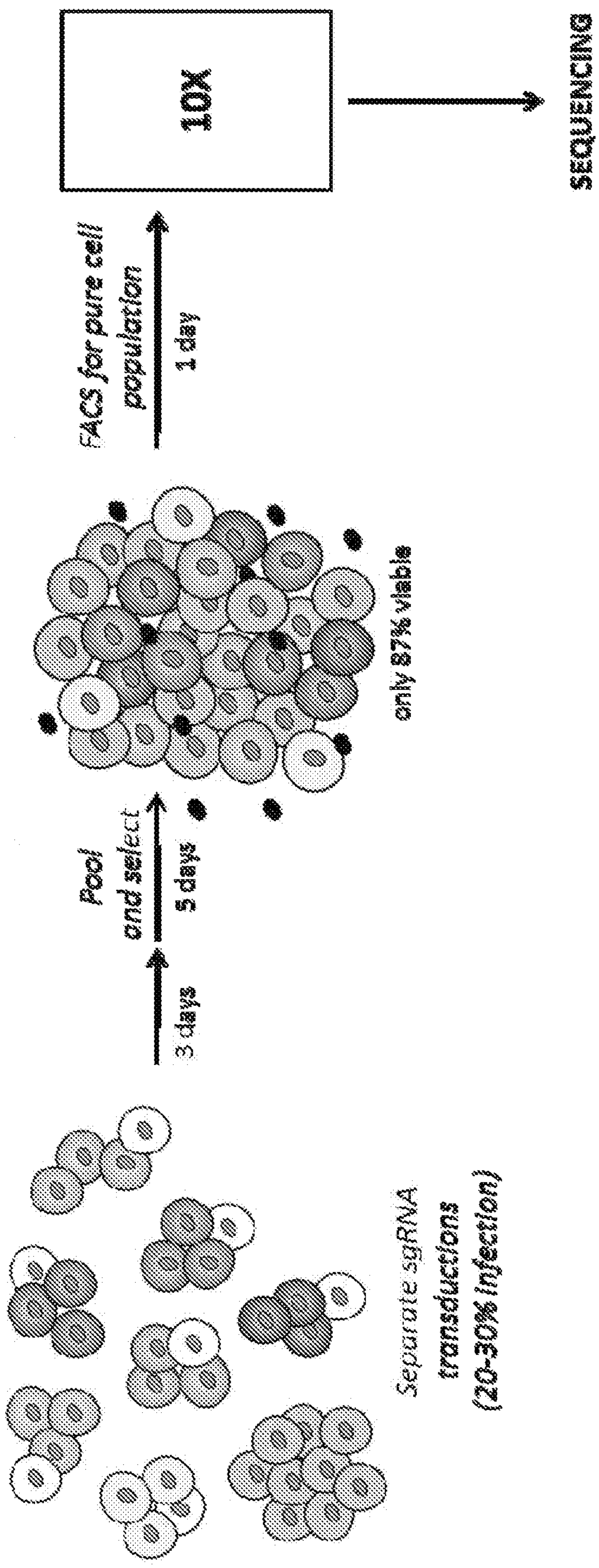
FIG. 77 illustrates a graphical embodiment of a perturb-Seq experiment.

The guide barcodes also permit overloading (FIG. 76). If barcodes are sufficiently diverse and recoverable with high confidence, then one can overload and discard doubles, triples, etc. The peak loading possible is 37.8%, although there is a "sweet spot" with sequencing costs.

Single cell sequencing may be performed by any method known in the art and each has advantages and disadvantages (FIG. 80).

Example 18: Discussion

Here, Applicants developed Perturb-seq a method to analyze the transcriptional defect associated with genetic manipulations as a readout of the cell's phenotype and the architecture of its molecular circuitry—from individual genes to specific processes to global states or types. Perturb-seq dramatically decreases the time and cost limitations associated with assaying the effects of large numbers of perturbations. By decomposing expression into the effects due to technical vs. biological covariates, Applicants recover expected expression changes and uncover new effects, from the effect on individual genes to cell states. Because of the single cell nature of the experiment, Perturb-seq can analyze heterogeneity in cell populations—distinguishing transcriptional effects associated with changes in cell state proportions from transcriptional responses within states.

The present invention shows novel methods to improve scalability, single cell phenotypes associated with perturbations, and interactions. As both the cost of both sequencing and high throughput library preparation methods decrease, the experimental and computational methods applicants have outlined should become versatile tools in armamentarium of the systems biologist. By sequencing shallowly across large numbers of cells, major transcriptional defects can be readily identified and, by sequencing deeper, smaller changes become apparent. In this invention, applicants exceeded the necessary scale to provide the community with a necessary resource to design future experiments. Excitingly, the signature analysis applicants describe, with as few cells as the number of cells that were analyzed in this work, could be used to gain a broad survey of transcriptional phenotypes across thousands of genes.

In certain examples, a diverse set of RNA barcodes can be used as an error correcting mechanism when more than one guide is present in a cell and sufficient clonality exists in the population. This feature can be leveraged in future studies to more intensively study the effects of combinations of perturbations and condition our regression framework on clonal similarity. Greater than 1 guide per cell can inform measurements of 1 guide per cell. Greater than 1 cell/drop can reduce costs by an order of magnitude.

Example 19: Perturb-Seq and MIMOSCA Correctly Determine Broad Phenotypic and Gene Specific Effects of Individual Perturbations and Genetic Interactions Perturb-Seq analysis of a set of TFs in BMDCs demonstrated the accuracy and resolution of our approach, as well as made specific new discoveries in this cell type. The grouping of individual guides and sets of TFs into TF modules, and many of the genes and processes that perturb-seq and our MIMOSCA framework predicted they regulate were coherent with respect to the extensive knowledge in the system. The specific regulatory connections were strongly supported by ChIP-Seq data. In addition, Applicants uncovered new and emerging regulatory connections, such as between Stat1 and 2 and mitochondrial biogenesis and Atf3, Irf2 and Rel and anti-viral responses, and showed that most programs induce both positive and negative feedback loops.

Because this novel approach supports such detailed dissection without pre-sorting the cells based on specific marker or state, Applicants could uncover two diametrically opposed programs that govern two global cell states, which precede stimulation with LPS, and may reflect distinct or mutually exclusive differentiation programs. The specific functional nature of "cluster disrupted cells" has been debated, including a suggestion that the two states represent dendritic cells ("cluster disrupted"; here, P2) and macrophages ("non cluster disrupted", here P4/5). Our result suggest that both states not only co-exist in unperturbed cells, but are coupled through a circuit with a specific set of positive and negative feedback loops, such that genetic perturbations (in single TFs or their combinations) that enhance one state inhibit the other and vice versa. The specific genes regulated in P2 include many recently highlighted in pre-DC cells, and may thus represent a less differentiated, arrested or abortive state.

Example 20: Alternative Embodiments to Enhance the Precision and Facility of Perturb-Seq Several enhancements can further improve Perturb-Seq. First, including a veritable cornucopia of sgRNAs that are non-targeting or target intergenic regions along with non-transduced controls in the same experiment would help create a stronger reference from which to evaluate the effect of perturbations.

Second, an important advantage of using Perturb-seq is that higher order interactions can be reached without further need to generate complex reagents (such as new vectors). The same experiment used for a single perturbation, due to the Poisson loading of perturbation per cell, can also uncover the genetic interactions between the perturbed genes. However, the number of sgRNAs present in each cell can vary over a large range. Applicants can leverage the cassette structure of the endogenous bacterial Cas9 crRNAs (Makarova et al., 2011) and the ability of Cpf1 to autonomously process an entire array, and deliver several sgRNAs (or an unprocessed array) on one construct (Kabadi et al., 2014; Wong et al., 2016; Zetsche et al., 2015, 2016). Such a system has advantages, such as having all members of the cassette be jointly detected or not, but depending on implementation disadvantages as well, such as cloning difficulty, and oligonucleotide synthesis scale.

Figure 54C:
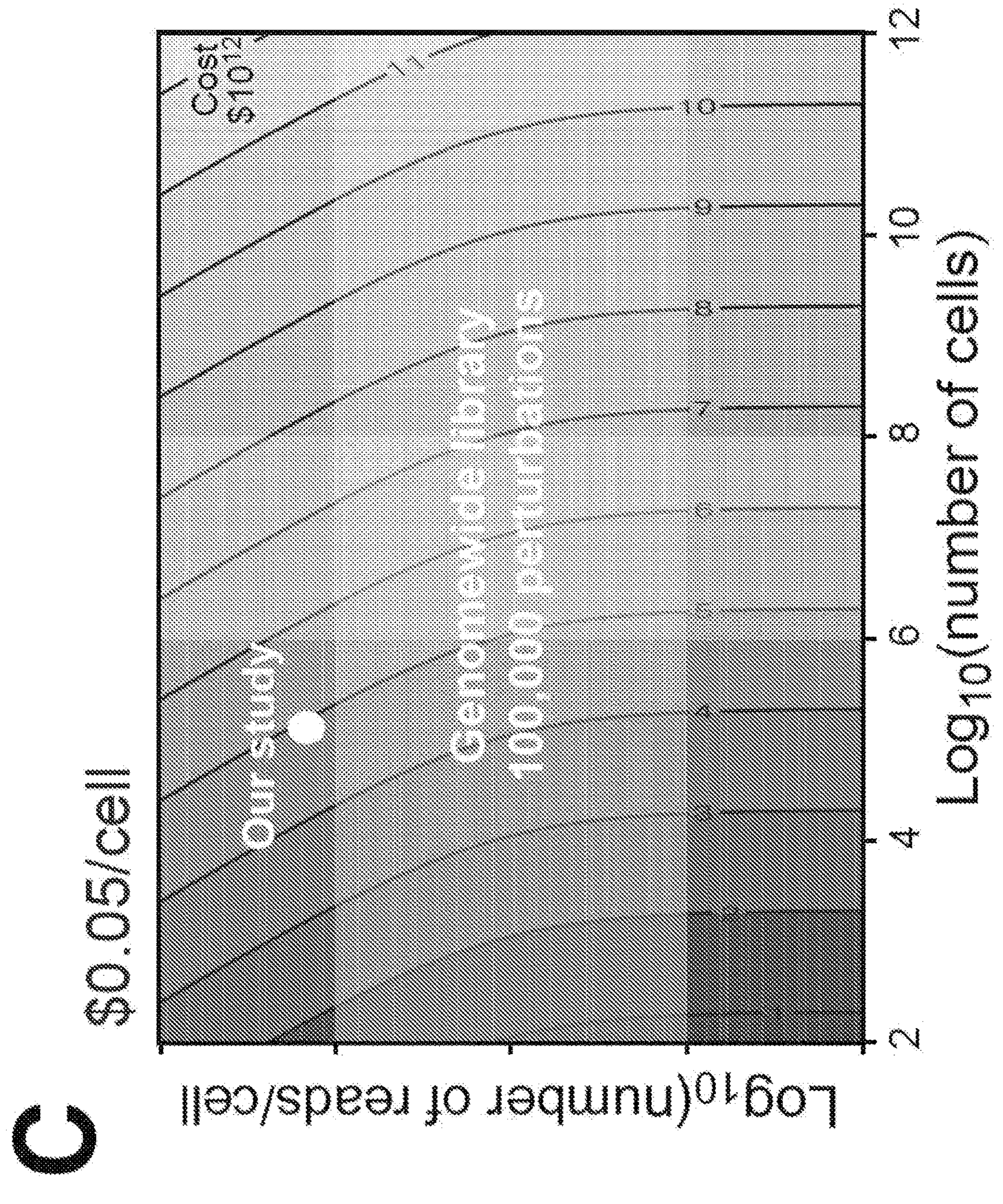
Figure 54D:
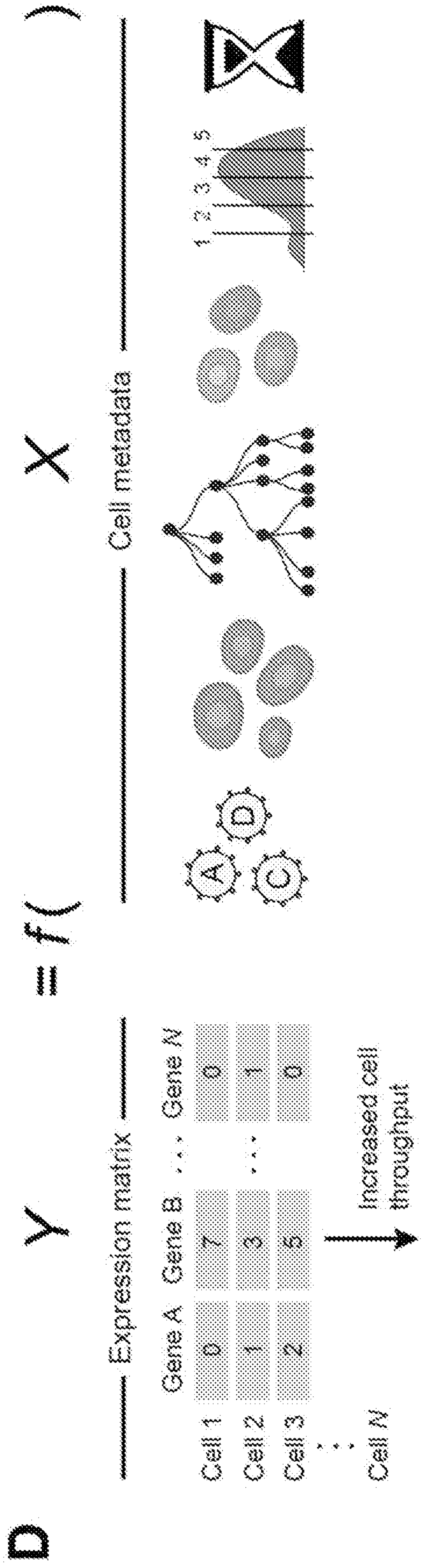

At its current scale, given the required number of cells and depth, and with reasonable estimates for the current cost of single cell assays (FIG. 54C), Perturb-seq can be readily applied for targeted screens of a subset of genes of interest and their interactions, as Applicants have done here for TFs and cell cycle regulators. In some systems, growth or marker based screens may first be performed to identify this subset upstream of Perturb-seq (as done for the unfolded protein response described herein as Applicants have done earlier in BMDCs (Parnas et al., 2015)). The scale of Perturb-seq, will increase as both the cost of both sequencing and of high throughput scRNA-seq preparation methods continues to decrease (FIG. 54C).

A researcher can balance the key parameters of the screens based on their wish to focus on major transcriptional phenotypes (cell states or signatures) vs. effects on individual genes' expression, by varying the number of surveyed cells and the sequencing depth. Major transcriptional defects can be readily identified when sequencing shallowly across large numbers of cells; by sequencing deeper (and more cells per perturbation), finer effects become readily apparent. Applicants purposefully exceeded in this study the sample size and sequencing depth required to reach saturation, thus providing the community with a necessary resource to design future experiments. Surprisingly, the signature analysis Applicants describe showed that with as few as ~10 cells per perturbation, a broad survey of transcriptional phenotypes across thousands of perturbations can be performed (FIG. 54B).

As cell numbers increase towards genome-wide or large combinatorial screens, Applicants will also need a concomitant increase in the bandwidth of computational methods. In our analysis framework, MIMOSCA (FIG. 56H), Applicants used a range of efficient algorithms, such as Facebook's Fast PCA implementation (research.facebook.com/blog/fast-randomized-svd/), Infomap clustering (Rosvall and Bergstrom, 2008), parallelizable regression frameworks, and binned permutation significance testing, foreseeing a need for scalability towards millions of cells. In future extensions, when the total number of perturbations is larger, expression matrices can be stored in chunked form, split by perturbation identity, and the relevant subsets can be read, combined with control cells, and analyzed in parallel.

Example 21: Challenges and Opportunities for Understanding the Vast Space of Possible Genetic Interactions By considering interactions between the covariates, Applicants showed that Perturb-seq can dissect molecular effects at unprecedented resolution. A key extension is to screen the combinatorial interaction space between perturbations (Hartl, 2014; Phillips, 2008; Sackton and Hartl, 2016; Shao et al., 2008; Zuk et al., 2012), to understand genetic interactions not only between pairs of genes but even at higher order, such as the three-way interaction between NFKB1-Rel-Stat2 Applicants uncovered in BMDC (FIG. 52C). This can also help uncover global principles of the genetic architecture of a system, such as how robust it is and what is the characteristic number of permissible perturbations (as in FIG. 60).

Figure 61A:
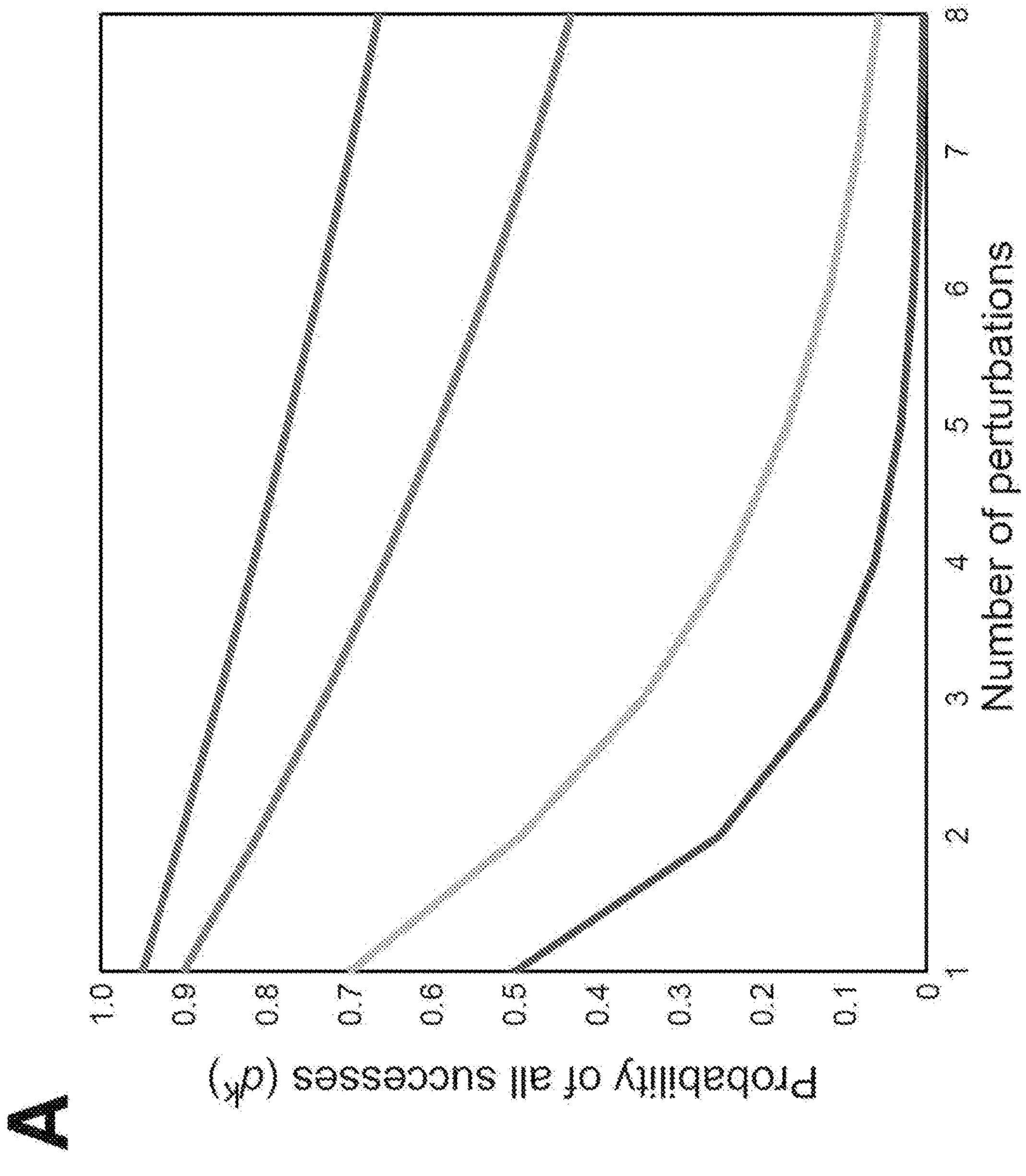
FIG. 61A-L illustrates a saturation analysis for differential expression, related to FIG. 54. (A) Theoretical probability of having a successful perturbation in every target as a function of the number of perturbations ($1\text{-}p^n$), assuming independence. (B-L) Saturation analysis. Shown is the effect of the fraction of cells (Y axis) and reads (X axis) on our ability to recover a given level of correlation (color bar) with either the PCA scores (B-D), gene signature effects (E-H) or per gene transcriptional defects (I-L) based on the BMDC 3 h stimulated screen data. The total number of cells (1.0) is, on average, 300 cells/perturbation and the total number of transcripts per cell is, on average 5,000. PCA scores (as the expression matrix Y) were obtained by projecting the data onto PCs defined by the wild type cells for the top 11 PCs conditioned on different effect sizes. Effect size units are arbitrary. For gene signatures, effects sizes are in units of average log 2 (UMI) across the gene signature. For an individual gene level, effect sizes are in units of log 2 (UMI).
Figure 61B:
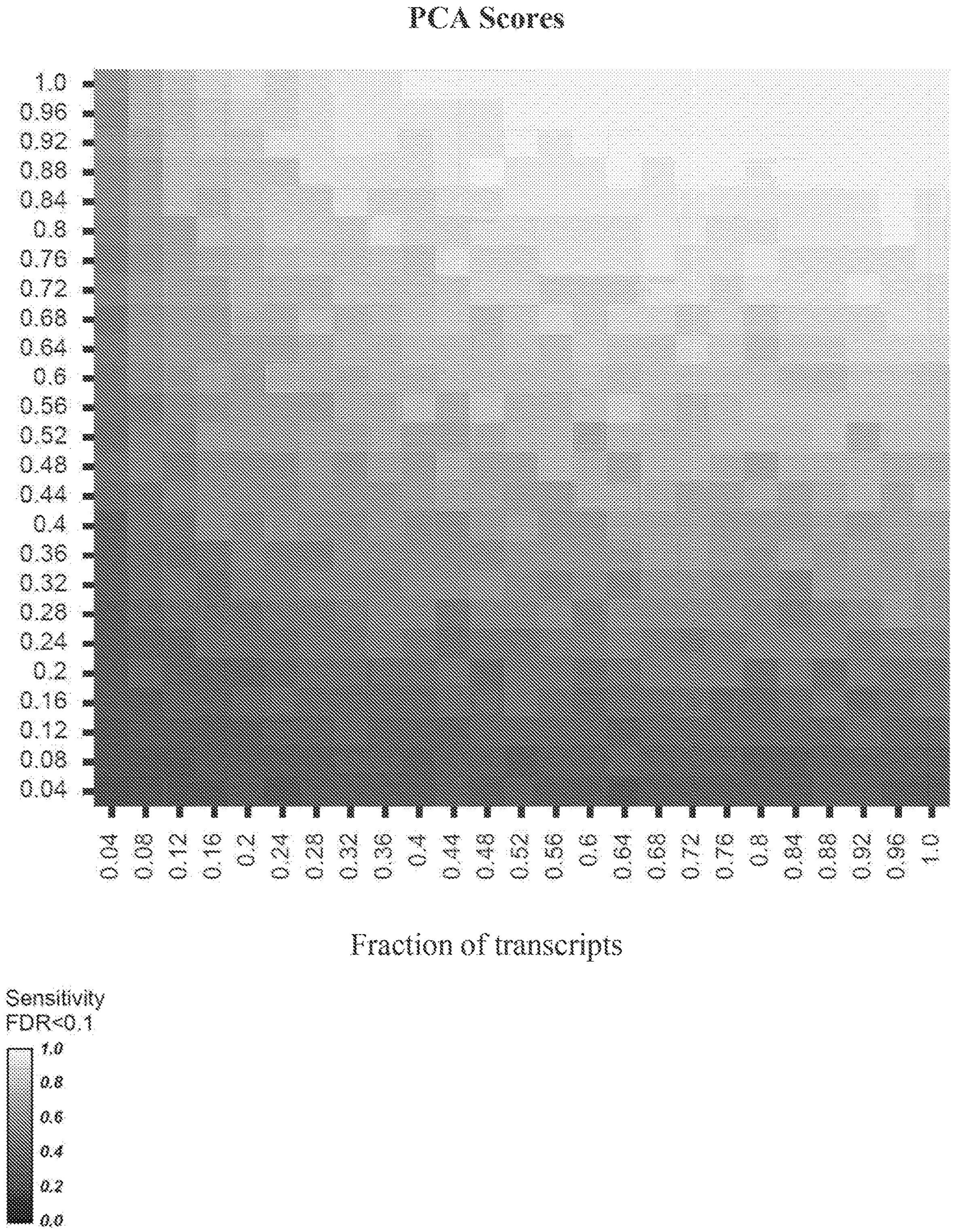
Figure 61C:
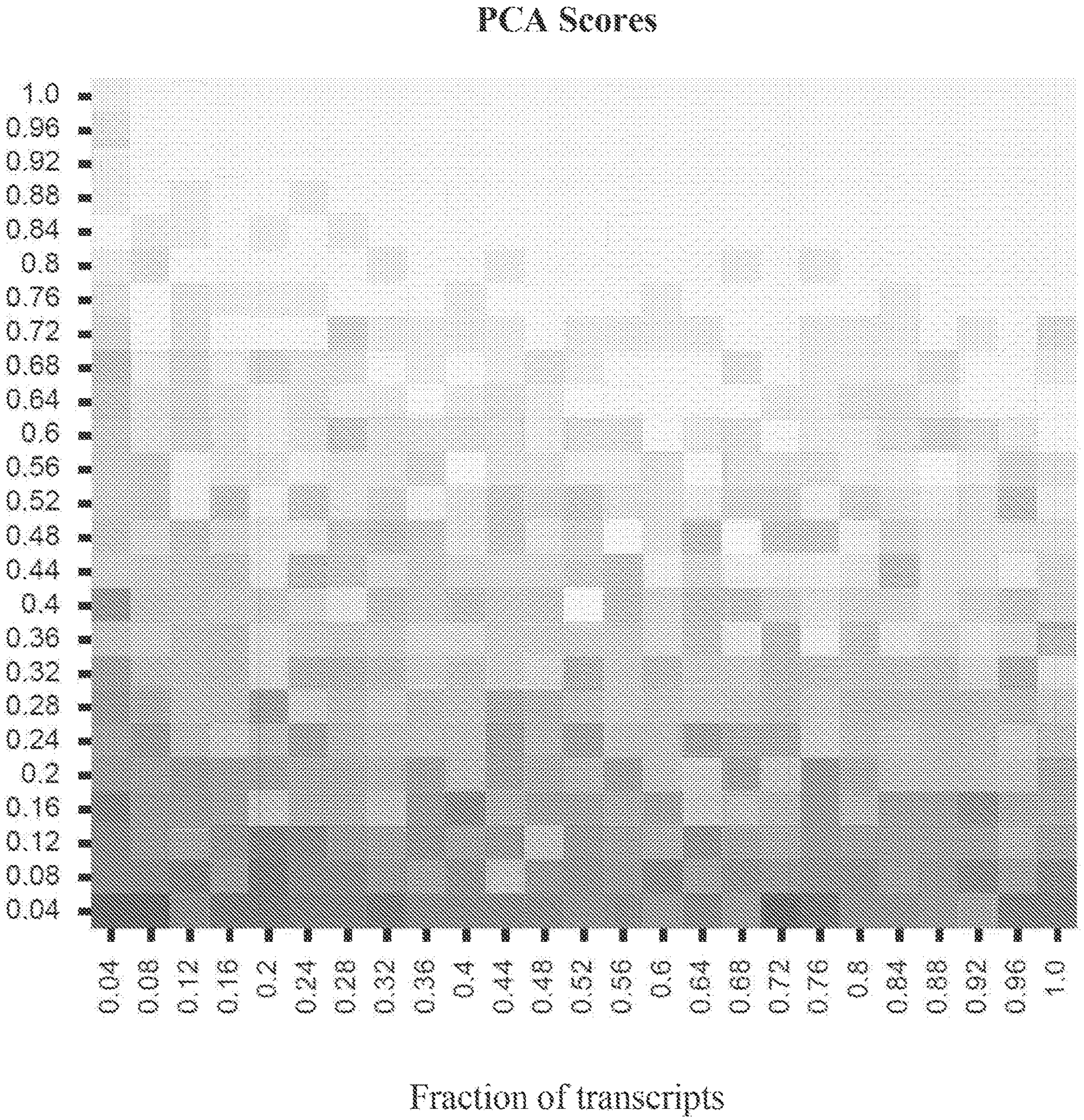
Figure 61D:
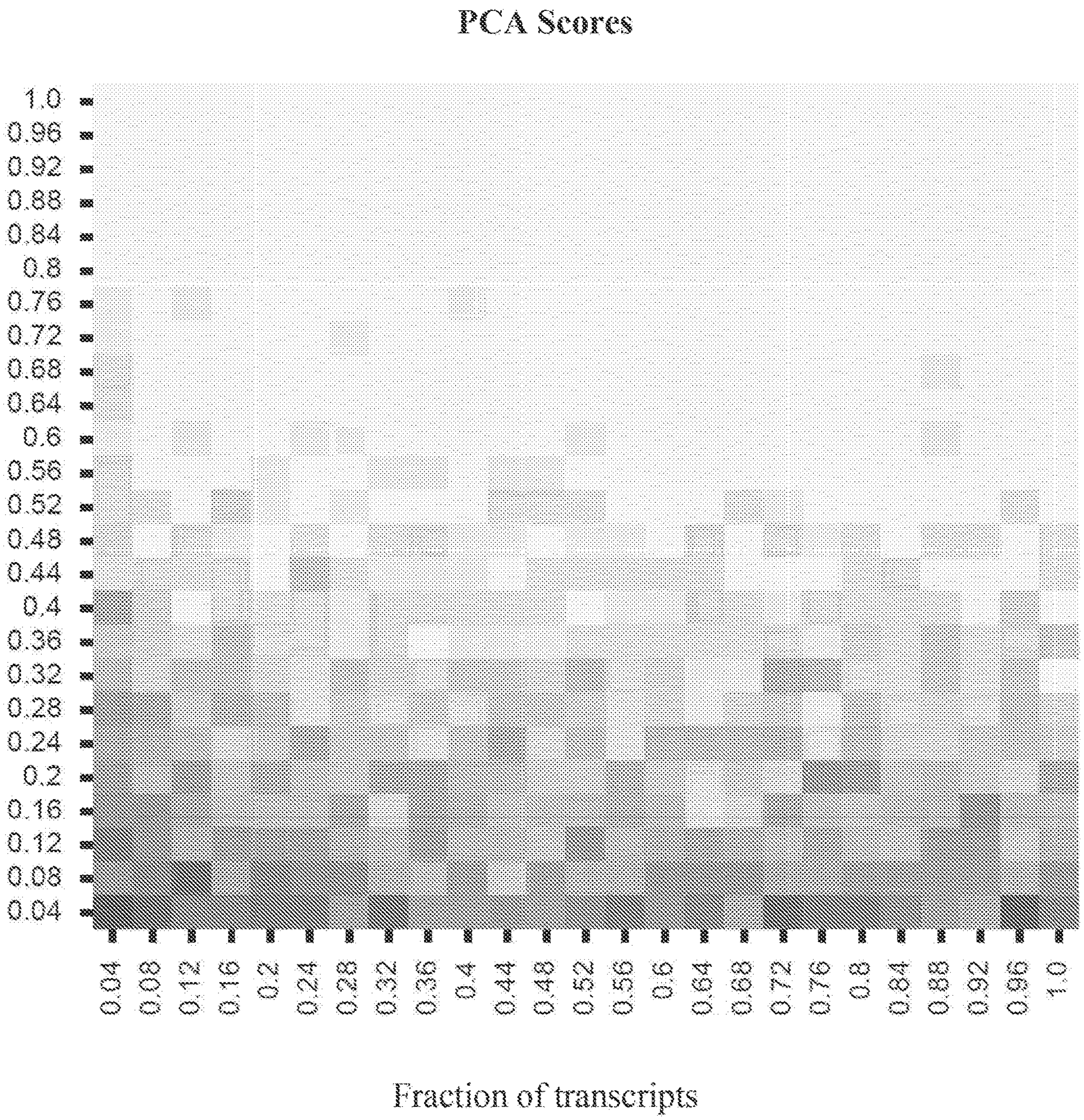
Figure 61E:
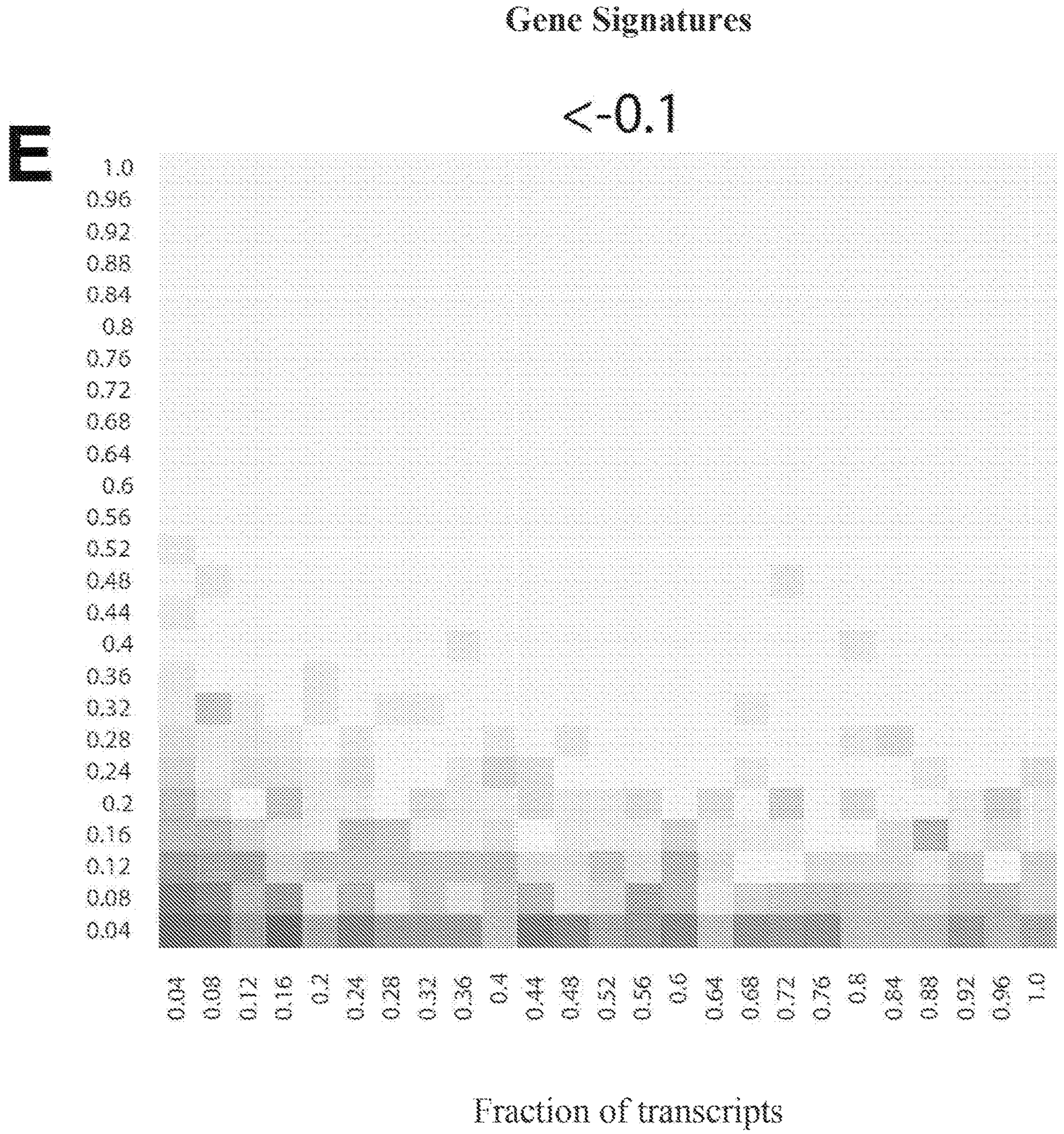
Figure 61F:
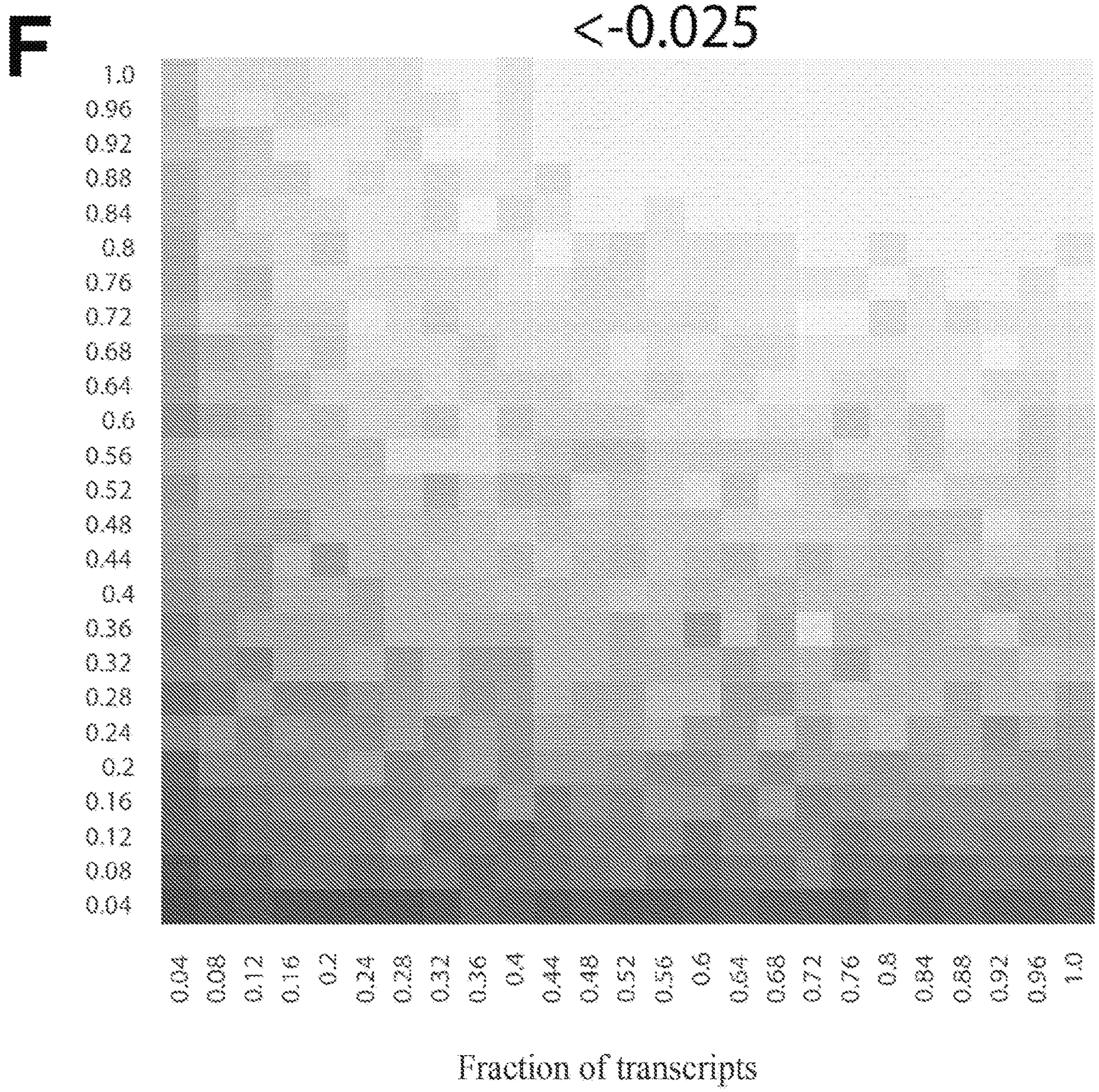
Figure 61G:
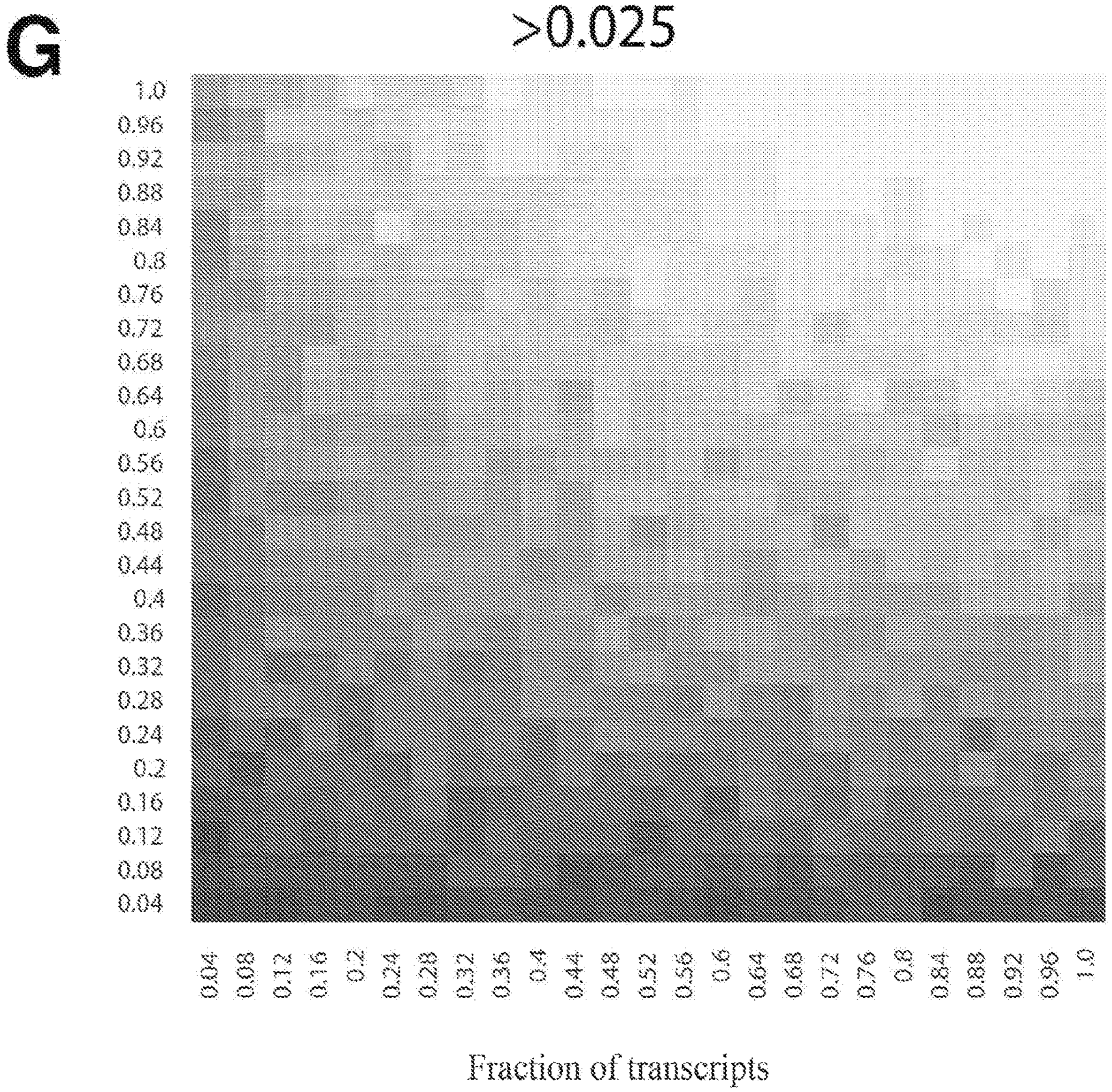
Figure 61H:
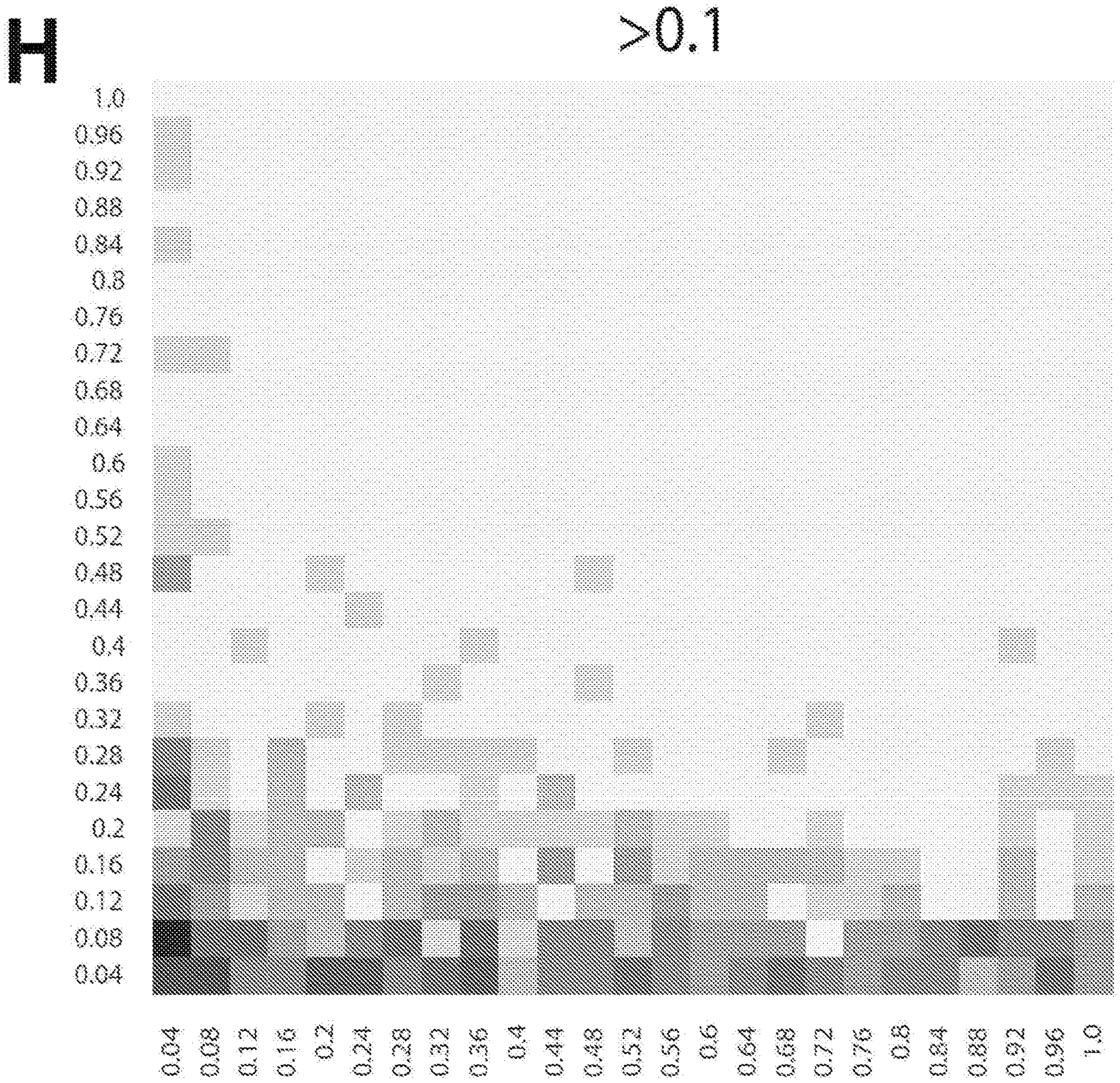
Figure 61I:
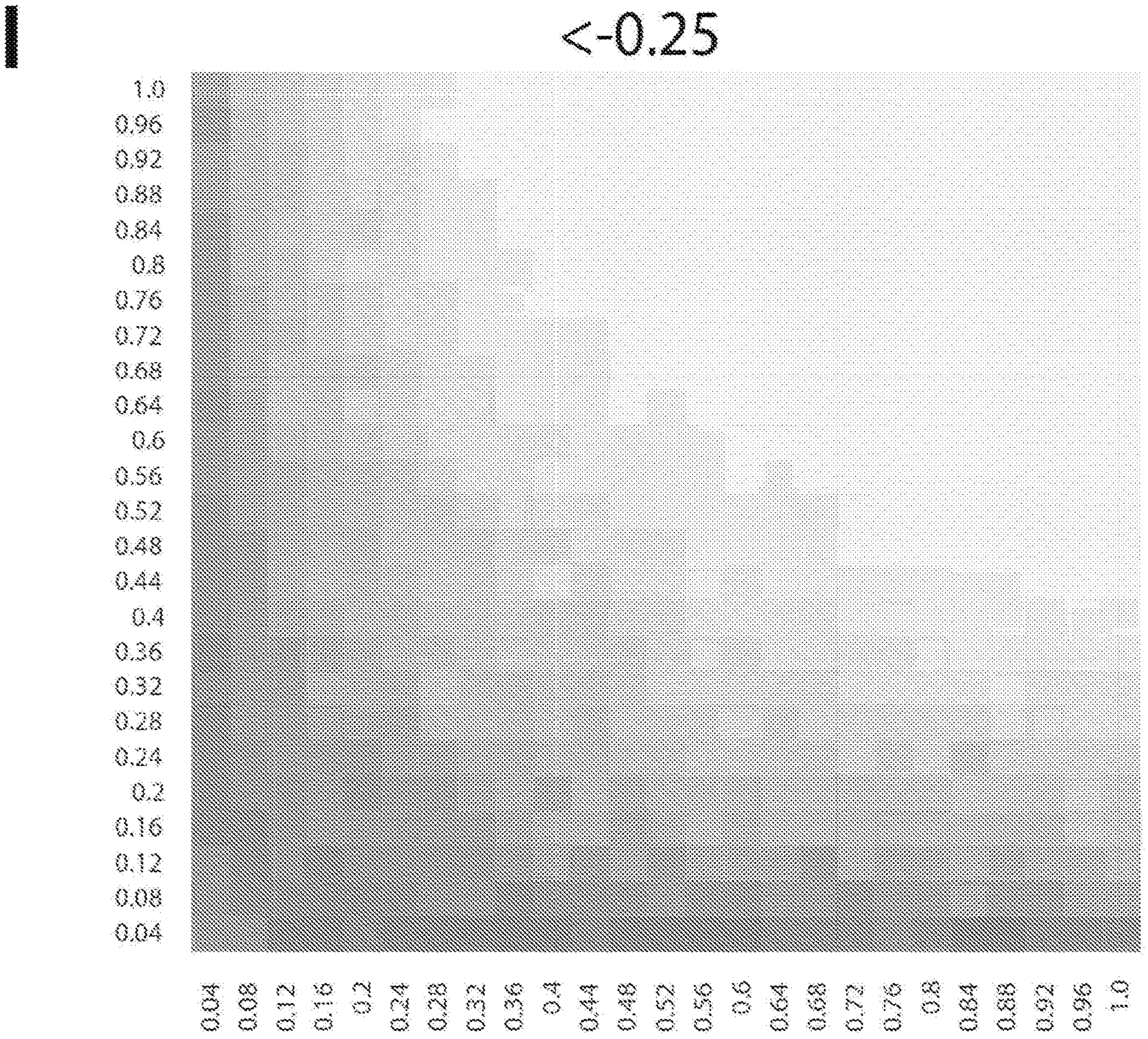
Figure 61J:
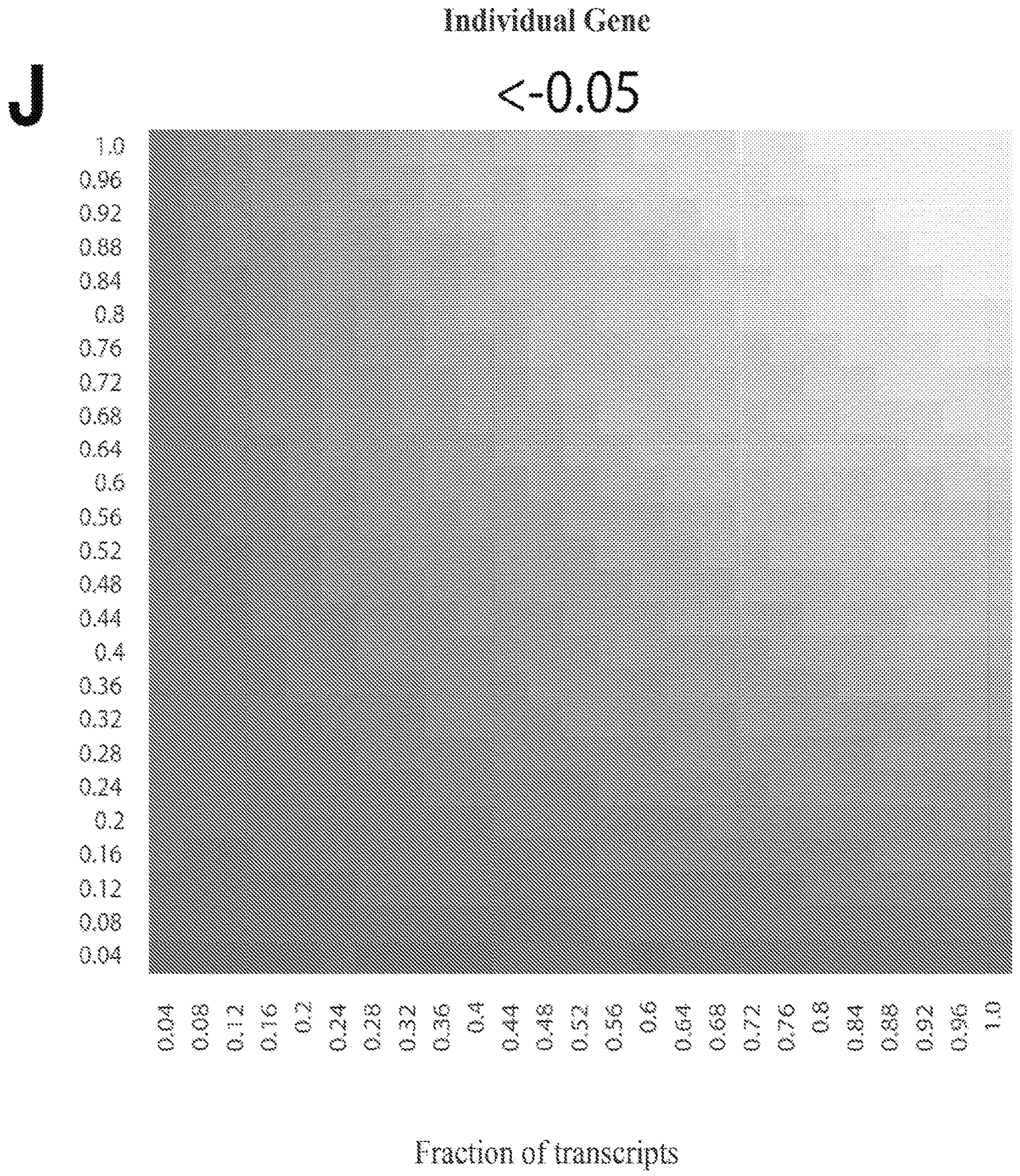
Figure 61K:
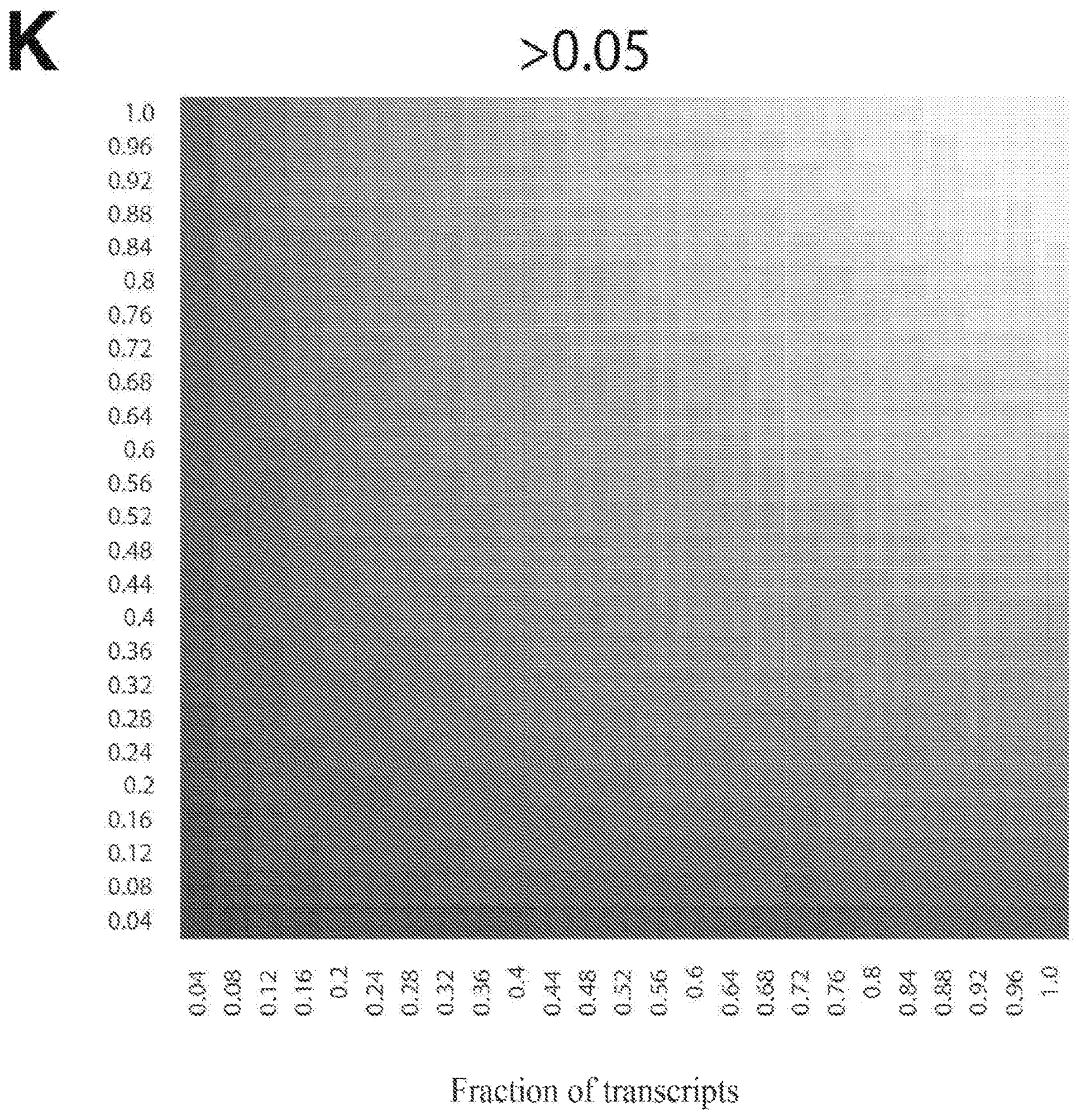
Figure 61L:
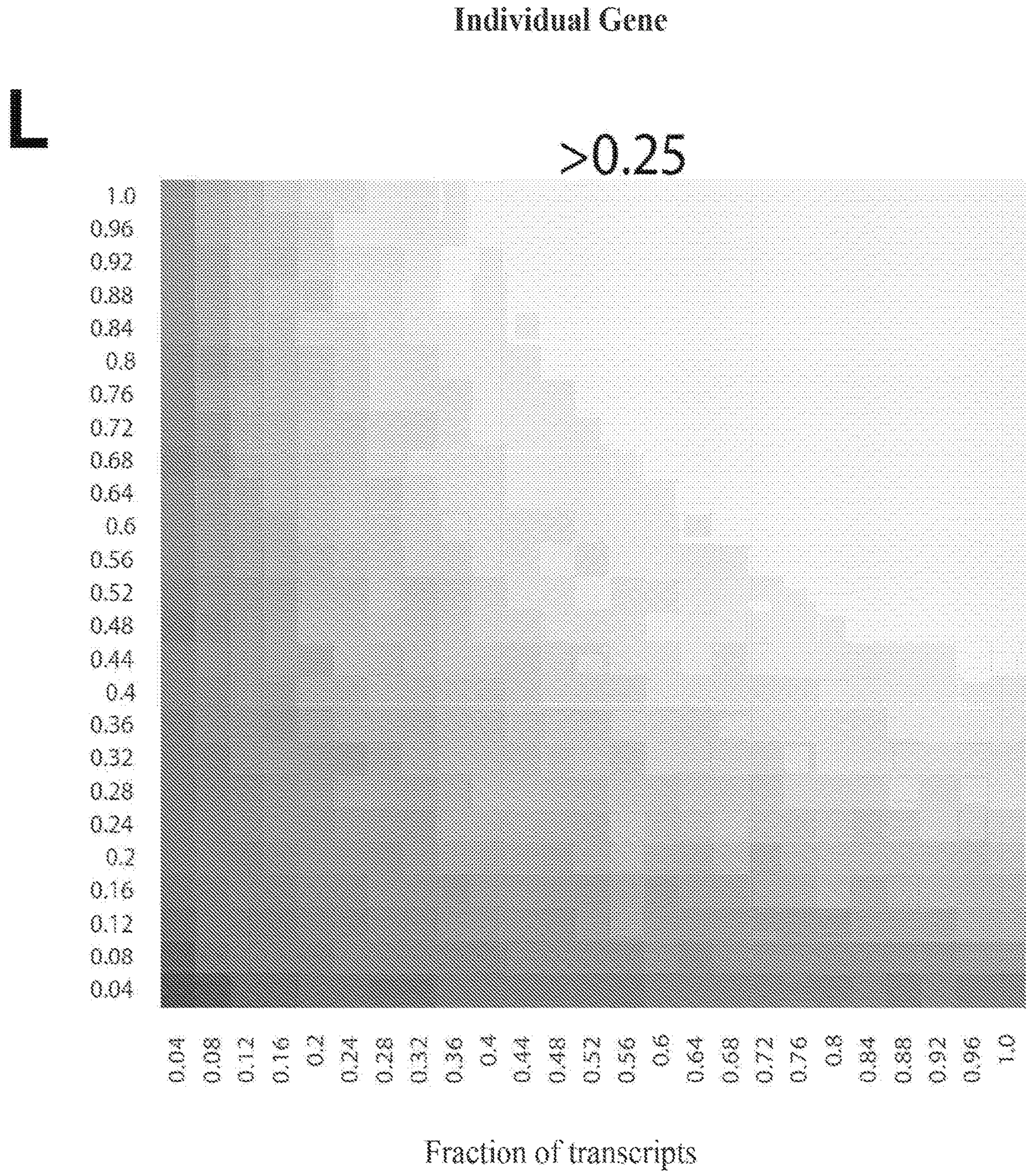
Figure 62:
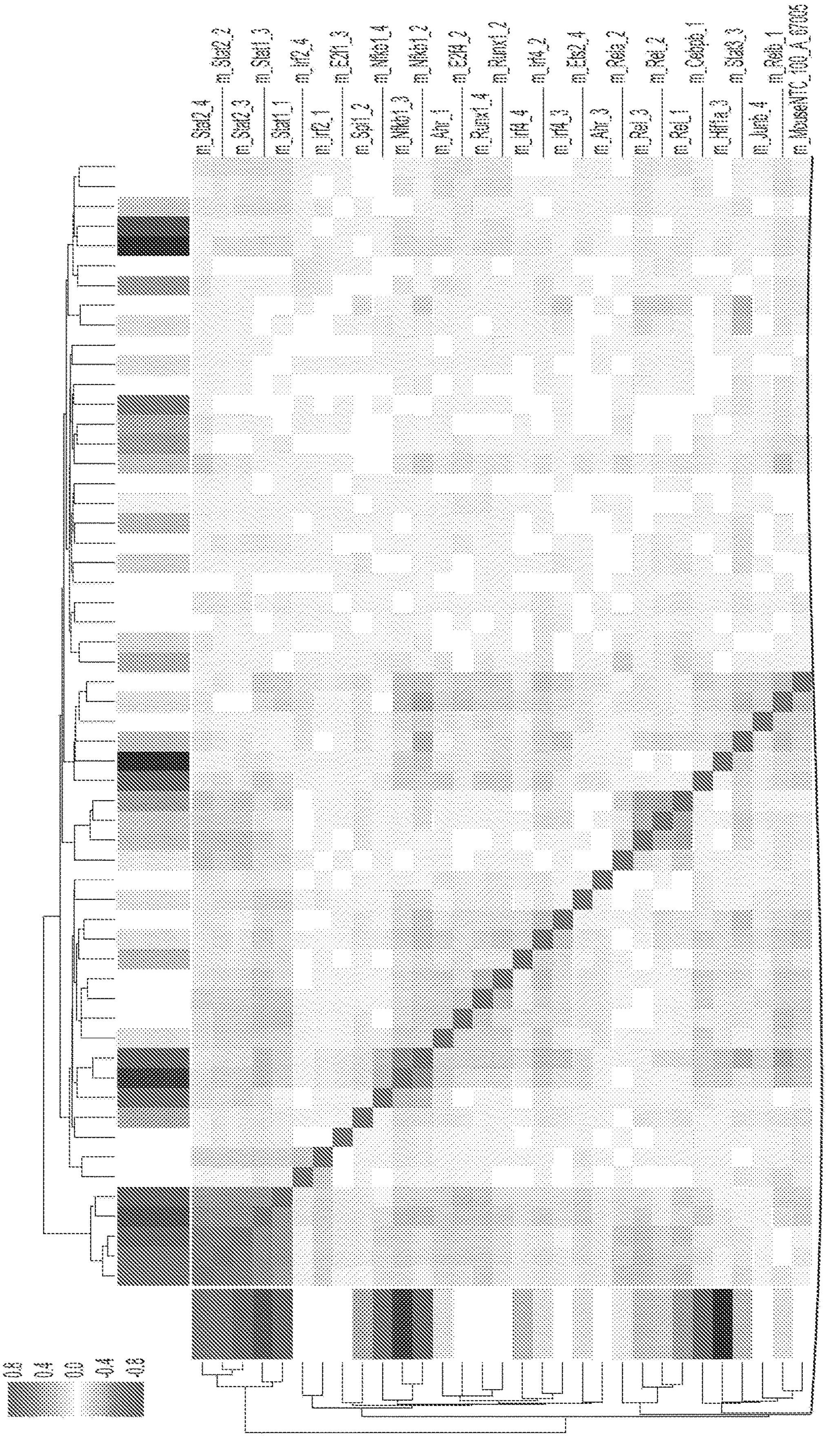
FIG. 62 illustrates Perturb-Seq analysis of the role of TFs in the response of BMDCs to LPS.
Figure 62:
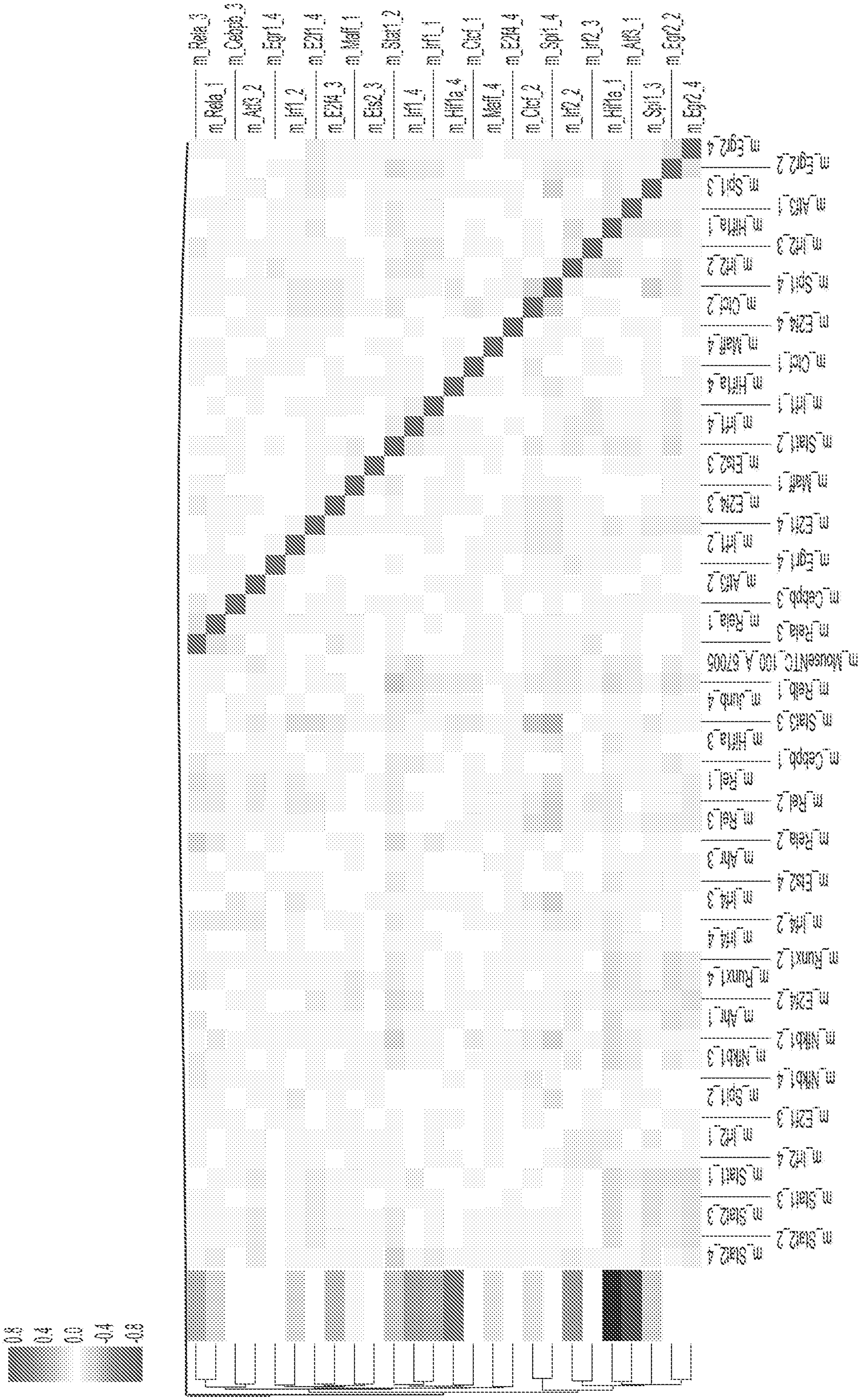
Figure 63D:
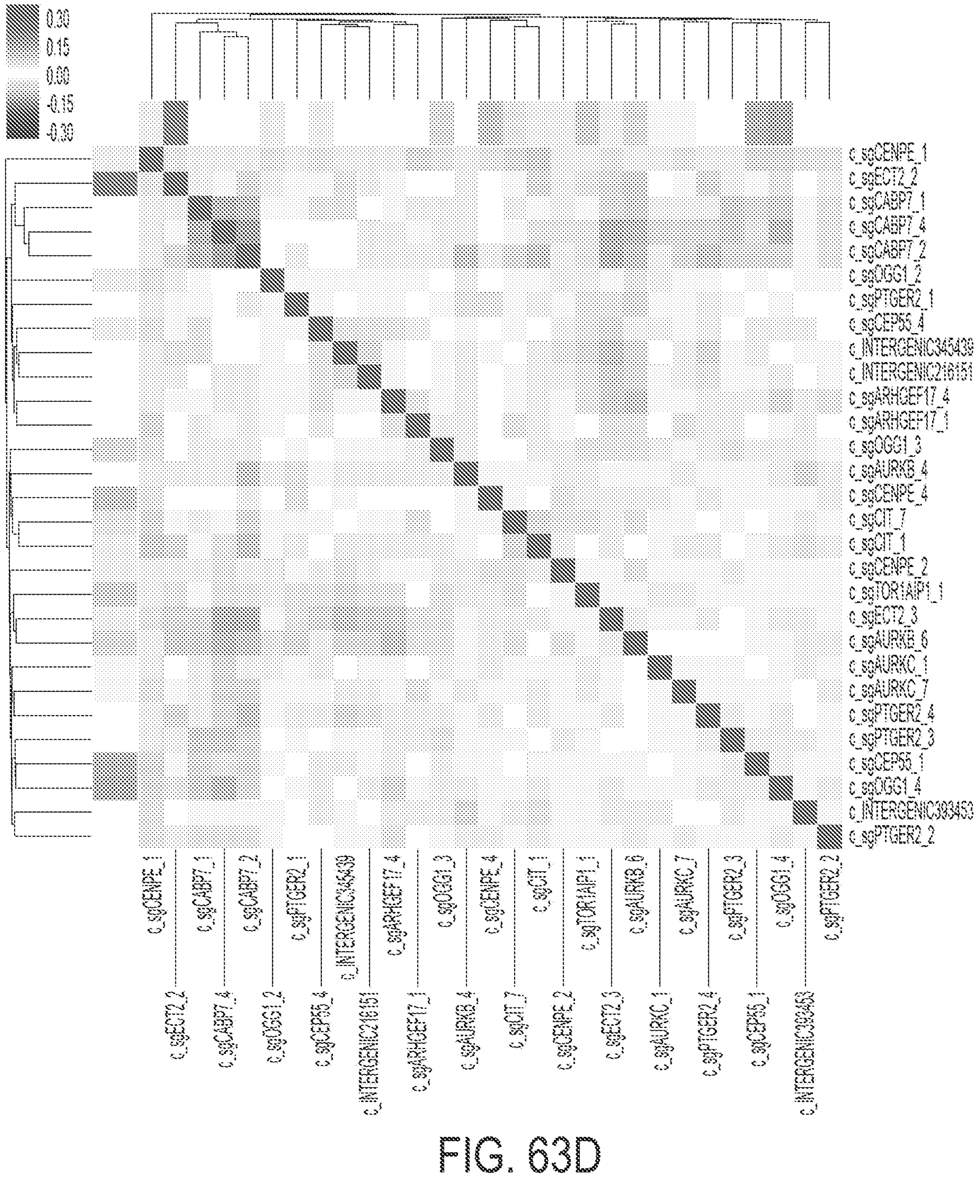
Figure 64:
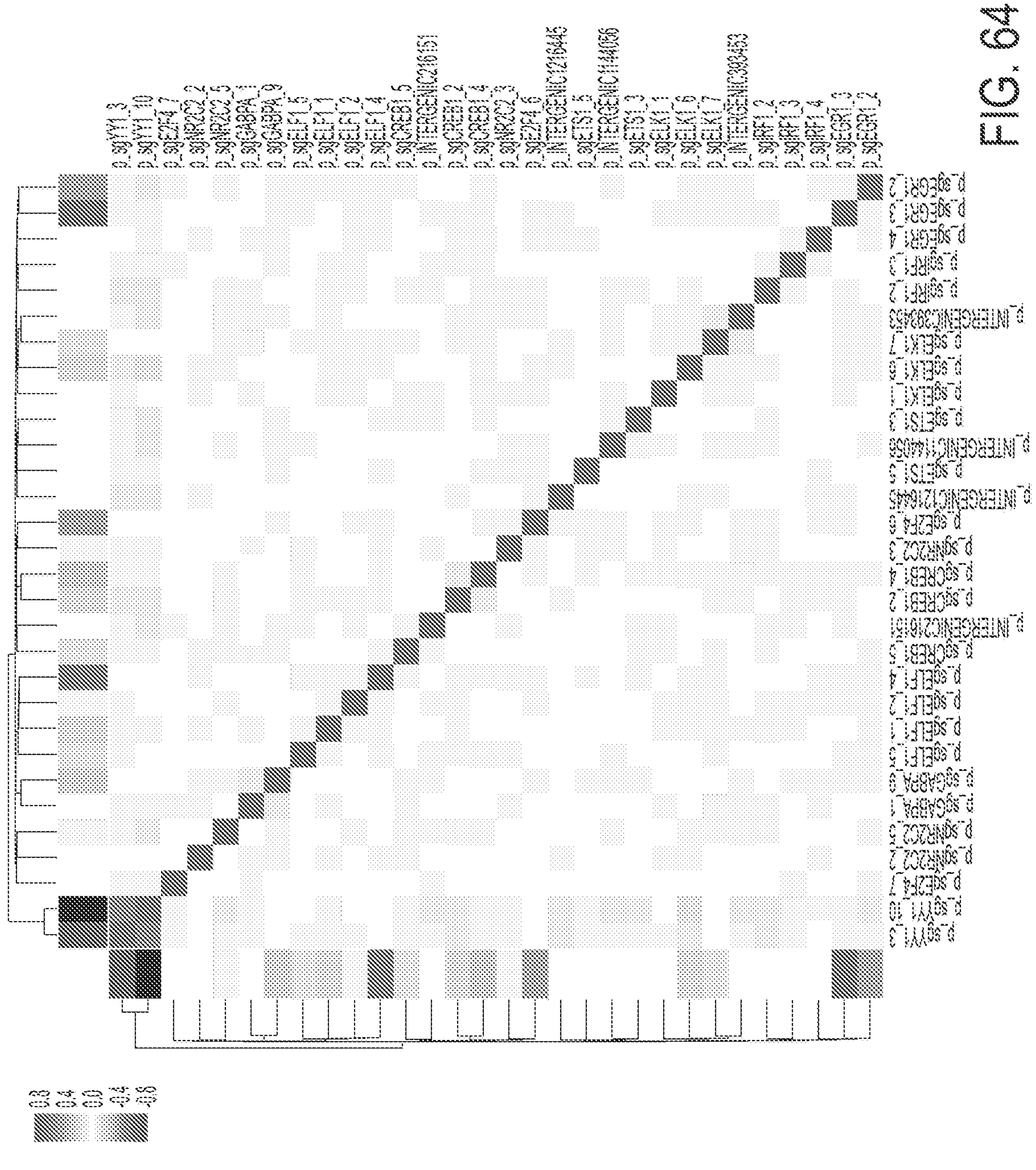
FIG. 64 illustrates Perturb-Seq analysis of the role of non-essential TFs in K562 cells.
Figure 65:
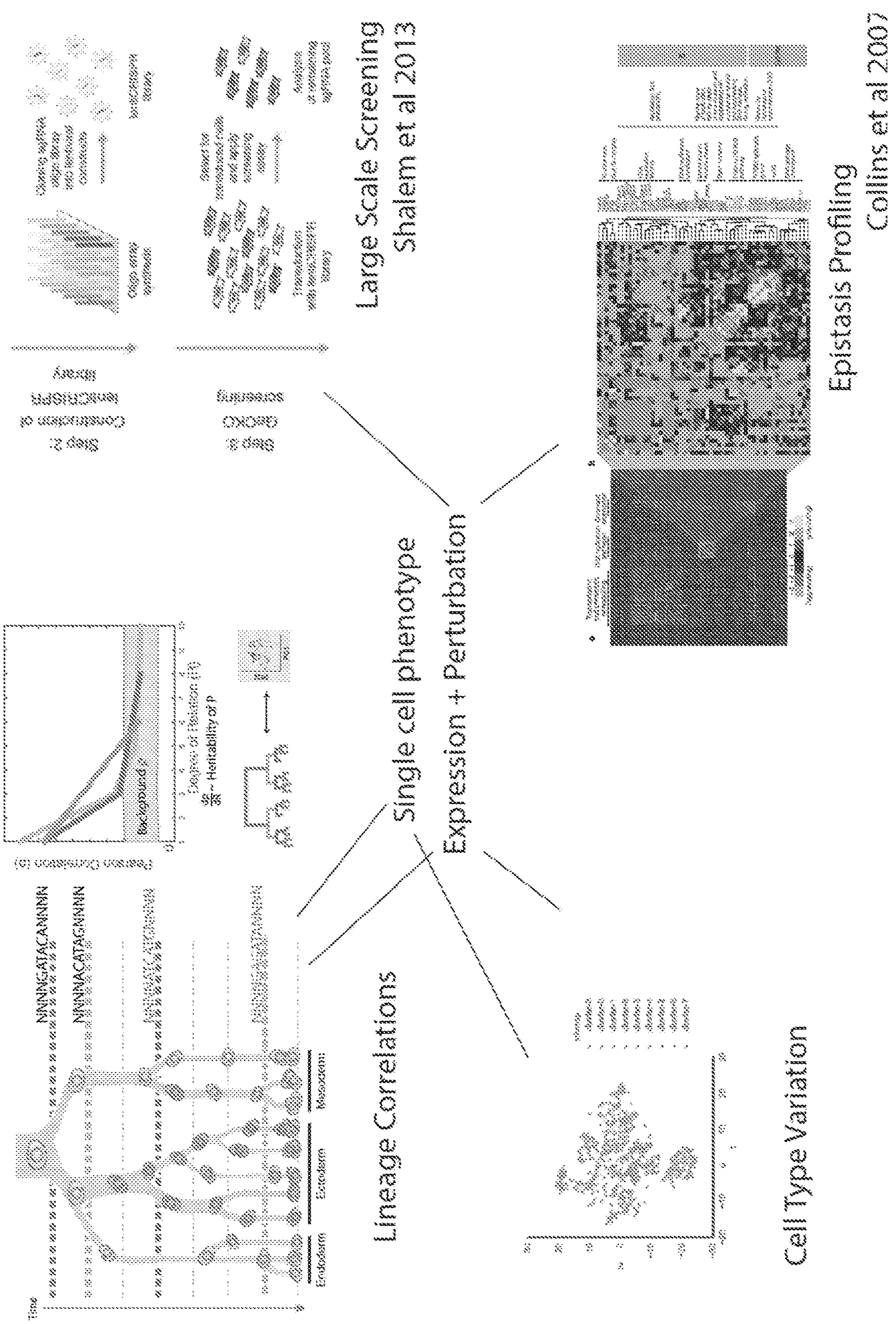
FIG. 65 illustrates the prospects for Perturb-Seq.

However, there are several major hurdles to achieve this ambitious goal. Both the probability of detecting all perturbations and the probability of all perturbations resulting in an effect scale exponentially with the order of perturbation (FIG. 61A). For example, when examining cells containing three sgRNAs, assuming half of the cells contain homozygous mutations, and all sgRNAs are independent, the probability of all targets being fully perturbed is one-eighth. Overcoming this source of noise will be a major challenge. However, the alternating-descent framework Applicants described (FIG. 82) and future improvements to it can help to deconvolve mixtures of knockouts, initialized by the observed assignments between cells and perturbations, and is potentially scalable to higher order interaction terms.

More critically, while Perturb-seq significantly reduces the time and cost required for transcriptional assays of many perturbations, these limiting factors still scale linearly with the number of perturbations assayed. The size of the combinatorially complete parameter space, p, scales as 28, where g is the number of perturbations. For any sizeable g, p is enormous; far more enormous, in fact, that the number of cells available in any imaginable setting, regardless of costs, efforts or other technological improvements.

Applicants hypothesize however, that an alternative strategy should combine a substantial under-sampling of this vast space, with appropriate analytical approaches-inspired by both classical and recent methods (Beerenwinkel et al., 2007; Carter et al., 2007; Jin et al., 2006; Weinberger, 1991), and should aid greatly in our endeavor to infer the impact of interactions even when p—the number of possible combinations—is much larger than n, the number of samples. Applicants are motivated in pursuing this framing by two assumptions on biomolecular systems, such as the circuits that control gene expression: (1) modularity, as Applicants have shown in this study for both the perturbations and the gene targets, and has been well-established in many genomic and genetic studies (e.g., PMID 14973197, 12134151, 15448693, 27708008); and (2) sparsity, for example, such that Applicants expect most genes not to have genetic interactions (this is supported by those studies—almost entirely in yeast—of pairwise genetic interactions; PMID 27708008). Under these two assumptions, it may be possible, for example, to perform a subset of experiments, when most cells receive a relatively large number of perturbations (e.g., 5) and infer both partially observed and unobserved interactions at a lower order (e.g., 2 or 3).

Perturb-seq was experimentally designed with such future studies in mind, and our initial framework already started to rely on such assumptions. One example is the Li penalty in the elastic net, in our regression framework. A similar $L_1$ penalty as Applicants apply to the coefficients of B could in principle be also applied to its rank (Candès and Recht, 2009); considering the group structure in our pathway analysis of perturbations, this may represent a reasonable constraint. More technically, when attempting to fit the combinatorial interaction space, our approach is consistent with the general machine learning framework of finding a function $f(x)$ that minimizes a loss function to best explain our observations y. Applicants effectively search for a sparse polynomial of the form $y=x_1+x_2+x_2+\ldots+x_1x_2+x_1x_2x_3\ldots$ to best explain our observations.

Example 22: Perturb-Seq is a First Example of a General Framework to Combine Rich Readout with Cellular Metadata The current implementation of Perturb-Seq can be readily extended to other traces of the cell's history and to additional rich readouts. First, other CRISPR-based perturbations are readily compatible with Perturb-Seq, including CRISPRi, CRISPRa, and alternative editors such as CRISPR/Cpf1. In particular, Modeling SNPs associated with common diseases or variants mutated in cancers requires efficient homologous recombination followed by cloning of edited cells, but this obstacle may be reduced by the ability to deconvolve wild type and perturbed cells based on expression signature, as Applicants have done here, or by assays that will directly detect the edited variant (through DNA+RNA assay or through its encoded transcript) in each cell in the pool.

The RNA barcodes (PAPIs) used in this study served to identify perturbations, but can also be used to mark cells derived from a common ancestor for the purposes of lineage tracing (FIG. 54D), thus relating cell lineage and cell fate maps. For example the PRISM pool contains a set of barcoded cell lines (Yu et al., 2016). Their expressed RNA barcodes could be combined with Perturb-seq to enable pooled measurements of the transcription effect of different perturbations across cell lines by fitting an interaction term between the cell line and the perturbation.

Other measurement platforms may be compatible within the experimental and computational framework Applicants describe. For example, multiplex PCR (Fan et al., 2015) can be used to dial-out a subset of transcripts on which to obtain more reliable information (similar to our PAPI protocol). Protein measurements across millions of cells may be feasible by fusing FISH probes to heavy metal and using CyTOF as the readout technique. It may also be possible to devise paracrine assays by co-culturing perturbed cells in droplets and merging the droplets with a massively parallel single cell sequencing technology.

The experiments and analysis provide a guide the design of future experiments that leverage the scale and tunable resolution possible by combining high throughput single cell sequencing and pooled screens. By rapidly and simultaneously testing causal relations between many genetic manipulations and the resulting molecular phenotypes, Applicants aspired to help bridge the gap between genetic screening and molecular follow up experiments and to provide a valuable tool to the systems biologist. In doing so, Applicants hope to facilitate casual research questions that infer mechanisms by which genotypes result in specific phenotypes.

Example 23: A Robust Strategy for Encoding Information in RNA Transcripts that Allows Parallel Profiling of Separately Perturbed Cells by Droplet-Based Single-Cell RNA-Sequencing A particularly fascinating example of a complex transcriptional response is the mammalian unfolded protein response (UPR), a branched pathway critical for maintaining homeostasis of the endoplasmic reticulum (ER). In metazoans, this response is coordinated by three distinct ER transmembrane sensor proteins (IRE1α, ATF6, and PERK), which activate three individual transcription factors (XBP1, the N-terminal cleavage product of ATF6, and ATF4, respectively) to promote survival or, when ER stress cannot be corrected, trigger cell death pathways (Ron, Walter 2007, Walter, Ron 2011, Hetz 2012). The molecular signaling events downstream of each UPR sensor protein are discrete. The resulting transcriptional responses, however, are overlapping and integrated and, therefore, the response to any given stress is likely to be heterogenous. Among stresses that can activate the UPR are potentially deleterious changes to protein folding, as well as disruption of normal nutrient flux, redox potential, calcium homeostasis, hormone stimulation, lipid biosynthesis, and membrane integrity. Considering the diversity of inputs monitored by the UPR and the necessary plasticity in outcome, comprehensive characterization of this system in mammalian cells requires both unbiased profiling of the physiological stresses that activate the sensors and delineation of the complex transcriptional phenotypes for each input.

Here, Applicants also apply perturb-seq to the systematic analysis of the mammalian UPR. To independently manipulate the three branches of the UPR, Applicants first developed a programmable strategy for simultaneously depleting up to three genes with high efficacy. Applicants then used perturb-seq with combinatorial depletion of the UPR sensors to delineate the distinct transcriptional programs of the UPR and the epistatic relationships among the three UPR branches. Next, Applicants used a two-tiered approach to interrogate the biological systems monitored by the UPR. Applicants identified hundreds of genes that contribute to ER homeostasis from a genome-wide CRISPRi screen and then applied perturb-seq to interrogate a diverse subset of these genes with single-cell resolution. These experiments allowed us to systematically define the functional relationships between genes with high precision and to dissect the complex, partially overlapping transcriptional responses to ER stress. Furthermore, analysis of the single-cell responses revealed bifurcation of the UPR branches at two levels: among individual cells subject to the same perturbation and at the population level, where differential activation of the three UPR branches occurred across perturbations. The latter indicated a dedicated feedback loop that enables a single arm of the UPR (the IRE1α/XBP1 branch) to specifically monitor the integrity of the protein translocation machinery. These data, alongside the parallel analysis of dendritic cell activation described herein, demonstrate the ability of perturb-seq to provide rich biological insights and systematically dissect complex biological responses.

The recent introduction of scalable, droplet-based approaches for single-cell gene expression profiling and the development of commercial devices (10X Genomics) have made measurement of complex phenotypes highly parallelizable (Macosko et al. 2015, Klein et al. 2015, Zheng et al. 2016). These methods incorporate two barcoding strategies that allow deconvolution of pooled RNA-seq data into single-cell transcriptomes. A cell barcode, affixed to cDNA molecules during reverse transcription of mRNAs from a single cell, is used to computationally link data from individual cells, and a similarly appended unique molecular identifier (UMI) collapses information gathered from individual mRNA molecules to allow molecular counting (FIG. 81A). A current limitation of these methods, however, is that they rely on oligo-dT priming during cDNA synthesis to capture mRNA identity and therefore report only on polyadenylated RNA transcripts. To enable the recording of other types of information, Applicants built a platform that allows genetically encoded barcodes to be expressed as polyadenylated transcripts and captured alongside endogenous mRNAs (FIG. 81A). These barcodes can be used to mark specific cell perturbations (e.g., the identity of a Cas9-targeting single guide RNA, sgRNA), and thus, allow complex pools of cells to be evaluated by single-cell RNA-sequencing on existing droplet-based platforms.

Central to this approach is our barcode delivery construct, a third generation lentiviral vector carrying a polymerase II-driven barcode expression cassette that terminates with a strong polyadenylation signal (PAS) (FIG. 81B) (Goodwin, Rottman 1992). To ensure that the PAS of this internal cassette does not disrupt transcription of the lentiviral genome, and therefore lentivirus production, the entire barcode expression cassette was placed in reverse orientation with respect to transcription initiated by the upstream hybrid long terminal repeat (LTR) promoter. Within this region, the PAS was encoded directly adjacent to the barcode site (127 nucleotides separate the barcode site from the AAUAAA hexanucleotide), a placement designed to favor faithful transmission of barcode sequences into single-cell RNA-sequencing libraries, which typically capture and count only the 3' ends of polyadenylated transcripts. To test barcode capture, Applicants performed single-cell RNA sequencing using the Chromium™ Single Cell 3' Solution (10X Genomics) on a pool of individually transduced chronic myeloid leukemia cells (K562) carrying 8 distinct barcodes. To ensure robust barcode capture with minimal sequencing depth, Applicants developed a protocol to specifically amplify barcode transcripts (FIG. 81A). In a pilot experiment of ~5,700 cells, Applicants observed a median of 45 independent observations (marked by unique molecular identifiers) of the "guide barcodes" per cell using this approach, allowing us to uniquely infer a guide barcode for 92.2% of cells (FIG. 81C,D). The guide barcodes also allowed us to discard droplets that fortuitously received more than one cell (marked by the presence of two or more distinct guide barcodes assigned to one cell barcodes) (FIG. 81D).

A practical way to build complex pools of cells experiencing different perturbations is by variably modulating gene expression, and the advent of CRISPR-based genetic approaches has revolutionized the specificity with which this can be done in mammalian cells (Shalem, Sanjana & Zhang 2015). By including an sgRNA expression cassette in our barcode delivery vector, Applicants tailored our barcoding system to the study of complex CRISPR-based phenotypes (FIG. 81B). To begin validating this "perturb-seq" approach, Applicants confirmed that sgRNA expression from our barcoded construct, the "perturb-seq vector," was capable of generating robust CRISPRi-mediated gene depletion phenotypes (FIG. 81E). Specifically, Applicants tested an EGFP-targeting sgRNA (programmed with a previously validated protospacer, EGFP-NT2 (Gilbert et al. 2013)) in the context of our perturb-seq vector for its ability to repress expression of a genomically integrated GFP reporter. Guide activity from this construct was robust and comparable to that from a previously validated sgRNA expression construct (Gilbert et al. 2014) (95.4% and 96.2% repression of GFP fluorescence, respectively). Importantly, this experiment also demonstrated that, consistent with previous findings (Gilbert et al. 2013), CRISPRi mediates highly homogenous protein depletion across a population of perturbed cells. This ability carried over to pooled experiments, in which the guide barcode can be used computationally to identify the subpopulations of cells bearing particular CRISPR perturbations. Within each subpopulation, the RNA-seq profiles always revealed knockdown of the expected target, as seen in example perturbations from our pilot experiment (FIG. 81F) demonstrating our ability to genetically encode and reliably capture the identity of CRISPRi-mediated perturbations in pooled format with single-cell resolution.

Example 24: A Strategy for Multiplexed sgRNA Delivery that Allows Systematic and Simultaneous Induction of Robust and Homogeneous Genetic Perturbations Having established the potential for perturb-seq as a high content screening platform, Applicants sought to interrogate the unfolded protein response (UPR). Although well studied at the level of mechanistic signaling and bulk population behavior (Ron, Walter 2007, Walter, Ron 2011, Hetz 2012), much remains unknown about how individual cells execute the UPR. Of particular interest is the potential for cell-to-cell heterogeneities in activation of the metazoan UPR, because, unlike the linear pathway in yeast, this branched stress response integrates distinct and separable signaling events to coordinate downstream transcriptional programs (FIG. 82A). Specifically, there are 3 signaling arms of the metazoan UPR, each controlled by a different ER transmembrane sensor protein. These sensor proteins are IRE1α, PERK, and ATF6 (Walter, Ron 2011). Briefly, IRE1α is an endoribonuclease that, upon sensing ER stress, mediates noncanonical splicing of XBP1 mRNA and facilitates stabilized expression of the active XBP1 transcription factor (XBP1s). PERK is a kinase that, upon activation, phosphorylates the alpha subunit of translation initiation factor eIF2 (eIF2α). This inhibitory phosphorylation event generally suppresses translation but paradoxically promotes translation of a small group of mRNAs, including one encoding the ATF4 transcription factor. Lastly, under stress conditions, ATF6 is targeted to the Golgi where proteolytic cleavage releases a cytosolic transcription factor domain. Once activated, XBP1, ATF4 and cleaved ATF6 translocate into the nucleus to initiate transcription.

Applicants sought to systematically interrogate the integrated programs of UPR-mediated transcription using perturb-seq with two motivations: first, to delineate the IRE1α, PERK, and ATF6 transcriptional regulons, which is inherently challenging because of cross-regulation between branches, and second, to evaluate both cell-to-cell and perturbation-to-perturbation heterogeneity in UPR activation. To accomplish our first goal, Applicants had to expand the perturb-seq platform for the systematic analysis of higher-order genetic interaction. Therefore, Applicants developed an approach that allows combinations of genes to be robustly and homogeneously perturbed in a single cell (FIG. 82B).

Previous efforts to multiplex genetic perturbations by expressing multiple sgRNAs for Cas9 or the alternative programmable nuclease Cpf1 have had limited success achieving consistent and uniform perturbation of multiple genes simultaneously (Kabadi et al. 2014, Nissim et al. 2014, Zetsche et al. 2016). To begin addressing this issue, Applicants adapted a previously reported strategy (Kabadi et al. 2014) of fusing three sgRNA expression cassettes (each composed of an RNA polymerase III promoter, the sgRNA targeting sequence, and the sgRNA constant region) into a lentiviral vector carrying our reverse barcode expression cassette (FIG. 82B). To minimize recombination at repetitive nucleotide sequences during lentiviral transduction (Sack et al. 2016, Smyth, Davenport & Mak 2012), Applicants used three different RNA polymerase III promoters (initially Applicants used a modified mouse U6 promoter (mU6), a modified human U6 promoter (hU6), and a modified human 7SK promoter (h7SK), but replaced h7SK with a more potent modified bovine U6 promoter (bU6) in later work). To evaluate the activity of our initial three-guide expression vectors, Applicants assembled three test constructs that each express EGFP-NT2 from one of the promoters (and negative control sgRNAs from the other two) and monitored GFP depletion in K562 cells using flow cytometry (FIG. 88A). Applicants found that the h7SK promoter generally performed poorly in the context of our perturb-seq vector (FIG. 88B). More importantly, however, cells transduced with our first generation three-guide vectors expressing EGFP-NT2 from the hU6 promoter or the mU6 promoter partitioned into two distinct subpopulations with either strong depletion (>90%) or no depletion of GFP (FIG. 88A). To exclude the possibility that dCas9-KRAB expression levels limited the activity of the three-guide vectors, Applicants engineered a GFP+K562 cell line with increased levels of dCas9-KRAB expression (FIG. 88C, see Methods). When transduced with a three-guide vector expressing EGFP-NT2, these cells still exhibited bimodal GFP expression (FIG. 82C). A likely source of this inactive population is intramolecular recombination within the 93-nt constant regions, which would lead to elimination of one or two sgRNA expression cassettes (Sack et al. 2016).

Figure 82D:
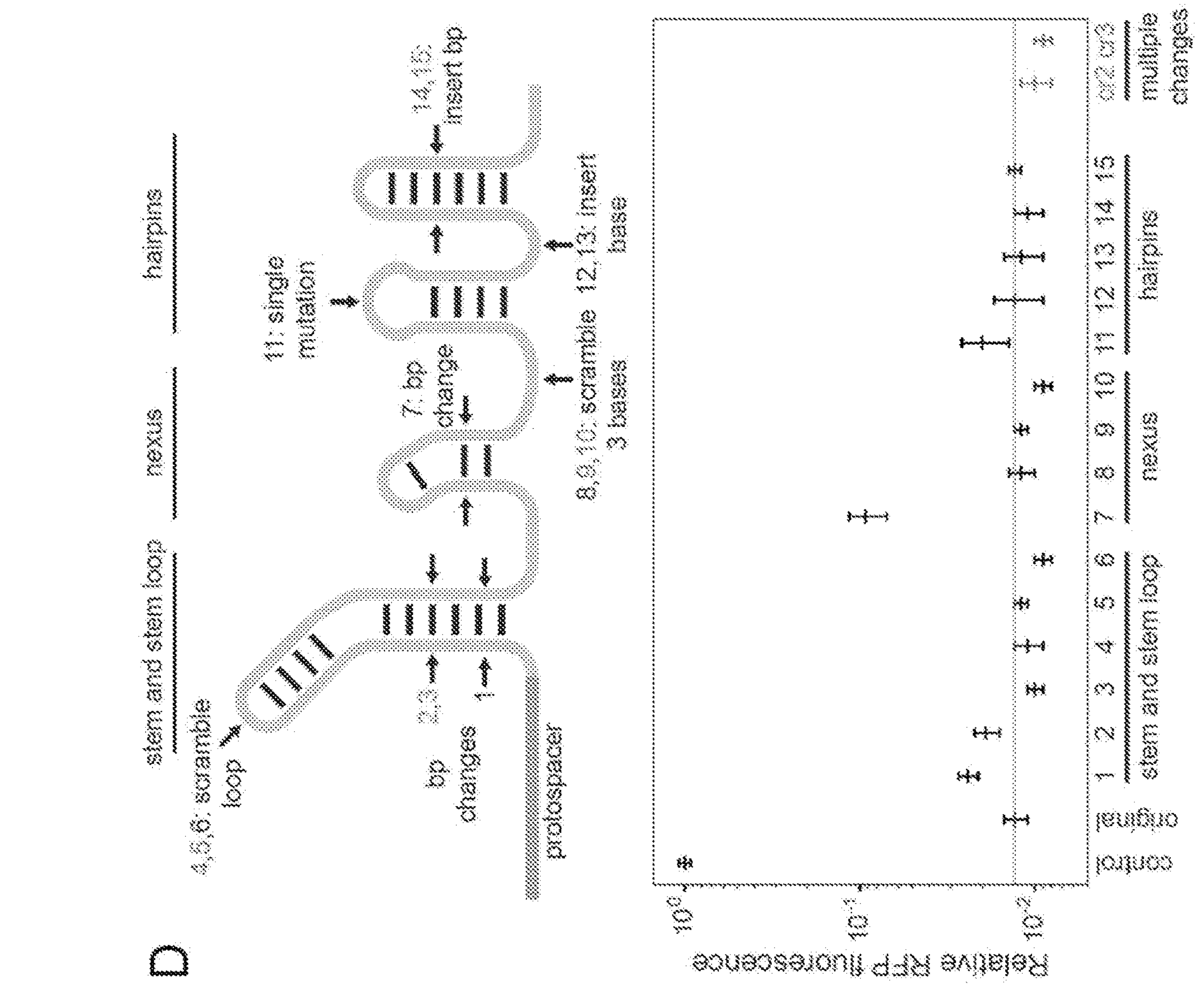

Consequently, Applicants sought to engineer modified sgRNA constant regions that were functionally equivalent but distinct enough in sequence to suppress recombination. Guided by crystal structures of Cas9 (Nishimasu et al. 2014, Anders et al. 2014, Jiang et al. 2015), literature reports of modified constant regions (Briner et al. 2014, Dang et al. 2015), and sequence conservation of tracrRNAs in *Streptococcus* species (Briner et al. 2014), Applicants identified bases that seemed amenable to mutation and designed a panel of variant constant regions (FIGS. 82D, 88D). Almost all constant region variants retained strong CRISPRi activity as indicated by a 97-99% reduction in mRFP levels using a bacterial CRISPRi assay suggesting that the introduced mutations do not disrupt sgRNA: Cas9 binding (FIG. 82D). By combining sets of neutral mutations, Applicants obtained two new constant regions (cr2 and cr3) that share at most 20 bases of continuous sequence homology with each other and the original constant region. Both cr2 and cr3 exhibit strong CRISPRi activity in *E. coli* (FIG. 82D).

To test the activity of cr2 and cr3 in human cells, Applicants generated sgRNA expression cassettes containing the mU6 promoter paired with cr2 and the hU6 promoter paired with cr3 in the context of our perturb-seq vector.

When used to express EGFP-NT2, both cassettes yielded GFP depletion that was indistinguishable from that of the original perturb-seq vector in K562 cells (FIG. 82E). Finally, to identify a third functional RNA polymerase III promoter, Applicants cloned a panel of U6 promoters from different mammalian species into our perturb-seq construct with the original constant region and tested them in our GFP depletion assay. Several U6 promoters mediated strong CRISPRi activity (FIG. 88E), with the bovine U6-2 promoter (bU6) (Lambeth et al. 2006) having the largest effect.

Using our three sgRNA expression cassettes (bU6-2 with original cr (cr1), mU6 with cr2, hU6 with cr3), Applicants then assembled our second iteration of three-guide expression vectors (FIGS. 82B, FIG. 88F) and tested them in our GFP depletion assay. GFP+K562 cells carrying dCas9-KRAB (higher expression levels) transduced with three-guide vectors expressing EGFP-NT2 from any of the three promoters exhibited near-uniform and strong knockdown of GFP (96-97%), nearly identical to that mediated by our single perturb-seq vector (FIG. 82F). These data establish that recombination at the constant regions during lentiviral transduction is an important limitation when fusing multiple sgRNA expression cassettes and that new highly active sgRNAs can be engineered to suppress recombination. Our final three-guide vectors, which use three different RNA polymerase III promoters and three different constant regions, can be faithfully transduced into cells alongside a single perturb-seq barcode to mediate robust depletion of targeted genes.

Example 25: Systematic Delineation of the Transcriptional Responses Controlled by the Unfolded Protein Response Using Perturb-Seq Applicants next sought to use the perturb-seq approach together with our ability to simultaneously repress expression of multiple genes to systematically explore the three branches of the mammalian UPR (FIG. 83A). Using our triple sgRNA expression vector, Applicants transduced sgRNAs targeting each UPR sensor gene (ERN1 encoding IRE1α, EIF2AK3 encoding PERK, or ATF6) in all possible combinations (i.e., single, double, or triple depletions) into K562 cells. Applicants chose K562 because they have a robust UPR and as suspension cells avoid heterogeneity due to difference in their microenvironment (Snijder et al. 2009). Transduced cells were then pooled, sorted for BFP expression (a marker for sgRNA delivery), and after 2 days of growth, cells were treated with thapsigargin, a non-competitive inhibitor of ER calcium pumps, or tunicamycin, an inhibitor of N-linked glycosylation, well-known pharmacological inducers of the UPR. Control cells were treated with DMSO. Applicants sequenced transcriptomes of ~15,000 cells, of which 5% were called as multiplets and 5% were unidentifiable, to a depth of ~120,000 reads per cell, and observed a median of ~25,000 UMIs per cell arising from ~4,300 unique genes. ERN1, EIF2AK3, and ATF6 were depleted >80% when targeted in any combination, and across the three chemical treatments (FIG. 82G).

Applicants then set out to construct an analytical approach for finding statistically robust features within the data (FIGS. 83B, 89A). Every perturb-seq experiment generates an extremely rich dataset, but single-cell RNA-seq data are both intrinsically noisy (due to efficiency limitations during library preparation and natural stochasticity of transcription at the single-cell level) and of very high-dimension (Grün, van Oudenaarden 2015). The latter problem is usually overcome using unsupervised dimensionality reduction methods like principal components analysis (PCA). As many genes share common regulation, cellular behavior is intrinsically low-dimensional (Heimberg et al. 2016, Pollen et al. 2014), thus cellular behavior can be effectively summarized in terms of tens of aggregated effects instead of thousands of individual genes. A limitation of PCA is that it can be arbitrarily corrupted by outliers, and principal components often do not have clear meanings. In our hands, PCA was strongly influenced by clear outliers, such as apoptotic cells (data not shown).

To mitigate these problems Applicants developed an analytical pipeline, Applicants term low rank independent component analysis (LRICA), which proceeds in two stages (See Methods). Applicants first leverage recent advances in the mathematics of sparse matrices (Candès et al. 2011, Lin, Chen & Ma 2010) to directly decompose the observed gene expression matrix (X) into a low-rank matrix (L), representing the low-dimensional dynamics shared across the population, and a sparse matrix(S), capturing noise and effects that are highly variable between cells:

$$X=L+S$$

The low rank matrix contains the major dynamic trends in the population. Applicants identified these trends using independent component analysis (ICA, Methods), which deconstructs the gene expression pattern in each cell into a linear sum of components that are maximally independent of each other (instead of uncorrelated, as in PCA). The components aid interpretation in two ways: by determining which cells are high or low for a particular component, Applicants can identify subpopulations, and by asking which genes maximally influence a component, Applicants can identify groups of related genes driving a particular behavior.

Applicants applied LRICA to our thapsigargin-treated population. Four components varied across the different perturbations, including three that tracked the presence of PERK, IRE1α, and ATF6 (Methods, FIG. 89B). When projected to two dimensions using t-distributed stochastic neighbor embedding (t-sne) (Van Der Maaten 2014), cells bearing a particular perturbation all grouped together, and biologically reasonable groups of perturbations also clustered in proximity to each other. Thus, the identity of the perturbation contained in each cell was distinguishable, which further validated our triple knockdown strategy. The same analysis applied to the four components that varied across the cell cycle arranged the cells in a circular pattern ordered correctly by cell cycle phase. Thus, LRICA identified and decomposed the two largest effects causing variation in the population in an unbiased way and also computationally decoupled them from each other, enabling them to be studied independently.

Figure 83E:
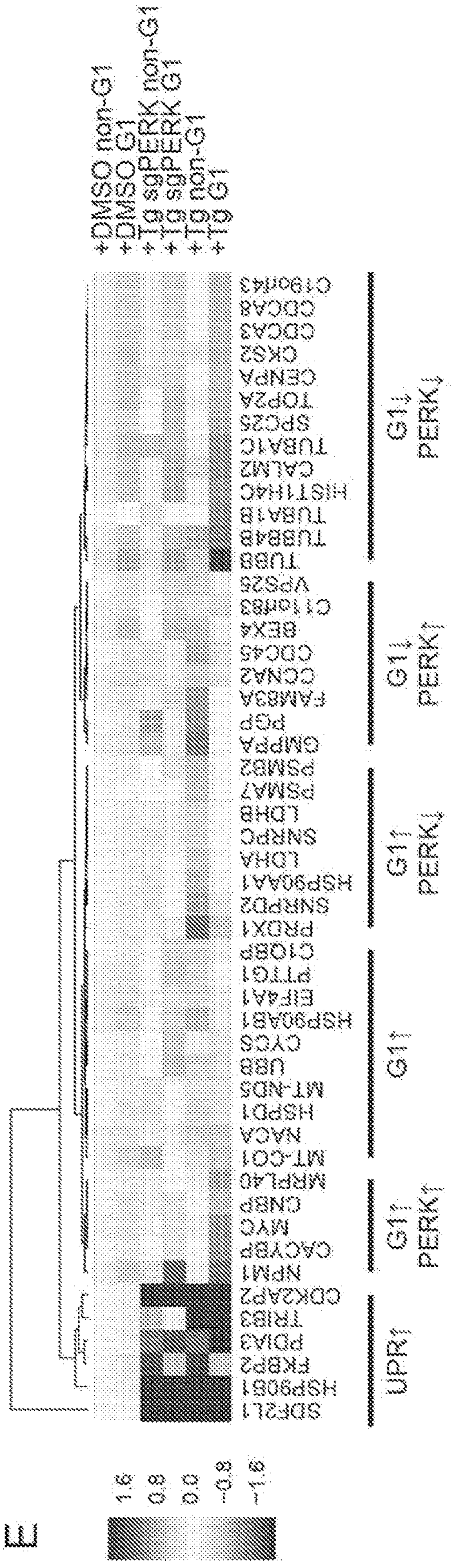

Applicants did observe a small but prominent interaction between the two effects, apparent in a "bulge" seen in the cell cycle analysis (highlighted in FIG. 83B) where cells bearing certain perturbations concentrated. Closer examination of a more targeted set of three perturbations suggested that this interaction was caused by PERK-dependent cell cycle arrest in G1 caused by thapsigargin treatment (FIGS. 83C,D) (Hamanaka et al. 2005). A particular component (right panel of FIG. 83C) was bimodal among the cells bearing each perturbation. Defining the cells with that component low as "G1 cells" (cf. middle and right panels of FIG. 83C), Applicants looked at the top fifty genes influencing the component (FIG. 83E). This list included a set of factors associated with cell cycle progression and the UPR. Intriguingly, it highlighted epistatic interactions between the two effects of PERK-dependent activation of the UPR and progression through G1, showing for example how for some genes the two programs cancel each other out, while for others they may act synergistically. A notable example of the latter was the expression of MYC, which has previously been identified as being thapsigargin-induced (Liang et al. 2006). Our data here show that MYC induction is most strongly associated with the G1-arrested subpopulation (FIG. 83E).

Figure 83F:
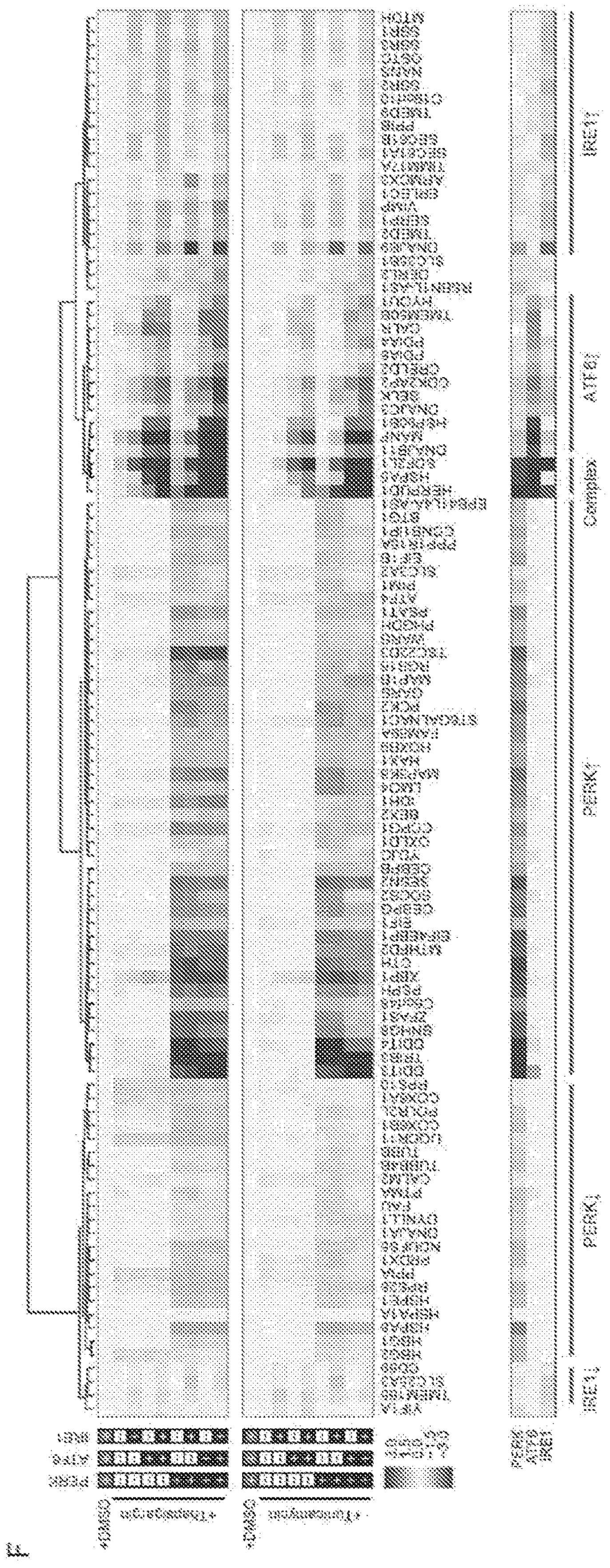

Given our success in decomposing independent effects, Applicants next turned to decomposing the distinct branches of the UPR itself. Applicants identified a set of genes that were most robustly induced in response to both thapsigargin and tunicamycin treatment and used hierarchical clustering to order them based on their pattern of co-expression in the 15,000 cells within our experiment (see Methods). Applicants constructed synthetic bulk RNA-seq profiles by averaging together all cells bearing the same perturbation. When these profiles were ordered according to our clustering, clear patterns of regulatory control were apparent (FIG. 83F). To estimate regulatory overlap, Applicants decomposed the changes across bulk responses using ICA (bottom of FIG. 83F, Methods). PERK/ATF4 had the largest regulon in our experiment, and had many targets uniquely under its control. ATF6 and IRE1α showed more overlap in their set of regulatory outputs, consistent with their common transcriptional regulatory mechanism. Of the two, IRE1α had more specific targets, notably components of the translocon (e.g. SEC61A1, SEC61B), which is consistent with previous reports (Shoulders et al. 2013), but ATF6 had stronger activating effects on common targets (FIG. 83F). Many genes showed some sensitivity to all branches, particularly a group of very high abundance core stress response genes (HSPA5, HERPUD1, SDFL21). Our epistasis experiment thus defined and decoupled the three overlapping branches of the mammalian UPR, both at the bulk level and within single cells.

Example 26: Unbiased Genome-Scale CRISPRi Screens Identify a Library of Genetic Perturbations that Induce the UPR Having systematically mapped the transcriptional programs controlled by each of the three UPR sensors, Applicants next sought to leverage this information and our platform to evaluate what role each branch plays in responding to different types of perturbations. A principal advantage of perturb-seq is the ability to evaluate transcriptional phenotypes for many genetic modifications in a single, internally controlled experiment. Thus Applicants can ask fundamental questions about how transcriptional pathways differentially respond to diverse and physiologically relevant inputs, and importantly, Applicants can do this in cells otherwise exposed to identical conditions. Applicants employed a two-tiered approach to use perturb-seq to systematically explore transcriptional pathways, such as the UPR. First, Applicants performed a genome-scale CRISPRi screen to identify genes that are important for ER homeostasis, as evidenced by induction of the UPR upon depletion. Applicants then applied perturb-seq to a diverse sub-library targeting the strongest hits to better understand their role.

To begin, Applicants constructed a fluorescence reporter of IRE1α activation. This reporter drives mCherry expression from a minimal c-fos promoter controlled by 5 IRE1α-responsive unfolded protein response elements (UPREs) (Wang et al. 2000) (FIG. 84A). The reporter was transduced into K562 cells stably expressing a dCas9-KRAB fusion protein and a clonally derived line (cBA010), which demonstrated strong reporter activation (FIG. 84B), was selected. To control for general effects on gene expression during screening, this cBA010 parental line was subsequently transduced with a constitutive GFP reporter (driven by the EF1a promoter) (FIG. 84A). Importantly, when treated with tunicamycin, these cells (cBA011) demonstrated XBPI-dependent mCherry induction (maximally 16-fold), which occurred subsequent to endogenous XBP1 splicing (FIGS. 84B, 90A). As expected, Applicants observed no similar induction of GFP.

Using our reporter cell line, Applicants separately screened two genome-scale CRISPRi libraries, our first generation library (hCRISPRi-v1) and our recently described second generation library (hCRISPRi-v2) (FIG. 84C) (Gilbert et al. 2014, Horlbeck et al. 2016). Briefly, cBA011 K562 cells were transduced with each library. After 8 days of growth, the cells were separated by fluorescence-activated cell sorting into bins according to the ratiometric reporter signal (mCherry/GFP). Cells in the top and bottom thirds of the reporter distribution were collected and processed to measure the frequency of sgRNAs contained within each bin by deep sequencing. Using these data, Applicants calculated the log 2 sgRNA enrichments in the top mCherry/GFP bin over the bottom bin, and defined gene-level reporter signal phenotypes as the average of the 3 most active sgRNAs targeting each gene. Our hCRISPRi-v2 screen identified 397 hit genes with high mCherry/GFP, indicative of UPR activation (FIG. 84D). Importantly, phenotypes were reproducible between replicates of this screen and minimal correlation was observed between hit phenotypes and previously calculated gene growth phenotypes (Spearman R=−0.2) (FIGS. 84E, 90B).

Our first generation CRISPRi library targets 15,977 genes (20,899 transcriptional start sites, TSSs) with 10 sgRNAs per TSS, and our hCRISPRi-v2 library targets 18,905 genes at 20,526 TSSs. hCRISPRi-v2 incorporates several improvements over hCRISPRi-v1, including a greater frequency of highly active sgRNAs and the flexibility to screen with either 10 sgRNAs per gene or a similarly active half-library containing the top 5 predicted sgRNAs for each gene (Horlbeck et al. 2016). Practically, the compact hCRISPRi-v2 library allowed us to maintain higher screen representation through the flow cytometer with similar sorting times (screen representations: hCRISPRi-v1 ~450, hCRISPRi-v2 ~600). Encouragingly, of the 141 hits from the hCRISPRi-v1 screen, 103 reproduced from screening the hCRISPRi-v2 library (Fisher's Exact p-value=8.97e-138) (FIG. 90C).

Figure 84F:
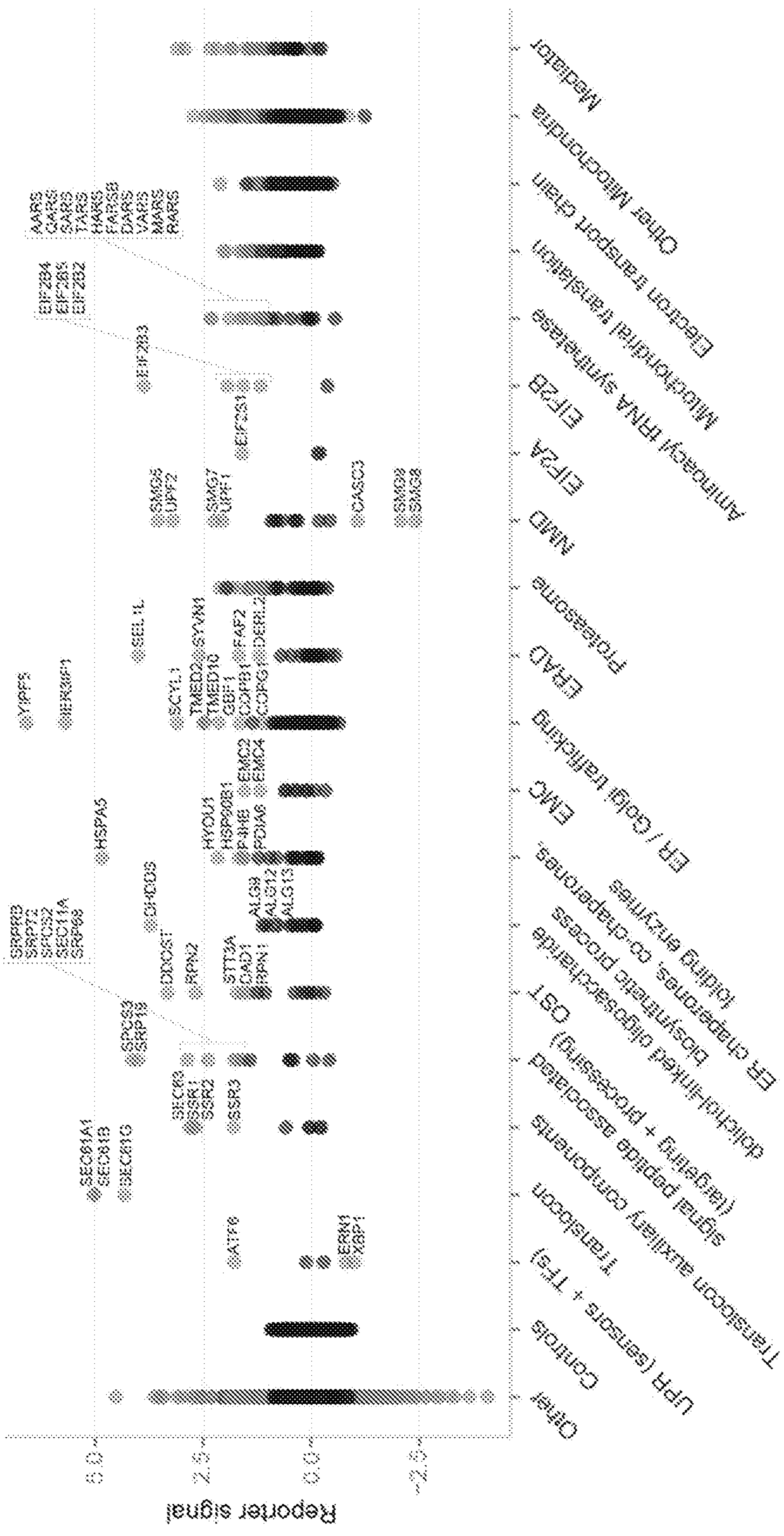

Among hits from the hCRISPRi-v2 screen are well-characterized regulators of protein folding in the ER, most notably HSPA5, which encodes the major ER Hsp70 chaperone BiP (FIG. 84F). Consistent with results from a similar screen in yeast (Jonikas et al. 2009), our hits also featured genes functionally involved in N-linked glycosylation, including components of the oligosaccharyltransferase (OST) and the dolichol-linked oligosaccharide biosynthesis pathway, ER-associated degradation (ERAD), and protein trafficking. Additionally, genes involved in protein targeting to the ER were enriched among hits (Fisher's Exact p-value=2.65e-09). This gene set consists of genes encoding components of the signal recognition particle (SRP), the SRP receptor, and the signal peptidase complex. Three out four of the translocon-associated protein complex (TRAP) scored; and strikingly, among the 7 hits with the strongest phenotype were all three genes that encode the ER protein-conducting channel or PCC (SEC61A1, SEC61B, SEC61G)

(FIG. 84D,F). The phenotypes of SRP targeting factors and PCC were surprising because recent reports have shown that SRP-mediated recruitment to the ER and IRE1α binding to PCC subunits are required for maximal pathway activation in response to exogenous stress (Plumb et al. 2015, Kanda et al. 2016). Satisfyingly, targeting of both ERN1 and XBP1 was observed to decrease reporter signal in the screen (FIG. 84D).

Figure 84G:
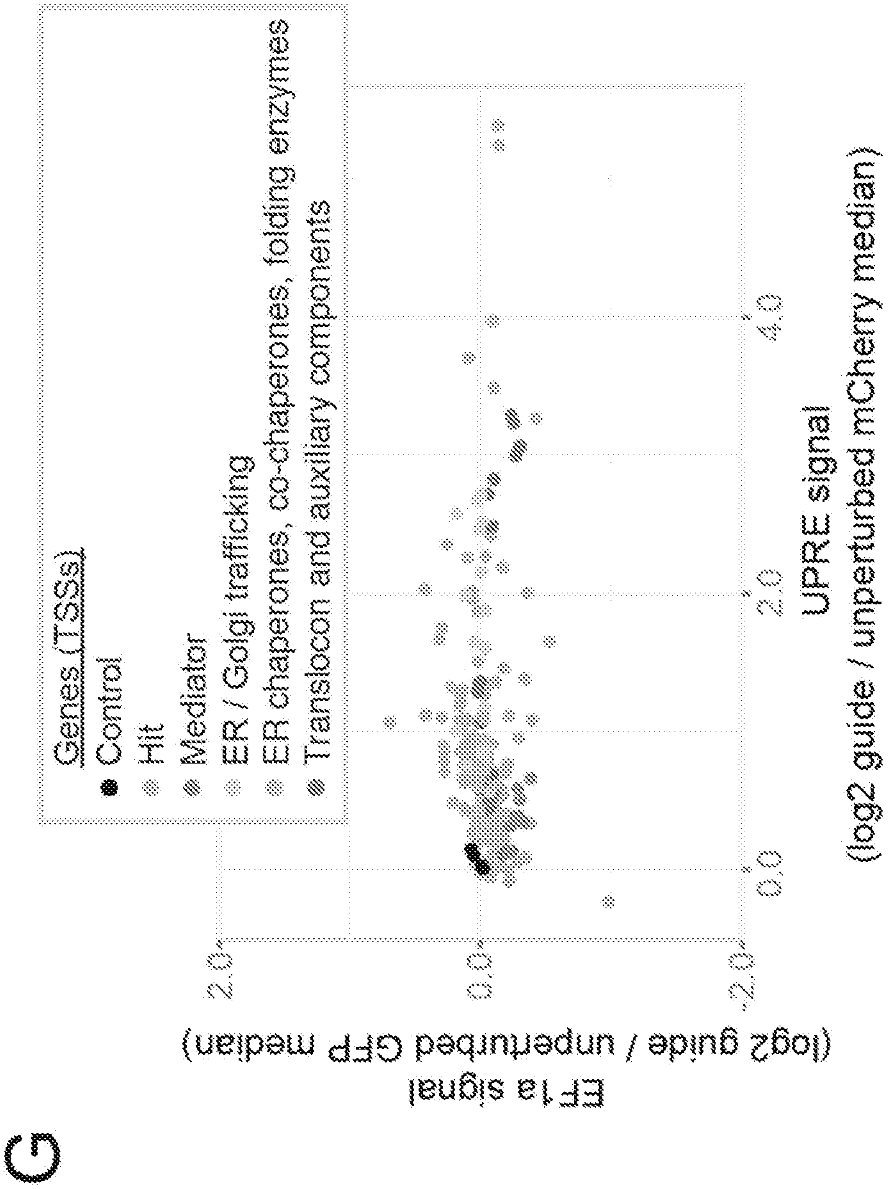

Of note, genes with biological functions unrelated or indirectly related to ER function also scored as UPR hits, some of which are distinct from functional classes seen in the analogous systematic yeast studies (Jonikas et al. 2009). Specifically, sets of genes that control general translation, transcription, and, perhaps most intriguingly, mitochondrial function were enriched among hits (FIGS. 84F, 90D). While disruption of the functions of these globally important genes may induce the UPR through impairment of ER function, it is also possible that such broad hits, especially the transcriptional components, represent perturbations of our reporter system. During individual testing of 257 sgRNAs targeting 152 select hit genes, Applicants confirmed that a majority induced reporter signaling from the UPRE reporter; however, for some sgRNAs, notably ones targeting the mediator transcriptional complex, Applicants found that GFP levels were also reduced, inflating the mCherry/GFP ratio (FIG. 84G). Moreover, from the magnitude of the phenotypes alone, Applicants cannot distinguish among the various mechanisms for disrupting ER homeostasis because perturbation of functionally diverse genes frequently resulted in similar levels of reporter induction whereas perturbation of genes with shared function, as in the case of ER protein targeting genes, often resulted in a range of phenotypes (FIG. 84F). Cumulatively, these data highlight the ability of the pooled screens to robustly identify diverse factors important for ER homeostasis but the challenges of making systematic conclusions about gene function from such simple phenotypic readouts.

Example 27: Perturb-Seq Analysis of a UPR-Inducing CRISPRi Sub-Library Demonstrates Functional Relationships Between Genes and Differential Activation of UPR Transcriptional Programs in Response to Distinct Forms of Stress Our next goal was to systematically characterize the role of these different classes of genes. Applicants hypothesized that a mechanistically diverse set of perturbations to ER homeostasis might reveal a richer picture of the underlying structure of its regulation than is possible with a small set of strong chemical perturbants (e.g., thapsigargin and tunicamycin). Applicants thus applied perturb-seq to a CRISPRi sub-library of 91 sgRNAs targeting 83 genes, including many of our strongest hits, and 2 negative controls (FIG. 90C). To test platform scalability, sgRNAs were delivered via pooled transduction in this experiment. Applicants then subjected the UPR-inducing CRISPRi sub-library to profiling via perturb-seq, collecting ~65,000 cells and sequencing to an average depth of ~67,000 reads per cell, which collapsed to ~15,300 UMIs arising from ~3,700 unique genes per cell. Approximately 50,500 cells were called a containing unique sgRNA, while ~9,000 contained multiple sgRNAs (either due to double infection during our pooled transduction or encapsulation of multiple cells during emulsion generation). ~6,000 cells were unidentifiable. All of the expected sgRNAs were detected, with nearly even representation across sgRNAs that were pooled equally during viral titering (457±108 cells per sgRNA, mean±standard deviation).

Figure 91C:
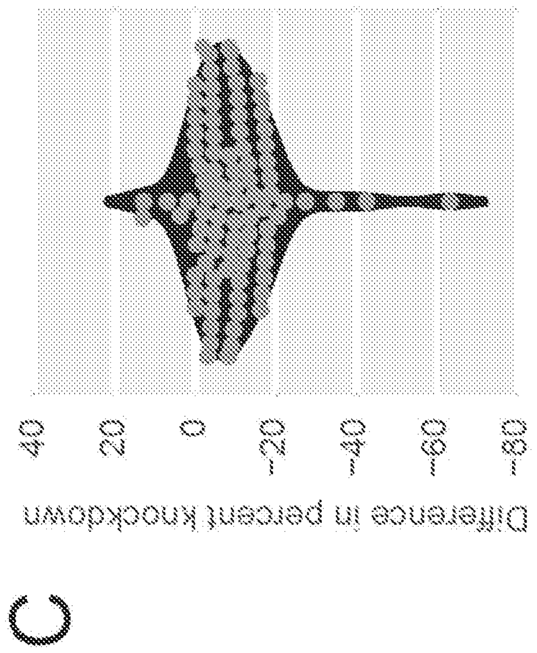

Applicants then constructed synthetic bulk expression profiles by averaging normalized expression across cells containing a given sgRNA. Hierarchical clustering of these average profiles revealed that sgRNAs targeting the same gene always clustered together (FIG. 91A), and the level of knockdown of guides targeting the same gene was similar (FIG. 85C). Knockdown was robust, with a median 90% depletion of the guide target (FIG. 85C). Knockdown appeared as a shift of the entire distribution of expression, rather than a bifurcation into perturbed and unperturbed subpopulations (FIG. 91B). To assess homogeneity, Applicants computationally assigned each cell a score measuring the deviation of its expression profile from the distribution of expression seen in control cells. Comparing the most perturbed cells (top third) to the least perturbed (bottom third) showed a median difference in knockdown of 8% (FIG. 91C). These findings establish the general robustness of the CRISPRi reagents in producing uniform knockdowns as well as the ability of the barcoding scheme to accurately assign sgRNAs to the appropriate cells. Given the similarity in phenotypes between sgRNAs targeting the same gene, in subsequent analyses Applicants grouped cells by sgRNA target, rather than by sgRNA.

At the level of bulk analysis, perturb-seq offers a simple and robust platform for highly parallel RNA-seq. Since sgRNAs can be introduced in pooled format, variability from exogenous factors is minimized, and the loss of information from shallow capture and sequencing is reduced once many cells are averaged together. These bulk profiles are a rich phenotypic fingerprint that can be used to understand how different perturbations relate to each other (Parnas et al. 2015). For example, hierarchical clustering of bulk profiles for each targeted gene revealed high precision functional clusters (apparent as lines on the diagonal in FIG. 85A), consistent with known protein-protein interactions such as the oligosaccharyltransferase complex (DDOST/DAD1/OST4) and Triple T complex (TELO2/TTI1/TTI2), as well as factors involved in the ubiquitylation reactions of ERAD (SYVN1/SEL1L), SRP-mediated protein targeting (SRP68/SRPRB/SRPR), protein trafficking (TMED2/TMED10), and UFMylation (UFML1/UFM1/DDRGK1). Genes also clustered by role, including ER-Golgi trafficking (the YIPF5/IER3IP1 complex clustering with SCYL1 and TMEM167A). Interestingly, genes encoding particular translation initiation factors, the EIF2B complex (EIF2B2/EIF2B3/EIF2B4) and eIF1α (EIF21), were part of a large, highly correlated cluster. Similar to inhibition of eIF1α, EIF2B loss-of-function is known to induce ATF4 signaling (Fogli, Boespflug-Tanguy 2006). This presents the possibility that the repression of other genes within this cluster also induce ATF4. Indeed, within this large cluster Applicants observed smaller clusters of genes whose common roles are monitored by ATF4, including a set of aminoacyl tRNA synthetases (LARS2/SARS/FARSB/HARS/QARS/CARS/AARS/MARS/DARS/TARS) and mitochondrial genes (TIMM23/SAMM50/ATP5B/MRPL39 and DNAJC19/HSPA9/IARS2) (Bao et al. 2016, Tyynismaa et al. 2010).

An advantage of perturb-seq is that these bulk properties can then be examined at the single-cell level to better understand the phenotypes. For example, decomposing the populations by cell cycle position (FIG. 85B) revealed that some perturbations, such as many of the aminoacyl tRNA synthetases, elicited an accumulation of cells in G2. In contrast, CAD, a gene essential for pyrimidine synthesis, elicited a clear accumulation of cells in S phase.

Applicants next sought to analyze how individual hits effect activation of the different branches of the UPR. As single-cell data are prone to dropouts, scoring systems based on defined linear combinations of gene expression are prone to wide variation. Applicants thus adopted a data-driven strategy, and trained random forest regressors to score branch activation using the cells in our epistasis experiment, in which the branches are definitively separated, as training data (Methods). This scoring method had superior accuracy compared to defined gene lists and superpositions derived from ICA (Methods, FIG. 91F).

Branch activation scores (FIG. 85D) showed that hits from the screen elicited activation of all three branches of the UPR with clear correlations in activation among functionally related groups of genes. Perhaps most interestingly, different groups of perturbations elicited differential activation of the three branches. For example, repression of HSPA5, which encodes the core component of the UPR and central ER chaperone BiP, robustly activated all three branches. The amino acid synthetases activated both IRE1α and ATF4 branches of the UPR, with the latter possibly influenced by GCN2 signaling, which is responsive to amino acid stress and, like PERK, inactivates elF2a. (Because our training data was experimentally obtained using PERK depletion in the presence of ER stress, Applicants score activation of the corresponding signature with a "PERK score." However, the activity of four separate kinases that upregulate ATF4 may formally contribute to these effects). Finally, all three components of the PCC (SEC61A1/SEC61G/SEC61B) appeared to selectively activate only the IRE1α branch. Comparison with alternate scoring methods and expression of branch-specific genes Applicants identified in the epistasis experiment showed good agreement with these calls (FIG. 91D,E). Thus at the bulk level, our data reveal how different genetic perturbations can selectively activate the different branches of the UPR.

Example 28: Single-Cell Expression Profiling of Cells Perturbed by HSPA5 Depletion Uncovers a Bifurcated Response The observation of differential activation of the different UPR branches in bulk raises an immediate question: do single cells coordinately carry out an identical response to a given perturbation, or might the branches also operate independently at the single-cell level? To explore this issue, Applicants examined cells depleted of BiP, where all three branches of the UPR are active.

When compared to cells containing control sgRNAs, cells transduced with HSPA5-targeting sgRNAs were readily distinguishable as a distinct population (FIG. 86A), and had markedly different patterns of gene expression (~2,100 genes differentially expressed at P<0.01). Using LRICA, Applicants decomposed these differences into sixteen independent components. Several of these reflected cell cycle effects, reflecting the altered composition seen previously (FIG. 85B).

Two of the independent components (IC1 and IC2) varied substantially between control and HSPA5-perturbed cells (FIG. 86B), and examination of the genes that most strongly affected these components showed they were driven by genes Applicants had previously identified as under UPR control. Comparing these hypothesis-free results to the branch activation scores given by our random forest regressors (FIG. 86C) showed that our analysis pipeline had independently discovered a subpopulation structure within the HSPA5-perturbed cells in which ATF6 alone was activated (IC1 and IC2 both low), ATF6 and IRE1α were activated (IC1 low, IC2 high), or ATF6, IRE1α, and ATF4 were simultaneously activated (IC1 high, IC2 low). Indeed, when Applicants ordered the cells by the value of IC1 and examined the expression of UPR-induced genes (as defined in FIG. 83F), the trends defining these subpopulations were apparent (FIG. 86D).

Of particular note was the switch-like induction of the ATF4 branch, revealing that these cells represented a discrete subpopulation. Importantly, these differences did not reflect differences in BiP depletion, as the subpopulations with IC1 low and high (FIGS. 86B,D) had indistinguishable expression of HSPA5 (FIG. 86E). They were distinguishable, however, in that the ATF4-induced subpopulation had a substantially altered cell cycle distribution, with many cells accumulating in G2 compared to control cells or HSPA5-perturbed cells without ATF4 induced (FIG. 86F). These results thus reveal that the phenotype observed at bulk level does not accurately capture the biology of single cells, and that the UPR can be executed in markedly different ways within an apparently homogeneous population.

Example 29: Gene-Gene Covariance Analysis of Perturb-Seq Data Reveals Transcriptional Regulons Perturb-seq offers substantial insights into the biology of individual cells, but also reveals the genes driving those behaviors. FIG. 86D underscores a key point: correlated up- or downregulation of genes can be a signature of shared regulation (Klein et al. 2015). As a single perturb-seq experiment provides tens of thousands of data points for each gene, these coordinated motions provide a rich phenotype that can be used to identify related genes by looking for correlated patterns of expression (FIG. 86G).

For example, Applicants identified 200 genes that were perturbation-induced and highly variable across the 50,500 cells in our perturb-seq experiment. When these genes were clustered based on their patterns of co-expression, obvious functional groupings appeared, including all three branches of the UPR (FIGS. 86H and 92A). Indeed, when Applicants clustered our defined list of UPR-induced genes (from FIG. 83F) using co-expression information from the epistasis experiment or the perturb-seq experiment, Applicants uncovered similar clusterings (cophenetic correlation 0.81, compared to 0.13 when control cells were used to cluster the genes), with differences tending to involve targets with overlapping regulation by ATF6 and IRE1α (FIG. 86I, FIG. 92B). The similarity between experiments indicates that much of the regulatory interactions between these genes is implicitly present in the perturb-seq experiment, and also suggests that the organization of the UPR is preserved between the very strong chemical inducers used in the epistasis experiment and the far more varied genetic perturbations used here.

A key advantage of perturb-seq is that the perturbations tend to elevate correlations above the levels induced by natural variation. These correlations can be further enhanced by a "fishing" strategy, where the population is subsampled to enrich for cells perturbed for a given group of genes. Related genes can then be discovered by how well their expression correlates with the original group (FIG. 86J,K, Methods). For example, our preliminary analysis (FIG. 86H) identified a five gene cluster of cholesterol biosynthesis genes with correlated expression. When Applicants confined our gene clustering analysis to the roughly ~9,000 cells most perturbed for this cluster, Applicants saw a general strengthening of correlations, and the core group now clustered with a group of genes related to cholesterol biosynthesis (FIG. 86K). Similarly, when Applicants selected out the cells most perturbed for the heat shock proteins HSPA1A and HSPA1B, the genes that clustered nearby were essentially all implicated in the heat shock response based on Reactome annotation, HSF1 binding profiles from Encode, or literature searches (FIG. 86L). When Applicants expanded the analysis to look at nearby gene clusters, Applicants noticed some apparent structure in co-expression (FIG. 86L). Intriguingly, the correlation structure seemed somewhat explainable in terms of the most enriched transcription factor binding sites among the gene set, with the middle group of genes for example linked to the first group by a possible regulatory overlap between HSF1 and KAT2A (FIG. 86L). Though these demonstrations are not definitive proof, they suggest that gene-gene correlation information from perturb-seq, potentially constrained by other sources of information like transcription factor binding, may enable automated functional clustering of genes of unknown function.

Example 30: Preferential Activation of the IRE1α-Controlled Arm of the UPR in Response to Translocon Dysfunction Initiates Homeostatic Feedback Among the genes targeted in the perturb-seq screen, the PCC genes (SEC61A1, SEC61G, and SEC61B) were perhaps the most intriguing outliers, in that they each displayed a marked preference for activation of the IRE1 branch (FIG. 85D), with widespread IRE1α activation and little or no activation of the other branches (FIGS. 87A, 87B, 93A). To confirm that our single-cell data were accurately calling IRE1α activation, Applicants directly probed for XBP1 splicing using RT-PCR (Calfon et al. 2002) (FIG. 87C). Depletion of all three PCC coding genes induced XBP1 splicing at levels consistent with the single-cell data and to a degree at or above that provoked by targeting HSPA5, a perturbation that induces all three branches of the UPR. Additionally, a time course experiment showed that depletion of PCC components led to sustained XBP1 splicing over the course of days. Expression of SSR2, a translocon-associated protein and strongly selective target of IRE1α (FIG. 87D, and cf. FIG. 83F), was also maintained over the same period. These results were in marked contrast to the transient XBP1 splicing seen when cells were challenged with chemical stress (FIG. 90A), which diminished on the scale of hours, consistent with previous reports (Lin et al. 2007).

The kinetics and magnitude of IRE1 activation in response to PCC gene repression varied with respect to the subunit targeted, which may reflect the fact that depletion of these factors also have variable effects on cell growth. SEC61A1 is an essential gene with strong growth phenotypes in both CRISPRi and CRISPR cutting cell viability screens (Gilbert et al. 2014, Wang et al. 2015), however across both analyses, SEC61B depletion demonstrated at most a relatively mild effect, which included analysis of a CRISPRi sgRNA (SEC61B-1), for which Applicants independently validated mRNA depletion (FIGS. 90B, 93B,C). Concordantly, Applicants observed a limited increase in CHOP expression upon depletion of SEC61A1 (FIG. 87D), which is indicative of ATF4 induction. The single-cell analyses nonetheless revealed that the majority of cells only induced the IRE1α branch (FIG. 87A, 93A), suggesting that the increase in CHOP expression might reflect general toxicity. Strikingly, depletion of SEC61B, which causes only mild growth defects, showed little to no CHOP induction over ten days of growth, while showing sustained markers of IRE1α induction (FIG. 87D). Applicants note that SEC61B appears to share a co-regulated promoter region with ALG2, a gene that functions in N-linked glycosylation, and that Applicants cannot formally separate the effects of repressing these genes (FIG. 93B). Nonetheless, the consistent phenotypes of SEC61A1, SEC61B, and SEC61G repression suggest that genetic disruption of the PCC elicited selective activation of the IRE1α branch. An alternative explanation for these observations is that depletion of PCC subunits induces general stress but impairs activation of the other branches of the UPR. ATF4 activation was intact, however, as cells transduced with sgRNAs targeting SEC61A1, SEC61B, or SEC61G showed robust CHOP induction in response to thapsigargin treatment (FIG. 87E). Additionally, without stress these cells showed strong XBP1 splicing and low levels of CHOP as compared to cells transduced with an HSPA5 targeting sgRNA, which demonstrated strong basal CHOP induction (FIG. 87C,E). Collectively, these results confirm that depletion of PCC subunits selectively induces the IRE1α branch.

Taken together with our single-cell epistasis data, these experiments suggest a selective role for the IRE1α branch of the UPR in monitoring PCC function. Many of the strongest and most selective IRE1α transcriptional targets in the epistasis experiment were PCC-associated genes (FIG. 83F), and by qPCR analysis, Applicants confirmed upregulation of the two other PCC coding genes in response to depletion of SEC61A1 or SEC61B (FIG. 93B). Conversely, PCC coding and translocon-associated genes were hits in our unbiased genome-wide screen for IRE1α activation and also showed preferential IRE1α pathway activation in our perturb-seq analysis. Given that the translocon has been shown to selectively interact with IRE1α (and not ATF6 or PERK) (Plumb et al. 2015, Kanda et al. 2016), these results suggest a model in which IRE1α actively monitors the function and number of translocons and acts to increase them as needed (FIG. 87F).

Example 31: Discussion

Here Applicants present perturb-seq, an experimental and analytical platform that enables multiplexed profiling of many perturbations with single-cell resolution, and used it to systematically dissect the mammalian unfolded protein response (UPR). Perturb-seq is enabled by a strategy Applicants developed for robustly encoding the identity of a perturbation in an expressed transcript. Because this information is specifically encoded in the genome of cells bearing a particular perturbation, different perturbations can be interrogated together in pooled format via massively parallel droplet-based single-cell RNA-seq. This approach fills a gap in our ability to interrogate biological systems, allowing measurement of rich, unbiased phenotypes for many perturbations in one experiment.

Perturb-seq addresses a pressing problem in modern genetics: with genome-wide screens now routine (Shalem, Sanjana & Zhang 2015), strategies must be developed to rapidly and systematically understand hits. Perturb-seq enables this in two ways. First and most simply, it is a powerful platform for highly parallelized RNA-seq in homogeneous experimental conditions. Combined with our approach for combinatorial genetic perturbations, perturb-seq has the potential to interrogate tens of thousands of distinct combinations of perturbations in one pool. On the other end, the single-cell nature of the data provides deep and precise insights into how cells behave. Indeed the analytical approaches Applicants have developed provide general tools for exploiting single-cell data to identify co-regulated genes in a hypothesis-free manner, reveal discrete subpopulations that make bulk phenotypes misleading, and separate specific effects from confounding phenomena like the cell cycle.

Applicants here focused on genetic perturbations using CRISPRi, but the platform can be used to encode the identity of a wide range of perturbations or changes, such as CRISPR cutting-mediated loss of function (Wang et al. 2015, Shalem et al. 2014), gene activation (Tanenbaum et al. 2014, Konermann et al. 2015, Chavez et al. 2015), targeted mutation (Komor et al. 2016), or the identity of a particular variant in a library of systematically mutagenized proteins. Applicants have shown that CRISPRi gives strong, highly homogeneous, and simultaneous depletion of up to three targets and enables the study of essential genes. It also has some potential advantages when scaling to high-order combinations relative to CRISPR cutting, as genetic variability (e.g., partially functional alleles due to in-frame indels (Shi et al. 2015)) and non-specific toxicity due to DNA cutting (Wang et al. 2015, Aguirre et al. 2016, Munoz et al. 2016, Horlbeck et al. 2016) both increase with the number of cut sites. On the other hand, CRISPR cutting provides complementary advantages including allowing domain-level analysis (Shi et al. 2015) and the generation of true null alleles (Shalem et al. 2014).

Perturb-seq is already a robust platform for in depth functional analysis of hit genes from screens. Scaling it further to genome-level coverage requires overcoming some obstacles, but none appear intractable. Cost per cell is a major consideration, but this will decline as technologies mature. With current techniques (Zheng et al. 2016), ~50, 000 cells can be profiled in ten minutes. Additionally, perturb-seq will enable higher loading, which usually has the undesirable effect of increasing the frequency at which multiple cells are encapsulated per droplet, because our guide barcodes allow computational removal of cell doublets. Sequencing costs are high, but can be mitigated at the library preparation stage through specific amplification of select targets, as demonstrated with our barcode capture, or by depletion of uninteresting high abundance genes (Gu et al. 2016). A more subtle point is that provirus recombination during lentivirus transduction can potentially scramble barcode identities during standard methods of pooled library delivery (Sack et al. 2016). Applicants took careful steps to avoid these problems (see Methods) and expect that altered library preparation protocols will circumvent this issue.

By far the biggest barrier Applicants anticipate is on the analytical side. Perturb-seq generates massive amounts of data, but these data are intrinsically noisy due both to the low capture efficiencies of single-cell RNA-seq protocols and more fundamentally, the intrinsic stochasticity of transcription at the single-cell level. Rigorously extracting meaningful conclusions will require new tools and algorithms (Satija et al. 2015, Heimberg et al. 2016, Trapnell 2015, Grün, van Oudenaarden 2015), as well as new statistical approaches for assessing the significance of claims. Applicants have made some progress on this front, and showed how single-cell data can be used for example to objectively decouple the branches of the UPR, uncover subtle subpopulations within cells of the same type, and infer larger programs of gene expression using correlated expression. Along with previous successes (Macosko et al. 2015, Klein et al. 2015, Jaitin et al. 2014), and the novel analytical approaches presented in an accompanying manuscript (Dixit et al., co-submitted manuscript), Applicants anticipate that large-scale analyses of single cell behavior will enable systematic discovery of the complex and overlapping regulatory programs at work within cells. As perturb-seq scales, it will present computational challenges on the same scale as other “big data” fields.

Applicants experiments also provide important insights into the understanding of the logic used by the mammalian UPR to sense and respond appropriately to the diversity of challenges faced by the ER. A central question in the field of ER homeostasis is why metazoan cells have evolved to have three independent and mechanistically distinct sensors of protein misfolding in the ER. As expected from previous work (Acosta-Alvear et al. 2007, Han et al. 2013, Lee, Iwakoshi & Glimcher 2003, Shoulders et al. 2013), epistasis analysis using combinatorial depletion of the three main regulators of the UPR revealed both distinct and overlapping programs of gene expression controlled by PERK, ATF6, and IRE1α. The clean divisions Applicants observed at the single-cell level highlight the importance of performing these experiments in a pooled format, as sensitive phenotypes like stress responses might otherwise be overwhelmed by experimental variation. PERK/ATF4 had the largest regulon in our data, while ATF6 and IRE1α had more overlapping targets, with IRE1 having more unique targets such as the translocon. Additionally, Applicants observed that the three UPR branches were able to operate independently both at the bulk level, as different genetic perturbations showed differential activation of the three branches, and at the single-cell level.

Our genome-wide screen identified a broad diversity of genetic perturbations that activate signaling from the IRE1α branch of the UPR, including some categories of genes that were not expected from analogous yeast screens (Jonikas et al. 2009). Subjecting these hits to perturb-seq showed that the screen in fact hit all three branches of the UPR, and that genes with similar functional roles induced the UPR in similar ways. Intriguingly, Applicants also found that the signatures of the three branches of the UPR were implicit in the correlations seen in the perturb-seq experiment, suggesting that in principle the hypothesis-driven epistasis experiment could be dispensable. Thus, perturb-seq could enable identification and characterization of novel pathways for which such a priori information is not available. The single-cell analysis also revealed a remarkable bifurcation of UPR branch activation within cells subject to identical perturbations. In particular, depletion of HSPA5 resulted in some cells primarily inducing ATF6, others both IRE1α and ATF6, and a distinct subset inducing all three UPR branches simultaneously. This example illustrates the utility of single-cell data: bulk RNA-seq would in this case describe an average state that no cell actually occupies, just as it obscures the effect of other factors like the cell cycle. As all HSPA5-perturbed cells were treated identically, the cause of such marked differences in behavior remains in question. The simplest answer, variability in knockdown efficiency, does not appear to play a role, though the time course of HSPA5 depletion might. But this possibility suggests a real, interesting biological hypothesis, namely that there is a temporal ordering to the activation of the three pathways in HSPA5-depleted cells (Lin et al. 2007).

Applicants also found that different perturbations show clear differences in their propensity to activate the different branches of the UPR. Particularly intriguing in this regard were the three components of the protein-conducting channel encoded by SEC61A1, SEC61G, and SEC61B, repression of which selectively activated the IRE1α branch of the UPR. These results are notable in light of recent studies suggesting that IRE1α acts in proximity to the translocon (Plumb et al. 2015, Kanda et al. 2016). Given that Applicants and others have observed regulation of translocon expression to be uniquely under IRE1α control (Shoulders et al. 2013), this suggests a feedback model in which IRE1α actively monitors the state of translocation. Interestingly, isolated IRE1α induction would enable repair to or upregulation of the translocation machinery without a broader UPR induction, preventing potentially inappropriate responses including cell death (Hetz 2012). Additionally, further study of selective UPR induction using genetic perturbations, as Applicants have shown here, could also inform efforts to pharmacologically manipulate the UPR to enhance specific repair and prosurvival pathways (Shoulders et al. 2013). More broadly, this provides a concrete example of how the three distinct sensors of ER homeostasis allow the cell to monitor distinct types of ER stress and provide nuanced responses tailored to the specific challenge.

Applicants believe that their study of the mammalian UPR serves as a blueprint for the study of complex and overlapping transcriptional networks, in which a primary genome-wide screen serves as the input to more detailed analysis via perturb-seq. Applicants independently uncovered both well-known features of the UPR and new and unexpected findings. As the technology scales, it should be possible to conduct saturating analyses of every major pathway. Our success here, and the parallel success in understanding dendritic cell activation described herein, speak well to potential of the perturb-seq approach to become a standard strategy for understanding regulatory interactions in the cell.

Materials and Methods

Pool construction and transduction. A lentivirus backbone was constructed containing antiparallel cassettes of a PolIII promoter for sgRNA construction and a PolII promoter for expression of a selection marker and a polyadenylated RNA barcode. This construction avoided early termination of the viral transcript. A diverse library of RNA barcodes was inserted (approximately 1,000). Finally, sgRNAs were inserted. Association between RNA barcodes and sgRNAs was performed using Sanger sequencing. Lentivirus was made using 293T cells transfected with pBA439, and pMD2.G (Addgene 12259) at a 10:10:1 ratio, using Lipofectamine LTX and plus reagents according to the manufacturer's instructions.

For the mouse experiments, BMDCs were isolated from 6- to 8-week-old constitutive Cas9-expressing female mice and used as described previously (Platt et al., 2014). Cells were infected with the pooled lentiviral library at an MOI of approximately 0.2 at day 2. At day 9, BMDCs were stimulated with 100 ng/ml LPS. Cells were harvested for library preparation at 0 hr and 3 hr post stimulation.

For the human experiments, k562 transduced with Cas9 were purified by high GFP expression. These cells were transduced with the pooled lentiviral library at an MOI of approximately 0.2 for most experiments and an MOI of 1 for the high MOI experiment. Cells were harvested for library preparation 7 days post transduction for most experiments and 14 days post transduction for the second time point promoters experiment.

Library preparation. After cells were collected they were processed into single cell RNA-seq libraries following the manufacturer's protocol of the commercial 10X Chromium system.

Bone marrow derived dendritic cells (BMDCs). All animal protocols were reviewed and approved by the MIT/Whitehead Institute/Broad Institute Committee on Animal Care (CAC protocol 0609-058-12). To obtain sufficient number of cells, Applicants implemented a modified version of the DCs isolation protocol as previously described (Amit et al. 2009; Chevrier et al. 2011; Garber et al. 2012; Lutz et al. 1999; Rabani et al. 2011). Briefly, for all CRISPR knockout experiments six- to eight-week old constitutive Cas9-expressing female mice were used as described previously (Platt et al. 2014). RPMI medium (Invitrogen) supplemented with 10% heat inactivated FBS (Invitrogen), β-mercaptoethanol (50 μM, Invitrogen), L-glutamine (2 mM, VWR), penicillin/streptomycin (100U/ml, VWR), MEM non-essential amino acids (1X, VWR), HEPES (10 mM, VWR), sodium pyruvate (1 mM, VWR), and GM-CSF (20 ng/ml; Peprotech) was used throughout the study. At day 0, cells were collected from femora and tibiae and plated in 100 mm non tissue culture treated plastic dishes using 10 ml medium per plate at concentration of $2\times10^5$/ml. At day 2, cells were fed with another 10 ml of medium per dish. At day 5, 12 ml of the medium were carefully removed (to avoid removal of cells) and 10 ml of fresh medium were added back to the original dish. Cells were fed with another 5 ml medium at day 7. At day 8, all non-adherent and loosely bound cells were collected and harvested by centrifugation. Cells were then re-suspended with medium, plated at a concentration of $10\times10^6$ cells in 10 ml medium per 100 mm dish. At day 9, cells were stimulated for with LPS (100 ng/ml, rough, ultrapure *E. coli* K12 strain, Invitrogen) and harvested. Cells were always plated at concentration of $2\times10^5$/ml at day 0. Cells were harvested post stimulation after 0 hr or 3 hr and cells from cultures that contained 10% BFP positive cells were sorted for BFP+ and GFP+ (contain CAS9).

Cell Culture. Human K562 cells were purchased; murine BMDC were isolated from 6- to 8-week-old constitutive Cas9-expressing female mice.

K562 cells were grown to a confluence of 30-60% and spun down at 300×g for 5 min. The supernatant was removed, and cells were resuspended in 1 mL of 1×PBS+0.2% BSA (Sigma cat #A8806) and re-spun at 300×g for 3 min. The supernatant was again removed, and the cells re-suspended in 1 mL of 1×PBS, passed through a 40-micron cell strainer (Falcon, VWR cat #21008-949), and counted. For 10X, cells were diluted to the final concentration in 1×PBS+200 μg/mL BSA (NEB, cat #B9000S).

K562 cell cultures. Applicants used transgenic K562 cells constitutively expressing Cas9. K562 cells were transduced using several titers of virus and cells where spin infected in 2000 rpm for 30 min. For the low MOI experiment Applicants used cultures that contained 10% BFP+ and for the high MOI 50% BFP+. Cells were grown in RPMI Medium 1640+GlutaMAX (Thermo Fisher)+10% heat inactivated FBS (Invitrogen). Cells were grown to a confluence of 30-60% and spun down at 300×g for 5 min. The supernatant was removed, and cells were suspended in 5 mL of 1×PBS+0.2% BSA (Sigma cat #A8806) for sorting: BFP+ and GFP+ (CAS9 expressing) cells were sorted. Cells were harvested for library preparation 7 days post transduction for most experiments and 13 days post transduction for the second time point of the TF pool experiment. After sorting BFP+ GFP+ cells passed through a 40-micron cell strainer (Falcon, VWR cat #21008-949), wash twice and counted.

Library preparation. After cells were collected, they were processed into single cell RNA-seq libraries following the manufacturer's protocol of the commercial 10X Chromium system.

Single cell library preparation. Prior to analysis, cells were diluted to the final concentration in 1×PBS+200 μg/mL BSA (NEB, cat #B9000S). Sorted cells (BMDCs or K562 cells) where loaded on the 10X Chromium system (Zheng et al., 2016) (8,000 cells/channel) and single cell RNA-seq libraries were generated following the manufacturer's instructions.

Following WTA, a fraction of the WTA was used to amplify sgRNA barcode using a dial-out PCR strategy with the primer sequences below (the full primer sequence is a concatenation of the columns). The template material was approximately 5 ng of WTA libraries. 25 cycles of PCR were performed using one of the dial-out primers below with the P7 Illumina reverse primer.

Preparation of RNA barcode sub-libraries. In order obtain high confidence information about the identities of which sgRNAs were present in each cell, a dial-out PCR strategy was performed using the primer sequences below (the full primer sequence is a concatenation of the columns). The template material was approximately 5 ng of whole transcriptome amplification libraries obtained after a 10X library, 25 cycles of PCR was performed using one of the dial-out primers below with the a P7 Ilumina primer reverse primer.

Primer Sequences:

| P5 | Barcode | R1 | Primer (BFP location of pBA439) |
|---|---|---|---|
| AATGATACGGCGACCACCGA GATCTACAC (SEQ. I.D. No. 3) | NNNNNN NN | TCGTCGGCAGCGTCAGATGTGTATAA GAGACAG (SEQ. I.D. No. 4) | TAGCAAACTGGGGCACAAGC (SEQ. I.D. No. 5) |
| AATGATACGGCGACCACCGA GATCTACAC (SEQ. I.D. No. 6) | TCGCCT TA | TCGTCGGCAGCGTCAGATGTGTATAA GAGACAG (SEQ. I.D. No. 7) | TAGCAAACTGGGGCACAAGC (SEQ. I.D. No. 8) |
| AATGATACGGCGACCACCGA GATCTACAC (SEQ. I.D. No. 9) | CTAGTA CG | TCGTCGGCAGCGTCAGATGTGTATAA GAGACAG (SEQ. I.D. No. 10) | TAGCAAACTGGGGCACAAGC (SEQ. I.D. No. 11) |
| AATGATACGGCGACCACCGA GATCTACAC (SEQ. I.D. No. 12) | TTCTGC CT | TCGTCGGCAGCGTCAGATGTGTATAA GAGACAG (SEQ. I.D. No. 13) | TAGCAAACTGGGGCACAAGC (SEQ. I.D. No. 14) |
| AATGATACGGCGACCACCGA GATCTACAC (SEQ. I.D. No. 15) | GCTCAG GA | TCGTCGGCAGCGTCAGATGTGTATAA GAGACAG (SEQ. I.D. No. 16) | TAGCAAACTGGGGCACAAGC (SEQ. I.D. No. 17) |
| AATGATACGGCGACCACCGA GATCTACAC (SEQ. I.D. No. 18) | CATGCC TA | TCGTCGGCAGCGTCAGATGTGTATAA GAGACAG (SEQ. I.D. No. 19) | TAGCAAACTGGGGCACAAGC (SEQ. I.D. No. 20) |
| AATGATACGGCGACCACCGA GATCTACAC (SEQ. I.D. No. 21) | GTAGAG AG | TCGTCGGCAGCGTCAGATGTGTATAA GAGACAG (SEQ. I.D. No. 22) | TAGCAAACTGGGGCACAAGC (SEQ. I.D. No. 23) |

P7 Illumina Reverse Primer:

(SEQ. I.D. No. 24)
CAAGCAGAAGACGGCATACGAGAT

The PCR protocol is as follows:

| | 1 rxn |
|---|---|
| Q5 2X master mix | 25 |
| P7 primer @ 10 uM | 1.25 |
| pBA439_rev @ 10 uM | 1.25 |

-continued

| | 1 rxn |
|---|---|
| Template (5 ng total) | x |
| water (qs up to final rxn of 50 ul) | y |
| total | 50 |

| Temp | time | |
|---|---|---|
| 98 C | 10 s | |
| 98 C | 2 s | repeat for |
| 65 C | 5 s | 25 cycles |
| 72 C | 10 s | |
| 72 C | 1 min | |

The resulting PCR product was purified with Agencourt AMPure XP beads at 0.7× and sequenced.

Read alignment and Generation of Expression Matrix. A digital expression matrix was obtained for each experiment using 10X's Cellranger pipeline with default parameters. The software uses STAR for alignment. All subsequence analysis information is available and maintained in current form in the following Git repository and documentation available through ReadtheDocs.

Alignment of initial abundances. Applicants compiled a dictionary of RNA barcodes associated with sgRNA from Sanger sequencing each part of the construct separately. Applicants devised an alternative cloning protocol for larger libraries to enable NGS pairing of sgRNA/RNA barcodes, but did not use it for any of the results in this paper. The initial abundance of each plasmid in the pool was quantified using NGS of the RNA barcode. The RNA barcode/sgRNA dictionary was used to convert the readout into a relative abundance estimate of sgRNA in the initial pool.

Alignment of Cell barcode/RNA barcodes libraries. In order to associate cell barcodes with guides, the same RNA barcode/sgRNA dictionary was used. Then NGS sequencing may have contained a complex library of molecules such as a full RNA-seq library reads. Paired end reads containing a cell barcode UMI on one side and an RNA barcode on another side were isolated and collapsed into unique molecules by first demultiplexing a sequencing run using bcl2fastq2 with the following options—create-fastq-for-index-reads—barcode-mismatches 1—no-lane-splitting—mask-short-adapter-reads 5—minimum-trimmed-read-length 5 using a sample-sheet containing one line with polyG tracts in the index read columns (see below). The resulting Undetermined fastq files were split using keentools into two folders called split1 and split2 containing chunked R1 and R2 reads respectively.

| Sample_ID | Sample_Name | I7_Index_ID | index | I5_Index_ID | index2 |
|---|---|---|---|---|---|
| 1 | placeholder | silly1 | GGGGGGGGGGGGGG (SEQ. I.D. No. 25) | silly2 | GGGGGGGG |

Then the reads were concatenated and RNA barcode reads isolated using the following UNIX commands.

```
(SEQ. I.D. No. 26)
paste ./split1/$f1 ./split2/$f2 | awk '{if
(NR%4==1) printf($2"\t"); else if
(NR%4==2)printf($0"\n")}' | grep
GGCACAAGCTTAATTAAGAATT
```

with GGCACAAGCTTAATTAAGAATT corresponding to a constant sequence within the RNA barcode, and $f1 and $f2 corresponding to input arguments containing the read1_splitfile and read2_splitfile respectively and creating an output split file.

All split files containing a particular index barcode are finally concatenated and collapsed to unique molecules using the following command.

cat*${inputbc}.txt|sort|uniq-c.|sort-k1,1g|awk"{print$1"\t"$2"\t"$3"-"$4}' the result file format looks as follows (grey highlighting for actual barcode portion of RNA barcode read):

```
(Seq. I.D. Nos. (27 and 28)
2791:N:0:GGTGATACCTCATT + TCGCATAA

(SEQ. I.D. Nos. 29 and 30)
CGCAAACTGGGGCACAAGCTTAATTAAGAATTCGATCAACGCAGAGACG

GCCTAGGCGTATAAGT

(SEQ. I.D. Nos. 31 and 32)
2821:N:0:TCGAGCCTTATGGC + TCGCATAA

(SEQ. I.D. Nos. 33 and 34)
CGCAAACTGGGGCACAAGCTTAATTAAGAATTGCTTGACTCGTTAGCGA

GCCTAGCACGATACCG

(SEQ. I.D. Nos. 35 and 36)
2861:N:0:ACTCGAGAGTTCGA + TCGCATAA

(SEQ. I.D. Nos. 37 and 38)
CGCAAACTGGGGCACAAGCTTAATTAAGAATTCGATCAACGCAGAGACG

GCCTAGGTCTAATGAA

(SEQ. I.D. Nos. 39 and 40)
2941:N:0: GCACGTCTACTAGC + TCGCATAA
```

-continued

```
(SEQ. I.D. Nos. 41 and 42)
CGCAAACTGGGGCACAAGCTTAATTAAGAATTCTAACTCAGCGACTGGA

GCCTAGCATGTGCCCG

(SEQ. I.D. Nos. 43 and 44)
2971:N:0:ATAGATTGTCCGAA + TCGCATAA

(SEQ. I.D. Nos. 45 and 46)
CGCAAACTGGGGCACAAGCTTAATTAAGAATTGCTTGACTCGTTAGCGA

GCCTAGAAAAGGATGG
```

-continued

```
(SEQ. I.D. Nos. 47 and 48)
2991:N:0:GAGCAGGAGCTATG + TCGCATAA

(SEQ. I.D. Nos. 49 and 50)
CGCAAACTGGGGCACAAGCTTAATTAAGAATTAAACCCTCACTGCCGAC

GCCTAGACCTGTTACG

(SEQ. I.D. Nos. 51 and 52)
3331:N:0:GGAGGCCTGTTACG + TCGCATAA

(SEQ. I.D. Nos.53 and 54)
CGCAAACTGGGGCACAAGCTTAATTAAGAATTAGGGCTTGCAGTGCACG

GCCTAGAACGTCAAGA

(SEQ. I.D. Nos. 55 and 56)
3391:N:0:CGACTCACGTTCAG+ + TCGCATAA

(SEQ. I.D. Nos. 57 and 58)
CGCAAACTGGGGCACAAGCTTAATTAAGAATTCGATCAACGCAGAGACG

GCCTAGCAGACTGGGC
```

Counts 1:N:0:Cellbarcode+Index/SampleBarcode RNAbarcoderead-UMI

The resulting file along with the preassociated RNA barcode, sgRNA dictionary is parsed using a custom python script to create a new table of probability estimates of which sgRNA are present in each cell. The probability estimate is thresholded to create a dictionary of which cell barcodes contain which sgRNAs.

Fit of distribution of guides per cell. The distribution of guides per cell was fit using a maximum likelihood approach.

Linear model. To fit the linear model Applicants compiled our covariate matrix X and our expression matrix (or one of the continuous covariates; as done for some assignments of cell states; below) as our matrix Y. Applicants then used the Python implementation of elastic net with the following parameters, to fit our model.

sklearn.linear_model.ElasticNet(11_ratio=0.5,alpha=0.0005,max_iter=10000)

Alternating descent fit of perturbation probability. To account for the contribution of unperturbed cells in the population containing a particular sgRNA, Applicants constructed an approach in which the presence of sgRNA in a given cell was converted into a probability measure of that sgRNA having a phenotypic effect on the cell, as follows:

First, Applicants fit using the multivariate regression on $$Y=X$$

$$LL(y)=\log\left(\frac{\frac{1}{2\pi\sigma}e^{-\frac{(y-\mu_1)^2}{2\sigma}}}{\frac{1}{2\pi\sigma}e^{-\frac{(y-\mu_0)^2}{2\sigma}}}\right)=\frac{(y-\mu_0)^2-(y-\mu_1)^2}{2\sigma}$$

$$P(X_j=1\mid Y)=\frac{P(Y\mid X_j=1)P(X_j=1)}{P(Y)}=\frac{P(Y\mid X_j=1)P(X_j=1)}{P(Y\mid X_j=0)P(X_j=0)+P(Y\mid X_j=1)P(X_j=1)}=\frac{1}{1+e^{-LL(Y)}}$$

Next, Applicants evaluate the fit with the guide covariate set to 0, Xo $$P(X_j=1)=\text{logistic}(\Sigma_t[[Y_{tj}-X_o\beta_t]^2-[Y_{tj}-\hat{Y}_{tj}]^2);\text{ where}$$

$$\text{logistic}(x)=\frac{1}{1+e^{-x}}$$

Finally, Applicants use the new covariate matrix $X_M$ to recompute $\beta_M$.

Significance testing for coefficients of linear model. Applicants devised a permutation strategy to obtain an empirical null distribution of the coefficients associated with our sgRNA effects. Specifically, Applicants randomized the guide assignments to cells (such that co-occurrence between guides was preserved) and the linear model was recomputed with all other covariates being held constant. Applicants repeated this ten times. Applicants noticed that three significant as-yet latent factors impacted the empirical null distribution of coefficients: (1) the mean expression level of a gene; (2) the variance in expression of a gene; and (3) the number of cells a particular sgRNA was present in.

To control for these factors when assessing significance, each empirical null coefficient's value was assigned a point in 4-space: [Gene mean, gene variance, number of cells, value]. Applicants then estimated the multivariate density using a binning approach (np.histogramdd in Python). True nonzero coefficients were evaluated for significance relative to a matched set of bins (to create an empirical conditional cumulative probability distribution) conditioned on the first three factors.

A less stringent null was generated by obtaining a permuted distribution of coefficients based on a permuted cell to guide assignment, but only calculating the significance on a per guide basis without consideration of the mean expression level or variance of the gene being considered.

In both cases, Applicants used a Benjamini-Hochberg procedure to control for multiple hypothesis testing.

Residuals analysis. To determine the marginal effect of each covariate in explaining the observed gene expression variation, Applicants estimated the model R2 by cross-validated (trained on 80% of the data and tested against 20%) for the addition of each of the covariates.

To determine the extent to which our covariates explained the major axes of variation in our data, Applicants decomposed the residuals using the same randomized PCA approach described in the Definition of Cell States section. Two major metrics were evaluated: (1) the eigenvalue distribution, and (2) the extent to which the top loadings were enriched for biological terms.

Cross validated $R^2$. To estimate the generalizability of the model, Applicants determined a cross-validated $R^2$ by training our model on 80% of our data and determining the fit on the remaining 20%.

Definition of cell states. Cell states were defined using cells that did not have sgRNAs introduced. Starting from an expression matrix Y, variable genes are selected based on fitting a nonparametric loess regression (using a moving window of 25 percent of the data) to the relationship between the average expression of a gene and its respective coefficient of variation (after normalizing each cell for complexity). Genes with high residuals (i.e more variable than genes at comparable expression levels) were selected (approximately 1000 genes).

Next, the cell normalized expression matrix (the sum of the number of transcripts is renormalized to 10,000) and then log 2 transformed with a pseudocount of 1. The final normalization is Z-transforming the genes of the matrix. Randomized PCA is performed on the Z transformed expression matrix using Facebook's implementation through the python package fbpca retaining the top 50 components.

A combination of the elbow method looking at the eigenvalue gap of each component, GO enrichment of each component using jackstraw (cite Story paper), and a PC robustness analysis (in which increasing amounts of random noise is added to the data and the stability of each principal component with respect to the original components is evaluated) was used to determine the number of principal components (which in general was approximately 10).

A two dimensional visualization of the relationship between cells was performed using TSNE. Clustering was performed using Infomap with k refined so that slightly more clusters are created than one would expect. Clusters are subsequently merged in an iterative fashion that have fewer than 100 differentially expressed genes between them.

Differential expression is evaluated using a Welch's t-test on the Z-transformed values between each cluster and the rest of the cells.

A Benjamini-Hochberg procedure was used to control for multiple hypothesis testing.

The clusters are evaluated for GO enrichment using FDR corrected p-values (see Interpretation of Results).

Relation of perturbed cells to unperturbed states. In order to define the relationship between the cell states in the unperturbed cells and the perturbed cells, applicants projected the perturbed cells onto the same significant principal component vectors derived from the unperturbed cells. The projection onto these components was used as a covariate by itself, especially with the K562 cells, where the major axes of variation such as cell cycle describe somewhat continuous processes. Alternatively, for the PBMDCs, discrete cell types are readily discernable. As such, a random forest classifier was trained using class labels obtained by the merged Infomap clusters with features consisting of PC scores from sklearn.ensemble import RandomForestClassifier clf=RandomForestClassifier (n_estimators=100, n_jobs=−1,oob_score=True,class_weight='balanced').

The out of bag probability estimates were used to generate ROC curves to determine the sensitivity and specificity of classification per cluster.

Finally, the random forest was applied to the projected PC scores of the perturbed cells to obtain class membership estimates.

Testing for significant association of guides with cell states. Applicants used several tests to assess guide-state associations and our reported results are coherent across the tests.

In a continuous test Applicants used the Wilcoxon-ranksum test to examine if the cells with a specific guide have significantly higher or lower cell-state scores compared to the cells with non-targeting or intergenic guides. The test is performed separately for each batch (to avoid batch-effects), and then the p-values are merged using Fisher's combined probability test.

In a discrete test, each cell is assigned with a single state (the one it scored highest in). Cells with low cell-state scores (<0.5) are classified as unclustered. For each guide-state pair <g,s>Applicants examine if the number of cells with guide g in state s is significantly larger or smaller than expected (using a binomial test). The expected is based on the probability of the cell-state in the cells with intergenic/non-targeting guides.

A guide-cell association is defined as significant if its p-value <0.05 after correcting for multiple hypotheses testing using the Benjamini-Hochberg procedure.

Tests of sgRNA effect on Covariate. In order to evaluate the effect of a sgRNA on a covariate such as genes detected, transcripts detected, or cell state, an Welch's t-test is performed between the covariate and the set of control sgRNAs.

Expectation Maximization. In order to account for the contribution of unperturbed cells in the population containing a particular sgRNA, an expectation maximization approach was constructed in which the presence of sgRNA in a given cell was converted into a probability measure. The approach is as follows:

First, fit β using the multivariate regression on $$Y=X\beta$$

Then evaluate the fit with guide covariate set to 0 $X_o$ $$P(X_j=1)=\log\ \mathrm{tstto}(\Sigma_t[Y_{ij}-X_o\beta]^2-[Y_{ij}-Y_{ij}]^2);\ \text{where}$$

$$\mathrm{logistic}(x)=\frac{1}{1+e^{-x}}$$

Finally, the new covariate matrix $X_M$ is used to recompute $\beta_M$.

Significance Testing for Coefficients of Linear Model. A permutation strategy was devised to get an empirical null distribution of the coefficients associated with our sgRNA effects. Specifically, the guide assignments to cells were randomized (such that co-occurrence between guides was preserved) and the linear model was recomputed with all other covariates being held constant ten times. Applicants noticed that three significant as-yet latent factors impacted the empirical null distribution of coefficients: 1) the mean expression level of a gene 2) the variance in expression of a gene 3) the number of cells a particular sgRNA was present in.

In order to control for these factors in assessing significance, each empirical null coefficient's value was assigned a point in 4-space: [Gene mean, Gene variance, number of cells, value] A multivariate density estimation was subsequently performed using a binning approach (np.histogramdd in Python). True coefficients were evaluated for significance relative to a matched set of bins (to create an empirical conditional cumulative probability distribution) conditioned on the first three factors.

A Benjamini-Hochberg procedure was used to control for multiple hypothesis testing.

Residuals Analysis. In order to determine the marginal effect of each covariate in explaining the observed gene expression variation a cross-validated estimation (trained on 80% of the data and tested against 20%) of the model $R^2$ was obtained for the addition of each of the covariates.

In order to determine the extent to which our covariates explained the major axes of variation in our data, applicants decomposed the residuals using the same randomized PCA approach described in the Definition of Cell States section. Two major metrics were evaluated: 1) the eigenvalue distribution 2) the extent to which the top loadings were enriched for biological terms using the aforementioned approach.

Interpretation of Results. GO analysis was performed using the goatools python package with an FDR threshold of 0.1.

Power Analysis/Design of Experiments. Power analysis was performed to determine as a function of observed effect size and baseline expression of a gene, how many cells are required to observe a signal.

Fitness effects of sgRNAs. Applicants used several approaches to assess the fitness effects of sgRNAs and all yielded qualitatively comparable results.

In the most straight forward approach, Applicants obtained estimates of the initial abundances of each sgRNA in the pool. The initial abundance of each plasmid in the pool was quantified using NGS of the RNA barcode. The RNA barcode/sgRNA dictionary was used to convert the readout into a relative abundance estimate of sgRNA in the initial pool. Then, Applicants calculated the fold change of the observed abundance of cells containing a particular sgRNA compared to its respective abundance in the original pool.

In an alternative approach, Applicants developed two complementary Bayesian probabilistic models that compute the expected probability of each guide in the resulting cell population. The first model assumes that none of the guides affect cell fitness and is suitable in situations where the perturbations are unlikely to effect cell survival or proliferations, as in BMDC TFs. The expected guide frequency is modeled as a function of the MOI, the guide frequency in the initial library, and the guide detection rate, such that multiple infections are considered to be independent Poisson processes. Applicants applied this model and examined if the observed guide frequencies deviate from the expected ones. Indeed, in K562 cells the observed guide distribution deviates significantly from the expected distribution, indicating that certain perturbations affect cell fitness. Applicants then extended the probabilistic model to account for these effects by introducing fitness parameters, which are set by solving a maximum likelihood optimization problem. In this setting Applicants model the fitness effects of multiple perturbations as additive, and identify perturbations that show different co-occurrence frequencies as indicators of genetic interactions.

In both Bayesian models the infection, selection, and detection processes are modeled such that: (1) the guide detection rate, denoted as d, is the same for all guides, (2) there are no falsely detected guides, (3) the infection with different guides is independent and, (4) due to BFP selection, denoted as B, all cells have at least one guide by the end of the screen. Let M, $f_g$, and $d_g$ denote the MOI, the frequency of guide g in the initial pool of the screen, and the event of detecting guide g, respectively. Applicants model the infection as a Poisson process, such that ig denotes the number of times the cell was infected with guide g, to $L_g$~Palstart ($f_s$·M). Let $I_{c,g}$, $N_0$, and $N_g$ be the indicator that cell c was detected with guide g in the screen, the number of cells in which no guide was detected, and the number of cells in which guide g was detected, respectively.

To find the most likely parameters and compute the expected guide probabilities without fitness effects Applicants solve the following maximum likelihood optimization problem.

$$L(M, p_d) = \prod_c P(d_1, \ldots, d_k, B)$$

$$P(d_1, \ldots, d_k, B) = P(B \mid d_1, \ldots, d_k)P(d_1, \ldots, d_k) = \begin{cases} P(d_1, \ldots, d_k) & \text{if } \sum_g d_g > 0 \\ P(B \mid \forall_g\, d_g = 0)P(\forall_g\, d_g = 0) & \text{otherwise} \end{cases}$$

$$L(M, p_d) = \prod_c \left[P(B \mid \forall_g\, d_g = 0)^{I_{\forall_g I_{c,g}=0}} \prod_g P(d_g = 1)^{I_{c,g}} \cdot P(d_g = 0)^{1-I_{c,g}}\right] = P(B \mid \forall_g\, d_g = 0)^{N_0}\left[\prod_g P(d_g = 1)^{N_g} \cdot P(d_g = 0)^{N-N_g}\right] = \left(1 - e^{-M(1-p_d)}\right)^{N_0}\left[\prod_g P(d_g = 1)^{N_g} \cdot P(d_g = 0)^{N-N_g}\right]$$

The log likelihood is $$\log[L(M, p_d)] = N_0 \log\left(1 - e^{-M(1-p_d)}\right) + \sum_g \{N_g \log[P(d_g = 1)] + (N - N_g)\log[P(d_g = 0)]\} = N_0 \log\left(1 - e^{-M(1-p_d)}\right) + \sum_g \left\{N_g \log\left(1 - e^{-f_g p_d M}\right) - (N - N_g) f_g p_d M\right\}$$

Below Applicants provide the equations used to compute the maximum likelihood function above.

$$F(d_g{=}0){=}e^{-f_g M_{Bd}}P(d_g{=}0|t_g){-}(1{-}p_d)^{t_g}{=}q^{t_g},\quad P(d_g{=}0){=}\Sigma_n q^n P(t_g{=}n){=}B[q^{t_g}] \tag{1.1}$$

Based on the moment-generating function $$E\left[e^{TX}\right] = e^{\lambda(e^t - 1)}, \text{ where } X \sim \text{Poisson}(\lambda) \text{ and } t \in \mathbb{R}$$

$$t = \ln q,\ \lambda = f_g \cdot M,\ E\left[q^{i_g}\right] = E\left[e^{i_g \cdot \ln q}\right] = e^{f_g M(q-1)} = e^{-f_g M p_d}$$

$$P(B) = 1 - e^{-M} \tag{1.2}$$

$$P(B) = 1 - P(\neg B)$$

$$P(\neg B) = P(\forall_g\, I_g = 0) = \prod_g P(I_g = 0) = \prod_g e^{-Mf_g} = e^{-M\Sigma_g f_g} = e^{-M}$$

$$P(B \mid \forall_g\, d_g = 0) = 1 - e^{-M(1-p_d)} \tag{1.3}$$

$$P(B \mid \forall_g\, d_g = 0) = 1 - P(\neg B \mid \forall_g\, d_g = 0)$$

$$P(\neg B \mid \forall_g\, d_g = 0) = P(\forall_g\, I_g = 0 \mid \forall_g\, d_g = 0) = \prod_g P(I_g = 0 \mid d_g = 0) = \prod_g \frac{P(d_g = 0 \mid I_g = 0)P(I_g = 0)}{P(d_g = 0)} = \prod_g \frac{1 \cdot e^{-Mf_g}}{e^{-f_g M p_d}} = \prod_g e^{-Mf_g(1-p_d)} = e^{-M(1-p_d)\Sigma_g f_g} = e^{-M(1-p_d)}$$

To account for fitness effects Applicants introduce a fitness parameter for each guide, denoted as $\theta_g$, and define the fitness normalization factor Z, such that $$Z = E_{P(i_g)}[\delta_g] = \delta_0 \prod_g \left(e^{-f_g M}(1 - \delta_g) + \delta_g\right) = \delta_0 \prod_g \alpha_g$$

$$Z = E_{P(i_g)}[\delta_g] = \sum_{(n_1, \ldots, n_k)} P(i_1 = n_1, \ldots, i_k = n_k)\delta_0 \delta_1^{i_1>0} \ldots \delta_k^{i_k>0} =$$

-continued $$\delta_0 \sum_{(n_2, \ldots, n_k)} \left[P(i_1 = 0, i_2 = n_2 \ldots, i_k = n_k)\delta_2^{i_2>0} \ldots \delta_k^{i_k>0} + P(i_1 > 0, i_2 = n_2 \ldots, i_k)\delta_1 \delta_2^{i_2>0} \ldots \delta_k^{i_k>0}\right] =$$

$$\delta_0 \sum_{(n_2, \ldots, n_k)} (P(i_1 = 0) + P(i_1 > 0)\delta_1) \prod_{2 \le g \le k} P(i_g = n_g)\delta_1^{i_g>0} =$$

$$\delta_0 \prod_g (P(i_g = 0) + P(i_g > 0)\delta_g) = \delta_0 \prod_g \left(e^{-f_g M}(1 - \delta_g) + \delta_g\right) = \delta_0 \prod_g \alpha_g$$

Where $\alpha_g = e^{-f_g M}(1 - \delta_g) + \delta_g$

Applicants adjust the probability that a cell that was infected i times with guide g to account for the fitness effects.

$$P_f(i_g = n_g) = \frac{\delta_g^{n_g>0} P(i_g = n_g)}{\alpha_g}$$

$$P_f(i_1 = n_1) = \frac{1}{Z} \sum_{(n_2, \ldots, n_k)} P(i_1 = n_1, i_2 = n_2 \ldots, i_k = n_k)\delta_0 \delta_1^{n_1>0} \ldots \delta_k^{i_k>0} = \frac{1}{\prod_g \left(e^{-f_g M}(1 - \delta_g) + \delta_g\right)} \delta_1^{n_1>0} P(i_1 = n_1) \prod_{g \ne 1} \left(e^{-f_g M}(1 - \delta_g) + \delta_g\right) = \frac{\delta_1^{n_1>0} P(i_1 = n_1)}{e^{-f_1 M}(1 - \delta_1) + \delta_1}$$

The probability that guide g was not detected in a specific cell is now $$P(d_g = 0) = \frac{e^{-f_g M}(1 - \delta_g) + \delta_g e^{-f_g M p_d}}{e^{-f_g M}(1 - \delta_g) + \delta_g}$$

$$P(d_g = 0 \mid i_g) = (1 - p_d)^{i_g} = q^{i_g}$$

$$P_f(d_g = 0) = \sum_n q^n P_f(i_g = n) = \sum_n q^n \frac{\delta_g^{n>0} P(i_g = n)}{\alpha_g} = \frac{1}{\alpha_g} \sum_n q^n \delta_g^{n>0} P(i_g = n) = \frac{1}{\alpha_g}\left[P(i_g = 0) - \delta_g P(i_g = 0) + \delta_g \sum_n q^n P(i_g = n)\right] = \frac{1}{\alpha_g}\left[e^{-f_g M}(1 - \delta_g) + \delta_g e^{-f_g M p_d}\right] = \frac{e^{-f_g M}(1 - \delta_g) + \delta_g e^{-f_g M p_d}}{e^{-f_g M}(1 - \delta_g) + \delta_g}$$

The probability of detecting guide g in a cell $$P_f(d_g = 1) = \frac{\delta_g\left(1 - e^{-f_g M p_d}\right)}{\alpha_g}$$

The probability that a cell survived BFP selection given that none of the guides was detected $$P(B \mid \forall_g\, d_g = 0) = 1 - \frac{1}{\prod_g \left(1 - \delta_g + \delta_g e^{-f_g M(p_d - 1)}\right)}$$

$$P(\neg B \mid \forall_g\, d_g = 0) =$$

-continued $$P(\forall_g\, i_g = 0 \mid \forall_g\, d_g = 0) = \frac{\overbrace{P(\forall_g\, d_g = 0 \mid \forall_g\, i_g = 0)}^{1} P(\forall_g\, i_g = 0)}{P(\forall_g\, d_g = 0)}$$

$$\prod_g \frac{\frac{P(i_g = 0)}{\alpha_g}}{\frac{1}{\alpha_g}\left[e^{-f_g M}(1-\delta_g) + \delta_g e^{-f_g M p_d}\right]} = \prod_g \frac{e^{-f_g M}}{e^{-f_g M}(1-\delta_g) + \delta_g e^{-f_g M p_d}} =$$

$$\prod_g \frac{e^{-f_g M}}{e^{-f_g M}\left(1-\delta_g + \delta_g e^{-f_g M(p_d - 1)}\right)} = \frac{1}{\prod_g \left(1-\delta_g + \delta_g e^{-f_g M(p_d - 1)}\right)}$$

The probability of the BFP selection $$P(B) = 1 - \frac{e^{-M}}{\prod_g e^{-f_g M}(1-\delta_g) + \delta_g}$$

$$P(\neg B) = P(\forall_g\, i_g = 0) = \prod_g \frac{P(i_g = n_1)}{e^{-f_g M}(1-\delta_g) + \delta_g} = \frac{e^{-M}}{\prod_g e^{-f_g M}(1-\delta_g) + \delta_g}$$

The new maximum likelihood function that accounts for the fitness parameters is $$\log[L(M, p_d, \delta)] =$$

$$N_0 \log P(B \mid \forall_g\, d_g = 0) + \overbrace{\sum_g \{N_g \log[P(d_g = 1)] + (N - N_g)\log[P(d_g = 0)]\}}^{\gamma}$$

$$\gamma =$$

$$\sum_g \left\{N_g \log \frac{\delta_g\left(1 - e^{-f_g M p_d}\right)}{\alpha_g} + (N - N_g)\log \frac{e^{-f_g M}(1-\delta_g) + \delta_g e^{-f_g M p_d}}{\alpha_g}\right\} =$$

$$\sum_g \left\{N_g \log\left[\delta_g\left(1 - e^{-f_g M p_d}\right)\right] - N_g \log \alpha_g + \right.$$

$$\left.(N - N_g)\log\left(e^{-f_g M}(1-\delta_g) + \delta_g e^{-f_g M p_d}\right) - (N - N_g)\log \alpha_g\right\} =$$

$$\sum_g \left\{N_g \log\left(1 - e^{-f_g M p_d}\right) + N_g \log \delta_g + \right.$$

$$\left.(N - N_g)\log\left(e^{-f_g M}(1-\delta_g) + \delta_g e^{-f_g M p_d}\right) - N \log \alpha_g\right\}$$

$$\log[L(M, p_d, \delta)] = N_0 \log\left(1 - \frac{1}{\prod_g \left(1-\delta_g + \delta_g e^{f_g M(1-p_d)}\right)}\right) +$$

$$\sum_g \left\{N_g \log\left(1 - e^{-f_g M p_d}\right) + N_g \log \delta_g + \right.$$

$$\left.(N - N_g)\log\left(e^{-f_g M}(1-\delta_g) + \delta_g e^{-f_g M p_d}\right) - N \log \alpha_g\right\}$$

Analysis of perturbation effects on individual genes and gene modules. The most variable genes from each Perturb-Seq experiment were filtered by using the jackstraw approach (Chung and Storey, 2015) to identify the most significant genes (q-value <0.01) in the top 20 PCs of the coefficient matrix. The genes were then clustered using k-means clustering by their coefficients. Optimal k was chosen by visual inspection of clustering results. Gene ontology (GO) enrichment analysis was performed on each cluster using goatools (Tang et al., 2015) with FDR threshold of 0.05.

Comparison to ChIP-seq binding profiles. Applicants analyzed assignments of TF binding in gene promoters in BMDCs following LPS stimulation across four time points (0 minutes, 30 minutes, 60 minutes, and 120 minutes) (Garber et al., 2012). To test for significant binding, two tests were used. First, the regulatory coefficients of bound genes were compared to those of unbound genes using a non-parametric Mann-Whitney test to identify significantly different means. Because of the possibility that this significance was driven by skewed covariates from unbound genes, Applicants also tested whether the coefficients of bound genes significantly deviated from 0, using the non-parametric one-sample Wilcox test. Finally, because TFs could both activate and repress genes, Applicants examined the number of bound genes significantly up- or down-regulated. To do this, Applicants used the distribution of covariates of unbound genes to define thresholds at the $5^{th}$ percentile of lowest negative and highest positive coefficients. Any bound genes with coefficients that surpassed the thresholds were considered significant. Between the set of genes with significant positive and negative coefficients, Applicants used the larger set to infer whether the transcription factor was activating or inhibiting gene expression. Only BMDC expressed genes were considered in all ChIP-Seq analysis.

Power analysis and experimental design considerations. Power analysis was performed to determine how many cells are required to observe a signal as a function of observed effect size and baseline expression of a gene.

As an estimate of required read depth, Applicants downsampled at the UMI level. For example, for a vector of gene expression for a cell with the following values: [2,0,1,6] Applicants convert it into the following vector [1,1,3,4,4,4,4,4,4] on which downsampling is performed with equal probability without replacement. It is reconstructed into the original probability space by binning the observed integer counts. Applicants also downsampled cells are without replacement from our observed set.

Applicants performed our regression analysis on the downsampled expression matrix for various amounts of downsampling and recomputed resulting regulatory matrix. For each level of downsampling, 10 instances are averaged. Applicants compared between the original regulatory matrix and the matrix that results after downsampling using either a Pearson or Spearman correlation.

Plasmid design and construction The perturb-seq expression vector (pBA439) was derived from a previously described CRISPRi expression vector (herein referred to as the "original CRISPRi expression vector") (Addgene plasmid #60955) (Gilbert et al. 2014). To construct pBA439, the mU6-sgRNA-EF1a-PURO-BFP region from the original CRISPRi vector and a BGH polyadenylation sequence amplified by PCR from pcDNA3.1 (+) (Invitrogen, V790-20) were inserted in reverse origination between the XbaI and EcoRI sites of the original CRISPRi expression vector. A random 18 nucleotide barcode was then inserted between the BFP and BGH polyA sequences (using disrupted EcoRI and AvrII sites) by Gibson assembly to construct the perturb-seq expression library (pBA571). The perturb-seq library was prepared with an estimated barcode diversity of >100,000 essentially as previously described (Kampmann, Bassik & Weissman 2014). Guide RNA protospacer sequences were individually cloned into both the original CRISPRi expression vector and the pBA571 library (between the BstXI and BlpI sites) by ligation. Each vector was then verified by Sanger sequencing of the protospacer and, if applicable, its corresponding barcode. Final guide expression vectors containing barcodes that introduced the conserved polyadenylation signal AATAAA were discarded. To construct pMH0001, a minimal ubiquitous chromatin opening element (UCOE) (Müller-Kuller et al. 2015) was inserted upstream of the SFFV promoter in the lentiviral dCas9-BFP-KRAB expression vector (Gilbert et al. 2014).

The UPRE reporter was built into a backbone for lentiviral expression that has been previously described (Addgene plasmid #44012) (Meerbrey et al. 2011). This parental vector was digested with AgeI and religated to remove unwanted functional cassettes, and the UPRE promoter region or EF1α promoter were inserted between the BamHI and XhoI site of the resulting product. The UPRE promoter region contains 5 UPR elements (UPREs, 5'-TGACGTGG-3') upstream of the c-fos minimal promoter (−53 to +45 of the human c-fos promoter) (Wang et al. 2000). Lastly, mCherry and sfGFP were cloned adjacent to UPRE and EF1α promoters, respectively (into an HpaI site). The resulting vectors are pBA407 (UPRE-mCh-Ubc-Neo) and pBA409 (EF1a-sfGFP-Ubc-Neo).

For testing of constant region variants in K562 cells, constant region variants fused to a GFP-targeting protospacer (EGFP-NT2, sequence GACCAGGATGGGCACCACCC) (SEQ. I.D. No. 59) or a negative control protospacer were PCR-amplified and inserted into BstXI/XhoI-digested pBA439 (perturb-seq expression vector) by Gibson assembly. For testing of U6 promoters, U6 promoters from cow (bU6-2, GenBank DQ150531 and bU6-3, GenBank DQ150532 (Lambeth et al. 2006)), sheep (sU6-1, GenBank HM641427 and sU6-2, GenBank HM641426 (Hu et al. 2011)), buffalo (buU6, GenBank JN417659 (Zhang et al. 2014)), and pig (pU6, GenBank EU520423 (Chuang et al. 2009)) spanning ~400-500 bp upstream of the TSS, modified to contain a BstXI site at the TSS, and fused to EGFP-NT2 and the original constant region were obtained as synthetic DNA segments (Integrated DNA technologies) and inserted into HpaI/XhoI-digested pBA439 (perturb-seq expression vector) by Gibson assembly.

Figure 88F:
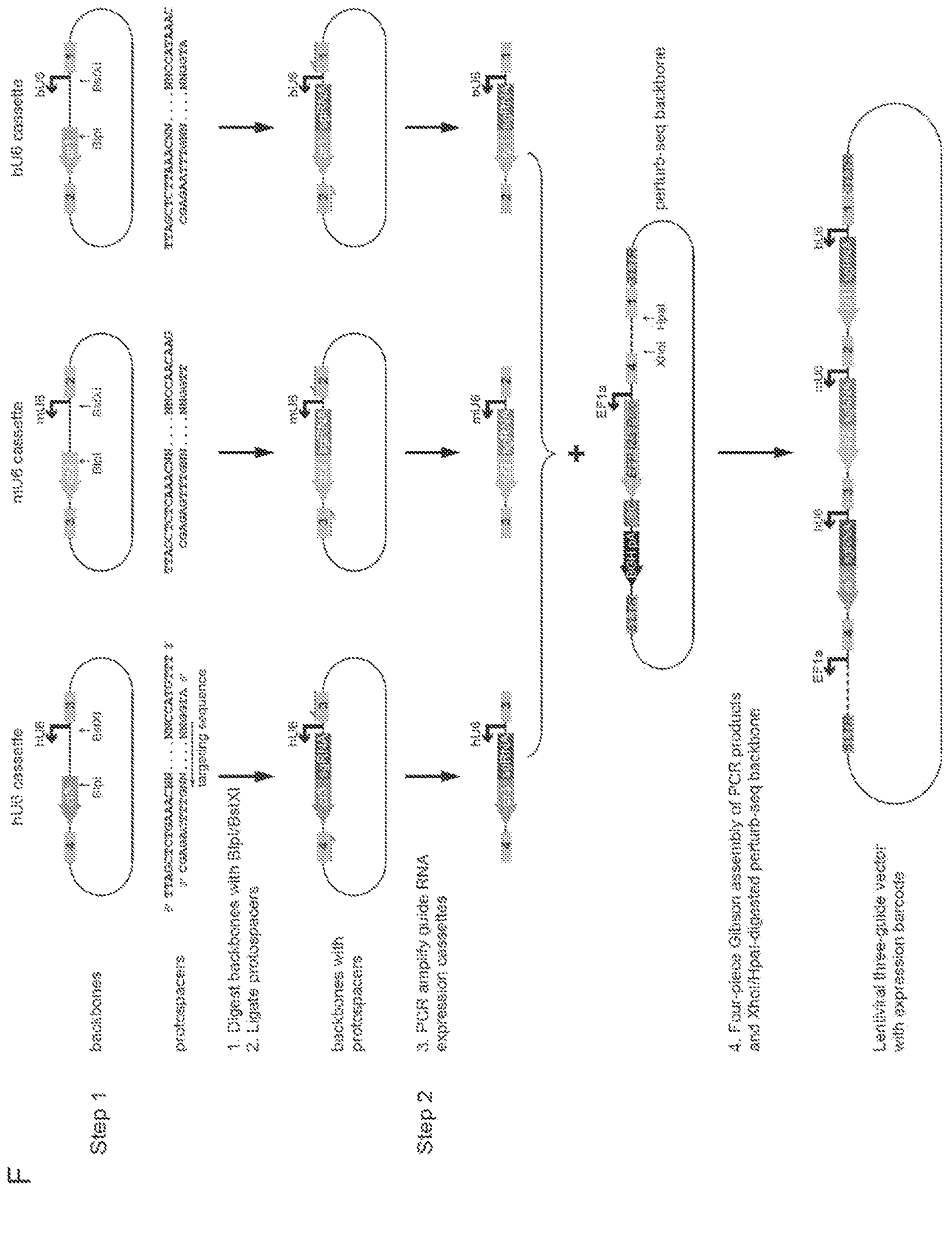

Three-guide vectors were assembled by a two-step cloning procedure (FIG. 88F). First, guide RNAs to be included were cloned into the corresponding single guide RNA expression vectors. Briefly, complementary oligonucleotides (Integrated DNA Technologies) containing the protospacer sequence and ligation overhangs were annealed and ligated into BstXI/BlpI-digested guide RNA expression vectors containing specific primer binding sites flanking the guide RNA expression cassette. The three-guide RNA expression cassettes were then PCR-amplified and assembled into HpaI/XhoI-digested pBA571 (perturb-seq expression library) by a single four-piece Gibson assembly step. Vectors were validated and barcodes were determined as described above. For three-guide vectors targeting the UPR branches, the bU6, mU6, and hU6 cassettes were designed to either express an sgRNA targeting ATF6, EIF2AK3 (PERK), or ERN1 (IRE1α), respectively, or a non-targeting negative control sgRNA. The following protospacer sequences were used: ATF6-targeting, gGGGATCTGAGAATGTACCA (SEQ. I.D. No. 60); EIF2AK3-targeting, gCGGGCTGAGACGTGGCCAG (SEQ. I.D. No. 61);; ERN1-targeting, gAGAACTGACTAGGCAGCGG (SEQ. I.D. No. 62); non-targeting sgRNA in bU6 cassette, gACGACTAGTTAGGCGTGTA (SEQ. I.D. No. 63); non-targeting sgRNA in mU6 cassette, gGCCAAACGTGCCCTGACGG (SEQ. I.D. No. 64); non-targeting sgRNA in hU6 cassette, gCCTTGGCTAAACCGCTCCC (SEQ. I.D. No. 65).

Cell culture, DNA transfections, viral production, and construction of reporter cell lines K562 cells were grown in RPMI-1640 with 25 mM HEPES, 2.0 g/L $NaHCO_3$, 0.3 g/L L-Glutamine supplemented with 10% FBS, 2 mM glutamine, 100 units/mL penicillin and 100 μg/mL streptomycin. HEK293T cells were grown in Dulbecco's modified eagle medium (DMEM) in 10% FBS, 100 units/mL penicillin and 100 μg/mL streptomycin. Cells were treated with tunicamycin or thapsigargin (Sigma, T9033) solubilized in DMSO. Lentivirus was produced by transfecting HEK293T with standard packaging vectors using TransIT®-LTI Transfection Reagent (Mirus, MIR 2306). Viral supernatant was harvested at least 2 days after transfection and filtered through a PVDF syringe filter and/or frozen prior to infection.

To construct the UPRE reporter cell line, K562 cells stably expressing dCas9-KRAB (Gilbert et al. 2014), originally constructed from K562 cells obtained from ATCC 536 (RRID:CVCL_0004), were stably transduced with pBA407 and selected in media supplemented with 500 μg/mL Geneticin (Gibco, 10131-035). The clonal line cBA010 was then selected by limiting dilution. cBA011 is a derivative of cBA010 containing pBA409. cBA011 was made by stable transduction and selection of GFP positive cells using fluorescence activated cell sorting on a BD FACSAria2. The GFP reporter cell line was constructed by infecting K562 cells stably expressing dCas9-KRAB with a Murine Stem Cell Virus (MSCV) retrovirus expressing GFP from the SV40 promoter. MSCV retrovirus was produced by transfecting amphotropic Phoenix packaging cell lines with standard packaging vectors. K562 cells stably expressing GFP were sorted to purity by flow cytometry using a BD FACS Aria2. To construct the GFP+K562 UCOE-dCas9-KRAB cell line, the GFP reporter cell line was transduced with pMH0001 at a multiplicity of infection of ~3. Transduced cells were sorted for BFP expression (top 33%) by: flow cytometry on a BD FACS Aria2. BFP fluorescence was monitored for several generations and found to be stable.

Design and cloning of constant region variants for testing in *E. coli*. Constant region bases to mutate were identified by inspection of the crystal structure of Cas9 bound to guide RNA and target DNA (FIG. 88D, PDB ID codes 4OO8, 4UN3, 4ZT0 (Nishimasu et al. 2014, Anders et al. 2014, Jiang et al. 2015)). Bases that did not form direct contacts with Cas9 or with other nucleotides of the constant region were deemed amenable for mutation. If applicable, sequence conservation patterns of the base in crRNAs/tracrRNAs of *Streptococcus* species and previous reports of constant regions carrying changes at the base (Briner et al. 2014, Dang et al. 2015) were used to determine the type of mutation. In this fashion, 15 constant region variants with mutations in different parts of the constant region were designed (FIG. 82D). The most diverse constant region variants cr2 and cr3 were designed by combining multiple individual mutations (FIG. 82D).

To rapidly assess the activity of the variant constant regions, the variants were fused to a mRFP-targeting guide RNA (mRFP-NT1, sequence AACTTTCAGTTTAGCGGTCT (SEQ. I.D. No. 66)) (Qi et al. 2013) and tested in an *E. coli* CRISPRi reporter strain for knockdown of mRFP (see below). To eliminate variability from copy number variation, guide RNAs were cloned into a plasmid for site-specific integration into the *E. coli* genome at attL and expressed from single copy from an IPTG-inducible $P_{LlacO\text{-}1}$ promoter (Lutz, Bujard 1997). To construct the integrating guide RNA expression plasmid, a guide RNA expression cassette was first PCR-amplified from pgRNA-bacteria (Addgene plasmid #44251) (Qi et al. 2013), modified to be flanked by the strong synthetic terminators L3S3P22 and L3S2P21 (Chen et al. 2013) and inserted into pCAH63 (Haldimann, Wanner 2001) at the ClaI/NheI sites.

The constitutive promoter from pgRNA-bacteria was replaced with the IPTG-inducible $P_{LlacO-1}$ promoter, generating pCs-550r. Then, pCs-550r was further modified to include the constant region used in mammalian CRISPRi (Gilbert et al. 2014), PCR-amplified with an mRFP-targeting protospacer and inserted into pCs-550r at the SpeI and KpnI sites to generate pMJ020. Finally, constant region variants 1-15 as well as cr2 and cr3 were cloned into pMJ020 by inverse PCR with mutations encoded in primer overhangs, by site-directed mutagenesis following standard procedures, or by insertion of a synthetic DNA segment encoding the constant region (Integrated DNA Technologies) into SpeI/KpnI-digested pMJ020 by Gibson assembly.

Construction of *E. coli* CRISPRi reporter strain and testing of constant region variants The *E. coli* CRISPRi reporter strain was constructed by sequential insertion of a construct for IPTG-inducible expression of dCas9, a construct for constitutive expression of mRFP, and a construct for IPTG-inducible guide RNA expression (described above) into the *E. coli* genome. First, a lacIq-t0-$P_{Llaco-1}$-dCas9 cassette (lacIq for strong expression of the Lac repressor; t0, a transcription terminator; $P_{LlacO-1}$-dCas9; for IPTG-inducible expression of *S. pyogenes* D10A/H840A Cas9 (dCas9)) was inserted into the chromosome of *E. coli* BW25113 at +19 attL via of lambda Red recombinase-mediated recombineering (Thomason et al. 2014). Then, a nfsA::mRFP-kan cassette for expression of mRFP from the J23119 promoter, a strong synthetic constitutive promoter from the Anderson promoter collection (http://parts.igem.org/Promoters/Catalog/Anderson), was inserted into an *E. coli* MG1655-derived strain by lambda Red recombinase-mediated recombineering as described previously (Qi et al. 2013), and moved from the MG1655-derived strain into the dCas9-expressing BW25113 strain by P1 transduction and selection on kanamycin following a published protocol (Thomason, Costantino & Court 2007). Plasmids for expression of mRFP-NT1 with the different constant region variants were integrated into the dCas9- and mRFP-expressing strain at attL using the helper plasmid pINT-ts (Haldimann, Wanner 2001), selecting for chloramphenicol resistance.

Single colonies of strains with the integrated guide RNA expression plasmids were inoculated into LB and grown overnight in deep 96-well blocks at 37 °C with shaking at 900 rpm. Stationary-phase cultures were back-diluted 1:30 and grown into mid-exponential phase, at which point they were back-diluted 1:10000 into LB with 1 mM IPTG for induction of guide RNA and dCas9 expression. Induced cultures were grown at 37 °C with shaking until $OD_{600\ nm}$ reached ~0.4-0.7 (approximately 5 hrs), at which point they were diluted 1:30 in PBS in a 96-well plate. RFP fluorescence was recorded on a LSR-II flow cytometer (BD Biosciences) equipped with a 96-well high-throughput sampler. Each experiment was carried out using three individual colonies for each constant region variant. RFP levels were normalized to those of a strain expressing a non-targeting guide RNA.

Testing of single- and three-guide vectors in K562 cells by GFP knockdown Vectors for expression of EGFP-NT2 in different contexts were delivered into GFP+ K562 cells with dCas9-KRAB or with UCOE-dCas9-KRAB by lentiviral transduction at MOI of 0.1-0.5. For all experiments using GFP+ K562 cells with UCOE-dCas9-KRAB, transduced cells were allowed to recover for 2 d, then selected to purity using 2 μg/mL puromycin for 3 d, and allowed to recover for another 2 d before GFP levels were recorded by flow cytometry on a LSR-II flow cytometer (BD Biosciences). For experiments involving only GFP+K562 cells with dCas9-KRAB, cells were grown out for 7-9 d after transduction and GFP levels were recorded by flow cytometry, using BFP expression to gate for transduced cells. Flow cytometry data were analyzed using FlowCytometryTools v0.4.5 (http://eyurtsev.github.io/FlowCytometryTools/). For plotting, flow cytometry events were normalized to population size and the histograms were smoothened by kernel density estimation. For estimating knockdowns, GFP levels of wild type (GFP-) K562 cells were subtracted.

Figure 1:
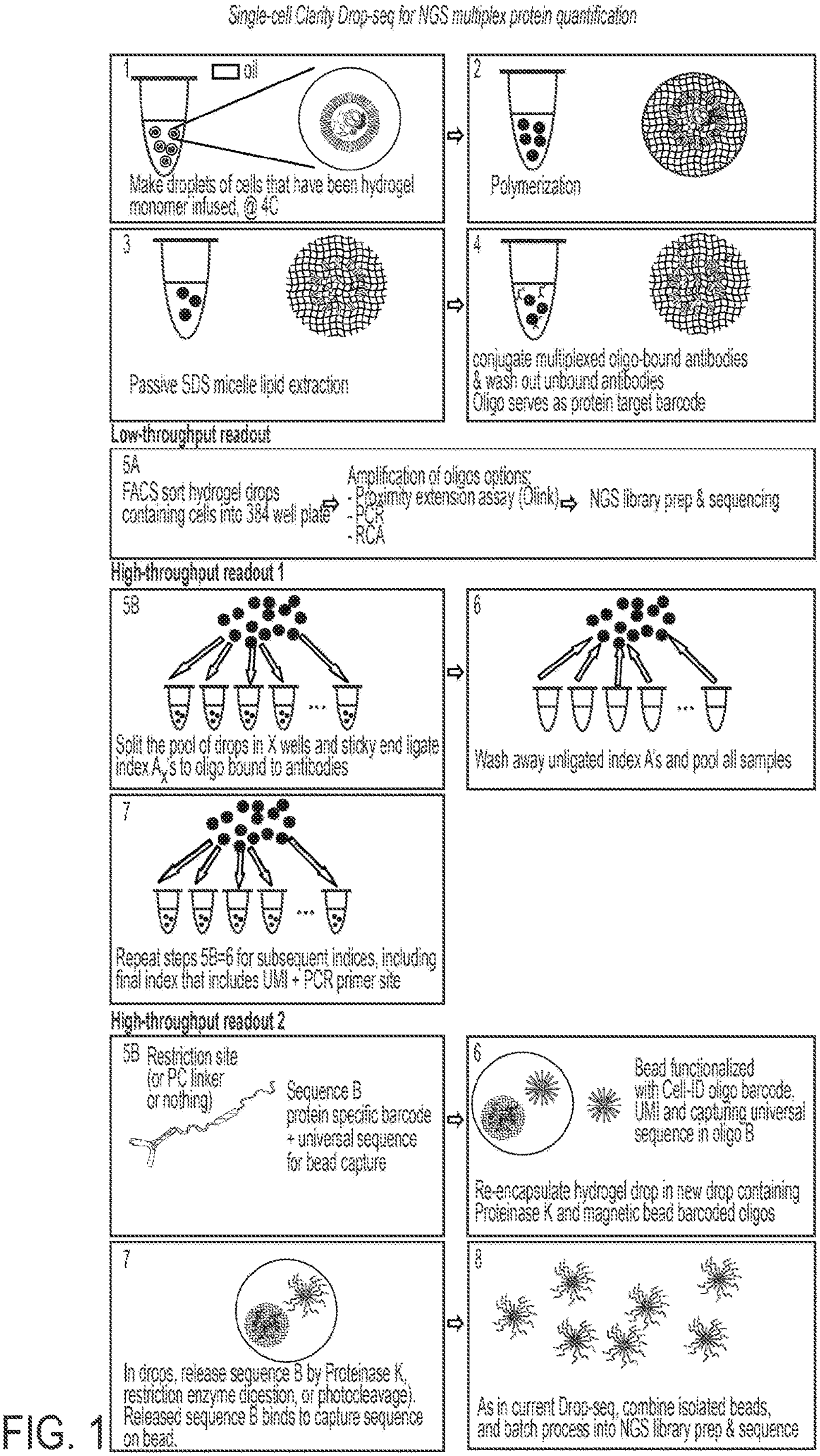
FIG. 1 illustrates a schematic overview of embodiments using hydrogel embedding of single cells, followed by lipid clearing and DNA-tagged antibody labeling. Also shown, are low-throughput and high-throughput readouts.
Figure 2A:
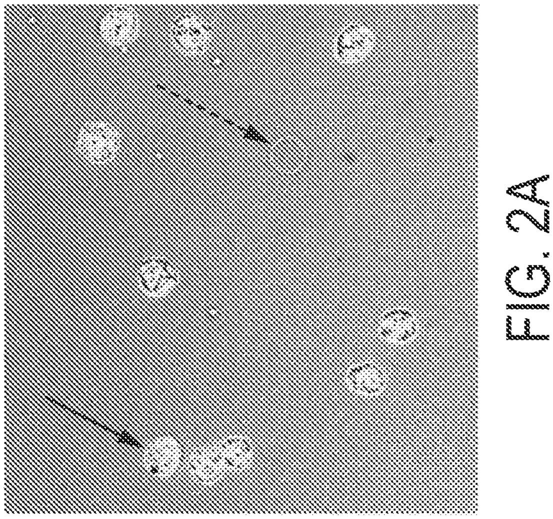
FIG. 2A-C illustrates a proof of principle. A) Overlay of transmission light microscopy image epifluorescent measurement of CD51/Alexa488 (green). Black arrow indicates an example of a hydrogel embedded cell, the white arrow indicates an empty hydrogel droplet, staining negative for CD51. B) same cells, stained for genomic DNA DAPI (blue) and intracellular PCNA/Alexa647 (red). C) Strong Pearson correlation (0.98) measured between fluorescence levels of 'endogenous' GFP levels from 293/GFP cells, and a detecting anti-GFP antibody conjugated to Alexa647. Similar staining with the BD cytofix/perm kit yielded a Pearson correlation of 0.36.
Figure 2B:
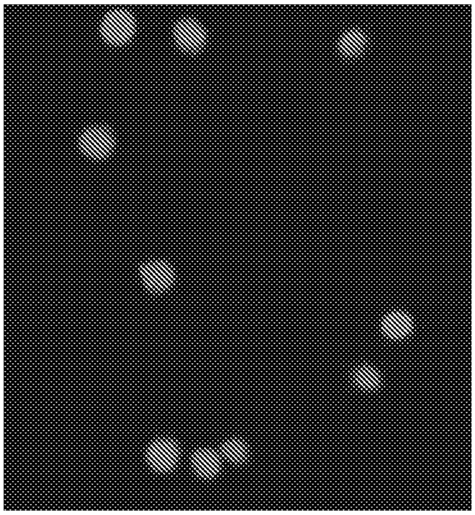
Figure 2C:
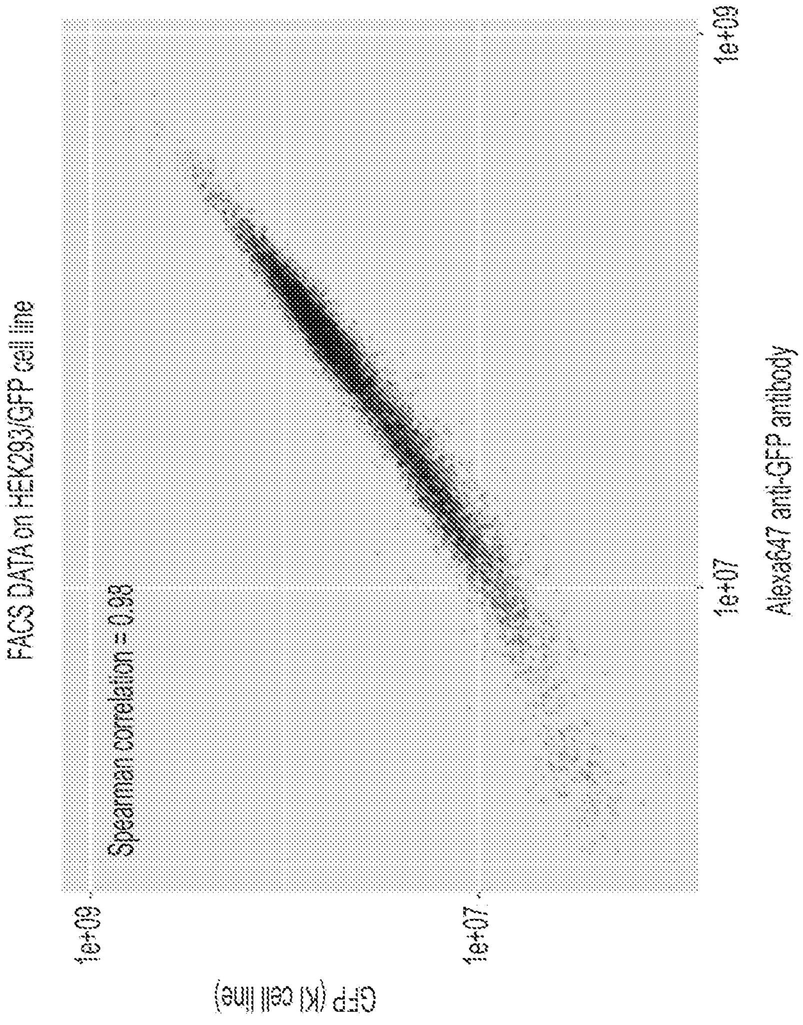

Perturb-seq screening Viruses were individually packaged and harvested in preparation for perturb-seq screening. Individual packaging of the lentivirus and pooling at the step of virus or cells was done to avoid intermolecular recombination of proviral genomes and to ensure maintenance of paired barcode-sgRNA coupling (Sack et al. 2016). For the pilot experiment represented in FIGS. 81C, 1D, 1F, cBA010 cells were individually spinfected with virus (at 33 °C for 2 hours at 1000×g) in media supplemented with 8 μg/mL polybrene; 5 hours post spinfection, virus was removed by centrifugation and cells were resuspended in fresh media. Three days later, a transduction efficiency of 20-30%, as determined by percentage of BFP positive (BFP+) cells, was measured by flow cytometry and cells were pooled with equal numbers of guide RNA-containing (BFP+) cells. Control cells were included in the pool at 3-fold. coverage. Pooled cells were then grown in the presence of puromycin (3 μg/mL) for 5 additional days. Seven days post transduction cells were sorted on a BD FACSAria2 to near purity and eight days post transduction the sorted cells were separated into droplet emulsion using the Chromium™ Single Cell 3' Solution according to manufacturer's instructions (10X Genomics).

For the perturb-seq epistasis experiment, seven three-guide vectors targeting every possible combination of ATF6, IRE1, and PERK as well as two independent three-guide vectors with three negative control guide RNAs and different barcodes were individually packaged into lentiviruses. Freshly produced (i.e. not frozen) lentiviruses were spinfected into cBA007 cells (at 33 °C for 2 h at 1000× g) in media supplemented with 8 μg/mL polybrene. The virus was removed by centrifugation and cells were resuspended in fresh media. Three days after infection, transduction efficiencies of 5-10% were measured by flow cytometry. Cells were combined into a pool with equal numbers of transduced (BFP+) cells for each vector (resulting in 2-fold excess of negative control vectors) and the combined cells were then sorted on a BD FACS Aria2 to near purity. To limit heterogenous effects of cell microenvironments caused by cell settling, the sorted cells were grown with continuous agitation on an orbital shaker. Five days after infection, the pooled and sorted cells were split into three populations, which were treated as follows: 1) DMSO control treatment for 6 hr; 2) treatment with 4 μg/mL tunicamycin for 6 hr; and 3) treatment with 100 nM thapsigargin for 4 hr. At the end of the treatment, the cells were separated into droplet emulsion using the Chromium™ Single Cell 3' Solution according to manufacturer's instructions (10X Genomics). Cells loaded onto the device were 90.4%, 87.9%, and 85.3% viable for the different treatment conditions, respectively.

For the large-scale perturb-seq screen of UPR-inducing guide RNAs, viruses were individually titered by test infections into cBA011 cells and then pooled evenly. To account for varied effects on cell viability across the guide RNA sub-library and minimize cell number difference, pooling titers were determined by the percentage of BFP+ cells remaining 6 days post transduction. Two negative control guides were included, NegCtrl-2 and NegCtrl-3. NegCtrl-2 and select guides (those encoded by pDS002, pDS017, pDS026, pDS032, pDS033, pDS044, pDS052, pDS088, pDS091, pDS160, pDS186) were included at higher representation within the lentivirus pool, 8-fold and 2-fold, respectively. The lentivirus library pool was then used to infect cBA010 cells (performed by spinfection at 33 °C for 3 hours at 1000×g) so that a single pooled cell population with all perturbations would be carried though subsequent steps. Post centrifugation, cells were immediately removed from virus and transferred to a spinner flask for growth in fresh media. Three days later, a transduction efficiency of 15% was measured by flow cytometry and BFP+ cells were sorted to near purity on a BD FACSAria2. To limit heterogenous effects of cell microenvironments caused by cell settling, the sorted cells were grown with continuous agitation on an orbital shaker. Approximately seven days post transduction cells were separated into droplet emulsion using the Chromium™ Single Cell 3' Solution across two separate runs totaling 10 lanes on the device according to manufacturer's instructions (10X Genomics). Cells loaded onto the device were 92% BFP+ and 93-94% viable, as determined by flow cytometry.

For all perturb-seq experiments single-cell RNA-seq libraries were prepared according to the Single Cell 3' Reagent Kits User Guide (10X Genomics). However, this protocol produces libraries that are not compatible with the HiSeq 4000 due to the presence of some sort of toxic byproducts that it is uniquely sensitive to. To remove this issue, Applicants implemented a short cleanup protocol taking place after library preparation. 120-200 ng of library material was split into parallel PCR reactions containing 0.3 μM each of the Illumina P5 and P7 primers, and amplified using Kapa HiFi ReadyMix according to the following protocol: (1) 95 °C 80 sec (2) 98 °C. 20 sec/65 °C. 30 sec/72 °C 20 sec for 6 cycles (3) 72 °C. 1 min. PCR products were then SPRI-purified at 1× rati, repooled during elution, and then fragments of length 350-525 bp were selected using the BluePippin (Sage Science).

Genome-scale CRISPRi screening Reporter screens were conducted using protocols similar to those previously described (Gilbert et al. 2014, Sidrauski et al. 2015). The hCRISPRi-v1 (Gilbert et al. 2014) or the compact (5 sgRNA/gene) hCRISPRi-v2 (Horlbeck et al. 2016) sgRNA libraries were transduced into cBA011 cells at an MOI <1 (percent BFP+ cells was ~45% and 26%, respectively). For the hCRISPRi-v1 screen, cells were grown in spinner flasks for 2 days without selection, followed by 3 days of selection with 1 μg/mL puromycin. Screen replicates were split post infection and carried separately throughout the remainder of the experiment. One replicate arm of the hCRISPRi-v1 screen was carried with media supplemented with 88-150 nM ISRIB throughout, although differences observed between the replicates at the level of both sgRNAs and genes (Table S3) were negligible. For the hCRISPRi-v2 screen, cells were grown in spinner flasks for 2 days without selection, followed by 5 days of selection with 1-3 μg/mL puromycin. Screen replicates were split into separate spinner flasks on day 3. For both screens, cells were separated into those with the highest (~28-33%) and lowest (~30-35%) mCherry/GFP ratio eight days post transduction by fluorescence-activated cell sorting. Cell pellets were frozen after collection. Approximately 23-30 million cells were collected per bin during screening of the hCRISPRi-v1 library (a representation of ~450) and 19-22 million cells per bin for hCRISPRi-v2 (a representation of ~600). Genomic DNA was isolated from frozen cells essentially as described previously (hCRISPRi-v2, 18239126) and the sgRNA-encoded regions were enriched, amplified, and prepared for sequencing (Gilbert et al. 2014).

Sequenced protospacer sequences were aligned and data were processed as described (Gilbert et al. 2014, Horlbeck et al. 2016) with custom Python scripts (available at github.com/mhorlbeck/ScreenProcessing). Reporter phenotypes (referred to as Reporter signal) for library sgRNAs were calculated as the log 2 enrichment of sgRNA sequences identified within the high mCherry/GFP cells over the low mCherry/GFP cells. Phenotypes for each transcription start site were then calculated as the average reporter phenotype of the 3 sgRNAs with the strongest phenotype by absolute value (most active sgRNAs). Mann-Whitney test p-values were calculated by comparing all sgRNAs targeting a given TSS to the full set of negative control sgRNAs. For data presented in FIGS. 84D-F and 90B,C, genes with multiple targeted TSSs were collapsed such that only the TSS with the lowest p-value was used. Screen hits were defined as those genes (or separately those TSSs) with a discriminate score, defined as the absolute value of a calculated reporter phenotype over the standard deviation of all evaluated phenotypes multiplied by the log 10 of the Mann-Whitney p-value for given candidate, greater than 7. Growth screen data in FIG. 90C has been reported elsewhere, and the unreported screen was conducted in parallel essential as described (Horlbeck et al. 2016). Gene ontology analysis was conducting using select databases (GOTERM_BP_FAT, GOTERM_CC_FAT, GOTERM_MF_FAT, KEGG_PATHWAY) and hits (calculated from all TSSs) with a phenotype of greater than 1 using DAVID Bioinformatic Resources 6.8 Beta (david-d.ncifcrf.gov/) with (Huang, Sherman & Lempicki 2009a, Huang, Sherman & Lempicki 2009b). Biological classifications reported in FIG. 84F-G were manually assembled from the literature and using resources from the HUGO Gene Nomenclature Committee (www.genenames.org), AmiGO, the GO Consortium's annotation and ontology toolkit (Carbon et al. 2009) (amigo.geneontology.org), DAVID Bioinformatic Resources (david.ncifcrf.gov) (Huang, Sherman & Lempicki 2009a, Huang, Sherman & Lempicki 2009b).

Individual re-test of sgRNA reporter phenotypes Viruses were individually packaged and harvested as described above. UPRE reporter-containing K562 cells (cBA011) cells were infected with thawed virus. Additionally, parental K562 dCas9-KRAB cells (Gilbert et al. 2014) were transduced with negative controls. Flow cytometer readings of the mCherry UPRE signal and GFP EF1α signal were taken periodically and 8 days post transduction. Median fluorescence signals were analyzed by subtracting an average background signal from control-transduced K562 dCas9-KRAB cells and normalizing the mCherry, GFP, or mCherry/GFP measurement from guide-containing cells (as determined by BFP fluorescence) in each well to untransduced cells. Data from wells with fewer than 500 transduced or untransduced cells or with lower than expected BFP signal (3 standard deviations below the mean of BFP median from all other experimental wells) were systematically discarded from further analysis. For experiments where a flow cytometer reading was taken on the second day post transduction, data was also filtered for a minimum day 2 viability percentage.

RT-qPCR and semi-quantitative PCR for XBP1 mRNA splicing Cells were harvested and total RNA was isolated using TRIzol® Reagent (Thermo Fisher Scientific, 15596-018) and Phase Lock Gel tubes (VWR, 10052-170) or NucleoSpin® RNA (Macherey-Nagel, 740955.50) essentially according to manufacturers' instructions. RNA prepared by TRIzol® extraction was treated with TURBO™ DNase (Thermo Fisher Scientific). RNA was converted to cDNA using SuperScript® II or SuperScript® III Reverse Transcriptase (Thermo Fisher Scientific) under standard conditions with oligo (dT) primers or random hexamers with or without RNaseOUT™ Recombinant Ribonuclease Inhibitor (Thermo Fisher Scientific). Quantitative PCR reactions were prepared with 1X master mix containing 1X Colorless GoTaq® Reaction Buffer (Promega, M792A), MgCl2 (0.7 mM), dNTPs (0.2 mM each), primers (0.75 μM each), and 1000X SYBR Green with GoTaq® DNA polymerase (Promega, M830B) in 22 μL reactions. Reactions were run on a LightCycler® 480 Instrument (Roche). Semi-quantitative XBP1-specific PCR reactions were prepared with 2 μL of cDNA diluted 1:10 using a master mix containing 0.9X Colorless GoTaq® Reaction Buffer (Promega, M792A), dNTPs (0.23 mM each), primers (0.45 μM each) with GoTaq® DNA polymerase (Promega, M830B) in 22.1 μL reactions. These reactions were run on a standard thermocycler program with 30 second at 60.5 °C for annealing and 28 cycles. PCR products were visualized on 8% TBE gels.

Quantification and Statistical Analysis. Applicants will first provide an overview of the methods used, and then describe their specific application to each figure.

Pipeline overview All analysis was performed in Python, using a combination of Numpy, Pandas, scikit-learn, and a custom-made perturb-seq library. The general outline is presented in FIG. 89A, and Applicants will outline the steps below.

Sequencing: Reads from 10X single-cell RNAseq experiments were aligned and collapsed to unique molecular identifier (UMI) counts using 10X's cellranger software (version 1.1). The result is a large digital expression matrix with cell barcodes as rows and gene identities as columns.

Perturbation identity mapping Specifically amplified guide barcode libraries were described as above and either sequenced as spike-ins or independently. The specific amplification strategy Applicants used preserved the 3' end of the transcript (and thus the cell barcode and UMI of a given captured molecule) and introduced an Illumina read 1 primer upstream of the guide barcode sequence. These reads were aligned using bowtie (flags:-v2-q-ml) to a library of expected barcode sequences. Applicants then collapsed all reads with common cell barcode, UMI, and read identity (as some reads were not mapped by bowtie due to low quality scores) to produce a table consisting of possible guide identities for each cell, and the number of molecules attributing a given guide identity to that cell. Applicants defined the coverage of a given proposed identity as the number of reads divided by the number of UMIs, and defined a proposed identity as having good coverage if it: (1) had a coverage level at or above the mean coverage level minus two times the standard deviation in coverage (2) had at least 50 raw reads and (3) had at least 3 UMIs. Any cell that had only a single identity that met these criteria was assigned that perturbation identity. Any cell that had two or more identities meeting these criteria was assigned as a multiple (either a multiple infection, or a multiple encapsulation during emulsion generation). Any cell that had no identities meeting these criteria was assigned as unidentifiable.

Expression normalization To normalize for differences in sequencing capture and coverage across emulsion droplets, Applicants rescaled all cells to have the median number of total UMIs (i.e. each row of the raw digital expression matrix is normalized to the same sum). Expression of each gene was then z-normalized with respect to the mean and standard deviation of that gene in the control (unperturbed) population:

$$x_{normalized} = \frac{x - \mu_{control}}{\sigma_{control}}$$

This normalization means that control cells always have mean normalized expression of 0 for all genes and standard deviation 1, so that the units of expression are "standard deviations above/below the control distribution."

In the epistasis experiment, the control population was the DMSO-treated cells. In the perturb-seq experiment, they were the cells containing the NegCtrl-2 guide. In the perturb-seq experiment, the mixed population was run in ten separate pools that were treated independently during library preparation (corresponding to lanes on the 10X Chromium instrument and on the Illumina sequencer). To avoid any lane-dependent batch effects, cells were normalized to the control cell distribution within the same lane.

Low cell count/inviable cell removal While developing the low rank ICA method described below, Applicants observed that all experiments always contained two subpopulations that were peculiar in that they contained roughly equal membership from all perturbations. Further investigation showed that these were a group of cells with systematically lower total UMI counts (visible as a small second mode in the distribution of total UMIs per cell) and a group of cells that contained markers of activation of apoptotic programs. Applicants attributed the first population to partly failed RNAseq library preparation occurring in a small number of emulsion droplets, and the second to inviable cells (which Applicants knew were present in the cells placed used in the 10X experiment). Neither population composed more than a few percent of the total number of cells. Though low rank ICA always isolated these in an unbiased way, Applicants generally excluded them from analysis. The low UMI count cells were simply removed using a threshold. To remove the apoptotic cells, Applicants trained a random forest regressor (described in more detail below in the section on UPR branch activation scoring below) to recognize them using the cells in our epistasis experiment as training data.

Identification of differentially expressed genes The end result of the previous steps is a normalized gene expression matrix where each cell has been assigned a perturbation identity. In general, Applicants were interested in analyzing differences between populations, and used two distinct strategies for isolating interesting genes.

Kolmogorov-Smirnov test/metric: The Kolmogorov-Smirnov test is a nonparametric test for equality of probability distributions based on a metric defined on their cumulative distribution functions. Specifically, if $F_{parturbed}$ and $F_{control}$ are the CDFs for a given gene in the perturbed and control distribution, the test statistic is $$D = \sup_x |F_{perturbed}(x) - F_{control}(x)|$$

This can be assigned a p-value in a standard way. However, the large scale of single-cell data means that many genes were often significantly perturbed without being interestingly perturbed, simply because of small differences detected by great sampling depth. Thus in some cases Applicants placed a direct threshold on the test statistic D itself, which ensured that changes were both significant (in the statistical sense) and also of reasonable magnitude, as it is valid metric on the space of CDFs.

Random forest classifier An advantage of perturb-seq is that the cell populations are known, which means that supervised learning methods can be brought to bear. Our strategy here was motivated by the idea that a gene is likely important for a given perturbation if its expression level can be used to accurately predict that perturbation's identity. This idea is particularly useful when many perturbations are being compared, as what you want then are the genes that best distinguish all of the perturbations from each other.

To leverage this idea, Applicants used random forest classifiers. Given a set of perturbations, Applicants would train a random forest classifier to predict perturbation identity using a subset of genes. Specifically, Applicants used the implementation of extremely randomized trees implemented in scikit-learn, generally with 1000 trees in the forest. Applicants performed a two-stage fitting process for a given number of desired features $N_{gamma}$. First, Applicants set aside 20% of the cells. The remaining 80% were used to train a random forest classifier (usually with 1000 estimators) to predict the perturbation identity using the normalized expression profile for each cell (with some threshold on gene expression level) as the set of features. The random forest assigns importances to features during training based on their predictive value, and Applicants would then take the top $N_{gansa}$ sorted by importance as the set of most informative genes. To evaluate how informative these genes were, Applicants would then retrain the classifier using only these genes, and predict the perturbation present in the 20% of cells Applicants had initially set aside. For sets of perturbations with large differences, Applicants routinely saw accuracies of 80-90%. The genes chosen by the random forest essentially always showed marked differences by the Kolmogorov-Smirnov approach outlined above, and the forests had the advantages that they scaled to an arbitrary number of perturbations, and that the selected genes were known to vary informatively across perturbations instead of simply having a difference in distribution.

Low rank ICA Single-cell data are intrinsically very noisy, either due to real biological variation or problems in capture efficiency. As described in the main text, these effects can affect the sensitivity of methods like principal components analysis, which is intrinsically variance-maximizing and hence very sensitive to outliers. To isolate larger trends within the data, Applicants developed a simple two-step approach called low rank ICA. The first step consists of isolating a low rank approximation of the dynamics within the experiment. To do this, Applicants used Robust PCA (Candès et al. 2011), which seeks a decomposition of the form $$X=L+S$$

where X is the normalized expression matrix, L is a low rank matrix, and S is a sparse matrix (most entries are zero). Specifically, Robust PCA solves the optimization problem $$\min_{L,S}\|L\|_* + \lambda\|S\|_1 \text{ subject to } X = L + S$$

where $\|\cdot\|$, is the nuclear norm (sum of singular values) and $\|\cdot\|$ is the sum of the absolute values of the entries of the matrix. These constraints naturally induce L to be low rank, and S to be sparse. In implementations, Applicants used the augmented Lagrange multiplier method (Lin, Chen & Ma 2010), which was fast and efficient.

Applicants should note that our interpretation of this optimization problem is slightly different from that seen in some other instances, where S is regarded as capturing noise corrupting the "true" dynamics seen in L. In single-cell data the "noise" may actually be biological in origin, but our primary intent is to isolate the low rank approximation L, which is effectively a smoothed version of the population's dynamics that leaves major trends intact. The advantage of the decomposition of course is that the S matrix is still available afterward, and it may in fact carry useful information about highly stochastic processes within the population.

Our next goal was to isolate the major trends within the low rank dynamics of the population. To do this Applicants applied independent components analysis (ICA). ICA posits a model in which the expression of a given gene ($y_j$) can be decomposed as a linear sum of various effects ($s_1$ to $s_n$) that are statistically independent of each other:

$$y_j=a_F s_1+a_{F2} s_2+ \ldots +a_{Fn} s_n$$

Solving this problem is beyond the scope of this section, but our interest lies primarily in the vector version of this formula, $$y=As$$

in which a cell's expression profile y (over all genes) is viewed as a linear sum of independent effects, and the equivalent matrix version $$Y=AS$$

in which Applicants decompose all of the dynamics of the cells within our population (the columns of Y) into sums of independent components (ICs). The matrix A above is called the mixing matrix, and in our context describes which genes contribute to which effects. As noted above, the key difference in this case from decompositions like principal components analysis is that the s components are derived in a way to make them as statistically independent as possible. Once the matrix A is estimated, Applicants can then "unmix" the dynamics of each cell in the population by applying the inverse operation (denoted here by W) to its expression profile:

$$s=Wy$$

This yields a low-dimensional description of what each cell is doing in terms of the independent factors given by s.

In this case Applicants apply ICA to the low rank matrix L, i.e. $Y=L^T$ above. Thus, Applicants try to separate the population's low rank dynamics into independent factors. As the ICA minimization problem posed in the strongest form cannot practically be solved, different algorithms will give somewhat different answers based on the tradeoffs they make. After trying several methods, Applicants settled on the ProDenICA algorithm (Friedman, Hastie & Tibshirani 2001), which Applicants found to frequently give the highest quality components.

In general Applicants applied low rank ICA in two ways. First, it can be used to partition cells into subpopulations. Strong trends often lead to independent components that are bimodal, so simply thresholding the value of a component is a means of clustering. Applicants note however that an advantage of this method of subpopulation identification is that it can also identify continuous trends, rather than enforcing discrete categories that may not exist like in other methods of clustering. Secondly, the mixing matrix A is very informative, as it determines the extent to which each gene contributes to a given component. This can be useful both in understanding what the component is measuring (if the most heavily weighted genes have a clear common function) and in identifying groups of genes that are co-expressed in an unbiased way.

Interpretation of independent components does have some caveats. First, they have no natural sign (so an "enriched" effect may appear as a low value of an independent component) or scale: thus there is no natural order where the first IC is somehow more informative than the next, consistent with the fact that they are meant to represent independent effects. Applicants do note that one pragmatic solution is to order the components by the norm of the corresponding column in the mixing matrix, which tends to place the most interesting components first.

t-sne visualization To obtain two-dimensional projections of the population's dynamics, Applicants first further reduce the dimensionality of the low rank matrix L using classical PCA (with the number of components determined from a scree plot), and then further reduce these components via t-distributed stochastic neighbor embedding. Applicants occasionally directly visualize the ICs in this way as well, but because they lack intrinsic scale like principal components, dominant effects can be crowded out by minor ones.

Hierarchical clustering of genes Several of the analyses in the paper use single-cell co-expression information to cluster genes. For a given list of genes, Applicants perform this clustering by first calculating the gene-gene correlation matrix p over all cells in the population. This is then converted to a dissimilarity matrix w via the transformation $\pi=\sqrt{2(1-p)}$. The dissimilarity matrix is then clustered using Ward's method. For visualization purposes, Applicants then apply the optimal leaf ordering algorithm in MATLAB. This reorders the leaves in the dendrogram by flipping tree branches to maximize the similarity between adjacent leaves, but without dividing any branches (i.e. the clustering is unchanged, but the dendrogram ordering is in some sense optimal). Applicants then reorder the columns and rows of the correlation matrix via the resulting ordering, so that groups of genes with correlated expression appear as blocks along the diagonal.

Cell cycle position Applicants used an approach previously described, in which the expression of sets of experimentally-derived genes specific for each cell cycle phase is used for each cell to score cell cycle phase (Macosko et al. 2015).

Average expression profiles Applicants often create synthetic bulk profiles for different populations. These are created by averaging the normalized expression profile of each cell within that population together.

Analytical steps for each figure. Applicants now describe the analysis behind each figure in the paper, with references as necessary to the above sections.

Single-cell analysis in FIG. 83. Applicants formed a population consisting of cells treated with 100 nM thapsigargin in each of our 8 genetic backgrounds, along with DMSO-treated control cells. As outlined in the "Low cell count/inviable cell removal" section, Applicants removed cells with substantially lower than average UMI counts or that scored strongly for inviability markers from analysis, as these groups partitioned away from the rest of the population in preliminary analyses. For each perturbation, Applicants then looked for genes that were differentially expressed relative to the control, as described in the "Identification of differentially expressed genes." Applicants made a list of all genes that had a mean expression of at least 0.5 UMI per cell in the population and for which the Kolmogorov-Smirnov test statistic D>0.15 in at least one perturbation. This led to a group of 1,711 differentially expressed genes. Applicants formed a reduced gene expression matrix containing only these genes, and performed low rank ICA to reduce the population's dynamics therein to 16 ICs (FIG. 89B). Applicants examined the raw trends in the population by reducing the low rank matrix to 16 components via PCA (16 components) and then to two dimensions via t-sne, revealing a general breakdown by perturbation and by cell cycle within each perturbation (FIG. 89B). Applicants then looked for ICs whose average value varied either across the perturbation, or across the cell cycle position. For each category, four components showed clear trends at the average level and in the t-sne plots (FIG. 89B). For example, several of the components clearly showed the expected epistasis patterns for PERK, ATF6, and IRE1 (FIG. 89B). The plots made in FIG. 83B of the main text were then made by furthering reducing only the ICs that varied across perturbation (IC1-IC4 in FIG. 89B) or across the cell cycle (IC5-IC8 in FIG. 89B) to two dimensions using t-sne. (I.e., Applicants constructed matrices with cells as rows and the given ICs as columns and reduced those matrices to two dimensions with t-sne.)

To make the plots in FIG. 83C, Applicants then subsampled our population to only look at cells treated with thapsigargin with or without depletion of PERK, and the DMSO-treated control. Applicants applied the same methodology as above, though with 12 ICs instead of 16. The "G1 cell" IC described in the main text was bimodal within each subpopulation (see inset in right panel of FIG. 83C), but with varying distances between the two modes (note that the IC takes a substantially lower value in the +Tg population than in any of the others, FIG. 83C). Applicants split each population at the location of the mode. The cell cycle position histograms were made as described above. To make FIG. 83E, Applicants took the 25 genes that most positively influenced the IC and the 25 genes that most negatively influenced the IC (by sorting the mixing matrix column for that IC by coefficient value) and then clustered them based on coexpression as described in the "Hierarchical clustering of genes" section. The meaning of each cluster was discerned by the pattern of up- and down-regulation observed within.

Branch epistasis analysis in FIG. 83F. Applicants created two populations: (1) consisting of cells treated with 100 nM thapsigargin in each of our 8 genetic backgrounds, along with DMSO-treated control cells, or (2) consisting of cells treated with 4 μg/mL tunicamycin in each of our 8 genetic backgrounds, along with DMSO-treated control cells. To identify informative differentially regulated genes, Applicants used the random forest classifier method described in the "Identification of differentially expressed genes," limiting the random forest to pick 100 genes for each of the two populations. Applicants then combined these two lists in one and discarded any duplicate genes. Applicants created average profiles of expression of these genes for each of the nine conditions present in the two populations, as visualized in FIG. 83F. The average epistatic phenotype of a gene can then be viewed as a 9-vector in either the thapsigargin- or tunicamycin-treated populations. Applicants discarded any genes where the correlation between these two conditions was less than 0.9, as Applicants were only interested in factors that showed the same regulation in response to both conditions. The end result was the 104 genes presented in FIG. 83F. These were then clustered based on their coexpression pattern as described in the "Hierarchical clustering of genes" section, with the exception that Spearman correlation was used instead of Pearson correlation (to emphasize the large shifts in expression across the population). Rough meanings were ascribed to clusters based on the average pattern of gene expression across perturbations, but Applicants emphasize that many targets show some degree of cross-regulation. To assess this in an unbiased way, Applicants constructed a matrix consisting of the average expression of the 104 assayed genes across the 17 unique conditions present in the experiment, and reduced it to four independent components using FastICA. Three of the components clearly corresponded to ATF6, IRE1, and PERK perturbations, as they showed banded patterns in the reduced matrix matching the pattern of epistasis for those regulators seen in FIG. 83F (e.g. the PERK component was high in all PERK conditions, and low everywhere else). The fourth component was low in the DMSO and all tunicamycin-treated conditions, and high in the thapsigargin-treated condition, so Applicants discarded it as representing the difference between the two perturbations. The panel at the bottom of FIG. 83F plots the mixing matrix coefficients for each gene in the indicated component, and thus determines how much that gene affects that component's value.

Genome-wide CRISPRi screen in FIG. 84. Analysis of the screen is described above along-side the experimental details above.

Figure 85A:
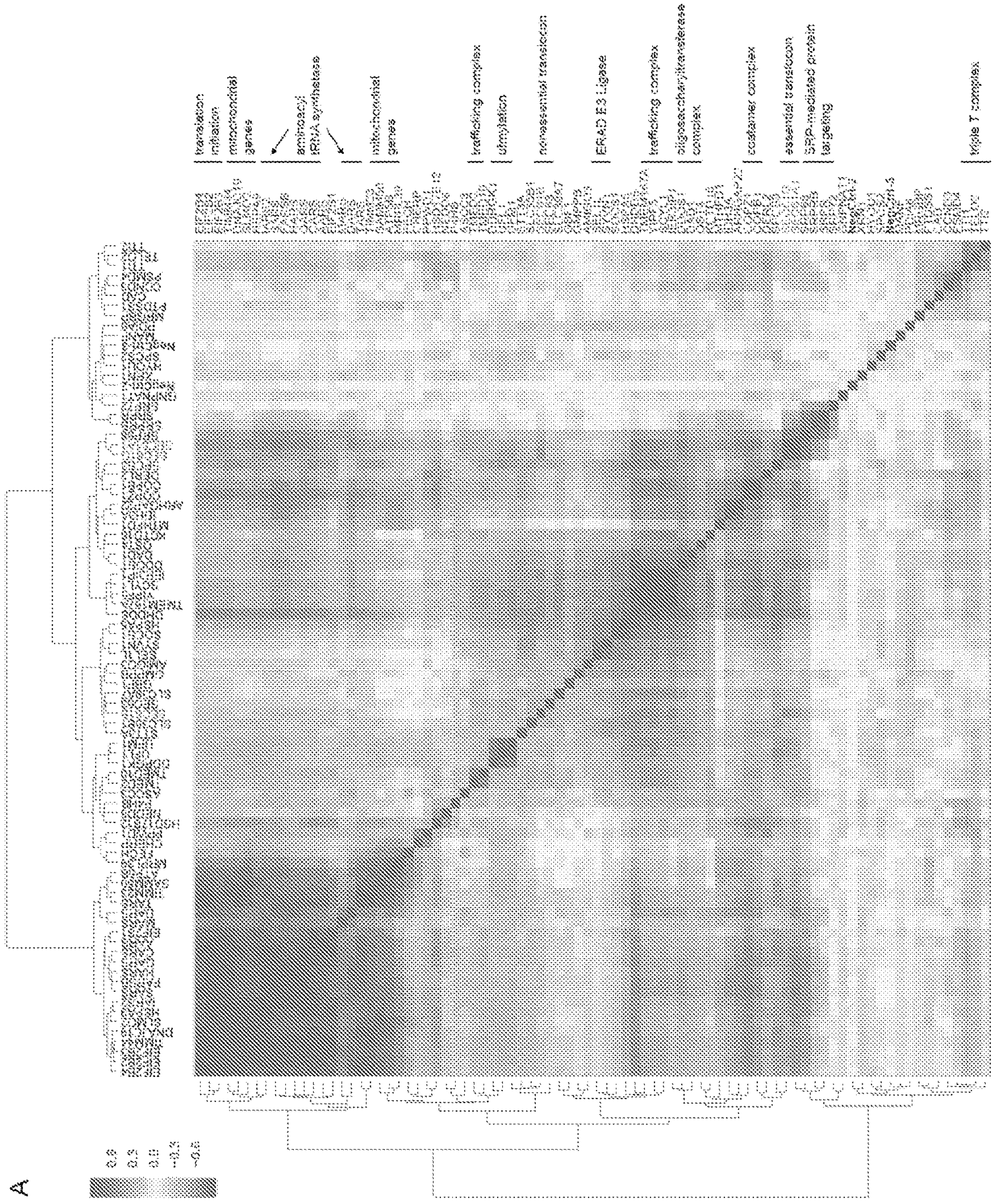

Clustering of guides and perturbations in FIG. 85. Applicants first split our large perturb-seq population into subpopulations based on guide identity and created average expression profiles (see "Average expression profiles" section) for each perturbations of all genes with mean representation >1 UMI per cell. Applicants calculated the perturbation-perturbation correlation matrix between all average expression profiles, and then clustering it using the same methodology described in the "Hierarchical clustering of genes." The ordering is seen in FIG. 91A. Because guides targeting the same gene behaved similarly in this analysis, in subsequent analyses Applicants instead split the population into subpopulations based on guide target (thus merging subpopulations that had different guides that targeted the same gene). Applicants clustered these profiles using the same criteria, and optimally ordered the resulting dendrogram and correlation matrix (as described in "Hierarchical clustering of genes") to produce FIG. 85A.

Assessing guide homogeneity and knockdown in FIG. 85. Most guide targets were too low abundance to interrogate directly at single-cell resolution. Applicants first directly visualized the shift in guide target expression induced by the guide, comparing the distribution of expression in control cells to cells perturbed for a given target (FIG. 91B). Applicants calculated mean knockdown per guide (FIG. 85C), and assigned 95% confidence intervals to our estimates via bootstrapping.

Applicants also attempted to assess to what extent knockdown varied throughout the population based on phenotype. To do this, Applicants needed an unbiased means of assessing deviation in behavior from the control cells. Applicants leveraged a method called OneClassSVM (Schölkopf et al. 2001) which is a means of novelty detection. Given a set of training exemplars, a OneClassSVM learns an estimate of how those points are distributed (potentially in a high-dimensional space). When given new observations, the OneClassSVM then estimates how likely it is that those observations came from the same distribution as the training set, or if they are outliers (potentially novel). In our case Applicants trained the OneClassSVM using control cells, and thus scored the extent to which perturbed cells scored as outliers, or if they fell within the expected range of behavior for unperturbed cells. Specifically, for each guide target, Applicants performed the following algorithm:

1. Form a population of all cells perturbed for that target, and an equal number of randomly sampled control cells.
2. Find all genes that are expressed at an average level of 0.5 UMI per cell or higher and that are differentially expressed between control and perturbed cells by the Kolmogorov-Smirnov test (as described in "Identification of differentially expressed genes") at P<0.01.
3. Form a reduced gene expression matrix consisting only of the differentially expressed genes. Create a low-dimensional picture of the dynamics within this population by reducing this matrix to 8 dimensions via PCA.
4. To form an estimate of "normal" behavior, train a OneClassSVM model to estimate the support of the control cells in this 8-dimensional space. The model was trained assuming a contamination rate with outliers of 5%.
5. Score each cell in the perturbed population using the OneClassSVM model to estimate the extent it deviates from control behavior.

These scores generally assigned most or all of the perturbed cells outlier status, except in guides where very few genes were perturbed to begin with (bottom panel of FIG. 85D). Ordering the cells by score, Applicants split each perturbed cell population into top third and bottom thirds (i.e. the most and least perturbed cells) and assessed the difference in average knockdown in each of these populations (FIG. 91C), with a difference of ~8% on average.

Applicants also reported the number of differentially expressed genes measured above in the bottom panel of FIG. 85D.

Scoring branch activation in FIG. 85D. As outlined in the main text, Applicants adopted a data-driven strategy to score activation of each of the UPR branches using the epistasis experiment as training data. To do this, Applicants assigned the label "ATF6 active", "IRE1 active", or "PERK active" to each cell in the epistasis experiment based on whether a given branch was present (i.e. not depleted) and induced (tunicamycin or thapsigargin had been added). For example, cells treated with thapsigargin and depleted for IRE1 would have ATF6 and PERK active, but not IRE1. Applicants converted these labels to scores of 0, for inactive, and 1, for active, and then trained three random forest regressors to predict activation of each branch. The training strategy was the same as outlined in the "Identification of differentially expressed genes" section: each cell was regarded as a training data point, with every gene of mean >1 UMI initially regarded as a possible feature for predicting branch activation. Each regressor was constrained to use the top 25 genes for predicting branch activation, as Applicants found no performance improvement when more genes were included. The genes isolated as most important by the three regressors for scoring activation of the three branches all appear in the epistasis analysis in FIG. 83F.

To assess performance, Applicants compared this approach to scoring based on two other strategies:

1. Gene list approach: A list of hand-picked branch-specific genes were chosen from FIG. 83F, and a score was defined as the sum of the normalized expression of those genes.
2. ICA approach: To allow for more complicated logic than simple sums, Applicants used the ICA decomposition seen in FIG. 83F and computed the value of each IC for every cell in the population.

Figure 91F:
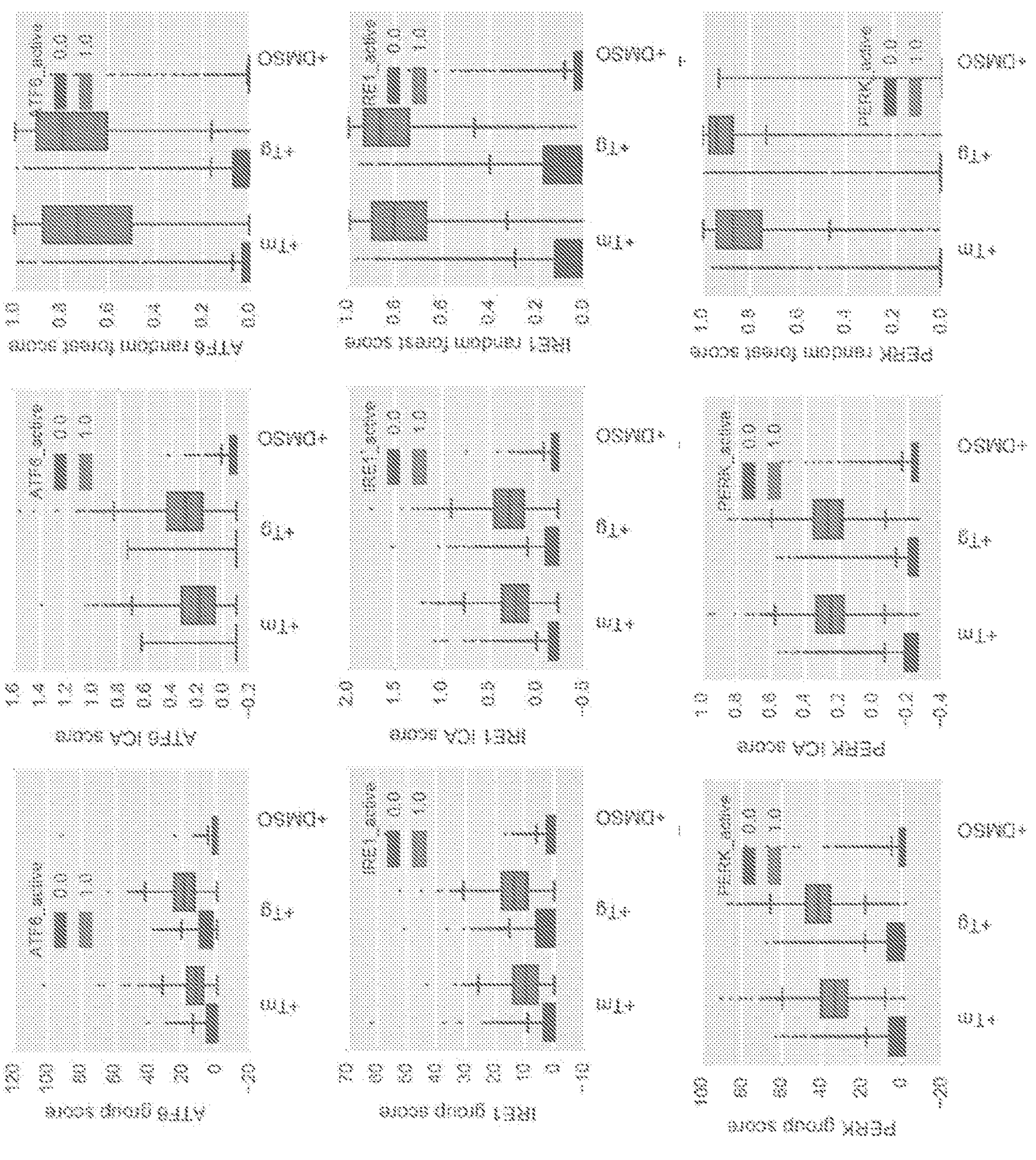

With each scoring system, Applicants subtracted the median of the DMSO-treated control cells' and thresholded all cells with negative scores to zero. Applicants then assessed the overlap of score distributions between cells expected to have a given branch active or inactive. Both the gene list approach and the ICA approach performed worse than the random forests in this analysis (FIG. 91F).

The branch scores seen in FIG. 85D are the result of applying the random forest regressor scoring system to each cell in the perturb-seq experiment, and then averaging the results within cells knocked down for the same gene. The average scores assigned by the ICA method agree well (cf. FIG. 85D and FIG. 91E).

Single-cell analysis in FIG. 86. Applicants formed a population of cells containing either our two guides targeting HSPA5, or the NegCtrl2 guide. Applicants found all genes that had mean abundance >0.5 UMI per cell and that were differentially expressed between the two populations by Kolmogorov-Smirnov test (P<0.01), resulting in ~2,100 genes. Applicants formed a reduced gene expression matrix consisting only of these genes and applied low rank ICA to reduce the population's dynamics therein to 12 ICs. The t-sne plots were made by reducing the low rank matrix to 16 components using PCA and then applying t-sne (see "t-sne visualization" section). Branch activation scores in FIG. 86C were assigned as described above in the "Scoring branch activation in FIG. 85D" section.

Two ICs varied substantially in average value between the control and perturbed cells (FIG. 86B). The first, IC1, had a two-phase distribution in which all control cells and the majority of HSPA5-perturbed cells fell in the large lower peak, and a subpopulation of HSPA5-perturbed cells fell into a long tail of higher values (FIG. 86B). Applicants defined the HSPA5 IC1 HIGH cells to be the ones that fell within this tail (FIG. 86B). FIG. 86D shows the normalized expression of genes found in our epistasis analysis (FIG. 83F) as columns, and the HSPA5-perturbed cells as rows, ordered by increasing IC1. FIG. 86E was created simply by averaging the expression of HSPA5 within the subpopulations defined in FIG. 86B. FIG. 86F was created using the cell cycle positions called in the "Cell cycle position" section.

Gene clustering analysis in FIG. 86H. Applicants first needed an unbiased approach to find programs of gene expression induced in the perturb-seq experiment. To do this Applicants separated the population into control cells (containing our two control guides) and perturbed cells (containing any guide). Applicants constructed average expression profiles (see "Average expression profiles" section) of each, and then restricted our analysis to genes of mean expression >0.5 UMI per cell on average in the perturbed population, and whose normalized expression was >0.5. (Control cells by definition have mean normalized expression 0 for all genes, see "Expression normalization" section.) Applicants then used a random forest classifier approach to select 200 of these induced genes that varied informatively across all of the perturbations in the perturb-seq experiment (see "Identification of differentially expressed genes" section). The genes were then clustered based on their co-expression throughout the population, with the dendrogram leaves optimally reordered (see "Hierarchical clustering of genes" section). Our assumption was that many of these "induced genes" were involved in the unfolded protein response. Applicants evaluated UPR dependence by examining the expression pattern of the induced genes within thapsigargin- and tunicamycin-treated cells (FIG. 92B). Applicants also assigned identities to some other clusters based on clear functional connections (as seen in FIG. 86H).

Comparison of clustering of UPR genes in FIG. 86I and FIG. 92A. As many UPR genes fell out of the previous analysis, Applicants wanted to evaluate the ability to go the opposite direction, and cluster known interactions. Applicants thus reexamined the list of UPR-regulated genes found in FIG. 83F. Applicants separated the perturb-seq population into control cells (containing our two control guides) and perturbed cells (containing any guide). Applicants constructed average expression profiles (see "Average expression profiles" section) of each, and then restricted our analysis to the UPR-regulated genes that showed the same pattern of induction or repression in the perturbed cell population as they did in the cells treated with thapsigargin in the epistasis experiment that had all branches of the UPR intact. Applicants then performed hierarchical clustering of these genes (see "Hierarchical clustering of genes" section) using co-expression information from either (1) all cells in the epistasis experiment, (2) all cells in the perturb-seq, and (3) only control cells in the perturb-seq experiment. Applicants assessed the similarity among clusterings using the cophenetic correlation coefficient, i.e. the correlation coefficient between dendrogram distances taken over all possible pairs of genes. Closeness in cophenetic correlation thus implies that the dendrograms tend to place the same genes close to each other. The figure is meant only as a visual aid, as the cophenetic correlation relies on information beyond the linear order. The genes were roughly grouped based on their epistasis pattern in the epistasis experiment (as in FIG. 83F), and then color was preserved as they were shuffled by the other two clusterings.

Enrichment of cholesterol genes in FIG. 86K. Our unbiased analysis in FIG. 86H contained a cluster of genes involved in cholesterol biosynthesis: ACAT2, FDPS, FADS1, INSIG1, TMEM97. Applicants made a "cholesterol score" by summing the normalized expression of this group of genes in each cell, and then created a subpopulation containing (1) cells with cholesterol scores at or above the 95% of the control cell population and (2) control cells. This gave ~9,000 cells. Within this subpopulation, Applicants then correlated the cholesterol score with the normalized expression of all genes with mean >0.25 UMI per cell. Applicants then selected all genes that had a correlation of 0.15 or higher with the cholesterol score for further analysis. Applicants clustered the genes by co-expression within the population (see "Hierarchical clustering of genes" section), and then selected a group of 23 genes that clustered together with the original five and that appeared as a distinct block on the diagonal of the gene-gene correlation matrix. To demonstrate the improvement in correlation obtained by this "fishing" approach, Applicants compared correlation matrices composed of these 23 genes and 23 random genes of similar average abundance between our enriched population, and control cells (seen in FIG. 86K). Finally, Applicants used Enrichr (Kuleshov et al. 2016) to obtain Reactome annotations and Encode SREBP binding state. Note that some of the genes that don't have annotations nevertheless are almost certainly cholesterol-related, such as the lncRNA RP11-660L16 which is directly next to DHC7R.

Enrichment of heat shock genes in FIG. 86L. Applicants followed an identical approach to the above, except starting with the genes HSPA1A and HSPA1B. In this case Applicants present all of the genes that had correlations of 0.15 or greater. Applicants again used Enrichr to find the top 3 most enriched transcription factor binding sites among the set of genes, as presented in FIG. 6L.

Single-cell analysis in FIG. 87. Applicants formed populations of cells containing guides targeting either SEC61A1 or SEC61B, along with cells containing the NegCtrl2 guide. Applicants found all genes that had mean abundance >0.5 UMI per cell and that were differentially expressed between the two populations by Kolmogorov-Smirnov test setting a threshold of D>0.15 for SEC61A1, and D>0.1 for SEC61B, which is a weaker perturbation (see "Identification of differentially expressed genes" section). The different thresholds were chosen largely for esthetic reasons: lowering the threshold with SEC61A1, which is a strong perturbation, resulted in the inclusion of a number of cell cycle genes that caused the control population to fragment into subpopulations by cell cycle phase, which Applicants felt was distracting. In each case Applicants formed a reduced gene expression matrix consisting only of differentially expressed genes, then applied robust PCA (see "Low rank ICA" section) to these matrices, and then visualized the dynamics using t-sne plots generated using the first 16 principal components (see "t-sne visualization" section). Branch activation scores in FIG. 87A,B, S6A were assigned as described above in the "Scoring branch activation in FIG. 85D" section.

Example 32: In Vivo Perturb-Seq

The perturbation methods and tools described herein allow reconstructing of a cellular network or circuit. In one embodiment, the method comprises (1) introducing single-order or combinatorial perturbations to a population of cells, (2) measuring genomic, genetic, proteomic, epigenetic and/or phenotypic differences in single cells and (3) assigning a perturbation(s) to the single cells. In certain embodiments, a perturbation may be linked to a phenotypic change, preferably changes in gene or protein expression. In preferred embodiments, measured differences that are relevant to the perturbations are determined by applying a model accounting for co-variates to the measured differences. The model may include the capture rate of measured signals, whether the perturbation actually perturbed the cell (phenotypic impact), the presence of subpopulations of either different cells or cell states, and/or analysis of matched cells without any perturbation. In certain embodiments, the measuring of phenotypic differences and assigning a perturbation to a single cell is determined by performing single cell RNA sequencing (RNA-seq). In preferred embodiments, the single cell RNA-seq is performed by any method as described herein (e.g., Drop-seq, InDrop, 10X genomics, Seq-well). In certain embodiments, a guide RNA is detected by RNA-seq using a transcript expressed from a vector encoding the guide RNA. In certain embodiments, unique barcodes are used to perform Perturb-seq (see, e.g., Datlinger, et al., 2017, CROP-seq, described further herein). The transcript may include a unique barcode specific to the guide RNA. In certain embodiments, a guide RNA and guide RNA barcode is expressed from the same vector and the barcode may be detected by single cell RNA-seq. In certain embodiments, detection of a guide RNA barcode is more reliable than detecting a guide RNA sequence, reduces the chance of false guide RNA assignment and reduces the sequencing cost associated with executing these screens. Thus, a perturbation may be assigned to a single cell by detection of a guide RNA barcode in the cell. In certain embodiments, a cell barcode is added to the RNA in single cells, such that the RNA may be assigned to a single cell. Generating cell barcodes is described herein for single cell sequencing methods. In certain embodiments, a Unique Molecular Identifier (UMI) is added to each individual transcript and protein capture oligonucleotide. Not being bound by a theory, the UMI allows for determining the capture rate of measured signals, preferably the binding events or the number of transcripts captured. Not being bound by a theory, the data is more significant if the signal observed is derived from more than one protein binding event or transcript. In preferred embodiments, perturbations are detected in single cells by detecting a guide RNA barcode expressed as a polyadenylated transcript, a cell barcode, and a UMI. In certain example embodiments, the guide RNA may further encode an optical barcode as described in WO/2016/149422 entitled "Encoding of DNA Vector Identity via Iterative Hybridization Detection of a Barcode Transcript" filed Mar. 16, 2016. Optical barcode allows for identification of delivery of guide RNAs and association of such delivery with a particular cell phenotype. Assessment of optical barcodes and cell phenotype may be carried our prior insertion into an experimental model or described below, in the experimental model, or after removal from the experimental model.

The ability to generate high throughput in vivo single cell data provides transcriptional insight to the heterogeneity of cell states. However, the ability to perturb each candidate gene (e.g., regulatory candidate) in in vivo mouse models is laborious and time-consuming, and has become a limiting factor in the mapping and annotation of regulatory drivers. To enable the efficient testing of tens of candidate regulators Applicants have adapted the Perturb-seq system to screen for regulators in vivo (e.g., tumor mouse models). In vivo Perturb-seq may be performed with a set of perturbations. The set of perturbations may be selected based on targets in a specific pathway or determined by RNA-seq or determined by performing Perturb-seq in vitro. The perturbations may preferably include up to 10, 20, 30, 40, 50, 60, 70, 80, 100 perturbations. In certain embodiments, more than 100 perturbations are screened by in vivo Perturb-seq.

In certain embodiments, Perturb-seq of target genes are performed in vivo. Methods and tools for genome-scale screening of perturbations in single cells using CRISPR-Cas9 have been described, herein referred to as perturb-seq (see e.g., Dixit et al., "Perturb-Seq: Dissecting Molecular Circuits with Scalable Single-Cell RNA Profiling of Pooled Genetic Screens" 2016, Cell 167, 1853-1866; Adamson et al., "A Multiplexed Single-Cell CRISPR Screening Platform Enables Systematic Dissection of the Unfolded Protein Response" 2016, Cell 167, 1867-1882; Feldman et al., Lentiviral co-packaging mitigates the effects of intermolecular recombination and multiple integrations in pooled genetic screens, bioRxiv 262121, doi: doi.org/10.1101/262121; Datlinger, et al., 2017, Pooled CRISPR screening with single-cell transcriptome readout. Nature Methods. Vol. 14 No. 3 DOI:10.1038/nmeth.4177; Hill et al., On the design of CRISPR-based single cell molecular screens, Nat Methods. 2018 April; 15(4): 271-274; and International publication serial number WO/2017/075294). The constructs described for introducing sgRNAs specific for perturbing a target gene and for identifying the perturbation may be used for in vivo analysis.

In certain embodiments, target genes may be perturbed in cells ex vivo and introduced to an animal model in vivo. As used herein "experimental models" refer to models that resemble human conditions in phenotype or response to treatment but are induced artificially in the laboratory. Some examples include, but are not limited to implanting animals with tumors to model cancers and immunization of animals with an auto-antigen to induce an immune response to model autoimmune diseases (e.g., Experimental autoimmune encephalomyelitis (EAE), see, WO 2015/130968). Cells perturbed ex vivo may include, but are not limited to tumor cells (e.g., melanoma, such as B16F10 and colon cancer, such as CT26), immune cells (e.g., tumor infiltrating lymphocytes (TIL)), or tumor microenvironment cells (e.g., cancer associated fibroblasts, microglia). Not being bound by a theory, perturbation of targets in vivo allows for measuring the effects of the perturbations on phenotype in single cells in an in vivo context and may advantageously provide network connections and/or regulatory drivers previously undetected.

In certain embodiments, perturbed cells are extracted from an in vivo organism. For example, methods for isolating TILs are known in the art. Perturbed cells may be further isolated by sorting cells expressing a selectable marker, such as a fluorescent marker as described herein.

In certain embodiments, after determining Perturb-seq effects in cancer cells and/or primary T cells, the cells are infused back to the tumor xenograft models to observe the phenotypic effects of genome editing. Not being bound by a theory, detailed characterization can be performed based on (1) the phenotypes related to tumor progression, tumor growth, immune response, etc. (2) the TILs that have been genetically perturbed by CRISPR-Cas9 can be isolated from tumor samples, subject to cytokine profiling, qPCR/RNA-seq, and single-cell analysis to understand the biological effects of perturbing the key driver genes within the tumor-immune cell contexts. Not being bound by a theory, this provides validation of TILs biology as well as novel therapeutic targets.

A CRISPR system may be delivered to primary mouse T cells. Over 80% transduction efficiency may be achieved with Lenti-CRISPR constructs in CD4 and CD8 T cells. Despite success with lentiviral delivery, recent work by Hendel et al, (Nature Biotechnology 33, 985-989 (2015) doi:10.1038/nbt.3290) showed the efficiency of editing human T cells with chemically modified RNA, and direct RNA delivery to T cells via electroporation. In certain embodiments, perturbation in mouse primary T cells may use these methods.

In one exemplary embodiment, Applicants perturb a list of ~50 candidate regulators by applying a pooled screen to CD8 T cells, followed by their transfer to a B16OVA tumor mouse model (see, e.g., Overwijk and Restifo, B16 as a Mouse Model for Human Melanoma, Curr Protoc Immunol. 2001 May; CHAPTER: Unit-20.1). The OT-1 TCR is expressed on CD8+ T cells and is specific for the peptide OVA257-264. After perturbation, OT1+ TILs are extracted and sequenced, enabling the identification of the gene modified by perturbation along with the transcriptional and/or proteomic profile of each cell. In certain embodiments, a regularized regression model is used to identify genes that are regulators of distinct TIL transcriptional states, or of transcriptional modules within some states but not others. Applicants have optimized conditions in the OT1/OVA tumor model, validating that sufficient numbers of cells can be extracted following transfer to conduct in vivo Perturb-seq.

In other embodiments, the Perturb-seq constructs described herein are introduced to cells in vivo (e.g., animal model). The cells may be extracted from an animal model and subjected to single cell RNA-seq and/or single cell proteomics. The perturbation may be identified and assigned to the proteomic and gene expression readouts of single cells. The constructs may include tissue specific expression of the CRISPR enzyme, whereby perturbation of target genes occurs in specific cell types. The constructs may be introduced by a vector, such as viral vector, configured for targeting a specific cell type. The expression of the CRISPR enzyme may be under the control of a tissue specific regulatory element (i.e., promoter). Specific cell types include, but are not limited to immune cells (e.g., CD8+ T cells, CD4+ T cells, Tregs, monocytes).

In certain embodiments, perturbed cells may comprise a cell in a model non-human organism, a model non-human mammal that expresses a Cas protein, a mouse that expresses a Cas protein, a mouse that expresses Cpf1, a mouse that expresses Cas13a, a mouse that expresses Cas13b, a cell in vivo or a cell ex vivo or a cell in vitro (see e.g., WO 2014/093622 (PCT/US13/074667); US Patent Publication Nos. 20120017290 and 20110265198 assigned to Sangamo BioSciences, Inc.; US Patent Publication No. 20130236946 assigned to Cellectis; Platt et al., "CRISPR-Cas9 Knockin Mice for Genome Editing and Cancer Modeling" Cell (2014), 159 (2): 440-455; "Oncogenic models based on delivery and use of the CRISPR-Cas systems, vectors and compositions," WO2014204723A1; "Delivery and use of the CRISPR-Cas systems, vectors and compositions for hepatic targeting and therapy," WO2014204726A1; and "Delivery, use and therapeutic applications of the CRISPR-Cas systems and compositions for modeling mutations in leukocytes," WO2016049251). The cell(s) may also comprise a human cell. Mouse cell lines may include, but are not limited to neuro-2a cells and EL4 cell lines (ATCC TIB-39). Primary mouse T cells may be isolated from C57/BL6 mice. Primary mouse T cells may be isolated from Cas9-expressing mice.

The mouse of Platt et al., 2014 may also be used in the present invention for in vivo Perturb-seq. Platt et al. established a Cre-dependent Cas9 knockin mouse and demonstrated in vivo as well as ex vivo genome editing using adeno-associated virus (AAV)-, lentivirus-, or particle-mediated delivery of guide RNA in neurons, immune cells, and endothelial cells. Using these mice, Platt et al. simultaneously modeled the dynamics of KRAS, p53, and LKB1, the top three significantly mutated genes in lung adenocarcinoma. Delivery of a single AAV vector in the lung generated loss-of-function mutations in p53 and Lkb1, as well as homology-directed repair-mediated Kras (G12D) mutations, leading to macroscopic tumors of adenocarcinoma pathology. In certain embodiments, Cre-dependent Cas9 knockin mice or any Cre-dependent CRISPR enzyme mouse (e.g., Cpf1) may be crossed with tissue-specific Cre transgenic or knockin mice to limit expression of the CRISPR enzyme to a specific cell type and limit in vivo Perturb-seq to specific cell types (see, e.g., Sharma and Zhu, Immunologic Applications of Conditional Gene Modification Technology in the Mouse, Curr Protoc Immunol. 2014; 105:10. 34.1-10.34.13). Most of the existing Cre mouse lines can be found at the CREATE (Coordination of resources for conditional expression of mutated mouse alleles) consortium (creline.org/), which includes the Cre mouse database at Mouse Genome Informatics (MGI, loxP.creportal.org/).

In certain embodiments, expression of Cre is limited to immune cells whereby the CRISPR enzyme is expressed exclusively in immune cells. In certain embodiments, the mouse is treated, such that the mouse has a disease phenotype (e.g., cancer, autoimmune disease). In one embodiment, the mouse expresses a CRISPR enzyme exclusively in immune cells in a mouse having a disease phenotype. In a specific embodiment, a Perturb-seq sgRNA library may be introduced to a tumor such that the perturbations occur in immune cells infiltrating the tumor. Tumor infiltrating lymphocytes may be extracted from the tumor and analyzed by a single cell RNA-seq and/or proteomics method as described herein. In alternative embodiments, immune cells are analyzed after perturbation in an autoimmune model.

Some commonly used Cre mice for studying the immune system and that are applicable for use in the present invention are summarized in the Table below (Tg refers to transgenic and KI refers to knock in).

| Name | Tg/KI | Expression in cell types | Note | Reference |
|---|---|---|---|---|
| ROSA26-CreER$^{T2}$ | KI | Most cells except those in the brain | High deletion efficiency with tamoxifen treatment both in vitro and in vivo | Seibler et al. (2003) |
| Vav-Cre | Tg | All hematopoietic lineages, testis and ovaries | High deletion efficiency; may cause germ line deletion in some offspring | de Boer et al. (2003) |
| CD2-Cre | Tg | Common lymphoid progenitors (CLPs) | High deletion efficiency; some modified CD2-Cre lines may only delete genes in T cells but not B cells | Zhumabekok et al. (1995); de Boer et al. (2003) |
| Lck-Cre | Tg | Early DN stage in the thymus | Deletion efficiency varies | Lee et al. (2001) |
| CD4-Cre | Tg | Late DN to DP stage, deleting floxed genes in both CD4 and CD8 T cells | High deletion efficiency | Lee et al. (2001) |
| CD4-CreER$^{T2}$ | Tg | Deleting floxed genes only CD4 but not CD8 T cells in the periphery | Inducible by tamoxifen; deletion efficiency up to 80% in vivo | Aghajani et al. (2012) |
| dLck-Cre (line 3779) | Tg | Late DP to SP stage | ~70% deletion efficiency in CD4 T cells; higher efficiency (80% to 90%) in CD8 T cells; very low in Tregs | Wang et al. (2001) |
| OX40-Cre | KI | Tregs and activated CD4$^+$ T cells | Endogenous OX40 gene is disrupted by Cre; very low efficiency in activated CD8 T cells | Yagi et al. (2010) |
| CD8a-Cre | Tg | Mature CD8$^+$ but not CD4$^+$ T cells | Also known as E8I-Cre; Cre expression driven by the core E8I enhancer and Cd8a promoter | Maekawa et al. (2008) |
| Granzyme-B-Cre | Tg | Activated CD4$^+$ and CD8$^+$ T cells | Cre driven by truncated granzyme B promoter | Jacob and Baltimore (1999) |
| Mb1-Cre | KI | Starting from Pre-Pro-B stage | Endogenous Mb1 gene encoding Igα signaling subunit of the BCR is disrupted by Cre; deletion efficiency is better than CD19-Cre | Hobeika et al. (2006) |
| CD19-Cre | KI | Starting Pro-B stage | Endogenous Cd19 gene is disrupted by Cre; deletion efficiency is 75% to 95% | Rickert et al. (1997) |
| CD19-CreER$^{T2}$ | BAC Tg | Similar to CD19-Cre, but its activity requires tamoxifen treatment | Inducible by tamoxifen; deletion efficiency 25% to 60% | Boross et al. (2009) |
| Foxp3-YFPCre | KI | Only in Foxp3$^+$ Tregs | YEP is dim; endogenous Foxp3 expression intact | Rubtsov et al. (2008) |
| Foxp3-GFPCreER$^{T2}$ | KI | Only in Foxp3$^+$ Tregs | Inducible but with low deletion efficiency (10% to 20%); endogenous Foxp3 expression intact | Rubtsov et al. (2010) |
| Id2-CreER$^{T2}$ | KI | Id2-expressing cells: epithelial cells in the lung distal tips as well as progenitor of ILCs and T cells | Inducible but with low deletion efficiency; endogenous Id2gene is disrupted by CreER$^{T2}$ | Rawlins et al. (2009) |

In one embodiment, CRISPR/Cas9 may be used to perturb protein-coding genes or non-protein-coding DNA. CRISPR/Cas9 may be used to knockout protein-coding genes by frameshifts, point mutations, inserts, or deletions. An extensive toolbox may be used for efficient and specific CRISPR/Cas9 mediated knockout as described herein, including a double-nicking CRISPR to efficiently modify both alleles of a target gene or multiple target loci and a smaller Cas9 protein for delivery on smaller vectors (Ran, F. A., et al., In vivo genome editing using *Staphylococcus aureus* Cas9. Nature. 520, 186-191 (2015)). In one embodiment, perturbation is by deletion of regulatory elements. Non-coding elements may be targeted by using pairs of guide RNAs to delete regions of a defined size, and by tiling deletions covering sets of regions in pools.

In certain embodiments, whole genome screens can be used for understanding the phenotypic readout of perturbing potential target genes. In preferred embodiments, perturbations target expressed genes as defined by a gene signature using a focused sgRNA library. Libraries may be focused on expressed genes in specific networks or pathways. In other preferred embodiments, regulatory drivers are perturbed. In certain embodiments, Applicants perform systematic perturbation of key genes that regulate T cell function in a high-throughput fashion. In certain embodiments, Applicants perform systematic perturbation of key genes that regulate cancer cell function in a high-throughput fashion (e.g., immune resistance or metastasis). Applicants can use gene and/or protein expression profiling data to define the target of interest and perform follow-up single-cell and population RNA-seq and/or protein analysis. Not being bound by a theory, this approach will accelerate the development of therapeutics for human disorders, in particular cancer. Not being bound by a theory, this approach will enhance the understanding of the biology of T cells and tumor immunity, and accelerate the development of therapeutics for human disorders, in particular cancer, as described herein.

In certain embodiments, signature genes may be perturbed in single cells in vivo and gene and/or protein expression analyzed: Not being bound by a theory, networks of genes that are disrupted due to perturbation of a signature gene may be determined in an in vivo context. Understanding the network of genes effected by a perturbation performed in vivo may allow for a gene to be linked to a specific pathway that may be targeted to modulate the signature and treat a disease (e.g., cancer, autoimmune disease). Thus, in certain embodiments, in vivo Perturb-seq is used to discover novel drug targets to allow treatment of patients having a specific gene signature.

In certain embodiments, the spatial location of perturbed genes in cells or tissues is determined. In regards to localizing proteins reference is made to WO2017/044893 "DNA Microscopy" and U.S. provisional application No. 62/309,680. In one embodiment, a tissue sample obtained from an in vivo animal model after perturbation is spatially tagged with functionalized barcoded probes, whereby the barcodes indicate the spatial location of the cells in the tissue upon single cell sequencing. Not being bound by a theory, cells may be perturbed in vivo and the cellular location of cells in response to the perturbations may be analyzed.

Example 33: Multiplex Screening of Perturbations in Different Cell Types

In certain embodiments, perturb-seq may be used to screen multiple cell types in a pooled screen. In one embodiment, a pool of barcode labeled cells is produced as in the PRISM method (see, e.g., Yu et al., Nature Biotechnology 34, 419-423 (2016)). A set of perturbation constructs is introduced to the pool of cells. After perturbation, cells are analyzed by single cell sequencing. The sequencing allows identification of the cell type perturbed, the perturbation, and the gene and/or protein expression in the single cells.

Example 34: ATAC-seq

The present invention may also be used with ATAC-seq (described herein and also see, e.g., US20160208323A1; US20160060691A1; WO2017156336A1; Buenrostro, J. D., Giresi, P. G., Zaba, L. C., Chang, H. Y., Greenleaf, W. J., Transposition of native chromatin for fast and sensitive epigenomic profiling of open chromatin, DNA-binding proteins and nucleosome position. Nature methods 2013; 10 (12): 1213-1218; J. D. Buenrostro et al., Single-cell chromatin accessibility reveals principles of regulatory variation. *Nature* 523, 486-490 (2015); Cusanovich, D. A., Daza, R., Adey, A., Pliner, H., Christiansen, L., Gunderson, K. L., Steemers, F. J., Trapnell, C. & Shendure, J. Multiplex single-cell profiling of chromatin accessibility by combinatorial cellular indexing. *Science.* 2015 May 22; 348(6237): 910-4. doi: 10.1126/science.aab1601. Epub 2015 May 7; and Cheng et al. "Genetic determinants of chromatin accessibility and gene regulation in T cell activation across human individuals" bioRxiv Dec. 6, 2016 dx.doi.org/10.1101/090241). In certain embodiments, single cells are perturbed either in vitro, in vivo, or ex vivo. The single cells are then analyzed by single cell ATAC-seq, whereby changes in chromatin accessibility in response to perturbations are detected. The barcoded transcripts for identifying the perturbation may be identified by sequencing.

Example 35: Multiplexing Single Cell RNA-Sequencing Using DNA Sample Barcodes

In certain embodiments, different samples of single cells are multiplexed to generate a multiplexed single sequencing library. The samples may be from different subjects, different tissues, different time points in an experiment, from different samples treated under different conditions in an experiment, or from different perturb-seq experiments (e.g., replicates). In certain embodiments, the sequencing library is sequenced and demultiplexed in silico.

Recently, droplet-based (see, e.g., Macosko, et al., Highly parallel genome-wide expression profiling of individual cells using nanoliter droplets. Cell, 161(5):1202-1214, 2015; and Dixit, et al., Perturb-seq: dissecting molecular circuits with scalable single-cell RNA profiling of pooled genetic screens. Cell, 167(7):1853-1866, 2016) and combinatorial split-pool methods (see, e.g., Vitak, et al., Sequencing thousands of single-cell genomes with combinatorial indexing. Nature Methods, 14(3):302-308, 2017; Cao, et al., Comprehensive single-cell transcriptional profiling of a multicellular organism. Science, 357(6352):661-667, 2017; and Rosenberg et al., Scaling single cell transcriptomics through split pool barcoding. bioRxiv preprint first posted online Feb. 2, 2017, doi:dx.doi.org/10.1101/105163) have significantly increased the throughput of single-cell assays and, enabled sequencing based quantification of transcriptional, proteomic and epigenetic states of thousands of cells from one microfluidic reaction.

Multiplexing samples would significantly reduce cost and technical variability associated with sample processing and library generation, improving the statistical power to resolve biological from technical effects.

Recently, sample multiplexing over different human donor samples in silico was performed by demultiplexing over a set of single nucleotide polymorphisms (SNPs) in the RNA-seq reads that provide a donor specific signature (Kanget et al., Multiplexing droplet-based single cell rna-sequencing using natural genetic barcodes. bioRxiv, page 118778, 2017).

Here, Applicants provide a method that allows pooling of samples in a single microfluidic (e.g., droplet based single cell sequencing, such as Drop-seq, InDrop, 10X) or split-pool reaction by labeling cells with DNA sample-barcodes, irrespective of their genomic profiles. By doing so, Applicants enable pooling multiple samples from a single patient, for instance isolated from different tissues, or analyzing different cell types. Or samples from a patient that have received different ex vivo treatments (for instance, responses to different drugs, or other perturbations). Similarly, one can pool samples from other organisms such as mice with isogenic backgrounds, that for instance, are sampled at different time points.

In one application, Applicants can stain cells with a sample specific barcoded antibody using methods and oligo linked antibodies similar to those described previously that target an epitope accessible from staining buffer (Stoeckius et al., Simultaneous epitope and transcriptome measurement in single cells. Nat Methods. 2017 September; 14(9):865-868). In certain embodiments, the epitope is selected such that it is expressed on all samples to be pooled. For each separate sample, the antibody barcoding the sample gets a different sample barcode, such that samples can be demultiplexed in silico. This approach only adds a short (5-10 minutes) antibody staining step to existing single-cell methods. In certain embodiments, cells are stained for less than 1 minute, 1 minute, 5 minutes, 10 minutes or more depending on the amount of antibody used or depending on the specific antibody. In certain embodiments, the antibody staining step uses a washing step to remove unbound antibodies that may crossreact across samples when the samples are multiplexed. One skilled in the art understands optimization of conditions for specific antibodies, such as for binding and washing steps.

In certain embodiments, more than one barcoded antibody is used to ensure every cell type in a sample is labeled with a sample barcode. In certain embodiments, panels of antibodies (e.g., 2 or 3 or more) are used to label cells in a sample. Not being bound by a theory a panel of two or three antibodies to common surface markers will label every cell type in a sample. In certain embodiments, the antibodies in the panel of antibodies are labeled with the same sample barcode oligonucleotide for each separate sample.

In certain embodiments, the antibody is selected from a group of generic antibodies specific for common antigens expressed by the cells in a sample. For example, if immune cells are analyzed an antibody against a common immune marker may be used.

In certain embodiments, common surface proteins applicable to the present invention include, but are not limited to human CD antigens selected from CD1a, CD1b, CD1c, CD1 d, CD1e, CD2, CD2R, CD3 gamma, CD3 delta, CD3 epsilon, CD4, CD5, CD6, CD7, CD8a, CD8b, CD9, CD10, CD11a, CD11b, CD11c, CD12, CD13, CD14, CD15, CD15s, CD15u, CD16a, CD16b, CD17, CD18, CD19, CD20, CD21, CD22, CD23, CD24, CD25, CD26, CD27, CD28, CD29, CD30, CD31, CD32, CD33, CD34, CD35, CD36, CD37, CD38, CD39, CD40, CD41, CD42a, CD42b, CD42c, CD42d, CD43, CD44, CD44v, CD45, CD45RA, CD45RB, CD45RO, CD46, CD47, CD47R, CD48, CD49a, CD49b, CD49c, CD49d, CD49e, CD49*f*, CD50, CD51, CD52, CD53, CD54, CD55, CD56, CD57, CD58, CD59, CD60a, CD60b, CD60c, CD61, CD62E, CD62L, CD62P, CD63, CD64, CD65, CD65s, CD66a, CD66b, CD66c, CD66d, CD66e, CD66*f*, CD68, CD69, CD70, CD71, CD72, CD73, CD74, CD75, CD75s, CD77, CD79a, CD79b, CD80, CD81, CD82, CD83, CDw84, CD85, CD86, CD87, CD88, CD89, CD90, CD91, CD92, CD93, CD94, CD95, CD96, CD97, CD98, CD99, CD99R, CD100, CD101, CD102, CD103, CD104, CD105, CD106, CD107a, CD107b, CD108, CD109, CD110, CD111, CD112, CD113, CD114, CD115, CD116, CD117, CD118, CD119, CD120a, CD120b, CD121a, CD121b, CD122, CD123, CD124, CD125, CD126, CD127, CD128, CD130, CD131, CD132, CD133, CD134, CD135, CD136, CD137, CD138, CD139, CD140a, CD140b, CD141, CD142, CD143, CD144, CD145, CD146, CD147, CD148, CD150, CD151, CD152, CD153, CD154, CD155, CD156a, CD156b, CD156c, CD157, CD158a, CD158b, CD159a, CD159c, CD160, CD161, CD162, CD162R, CD163, CD164, CD165, CD166, CD167a, CD168, CD169, CD170, CD171, CD172a, CD172b, CD172g, CD173, CD174, CD175, CD175s, CD176, CD177, CD178, CD179a, CD179b, CD180, CD181, CD182, CD183, CD184, CD185, CD186, CD191, CD192, CD193, CD195, CD196, CD197, CD198, CD199, CD200, CD201, CD202b, CD203c, CD204, CD205, CD206, CD207, CD208, CD209, CD210, CD212, CD213al, CD213a2, CD217, CD218a, CD218b, CD220, CD221, CD222, CD223, CD224, CD225, CD226, CD227, CD228, CD229, CD230, CD231, CD232, CD233, CD234, CD235a, CD235ab, CD235b, CD236, CD236R, CD238, CD239, CD240CE, CD240D, CD241, CD242, CD243, CD244, CD245, CD246, CD247, CD248, CD249, CD252, CD253, CD254, CD256, CD257, CD258, CD261, CD262, CD263, CD265, CD266, CD267, CD268, CD269, CD271, CD272, CD273, CD274, CD275, CD276, CD277, CD278, CD279, CD280, CD281, CD282, CD283, CD284, CD289, CD292, CD293, CD294, CD295, CD296, CD297, CD298, CD299, CD300a, CD300c, CD300e, CD301, CD302, CD303, CD304, CD305, CD306, CD307, CD309, CD312, CD314, CD315, CD316, CD317, CD318, CD319, CD320, CD321, CD322, CD324, CD325, CD326, CD327, CD328, CD329, CD331, CD332, CD333, CD334, CD335, CD336, CD337, CD338 or CD339; other human non-CD cellular antigens selected from 4-1BB Ligand, AID, AITR, AITRL, B7 family, B7-H4, BAMBI, BCMA, BLyS, BR3, BTLA, CCR7, c-Met, CMKLR1, DcR3, DEC-205, DR3, DR6, Fc epsilonRI alpha, Foxp3, Granzyme B, HLA-ABC, HLA-DR, HVEM, ICOS, ICOSL, IL-15R alpha, Integrin beta5, MD-2, MICA/MICB, Nanog, NKG2D, NOD2, Notch-1, OPG, OX-40, OX-40 Ligand, p38, PD-1, PD-L1, PD-L2, Perforin, RP105, RANK, RANKL, SAP, SLP-76, SSEA-1, SSEA-3, SSEA-4, Stro-1, TACI, T-bet, TCL1, TCR alpha beta, TCR gamma delta, TLR1-TLR4, TLR5, TLR6, TLR7, TLR8, TLR9, TLR10, TNFR1, TRAIL, TSLPR, TWEAK, TWEAK Receptor, ULBPs, ZAP-70; mouse CD antigens selected from CD1 d, CD2, CD3 d, CD3e, CD3g, CD4, CD5, CD6, CD7, CD8a, CD8b, CD9, CD10, CD11a, CD11b, CD11c, CD13, CD14, CD15, CD16, CD18, CD19, CD20, CD21, CD22, CD23, CD24a, CD25, CD26, CD27, CD28, CD29, CD30, CD31, CD32, CD33, CD34, CD35, CD36, CD37, CD38, CD39, CD40, CD41, CD42, CD43, CD44, CD44R, CD45, CD45.1, CD45.2, CD45R/CT1, CD45R, CD45RA, CD45RB, CD45RC, CD45RO, CD46, CD47, CD48, CD49a, CD49b, CD49c, CD49d, CD49e, CD49*f*, CD50, CD51, CD52, CD53, CD54, CD55, CD56, CD57, CD58 (H), CD59, CD60 (H), CD61, CD62E, CD62L, CD62P, CD63, CD64, CD65 (H), CD66a, CD68, CD69, CD70, CD71, CD72, CD73, CD74, CD75, CD77 (H), CD79a, CD79b, CD80, CD81, CD82, CD83, CD84, CD85, CD86, CD87, CD88, CD89, CD90, CD90.1, CD90.2, CD91, CD92 (H), CD93, CD94, CD95, CD96, CD97, CD98, CD99, CD100, CD101, CD102, CD103, CD104, CD105, CD106, CD107a, CD107b, CD108, CD109, CD110, CD111, CD112, CD113, CD114, CD115, CD116, CD117, CD118, CD119, CD120a, CD120b, CD121a, CD121b, CD122, CD123, CD124, CD125, CD126, CD127, CD128, CD130, CD131, CD132, CD133, CD134, CD135, CD136, CD137, CD138, CD139 (H), CD140a, CD140b, CD141, CD142, CD143, CD144, CD146, CD147, CD148, CD150, CD151, CD152, CD153, CD154, CD155, CD156a, CD156b, CD156c, CD157, CD158 (H), CD159a, CD159c, CD160, CD161c, CD162, CD162R (H), CD163, CD164, CD165, CD166, CD167a, CD168, CD169, CD170 (H), CD171, CD172a, CD172b, CD172g (H), CD173-CD175 (H), CD176, CD177, CD178, CD179a, CD179b, CD180, CD181, CD182, CD183, CD184, CD185, CD186, CD191, CD192, CD193, CD195, CD196, CD197, CD198, CD199, CD200, CD201, CD202b, CD203c, CD204, CD205, CD206, CD207, CD208 (H), CD209, CD210, CD212, CD213a1, CD213a2, CD217, CD218a, CD218b, CD220, CD221, CD222, CD223, CD224, CD225, CD226, CD227, CD228, CD229, CD230, CD231, CD232, CD233, CD234, CD235a, CD236R, CD238, CD239 (H), CD240CE (H), CD241, CD242 (H), CD243, CD244, CD246, CD247, CD248, CD249 (H), CD252, CD253, CD254, CD256, CD257, CD258, CD261 (H), CD262, CD263 (H), CD264 (H), CD265, CD266, CD267, CD268, CD269, CD271, CD272, CD273, CD274, CD275, CD276, CD277 (H), CD278, CD279, CD280, CD281, CD282, CD283, CD284, CD289, CD292, CD293, CD294, CD295, CD296, CD297, CD298, CD299 (H), CD301-302 (H), CD303, CD304, neuropilin 1, Nrp, NP-1, CD305, CD306-307 (H), CD309, CD312 (H), CD314, CD315, CD316, CD317, CD318, CD319, CD320, CD321, CD322, CD324, CD325, CD326, CD327 (H), CD328 (H), CD329, CD331, CD332, CD333, CD334, CD335, CD336 (H), CD337 (H), CD338 or CD339; or mouse non-CD cellular antigen selected from 4-1BBL, 33D1 antigen, AA4.1 antigen, ABCG2, AC133, AID, B7-DC, B7-H1, B7-H2, B7-H3, B7-H4, BP-1, BTLA, CCR7, CIRE, c-Met, CMKLR1, DC maturation marker, DR5, DX5, F4/80 antigen, FIRE, Flk-1, Flt-4, Foxp3, GITR, GITRL, Granzyme B, HVEM, ICOS, IgD, IgE Receptor high affinity, IgM, IL-15R alpha, IL-21R, Jagged-1, JAML, KLRG1, Lymphotoxin beta Receptor, Ly-6A/E, Ly-6B, Ly-6C, Ly-6D, Ly-6F, Ly-6G, Ly-49A, Ly-49B, Ly-49C, Ly-49D, Ly-49E, Ly-49F, Ly-49G, Ly-49H, Ly-49I, Mac-3, MAdCAM-1, MCP-1, MD-1, Nanog, NKG2A, NKG2A B6, NKG2B, NKG2C, NKG2D, NKG2E, Notch-1, OX40 Ligand, PD-1, Perforin, Plexin B2, Prominin-1, RAE-1 gamma, RANK, ROR gamma (t), ROR gamma (t) Products, SAP, Sca-1, Sema4A, SLP-76, SSEA-1, T-bet, TCR alpha beta, TCR gamma delta, TCR-HY, Ter-119, TIE2, TIM-1, TIM-2, TIM-3, TLR1-TLR4, TLR5, TLR6, TLR7, TLR8, TLR9, TLR11, TLR13, TRAIL, TRANCE, TWEAK, TWEAK Receptor or ZAP-70 (see also, CD Marker Handbook, available at www.bdbiosciences.com/documents/cd_marker_handbook.pdf). In a preferred embodiment, CD47 antibodies are used. Antibodies to any of the antigens described herein may be purchased (see, e.g., BD Biosciences, San Jose, CA; Biolegend, San Diego, CA; or Thermo Fisher, Waltham, MA). In certain embodiments, the generic antibody may be linked to the sample barcode oligonucleotide in pools, such that each pool includes an oligonucleotide with a different barcode sequence. Any method of attaching oligonucleotides to an antibody may be used herein. In certain embodiments, a streptavidin-biotin interaction may be used to link oligonucleotides to antibodies. In certain embodiments, the antibody-oligonucleotide includes a disulfide link at the 5' end of the oligonucleotide which allows the oligo to be released from the antibody with reducing agents. In certain embodiments, highly specific, FACS optimized monoclonal or polyclonal antibodies are selected.

Antibodies may be conjugated to oligonucleotides containing sample barcode sequences and a polyA tail. Oligonucleotides may be conjugated to antibodies by streptavidin-biotin conjugation using the LYNX Rapid Streptavidin Antibody Conjugation Kit (Bio-Rad, USA), according to manufacturer's instructions with modifications. Specifically, Applicants can label 15 μg of antibody with 10 μg of streptavidin. At this ratio, up to two streptavidin tetramers can theoretically be conjugated to one antibody, which results in 4-8 binding sites for biotin on each antibody. DNA-oligonucleotides can be purchased and/or synthesized with a 5' biotin modification or with a 5' amine modification and biotinylated using NHS-chemistry according to manufacturer's instructions (EZ Biotin S-S NHS, Thermo Fisher Scientific, USA). The disulfide bond allows separation of the oligo from the antibody with reducing agents. Separation of the oligo from the antibody may not be needed for all applications. Excess Biotin-NHS can be removed by gel filtration (Micro Biospin 6, Bio-Rad) and ethanol precipitation. Streptavidin-labelled antibodies can be incubated with biotinylated oligonucleotides in excess (1.5× theoretically available free streptavidin) overnight at 4 °C in PBS containing 0.5M NaCl and 0.02% Tween. Unbound oligo can be removed from antibodies using centrifugal filters with a 100KDa MW cutoff (Millipore, USA). Removal of excess oligo can be verified by 4% agarose gel electrophoresis. Antibody-oligo conjugates can be stored at 4 °C supplemented with sodium azide and BSA.

Cells can be labeled with oligonucleotide linked antibodies by resuspending cells in cold PBS containing 2% BSA and 0.01% Tween (PBT) and filtering through 40 μm cell strainers (Falcon, USA) to remove potential clumps and large particles. Cells can be incubated for 10 minutes with Fc receptor block (TruStain FcX, BioLegend, USA) to block non-specific antibody binding. Subsequently cells can be incubated in with mixtures of barcoded antibodies for 5-30 minutes at 4 °C. Cells can be washed 1-3× by resuspension in PBS containing 2% BSA and 0.01% Tween, followed by centrifugation (~480×g 5 minutes) and supernatant exchange. After the final wash cells can be resuspended at appropriate cell concentration for library construction applications (e.g., Drop-seq, 10X Genomics, or split-pool applications).

In alternative embodiments, cells can be non-specifically labeled with DNA sample barcodes. For instance, primary amines or thiols of extracellular domains of membrane proteins can be labeled with click chemistry moieties (see, e.g., Niki'c et al., Labeling proteins on live mammalian cells using click chemistry. Nature protocols, 10(5):780-791, 2015; Chang, et al., Copper-free click chemistry in living animals. PNAS 2010 107 (5) 1821-1826; published ahead of print Jan. 14, 2010; Hong et al., Labeling Live Cells by Copper-Catalyzed Alkyne-Azide Click Chemistry. Bioconjug Chem. 2010 Oct. 20; 21(10): 1912-1916; Kolb, H. C., Finn, M. G. and Sharpless, K. B. (2001), Click Chemistry: Diverse Chemical Function from a Few Good Reactions. Angewandte Chemie International Edition, 40:2004-2021; and Hoyle, Charles E. and Bowman, Christopher N. (2010), Thiol-Ene Click Chemistry. Angewandte Chemie International Edition, 49:1540-1573), and in a staining step, oligonucleotides functionalized with compatible click chemistry groups can be covalently attached. In certain embodiments, copper-less click chemistry reagents may be used to label the surface of cells (e.g., Click-iT® DIBO-maleimide can be used to label thiols and Click-iT® DIBO-succinimidyl ester can be used to label primary amines).

In additional embodiments, one could biotinylate primary amines of extracellular domains of membrane proteins, and stain samples with monomeric avidin (see, e.g., Jeong Min Lee, et al., A rhizavidin monomer with nearly multimeric avidin-like binding stability against biotin conjugates. Angewandte Chemie International Edition, 55(10):3393-3397, 2016), or antibodies that recognize biotin (see, e.g., Udeshi, et al., Antibodies to biotin enable large-scale detection of biotinylation sites on proteins. Nature Methods, 2017) that are conjugated to DNA sample barcodes. This reaction would be non-specific, and efficient.

In certain embodiments, the surface of the cells is labeled with a biotin ester. Biotin-XX sulfosuccinimidyl ester is a cell-impermeant, amine-reactive compound that can be used to label proteins exposed on the surface of live cells (see, e.g., Cell-Surface Biotinylation Kit, Thermo Fisher Scientific). The sulfosuccinimidyl ester forms an extremely stable conjugate (Bioconjugate Chem 6, 447 (1995)) with cell-surface proteins, and the biotin provides a convenient hapten for subsequent analysis or binding with an avidin-based protein (e.g., linked to a sample barcode oligonucleotide), including streptavidin, NeutrAvidin or CaptAvidin biotin-binding proteins (Cell Biology: A Laboratory Handbook 2nd Edition, J. Celis, Ed., pp. 341-350, Academic Press (1998)) Cell-surface biotinylation techniques have been employed to differentially label proteins in the apical and basolateral plasma membranes of epithelial cells (J Neurochem 77, 1301 (2001); J Cell Sci 109, 3025 (1996)). The technique is also suited to the study of internalization of membrane proteins and cell-surface targeting of proteins (J Cell Biol 153, 957 (2001); J Virol 75, 4744 (2001); J Biol Chem 274, 36801 (1999)).

In certain embodiments, the sample barcode oligonucleotides are compatible with oligo dT-based RNA-sequencing library preparations so that they can be captured and sequenced together with mRNAs. In certain embodiments, the sample barcode oligonucleotide includes a poly A tail. In certain embodiments, a poly T oligo is used to capture mRNA and polyadenylated sample barcode oligonucleotides and prime a reverse transcription reaction to obtain cDNA molecules. Commonly used reverse transcriptases have DNA-dependent DNA polymerase activity. This activity allows DNA sample barcoding oligonucleotides to be copied into cDNA during reverse transcription. In certain embodiments, the sample barcode oligonucleotides comprise a PCR handle compatible with single cell sequencing methods as described herein (e.g., Drop-seq, InDrop, 10X Genomics). Depending on the application, the PCR-amplification handle in the sample barcode oligonucleotides can be changed depending on which sequence read is used for RNA readout (e.g. Drop-seq uses read 2, 10X v1 uses read 1). In certain embodiments, the sample barcode oligonucleotides comprise a PCR handle for amplification and next-generation sequencing library preparation, a barcode sequence specific for each sample, and a polyA stretch at the 3' end designed to anneal to polyT stretches on primers used to initiate reverse transcription. In certain embodiments, the sample barcode oligonucleotide comprises an UMI. In certain embodiments, random priming may be used for reverse transcription. The sample barcode oligonucleotides may be RNA or DNA. The sample barcode oligonucleotides may incorporate any modified nucleotides known in the art. In certain embodiments, the sample barcode oligonucleotides include a 3-20 nucleotide barcode sequence.

In certain embodiments, the multiplexing strategy can be applied to any membrane enclosed biological entity, such as membrane enclosed organelles, isolated nuclei, single-cells, and the like. In certain embodiments, organelle specific antibodies may be used.

In certain embodiments, the invention involves plate based single cell RNA sequencing (see, e.g., Picelli, S. et al., 2014, "Full-length RNA-seq from single cells using Smart-seq2" Nature protocols 9, 171-181, doi:10.1038/nprot.2014.006). In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi:10.1038/ncomms14049; International patent publication number WO 2014210353 A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; and Cao, et al., Comprehensive single-cell transcriptional profiling of a multicellular organism. Science, 357(6352): 661-667, 2017.

The multiplexing strategy described herein is also applicable to samples obtained by single nucleus sequencing and/or Div-seq (see, e.g., Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; and Habib et al., 2017, "Massively parallel single-nucleus RNA-seq with DroNc-seq" Nat Methods. 2017 October; 14(10):955-958). In certain embodiments, nuclei are labeled chemically (e.g., Click chemistry, biotin) or with an antibody specific for a nuclear membrane protein (e.g., nuclear pore protein). Nuclear membrane proteins common to all nuclei include, but are not limited to Lamin-A, B or C, NUP98, NUP153, or NUP214.

The multiplexing strategy described herein is also applicable to single-cell profiling of chromatin accessibility (see, e.g., Cusanovich, et al., Multiplex single-cell profiling of chromatin accessibility by combinatorial cellular indexing. *Science.* 2015 May 22; 348(6237):910-4. doi: 10.1126/science.aab1601. Epub 2015 May 7). In certain embodiments, the sample barcode oligonucleotides are adapted for tagmentation with the adapters used in the first step of generating cell of origin barcodes.

In certain embodiments, multiplexing may be used in single cell proteomics as discussed herein or in other protocols (see e.g., WO2012106385A2). In certain embodiments, cells or fixed cells are labeled (e.g., antibody, click chemistry, biotin-avidin) with a sample barcode oligonucleotide compatible with a cell of origin barcoding strategy as described herein (e.g., split and pool).

In one exemplary embodiment, samples for use in droplet based single sequencing as described herein are multiplexed. Cells belonging to different samples are labeled with sample barcode oligonucleotides as described herein. The single cells from multiple samples may then be loaded into a microfluidic device. The labeled cells are encapsulated with reagents and cell of origin barcode containing beads in emulsion droplets. The sample barcode oligonucleotide may then be released from the cell in the droplet (e.g., by lysis of the cell or reducing conditions in the droplet) and processed to generate a cDNA molecule comprising the sample barcode and cell of origin barcode. Since every cDNA molecule (i.e., derived from mRNA and sample barcode oligonucleotide) from a single cell includes the same cell of origin barcode, the sequencing data can be demultiplexed to determine the cell and sample of origin.

In another exemplary embodiment, single cell analysis uses split and pool barcoding. In certain embodiments, split and pool barcoding requires the cells or nuclei to be fixed. In certain embodiments, the label needs to remain bound to the cells during the split and pool steps. In certain embodiments, cells are labeled with sample barcode oligonucleotides (e.g., oligo-linked antibodies, chemical means or biotin-avidin binding). In certain embodiments, the cells in different samples are fixed and permeabilized. The cells are then labeled with a sample barcode oligonucleotide as described herein. Fixation may be by methanol fixation or aldehyde fixation (e.g., formaldehyde, paraformaldehyde, glutaraldehyde). In certain embodiments, the labeled cells are pooled and in situ reverse transcription is performed, thus cDNA is obtained for mRNA and the sample barcode oligonucleotides. The cells from all samples are split into pools for labeling with a first barcode. The split and pool process may be repeated any number of "n" times to ensure each cell has a unique barcode sequence. The last barcode may include an UMI and a PCR handle.

In certain embodiments, the cells in different samples are fixed and permeabilized. The cells are then labeled with a sample barcode oligonucleotide as described herein. The cells from all samples are split into pools. In situ reverse transcription is then performed in the pools to introduce a first barcode sequence to the mRNA and sample barcode oligonucleotides. The cells may be pooled again and split into second pools. Second strand synthesis, tagmentation and PCR may be performed to add a second barcode sequence to the cDNA.

REFERENCES

Acosta-Alvear, D., Zhou, Y., Blais, A., Tsikitis, M., Lents, N. H., Arias, C., Lennon, C. J., Kluger, Y. & Dynlacht, B. D. 2007, "XBP1 controls diverse cell type- and condition-specific transcriptional regulatory networks", *Molecular Cell*, vol. 27, no. 1, pp. 53-66.

Adiconis, X., Borges-Rivera, D., Satija, R., DeLuca, D. S., Busby, M. A., Berlin, A. M., Sivachenko, A., Thompson, D. A., Wysoker, A., Fennell, T., Gnirke, A., Pochet, N., Regev, A. & Levin, J. Z. Comparative analysis of RNA sequencing methods for degraded or low-input samples: *Nat Methods.* 10, 623-629, doi:10.1038/nmeth.2483 (2013). PMCID:3821180.

Aguirre, A. J., Meyers, R. M., Weir, B. A., Vazquez, F., Zhang, C., Ben-David, U., Cook, A., Ha, G., Harrington, W. F., Doshi, M. B., et al 2016, "Genomic Copy Number Dictates a Gene-Independent Cell Response to CRISPR/Cas9 Targeting", *Cancer Discovery*, vol. 6, no. 8, pp. 914-929.

Altshuler, D., Daly, M. J., and Lander, E. S. (2008). Genetic Mapping in Human Disease. Science (80-.). 322, 881-888.

Amit, I., Garber, M., Chevrier, N., Leite, A. P., Donner, Y., Eisenhaure, T., Guttman, M., Grenier, J. K., Li, W., Zuk, O., et al. (2009). Unbiased Reconstruction of a Mammalian Transcriptional Network Mediating Pathogen Responses. Science (80-.). 326, 257-263.

Anders, C., Niewoehner, O., Duerst, A. & Jinek, M. 2014, "Structural basis of PAM-dependent target DNA recognition by the Cas9 endonuclease", *Nature*, vol. 513, no. 7519, pp. 569-573.

Assarsson, E., Lundberg, M., Holmquist, G., Bjorkesten, J., Thorsen, S. B., Ekman, D., Eriksson, A., Rennel Dickens, E., Ohlsson, S., Edfeldt, G., et al. (2014). Homogenous 96-plex PEA immunoassay exhibiting high sensitivity, specificity, and excellent scalability. PloS one 9, e95192.

Bamshad, M. J., Ng, S. B., Bigham, A. W., Tabor, H. K., Emond, M. J., Nickerson, D. A., and Shendure, J. (2011). Exome sequencing as a tool for Mendelian disease gene discovery. Nat. Rev. Genet. 12, 745-755.

Bandyopadhyay, S., Mehta, M., Kuo, D., Sung, M.-K., Chuang, R., Jaehnig, E. J., Bodenmiller, B., Licon, K., Copeland, W., Shales, M., et al. (2010). Rewiring of Genetic Networks in Response to DNA Damage. Science (80-.). 330, 1385-1389.

Bao, X. R., Ong, S., Goldberger, O., Peng, J., Sharma, R., Thompson, D. A., Vafai, S. B., Cox, A. G., Marutani, E., Ichinose, F., et al 2016, "*Mitochondrial dysfunction remodels one-carbon metabolism in human cells", eLife*, vol. 5.

Bassik, M. C., Kampmann, M., Lebbink, R. J., Wang, S., Hein, M. Y., Poser, I., Weibezahn, J., Horlbeck, M. a, Chen, S., Mann, M., et al. (2013a). A systematic mammalian genetic interaction map reveals pathways underlying ricin susceptibility. Cell 152, 909-922.

Bassik, M. C., Kampmann, M., Lebbink, R. J., Wang, S., Hein, M. Y., Poser, I., Weibezahn, J., Horlbeck, M. A., Chen, S., Mann, M., et al. (2013b). A Systematic Mammalian Genetic Interaction Map Reveals Pathways Underlying Ricin Susceptibility. Cell 152, 909-922.

Beerenwinkel, N., Pachter, L., and Sturmfels, B. (2007). Epistasis and Shapes of Fitness Landscapes. Stat. Sin. 17, 1317-1342.

Bendall, S. C., Simonds, E. F., Qiu, P., Amir el, A. D., Krutzik, P. O., Finck, R., Bruggner, R. V., Melamed, R., Trejo, A., Ornatsky, O. I., et al. (2011). Single-cell mass cytometry of differential immune and drug responses across a human hematopoietic continuum. Science 332, 687-696.

Berger, A. H., Brooks, A. N., Wu, X., Shrestha, Y., Chouinard, C., Piccioni, F., Bagul, M., Kamburov, A., Imielinski, M., Hogstrom, L., et al. (2016). High-throughput Phenotyping of Lung Cancer Somatic Mutations. Cancer Cell 0, 248-249.

Blecher-Gonen, R., Barnett-Itzhaki, Z., Jaitin, D., Amann-Zalcenstein, D., Lara-Astiaso, D. & Amit, I. High-throughput chromatin immunoprecipitation for genome-wide mapping of in vivo protein-DNA interactions and epigenomic states. *Nat Protoc.* 8, 539-554, doi:10.1038/nprot.2013.023 (2013).

Bochkis, I. M., Przybylski, D., Chen, J. & Regev, A. Changes in nucleosome occupancy associated with metabolic alterations in aged mammalian liver. *Cell reports.* 9, 996-1006, doi:10.1016/j.celrep.2014.09.048 (2014). PMCID:4250828.

Boone, C., Bussey, H., and Andrews, B. J. (2007). Exploring genetic interactions and networks with yeast. 8, 437-449.

Bornstein, C., Winter, D., Barnett-Itzhaki, Z., David, E., Kadri, S., Garber, M. & Amit, I. A negative feedback loop of transcription factors specifies alternative dendritic cell chromatin States. *Mol Cell.* 56, 749-762, doi:10.1016/j.molcel.2014.10.014 (2014). PMCID:4412443.

Botstein, D., and Risch, N. (2003). Discovering genotypes underlying human phenotypes: past successes for mendelian disease, future approaches for complex disease. Nat. Genet. 33, 228-237.

Briner, A. E., Donohoue, P. D., Gomaa, A. A., Selle, K., Slorach, E. M., Nye, C. H., Haurwitz, R. E., Beisel, C. L., May, A. P. & Barrangou, R. 2014, "Guide RNA functional modules direct Cas9 activity and orthogonality", *Molecular Cell*, vol. 56, no. 2, pp. 333-339.

Buettner, F., Natarajan, K. N., Casale, F. P., Proserpio, V., Scialdone, A., Theis, F. J., Teichmann, S. A., Marioni, J. C., and Stegle, O. (2015). Computational analysis of cell-to-cell heterogeneity in single-cell RNA-sequencing data reveals hidden subpopulations of cells. Nat. Biotechnol. 33, 155-160.

Cabili, M. N., Dunagin, M. C., McClanahan, P. D., Biaesch, A., Padovan-Merhar, O., Regev, A., Rinn, J. L. & Raj, A. Localization and abundance analysis of human lncRNAs at single-cell and single-molecule resolution. *Genome Biol.* 16, 20, doi:10.1186/s13059-015-0586-4 (2015). PMCID:4369099.

Cabili, M. N., Trapnell, C., Goff, L., Koziol, M., Tazon-Vega, B., Regev, A. & Rinn, J. L. Integrative annotation of human large intergenic noncoding RNAs reveals global properties and specific subclasses. *Genes Dev.* 25, 1915-1927, doi:10.1101/gad.17446611 (2011). PMCID: 3185964.

Calfon, M., Zeng, H., Urano, F., Till, J. H., Hubbard, S. R., Harding, H. P., Clark, S. G. & Ron, D. 2002, "IRE1 couples endoplasmic reticulum load to secretory capacity by processing the XBP-1 mRNA", *Nature*, vol. 415, no. 6867, pp. 92-96.

Candès, E. J., and Recht, B. (2009). Exact Matrix Completion via Convex Optimization. *Found. Comput. Math.* 9, 717-772.

Candès, E. J., Li, X., Ma, Y. & Wright, J. 2011, "Robust principal component analysis?", Journal of the ACM (JACM), vol. 58, no. 3, pp. 11.

Capaldi, A. P., Kaplan, T., Liu, Y., Habib, N., Regev, A., Friedman, N., and O'Shea, E. K. (2008). Structure and function of a transcriptional network activated by the MAPK Hog1. *Nat. Genet.* 40, 1300-1306.

Carter, G. W., Prinz, S., Neou, C., Shelby, J. P., Marzolf, B., Thorsson, V., and Galitski, T. (2007). Prediction of phenotype and gene expression for combinations of mutations. Mol. Syst. Biol. 3, 96.

Carbon, S., Ireland, A., Mungall, C. J., Shu, S., Marshall, B. & Lewis, S. 2009, "AmiGO: online access to ontology and annotation data", *Bioinformatics* (*Oxford, England*), vol. 25, no. 2, pp. 288-289.

Cartwright, T., Perkins, N. D., and L Wilson, C. (2016). NFKB1: a suppressor of inflammation, ageing and cancer. *FEBS J.* 283, 1812-1822.

Chan, M. M., Smith, Z. D., Egli, D., Regev, A. & Meissner, A. Mouse ooplasm confers context-specific reprogramming capacity. *Nature genetics*. 44, 978-980, doi:10.1038/ng.2382 (2012). PMCID:3432711.

Chavez, A., Scheiman, J., Vora, S., Pruitt, B. W., Tuttle, M., P R Iyer, E., Lin, S., Kiani, S., Guzman, C. D., Wiegand, D. J., et al 2015, "Highly efficient Cas9-mediated transcriptional programming", *Nature Methods*, vol. 12, no. 4, pp. 326-328.

Chen, Y., Liu, P., Nielsen, A. A. K., Brophy, J. A. N., Clancy, K., Peterson, T. & Voigt, C. A. 2013, "Characterization of 582 natural and synthetic terminators and quantification of their design constraints", *Nature Methods*, vol. 10, no. 7, pp. 659-664.

Chen, S., Sanjana, N. E., Zheng, K., Shalem, O., Lee, K., Shi, X., Scott, D. A., Song, J., Pan, J. Q., Weissleder, R., et al. (2015). Genome-wide CRISPR Screen in a Mouse Model of Tumor Growth and Metastasis. Cell 160, 1246-1260.

Cheng, C. S., Rai, K., Garber, M., Hollinger, A., Robbins, D., Anderson, S., Macbeth, A., Tzou, A., Carneiro, M. O., Raychowdhury, R., Russ, C., Hacohen, N., Gershenwald, J. E., Lennon, N., Nusbaum, C., Chin, L., Regev, A. & Amit, I. Semiconductor-based DNA sequencing of histone modification states. *Nat Commun.* 4, 2672, doi:10.1038/ncomms3672 (2013). PMCID:3917140.

Chevrier, N., Mertins, P., Artyomov, M. N., Shalek, A. K., Iannacone, M., Ciaccio, M. F., Gat-Viks, I., Tonti, E., DeGrace, M. M., Clauser, K. R., Garber, M., Eisenhaure, T. M., Yosef, N., Robinson, J., Sutton, A., Andersen, M. S., Root, D. E., von Andrian, U., Jones, R. B., Park, H., Carr, S. A., Regev, A., Amit, I. & Hacohen, N. Systematic discovery of TLR signaling components delineates viral-sensing circuits. *Cell.* 147, 853-867, doi:10.1016/j.cell.2011.10.022 (2011). PMCID:3809888.

Chuang, C., Lee, K., Fan, C. & Su, Y. 2009, "Porcine type III RNA polymerase III promoters for short hairpin RNA expression", *Animal Biotechnology*, vol. 20, no. 1, pp. 34-39.

Chung, K., Wallace, J., Kim, S. Y., Kalyanasundaram, S., Andalman, A. S., Davidson, T. J., Mirzabekov, J. J., Zalocusky, K. A., Mattis, J., Denisin, A. K., et al. (2013). Structural and molecular interrogation of intact biological systems. Nature 497, 332-337.

Chung, N. C., and Storey, J. D. (2015). Statistical significance of variables driving systematic variation in high-dimensional data. Bioinformatics 31, 545-554.

Cohen, A., and Sheva, B.-(1998). HIDDEN MARKOV MODELS IN BIOMEDICAL SIGNAL PROCESSING. 20, 1145-1150.

Cong, L., Ran, F. A., Cox, D., Lin, S., Barretto, R., Habib, N., Hsu, P. D., Wu, X., Jiang, W., Marraffini, L. a, et al. (2013). Multiplex genome engineering using CRISPR/Cas systems. Science 339, 819-823.

Costanzo, M., Baryshnikova, A., Bellay, J., Kim, Y., Spear, E. D., Sevier, C. S., Ding, H., Koh, J. L. Y., Toufighi, K., Mostafavi, S., et al. (2010). The Genetic Landscape of a Cell. Science (80-.). 327, 425-431.

Dang, Y., Jia, G., Choi, J., Ma, H., Anaya, E., Ye, C., Shankar, P. & Wu, H. 2015, "Optimizing sgRNA structure to improve CRISPR-Cas9 knockout efficiency", Genome Biology, vol. 16, pp. 280.

Duan, Q., Flynn, C., Niepel, M., Hafner, M., Muhlich, J. L., Fernandez, N. F., Rouillard, A. D., Tan, C. M., Chen, E. Y., Golub, T. R., et al. (2014). LINCS Canvas Browser: interactive web app to query, browse and interrogate LINCS L1000 gene expression signatures. Nucleic Acids Res. 42, W449-W460.

Elsharkawy, A. M., Oakley, F., Lin, F., Packham, G., Mann, D. A., and Mann, J. (2010). The NF-kappaB p50: p50: HDAC-1 repressor complex orchestrates transcriptional inhibition of multiple pro-inflammatory genes. J. Hepatol. 53, 519-527.

Engreitz, J. M., Pandya-Jones, A., McDonel, P., Shishkin, A., Sirokman, K., Surka, C., Kadri, S., Xing, J., Goren, A., Lander, E. S., Plath, K. & Guttman, M. The Xist lncRNA exploits three-dimensional genome architecture to spread across the X chromosome. *Science.* 341, 1237973, doi:10.1126/science.1237973 (2013). PMCID:3778663.

Fan, H. C., Fu, G. K., and Fodor, S. P. a. (2015). Combinatorial labeling of single cells for gene expression cytometry. Science. 347, 1258367-1258367.

Fogli, A. & Boespflug-Tanguy, O. 2006, “The large spectrum of eIF2B-related diseases”, *Biochemical Society Transactions*, vol. 34, no. Pt 1, pp. 22-29.

Friedman, J., Hastie, T. & Tibshirani, R. 2001, *The elements of statistical learning*, Springer series in statistics Springer, Berlin.

Galonska, C., Smith, Z. D. & Meissner, A. In Vivo and in vitro dynamics of undifferentiated embryonic cell transcription factor 1. *Stem Cell Reports.* 2, 245-252, doi: 10.1016/j.stemcr.2014.01.007 (2014). PMCID:3964277.

Garber, M., Yosef, N., Goren, A., Raychowdhury, R., Thielke, A., Guttman, M., Robinson, J., Minie, B., Chevrier, N., Itzhaki, Z., et al. (2012). A High-Throughput Chromatin Immunoprecipitation Approach Reveals Principles of Dynamic Gene Regulation in Mammals. Mol. Cell 47, 810-822.

Gat-Viks, I., Chevrier, N., Wilentzik, R., Eisenhaure, T., Raychowdhury, R., Steuerman, Y., Shalek, A. K., Hacohen, N., Amit, I. & Regev, A. Deciphering molecular circuits from genetic variation underlying transcriptional responsiveness to stimuli. *Nature biotechnology.* 31, 342-349, doi:10.1038/nbt.2519 (2013). PMCID:3622156.

Gilbert, L. A., Horlbeck, M. A., Adamson, B., Villalta, J. E., Chen, Y., Whitehead, E. H., Guimaraes, C., Panning, B., Ploegh, H. L., Bassik, M. C., et al. (2014). Genome-Scale CRISPR-Mediated Control of Gene Repression and Activation. Cell 159, 647-661.

Gilbert, L. a, Larson, M. H., Morsut, L., Liu, Z., Brar, G. a, Torres, S. E., Stern-Ginossar, N., Brandman, O., Whitehead, E. H., Doudna, J. a, et al. (2013). CRISPR-mediated modular RNA-guided regulation of transcription in eukaryotes. Cell 154, 442-451.

Gomez, D., Shankman, L. S., Nguyen, A. T., and Owens, G. K. (2013). Detection of histone modifications at specific gene loci in single cells in histological sections. Nature methods 10, 171-177.

Goodwin, E. C. & Rottman, F. M. 1992, “The 3'-flanking sequence of the bovine growth hormone gene contains novel elements required for efficient and accurate polyadenylation”, *The Journal of Biological Chemistry*, vol. 267, no. 23, pp. 16330-16334.

Grün, D. & van Oudenaarden, A. 2015, “Design and Analysis of Single-Cell Sequencing Experiments”, *Cell*, vol. 163, no. 4, pp. 799-810.

Gu, W., Crawford, E. D., O'Donovan, B. D., Wilson, M. R., Chow, E. D., Retallack, H. & DeRisi, J. L. 2016, “Depletion of Abundant Sequences by Hybridization (DASH): using Cas9 to remove unwanted high-abundance species in sequencing libraries and molecular counting applications”, *Genome Biology*, vol. 17, pp. 41.

Guttman, M., Donaghey, J., Carey, B. W., Garber, M., Grenier, J. K., Munson, G., Young, G., Lucas, A. B., Ach, R., Bruhn, L., Yang, X., Amit, I., Meissner, A., Regev, A., Rinn, J. L., Root, D. E. & Lander, E. S. lincRNAs act in the circuitry controlling pluripotency and differentiation. *Nature.* 477, 295-300, doi:10.1038/nature10398 (2011). PMCID:3175327.

Haas, B. J., Papanicolaou, A., Yassour, M., Grabherr, M., Blood, P. D., Bowden, J., Couger, M. B., Eccles, D., Li, B., Lieber, M., Macmanes, M. D., Ott, M., Orvis, J., Pochet, N., Strozzi, F., Weeks, N., Westerman, R., William, T., Dewey, C. N., Henschel, R., Leduc, R. D., Friedman, N. & Regev, A. De novo transcript sequence reconstruction from RNA-seq using the Trinity platform for reference generation and analysis. *Nat Protoc.* 8, 1494-1512, doi:10.1038/nprot.2013.084 (2013). PMCID: 3875132.

Haber, J. E., Braberg, H., Wu, Q., Alexander, R., Haase, J., Ryan, C., Lipkin-Moore, Z., Franks-Skiba, K. E., Johnson, T., Shales, M., et al. (2013). Systematic triple-mutant analysis uncovers functional connectivity between pathways involved in chromosome regulation. Cell Rep. 3, 2168-2178.

Hacisuleyman, E., Goff, L. A., Trapnell, C., Williams, A., Henao-Mejia, J., Sun, L., McClanahan, P., Hendrickson, D. G., Sauvageau, M., Kelley, D. R., Morse, M., Engreitz, J., Lander, E. S., Guttman, M., Lodish, H. F., Flavell, R., Raj, A. & Rinn, J. L. Topological organization of multichromosomal regions by the long intergenic noncoding RNA Firre. *Nat Struct Mol Biol.* 21, 198-206, doi: 10.1038/nsmb.2764 (2014). PMCID:3950333.

Haldimann, A. & Wanner, B. L. 2001, “Conditional-replication, integration, excision, and retrieval plasmid-host systems for gene structure-function studies of bacteria”, *Journal of Bacteriology*, vol. 183, no. 21, pp. 6384-6393.

Hamanaka, R. B., Bennett, B. S., Cullinan, S. B. & Diehl, J. A. 2005, “PERK and GCN2 Contribute to eIF2α Phosphorylation and Cell Cycle Arrest after Activation of the Unfolded Protein Response Pathway”, *Molecular Biology of the Cell*, vol. 16, no. 12, pp. 5493-5501.

Han, J., Back, S. H., Hur, J., Lin, Y., Gildersleeve, R., Shan, J., Yuan, C. L., Krokowski, D., Wang, S., Hatzoglou, M., et al 2013, “ER-stress-induced transcriptional regulation increases protein synthesis leading to cell death”, *Nature Cell Biology*, vol. 15, no. 5, pp. 481-490.

Hartl, D. L. (2014). What can Applicants learn from fitness landscapes? Curr. Opin. Microbiol. 21, 51-57.

Heckl, D., Kowalczyk, M. S., Yudovich, D., Belizaire, R., Puram, R. V., McConkey, M. E., Thielke, A., Aster, J. C., Regev, A. & Ebert, B. L. Generation of mouse models of myeloid malignancy with combinatorial genetic lesions using CRISPR-Cas9 genome editing. *Nature biotechnology.* 32, 941-946, doi:10.1038/nbt.2951 (2014). PMCID: 4160386.

Heimberg, G., Bhatnagar, R., El-Samad, H., and Thomson, M. (2016). Low Dimensionality in Gene Expression Data Enables the Accurate Extraction of Transcriptional Programs from Shallow Sequencing. Cell Syst. 2, 239-250.

Helft, J., Böttcher, J., Chakravarty, P., Zelenay, S., Huotari, J., Schraml, B. U., Goubau, D., and Reis e Sousa, C. (2015). GM-CSF Mouse Bone Marrow Cultures Comprise a Heterogeneous Population of CD11c+MHCII+ Macrophages and Dendritic Cells. Immunity 42, 1197-1211.

Hetz, C. 2012, “The unfolded protein response: controlling cell fate decisions under ER stress and beyond”, *Nature Reviews. Molecular Cell Biology*, vol. 13, no. 2, pp. 89-102.

Horlbeck, M. A., Gilbert, L. A., Villalta, J. E., Adamson, B., Pak, R. A., Chen, Y., Fields, A. P., Park, C. Y., Corn, J. E. & Kampmann, M. 2016, “Compact and highly active next-generation libraries for CRISPR-mediated gene repression and activation”, *eLife*, vol. 5, pp. e19760.

Hu, S., Ni, W., Hazi, W., Zhang, H., Zhang, N., Meng, R. & Chen, C. 2011, “Cloning and functional analysis of sheep U6 promoters”, *Animal Biotechnology*, vol. 22, no. 3, pp. 170-174.

Huang, D. W., Sherman, B. T. & Lempicki, R. A. 2009a, “Bioinformatics enrichment tools: paths toward the comprehensive functional analysis of large gene lists”, *Nucleic Acids Research*, vol. 37, no. 1, pp. 1-13.

Huang, D. W., Sherman, B. T. & Lempicki, R. A. 2009b, "Systematic and integrative analysis of large gene lists using DAVID bioinformatics resources", *Nature Protocols*, vol. 4, no. 1, pp. 44-57.

Hughes, T. R., Marton, M. J., Jones, A. R., Roberts, C. J., Stoughton, R., Armour, C. D., Bennett, H. a, Coffey, E., Dai, H., He, Y. D., et al. (2000). Functional Discovery via a Compendium of Expression Profiles. Cell 102, 109-126.

Jaitin, D. A., Kenigsberg, E., Keren-Shaul, H., Elefant, N., Paul, F., Zaretsky, I., Mildner, A., Cohen, N., Jung, S., Tanay, A. & Amit, I. Massively parallel single-cell RNA-seq for marker-free decomposition of tissues into cell types. *Science.* 343, 776-779, doi:10.1126/science.1247651 (2014). PMCID:4412462.

Janssen, K. P., Knez, K., Spasic, D., and Lammertyn, J. (2013). Nucleic acids for ultra-sensitive protein detection. Sensors 13, 1353-1384.

Jiang, F., Zhou, K., Ma, L., Gressel, S. & Doudna, J. A. 2015, "STRUCTURAL BIOLOGY. A Cas9-guide RNA complex preorganized for target DNA recognition", *Science* (*New York, N.Y.*), vol. 348, no. 6242, pp. 1477-1481.

Jin, F., Hazbun, T., Michaud, G. A., Salcius, M., Predki, P. F., Fields, S., and Huang, J. (2006). A pooling-deconvolution strategy for biological network elucidation. Nat Methods 3, 183-189.

Joensson, H. N., and Andersson Svahn, H. (2012). Droplet Microfluidics-A Tool for Single-Cell Analysis. Angew. Chemie Int. Ed. 51, 12176-12192.

Jonikas, M. C., Collins, S. R., Denic, V., Oh, E., Quan, E. M., Schmid, V., Weibezahn, J., Schwappach, B., Walter, P., Weissman, J. S., et al 2009, "Comprehensive characterization of genes required for protein folding in the endoplasmic reticulum", *Science* (*New York, N.Y.*), vol. 323, no. 5922, pp. 1693-1697.

Jovanovic, M., Rooney, M. S., Mertins, P., Przybylski, D., Chevrier, N., Satija, R., Rodriguez, E. H., Fields, A. P., Schwartz, S., Raychowdhury, R., Mumbach, M. R., Eisenhaure, T., Rabani, M., Gennert, D., Lu, D., Delorey, T., Weissman, J. S., Carr, S. A., Hacohen, N. & Regev, A. Dynamic profiling of the protein life cycle in response to pathogens. *Science.* 347, 1259038, doi:10.1126/science.1259038 (2015). PMCID: PMC Journa—In Process.

Jovanovic, M., Rooney, M. S., Mertins, P., Przybylski, D., Chevrier, N., Satija, R., Rodriguez, E. H., Fields, A. P., Schwartz, S., Raychowdhury, R., et al. (2015). Dynamic profiling of the protein life cycle in response to pathogens. Science (80-.). 347, 1259038-1259038.

Kabadi, A. M., Ousterout, D. G., Hilton, I. B., and Gersbach, C. A. (2014). Multiplex CRISPR/Cas9-based genome engineering from a single lentiviral vector. Nucleic Acids Res. 42, 1-11.

Kampmann, M., Bassik, M. C., and Weissman, J. S. (2014). Functional genomics platform for pooled screening and generation of mammalian genetic interaction maps. Nat. Protoc. 9, 1825-1847.

Kanda, S., Yanagitani, K., Yokota, Y., Esaki, Y. & Kohno, K. 2016, "Autonomous translational pausing is required for XBP1u mRNA recruitment to the ER via the SRP pathway", *Proceedings of the National Academy of Sciences of the United States of America*, vol. 113, no. 40, pp. E5895.

Kantlehner, M., Kirchner, R., Hartmann, P., Ellwart, J. W., Alunni-Fabbroni, M., and Schumacher, A. (2011). A high-throughput DNA methylation analysis of a single cell. Nucleic acids research 39, e44.

Kearns, N. A., Genga, R. M., Enuameh, M. S., Garber, M., Wolfe, S. A. & Maehr, R. Cas9 effector-mediated regulation of transcription and differentiation in human pluripotent stem cells. *Development.* 141, 219-223, doi:10.1242/dev.103341 (2014). PMCID:3865759.

Kelley, D. & Rinn, J. Transposable elements reveal a stem cell-specific class of long noncoding RNAs. *Genome Biol.* 13, R107, doi:10.1186/gb-2012-13-11-r107 (2012). PMCID:3580499.

Kemmeren, P., Sameith, K., Van De Pasch, L. A. L., Benschop, J. J., Lenstra, T. L., Margaritis, T., O'Duibhir, E., Apweiler, E., Van Wageningen, S., Ko, C. W., et al. (2014). Large-scale genetic perturbations reveal regulatory networks and an abundance of gene-specific repressors. Cell 157, 740-752.

Kharchenko, P. V, Silberstein, L., and Scadden, D. T. (2014). Bayesian approach to single-cell differential expression analysis. Nat. Methods 11, 740-742.

Klein, A. M., Mazutis, L., Akartuna, I., Tallapragada, N., Veres, A., Li, V., Peshkin, L., Weitz, D. A., and Kirschner, M. W. (2015). Droplet barcoding for single-cell transcriptomics applied to embryonic stem cells. Cell 161, 1187-1201.

Komor, A. C., Kim, Y. B., Packer, M. S., Zuris, J. A. & Liu, D. R. 2016, "Programmable editing of a target base in genomic DNA without double-stranded DNA cleavage", Nature, vol. 533, no. 7603, pp. 420-424.

Konermann, S., Brigham, M. D., Trevino, A. E., Joung, J., Abudayyeh, O. O., Barcena, C., Hsu, P. D., Habib, N., Gootenberg, J. S., Nishimasu, H., et al. (2014). Genome-scale transcriptional activation by an engineered CRISPR-Cas9 complex. Nature 517, 583-588.

Kowalczyk, M. S., Tirosh, I., Heckl, D., Rao, T. N., Dixit, A., Haas, B. J., Schneider, R. K., Wagers, A. J., Ebert, B. L., and Regev, A. (2015). Single-cell RNA-seq reveals changes in cell cycle and differentiation programs upon aging of hematopoietic stem cells. Genome Res. 25, 1860-1872.

Kuleshov, M. V., Jones, M. R., Rouillard, A. D., Fernandez, N. F., Duan, Q., Wang, Z., Koplev, S., Jenkins, S. L., Jagodnik, K. M., Lachmann, A., et al 2016, "Enrichr: a comprehensive gene set enrichment analysis web server 2016 update", *Nucleic Acids Research*, vol. 44, no. W1, pp. 90.

Kumar, R. M., Cahan, P., Shalek, A. K., Satija, R., DaleyKeyser, A. J., Li, H., Zhang, J., Pardee, K., Gennert, D., Trombetta, J. J., Ferrante, T. C., Regev, A., Daley, G. Q. & Collins, J. J. Deconstructing transcriptional heterogeneity in pluripotent stem cells. *Nature.* 516, 56-61, doi:10.1038/nature13920 (2014). PMCID:4256722.

Labzin, L. I., Schmidt, S. V, Masters, S. L., Beyer, M., Krebs, W., Klee, K., Stahl, R., Lütjohann, D., Schultze, J. L., Latz, E., et al. (2015). ATF3 Is a Key Regulator of Macrophage IFN Responses. J. Immunol. 195, 4446-4455.

Lamb, J., Crawford, E. D., Peck, D., Modell, J. W., Blat, I. C., Wrobel, M. J., Lerner, J., Brunet, J., Subramanian, A., Ross, K. N., et al. (2006). The Connectivity Map: Using. Science (80-.). 313, 1929-1935.

Lambeth, L. S., Wise, T. G., Moore, R. J., Muralitharan, M. S. & Doran, T. J. 2006, "Comparison of bovine RNA polymerase III promoters for short hairpin RNA expression", *Animal Genetics*, vol. 37, no. 4, pp. 369-372.

Lara-Astiaso, D., Weiner, A., Lorenzo-Vivas, E., Zaretsky, I., Jaitin, D. A., David, E., Keren-Shaul, H., Mildner, A., Winter, D., Jung, S., Friedman, N. & Amit, I. Immunogenetics. Chromatin state dynamics during blood formation. *Science.* 345, 943-949, doi:10.1126/science.1256271 (2014). PMCID:4412442.

Laufer, C., Fischer, B., Billmann, M., Huber, W., and Boutros, M. (2013). Mapping genetic interactions in human cancer cells with RNAi and multiparametric phenotyping. Nat. Methods 10, 427-431.

Lawrence, M. S., Stojanov, P., Mermel, C. H., Robinson, J. T., Garraway, L. A., Golub, T. R., Meyerson, M., Gabriel, S. B., Lander, E. S., and Getz, G. (2014). Discovery and saturation analysis of cancer genes across 21 tumour types. Nature 505, 495-501.

Lee, A., Iwakoshi, N,N. & Glimcher, L. H. 2003, "XBP-1 regulates a subset of endoplasmic reticulum resident chaperone genes in the unfolded protein response", *Molecular and Cellular Biology*, vol. 23, no. 21, pp. 7448-7459.

Lee, M. N., Ye, C., Villani, A. C., Raj, T., Li, W., Eisenhaure, T. M., Imboywa, S. H., Chipendo, P. I., Ran, F. A., Slowikowski, K., Ward, L. D., Raddassi, K., McCabe, C., Lee, M. H., Frohlich, I. Y., Hafler, D. A., Kellis, M., Raychaudhuri, S., Zhang, F., Stranger, B. E., Benoist, C. O., De Jager, P. L., Regev, A. & Hacohen, N. Common genetic variants modulate pathogen-sensing responses in human dendritic cells. *Science*. 343, 1246980, doi: 10.1126/science.1246980 (2014). PMCID:4124741.

Liang, S., Zhang, W., McGrath, B. C., Zhang, P. & Cavener, D. R. 2006, "PERK (eIF2alpha kinase) is required to activate the stress-activated MAPKs and induce the expression of immediate-early genes upon disruption of ER calcium homoeostasis", *The Biochemical Journal*, vol. 393, no. Pt 1, pp. 201-209.

Liberali, P., Snijder, B., and Pelkmans, L. (2014). Single-cell and multivariate approaches in genetic perturbation screens. Nat. Rev. Genet. 16, 18-32.

Lin, J. H., Li, H., Yasumura, D., Cohen, H. R., Zhang, C., Panning, B., Shokat, K. M., Lavail, M. M. & Walter, P. 2007, "IRE1 signaling affects cell fate during the unfolded protein response", *Science* (*New York, N.Y.*), vol. 318, no. 5852, pp. 944-949.

Lin, Z., Chen, M. & Ma, Y. 2010, "The augmented lagrange multiplier method for exact recovery of corrupted low-rank matrices", *arXiv preprint arXiv:*1009.5055.

Lorthongpanich, C., Cheow, L. F., Balu, S., Quake, S. R., Knowles, B. B., Burkholder, W. F., Solter, D., and Messerschmidt, D. M. (2013). Single-cell DNA-methylation analysis reveals epigenetic chimerism in preimplantation embryos. Science 341, 1110-1112.

Lutz, R. & Bujard, H. 1997, "Independent and tight regulation of transcriptional units in *Escherichia coli* via the LacR/O, the TetR/O and AraC/11-12 regulatory elements", *Nucleic Acids Research*, vol. 25, no. 6, pp. 1203-1210.

Macosko, E. Z., Basu, A., Satija, R., Nemesh, J., Shekhar, K., Goldman, M., Tirosh, I., Bialas, A. R., Kamitaki, N., Martersteck, E. M., et al. (2015). Highly Parallel Genome-wide Expression Profiling of Individual Cells Using Nanoliter Droplets. Cell 161, 1202-1214.

Makarova, K. S., Haft, D. H., Barrangou, R., Brouns, S. J. J., Charpentier, E., Horvath, P., Moineau, S., Mojica, F. J. M., Wolf, Y. I., Yakunin, A. F., et al. (2011). Evolution and Classification of the CRISPR-Cas Systems. Nat. Rev. Microbiol. 9, 467-477.

Manolio, T. A., Collins, F. S., Cox, N. J., Goldstein, D. B., Hindorff, L. A., Hunter, D. J., McCarthy, M. I., Ramos, E. M., Cardon, L. R., Chakravarti, A., et al. (2009). Finding the missing heritability of complex diseases. Nature 461, 747-753.

Martincorena, I., and Campbell, P. J. (2015). Somatic mutation in cancer and normal cells. Science (80-.). 349, 1483-1489.

Meerbrey, K. L., Hu, G., Kessler, J. D., Roarty, K., Li, M. Z., Fang, J. E., Herschkowitz, J. I., Burrows, A. E., Ciccia, A., Sun, T., et al 2011, "The pINDUCER lentiviral toolkit for inducible RNA interference in vitro and in vivo", *Proceedings of the National Academy of Sciences of the United States of America*, vol. 108, no. 9, pp. 3665-3670.

Meier, J. A., and Larner, A. C. (2014). Toward a new STATe: the role of STATs in mitochondrial function. Semin. Immunol. 26, 20-28.

Melnikov, A., Murugan, A., Zhang, X., Tesileanu, T., Wang, L., Rogov, P., Feizi, S., Gnirke, A., Callan, C. G., Kinney, J. B., et al. (2012). Systematic dissection and optimization of inducible enhancers in human cells using a massively parallel reporter assay. Nat. Biotechnol. 30, 271-277.

Müller-Kuller, U., Ackermann, M., Kolodziej, S., Brendel, C., Fritsch, J., Lachmann, N., Kunkel, H., Lausen, J., Schambach, A., Moritz, T., et al 2015, "A minimal ubiquitous chromatin opening element (UCOE) effectively prevents silencing of juxtaposed heterologous promoters by epigenetic remodeling in multipotent and pluripotent stem cells", *Nucleic Acids Research*, pp. gkv019.

Munoz, D. M., Cassiani, P. J., Li, L., Billy, E., Korn, J. M., Jones, M. D., Golji, J., Ruddy, D. A., Yu, K., McAllister, G., et al 2016, "CRISPR Screens Provide a Comprehensive Assessment of Cancer Vulnerabilities but Generate False-Positive Hits for Highly Amplified Genomic Regions", *Cancer Discovery*, vol. 6, no. 8, pp. 900-913.

Na, Y. R., Kim, S. Y., Gaublomme, J. T., Shalek, A. K., Jorgolli, M., Park, H. & Yang, E. G. Probing enzymatic activity inside living cells using a nanowire-cell "sandwich" assay. *Nano Lett.* 13, 153-158, doi:10.1021/n13037068 (2013). PMCID:3541459.

Nagano, T., Lubling, Y., Stevens, T. J., Schoenfelder, S., Yaffe, E., Dean, W., Laue, E. D., Tanay, A., and Fraser, P. (2013). Single-cell Hi-C reveals cell-to-cell variability in chromosome structure. Nature 502, 59-64.

Neumann, B., Walter, T., Hériché, J.-K., Bulkescher, J., Erfle, H., Conrad, C., Rogers, P., Poser, I., Held, M., Liebel, U., et al. (2010). Phenotypic profiling of the human genome by time-lapse microscopy reveals cell division genes. Nature 464, 721-727.

Nishimasu, H., Ran, F. A., Hsu, P. D., Konermann, S., Shehata, S. I., Dohmae, N., Ishitani, R., Zhang, F. & Nureki, O. 2014, "Crystal structure of Cas9 in complex with guide RNA and target DNA", *Cell*, vol. 156, no. 5, pp. 935-949.

Nissim, L., Perli, S. D., Fridkin, A., Perez-Pinera, P. & Lu, T. K. 2014, "Multiplexed and programmable regulation of gene networks with an integrated RNA and CRISPR/Cas toolkit in human cells", *Molecular Cell*, vol. 54, no. 4, pp. 698-710.

Okabe, Y., and Medzhitov, R. (2014). Tissue-Specific Signals Control Reversible Program of Localization and Functional Polarization of Macrophages. Cell 157, 832-844.

Pardon, E., Laeremans, T., Triest, S., Rasmussen, S. G., Wohlkonig, A., Ruf, A., Muyldermans, S., Hol, W. G., Kobilka, B. K., and Steyaert, J. (2014). A general protocol for the generation of Nanobodies for structural biology. Nature protocols 9, 674-693.

Parnas, O., Jovanovic, M., Eisenhaure, T. M., Herbst, R. H., Dixit, A., Ye, C. J., Przybylski, D., Platt, R. J., Tirosh, I., Sanjana, N. E., et al. (2015). A Genome-wide CRISPR Screen in Primary Immune Cells to Dissect Regulatory Networks. Cell 162, 675-686.
Perfetto, S. P., Chattopadhyay, P. K., and Roederer, M. (2004). Seventeen-colour flow cytometry: unravelling the immune system. Nature reviews Immunology 4, 648-655.
Phillips, P. C. (2008). Epistasis—the essential role of gene interactions in the structure and evolution of genetic systems.
Platt, R. J., Chen, S., Zhou, Y., Yim, M. J., Swiech, L., Kempton, H. R., Dahlman, J. E., Parnas, O., Eisenhaure, T. M., Jovanovic, M., et al. (2014). CRISPR-Cas9 Knockin Mice for Genome Editing and Cancer Modeling. Cell 159, 440-455.
Plumb, R., Zhang, Z., Appathurai, S. & Mariappan, M. 2015, "A functional link between the co-translational protein translocation pathway and the UPR", *eLife*, vol. 4.
Pollen, A. A., Nowakowski, T. J., Shuga, J., Wang, X., Leyrat, A. A., Lui, J. H., Li, N., Szpankowski, L., Fowler, B., Chen, P., et al 2014, "Low-coverage single-cell mRNA sequencing reveals cellular heterogeneity and activated signaling pathways in developing cerebral cortex", *Nature Biotechnology*, vol. 32, no. 10, pp. 1053-1058.
Qi, L. S., Larson, M. H., Gilbert, L. A., Doudna, J. A., Weissman, J. S., Arkin, A. P., and Lim, W. A. (2013). Repurposing CRISPR as an RNA-Guided Platform for Sequence-Specific Control of Gene Expression. Cell 152, 1173-1183.
Rabani, M., Raychowdhury, R., Jovanovic, M., Rooney, M., Stumpo, D. J., Pauli, A., Hacohen, N., Schier, A. F., Blackshear, P. J., Friedman, N., Amit, I. & Regev, A. High-resolution sequencing and modeling identifies distinct dynamic RNA regulatory strategies. *Cell.* 159, 1698-1710, doi:10.1016/j.cell.2014.11.015 (2014). PMCID: 4272607.
Rajagopal, N., Srinivasan, S., Kooshesh, K., Guo, Y., Edwards, M. D., Banerjee, B., Syed, T., Emons, B. J. M., Gifford, D. K., and Sherwood, R. I. (2016). High-throughput mapping of regulatory DNA. Nat. Biotechnol. 34, 167-174.
Ramsauer, K., Farlik, M., Zupkovitz, G., Seiser, C., Kröger, A., Hauser, H., and Decker, T. (2007). Distinct modes of action applied by transcription factors STAT1 and IRF1 to initiate transcription of the IFN-gamma-inducible gbp2 gene. Proc. Natl. Acad. Sci. U.S.A 104, 2849-2854.
Ram, O., Goren, A., Amit, I., Shoresh, N., Yosef, N., Ernst, J., Kellis, M., Gymrek, M., Issner, R., Coyne, M., Durham, T., Zhang, X., Donaghey, J., Epstein, C. B., Regev, A. & Bernstein, B. E. Combinatorial patterning of chromatin regulators uncovered by genome-wide location analysis in human cells. *Cell.* 147, 1628-1639, doi: 10.1016/j.cell.2011.09.057 (2011). PMCID:3312319.
Ran, F. A., Cong, L., Yan, W. X., Scott, D. A., Gootenberg, J. S., Kriz, A. J., Zetsche, B., Shalem, O., Wu, X., Makarova, K. S., et al. (2015). In vivo genome editing using *Staphylococcus aureus* Cas9. Nature 520, 186-191.
Ron, D. & Walter, P. 2007, "Signal integration in the endoplasmic reticulum unfolded protein response", *Nature Reviews. Molecular Cell Biology*, vol. 8, no. 7, pp. 519-529.
Rosvall, M., and Bergstrom, C. T. (2008). Maps of random walks on complex networks reveal community structure. Proc. Natl. Acad. Sci. 105, 1118-1123.
Sack, L. M., Davoli, T., Xu, Q., Li, M. Z. & Elledge, S. J. 2016, "Sources of Error in Mammalian Genetic Screens", *G3* (*Bethesda, Md.*), vol. 6, no. 9, pp. 2781-2790.
Sackton, T. B., and Hartl, D. L. (2016). Perspective Genotypic Context and Epistasis in Individuals and Populations. Cell 166, 279-287.
Satija, R., Farrell, J. A., Gennert, D., Schier, A. F. & Regev, A. Spatial reconstruction of single-cell gene expression data. *Nature biotechnology.* 33, 495-502, doi:10.1038/nbt.3192 (2015).
Sauvageau, M., Goff, L. A., Lodato, S., Bonev, B., Groff, A. F., Gerhardinger, C., Sanchez-Gomez, D. B., Hacisuleyman, E., Li, E., Spence, M., Liapis, S. C., Mallard, W., Morse, M., Swerdel, M. R., D'Ecclessis, M. F., Moore, J. C., Lai, V., Gong, G., Yancopoulos, G. D., Frendewey, D., Kellis, M., Hart, R. P., Valenzuela, D. M., Arlotta, P. & Rinn, J. L. Multiple knockout mouse models reveal lincRNAs are required for life and brain development. *eLife.* 2, e01749, doi:10.7554/eLife.01749 (2013). PMCID: 3874104.
Sawyers, C. (2004). Targeted cancer therapy. Nature 432, 294-297.
Schölkopf, B., Platt, J. C., Shawe-Taylor, J., Smola, A. J. & Williamson, R. C. 2001, "Estimating the support of a high-dimensional distribution", *Neural computation*, vol. 13, no. 7, pp. 1443-1471.
Schwartz, S., Agarwala, S. D., Mumbach, M. R., Jovanovic, M., Mertins, P., Shishkin, A., Tabach, Y., Mikkelsen, T. S., Satija, R., Ruvkun, G., Carr, S. A., Lander, E. S., Fink, G. R. & Regev, A. High-resolution mapping reveals a conserved, widespread, dynamic mRNA methylation program in yeast meiosis. *Cell.* 155, 1409-1421, doi:10.1016/j.cell.2013.10.047 (2013). PMCID:3956118.
Schwartz, S., Bernstein, D. A., Mumbach, M. R., Jovanovic, M., Herbst, R. H., Leon-Ricardo, B. X., Engreitz, J. M., Guttman, M., Satija, R., Lander, E. S., Fink, G. & Regev, A. Transcriptome-wide mapping reveals widespread dynamic-regulated pseudouridylation of ncRNA and mRNA. *Cell.* 159, 148-162, doi:10.1016/j.cell.2014.08.028 (2014). PMCID:4180118.
Schwartz, S., Mumbach, M. R., Jovanovic, M., Wang, T., Maciag, K., Bushkin, G. G., Mertins, P., Ter-Ovanesyan, D., Habib, N., Cacchiarelli, D., Sanjana, N. E., Freinkman, E., Pacold, M. E., Satija, R., Mikkelsen, T. S., Hacohen, N., Zhang, F., Carr, S. A., Lander, E. S. & Regev, A. Perturbation of m6A writers reveals two distinct classes of mRNA methylation at internal and 5' sites. *Cell reports.* 8, 284-296, doi:10.1016/j.celrep.2014.05.048 (2014). PMCID:4142486.
Shahni, R., Cale, C. M., Anderson, G., Osellame, L. D., Hambleton, S., Jacques, T. S., Wedatilake, Y., Taanman, J.-W., Chan, E., Qasim, W., et al. (2015). Signal transducer and activator of transcription 2 deficiency is a novel disorder of mitochondrial fission. Brain 138, 2834-2846.
Shakya, A., Callister, C., Goren, A., Yosef, N., Garg, N., Khoddami, V., Nix, D., Regev, A. & Tantin, D. Pluripotency transcription factor Oct4 mediates stepwise nucleosome demethylation and depletion. *Mol Cell Biol.* 35, 1014-1025, doi:10.1128/MCB.01105-14 (2015). PMCID: 4333097.
Shalek, A. K., Gaublomme, J. T., Wang, L., Yosef, N., Chevrier, N., Andersen, M. S., Robinson, J. T., Pochet, N., Neuberg, D., Gertner, R. S., Amit, I., Brown, J. R., Hacohen, N., Regev, A., Wu, C. J. & Park, H. Nanowire-mediated delivery enables functional interrogation of primary immune cells: application to the analysis of chronic lymphocytic leukemia. Nano Lett. 12, 6498-6504, doi: 10.1021/n13042917 (2012). PMCID:3573729.
Shalek, A. K., Satija, R., Adiconis, X., Gertner, R. S., Gaublomme, J. T., Raychowdhury, R., Schwartz, S., Yosef, N., Malboeuf, C., Lu, D., et al. (2013). Single-cell transcriptomics reveals bimodality in expression and splicing in immune cells. Nature 498, 236-240.
Shalek, A. K., Satija, R., Shuga, J., Trombetta, J. J., Gennert, D., Lu, D., Chen, P., Gertner, R. S., Gaublomme, J. T., Yosef, N., et al. (2014). Single-cell RNA-seq reveals dynamic paracrine control of cellular variation. Nature 510, 363-369.
Shalem, O., Sanjana, N. E., Hartenian, E., Shi, X., Scott, D. A., Mikkelsen, T. S., Heckl, D., Ebert, B. L., Root, D. E., Doench, J. G., et al. (2014). Genome-scale CRISPR-Cas9 knockout screening in human cells. Science 343, 84-87.
Shalem, O., Sanjana, N. E. & Zhang, F. 2015, "High-throughput functional genomics using CRISPR-Cas9", *Nature Reviews Genetics*, vol. 16, no. 5, pp. 299-311.
Shao, H., Burrage, L. C., Sinasac, D. S., Hill, A. E., Ernest, S. R., O'Brien, W., Courtland, H.-W., Jepsen, K. J., Kirby, A., Kulbokas, E. J., et al. (2008). Genetic architecture of complex traits: large phenotypic effects and pervasive epistasis. Proc. Natl. Acad. Sci. U.S.A 105, 19910-19914.
Shendure, J., and Akey, J. M. (2015). The origins, determinants, and consequences of human mutations. Science (80-.). 349, 1478-1483.
Shendure, J., and Fields, S. (2016). Massively Parallel Genetics. Genetics 203, 617-619.
Shi, J., Wang, E., Milazzo, J. P., Wang, Z., Kinney, J. B. & Vakoc, C. R. 2015, "Discovery of cancer drug targets by CRISPR-Cas9 screening of protein domains", *Nature biotechnology*, vol. 33, no. 6, pp. 661-667.
Shoulders, M. D., Ryno, L. M., Genereux, J. C., Moresco, J. J., Tu, P. G., Wu, C., Yates, J. R., Su, A. I., Kelly, J. W. & Wiseman, R. L. 2013, "Stress-independent activation of XBP1s and/or ATF6 reveals three functionally diverse ER proteostasis environments", *Cell Reports*, vol. 3, no. 4, pp. 1279-1292.
Sidrauski, C., Tsai, J. C., Kampmann, M., Hearn, B. R., Vedantham, P., Jaishankar, P., Sokabe, M., Mendez, A. S., Newton, B. W., Tang, E. L., et al 2015, "Pharmacological dimerization and activation of the exchange factor eIF2B antagonizes the integrated stress response", *eLife*, vol. 4, pp. e07314.
Sisler, J. D., Morgan, M., Raje, V., Grande, R. C., Derecka, M., Meier, J., Cantwell, M., Szczepanek, K., Korzun, W. J., Lesnefsky, E. J., et al. (2015). The Signal Transducer and Activator of Transcription 1 (STAT1) Inhibits Mitochondrial Biogenesis in Liver and Fatty Acid Oxidation in Adipocytes. PLoS One 10, e0144444.
Smith, R. P., Taher, L., Patwardhan, R. P., Kim, M. J., Inoue, F., Shendure, J., Ovcharenko, I., and Ahituv, N. (2013). Massively parallel decoding of mammalian regulatory sequences supports a flexible organizational model. Nat. Genet. 45, 1021-1028.
Smith, Z. D., Chan, M. M., Humm, K. C., Karnik, R., Mekhoubad, S., Regev, A., Eggan, K. & Meissner, A. DNA methylation dynamics of the human preimplantation embryo. *Nature*. 511, 611-615, doi:10.1038/nature13581 (2014). PMCID:4178976.
Smith, Z. D., Chan, M. M., Mikkelsen, T. S., Gu, H., Gnirke, A., Regev, A. & Meissner, A. A unique regulatory phase of DNA methylation in the early mammalian embryo. *Nature*. 484, 339-344, doi:10.1038/nature10960 (2012). PMCID:3331945.
Smyth, R. P., Davenport, M. P. & Mak, J. 2012, "The origin of genetic diversity in HIV-1", *Virus Research*, vol. 169, no. 2, pp. 415-429.
Snijder, B., Sacher, R., Rämö, P., Damm, E., Liberali, P. & Pelkmans, L. 2009, "Population context determines cell-to-cell variability in endocytosis and virus infection", *Nature*, vol. 461, no. 7263, pp. 520-523.
Sokolov, A., Carlin, D. E., Paull, E. O., Baertsch, R., and Stuart, J. M. (2016). Pathway-Based Genomics Prediction using Generalized Elastic Net. PLOS Comput. Biol. 12, e1004790.
Stegle, O., Teichmann, S. A., and Marioni, J. C. (2015). Computational and analytical challenges in single-cell transcriptomics. Nat. Rev. Genet. 16, 133-145.
Sun, L., Goff, L. A., Trapnell, C., Alexander, R., Lo, K. A., Hacisuleyman, E., Sauvageau, M., Tazon-Vega, B., Kelley, D. R., Hendrickson, D. G., Yuan, B., Kellis, M., Lodish, H. F. & Rinn, J. L. Long noncoding RNAs regulate adipogenesis. *Proceedings of the National Academy of Sciences of the United States of America*. 110, 3387-3392, doi:10.1073/pnas.1222643110 (2013). PMCID:3587215.
Tanenbaum, M. E., Gilbert, L. A., Qi, L. S., Weissman, J. S. & Vale, R. D. 2014, "A protein-tagging system for signal amplification in gene expression and fluorescence imaging", *Cell*, vol. 159, no. 3, pp. 635-646.
Tang, H., Klopfenstein, D., Pedersen, B., Flick, P., Sato, K., Ramirez, F., Yunes, J., and Mungall, C. (2015). GOATOOLS: Tools for Gene Ontology.
Theile, C. S., Witte, M. D., Blom, A. E., Kundrat, L., Ploegh, H. L., and Guimaraes, C. P. (2013). Site-specific N-terminal labeling of proteins using sortase-mediated reactions. Nature protocols 8, 1800-1807.
Thomason, L. C., Costantino, N. & Court, D. L. 2007, "*E. coli* genome manipulation by P1 transduction", *Current Protocols in Molecular Biology*, vol. Chapter 1, pp. Unit 1.17.
Thomason, L. C., Sawitzke, J. A., Li, X., Costantino, N. & Court, D. L. 2014, "Recombineering: genetic engineering in bacteria using homologous recombination", *Current Protocols in Molecular Biology*, vol. 106, pp. 39.
Tong, A. H. Y. (2004). Global Mapping of the Yeast Genetic Interaction Network. Science (80-.). 303, 808-813.
Trapnell, C. 2015, "Defining cell types and states with single-cell genomics", *Genome Research*, vol. 25, no. 10, pp. 1491-1498.
Trapnell, C., Cacchiarelli, D., Grimsby, J., Pokharel, P., Li, S., Morse, M., Lennon, N. J., Livak, K. J., Mikkelsen, T. S. & Rinn, J. L. The dynamics and regulators of cell fate decisions are revealed by pseudotemporal ordering of single cells. *Nature biotechnology*. 32, 381-386, doi:10.1038/nbt.2859 (2014). PMCID:4122333.
Trapnell, C., Hendrickson, D. G., Sauvageau, M., Goff, L., Rinn, J. L. & Pachter, L. Differential analysis of gene regulation at transcript resolution with RNA-seq. *Nature biotechnology*. 31, 46-53, doi:10.1038/nbt.2450 (2013). PMCID:3869392.
Trombetta, J. J., Gennert, D., Lu, D., Satija, R., Shalek, A. K. & Regev, A. Preparation of Single-Cell RNA-Seq Libraries for Next Generation Sequencing. *Curr Protoc Mol Biol*. 107, 4 22 21-24 22 17, doi:10.1002/0471142727.mb0422s107 (2014). PMCID:4338574.
Tsumura, A., Hayakawa, T., Kumaki, Y., Takebayashi, S., Sakaue, M., Matsuoka, C., Shimotohno, K., Ishikawa, F., Li, E., Ueda, H. R., et al. (2006). Maintenance of self-renewal ability of mouse embryonic stem cells in the absence of DNA methyltransferases Dnmt1, Dnmt3a and Dnmt3b. Genes to Cells 11, 805-814.
Tussiwand, R., Lee, W.-L., Murphy, T. L., Mashayekhi, M., KC, W., Albring, J. C., Satpathy, A. T., Rotondo, J. A., Edelson, B. T., Kretzer, N. M., et al. (2012). Compensatory dendritic cell development mediated by BATF-IRF interactions. Nature 490, 502-507.

Tyynismaa, H., Carroll, C. J., Raimundo, N., Ahola-Erkkilä, S., Wenz, T., Ruhanen, H., Guse, K., Hemminki, A., Peltola-Mjøsund, K. E., Tulkki, V., et al 2010, “Mitochondrial myopathy induces a starvation-like response”, *Human Molecular Genetics, vol.* 19, no. 20, pp. 3948-3958.

Van Der Maaten, L. 2014, “Accelerating t-SNE using tree-based algorithms.”, *Journal of machine learning research*, vol. 15, no. 1, pp. 3221-3245.

Visscher, P. M., Brown, M. A., Mccarthy, M. I., and Yang, J. (2012). Five Years of GWAS Discovery. Am. J. Hum. Genet. 90, 7-24.

Walter, P. & Ron, D. 2011, “The unfolded protein response: from stress pathway to homeostatic regulation”, *Science* (*New York, N.Y.*), vol. 334, no. 6059, pp. 1081-1086.

Wang, L., Shalek, A. K., Lawrence, M., Ding, R., Gaublomme, J. T., Pochet, N., Stojanov, P., Sougnez, C., Shukla, S. A., Stevenson, K. E., Zhang, W., Wong, J., Sievers, Q. L., MacDonald, B. T., Vartanov, A. R., Goldstein, N. R., Neuberg, D., He, X., Lander, E., Hacohen, N., Regev, A., Getz, G., Brown, J. R., Park, H. & Wu, C. J. Somatic mutation as a mechanism of Wnt/beta-catenin pathway activation in CLL. *Blood.* 124, 1089-1098, doi: 10.1182/blood-2014-01-552067 (2014). PMCID: 4133483.

Wang, T., Wei, J. J., Sabatini, D. M., and Lander, E. S. (2014). Genetic screens in human cells using the CRISPR-Cas9 system. Science 343, 80-84.

Wang, T., Birsoy, K., Hughes, N. W., Krupczak, K. M., Post, Y., Wei, J. J., Lander, E. S., and Sabatini, D. M. (2015). Identification and characterization of essential genes in the human genome. Science (80-.). 350, 1096-1101.

Wang, Y., Shen, J., Arenzana, N., Tirasophon, W., Kaufman, R. J. & Prywes, R. 2000, “Activation of ATF6 and an ATF6 DNA binding site by the endoplasmic reticulum stress response”, *The Journal of Biological Chemistry*, vol. 275, no. 35, pp. 27013-27020.

Wei, L., Fan, M., Xu, L., Heinrich, K., Berry, M. W., Homayouni, R., and Pfeffer, L. M. (2008). Bioinformatic analysis reveals cRel as a regulator of a subset of interferon-stimulated genes. J. Interferon Cytokine Res. 28, 541-551.

Washietl, S., Kellis, M. & Garber, M. Evolutionary dynamics and tissue specificity of human long noncoding RNAs in six mammals. *Genome Res.* 24, 616-628, doi:10.1101/gr.165035.113 (2014). PMCID:3975061.

Weinberger, E. D. (1991). Fourier and Taylor series on fitness landscapes. Biol. Cybern. 65, 321-330.

Wong, A. S. L., Choi, G. C. G., Cui, C. H., Pregernig, G., Milani, P., Adam, M., Perli, S. D., Kazer, S. W., Gaillard, A., Hermann, M., et al. (2016). Multiplexed barcoded CRISPR-Cas9 screening enabled by CombiGEM. Proc. Natl. Acad. Sci. 113, 2544-2549.

Wu, C., Yosef, N., Thalhamer, T., Zhu, C., Xiao, S., Kishi, Y., Regev, A. & Kuchroo, V. K. Induction of pathogenic TH17 cells by inducible salt-sensing kinase SGK1. *Nature.* 496, 513-517, doi:10.1038/nature11984 (2013). PMCID:3637879.

Yosef, N., and Regev, A. (2016). Writ large: Genomic dissection of the effect of cellular environment on immune response. Science (80-.). 354, 64-68.

Yosef, N., Shalek, A. K., Gaublomme, J. T., Jin, H., Lee, Y., Awasthi, A., Wu, C., Karwacz, K., Xiao, S., Jorgolli, M., Gennert, D., Satija, R., Shakya, A., Lu, D. Y., Trombetta, J. J., Pillai, M. R., Ratcliffe, P. J., Coleman, M. L., Bix, M., Tantin, D., Park, H., Kuchroo, V. K. & Regev, A. Dynamic regulatory network controlling TH17 cell differentiation. *Nature.* 496, 461-468, doi:10.1038/nature11981 (2013). PMCID:3637864.

Yu, C., Mannan, A. M., Yvone, G. M., Ross, K. N., Zhang, Y.-L., Marton, M. A., Taylor, B. R., Crenshaw, A., Gould, J. Z., Tamayo, P., et al. (2016). High-throughput identification of genotype-specific cancer vulnerabilities in mixtures of barcoded tumor cell lines. Nat. Biotechnol. 34, 419-423.

Zalatan, J. G., Lee, M. E., Almeida, R., Gilbert, L. A., Whitehead, E. H., La Russa, M., Tsai, J. C., Weissman, J. S., Dueber, J. E., Qi, L. S., et al. (2015). Engineering Complex Synthetic Transcriptional Programs with CRISPR RNA Scaffolds. Cell 160, 339-350.

Zetsche, B., Gootenberg, J. S., Abudayyeh, O. O., Slaymaker, I. M., Makarova, K. S., Essletzbichler, P., Volz, S. E., Joung, J., van der Oost, J., Regev, A., et al. (2015). Cpf1 Is a Single RNA-Guided Endonuclease of a Class 2 CRISPR-Cas System. Cell 163, 759-771.

Zetsche, B., Heidenreich, M., Mohanraju, P., Fedorova, I., Kneppers, J., DeGennaro, E. M., Winblad, N., Choudhury, S. R., Abudayyeh, O. O., Gootenberg, J. S., et al 2016, “Multiplex gene editing by CRISPR-Cpf1 through autonomous processing of a single crRNA array”, *bioRxiv.*

Zhang, X., Liu, Q., Luo, C., Deng, Y., Cui, K. & Shi, D. 2014, “Identification and characterization of buffalo 7SK and U6 pol III promoters and application for expression of short hairpin RNAs”, *International Journal of Molecular Sciences*, vol. 15, no. 2, pp. 2596-2607.

Zheng, G. X. Y., Terry, J. M., Belgrader, P., Ryvkin, P., Bent, Z. W., Wilson, R., Ziraldo, S. B., Wheeler, T. D., McDermott, G. P., Zhu, J., et al 2016, “Massively parallel digital transcriptional profiling of single cells”, *bioRxiv.*

Zuk, O., Hechter, E., Sunyaev, S. R., and Lander, E. S. (2012). The mystery of missing heritability: Genetic interactions create phantom heritability. Proc. Natl. Acad. Sci. U.S.A 109, 1193-1198.

Example 36: Growth-Based Group Testing: Shuffle-Seq

This example shows exemplary methods for performing Shuffle-seq, high-throughput testing of synergistic gene interactions in mammalian cells.

Biological functions arise from the collective activities of gene products. The emergent synergies which shape and are in turn shaped by the processes of evolution have been harnessed for the creation of stem cell therapeutics and combinatorial cancer treatments. Large scale screening efforts have been extended to quantify pairwise interactions between genes and a limited number of sets of three-way interactions. However, due to the exponential growth in the number of combinations possible as the size of the set being tested increases, the logic by which genes synergistically compute function is impossible to completely enumerate. This example shows exemplary methods that enable screening of large sets of genetic perturbations. Applicants applied it to screening for mechanisms of drug resistance in a melanoma model. The methods for generating and analyzing combinatorial genetic manipulations can have broad utility for drug discovery. The methods described herein provide a new paradigm for genetic screening using group testing approaches.

As the scale of genomics datasets increases, many phenotypes can be modulated by almost any gene through the network propagation of its impact. This finding motivates the importance of understanding how these networks are structured. However, it is challenging to generate datasets of a sufficient scale to test for all possible interactions between any sizeable set. In the case of genetic networks, the size of gene sets of interest can range from the tractable tens to genome-wide analyses over tens of thousands. As larger genomic datasets are generated, the pairwise interaction space for cancer vulnerabilities, modulation of gene expression, and population fitness effects can be tested using observational data. As an alternative, combinations of genetic manipulations can be experimentally generated in cell models, thus controlling for diverse genetic background. In mammalian systems, studies have examined the impact of pairwise gene interactions for cell growth, drug resistance, cell morphology, and gene expressio—for small subsets genes.

In yeast, all pairs of genetic deletions have been constructed over the course of ten years. Recently, the work was extended to a small percentage of the total number of sets of three gene deletions. It was shown that the prevalence of pairwise interactions is sparse (<2% overall). While it is likely that the total number of three-way interactions is far larger numerically, they are fewer as a percentage of the total set of possibilities. Still, these higher order genetic interactions can play a major role in the evolution of genetic networks, and be translationally leveraged for cellular reprogramming.

Current combinatorial screening methods are limited in their ability to screen to pairwise or three-way interactions. Broadly, these methods can be grouped into those that create a single barcoded vector containing multiple perturbations and those that perform single cell measurements to determine the set of perturbations present in a cell. The former group of methods is limited in the total number of perturbations that can be introduced by the titer of viral vectors that become progressively longer and their stability as increasing numbers of repetitive elements are introduced. The later group of methods rely on massively parallel single cell methods like droplet microfluidics to achieve scales on the order of hundreds of thousands of cells. However, it is cost prohibitive to use these methods for combinatorial screening beyond small sets of genes (See table below). The Shuffle-seq methods described herein allow for simultaneously profiling the effect of 1 million combinations of perturbations on cell phenotypes, e.g., cell viability.

Guide to the Miserly-Costs to Profile 1 million cells

| | Shuffle-seq | CRISPR screen | Perturb-seq |
|---|---|---|---|
| Oligo Array | 4,000 | 5,000 | 4,000 |
| Cloning Cost | 500 | 500 | 500 |
| NGS Verification | 500 | 500 | 500 |
| Virus Preparation | 500 | 500 | 500 |
| Tissue Culture | 1,000 | 1,000 | 1,000 |
| Library Prep | 200 | 1,000 | 200,000 |
| Perturbation Readout | 1,200 | 2,500 | 2,500 |
| RNA-seq | N/A | N/A | 48,000 |
| Totals | $7,900 | $11,000 | $257,000 |

The methods herein took advantage of the ability to couple perturbation information at a single cell level with the cost and scale of standard pooled screening approaches. This method, called Shuffle-seq, was able to infer the clonal effects associated with millions of genetic perturbations using standard pooled screening reagents (FIGS. 94A-94B and 95A-95F). It used unique transduction barcodes (UTB) such that the probability of two cells getting the same combination of perturbation and barcode was extremely low. Multiple perturbations were delivered into the cell using a high multiplicity of infection. The cells were allowed to expand and then sorted into a multiwell plate (FIG. 94A). The probability of barcode perturbation pairs co-occurring was significantly higher for those that originated from the same original cell and could be used for inference. If, for a given phenotype, like drug resistance or reprogramming, only a small number of perturbations create the phenotype, it is possible to leverage Shuffle-seq to perform group testing of perturbations at large scale to rapidly identify the relevant synergies (FIG. 94B).

When implementing a Shuffle-seq screen, detection of the perturbation-UTB may be maximized. To achieve this goal, we modified the CROP-seq plasmid, which generated a polyadenylated sgRNA transcript, to include an optimized trRNA and a UTB (FIG. 96A). These modifications were inserted during the sgRNA cloning step (FIG. 96B) and did not reduce cutting efficiency (FIG. 96C). By deep sequencing our CRISPR-UTB library, we showed that the number of distinct sgRNA-UTB pairs we had was greater than 50 million (FIGS. 96D and 96E).

Next, clones may present in an intermediate number of wells in order to allow for accurate inference with reasonable sequencing depth (FIG. 96B). We developed a procedure, akin to high dynamic range photography, in which a sort schematic was devised to optimally match the observed distribution of clonal abundances seen through bulk sequencing when encoding was determined as the presence or absence of a particular sgRNA-UTB across wells (FIGS. 96C and 96D). We noted that it was also possible to use quantitative information with respect to the number of cells present in each well to encode clonal association between sgRNA-UTBs. We performed simulations to determine the relationship between detection probability, clonal fraction, and barcode complexity with statistical power to infer clones (FIGS. 95E and 95F) and found that for reasonable detection efficiency and sequencing depth a 96 well plate could be used to encode a million clones, while a 384 well plate could be used to encode well over a billion.

To assess the feasibility of the method, we applied Shuffle-seq to a melanoma drug resistance model of vemurafenib (B-Raf inhibitor) to A375 cells (a malignant melanoma model) that had previously been used for a positive selection CRISPR screen with vemurafenib (FIG. 97A). [30] Between 1 and 160 sgRNA-UTBs were present per cell as determined by clonal outgrowth of a subset of cells (FIG. 97B). By applying Shuffle-seq to the resulting clones, we found 60% of surviving clones contained at least one gene perturbation that overlapped with those found in the previous study (FIG. 97C).

Spatially encoded barcodes can be used to infer clonal effects associated with millions of genetic perturbations. Parameter of the shuffle-seq methods include number of wells a clone is in, detection efficiency or p (observing a barcode/barcode was present), and barcode diversity. The probability of barcode perturbation pairs cooccurring was significantly higher for those that originated from the same original cell and can be used for inference (FIG. 98).

The methods shown herein are described below:

Plasmid generation: The CROP-seq plasmid (Addgene 86708) was digested to remove the scaf-fold, and three plasmids containing different resistance markers (Puromycin, Hygromycin, and Blasticidin) were created. An oligo array was constructed to contain CRISPR knockout guides and CRISPRi guides that were depleted for guides targeting essential genes and control guides (targeting both intergenic regions and non-targeting guides) based on sgRNAs derived from Doench et al. (2016), Horlbeck, et al. (2016), Morgens et al. (2017).

The oligo pool was amplified first using subpool specific primers, and then with the following primers to add on the UTB and plasmid homology result in a 220 bp product.

```
Primer 1
                                        (SEQ. I.D. No. 67)
TAACTTGAAAGTATTTCGATTTCTTGGCTTTATATATCTTGTGGAAAGG

ACGAAACACCG

Primer 2
                                        (SEQ. I.D. No. 68)
TCTCAAGATCTAGTTACGCCAAGCTTNNNNNNNNNNNNNNNaaaaaagca

ccgactcggtgccac tttttcaagttgataacggactagcc
```

Cloning proceeds as described by Fulco et al. (2016).

Lentivirus production: Applicants plated 700,000 HEK293T cells on 6-well plates and 24 hours later transfected with 1 μg dVPR, 300 ng VSVG, and 1.2 μg transfer plasmid using lipofectamine 2000.

Statistical Inference of Clones: Two procedures were used to infer clonal associations between sgRNA-UTB pairs. Both started with a matrix of sgRNA-UTBs read counts across wells of a multiwell plate. In the first approach, when the loading of a given clone into the multiwell plate was less than one per well on average, association is encoded as by binarization of this matrix (after within well normalization and filtering to remove spurious sgRNA-UTBs associated with sequencing and PCR errors). Permutations of nonzero elements of the matrix were performed which preserve the number of nonzero elements in each row and in each column. The permuted was matrix was used to compute a null distribution of sgRNA-UTB correlations to determine thresholds for significance when compared to those from the non-permuted matrix.

Similarly, for cases in which the number of cells per well greatly exceeded one per well, permutation was performed within sets of wells that have similar numbers of clones in them. Again, the observed correlations of sgRNA-UTBs pairs were compared to the empirical null distribution in order to compute significance. Locally sensitive hashing (LSH) was used when the number of sgRNA-UTBs to be tested was larger than several thousand.

The Shuffle-seq methods described herein enabled large scale combinatorial screening by leveraging the encoding capacity of multiwell plates. The technology is applied to a melanoma resistance screen. It recovered previously identified single gene hits as well as uncovers potential new synergistic paths to resistance. The methods herein provide a new paradigm of combinatorial screening in which each cell contains tens to hundreds of perturbations. This approach can accelerate the discovery of new synergistic combinations of perturbations that lead to translationally relevant phenotypes.

REFERENCES

Takahashi, K. & Yamanaka, S. Induction of pluripotent stem cells from mouse embryonic and adult fibroblast cultures by defined factors. Cell 126, 663-76 (2006).

Jaenisch, R. & Young, R. Stem Cells, the Molecular Circuitry of Pluripotency and Nuclear Reprogramming. Cell 132, 567-582 (2008).

O'Neil, N. J., Bailey, M. L. & Hieter, P. Synthetic lethality and cancer. Nat. Rev. Genet. 18, 613-623 (2017).

Rauscher, B., Heigwer, F., Boutros, M., Henkel, L. & Hielscher, T. Toward an integrated map of genetic interactions in cancer cells. 1-17 (2018). doi:10.15252/msb.20177656

Ashworth, A., Lord, C. J. & Reis-Filho, J. S. Genetic Interactions in Cancer Progression and Treatment. Cell 145, 30-38 (2011).

Costanzo, M. et al. A global genetic interaction network maps a wiring diagram of cellular function. Science 353, (2016).

Boyle, E. A., Li, Y. I. & Pritchard, J. K. An Expanded View of Complex Traits: From Polygenic to Omnigenic. Cell 169, 1177-1186 (2017).

Jerby-Arnon, L. et al. Predicting cancer-specific vulnerability via data-driven detection of synthetic lethality. Cell 158, 1199-1209 (2014).

Bloom, J. et al. The role of genetic interactions in yeast quantitative traits. 1-22 (2015). doi:10.1101/019513

Sohail, M. et al. Negative selection in humans and fruit flies involves synergistic epistasis. 542, 539-542 (2017).

Shen, J. P. et al. Combinatorial CRISPR-Cas9 screens for de novo mapping of genetic interactions. 14, (2017).

Najm, F. J. et al. Orthologous CRISPR-Cas9 enzymes for combinatorial genetic screens. Nat. Publ. Gr. 36, 179-189 (2018).

Han, K. et al. Synergistic drug combinations for cancer identified in a CRISPR screen for pairwise genetic interactions. (2017). doi:10.1038/nbt.3834

Wong, A. S. L. et al. Multiplexed barcoded CRISPR-Cas9 screening enabled by CombiGEM. Proc. Natl. Acad. Sci. 113, 2544-2549 (2016).

Bassik, M. C. et al. A systematic mammalian genetic interaction map reveals pathways underlying ricin susceptibility. Cell 152, 909-22 (2013).

Laufer, C., Fischer, B., Billmann, M., Huber, W. & Boutros, M. Mapping genetic interactions in human cancer cells with RNAi and multiparametric phenotyping. Nat. Methods 10, 427-31 (2013).

Dixit, A. et al. Perturb-Seq: Dissecting Molecular Circuits with Scalable Single-Cell RNA Profiling of Pooled Genetic Screens. Cell 167, 1853-1866.e17 (2016).

Adamson, B. et al. A Multiplexed Single-Cell CRISPR Screening Platform Enables Systematic Dissection of the Resource A Multiplexed Single-Cell CRISPR Screening Platform Enables Systematic Dissection. 1867-1882 (2016). doi:10.1016/j.cell.2016.11.048

Jaitin, D. A. et al. Dissecting Immune Circuits by Linking CRISPR-Pooled Screens with Single-Cell RNA-Seq Resource Dissecting Immune Circuits by Linking CRISPR-Pooled Screens with Single-Cell RNA-Seq. Cell 167, 1883-1888.e15 (2016).

Tong, A. Y. et al. Global Mapping of the Yeast Genetic Interaction Network. 303, 808-814 (2004).

Costanzo, M. et al. The Genetic Landscape of a Cell. Science (80-.). 327, 425-431 (2010).

Kuzmin, E. et al. Systematic analysis of complex genetic interactions. Science (80-.). 360, eaao1729 (2018).

Hartl, D. L. What can we learn from fitness landscapes? Curr. Opin. Microbiol . . . 21, 51-57 (2014).

Weinreich, D. M., Lan, Y., Wylie, C. S. & Heckendorn, R. B. Should evolutionary geneticists worry about higher-order epistasis? Curr. Opin. Genet. Dev. 23, 700-707 (2013).

Michlits, G. et al.CRISPR-UMI: single-cell lineage tracing of pooled CRISPR-Cas9 screens. Nat. Methods 14, 1191-1197 (2017).

Schmierer, B. et al. CRISPR/Cas9 screening using unique molecular identifiers. Mol. Syst. Biol. 13, 945 (2017).

Howie, B. et al. High-throughput pairing of T cell receptor and sequences. Sci. Transl. Med. 7, 301ra131-301ra131 (2015).

Datlinger, P. et al. Pooled CRISPR screening with single-cell transcriptome readout. Nat. Methods 14, 297-301 (2017).

Chen, B. et al. Dynamic Imaging of Genomic Loci in Living Human Cells by an Optimized CRISPR/Cas System. Cell 155, 1479-1491 (2013).

Shalem, O. et al. Genome-scale CRISPR-Cas9 knockout screening in hu-man cells. Science 343, 84-7 (2014).

Doench, J. G. et al. Optimized sgRNA design to maximize activity and minimize off-target effects of CRISPR-Cas9. Nat. Biotechnol. 34, 184-191 (2016).

Horlbeck, M. A. et al. Compact and highly active next-generation libraries for CRISPR-mediated gene repression and activation. Elife 5, 1-20 (2016).

Morgens, D. W. et al. Genome-scale measurement of off-target activity us-ing Cas9 toxicity in high-throughput screens. Nat. Commun. 8, 1-8 (2017).

Fulco, C. P. et al. Systematic mapping of functional enhancer-promoter connections with CRISPR interference. Science (80-.). 354, 769-773 (2016).

Strona, G., Nappo, D., Boccacci, F., Fattorini, S. & San-Miguel-Ayanz, J. A fast and unbiased procedure to randomize ecological binary matrices with fixed row and column totals. Nat. Commun. 5, (2014).

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

Exemplary embodiments of the invention may be further described by the following numbered paragraphs:

1. A method of reconstructing a cellular network or circuit, comprising introducing at least 1, 2, 3, 4 or more single-order or combinatorial perturbations to each cell in a population of cells;

measuring genomic, genetic and/or phenotypic differences of each cell and coupling combinatorial perturbations with measured differences to infer intercellular and/or intracellular networks or circuits.

2. The method of paragraph 1, wherein the single-order or combinatorial perturbations comprise 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98 or 99 or massively parallel perturbations.

3. The method of paragraph 1 or 2 wherein the perturbation(s) comprise one or more genetic perturbation.

4. The method of paragraph 1, 2 or 3 wherein the perturbation(s) comprise one or more epigenetic or epigenomic perturbation.

5. The method of any of the preceding paragraphs wherein at least one perturbation is introduced with RNAi- or a CRISPR-Cas system.

6. The method of any of the preceding paragraphs wherein at least one perturbation is introduced via a chemical agent, an intracellular spatial relationship between two or more cells, an increase or decrease of temperature, addition or subtraction of energy, electromagnetic energy, or ultrasound.

7. The method of any one of the preceding paragraphs wherein the cell comprises a cell in a model non-human organism, a model non-human mammal that expresses a Cas protein, a mouse that expresses a Cas protein, a cell in vivo or a cell ex vivo or a cell in vitro.

8. The method of any one of the preceding paragraphs wherein measuring or measured differences comprises measuring or measured differences of DNA, RNA, protein or post translational modification; or measuring or measured differences of protein or post translational modification correlated to RNA and/or DNA level(s).

9. The method of any preceding paragraph wherein the method includes sequencing, and prior to sequencing:

(a) perturbing and isolating a single cell with at least one labeling ligand specific for binding at one or more target RNA transcripts, or isolating a single cell with at least one labeling ligand specific for binding at one or more target RNA transcripts and perturbing the cell; and/or (b) lysing the cell under conditions wherein the labeling ligand binds to the target RNA transcript(s).

10. The method of paragraph 9 wherein step (a) comprises perturbing and isolating a single cell with at least one labeling ligand specific for binding at one or more target RNA transcripts.

11. The method of paragraph 9 wherein step (a) comprises isolating a single cell with at least one labeling ligand specific for binding at one or more target RNA transcripts and perturbing the cell.

12. The method of any preceding paragraph wherein perturbing or perturbation(s) comprise(s) genetic perturbing.

13. The method of any preceding paragraph wherein perturbing or perturbation(s) comprise(s) single-order perturbations.

14. The method of any preceding paragraph wherein perturbing or perturbation(s) comprise(s) combinatorial perturbations.

15. The method of any preceding paragraph wherein perturbing or perturbation(s) comprises gene knock-down, gene knock-out, gene activation, gene insertion, or regulatory element deletion.

16. The method of any preceding paragraph wherein perturbing or perturbation(s) comprises genome-wide perturbation.

17. The method of any preceding paragraph wherein perturbing or perturbation(s) comprises performing CRISPR-Cas-based perturbation.

18. The method of any preceding paragraph wherein perturbing or perturbation(s) comprises performing pooled single or combinatorial CRISPR-Cas-based perturbation with a genome-wide library of sgRNAs.

19. The method of any preceding paragraph wherein perturbing or perturbation(s) comprises performing pooled combinatorial CRISPR-Cas-based perturbation with a genome-wide library of sgRNAs.

20. The method of any one of paragraphs 18 or 19, wherein each sgRNA comprises a unique molecular identifier.

21. The method of any one of paragraphs 18 or 19, wherein each sgRNA is co-delivered with a reporter mRNA.

22. The method of any preceding paragraph wherein perturbing or perturbation(s) comprises subjecting the cell to an increase or decrease in temperature.

23. The method of any preceding paragraph wherein perturbing or perturbation(s) comprises subjecting the cell to a chemical agent.

24. The method of any preceding paragraph wherein perturbing or perturbation(s) comprises subjecting the cell to a chemical agent and/or temperature increase or decrease across a gradient.

25. The method of any preceding paragraph wherein the cell is in a microfluidic system.

26. The method of any preceding paragraph wherein the cell is in a droplet.

27. The method of any preceding paragraph wherein perturbing or perturbation(s) comprises transforming or transducing the cell or a population that includes and from which the cell is isolated with one or more genomic sequence-perturbation constructs that perturbs a genomic sequence in the cell.

28. The method of any preceding paragraph wherein perturbing or perturbation(s) comprises multiplex transformation with a plurality of genomic sequence-perturbation constructs.

29. The method of any one of the preceding paragraphs, wherein the labeling ligand comprises a unique perturbation identifier (UPI) sequence attached to a perturbation-sequence-capture sequence, and sequencing includes isolating via microbeads comprising a perturbation-sequence-capture-binding-sequence having specific binding affinity for the perturbation-sequence-capture sequence attached to the UPI sequence.

30. The method of paragraph 29, wherein the UPI sequence is attached to a universal ligation handle sequence, whereby a unique source identifier USI may be generated by split-pool ligation.

31. The method of any preceding paragraph wherein the labeling ligand comprises an oligonucleotide label comprising a regulatory sequence configured for amplification by T7 polymerase.

32. The method of any preceding paragraph wherein the labeling ligands comprises oligonucleotide sequences configured to hybridize to a transcript specific region.

33. The method of any preceding paragraph wherein the labeling ligands comprises an oligonucleotide label.

34. The method of paragraph, 33, wherein the oligonucleotide label further comprises a photocleavable linker.

35. The method of paragraph 33 or 34 wherein the oligonucleotide label further comprises a restriction enzyme site between the labeling ligand and unique constituent identifier (UCI).

36. The method of any preceding paragraph, wherein isolating comprises forming discrete unique-identifier-transfer compositions, each comprising the cell and a transfer particle, wherein:

(a) an oligonucleotide label further comprises a capture sequence, and unique constituent identifier (UCI) and capture sequence are together releasably attached to the labeling ligand;

(b) the labelling ligand is bound to the target cellular constituent; and, (c) a transfer particle comprises:

(i) a capture-binding-sequence having specific binding affinity for the capture sequence attached to the UCI, and, (ii) a unique source identifier (USI) sequence that is unique to each transfer particle.

37. The method of paragraph 36 wherein, the USI comprises 4-15 nucleotides.

38. The method of paragraph 36 or 37, further comprising releasing the UCI from the labeled ligand, under conditions within the unique-identifier-transfer composition so that the released capture sequence binds to the capture-binding-sequence on the transfer particle, thereby transferring the UCI to the transfer particle.

39. The method of any preceding paragraph wherein the ligation handle comprises a restriction site for producing an overhang complementary with a first index sequence overhang, and wherein the method further comprises digestion with a restriction enzyme.

40. The method of any preceding paragraph wherein the ligation handle comprises a nucleotide sequence complementary with a ligation primer sequence and wherein the overhang complementary with a first index sequence overhang is produced by hybridization of the ligation primer to the ligation handle.

41. The method of any one of the preceding paragraphs further comprising quantitating relative amount of UCI sequence associated with a first cell to the amount of the same UCI sequence associated with a second cell, whereby the relative differences of a cellular constituent between cell(s) are determined.

42. The method of any one of the preceding paragraphs wherein the labeling ligand comprises an antibody or an antibody fragment.

43. The method of any one of the preceding paragraphs wherein the antibody fragment is a nanobody, Fab, Fab', (Fab')2, Fv, ScFv, diabody, triabody, tetrabody, Bis-scFv, minibody, Fab2, or Fab3 fragment.

44. The method of any preceding paragraph wherein the labeling ligand comprises an aptamer.

45. The method of any preceding paragraph wherein the labeling ligand is a nucleotide sequence complementary to a target sequence.

46. The method of any preceding paragraph wherein the cell or a population that includes wherein the cell(s) are a member of a cell population, and the method further comprises transforming or transducing the cell population with one or more genomic sequence-perturbation constructs that perturb a genomic sequence in the cells, wherein each distinct genomic sequence-perturbation construct comprises a unique-perturbation-identified (UPI) sequence unique to that construct.

47. The method of paragraph 46, wherein the genomic sequence-perturbation construct comprises a sequence encoding a guide RNA sequence of a CRISPR-Cas targeting system.

48. The method of paragraph 46 or 47, further comprising multiplex transformation of the population of cells with a plurality of genomic sequence-perturbation constructs.

49. The method of any one of paragraphs 46, 47 or 48, wherein the UPI sequence is attached to a perturbation-sequence-capture sequence, and the transfer particle comprise a perturbation-sequence-capture-binding-sequence having specific binding affinity for the perturbation-sequence-capture sequence attached to the UPI sequence.
50. The method of any one of paragraphs 46 or 47, wherein the UPI sequence is attached to a universal ligation handle sequence, whereby a USI is generated by split-pool ligation.
51. A method of determining any combination of protein detection, RNA detection, open chromatin detection, protein-protein interactions, protein-RNA interactions, or protein-DNA interactions comprising any of the preceding methods.
52. A method according to any of the preceding paragraphs including whole transcriptome amplification.
53. The method according to any one of the preceding paragraphs including comparing an RNA profile of the perturbed cell with any mutations in the cell to also correlate phenotypic or transcriptome profile and genotypic profile.
54. A method for determining genetic interactions by causing a set of P genetic perturbations in cells,
wherein the method comprises:
(a) Determining, based upon random sampling, a subset of a genetic perturbations from the set of P genetic perturbations;
(b) Performing said subset of π genetic perturbations in a population of cells;
(c) Performing single-cell molecular profiling of the population of genetically perturbed cells of step (b);
(d) Inferring, from the results of step (c) and based upon the random sampling of step (a), single-cell molecular profiles for the set of P genetic perturbations in cells.
55. The method according to paragraph 54,
wherein the method further comprises:
(e) From the results of step (d), determining genetic interactions.
56. The method according to paragraph 54,
wherein the method further comprises:
(f) Confirming genetic interactions determined at step (e) with additional genetic manipulations.
57. The method according to any one of paragraphs 54-56, wherein said set of P genetic perturbations or said subset of π genetic perturbations comprises single-order genetic perturbations.
58. The method according to any one of paragraphs 54-57, wherein said set of P genetic perturbations or said subset of π genetic perturbations comprises combinatorial genetic perturbations.
59. The method according to any one of paragraphs 54-58, wherein said genetic perturbation comprises gene knock-down, gene knock-out, gene activation, gene insertion, or regulatory element deletion.
60. The method according to any one of paragraphs 54-59, wherein said set of P genetic perturbations or said subset of π genetic perturbations comprises genome-wide perturbations.
61. The method according to any one of paragraphs 54-60, wherein said set of P genetic perturbations or said subset of π genetic perturbations comprises k-order combinations of single genetic perturbations, wherein k is an integer ranging from 2 to 15, and wherein step (e) comprises determining k-order genetic interactions.
62. The method according to any one of paragraphs 54-61, wherein said set of P genetic perturbations comprises combinatorial genetic perturbations, such as k-order combinations of single-order genetic perturbations, wherein k is an integer ranging from 2 to 15, and wherein step (e) comprises determining j-order genetic interactions, with j<k.
63. The method according to any one of paragraphs 54-62, wherein step (b) comprises performing RNAi- or CRISPR-Cas-based perturbation.
64. The method according to any one of paragraphs 54-63, wherein step (b) comprises array-format or pool-format perturbation.
65. The method according to any one of paragraphs 54-64, wherein step (b) comprises pooled single or combinatorial CRISPR-Cas-based perturbation with a genome-wide library of sgRNAs.
66. The method according to any one of paragraphs 54-65, wherein step (b) comprises pooled combinatorial CRISPR-Cas-based perturbation with a genome-wide library of sgRNAs.
67. The method of paragraph 65 or 66, wherein each sgRNA comprises a unique molecular identifier.
68. The method of paragraph 65, 66 or 67, wherein each sgRNA is co-delivered with a reporter mRNA.
69. The method according to any one of paragraphs 54-68, wherein random sampling comprises matrix completion, tensor completion, compressed sensing, or kernel learning.
70. The method according to any one of paragraphs 54-69, wherein random sampling comprises matrix completion, tensor completion, or compressed sensing, and wherein π is of the order of log P.
71. The method of any one of the preceding paragraphs, wherein the cell comprises a eukaryotic cell.
72. The method of paragraph 71, wherein the eukaryotic cell comprises a mammalian cell.
73. The method of paragraph 72, wherein the mammalian cell comprises a human cell.
74. The method of any one of the preceding paragraphs, wherein the cell is from a population comprising $10^2$ to $10^8$ cells and/or DNA or RNA or protein or post translational modification measurements or variables per cell comprise 50 or more.
75. A method for screening a collection of compounds or agents comprising performing a method as paragraphed in any of the preceding paragraphs wherein perturbing comprises exposing the cell to each compound or agent.
76. A therapeutic identified by the method of paragraph 75.
77. The method of any one of the preceding paragraphs wherein the perturbing is across a library of cells to thereby obtain RNA level and optionally protein level cell-to-cell circuit data at genomic or transcript or expression level.
78. The method of paragraph 77, wherein the library of cells comprises or is from a tissue sample.
79. The method of paragraph 78, wherein the tissue sample comprises or is from a biopsy from a mammalian subject.
80. The method of paragraph 79, wherein the mammalian subject comprises a human subject.
81. The method of paragraph 80, wherein the biopsy is from a tumor.

82. The method of any one of paragraphs 77 to 81, further comprising reconstructing cell-to-cell circuits.
83. The method of any preceding paragraph wherein open chromatin detection includes fragmenting chromatin inside isolated intact nuclei from a cell, adding universal primers at cutting sites, and uniquely tagging DNA that originated from the cell.
84. A method of screening a combination of perturbations correlating to a phenotype:
    introducing a plurality of perturbations to a plurality of cells, wherein each perturbation comprises a barcode and each cell receives at least one perturbation;
    expanding the plurality of cells introduced with the plurality of perturbations, thereby generating a plurality of clonal cell populations wherein each clonal cell population results from expanding one of the plurality of cells introduced with the plurality of perturbations;
    selecting a subpopulation from the clonal cell populations, wherein cells in the subpopulation has the phenotype; and
    identifying perturbations in the cells in the subpopulation.
85. The method of paragraph 84, wherein the plurality of perturbations is a pooled plurality of perturbations.
86. The method of any of one of paragraphs 84-85, wherein the plurality of perturbations comprise polynucleotides with guide RNA sequences.
87. The method of paragraph 86, wherein each of the polynucleotides comprises a barcode sequence.
88. The method of any of one of paragraphs 84-87, further comprise identifying correlation between the barcode and the perturbation.
89. The method of any of one of paragraphs 84-88, wherein the barcode is a unique transduction barcode.
90. The method of any of one of paragraphs 84-89, wherein selecting the subpopulation comprises sorting cells into multiple containers.
91. The method of paragraph 90, wherein the multiple containers are wells in a multi-well plate.
92. The method of any of one of paragraphs 84-91, wherein identifying the perturbations in the cells in the subpopulation comprise sequencing.
93. The method of paragraph 92, wherein the sequencing is deep sequencing.
94. The method of any of one of paragraphs 84-93, wherein the plurality of perturbations are introduced via a chemical agent, biological agent, an intracellular spatial relationship between two or more cells, an increase or decrease of temperature, addition or subtraction of energy, electromagnetic energy, ultrasound, or combination thereof.
95. The method of any of one of paragraphs 84-94, wherein the plurality of perturbations are CRISPR-Cas-based perturbations.
96. The method of any of one of paragraphs 84-95, wherein the plurality of perturbations comprise a genome-wide library of sgRNA.
97. The method of any of one of paragraphs 84-96, wherein introducing the plurality of perturbations to the plurality of cells comprise transducing, transfecting, transforming, or a combination thereof.
98. The method of any of one of paragraphs 84-97, further comprising detecting the phenotype.
99. The method of any of one of paragraphs 84-98, wherein the phenotype indicates the subpopulation's response to a treatment of a disease.
100. The method of any of one of paragraphs 84-99, wherein the plurality of cells are derived from a patient or a disease model.

Exemplary embodiments of the invention may be further described by the following numbered statement:

A method of reconstructing a cellular network or circuit, comprising:

(a) introducing at least 1, 2, 3, 4 or more single-order or combinatorial perturbations to a plurality of cells in a population of cells, wherein each cell in the plurality of the cells receives at least 1 perturbation; and (b) measuring comprising:

(i) detecting genomic, genetic, proteomic, epigenetic and/or phenotypic differences in single cells compared to one or more cells that did not receive any perturbation, and (ii) detecting the perturbation(s) in single cells.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of screening for combinations of a plurality of genetic perturbations correlating to a phenotype, said method comprising:

introducing the plurality of genetic perturbations to a plurality of cells using a plurality of lentiviral vectors, wherein the plurality of cells express CRISPR-associated protein 9 (Cas9) or dead Cas9 (dCas9), and wherein each of the plurality of lentiviral vectors comprises a unique guide barcode for identifying each of the plurality of genetic perturbations, and each of the plurality of cells receives at least two of the plurality of genetic perturbations, and wherein each lentiviral vector in the plurality of lentiviral vectors comprises two expression units: (1) a polymerase III-driven single-guide RNA (sgRNA); and (2) a guide barcode expression cassette encoding the unique guide barcode and comprising a polyadenylation signal, wherein the unique guide barcode is unique for each sgRNA and uniquely identifies the genetic perturbation associated with each lentiviral vector, and wherein the two expression units are each encoded in reverse orientation with respect to lentiviral genes and are positioned between a 3' long terminal repeat (LTR) and a 5' LTR of each of the plurality of lentiviral vectors;

expanding the plurality of cells introduced with the plurality of genetic perturbations;

generating a plurality of clonal cell populations, wherein each clonal cell population results from the expanding one of the plurality of cells introduced with the plurality of genetic perturbations;

positively selecting a subpopulation of cells from the plurality of clonal cell populations having a phenotype; and sorting the subpopulation of cells from the plurality of clonal cell populations into multiple containers, wherein each of the multiple containers comprises a plurality of cells from the subpopulation of cells having the phenotype;

sequencing the unique guide barcodes in each of the multiple containers and determining the unique guide barcodes that co-occur in one or more of the multiple containers; and identifying, based on the co-occurrence of the unique guide barcodes in the one or more of the multiple containers, combinations of genetic perturbations from the plurality of genetic perturbations in the subpopulation of cells from the plurality of clonal cell populations having the phenotype, wherein each of the plurality of genetic perturbations comprises one or more of a gene knock-down, a gene knock-out, a gene activation, a gene insertion, or a deletion of a regulatory or functional element introduced by one of the plurality of lentiviral vectors; and wherein the plurality of lentiviral vectors are introduced at a multiplicity of infection (MOI) such that each cell of the plurality of cells receives at least 2 of the plurality of genetic perturbations.

2. The method of claim 1, wherein the plurality of lentiviral vectors are introduced at a multiplicity of infection (MOI) such that each of the plurality of cells receives more than two of the plurality of genetic perturbations.

3. The method of claim 1, wherein the plurality of lentiviral vectors are introduced at a multiplicity of infection (MOI) such that each of the plurality of cells receives at least four of the plurality of genetic perturbations.

4. The method of claim 1, wherein the plurality of lentiviral vectors are introduced at a multiplicity of infection (MOI) such that each cell of the plurality of cells receives at least 5 of the plurality of genetic perturbations.

5. The method of claim 1, wherein the plurality of genetic perturbations comprises a plurality of polynucleotides encoding a genetic perturbation.

6. The method of claim 5, wherein each polynucleotide further comprises a unique transduction barcode (UTB) that is unique to each polynucleotide encoding a genetic perturbation.

7. The method of claim 1, wherein the multiple containers comprise wells in a multi-well plate.

8. The method of claim 1, wherein the sequencing is deep sequencing.

9. The method of claim 1, wherein introducing the plurality of genetic perturbations to the plurality of cells comprises a process selected from the group consisting of transducing, transfecting, transforming, and a combination thereof.

10. The method of claim 1, further comprising obtaining the plurality of cells from a patient prior to introducing the plurality of genetic perturbations to the plurality of cells.

* * * * *